(12) United States Patent
Shluzas et al.

(10) Patent No.: US 7,976,464 B2
(45) Date of Patent: Jul. 12, 2011

(54) ACCESS SYSTEMS AND METHODS FOR MINIMALLY INVASIVE SURGERY

(75) Inventors: Alan E. Shluzas, West Roxbury, MA (US); Karl Dallas Kirk, III, New York, NY (US); Walter Stoeckmann, Hoboken, NJ (US)

(73) Assignee: Zimmer Spine, Inc., Minneapolis, MN (US)

( * ) Notice: Subject to any disclaimer, the term of this patent is extended or adjusted under 35 U.S.C. 154(b) by 1998 days.

(21) Appl. No.: 10/926,579

(22) Filed: Aug. 26, 2004

(65) Prior Publication Data
US 2005/0273131 A1 Dec. 8, 2005

Related U.S. Application Data

(60) Provisional application No. 60/497,822, filed on Aug. 26, 2003, provisional application No. 60/497,763, filed on Aug. 26, 2003, provisional application No. 60/514,559, filed on Oct. 24, 2003, provisional application No. 60/545,587, filed on Feb. 18, 2004, provisional application No. 60/579,643, filed on Jun. 15, 2004.

(51) Int. Cl.
*A61B 1/32* (2006.01)
(52) U.S. Cl. .................. 600/219; 604/104; 606/198
(58) Field of Classification Search .............. 600/190, 600/196, 201, 208, 210, 215, 225, 219, 220, 600/222; 606/108, 86, 198; 604/104, 106
See application file for complete search history.

(56) References Cited

U.S. PATENT DOCUMENTS

| 151,228 | A | 5/1874 | Knaffl |
|---|---|---|---|
| 530,728 | A | 12/1894 | Sherbrook |
| 2,083,573 | A | 6/1937 | Morgan |
| 2,313,164 | A | 3/1943 | Nelson |
| 2,594,086 | A | 4/1952 | Smith |

(Continued)

FOREIGN PATENT DOCUMENTS

AU 13672/95 9/1995

(Continued)

OTHER PUBLICATIONS

Invitation to Pay Additional Fees with Partial International Search Report, PCT/US2004/035072 dated Jan. 28, 2005.

(Continued)

*Primary Examiner* — Cris L Rodriguez
*Assistant Examiner* — Hao D Mai
(74) *Attorney, Agent, or Firm* — Seager, Tufte & Wickhem, LLC

(57) ABSTRACT

A device for retracting tissue provides access to a spinal location within a patient. The device includes an elongate body and a passage. The elongate body has a proximal portion and a distal portion. The elongate body defines a length between the proximal and distal portions along a longitudinal axis such that the distal portion can be positioned inside the patient adjacent the spinal location while the proximal portion is accessible. A transverse cross-section of the elongate body in the proximal portion has a first dimension that is longer than a second dimension. The first dimension is perpendicular to the second dimension. The passage extends through the elongate body between the proximal and distal portions. The elongate body is configured such that the proximal portion may be tilted with respect to the distal portion in a first direction generally aligned with the first dimension and in a second direction generally aligned with the second dimension.

6 Claims, 148 Drawing Sheets

U.S. PATENT DOCUMENTS

| | | |
|---|---|---|
| 2,623,517 A | 12/1952 | Barlow et al. |
| 3,044,461 A | 7/1962 | Murdock |
| 3,070,088 A | 12/1962 | Brahos |
| 3,509,873 A | 5/1970 | Karlin et al. |
| 3,749,088 A | 7/1973 | Kohlmann |
| 3,965,890 A | 6/1976 | Gauthier |
| 3,998,217 A | 12/1976 | Trumbull et al. |
| 4,010,741 A | 3/1977 | Gauthier |
| 4,130,113 A | 12/1978 | Graham |
| 4,155,355 A | 5/1979 | Yamamoto |
| 4,254,763 A | 3/1981 | McCready et al. |
| 4,414,962 A | 11/1983 | Carson |
| 4,421,107 A | 12/1983 | Estes et al. |
| 4,653,476 A | 3/1987 | Bonnet |
| 4,706,656 A | 11/1987 | Kuboto |
| 4,848,323 A | 7/1989 | Marijnissen et al. |
| 4,863,133 A | 9/1989 | Bonnell |
| 4,877,016 A | 10/1989 | Kantor et al. |
| 5,131,382 A | 7/1992 | Meyer |
| 5,163,949 A | 11/1992 | Bonutti |
| 5,197,971 A | 3/1993 | Bonutti |
| 5,231,974 A | 8/1993 | Giglio et al. |
| 5,269,772 A | 12/1993 | Wilk |
| 5,287,845 A | 2/1994 | Faul et al. |
| 5,295,994 A | 3/1994 | Bonutti |
| 5,313,962 A | 5/1994 | Obenchain |
| 5,345,927 A | 9/1994 | Bonutti |
| 5,354,302 A | 10/1994 | Ko |
| 5,400,774 A | 3/1995 | Villalta et al. |
| 5,454,365 A | 10/1995 | Bonutti |
| 5,503,617 A | 4/1996 | Jako |
| 5,505,690 A | 4/1996 | Patton et al. |
| 5,569,205 A | 10/1996 | Hart et al. |
| 5,601,590 A | 2/1997 | Bonutti et al. |
| 5,667,481 A | 9/1997 | Villalta et al. |
| 5,667,520 A | 9/1997 | Bonutti et al. |
| 5,681,265 A | 10/1997 | Maeda et al. |
| 5,688,223 A | 11/1997 | Rosendahl |
| 5,728,046 A | 3/1998 | Mayer et al. |
| 5,762,629 A | 6/1998 | Kambin |
| 5,792,044 A | 8/1998 | Foley et al. |
| 5,795,291 A | 8/1998 | Koros et al. |
| 5,813,978 A | 9/1998 | Jako |
| 5,868,668 A | 2/1999 | Weiss |
| 5,902,231 A | 5/1999 | Foley et al. |
| 5,944,658 A | 8/1999 | Koros et al. |
| 5,961,499 A | 10/1999 | Bonutti et al. |
| 6,024,697 A | 2/2000 | Pisarik |
| 6,036,638 A | 3/2000 | Nwawka |
| 6,083,154 A | 7/2000 | Liu et al. |
| 6,096,046 A | 8/2000 | Weiss |
| 6,139,493 A | 10/2000 | Koros et al. |
| 6,171,299 B1 | 1/2001 | Bonutti |
| 6,187,000 B1 | 2/2001 | Davison et al. |
| 6,193,715 B1 | 2/2001 | Wrublewski et al. |
| 6,206,826 B1 | 3/2001 | Mathews et al. |
| 6,338,730 B1 | 1/2002 | Bonutti et al. |
| 6,354,995 B1 | 3/2002 | Hoftman et al. |
| 6,358,266 B1 | 3/2002 | Bonutti |
| 6,361,488 B1 | 3/2002 | Davison et al. |
| 6,364,832 B1 | 4/2002 | Propp |
| 6,371,968 B1 | 4/2002 | Kogasaka et al. |
| 6,432,048 B1 | 8/2002 | Francois |
| 6,464,634 B1 | 10/2002 | Fraser |
| 6,524,320 B2 | 2/2003 | DiPoto |
| 6,530,880 B2 | 3/2003 | Pagliuca |
| 6,530,926 B1 | 3/2003 | Davison |
| 6,554,832 B2 | 4/2003 | Shluzas |
| 6,596,008 B1 | 7/2003 | Kambin |
| 6,616,605 B2 | 9/2003 | Wright et al. |
| 6,641,583 B2 | 11/2003 | Shluzas et al. |
| 6,648,888 B1 | 11/2003 | Shluzas |
| 6,652,553 B2 | 11/2003 | Davison et al. |
| 6,673,074 B2 | 1/2004 | Shluzas |
| 6,679,833 B2 | 1/2004 | Smith et al. |
| 6,712,795 B1 | 3/2004 | Cohen |
| 6,800,084 B2 | 10/2004 | Davison et al. |
| 6,811,558 B2 | 11/2004 | Davison et al. |
| 6,821,243 B2 | 11/2004 | Pagliuca et al. |
| 6,837,889 B2 | 1/2005 | Shluzas |
| 6,837,891 B2 | 1/2005 | Davison et al. |
| 6,849,064 B2 | 2/2005 | Hamada |
| 6,945,933 B2 | 9/2005 | Branch et al. |
| 7,001,397 B2 | 2/2006 | Davison et al. |
| 7,004,947 B2 | 2/2006 | Shluzas et al. |
| 7,014,608 B2 | 3/2006 | Larson et al. |
| 7,029,124 B2 | 4/2006 | Dubin et al. |
| 7,033,369 B2 | 4/2006 | Davison et al. |
| 7,056,321 B2 | 6/2006 | Pagliuca et al. |
| 7,066,937 B2 | 6/2006 | Shluzas |
| 7,144,393 B2 | 12/2006 | DiPoto et al. |
| 7,144,396 B2 | 12/2006 | Shluzas |
| 7,179,225 B2 | 2/2007 | Shluzas et al. |
| 7,226,451 B2 | 6/2007 | Shluzas et al. |
| 2001/0011170 A1 | 8/2001 | Davison et al. |
| 2002/0173798 A1 | 11/2002 | DiPoto |
| 2003/0014068 A1 | 1/2003 | Bonutti et al. |
| 2003/0073998 A1 | 4/2003 | Unger et al. |
| 2003/0097045 A1 | 5/2003 | Kashyap |
| 2003/0153927 A1 | 8/2003 | DiPoto et al. |
| 2003/0191371 A1 | 10/2003 | Smith et al. |
| 2003/0195550 A1 | 10/2003 | Davison et al. |
| 2003/0195551 A1 | 10/2003 | Davison et al. |
| 2003/0199885 A1 | 10/2003 | Davison et al. |
| 2003/0199915 A1 | 10/2003 | Shimm |
| 2004/0078051 A1 | 4/2004 | Davison et al. |
| 2004/0098012 A1 | 5/2004 | Davison et al. |
| 2004/0098016 A1 | 5/2004 | Bonutti |
| 2004/0116954 A1 | 6/2004 | Pagliuca et al. |
| 2004/0133201 A1 | 7/2004 | Shluzas et al. |
| 2004/0176665 A1 | 9/2004 | Branch et al. |
| 2004/0181231 A1 | 9/2004 | Emstad et al. |
| 2004/0230100 A1 | 11/2004 | Shluzas |
| 2005/0065517 A1 | 3/2005 | Chin |
| 2005/0075540 A1 | 4/2005 | Shluzas et al. |
| 2005/0075644 A1 | 4/2005 | DiPoto et al. |
| 2005/0090822 A1 | 4/2005 | DiPoto |
| 2005/0090833 A1 | 4/2005 | DiPoto |
| 2005/0090899 A1 | 4/2005 | DiPoto |
| 2005/0137461 A1 | 6/2005 | Marchek et al. |
| 2005/0159650 A1 | 7/2005 | Raymond et al. |
| 2005/0159651 A1 | 7/2005 | Raymond et al. |
| 2005/0215866 A1* | 9/2005 | Kim .......................... 600/233 |
| 2005/0234304 A1 | 10/2005 | Dewey et al. |
| 2005/0245942 A1 | 11/2005 | DiPoto |
| 2005/0251192 A1 | 11/2005 | Shluzas et al. |
| 2005/0273131 A1 | 12/2005 | Shluzas et al. |
| 2005/0273132 A1 | 12/2005 | Shluzas et al. |
| 2005/0273133 A1 | 12/2005 | Shluzas et al. |
| 2006/0052812 A1 | 3/2006 | Winer |
| 2006/0106416 A1 | 5/2006 | Raymond et al. |
| 2006/0195017 A1 | 8/2006 | Shluzas et al. |
| 2007/0021750 A1 | 1/2007 | Shluzas et al. |

FOREIGN PATENT DOCUMENTS

| | | |
|---|---|---|
| DE | 4133298 | 4/1993 |
| EP | 807 415 A | 11/1997 |
| FR | 610466 | 6/1926 |
| FR | 2701379 | 8/1994 |
| WO | 03068083 | 8/2003 |
| WO | 2004021899 | 3/2004 |
| WO | 2004022108 | 3/2004 |
| WO | 2004103188 | 12/2004 |
| WO | 2005018466 | 3/2005 |
| WO | 2005041863 | 5/2005 |
| WO | 2005046492 | 5/2005 |
| WO | 2005096968 | 10/2005 |
| WO | 2006045089 | 4/2006 |
| WO | 2006058079 | 6/2006 |

OTHER PUBLICATIONS

Invitation to Pay Additional Fees with Partial International Search Report, PCT/US2004/027761 dated Jan. 27, 2005.

International Search Report with Written Opinion, PCT/US2004/027761 dated Apr. 12, 2005.

Kamblin, "Arthroscopic Techniques for Spinal Surgery," Operative Anthroscopy, Second Edition, Ch. 89, pp. 1215-1225 (1996).

Kamblin, "Arthroscopic Lumbar Intervertebral Fusion," The Adult Spine: Principals and Practice Second Edition, Ch. 95, 2:2037-2046 (1997).

U.S. Appl. No. 07/328,952, "Endoscopic Percutaneous Discectomy Device," Material cancelled from Meyer Application filed Mar. 27, 1989.

Wolfhard Caspar, The Caspar Microsurgical Discectomy and Comparison with a Conventional Standard Lumbar Disc Procedure, Neurosurgery, Jan. 1991, pp. 78-87, vol. 28, No. 1, Williams and Wilkins, Baltimore.

* cited by examiner

FIG.2
FIG.3
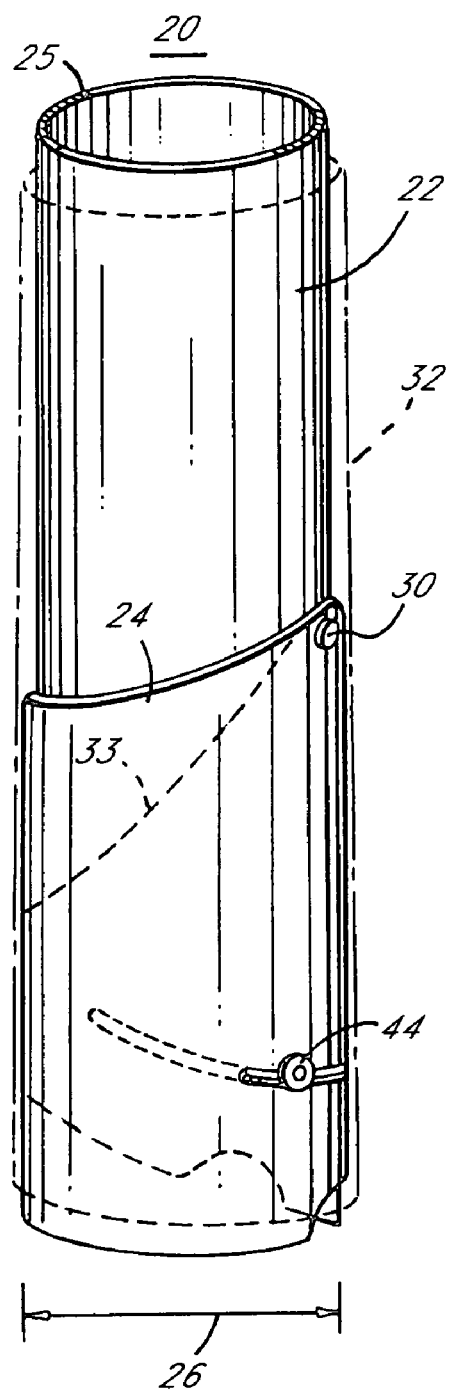
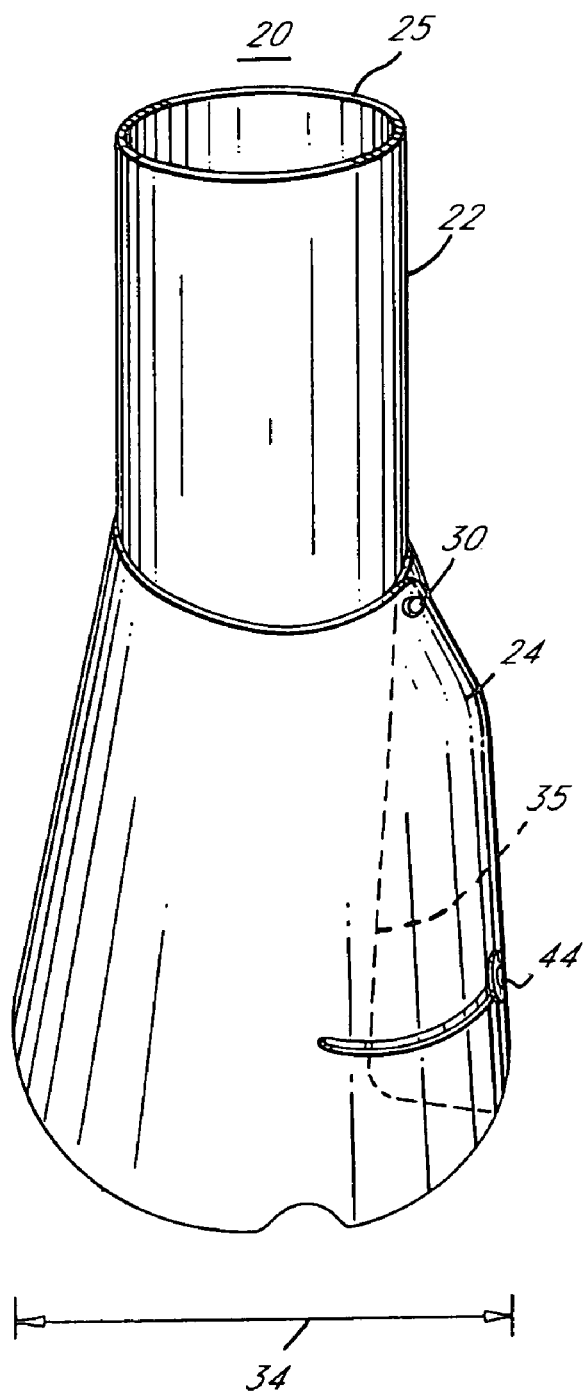

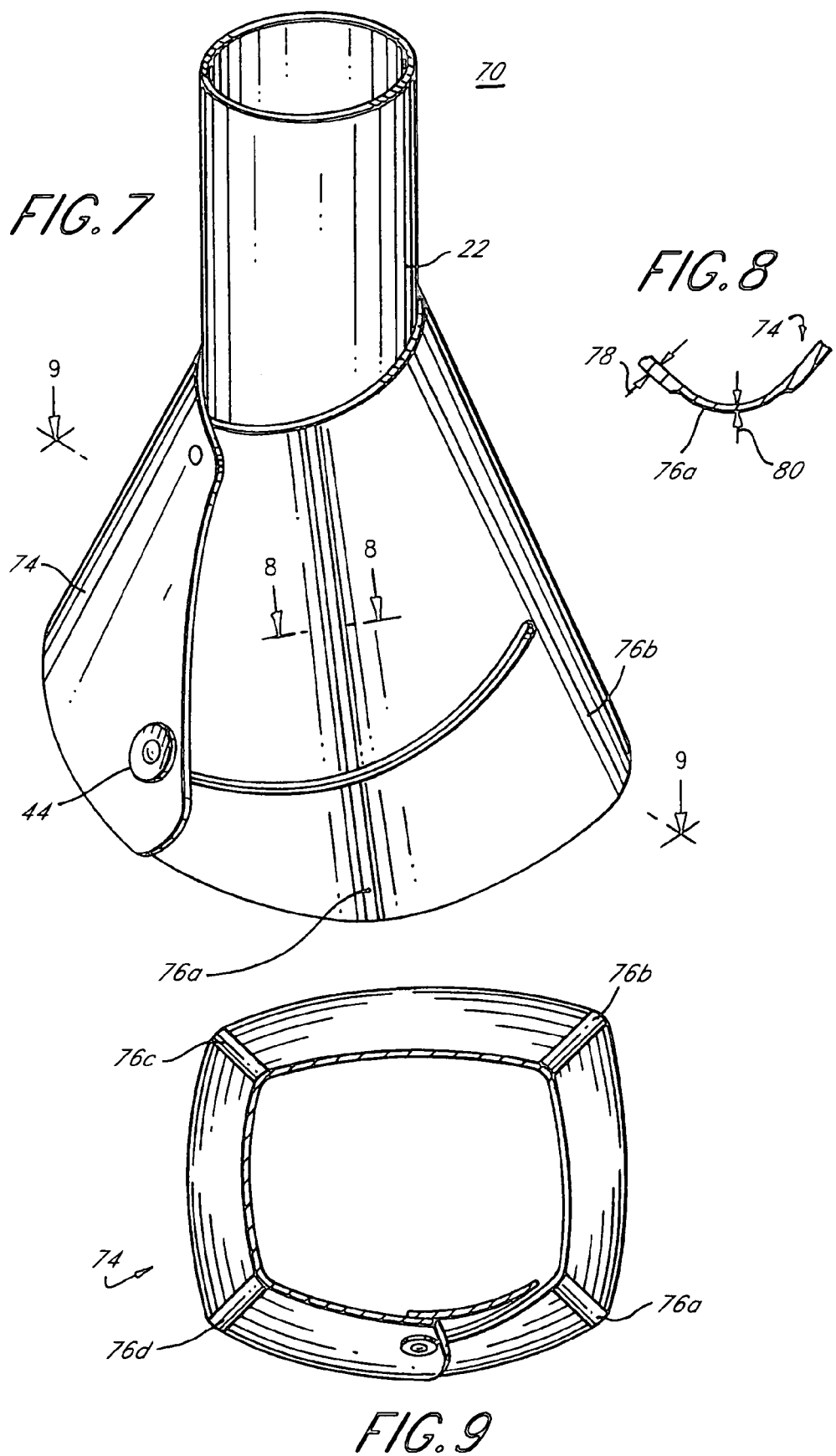

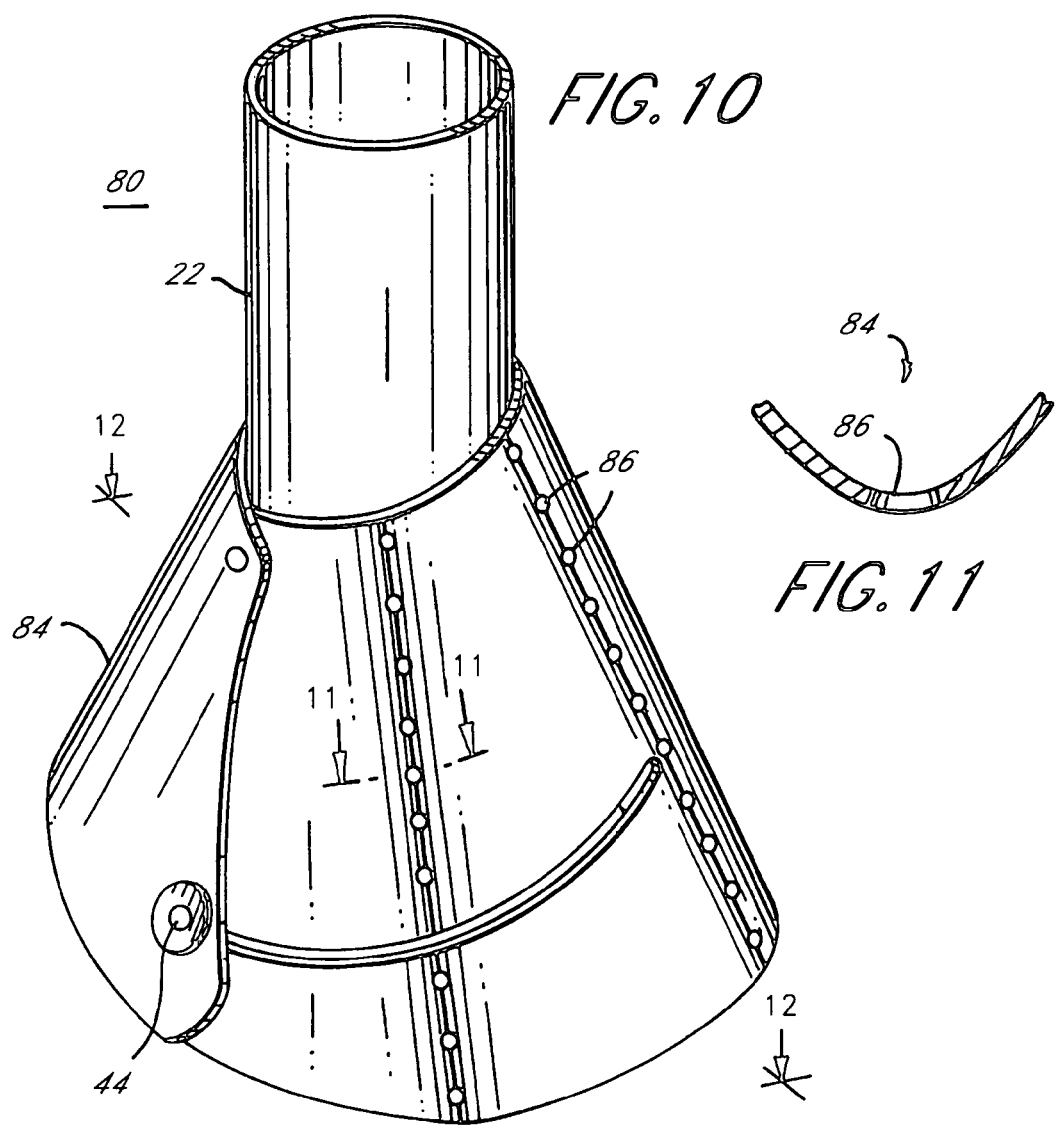
FIG. 10
FIG. 11
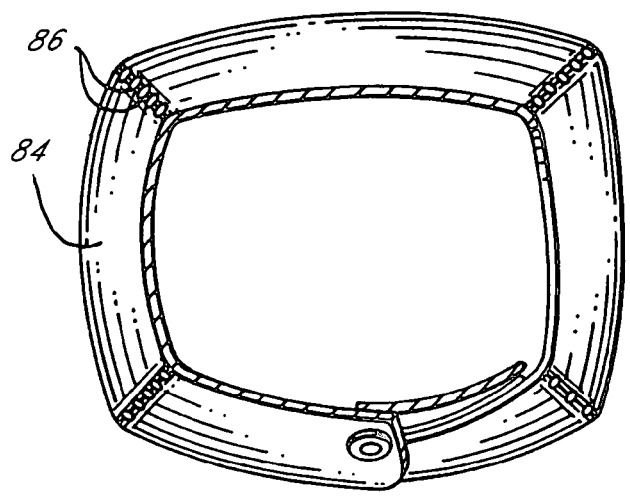
FIG. 12

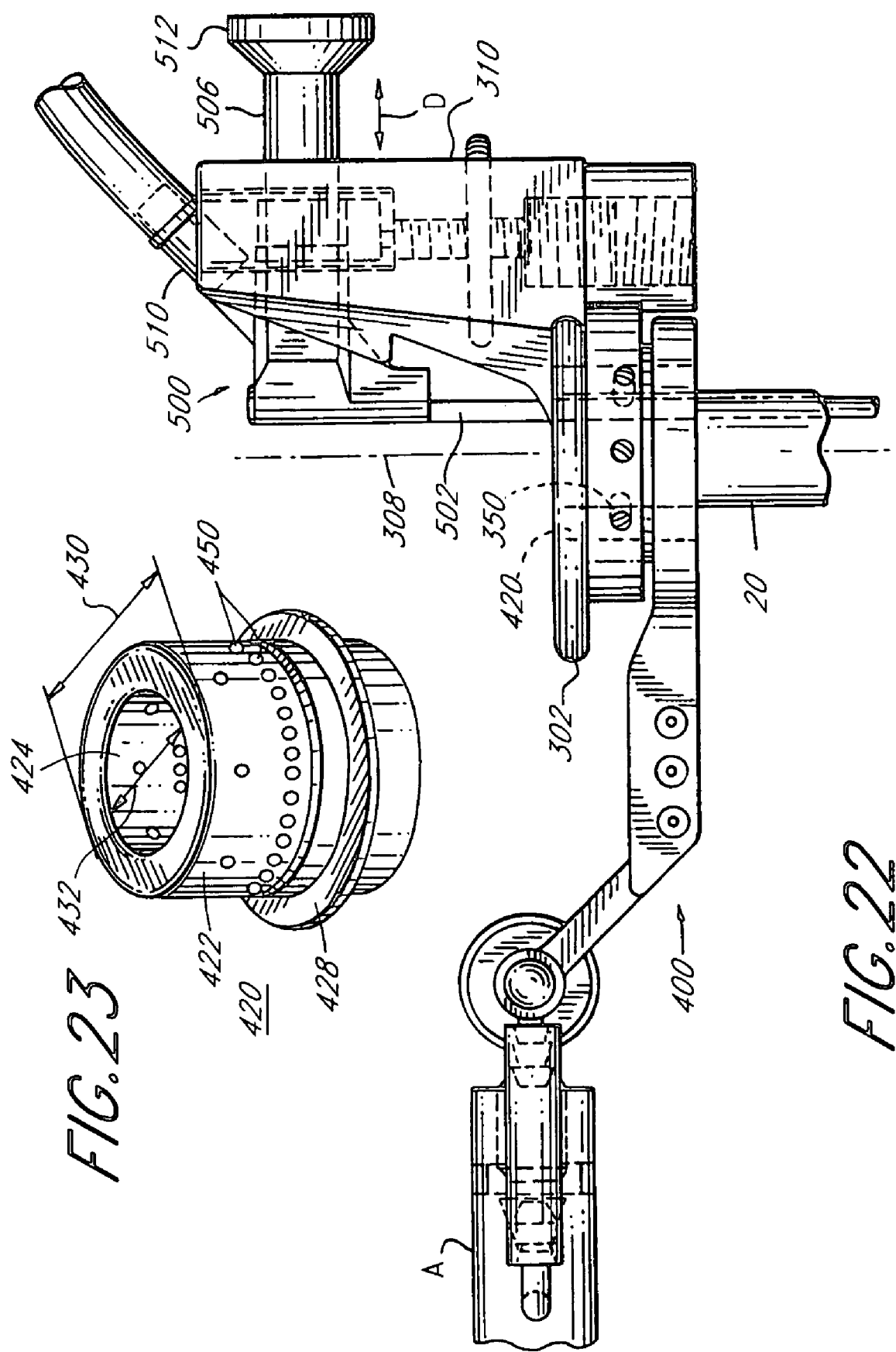

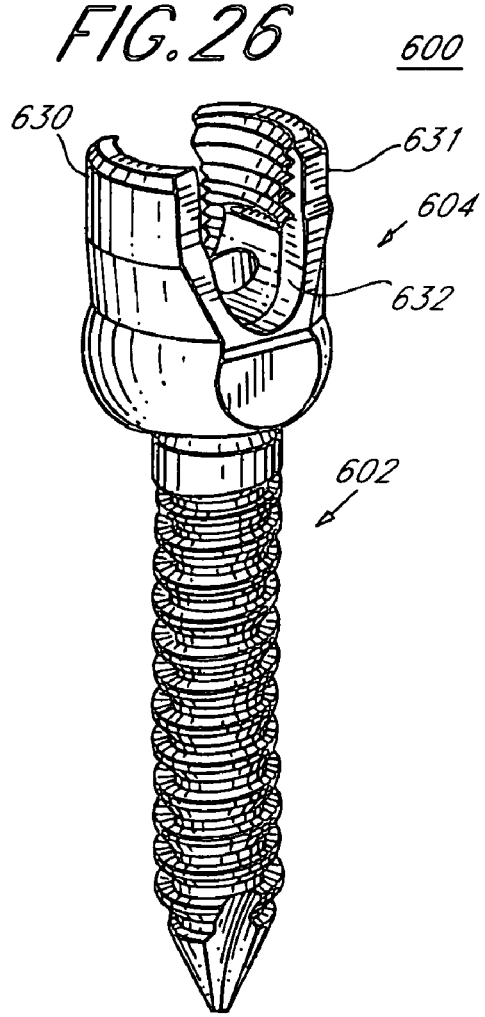
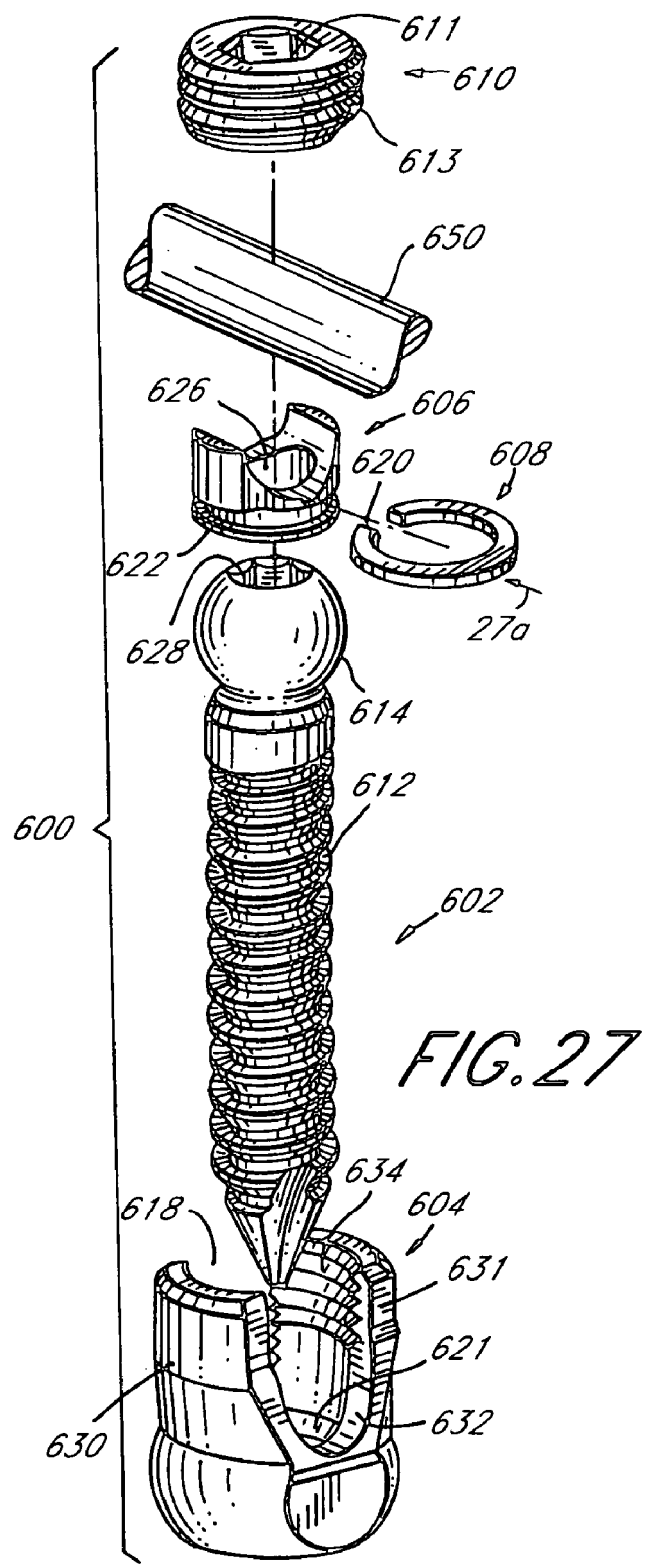

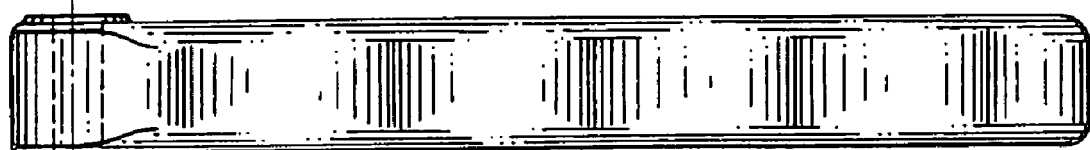
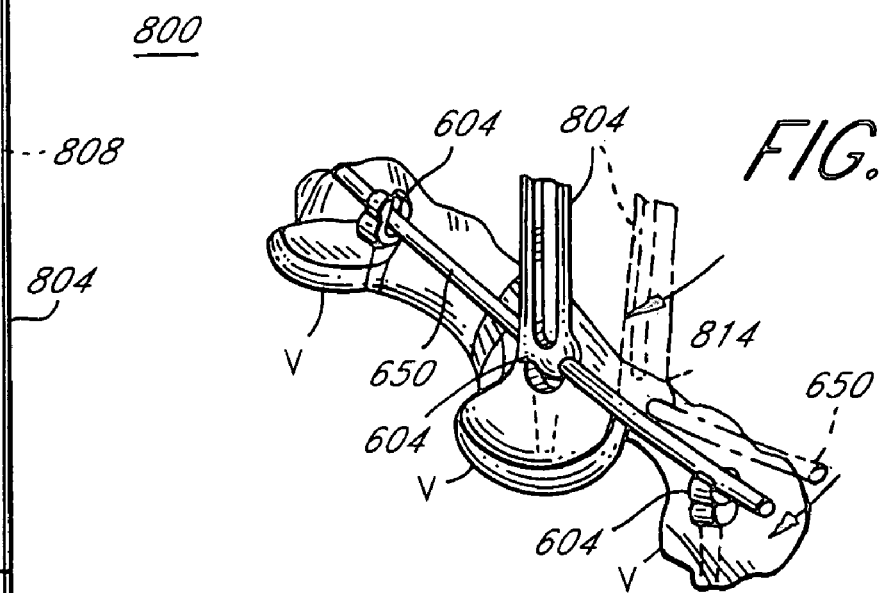
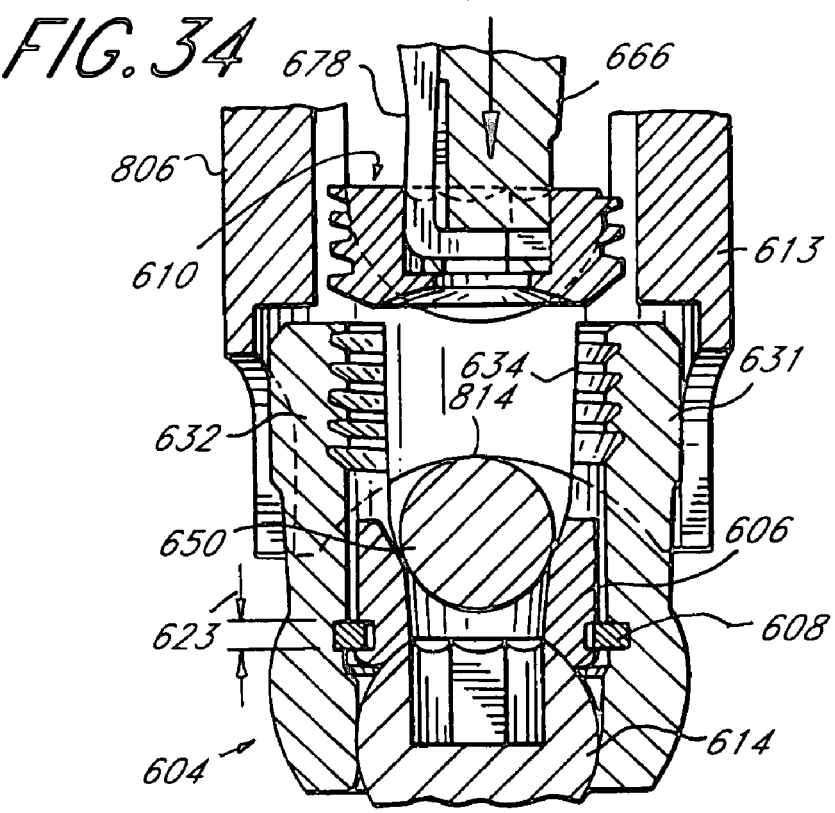

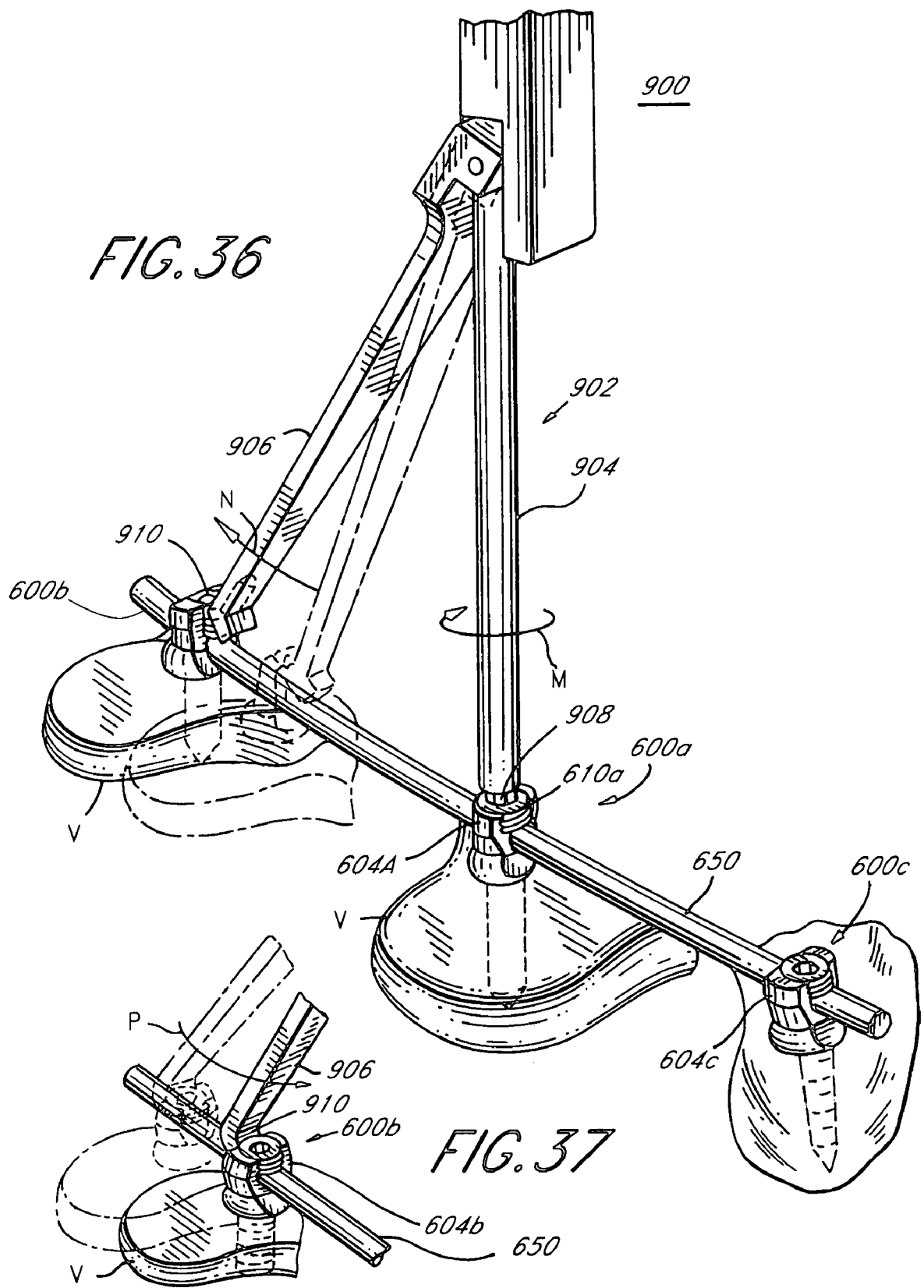

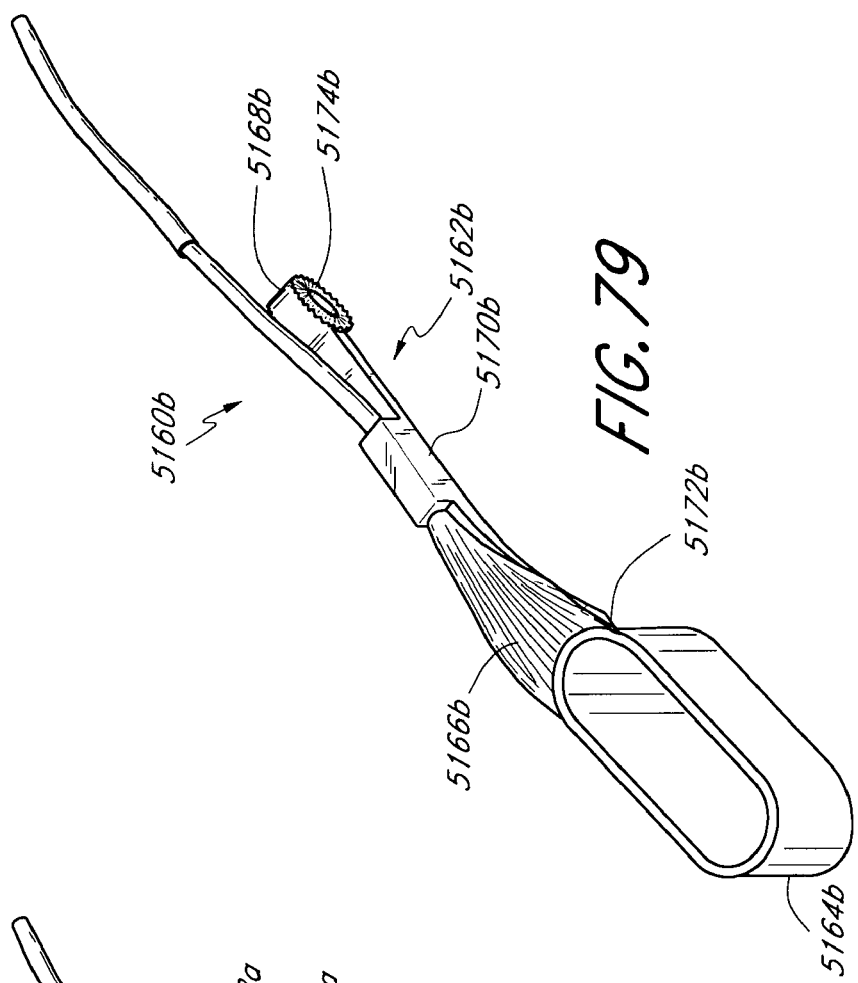
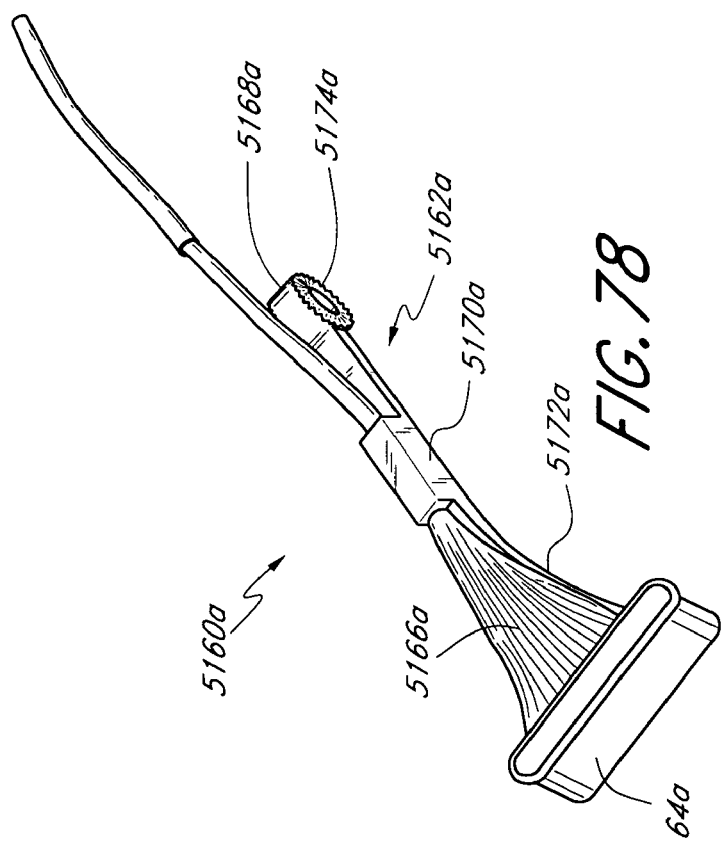

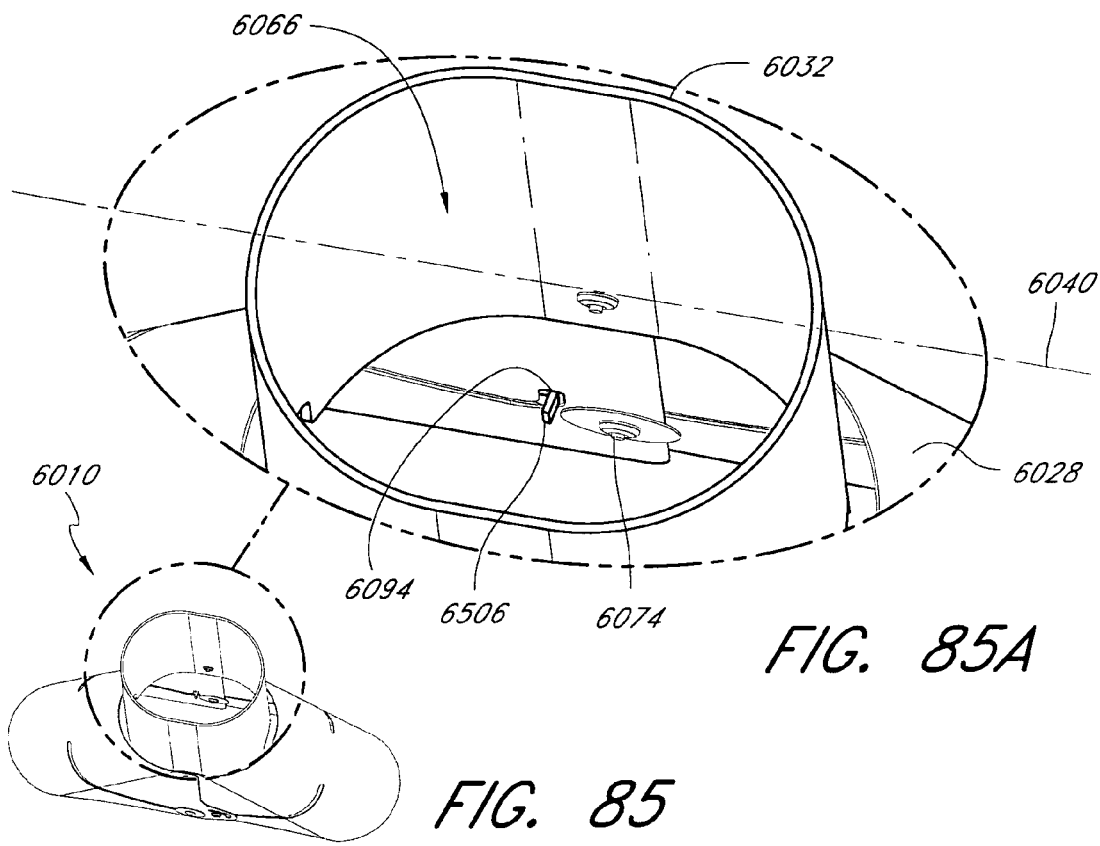
FIG. 85A
FIG. 85
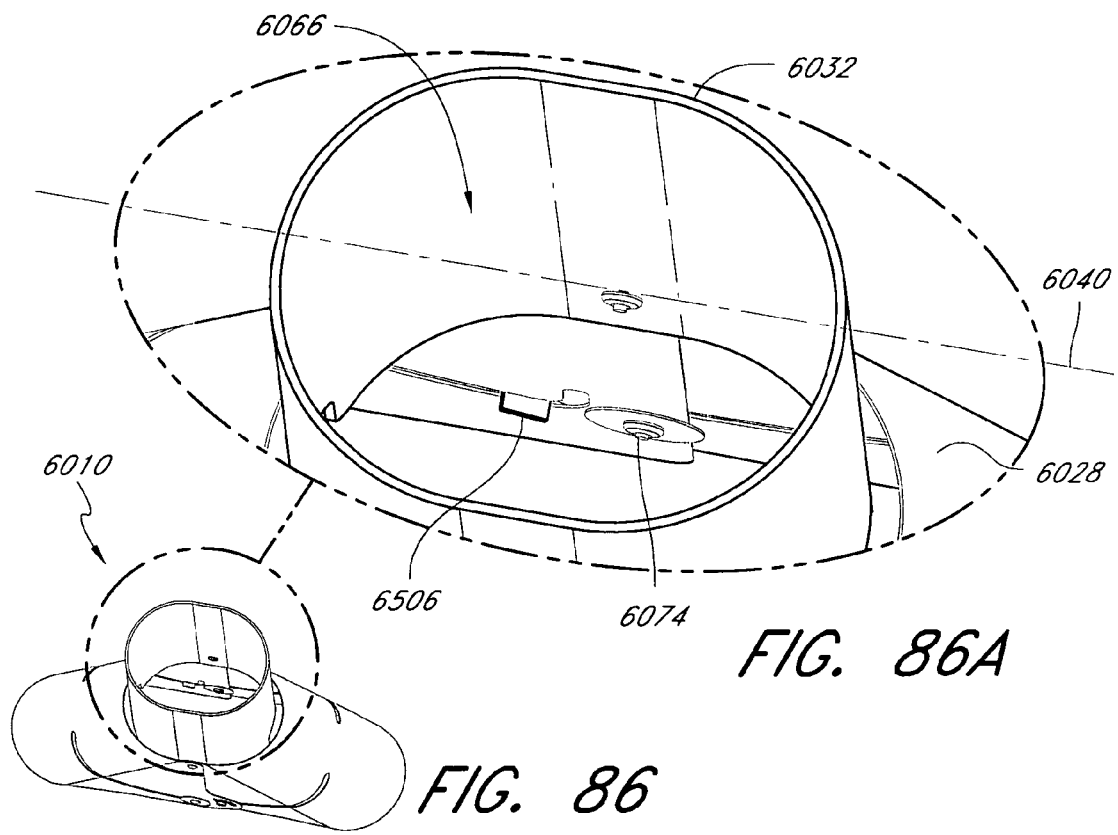
FIG. 86A
FIG. 86

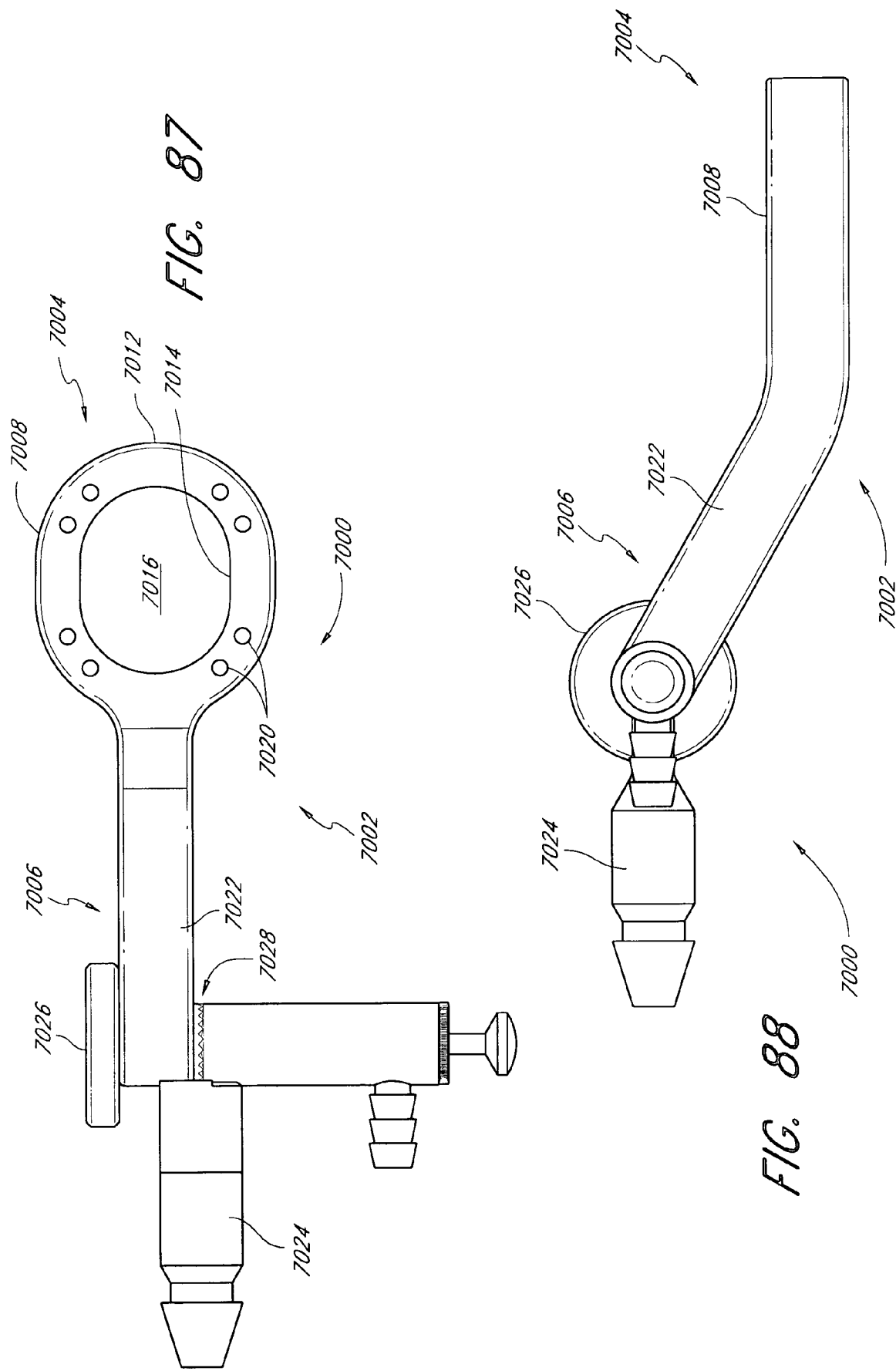

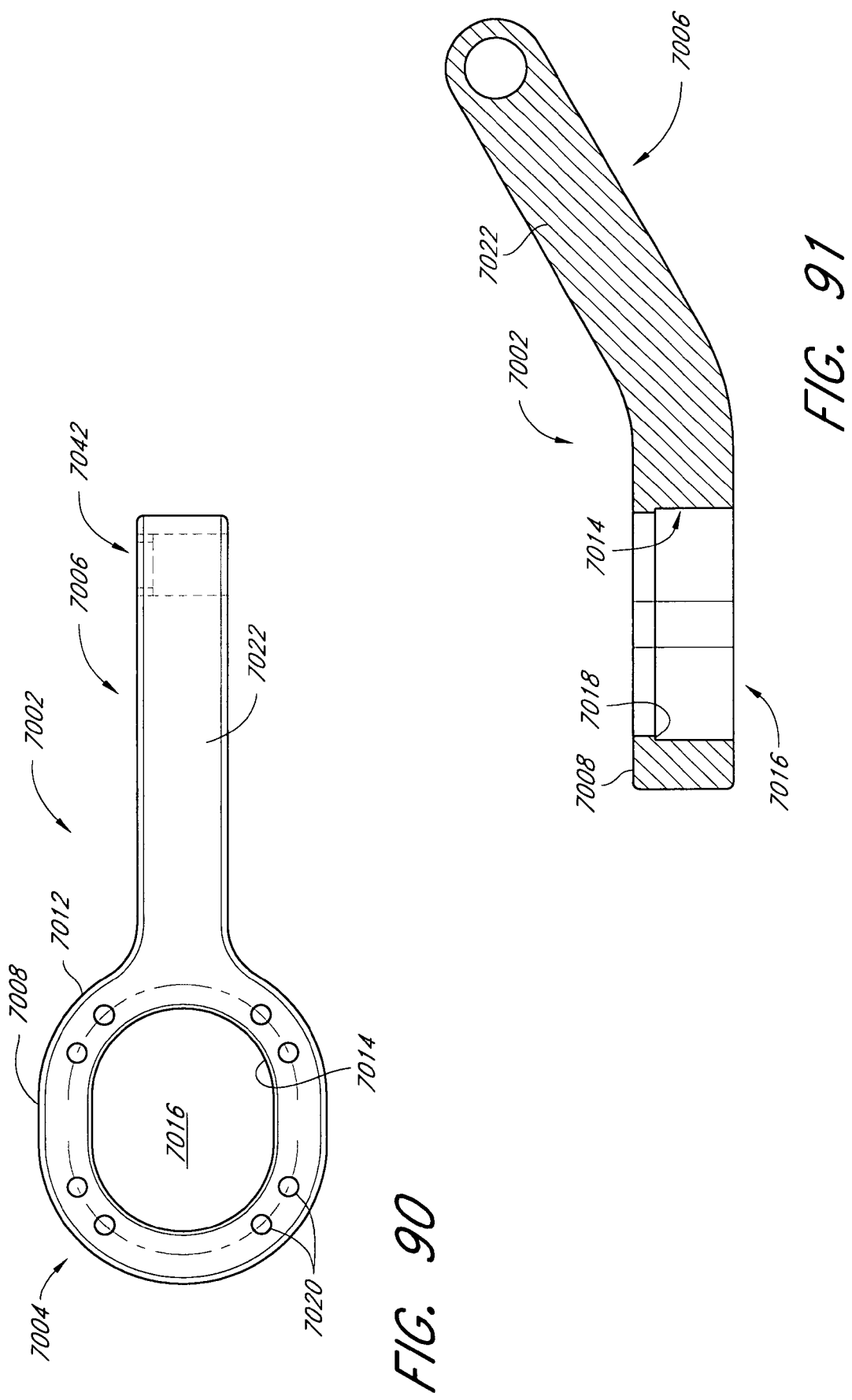

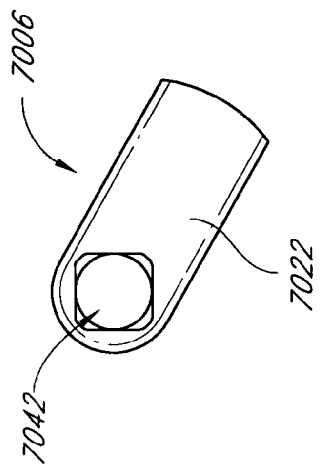
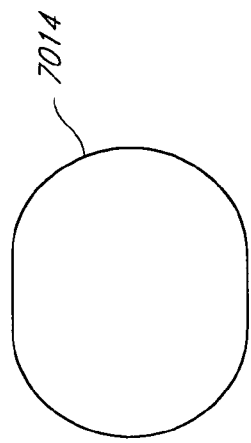
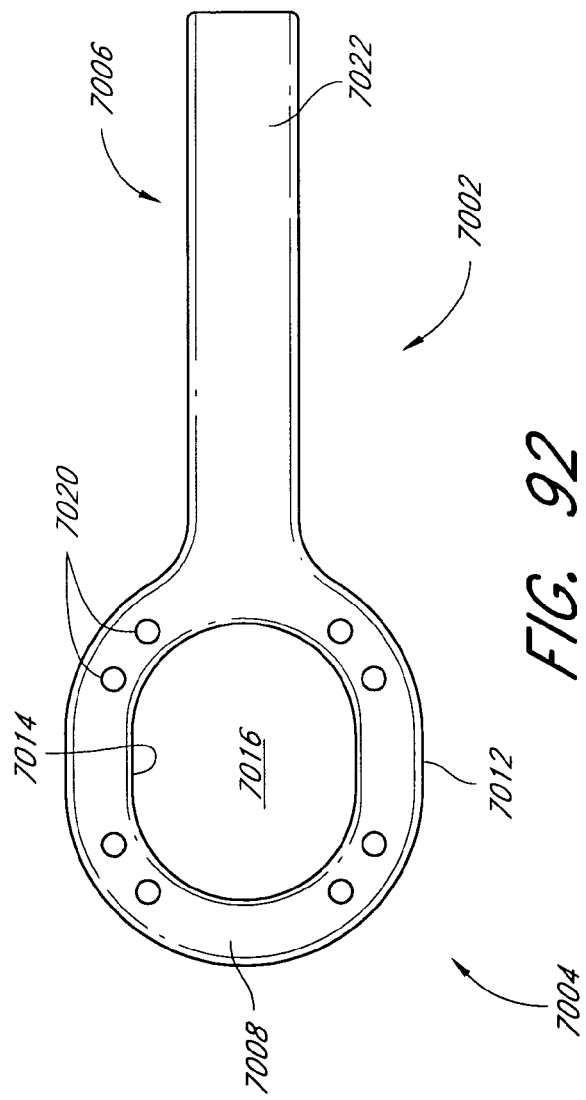
FIG. 93
FIG. 94
FIG. 92

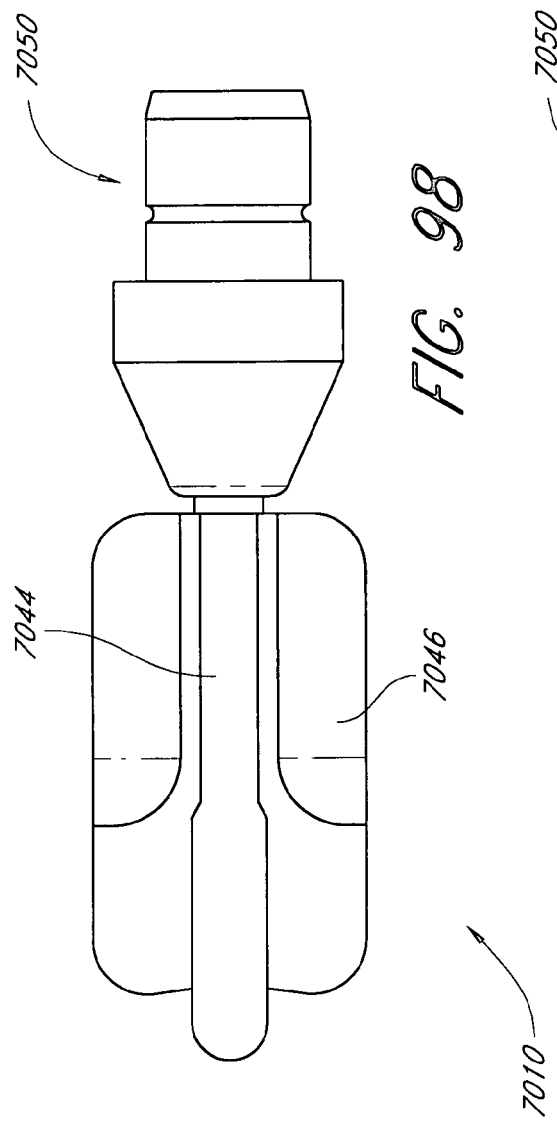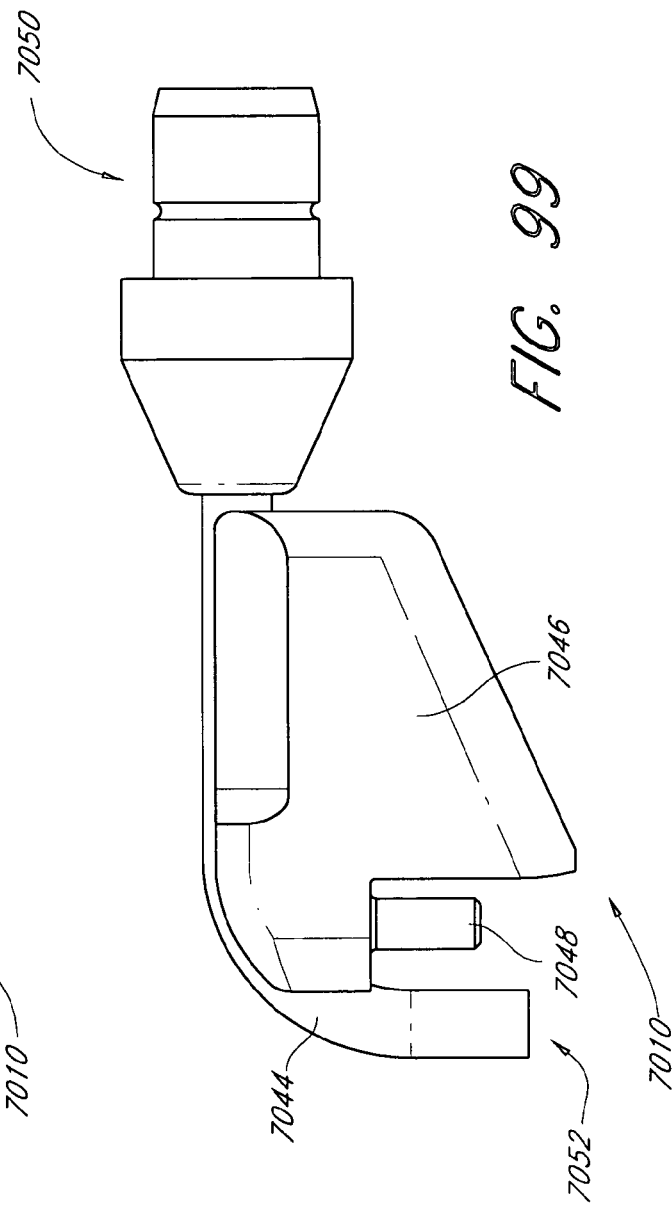

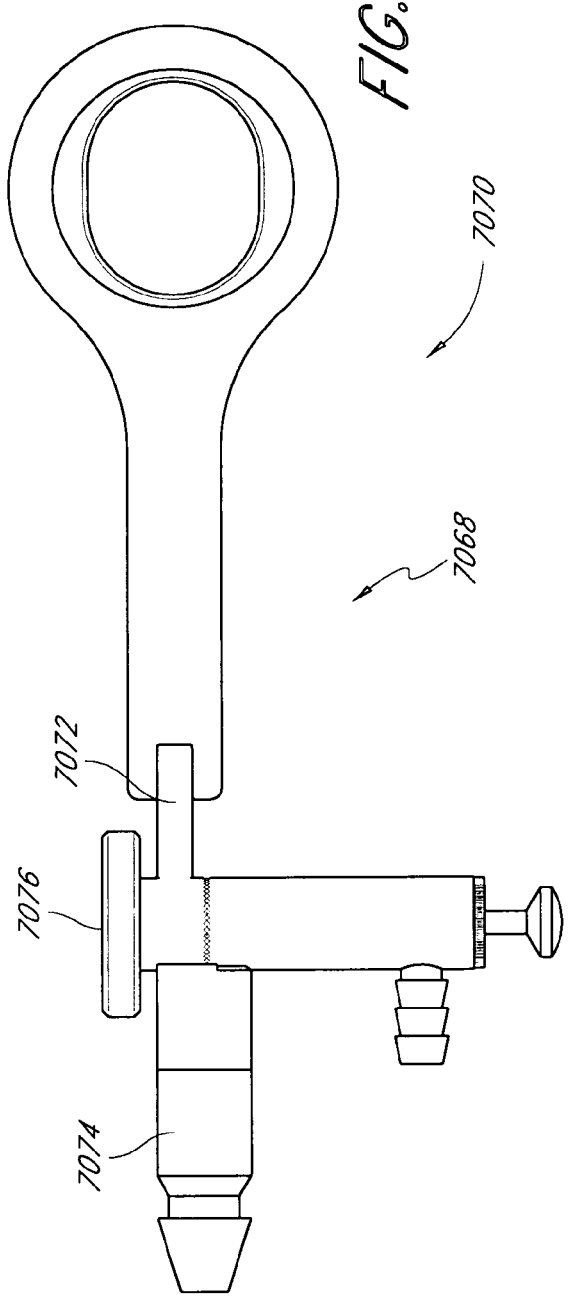
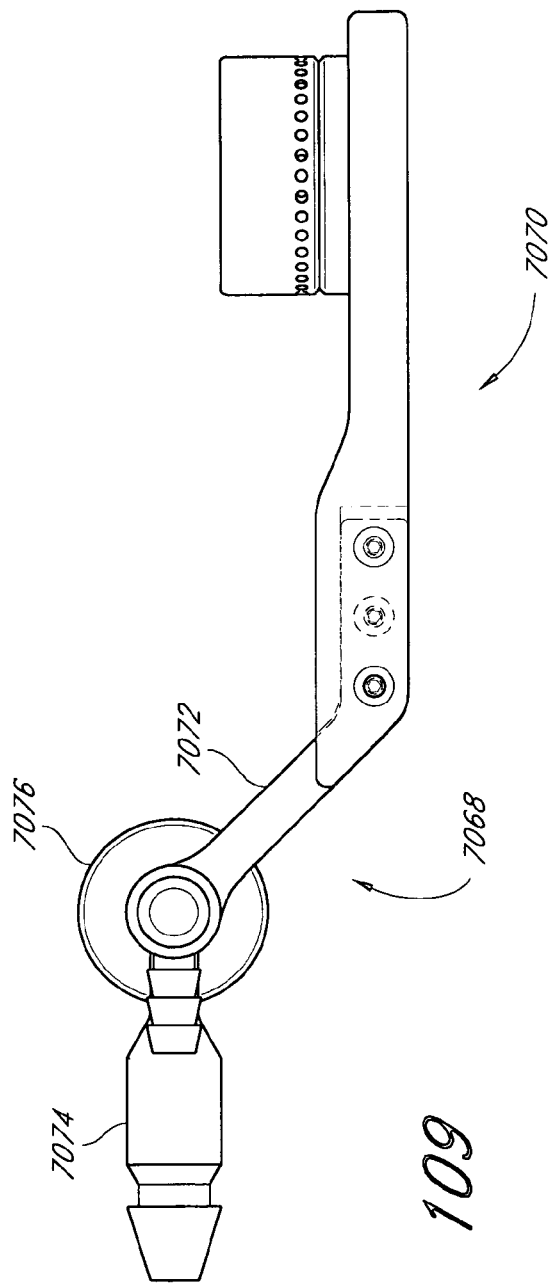
FIG. 108
FIG. 109

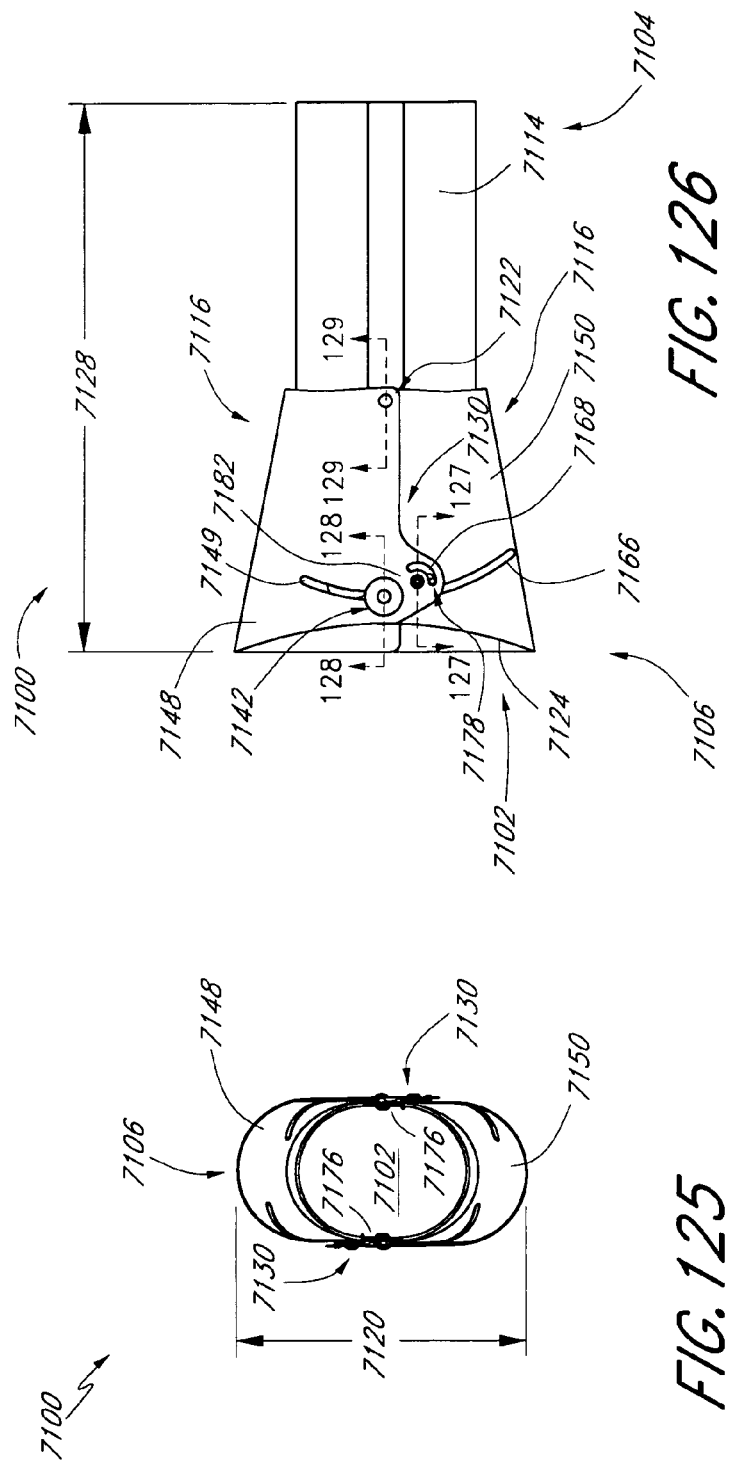

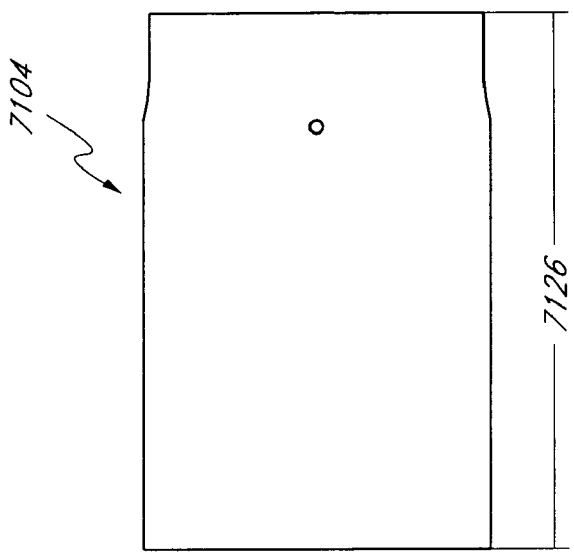
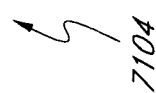
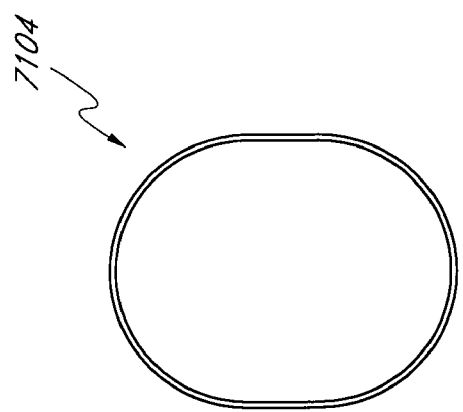
FIG. 131
FIG. 132
FIG. 130

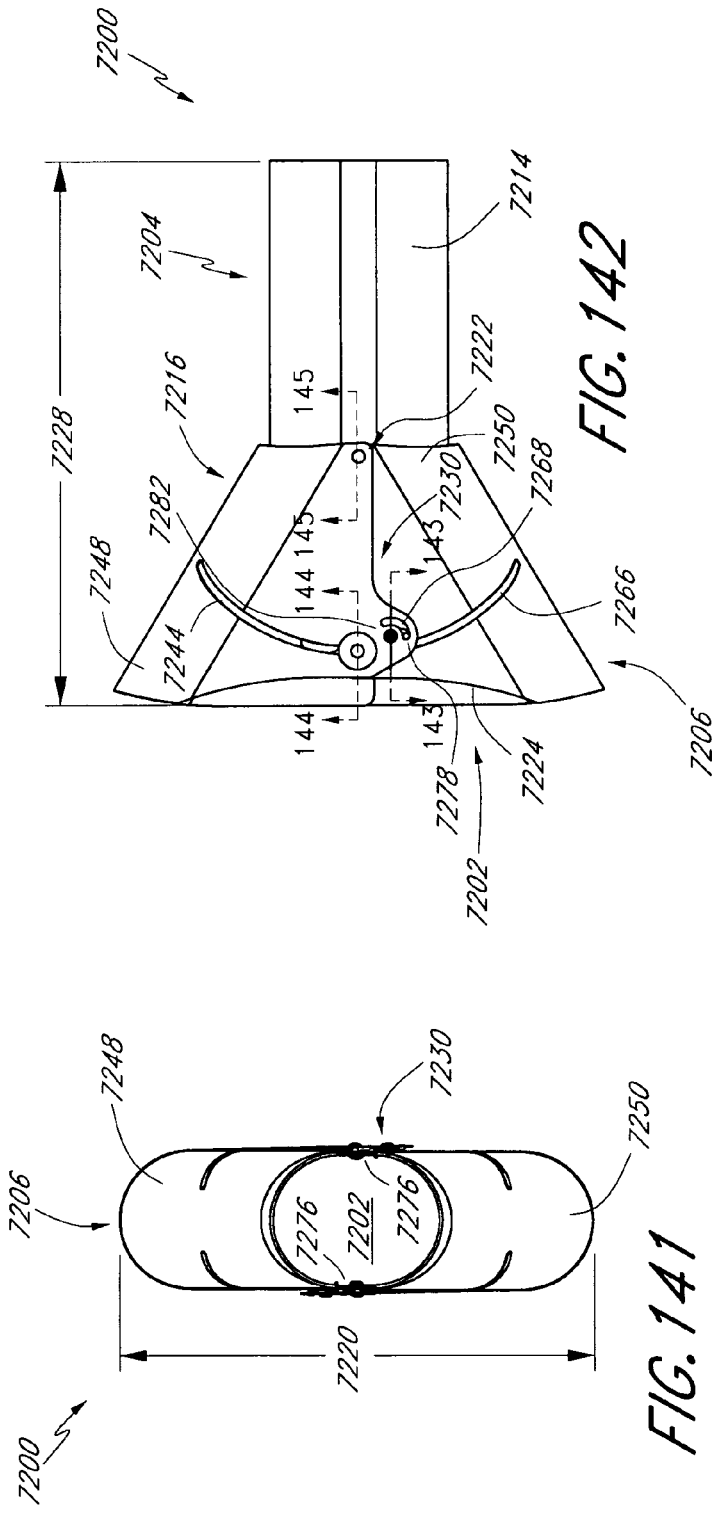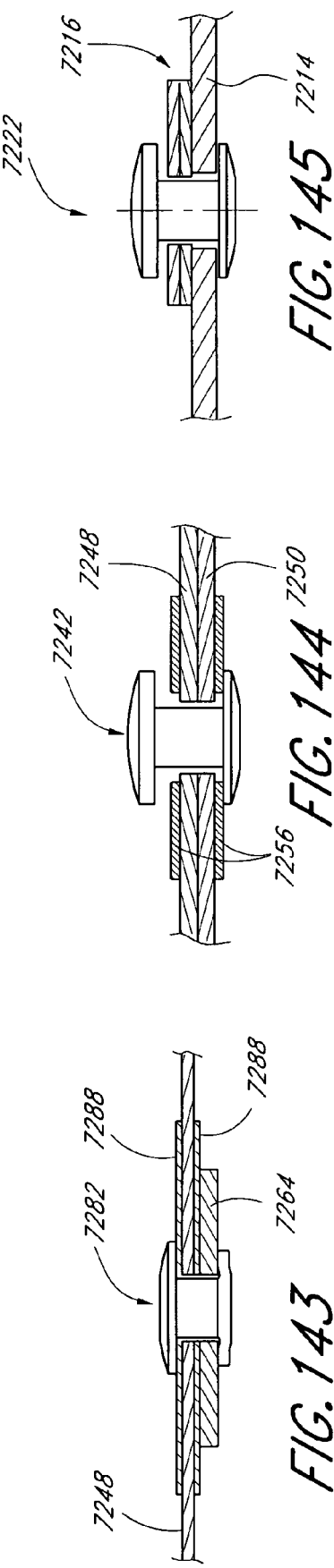

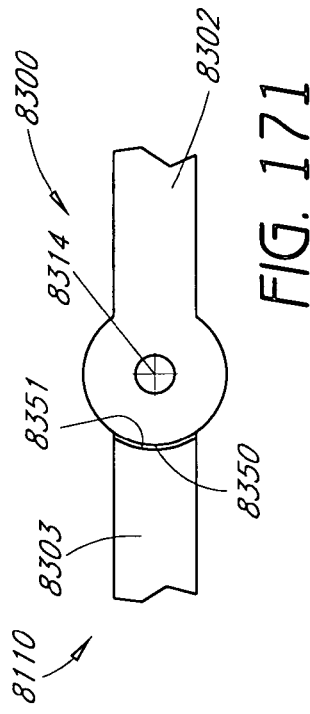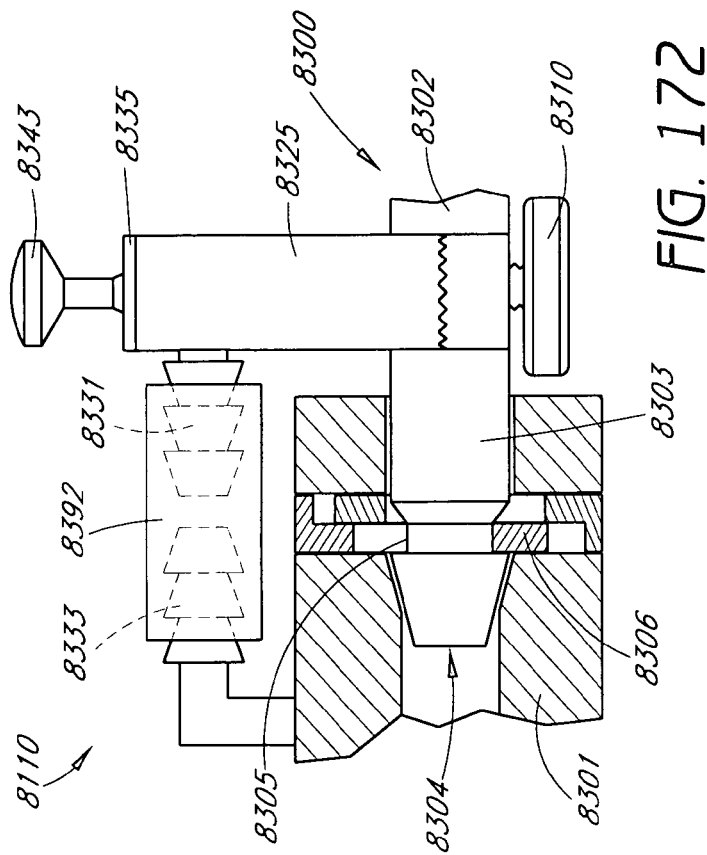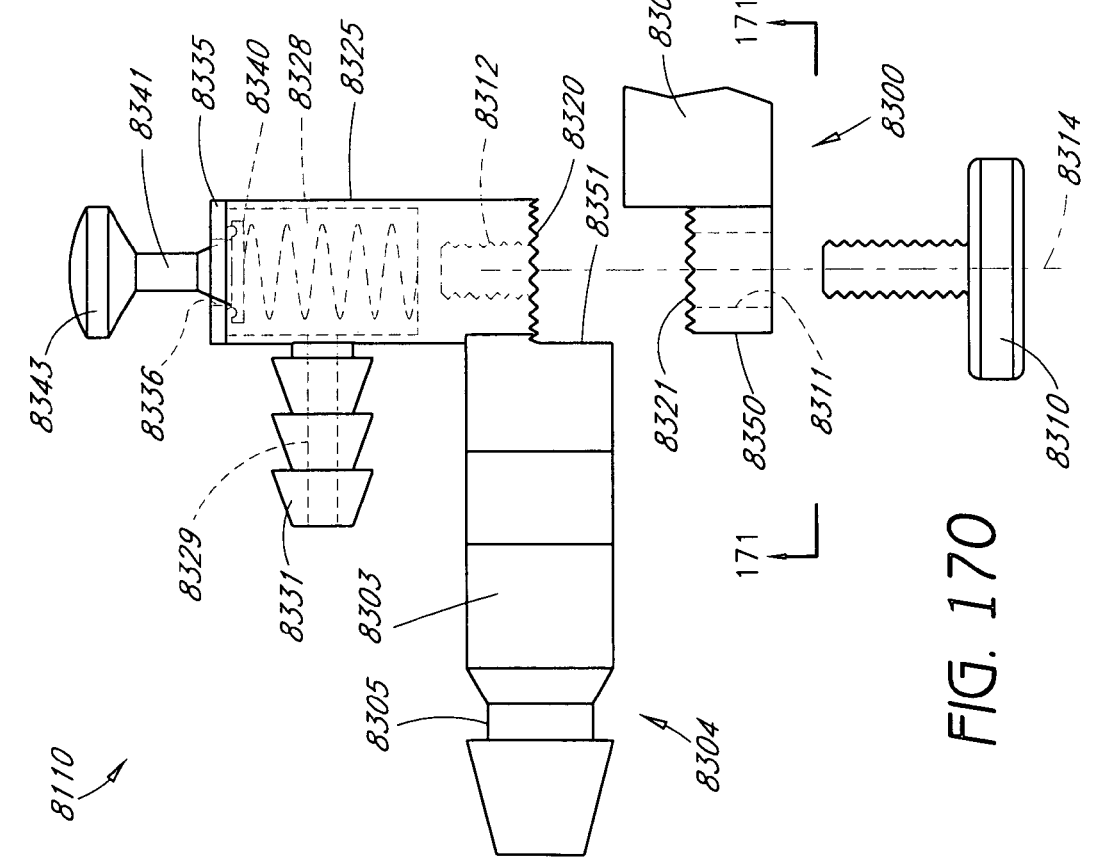

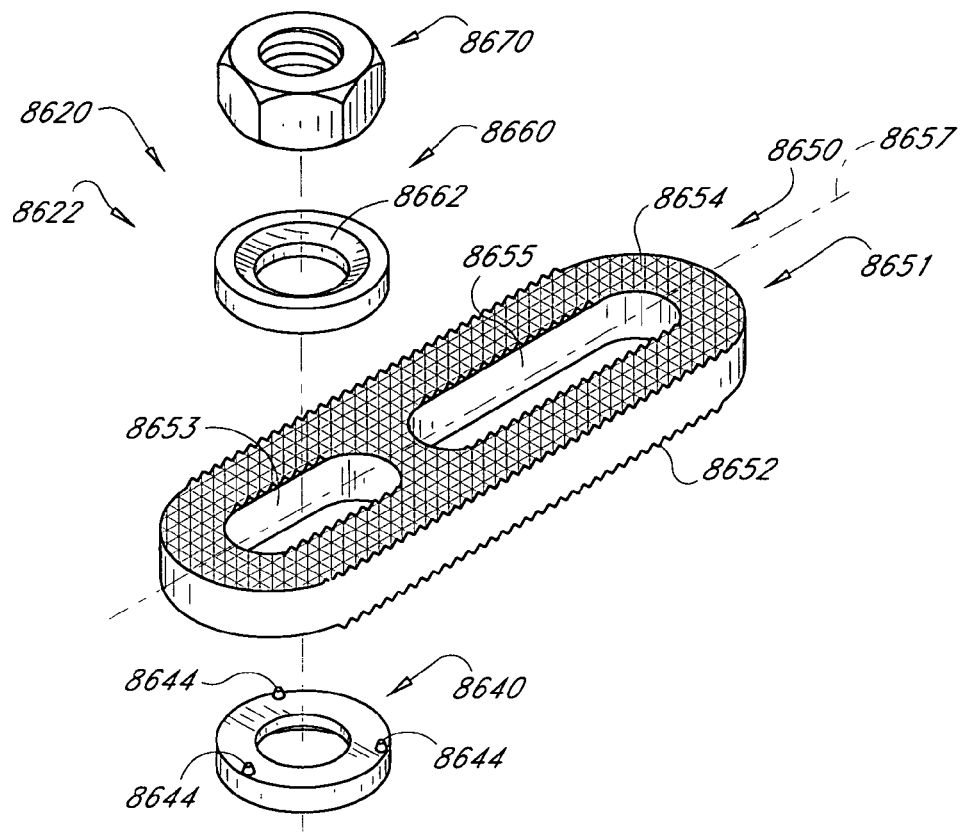
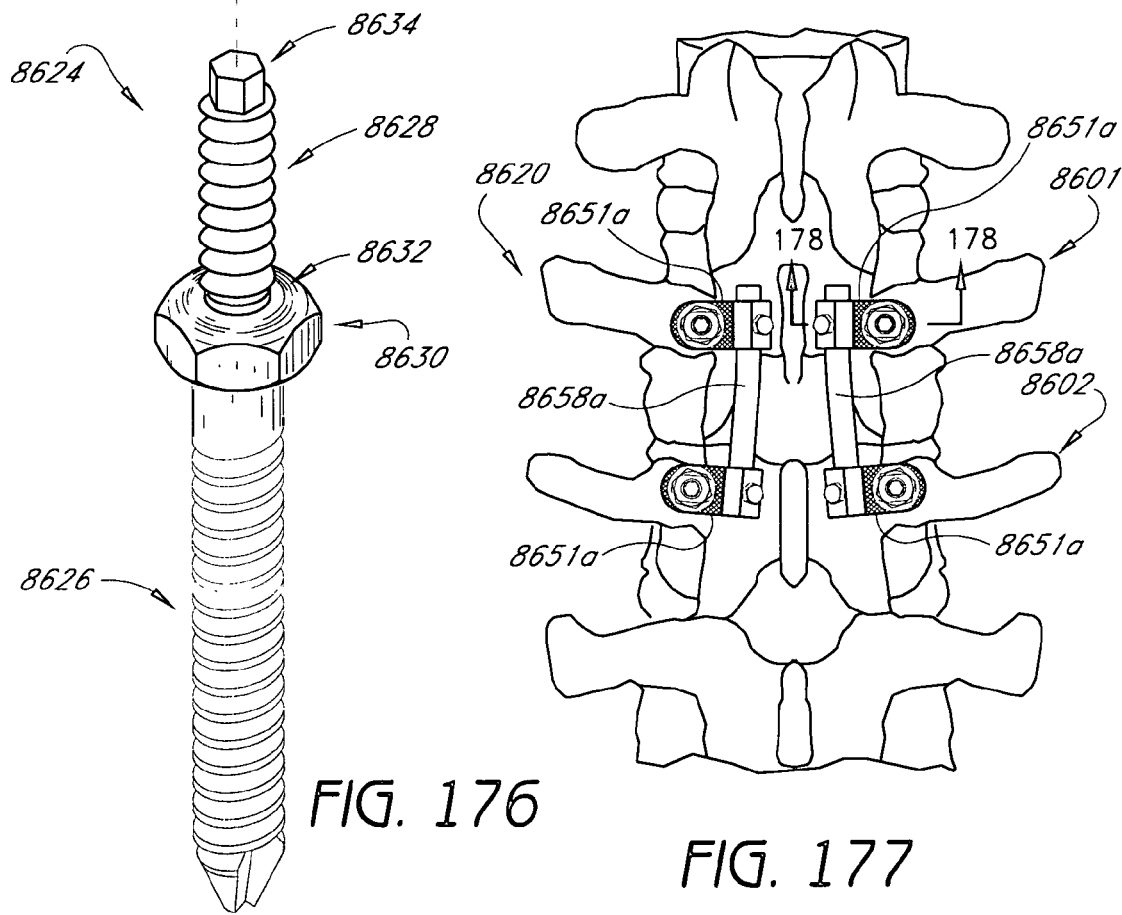
FIG. 176
FIG. 177

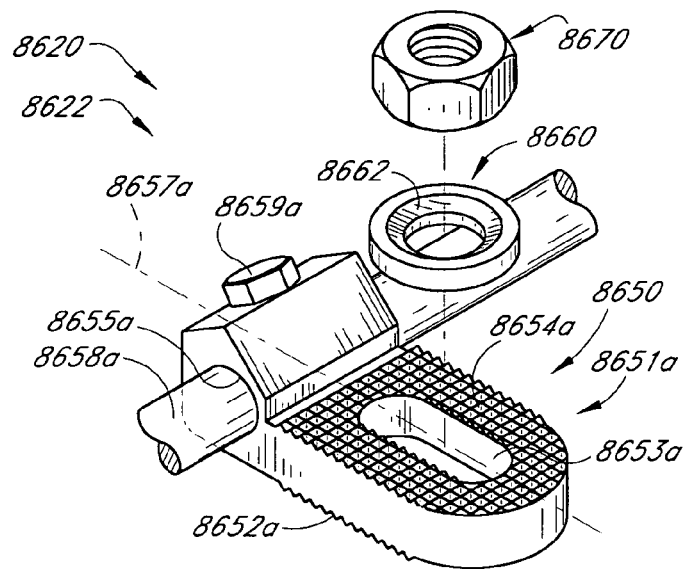
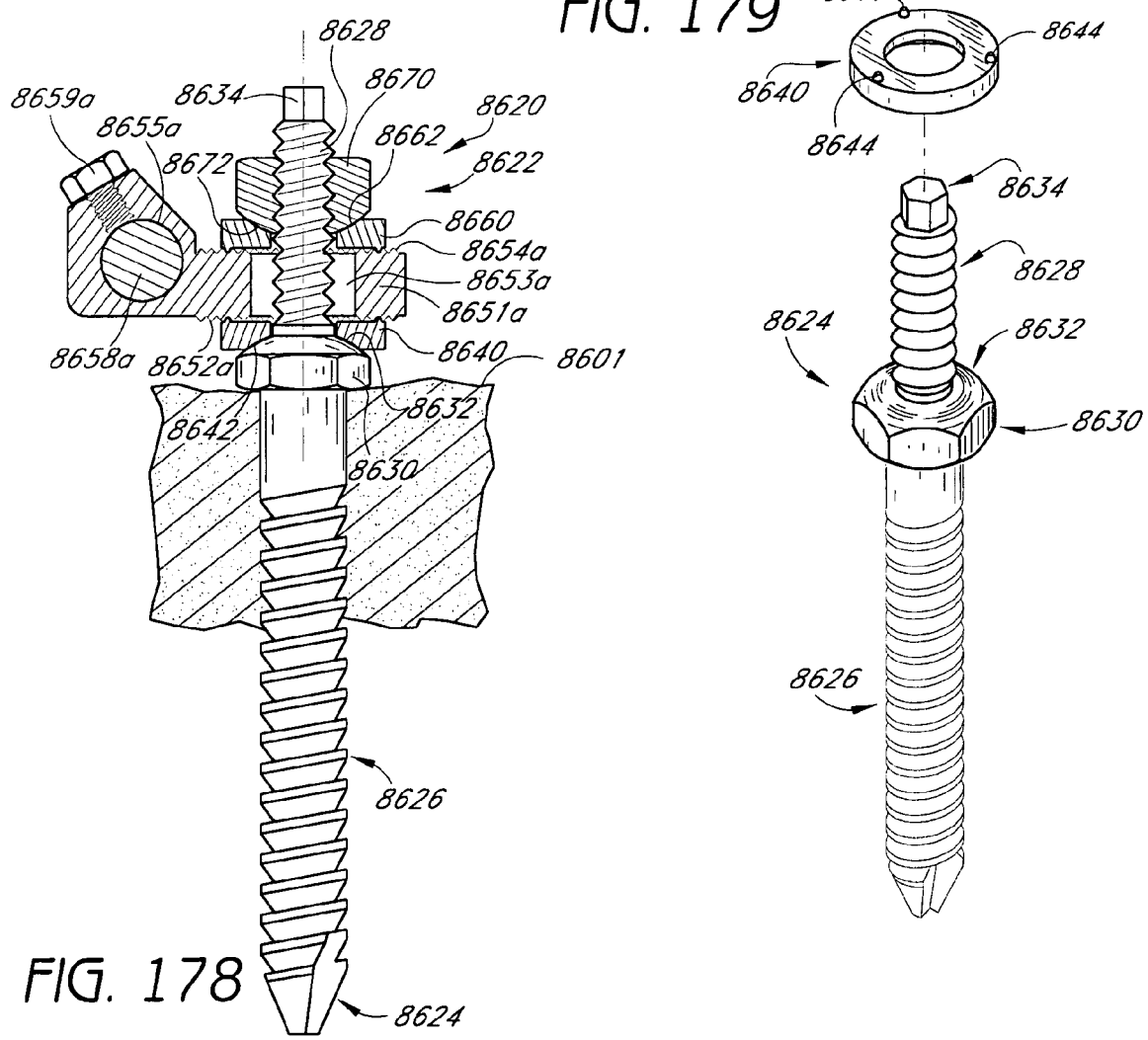
FIG. 179
FIG. 178

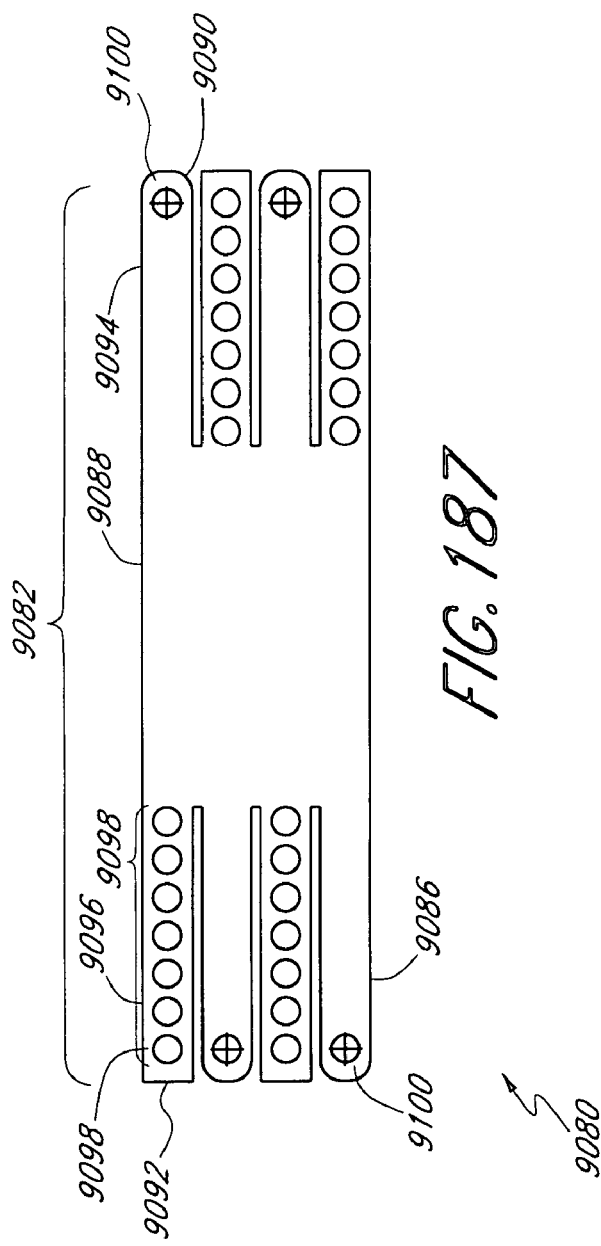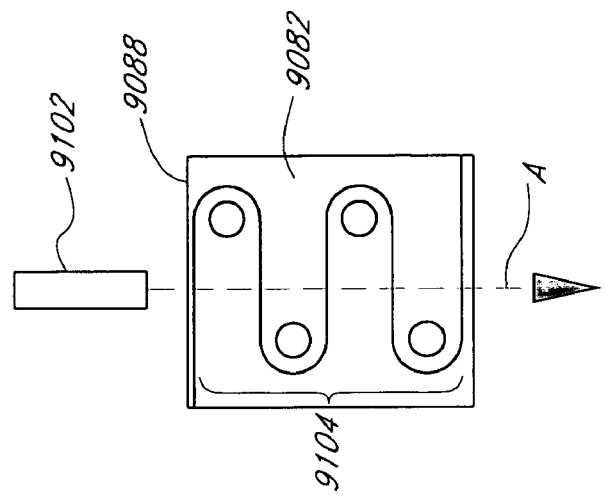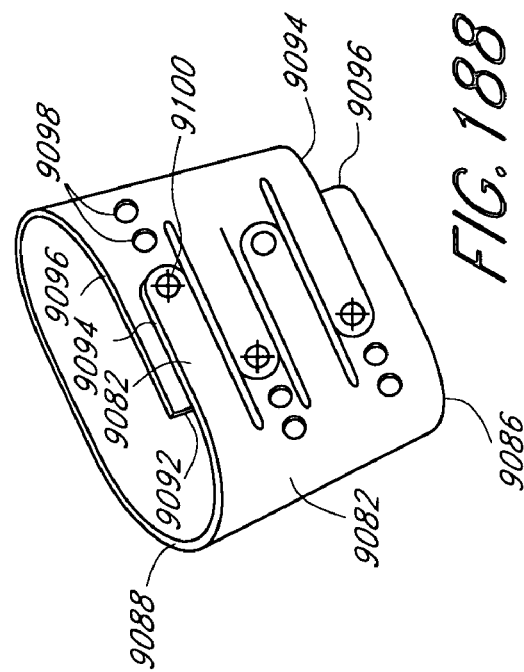

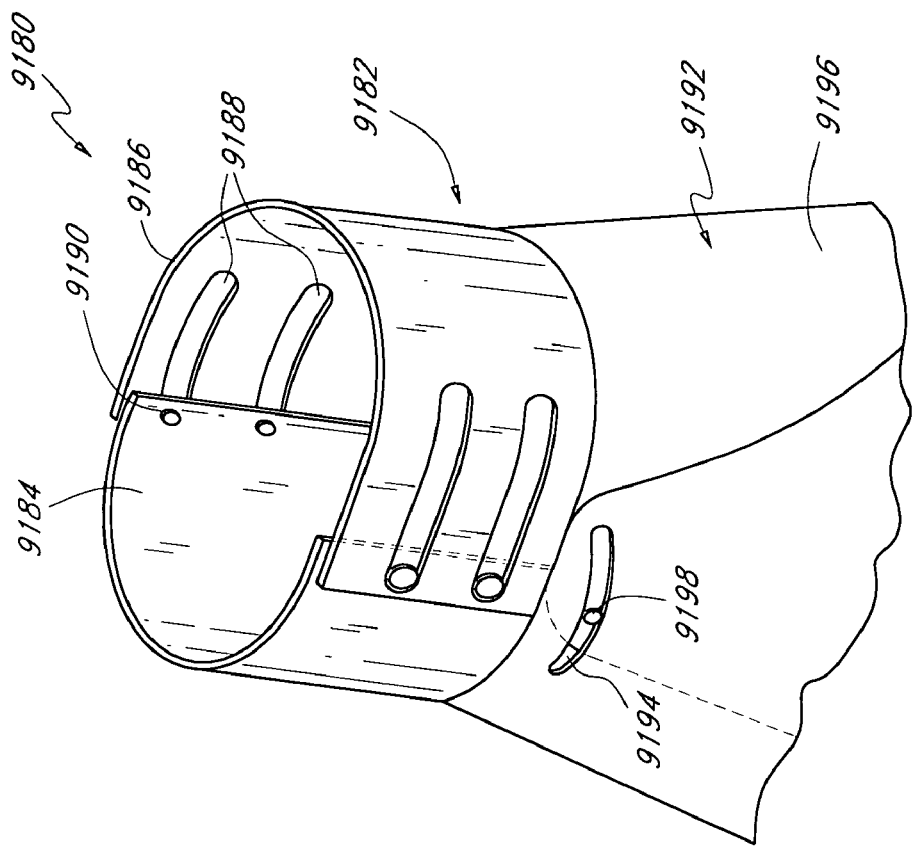
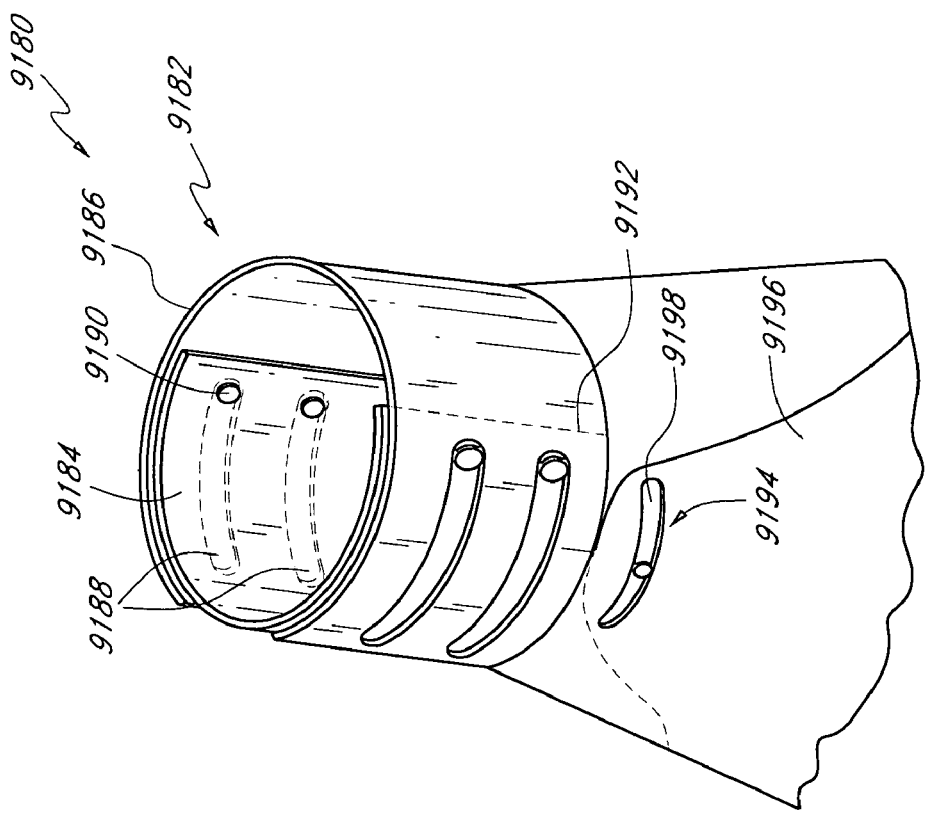

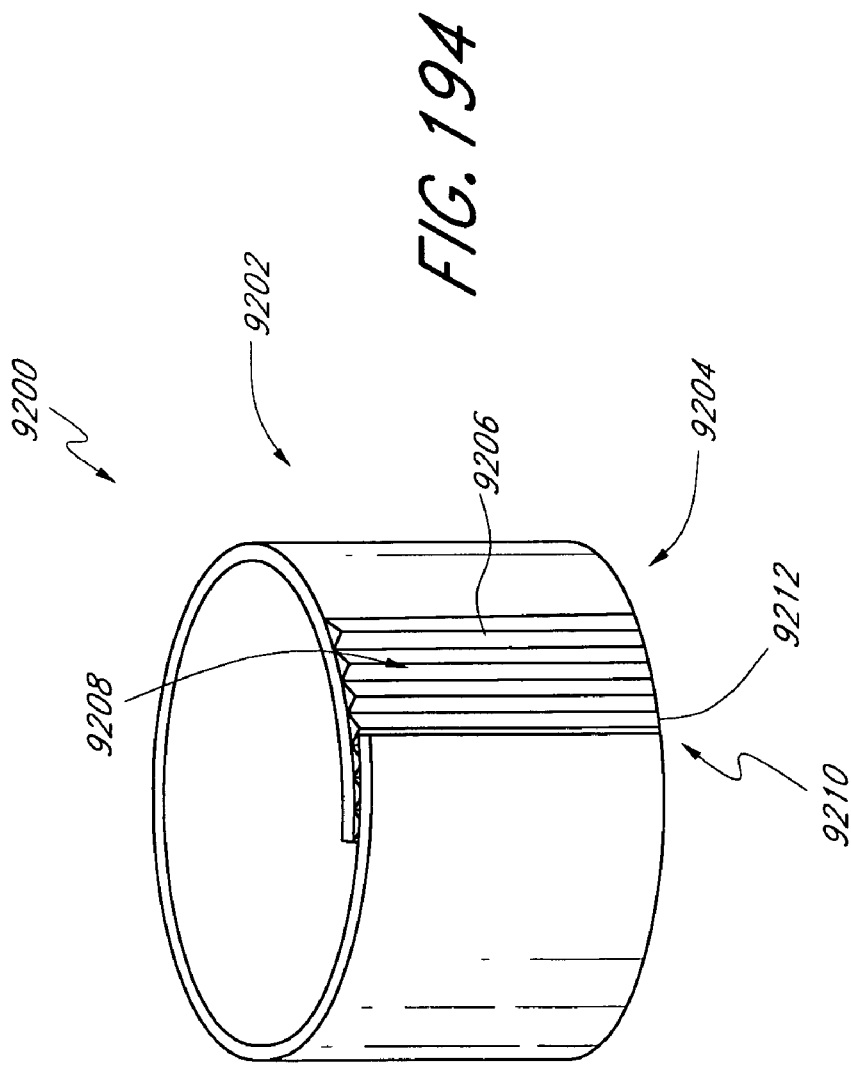
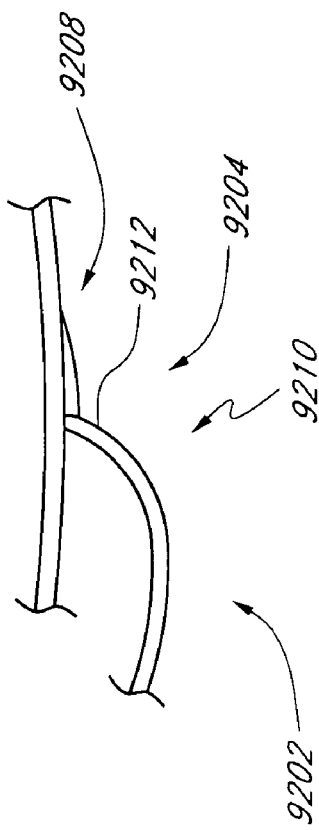

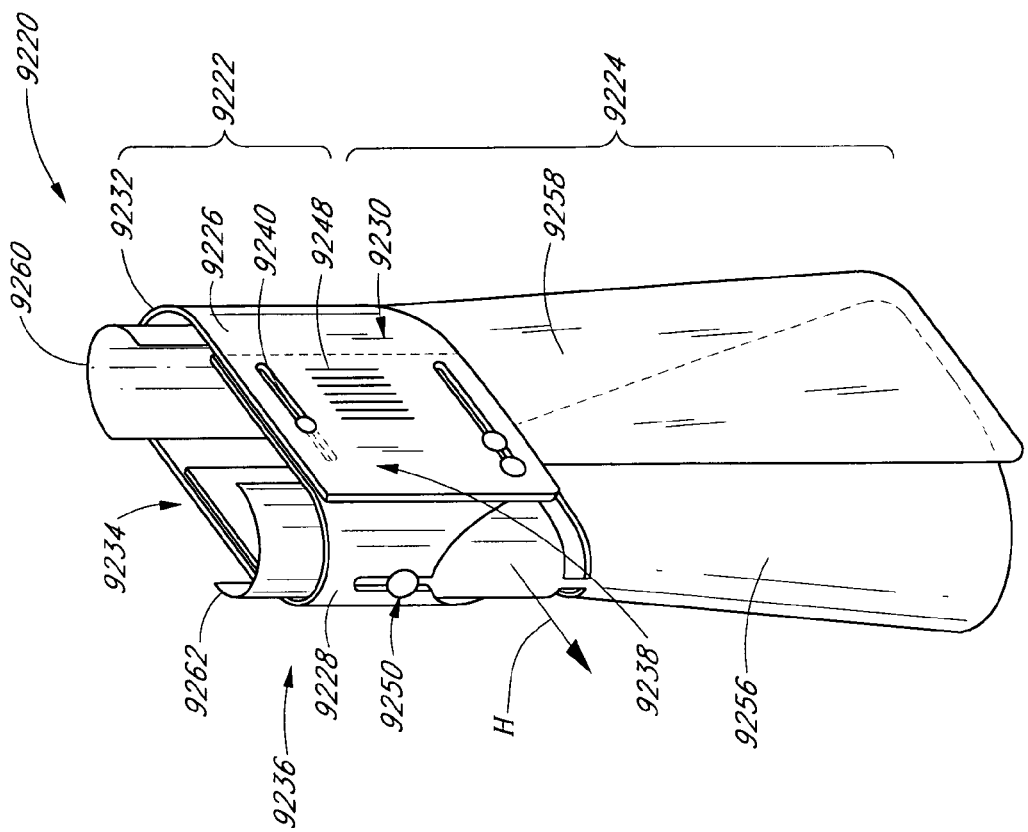
FIG. 196
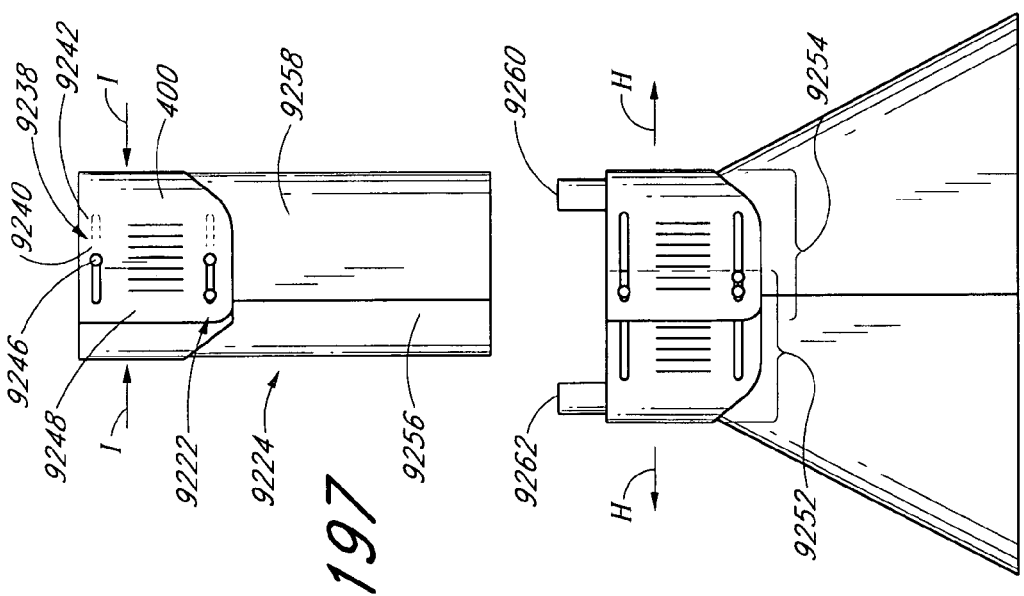
FIG. 197
FIG. 198

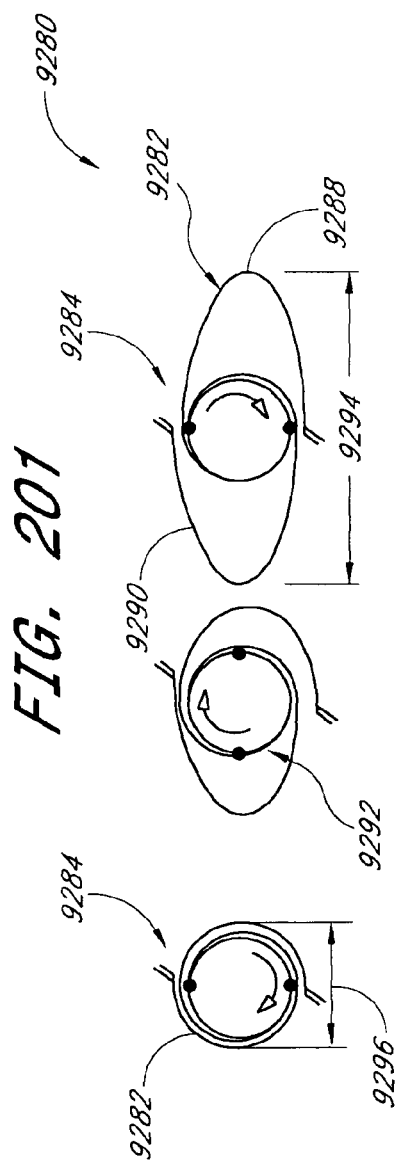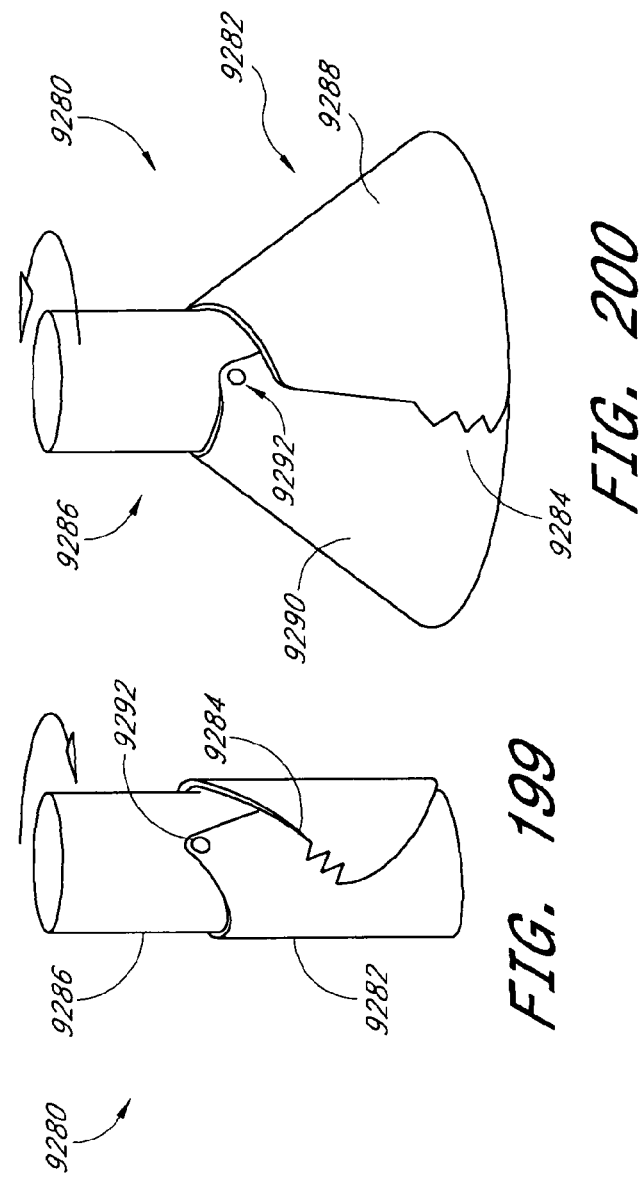

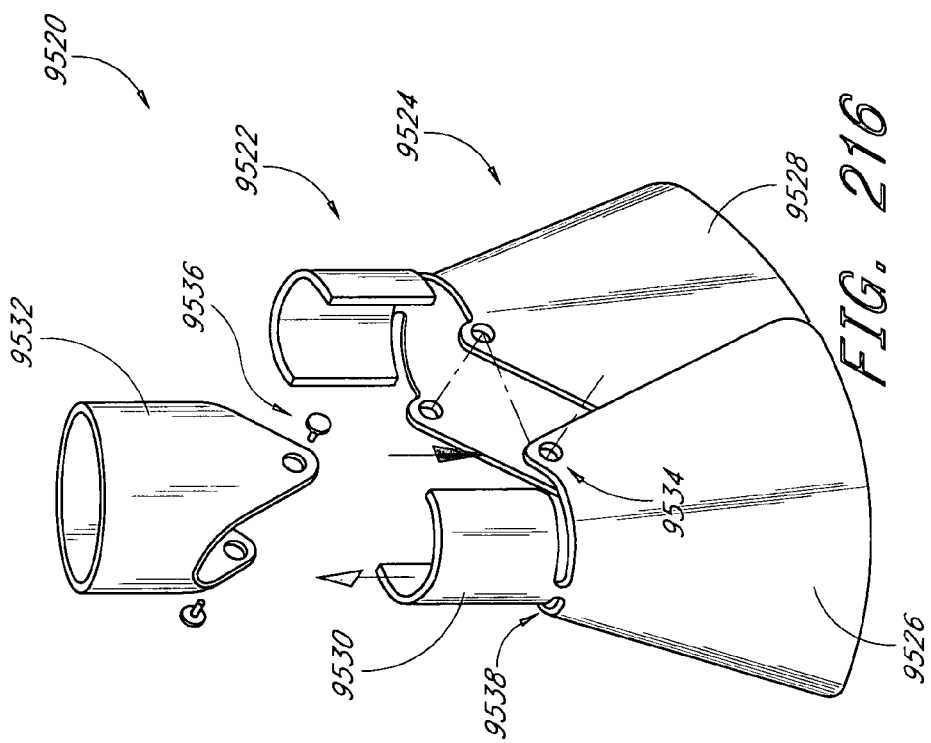
FIG. 216
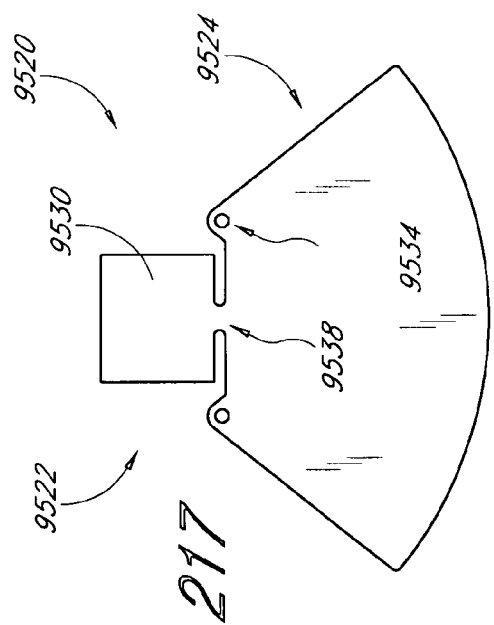
FIG. 217
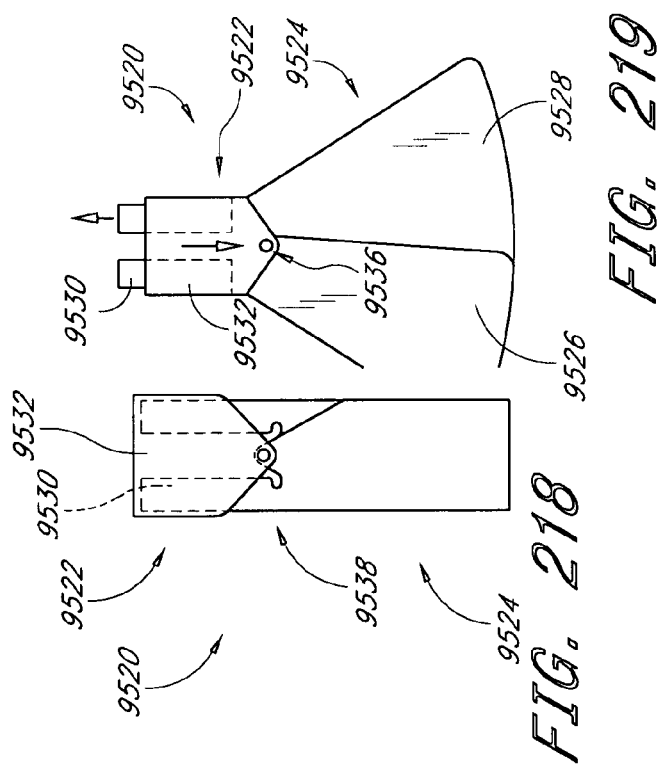
FIG. 218
FIG. 219

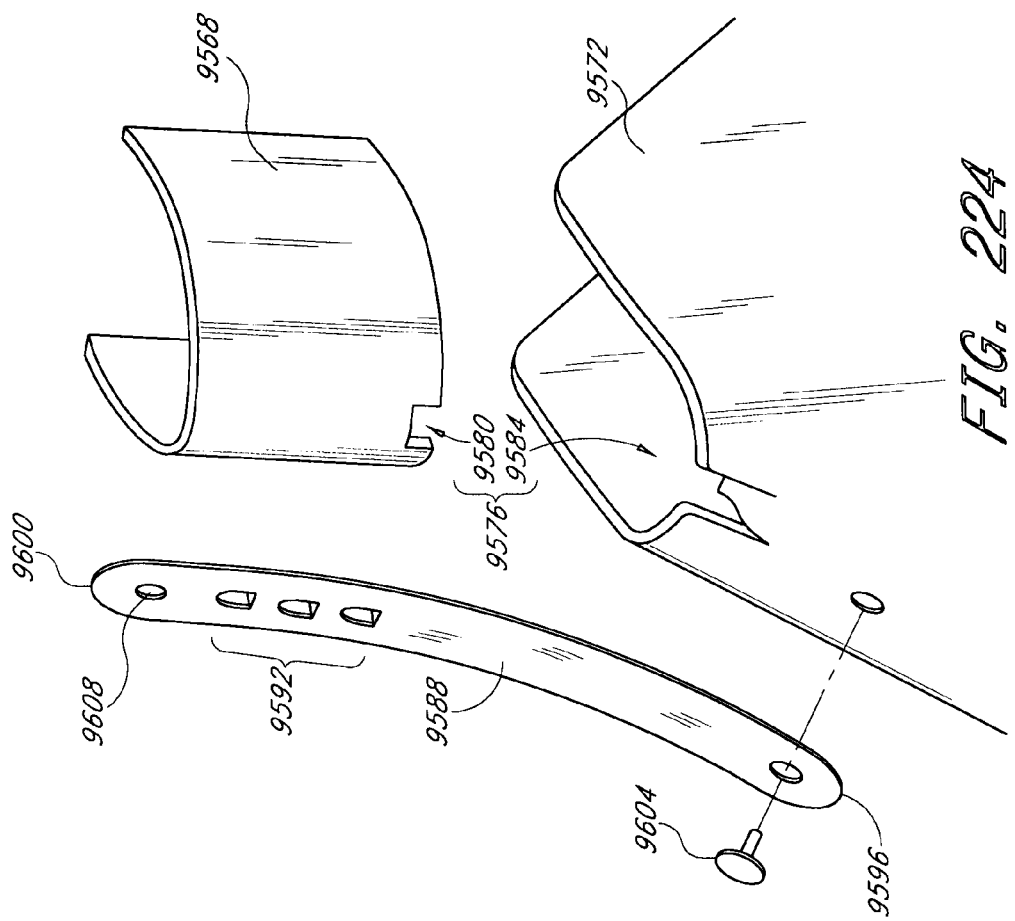
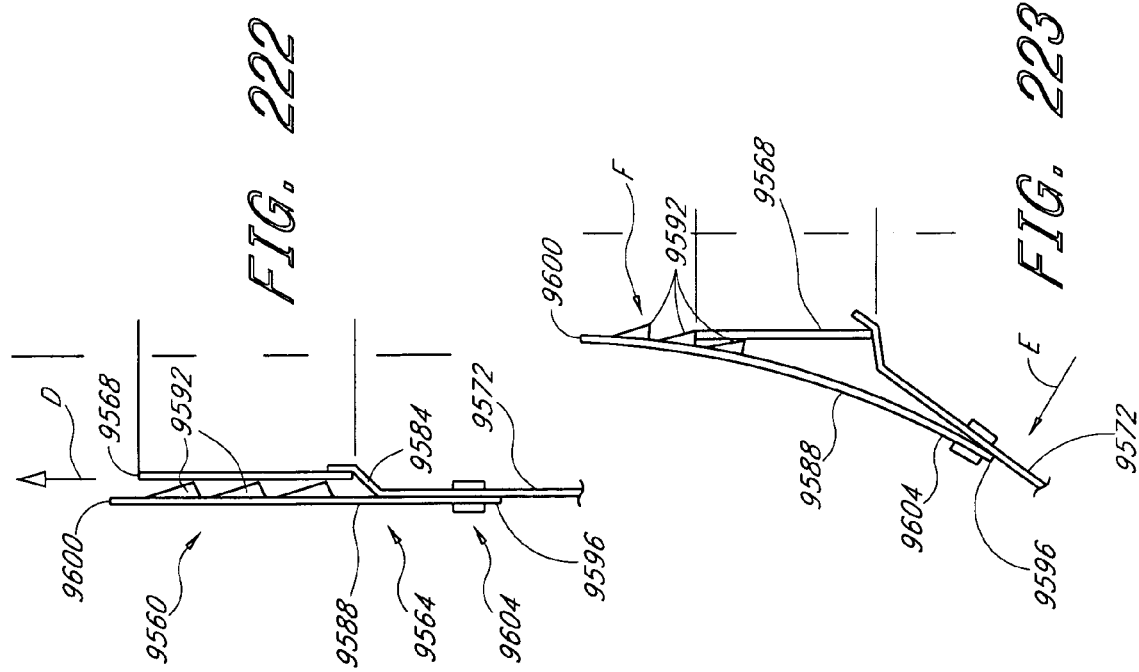
FIG. 224
FIG. 222
FIG. 223

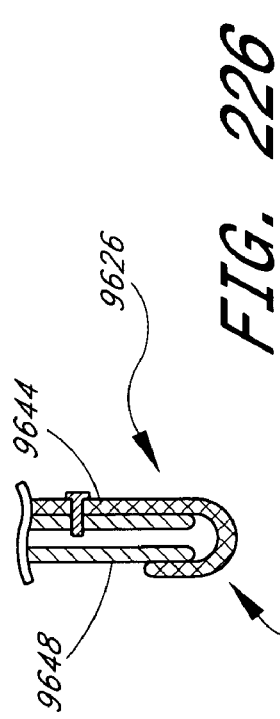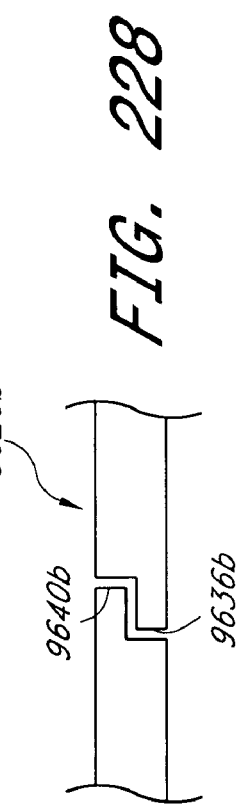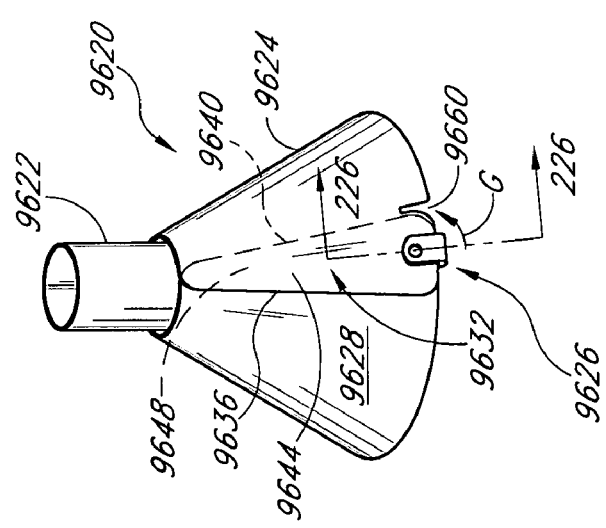
FIG. 226
FIG. 227
FIG. 228
FIG. 225

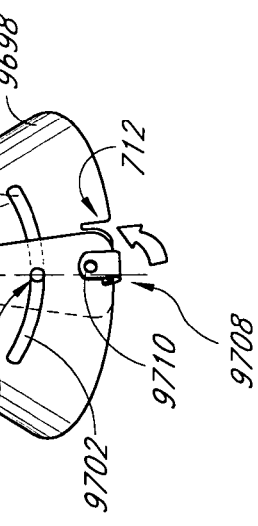
FIG. 231
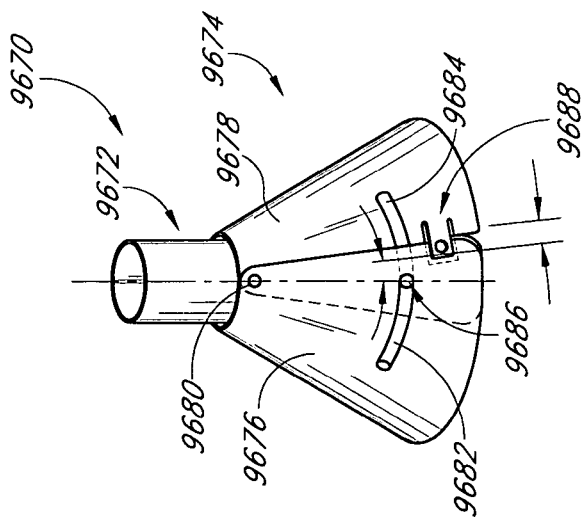
FIG. 230
FIG. 229

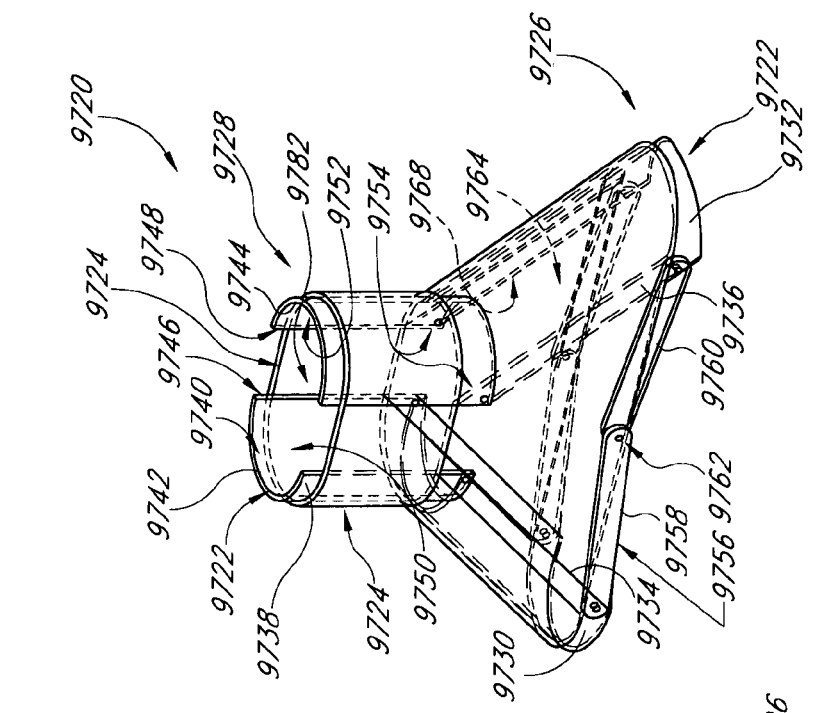
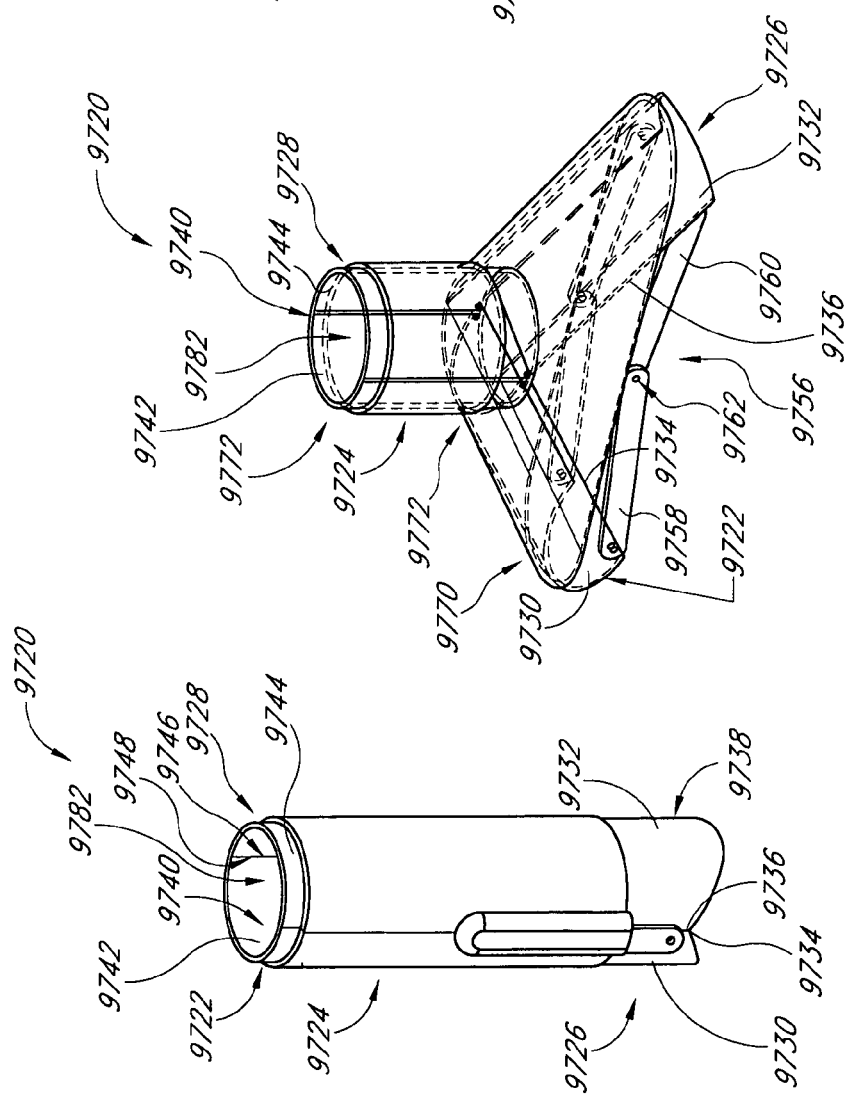

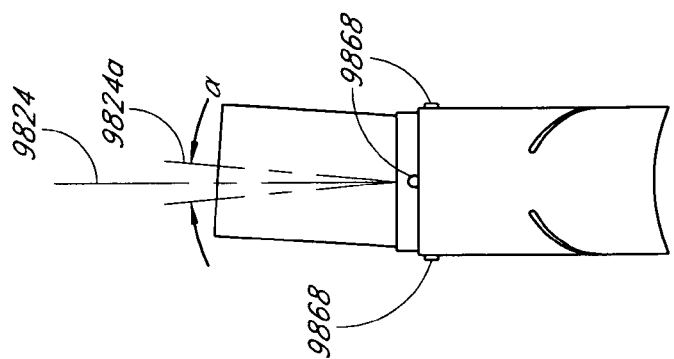
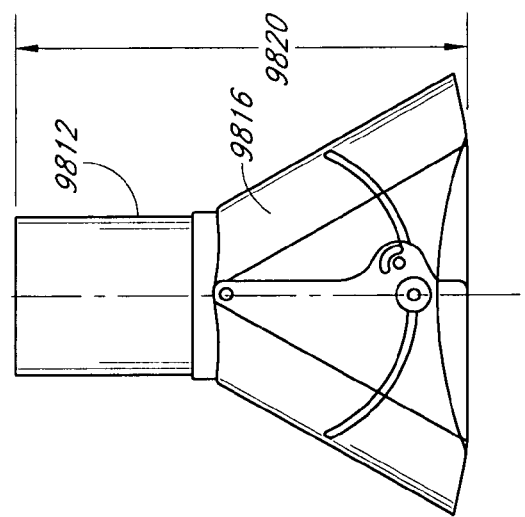
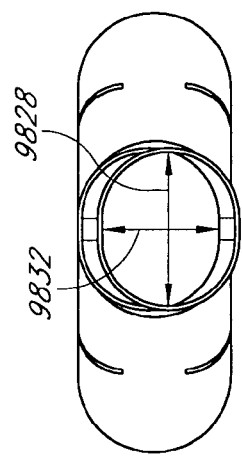
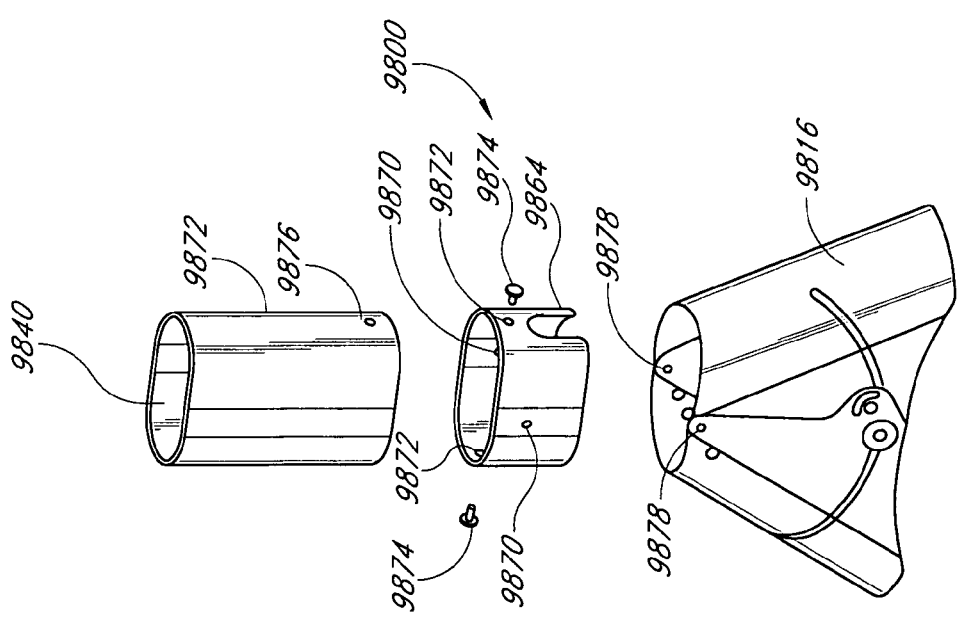

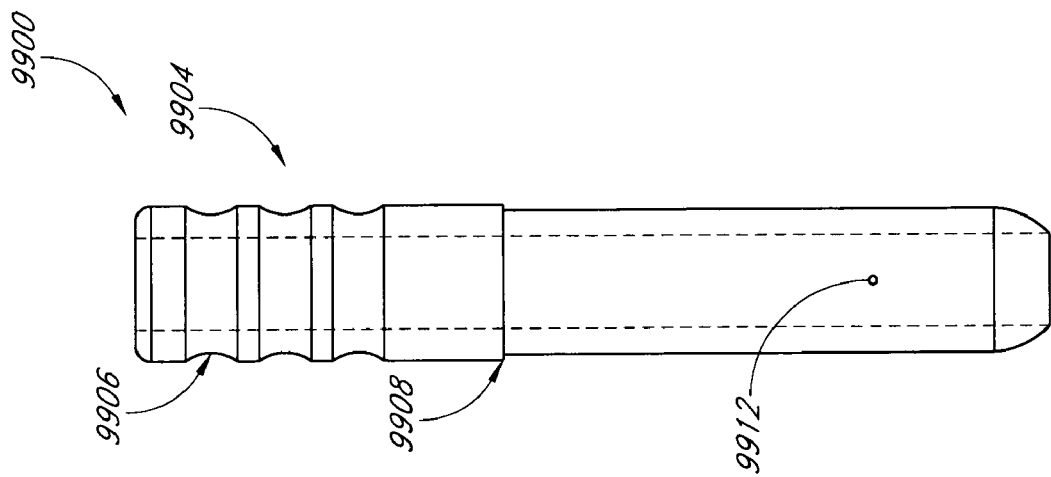
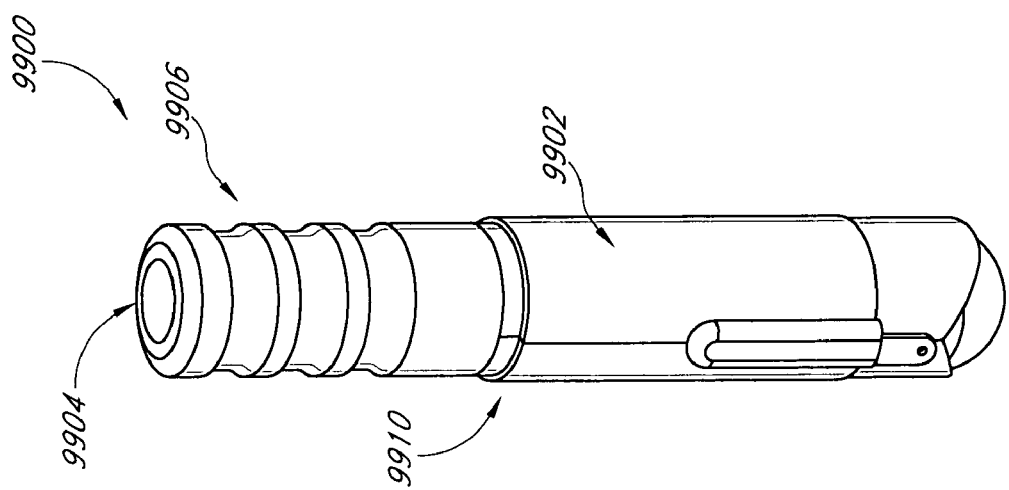

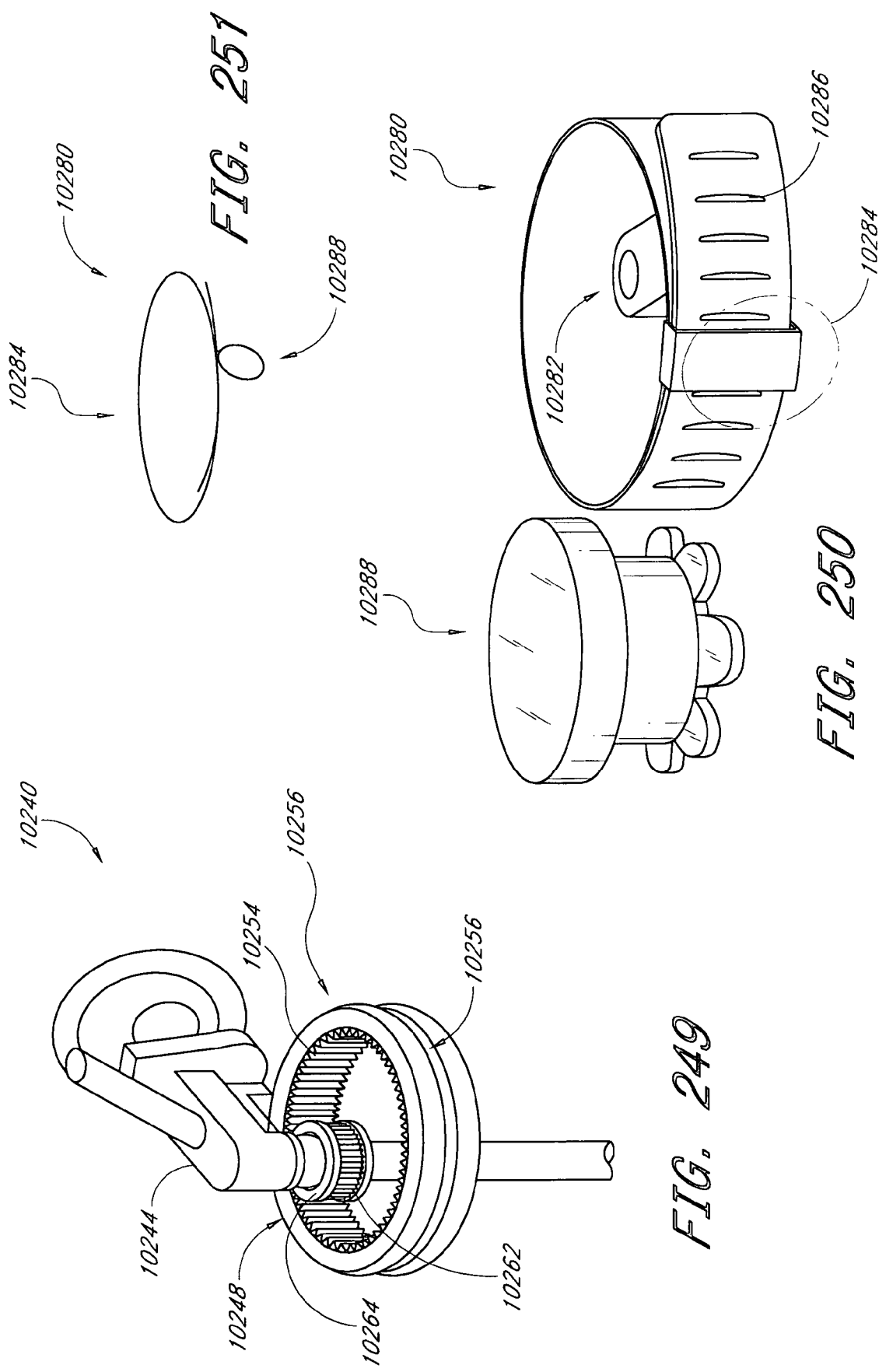

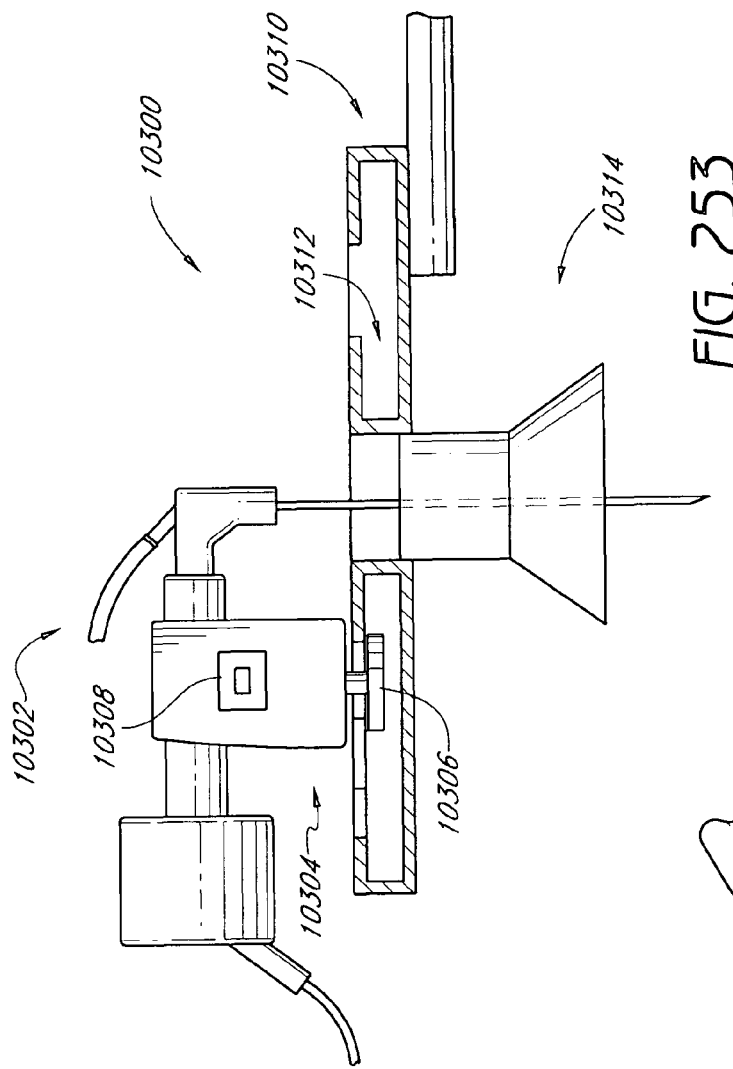
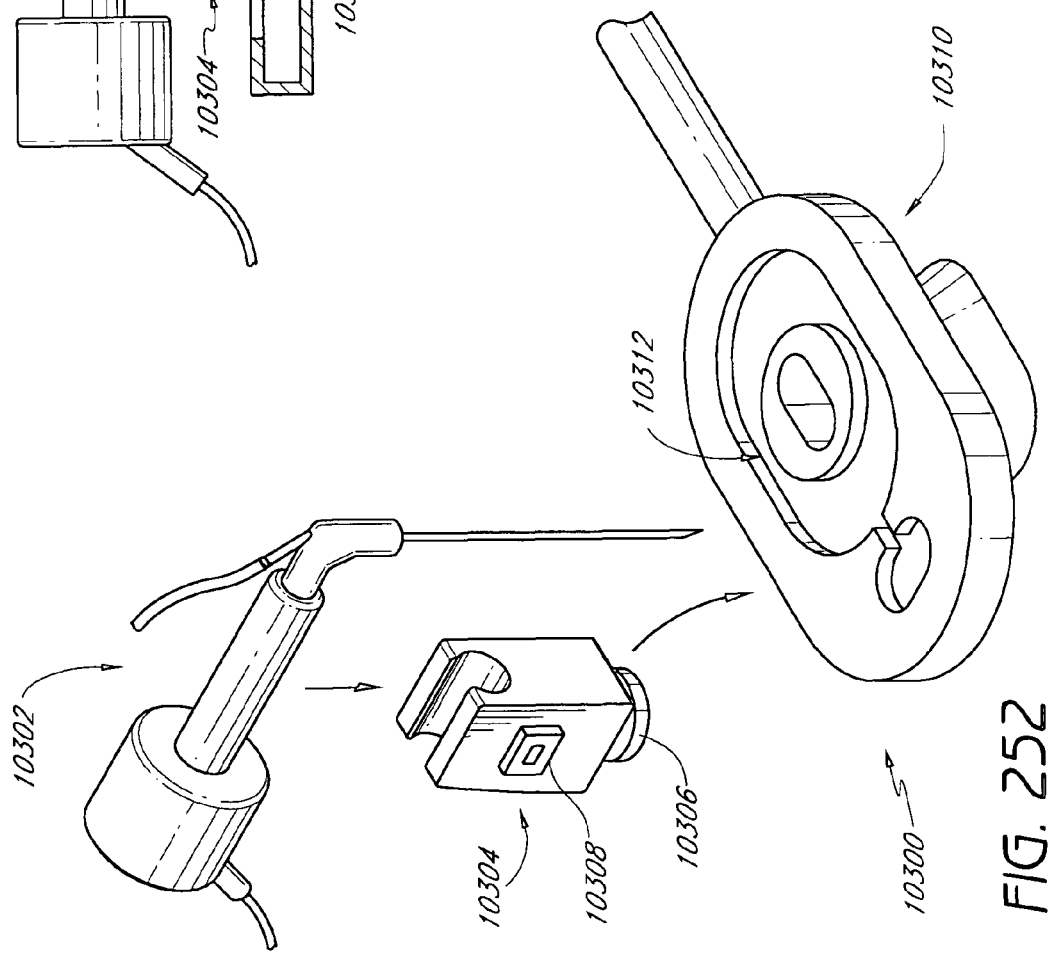
FIG. 253
FIG. 252

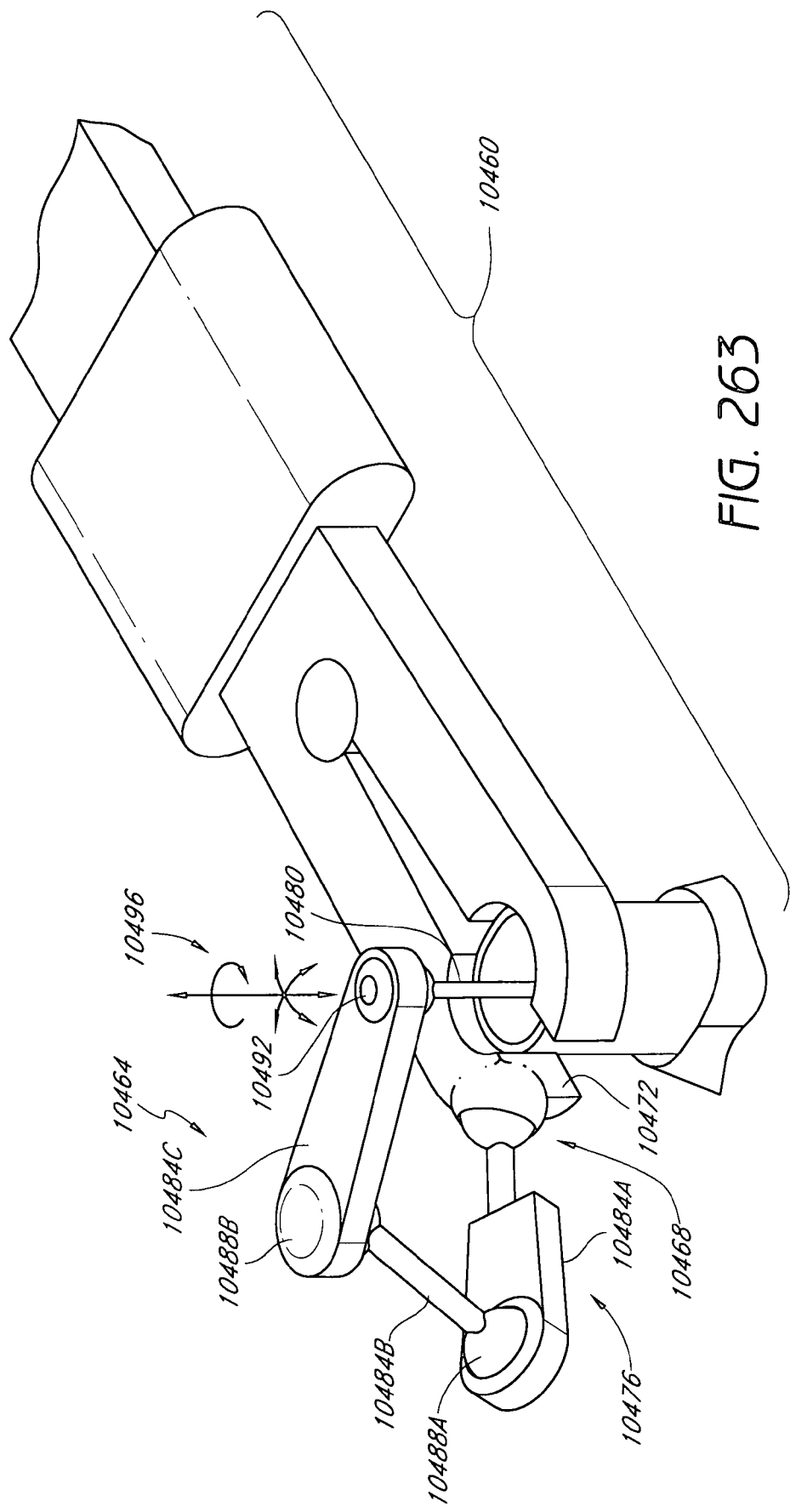

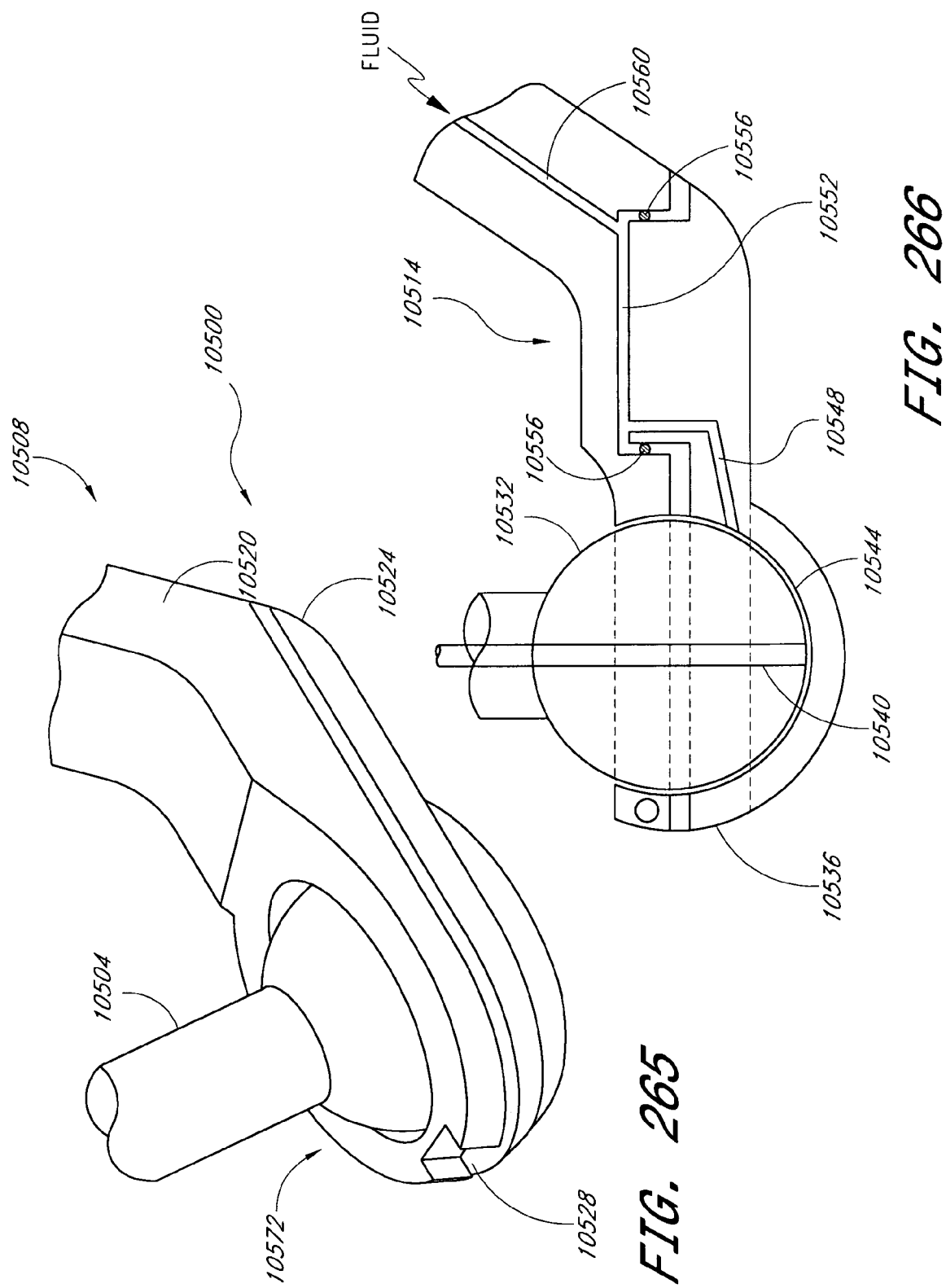

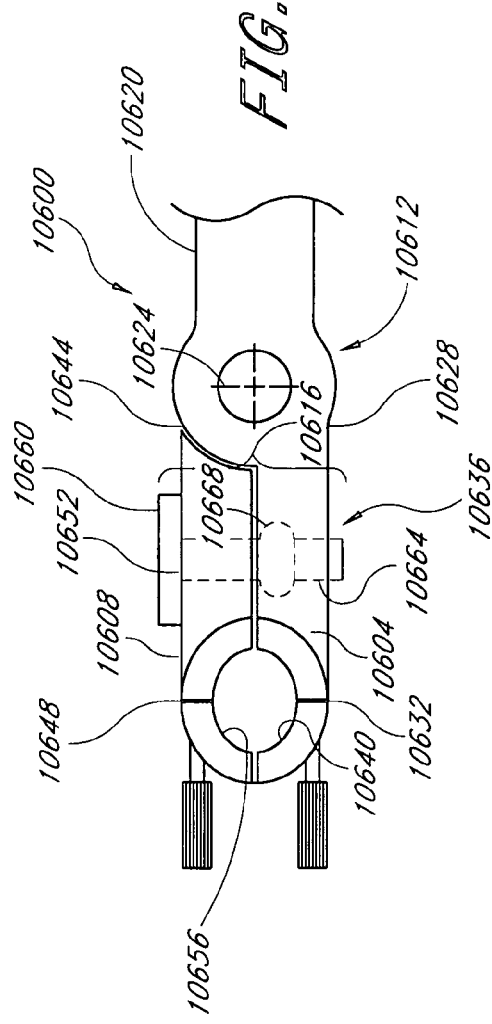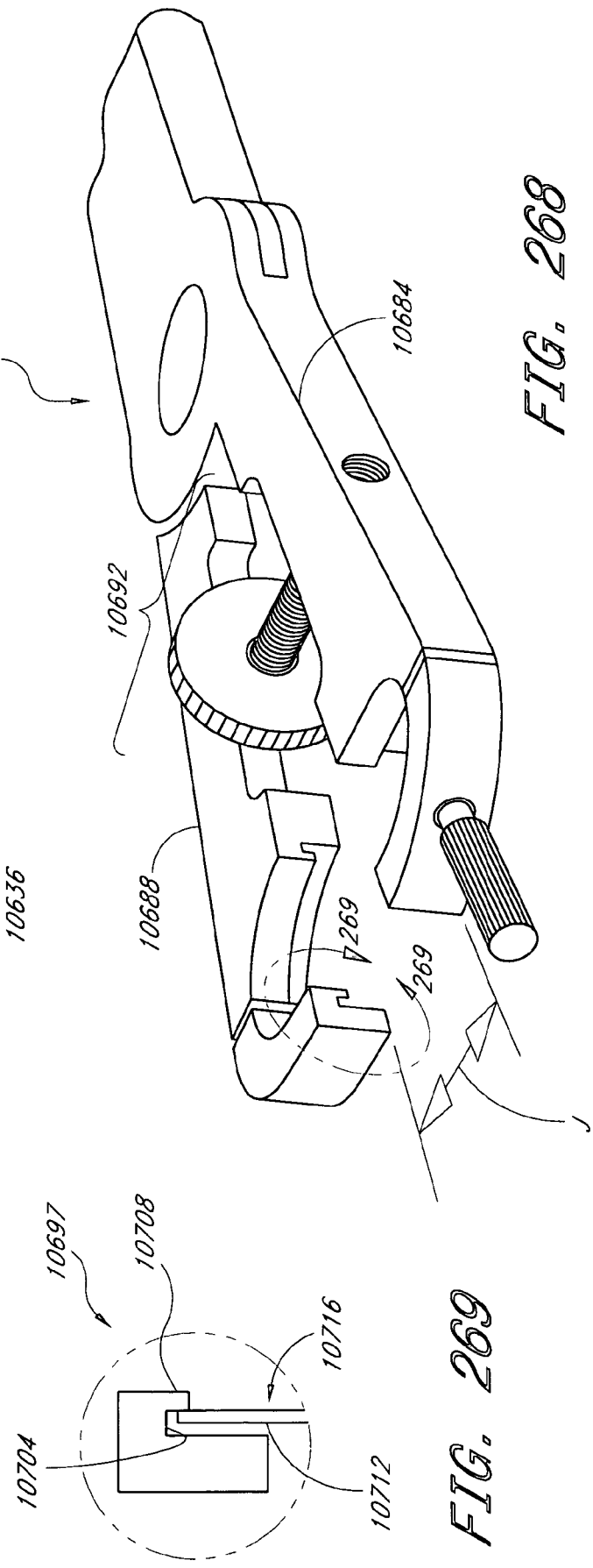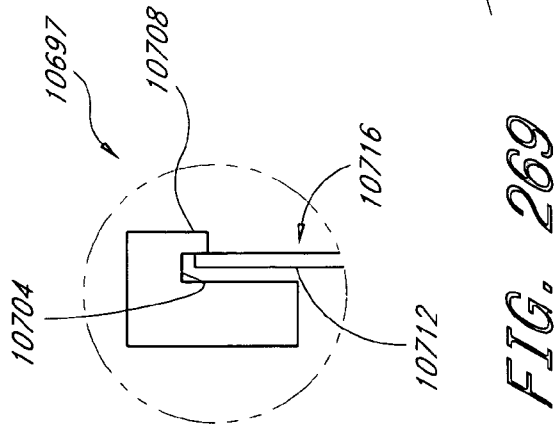

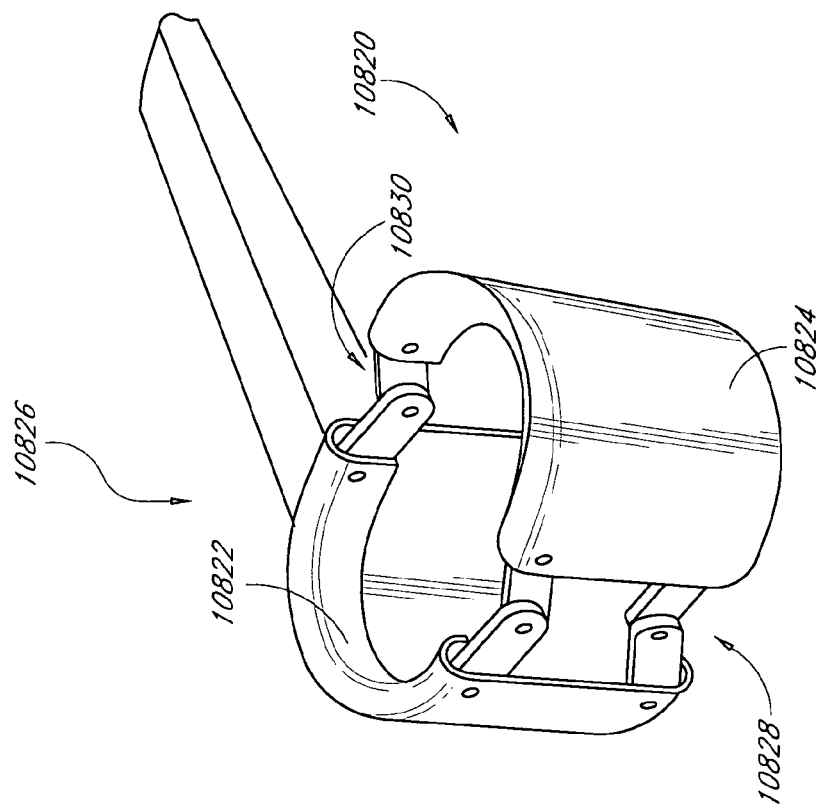
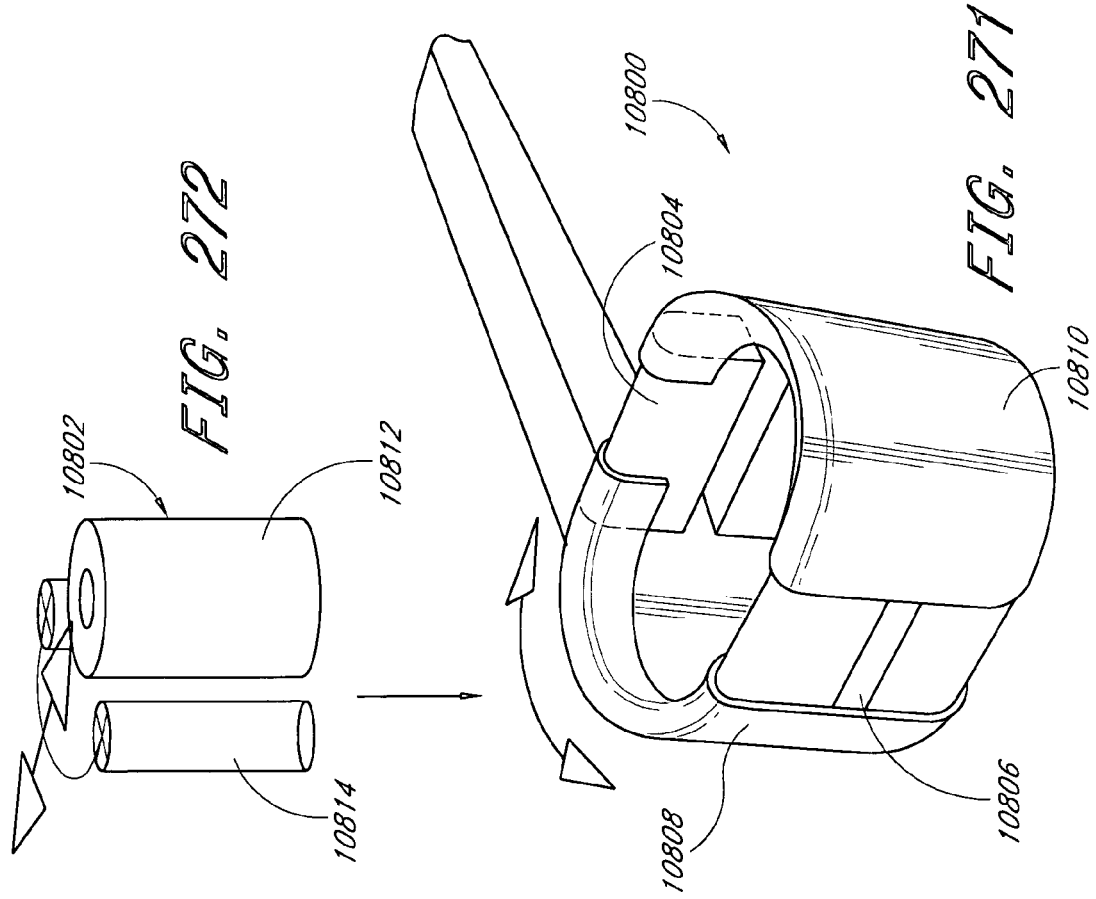

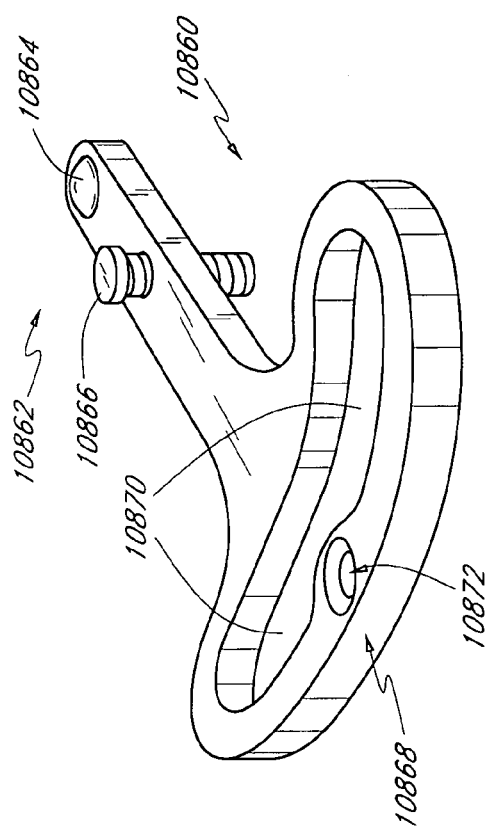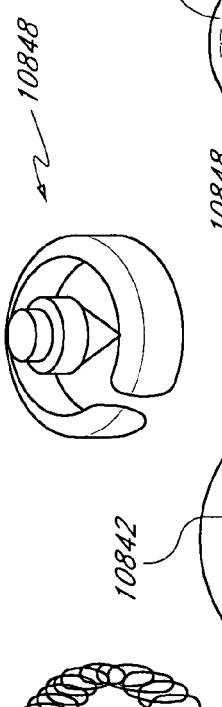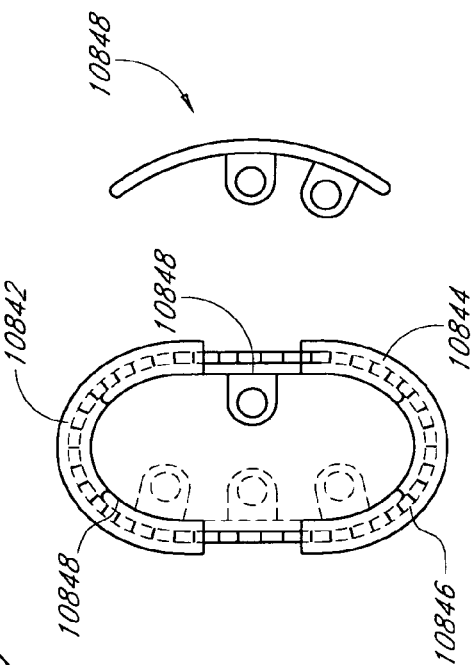
FIG. 275
FIG. 274

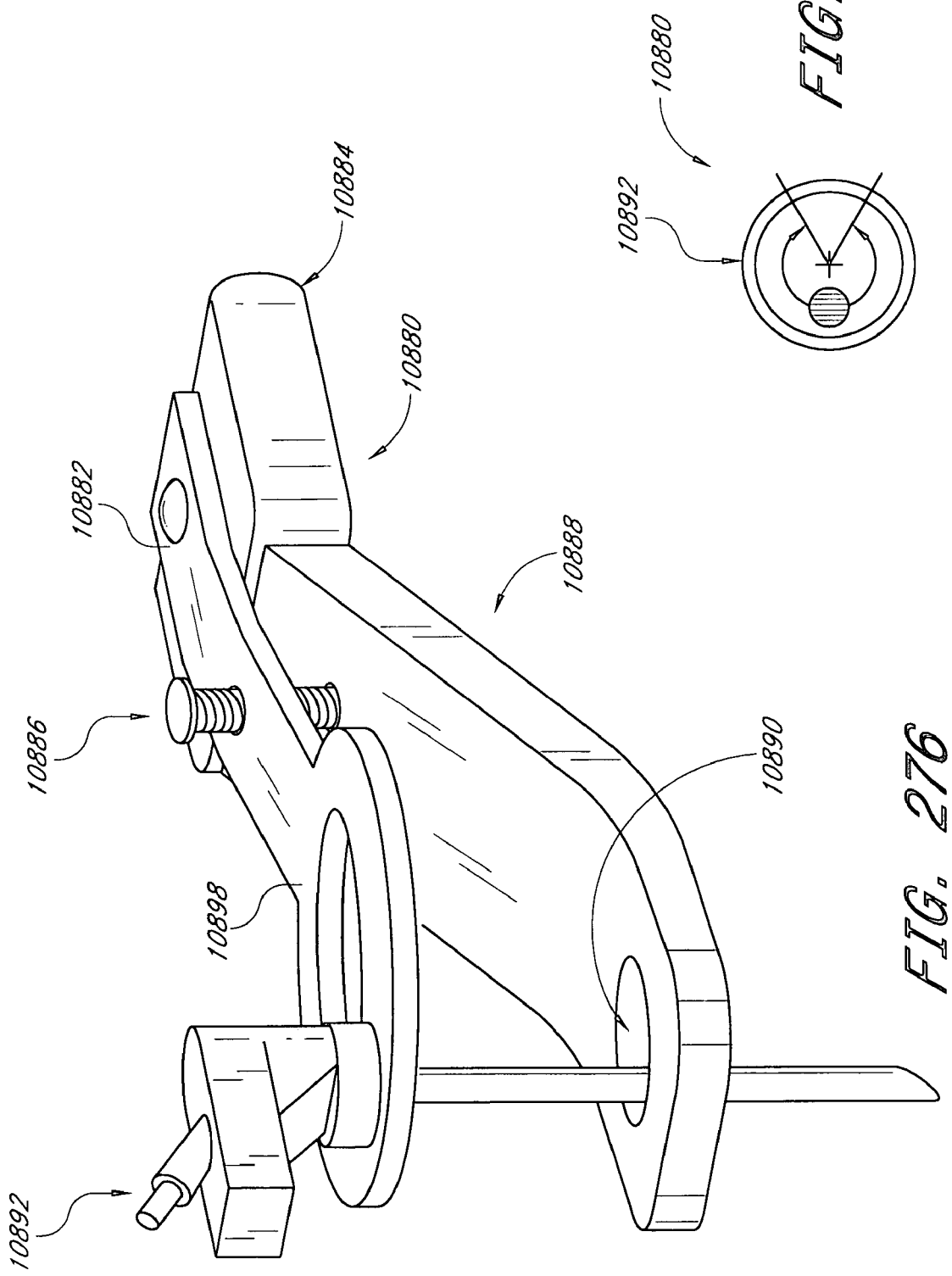

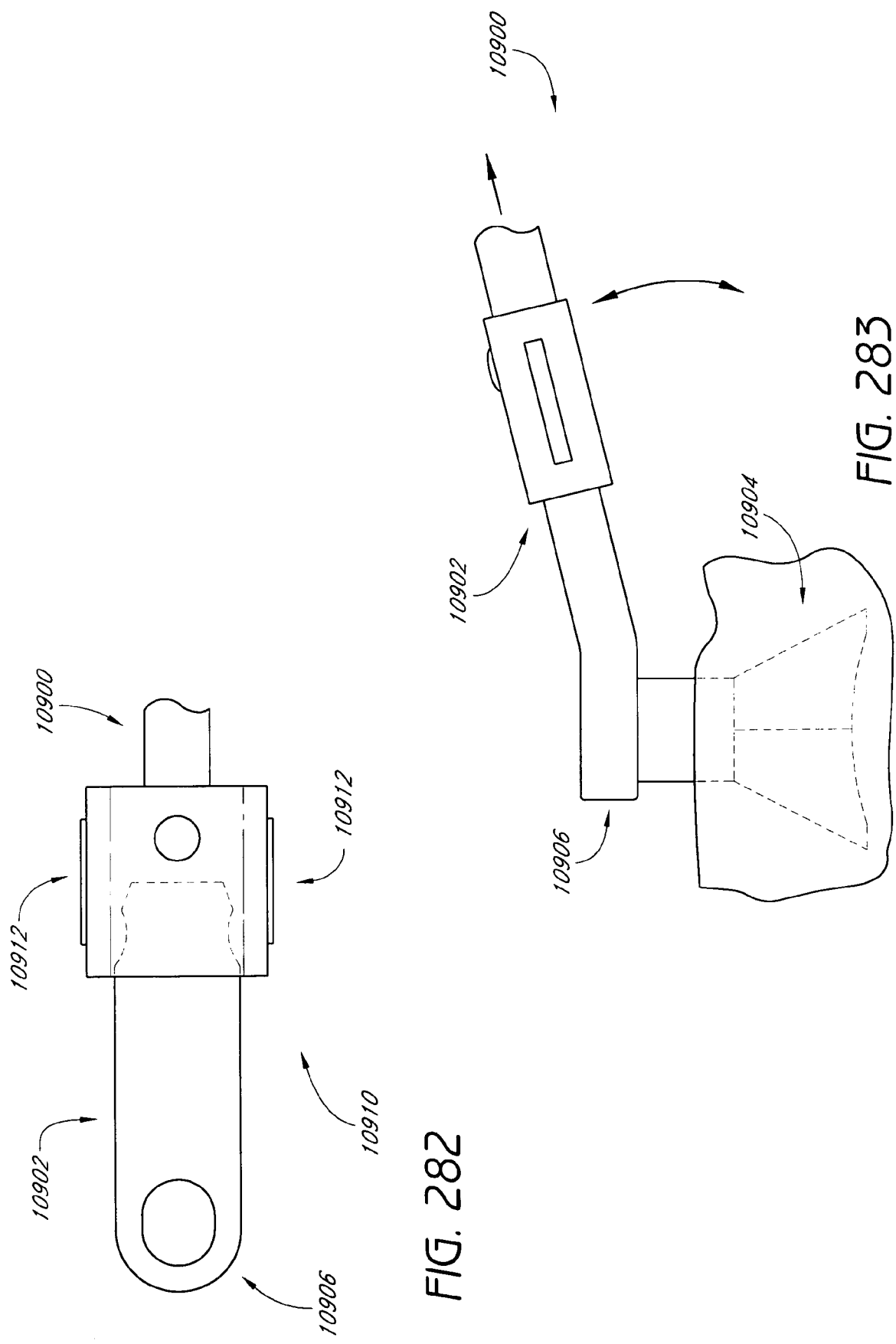

ACCESS SYSTEMS AND METHODS FOR MINIMALLY INVASIVE SURGERY

PRIORITY INFORMATION

This application is based on and claims priority to U.S. Provisional Patent Applications Nos. 60/497,822 (filed Aug. 26, 2003), 60/497,763 (filed Aug. 26, 2003), 60/514,559 (filed Oct. 24, 2003), 60/545,587 (filed Feb. 18, 2004), 60/579,643 (filed Jun. 15, 2004), the entire contents of all of which are hereby expressly incorporated by reference herein.

BACKGROUND OF THE INVENTION

1. Field of the Invention

This application relates to surgical systems and assemblies that include an access device for minimally invasive surgery, and in particular relates to systems and devices that provide access to a surgical location, e.g. adjacent a spine, for one or more instruments to perform a procedure at the surgical location.

2. Description of the Related Art

Spinal surgery presents significant difficulties to the physician attempting to reduce chronic back pain or correct spinal deformities without introducing additional trauma due to the surgical procedure itself. In order to access the vertebrae to perform spinal procedures, the physician is typically required to make large incisions and cut or strip muscle tissue surrounding the spine. In addition, care must be taken not to injure nerve tissue in the area. Consequently, traditional surgical procedures of this type carry high risks of scarring, pain, significant blood loss, and extended recovery times.

Apparatuses for performing minimally invasive techniques have been proposed to reduce the trauma of posterior spinal surgery by reducing the size of the incision and the degree of muscle stripping in order to access the vertebrae. One such apparatus provides a constant diameter cannula that is made narrow in order to provide a small entry profile. As a result, the cannula provides minimal space for the physician to observe the body structures and manipulate surgical instruments in order to perform the required procedures. A narrow cannula is typically insufficient to perform one level spinal fixation procedures, which requires visualization of two vertebrae and introduction of screws, rods, as well as other large spinal fixation devices.

SUMMARY OF THE INVENTION

Accordingly, there is a need in the art for systems and methods for treating the spine that provide minimally invasive access to the spine such that a variety of procedures, and preferably the entire procedure or at least a substantial portion thereof, can be performed via a single access device.

In one embodiment, a device is provided for accessing a surgical location within a patient. The device comprises an elongate body having an outer surface and an inner surface. The inner surface defines a passage extending through the elongate body and through which multiple surgical instruments can be inserted simultaneously to the surgical location. The elongate body is capable of having a configuration when inserted within the patient wherein the cross-sectional area of the passage at a first location is greater than the cross-sectional area of the passage at a second location. The first location is distal to the second location. The proximal portion of the device may be coupled with, e.g., supporting, a mount outside the body. The mount may include an indexing collar that rests on one section of the proximal portion.

Advantageously, in some embodiments the devices as described herein can allow for improved access to a surgical location, such as for performing a procedure on a spinal location. In one embodiment the device can have an expandable distal portion. In one embodiment, the device can have an expandable proximal portion. Expandable portions of the device can provide the operator with an enlarged passage to improve the field of vision and/or the working space within the access device. Moreover, the enlarged passage can allow for multiple instruments to be placed in the passage, with the ability to articulate the instruments at desired angles to reach desired locations in the working space.

In one embodiment a device for retracting tissue provides access to a spinal location within a patient. The device has an elongate body that has a proximal end and a distal end. The elongate body has a length between the proximal and distal ends such that the distal end can be positioned inside the patient adjacent the spinal location. The elongate body has a generally oval shaped proximal portion and an expandable distal portion. A passage extends through the elongate body between the proximal and distal ends. The passage is defined by a smooth metal inner surface extending substantially entirely around the perimeter of the passage between the proximal and distal ends. The elongate body is expandable between a first configuration sized for insertion into the patient and a second configuration wherein the cross-sectional area of the passage at the distal end is greater than the cross-sectional area of the passage at the proximal end.

In another embodiment, a device provides access to a surgical location within a patient. The device has an elongate body that has a proximal end, a distal end, and an inner surface. The inner surface defines a passage that extends through the elongate body. Surgical instruments can be inserted through the passage to the surgical location. The elongate body is capable of having a configuration when located within the patient wherein the cross-sectional area of the passage at a first location is greater than the cross-sectional area of the passage at a second location. The first location is distal to the second location. The passage is capable of having an oblong shaped cross section between the second location and the proximal end.

In another embodiment, a device provides access to a surgical location within a patient. The device has an elongate body that has a proximal end, a distal end, and an inner surface. The inner surface defines a passage that extends through the elongate body. Surgical instruments can be inserted through the passage to the surgical location. The elongate body is expandable from a first configuration to a second configuration when located within the patient. In the second configuration the cross-sectional area of the passage at a first location is greater than the cross-sectional area of the passage at a second location. The first location is distal to the second location. The passage is capable of having a generally oval shaped cross section between the second location and the proximal end.

In another embodiment, a device provides access to a surgical location within a patient. The device has an elongate body that has a proximal end, a distal end, and an inner surface. The inner surface defines a passage that extends through the elongate body. Surgical instruments can be inserted through the passage to the surgical location. The elongate body is capable of having a configuration when inserted within the patient wherein the cross-sectional area of the passage at a first location is greater than the cross-sectional area of the passage at a second location. The first location is distal to the second location. The passage is capable of having a cross section between the second location and the proximal end. The cross section is defined by first and second generally parallel opposing side portions and first and second generally arcuate opposing side portions.

In another embodiment, a method for accessing a surgical location within a patient comprises providing a device that has an elongate body. The elongate body has a proximal end, a distal end, and an inner surface. The inner surface defines a passage extending through the elongate body. Surgical instruments can be inserted through the passage to the surgical location. The passage is capable of having an oblong shaped cross section between the second location and the proximal end. The elongate body has an expanded configuration. The elongate body is configured for insertion into the patient. The device is inserted into the patient to the surgical location. The device is expanded to the expanded configuration.

In another embodiment, a device provides access to a surgical location within a patient. The device has an elongate body that has a proximal end, a distal end, and an inner surface. The inner surface defines a passage that extends through the elongate body. Surgical instruments can be inserted through the passage to the surgical location. The elongate body is capable of having a configuration when located within the patient wherein the cross-sectional area of the passage at a first location is greater than the cross-sectional area of the passage at a second location. The first location is distal to the second location. A lighting element is coupled with the elongate body to provide light to the surgical location.

In another embodiment, a method for providing access to a spinal location within a patient, comprises providing an elongate body having a proximal portion, a distal portion, a passage extending therethrough, and a locking element. The proximal portion is positioned at least partially outside the patient and the distal portion is positioned at least partially inside the patient adjacent the spinal location. The elongate body is actuated from a contracted configuration to an expanded configuration. The locking element is manipulated to retain the elongate body in the expanded configuration.

In another embodiment, a device for providing access to a surgical location within a patient comprises an elongate body having a proximal portion, a distal portion, a first slot segment, and a second slot segment that is angled relative to said first slot segment. The elongate body defines a passage for accessing the surgical location with surgical instruments. The elongate body has a contracted configuration for insertion into the patient and an expanded configuration for providing access to the surgical location. The cross-sectional area of the passage at a first location of the elongate body is greater than the cross-sectional area of said passage at a second location of the elongate body. A movable tab is configured to extend into the second slot segment when the elongate body is in the expanded configuration to retain the elongate body in the expanded configuration.

In another embodiment, a device for providing access to a surgical location within a patient comprises an elongate body having a proximal portion, a distal portion, and an inner surface defining a passage extending through the elongate body. The passage is capable of providing access for surgical instruments to be inserted to the surgical location. The elongate body is capable of having a configuration wherein the cross-sectional area of the passage at a first location is greater than the cross-sectional area of said passage at a second location. The first location is distal to the second location. A lock is coupled with the elongate body. The lock is actuatable to maintain the elongate body in the configuration.

In another embodiment, a device for providing access to a surgical location within a patient comprises an elongate body having a proximal portion, a distal portion coupled with the proximal portion, and an inner surface defining a passage extending through the elongate body and through which surgical instruments can be inserted to the surgical location. The elongate body is expandable from a contracted configuration to an expanded configuration wherein the cross-sectional area of the passage at a first location in the distal portion is greater than the cross-sectional area of the passage at a second location in the proximal portion. The passage has an oblong shaped cross-section at the second location. The elongate body is capable of resisting actuation from the expanded configuration to the contracted configuration when deployed.

In another embodiment, a retractor is provided that has an elongate body and an expandable shroud. The elongate body has an outer surface and an inner surface partially defining a passage. The elongate body also has a first longitudinal edge and a second longitudinal edge. The elongate body is capable of having an enlarged configuration when inserted within the patient. In the enlarged configuration the first longitudinal edge is spaced apart from the second longitudinal edge. The expandable shroud is configured to extend from the first longitudinal edge to the second longitudinal edge when the first and second edges are spaced apart. The shroud partially defines the passage. The cross-sectional area of said passage at a first location is greater than the cross-sectional area of the passage at a second location, wherein the first location is distal to the second location.

In another embodiment, a method provides access to a surgical location within a patient. A retractor is provided for insertion into the patient. The retractor has an elongate body that has an outer surface, an inner surface partially defining a passage, a first longitudinal edge, and a second longitudinal edge. The retractor also has an expandable shroud that extends from the first longitudinal edge to the second longitudinal edge. The retractor is positioned in a low-profile configuration for insertion into the patient. In the low-profile configuration, the first longitudinal edge is adjacent the second longitudinal edge. The retractor is positioned in an enlarged configuration wherein the cross-sectional area of the passage at a first location is greater than the cross-sectional area of said passage at a second location, wherein the first location is distal to the second location. The shroud is expanded to cover a gap formed between the first and second longitudinal edges.

In another embodiment, a device for retracting tissue provides access to a spinal location within a patient. The device includes an elongate body and a passage. The elongate body has a proximal portion and a distal portion. The elongate body defines a length between the proximal and distal portions along a longitudinal axis such that the distal portion can be positioned inside the patient adjacent the spinal location while the proximal portion is accessible. A transverse cross-section of the elongate body in the proximal portion has a first dimension that is longer than a second dimension. The first dimension is perpendicular to the second dimension. The passage extends through the elongate body between the proximal and distal portions. The elongate body is configured such that the proximal portion may be tilted with respect to the distal portion in a first direction generally aligned with the first dimension and in a second direction generally aligned with the second dimension.

In another embodiment, a device for retracting tissue provides access to a spinal location within a patient. The device includes a proximal portion, a distal portion, a first joint, and a second joint. The proximal portion partially defines a passage through which surgical instruments can be inserted to the surgical location. The distal portion partially defines the passage. The first joint is located on a first side of the device. The second joint is located on a second side of the device opposite the first joint. The proximal portion is capable of being positioned with respect to the distal portion about a first axis extending through the first and second joints and about a second axis that is perpendicular to the first axis.

In another embodiment, a method of accessing a surgical location within a patient is provided. A retractor that has a proximal portion, a distal portion, and a passage extending therethrough is provided. At least one of the proximal and distal portions is configured such that the portion has a first dimension and a second dimension, the first dimension being longer than and perpendicular to the second dimension. The elongate body is configured such that the proximal portion may be tilted with respect to the distal portion in a first direction generally aligned with the first dimension and in a second direction generally aligned with the second dimension. The retractor is advanced into the patient until the distal portion is adjacent a spinal location.

BRIEF DESCRIPTION OF THE DRAWINGS

Further objects, features and advantages of the invention will become apparent from the following detailed description taken in conjunction with the accompanying figures showing illustrative embodiments of the invention, in which:

FIG. 2 is a perspective view of one embodiment of an access device in a reduced profile configuration.

FIG. 3 is a perspective view of the access device of FIG. 2 in a first enlarged configuration.

FIG. 7 is a perspective view of another embodiment of an access device in an enlarged configuration.

FIG. 8 is an enlarged sectional view of the access device of FIG. 7 taken along lines 8-8 of FIG. 7.

FIG. 9 is a sectional view of the access device of FIG. 7 taken along lines 9-9 of FIG. 7.

FIG. 10 is a perspective view of another embodiment of an access device in an enlarged configuration.

FIG. 11 is an enlarged sectional view of the access device of FIG. 10 taken along lines 11-11 of FIG. 10.

FIG. 12 is a sectional view of the access device of FIG. 10 taken along lines 12-12 of FIG. 10.

FIG. 22 is a side view of the endoscope mount platform of FIG. 20 illustrated with one embodiment of an indexing arm and one embodiment of an endoscope.

FIG. 23 is a perspective view of one embodiment of an indexing collar of the endoscope mount platform FIG. 20.

FIG. 26 is a perspective view of one embodiment of a fastener.

FIG. 27 is an exploded perspective view of the fastener of FIG. 26.

FIG. 27(a) is an enlarged side view of one embodiment of a biasing member illustrated in FIG. 27 taken from the perspective of the arrow 27a.

FIG. 32 is a side view of one embodiment of another surgical instrument.

FIG. 33 is a perspective view similar to FIG. 31 illustrating the apparatuses of FIGS. 26 and 32, in one embodiment of a stage of one embodiment of a method for treating the spine of a patient.

FIG. 34 is an enlarged sectional view of the apparatus of FIGS. 26 and 32, illustrating one embodiment of a stage of one embodiment of a method for treating the spine of a patient.

FIG. 36 is an enlarged view in partial section illustrating one embodiment of a stage of one embodiment of a method for treating the spine of a patient.

FIG. 37 is a partial view of illustrating one embodiment of a stage of one embodiment of a method for treating the spine of a patient.

FIG. 78 is a perspective view of another embodiment of a lighting element.

FIG. 79 is a perspective view of another embodiment of a lighting element.

FIGS. 85 and 85A are top perspective and detailed views respectively of the access device of FIG. 82 with the lock in a locked position.

FIGS. 86 and 86A are top perspective and detailed views respectively of the access device of FIG. 82 with the lock in an unlocked position.

FIG. 87 is a top view of a viewing element mounting assembly having a light post mount or visualization mount, according to one embodiment.

FIG. 88 is a side view of the viewing element mounting assembly of FIG. 87.

FIG. 90 is a top view of the light post mount or visualization mount of FIG. 89.

FIG. 91 is a side cross section view of the light post mount or visualization mount of FIG. 89.

FIG. 92 is a bottom view of the light post mount or visualization mount of FIG. 89.

FIG. 93 is a side view of a support portion of the light post mount or visualization mount of FIG. 89.

FIG. 94 is a schematic view of the cross section of a passage of the light post mount or visualization mount of FIG. 89.

FIG. 98 is a top view of a light post or visualization element, according to one embodiment.

FIG. 99 is a side view of the light post or visualization element of FIG. 98.

FIG. 108 is a top view of an indexing collar assembly, having an indexing collar, according to one embodiment.

FIG. 109 is a side view of the indexing collar assembly of FIG. 108.

FIG. 116 is a bottom view of the indexing collar of FIG. 108.

FIG. 117 illustrates a portion of the indexing collar of FIG. 108.

FIG. 118 is a bottom perspective view of the indexing collar of FIG. 108.

FIG. 119 is a top perspective view of the indexing collar of FIG. 108.

FIG. 120 is a side view of an oval or oblong shaped dilator, according to one embodiment.

FIG. 121 is an end view of the dilator of FIG. 120.

FIG. 122 is another side view of the dilator of FIG. 120.

FIG. 123 is a side view of an access device assembly in a low profile configuration, according to one embodiment.

FIG. 124 is a front view of the access device assembly of FIG. 123.

FIG. 125 is a top view of the access device assembly of FIG. 123 in an expanded configuration.

FIG. 126 is a front view of the access device assembly of FIG. 123 in an expanded configuration.

FIG. 127 is a cross section view of a lock coupling location of the access device assembly of FIG. 123, taken along section plane 127-127.

Figure 123:
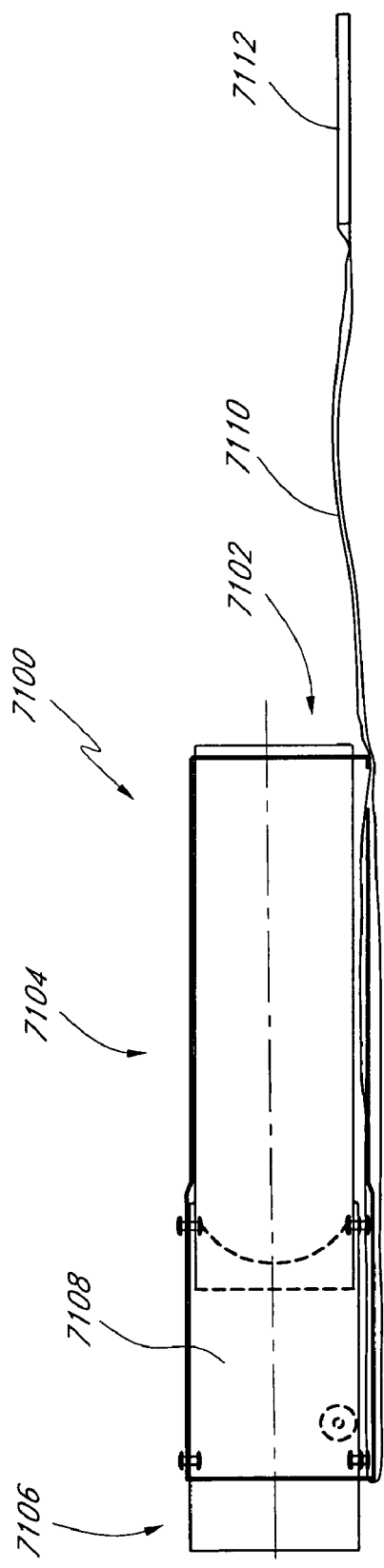

FIG. 128 is a cross section view of a skirt coupling location of the access device assembly of FIG. 123, taken along section plane 128-128.

FIG. 129 is a cross section view of a proximal portion coupling location of the access device assembly of FIG. 123, taken along section plane 129-129.

FIG. 130 is a top view of a proximal portion of the access device of FIG. 123.

FIG. 131 is a front view of the proximal portion of the access device of FIG. 123.

FIG. 132 is a side view of the proximal portion of the access device of FIG. 123.

Figure 133:
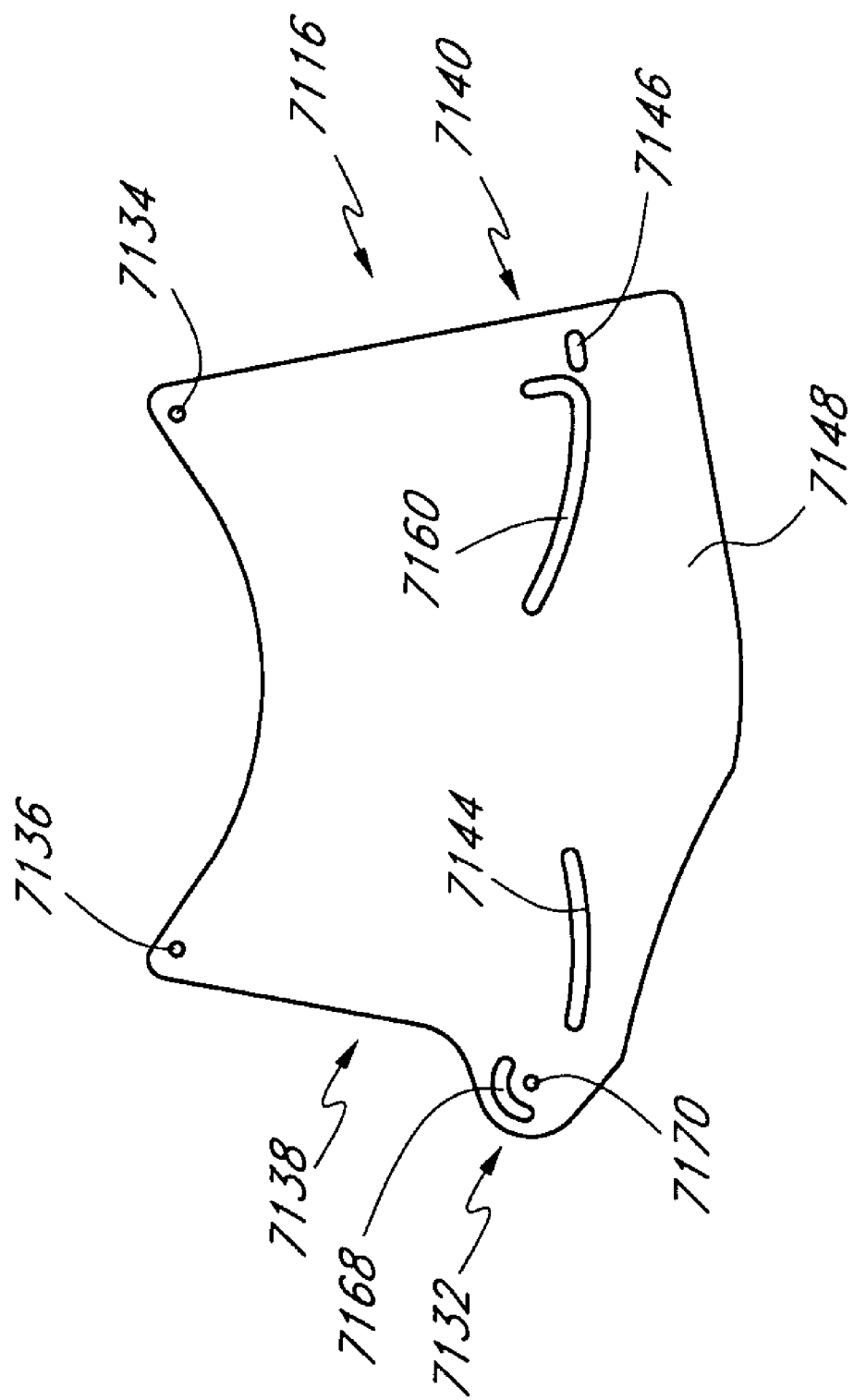

FIG. 133 illustrates a first locking skirt portion of a distal portion of the access device of FIG. 123.

Figure 134:
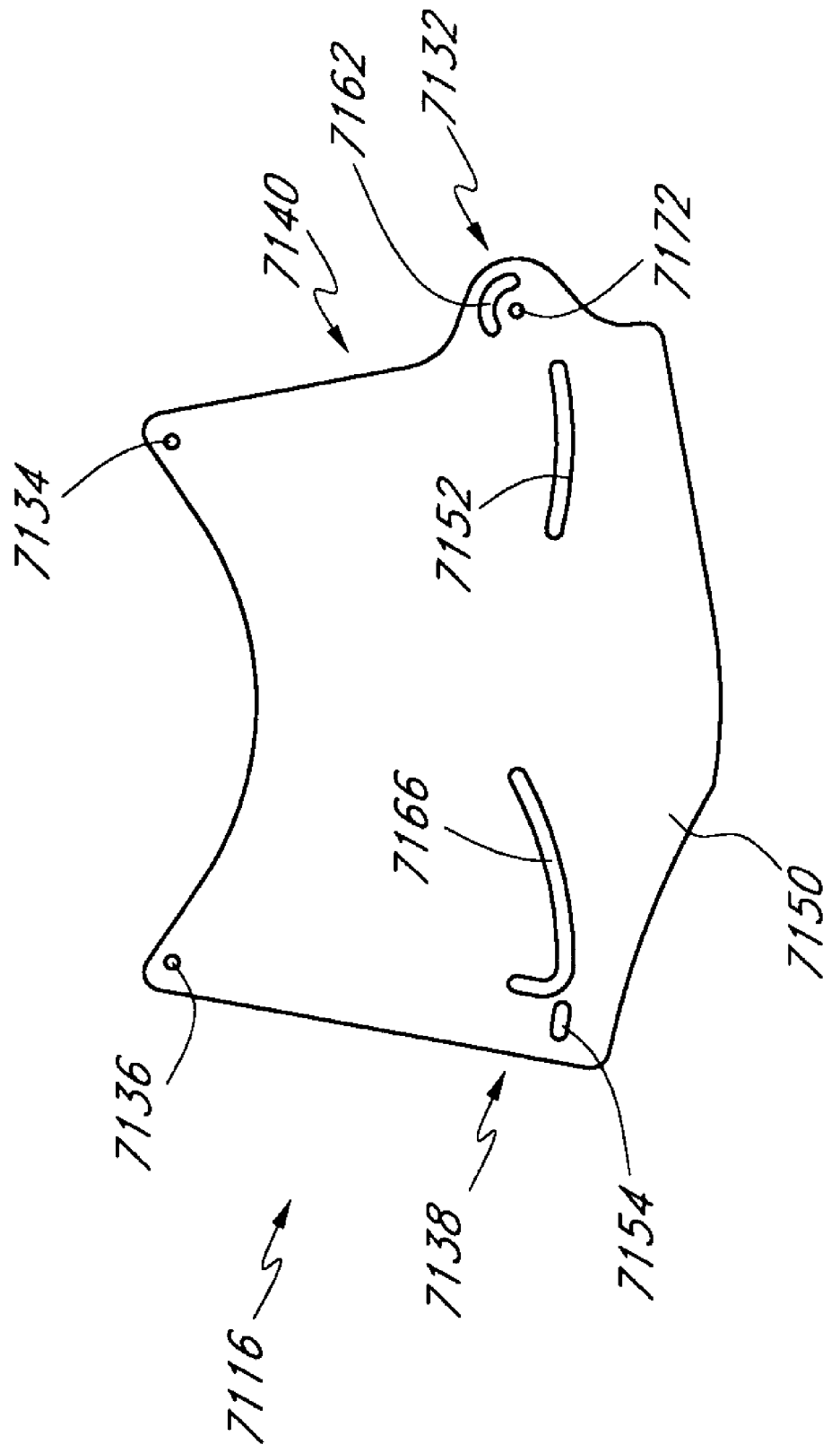

FIG. 134 illustrates a second locking skirt portion of the distal portion of the access device of FIG. 123.

Figure 135:
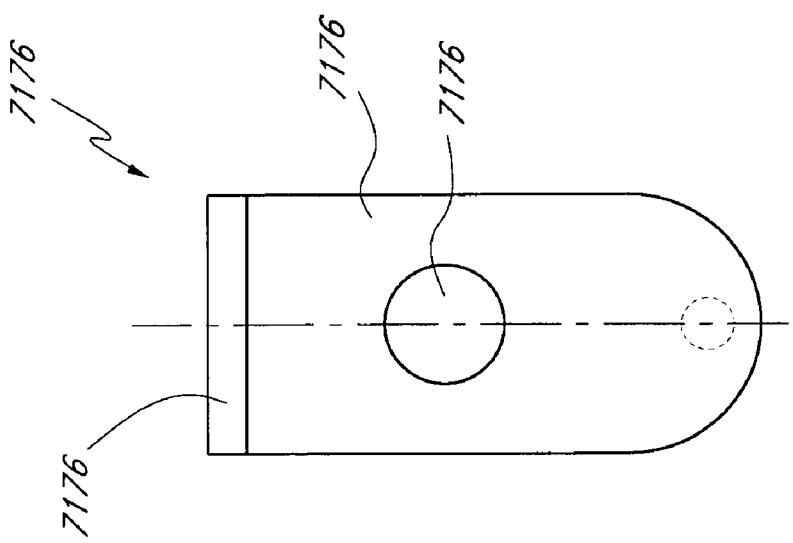

FIG. 135 is a side view of a locking element of the access device of FIG. 123.

Figure 136:
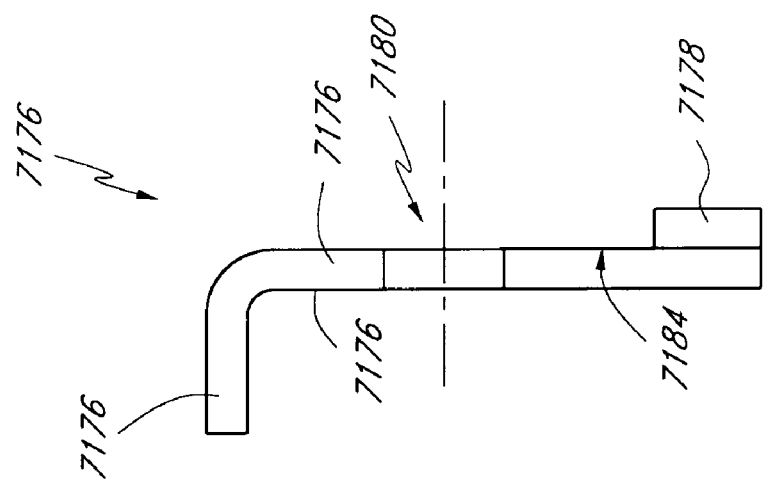

FIG. 136 is a side view of a locking element of the access device of FIG. 123.

Figure 137:
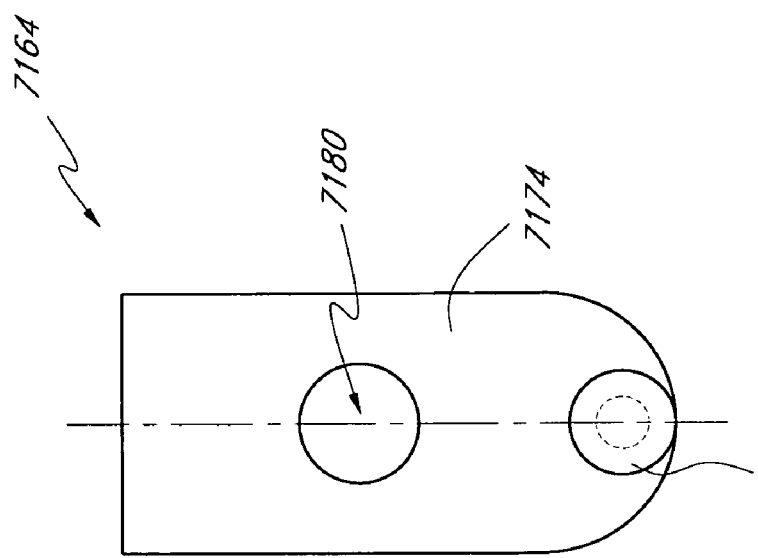

FIG. 137 is a side view of a locking element of the access device of FIG. 123.

Figure 138:
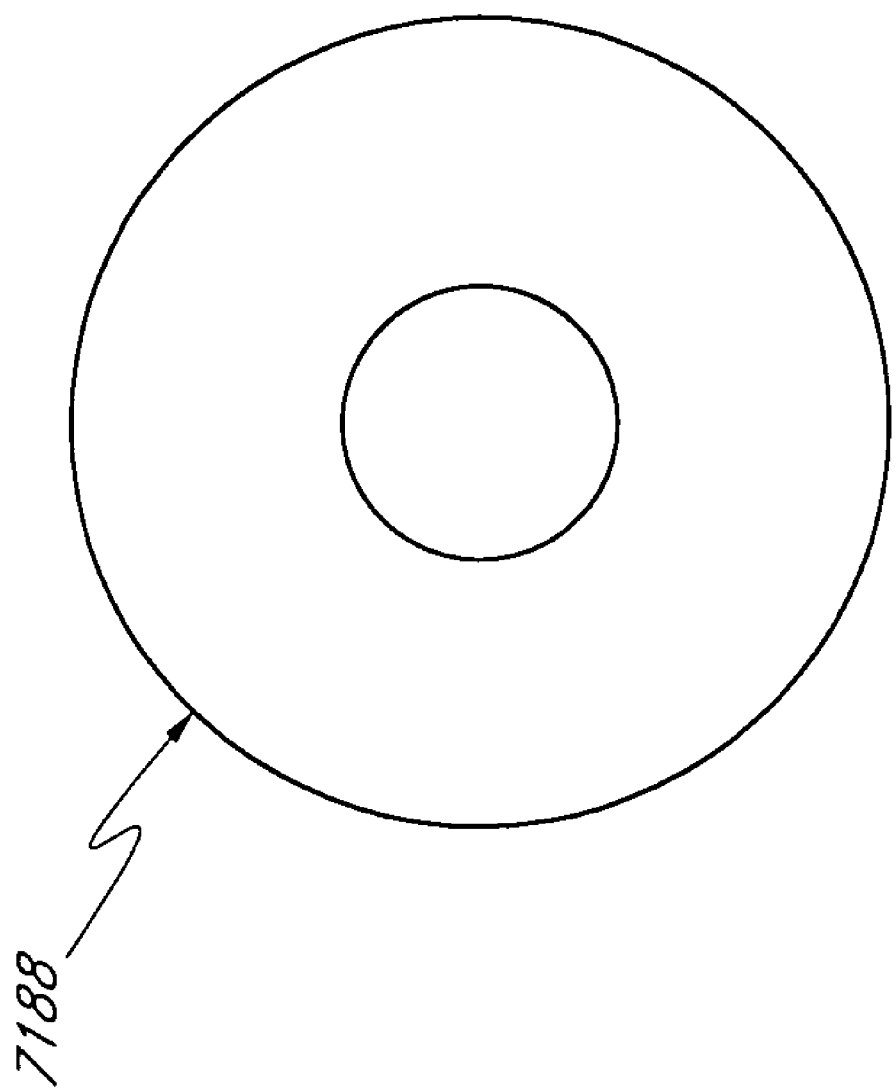

FIG. 138 illustrates a friction washer of the access device of FIG. 123.

Figure 139:
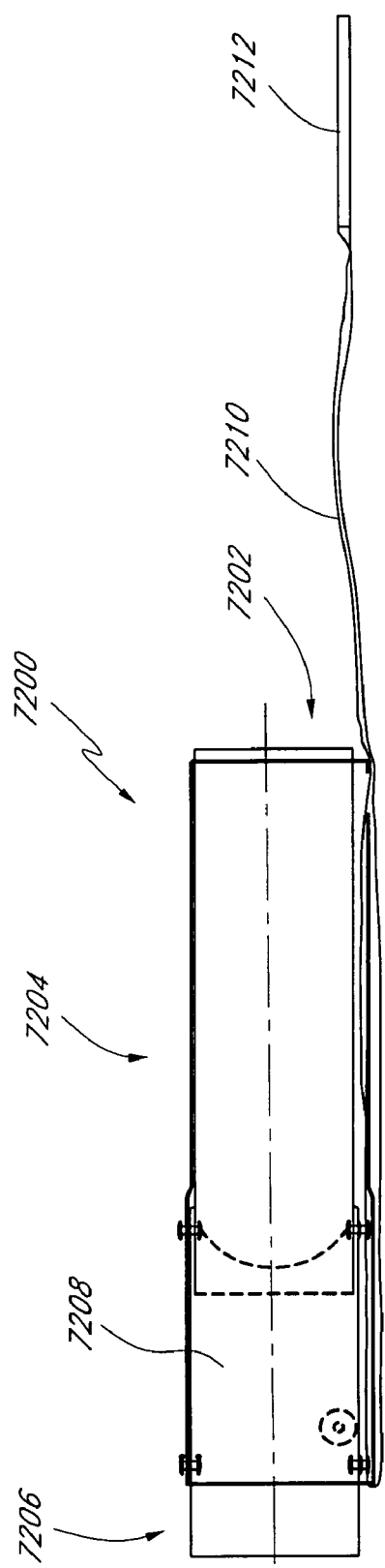

FIG. 139 is a side view of an access device assembly in a low profile configuration, according to another embodiment.

Figure 140:
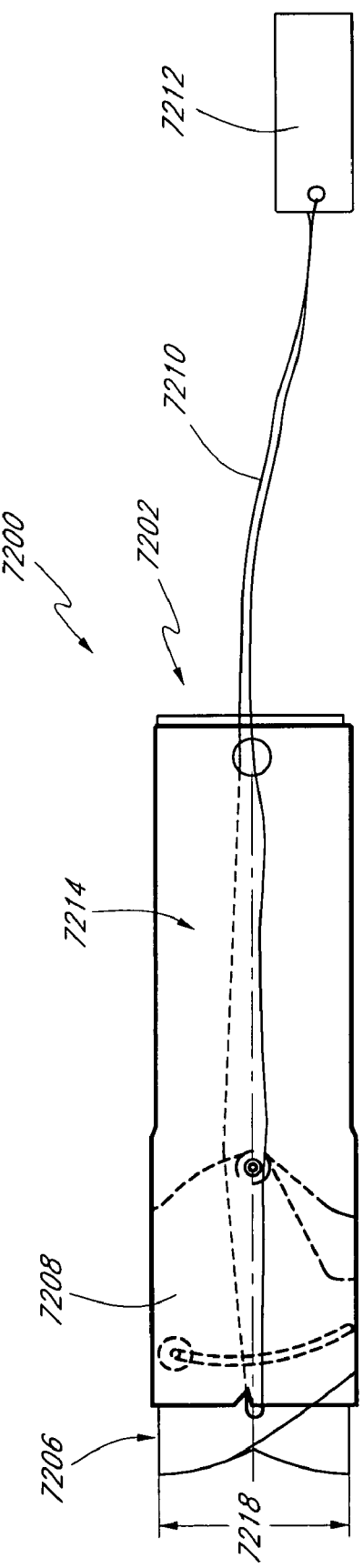

FIG. 140 is a front view of the access device assembly of FIG. 139.

FIG. 141 is a top view of the access device assembly of FIG. 139 in an expanded configuration.

FIG. 142 is a front view of the access device assembly of FIG. 139 in an expanded configuration.

FIG. 143 is a cross section view of a lock coupling location of the access device assembly of FIG. 139, taken along section plane 143-143.

FIG. 144 is a cross section view of a skirt coupling location of the access device assembly of FIG. 139, taken along section plane 144-144.

FIG. 145 is a cross section view of a proximal portion coupling location of the access device assembly of FIG. 139, taken along section plane 145-145.

Figure 146:
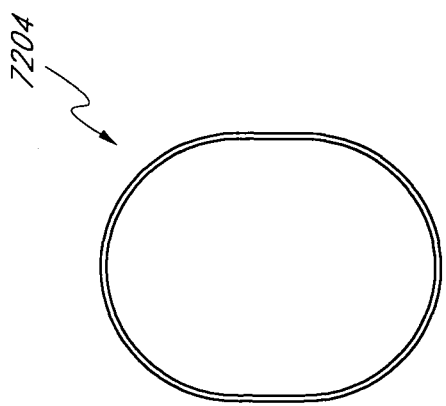

FIG. 146 is a top view of a proximal portion of the access device of FIG. 139.

Figure 147:
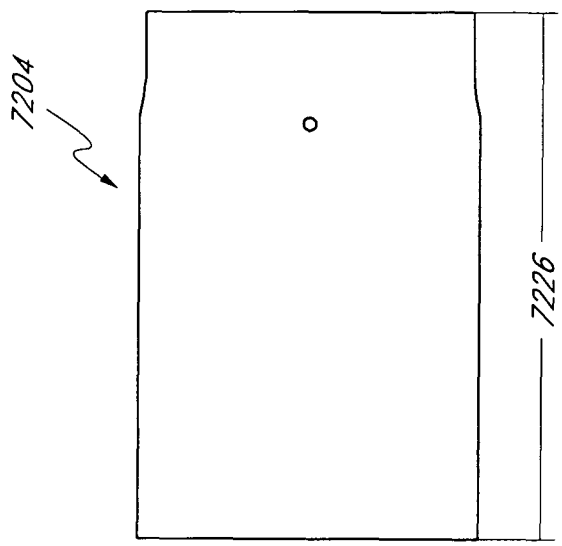

FIG. 147 is a front view of the proximal portion of the access device of FIG. 139.

Figure 148:
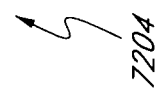

FIG. 148 is a side view of the proximal portion of the access device of FIG. 139.

Figure 149:
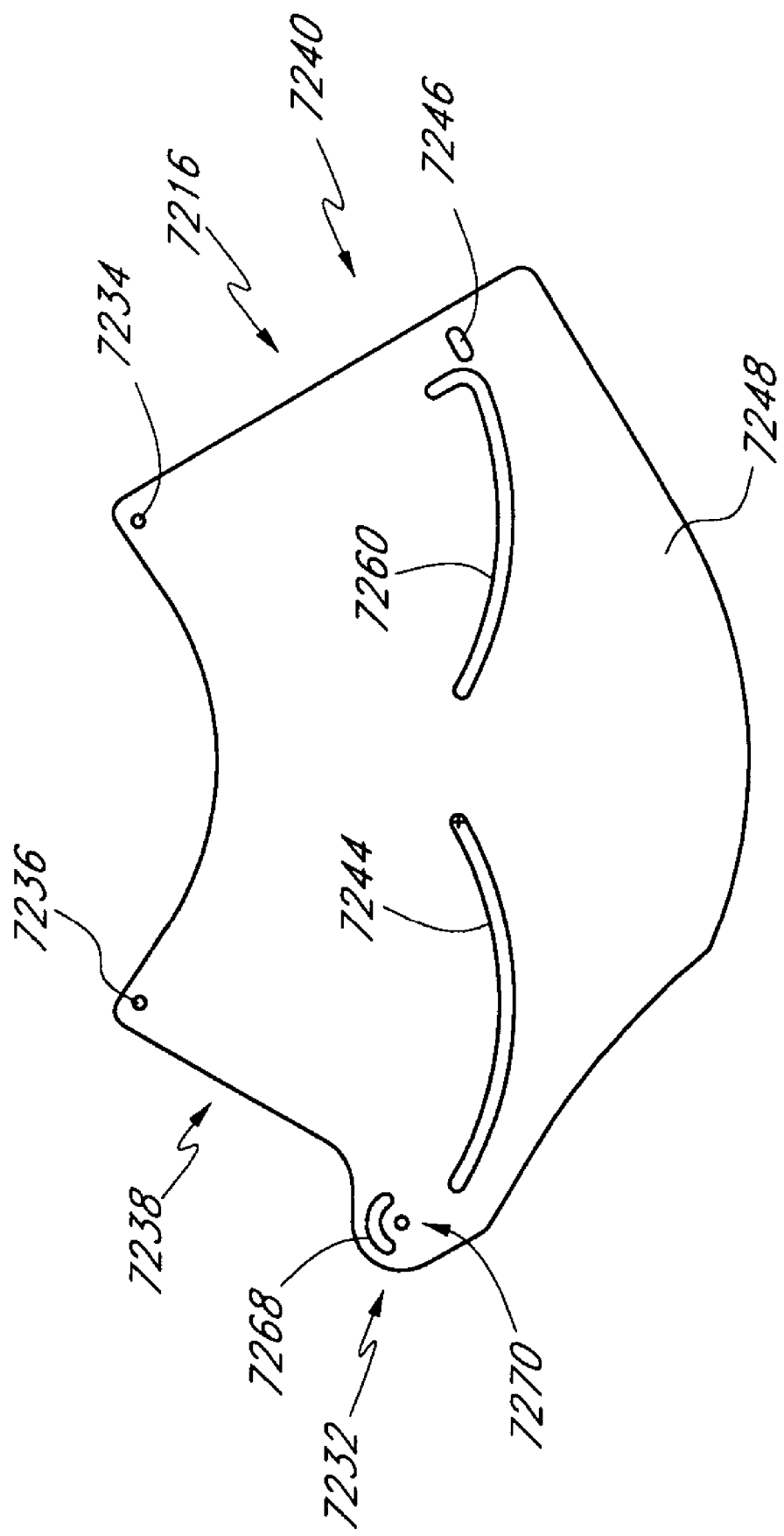

FIG. 149 illustrates a first locking skirt portion of a distal portion of the access device of FIG. 139.

Figure 150:
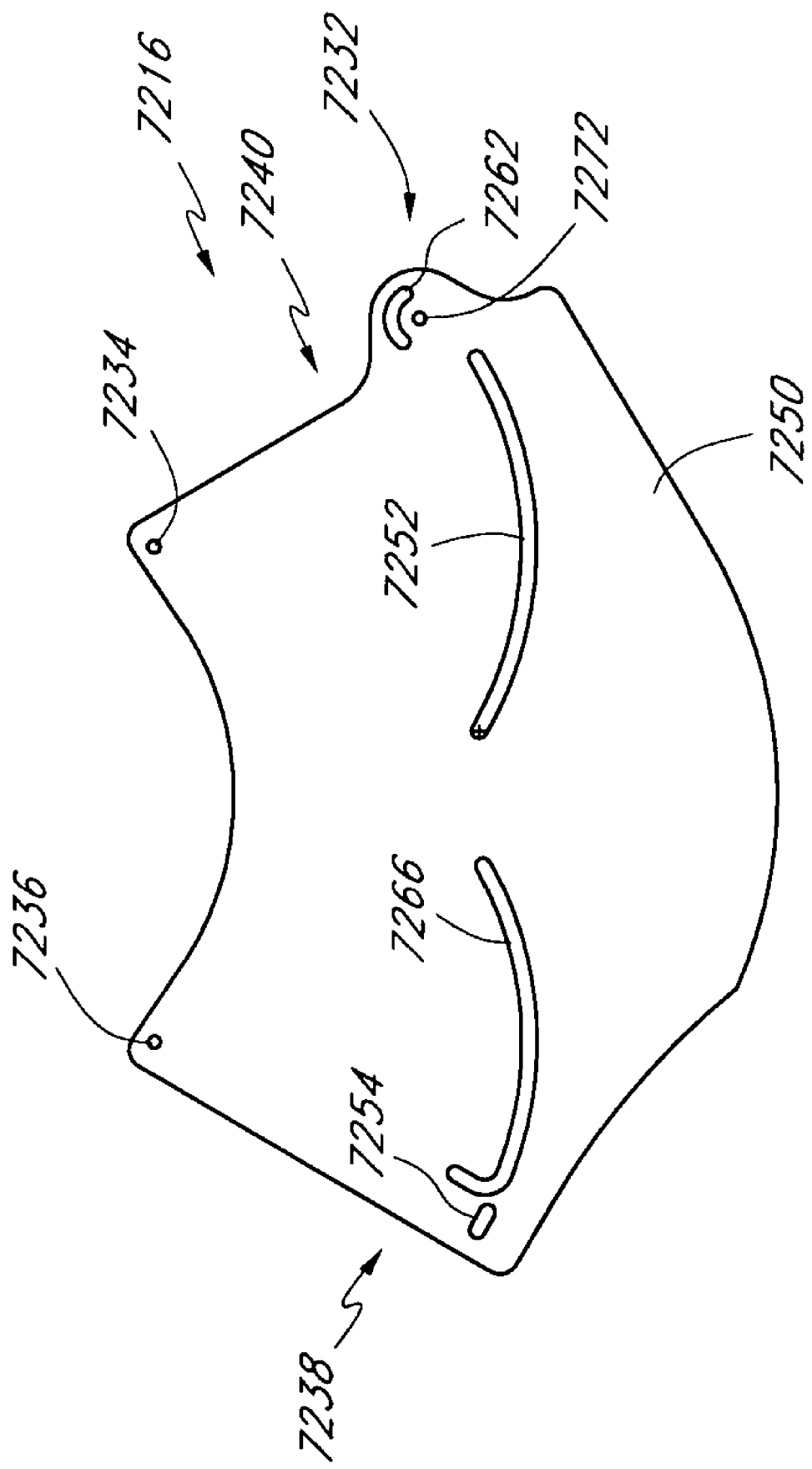

FIG. 150 illustrates a second locking skirt portion of the distal portion of the access device of FIG. 139.

Figure 151:
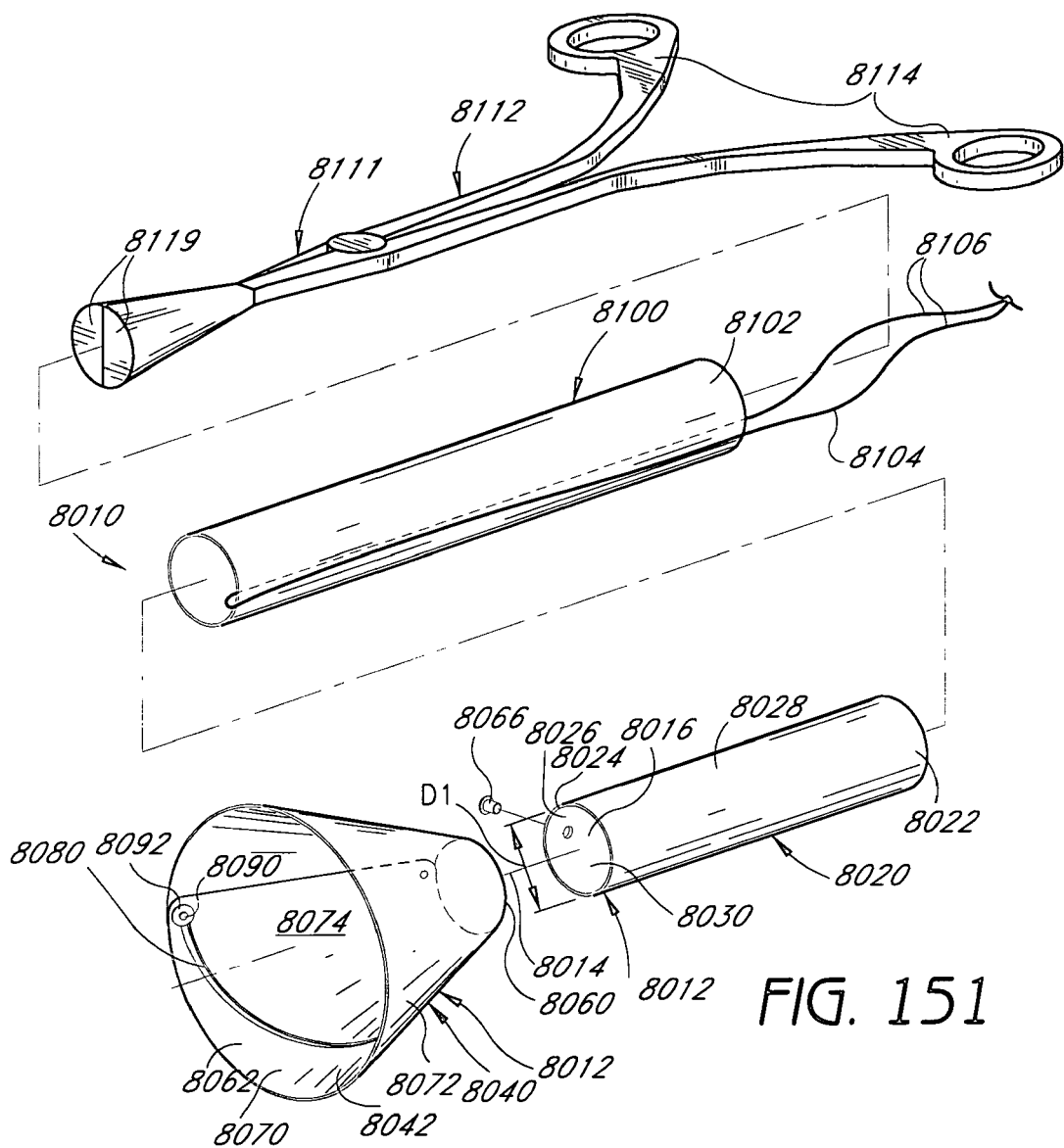

FIG. 151 is an exploded perspective view of a surgical cannula according to one embodiment of the present invention, the cannula being shown in an expanded condition.

Figure 152:
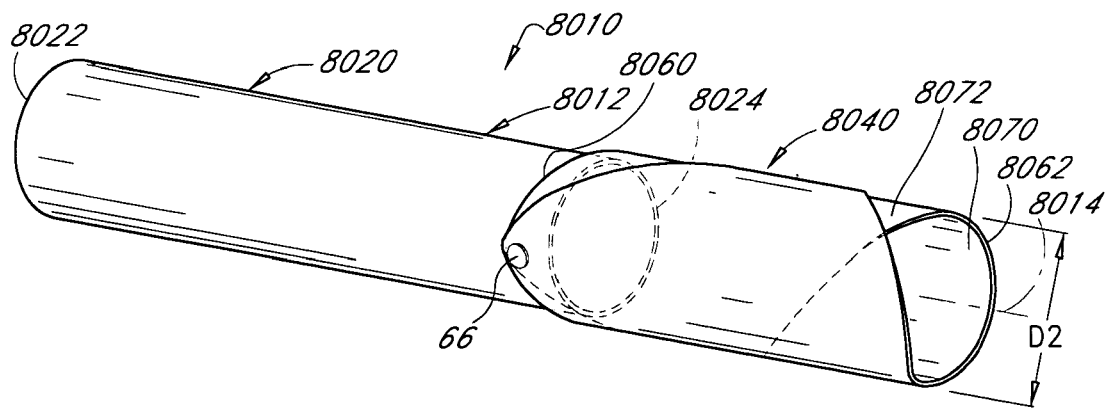

FIG. 152 is a perspective view of the cannula of FIG. 151 with parts removed for clarity, the cannula being shown in a contracted condition.

Figure 153:
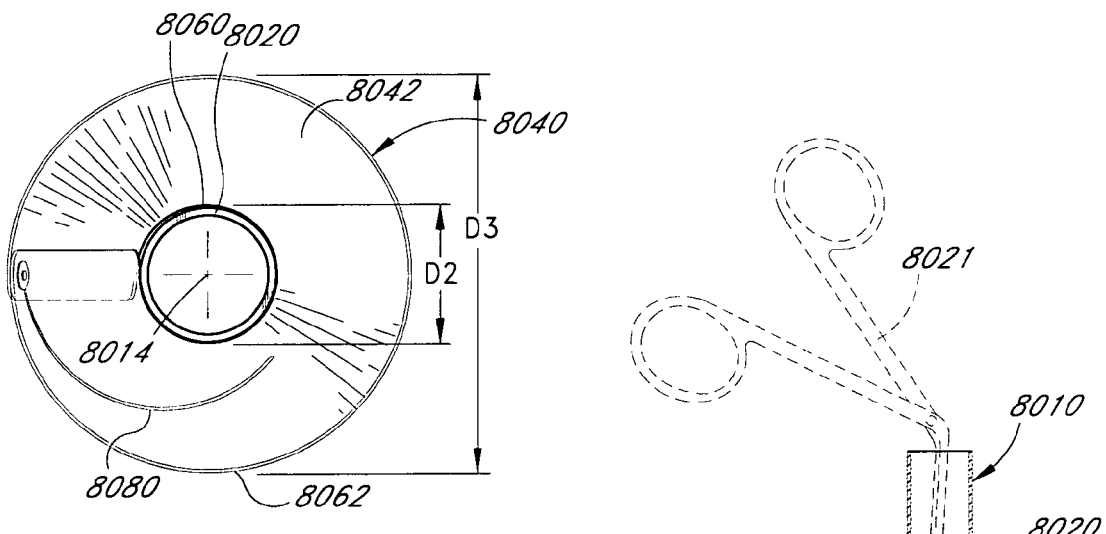

FIG. 153 is a schematic end view showing the cannula of FIG. 151 in the expanded condition.

Figure 154:
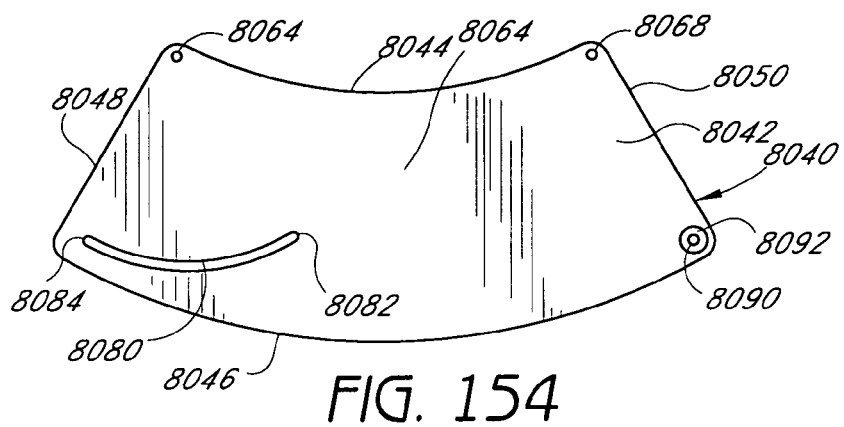

FIG. 154 is a rollout view of a part of the cannula of FIG. 151.

Figure 155:
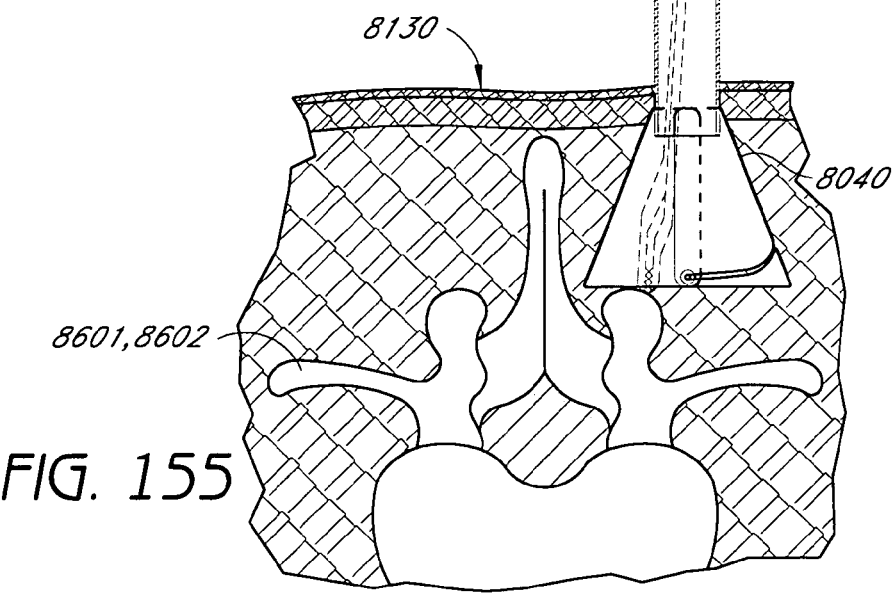

FIG. 155 is a schematic sectional view of the cannula of FIG. 151 during a surgical procedure.

Figure 156:
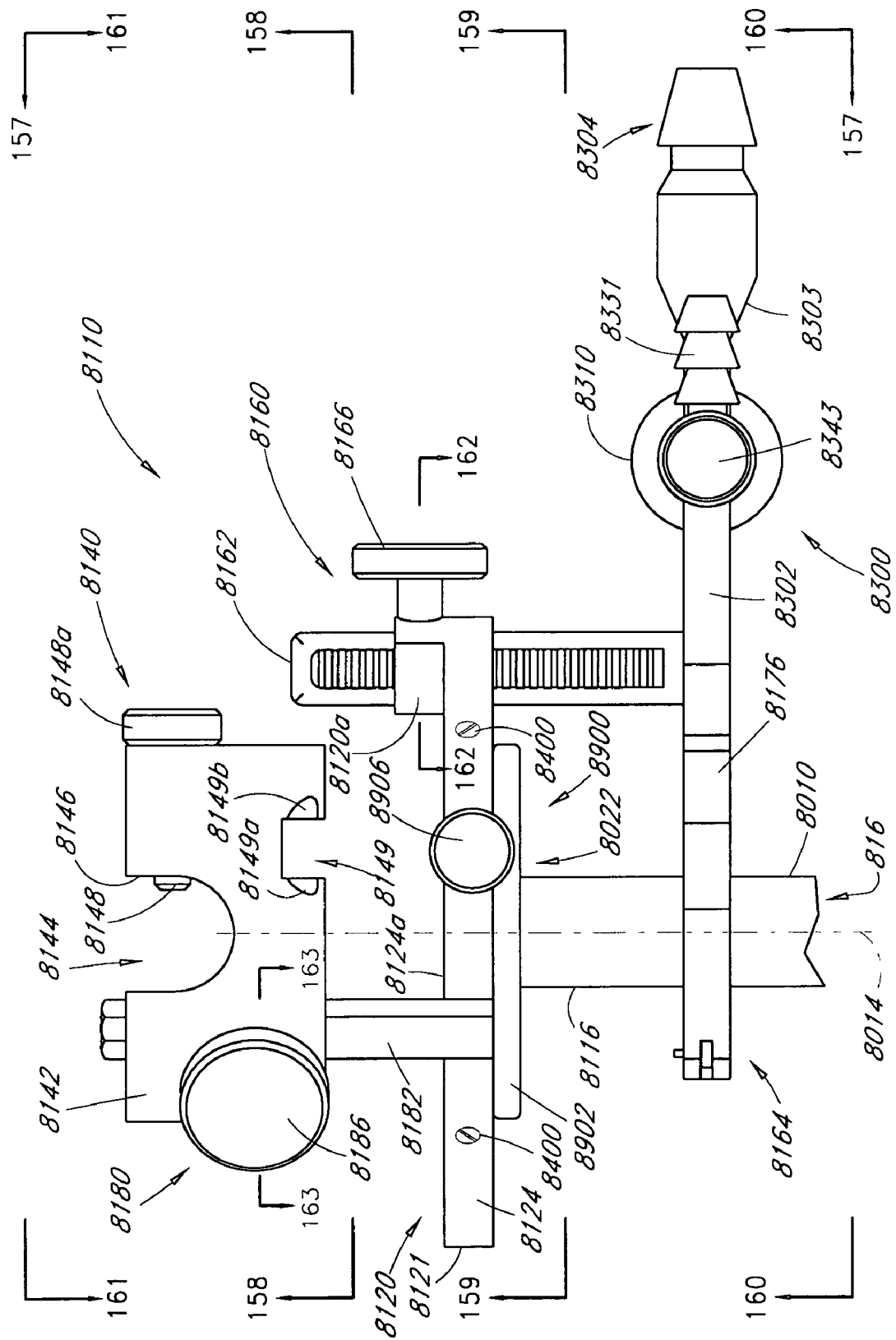

FIG. 156 is a schematic view of a support apparatus constructed according to another embodiment.

Figure 157:
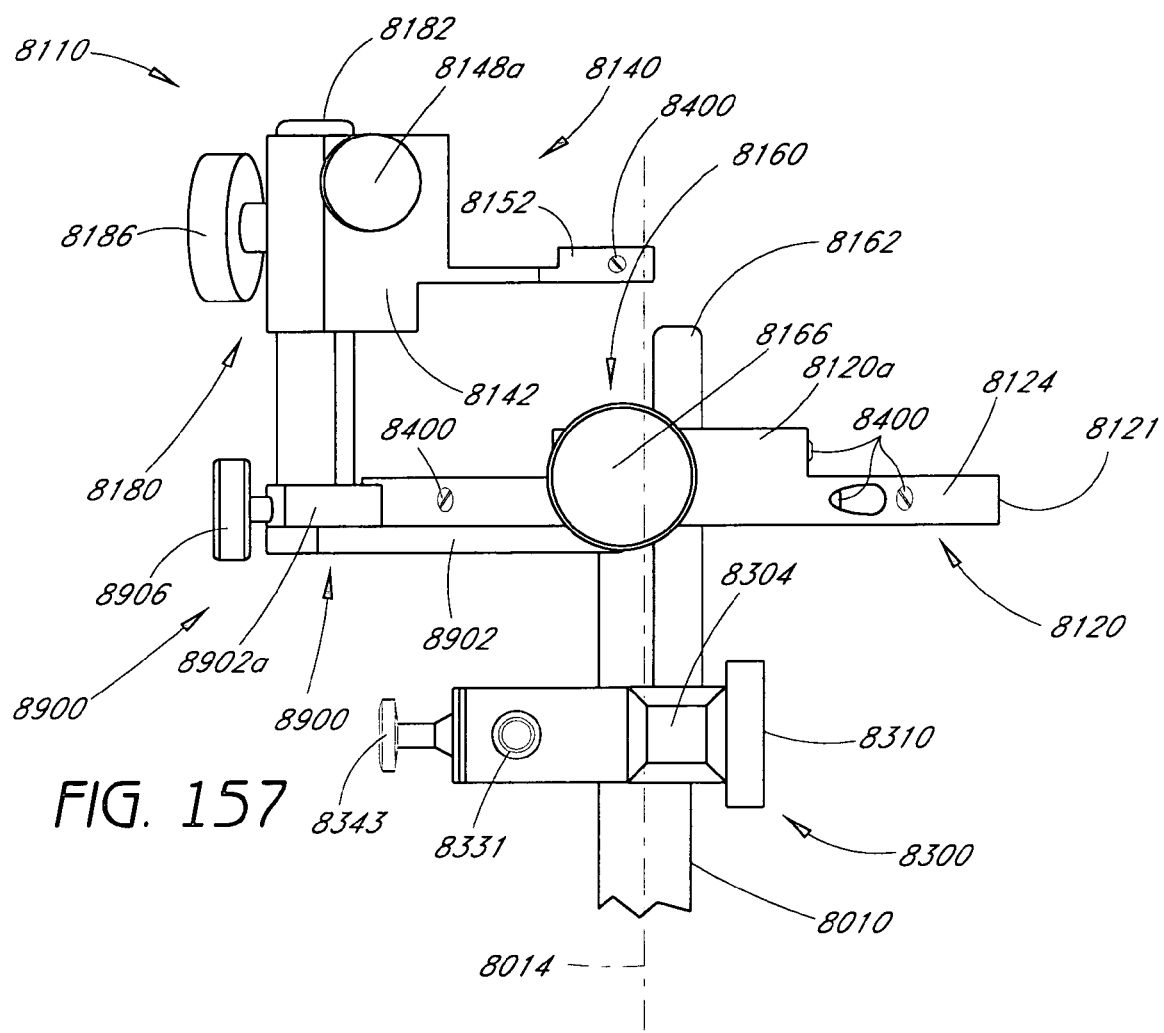

FIG. 157 is a schematic view taken along line 157-157 in FIG. 156.

Figure 158:
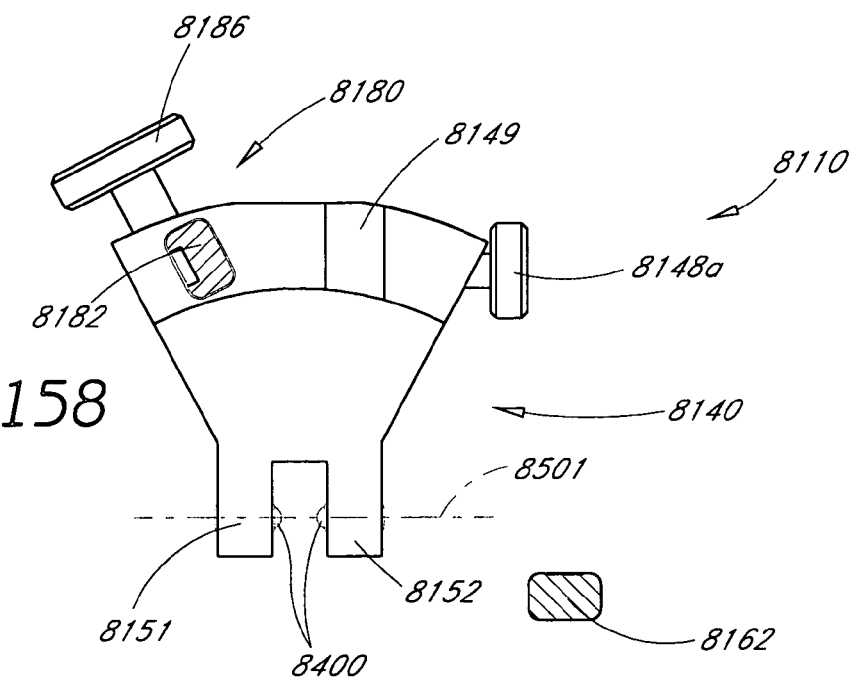

FIG. 158 is a schematic view taken along line 158-158 in FIG. 156 showing part of the support of FIG. 156.

Figure 159:
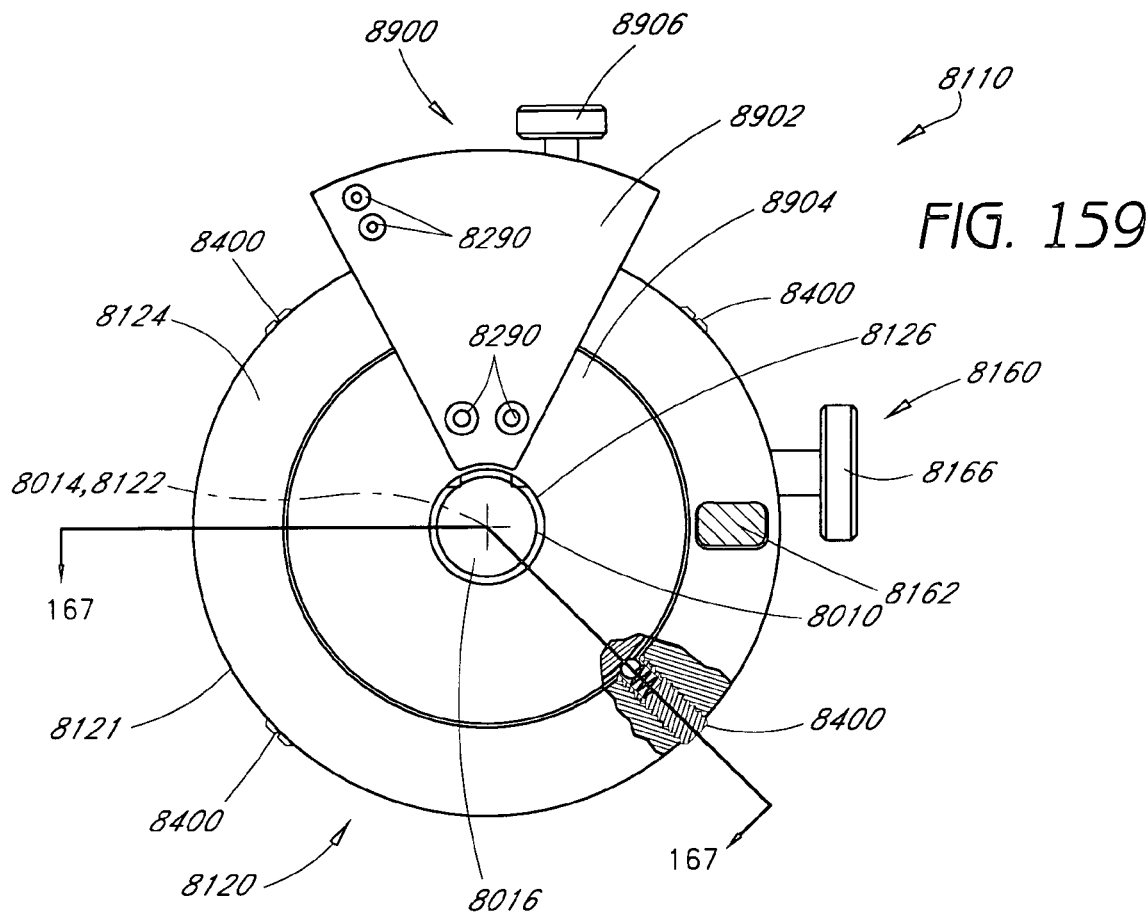

FIG. 159 is a schematic view taken along line 159-159 in FIG. 156 showing part of the support apparatus of FIG. 156.

Figure 160:
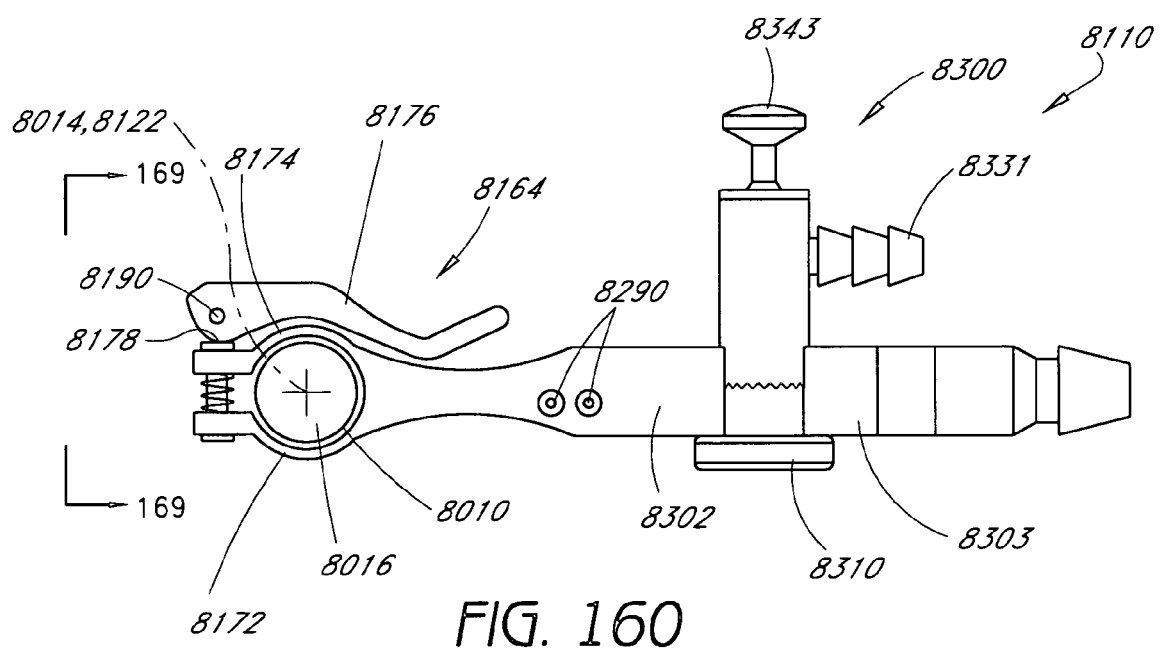

FIG. 160 is a schematic view taken along line 160-160 in FIG. 156 with parts removed.

Figure 161:
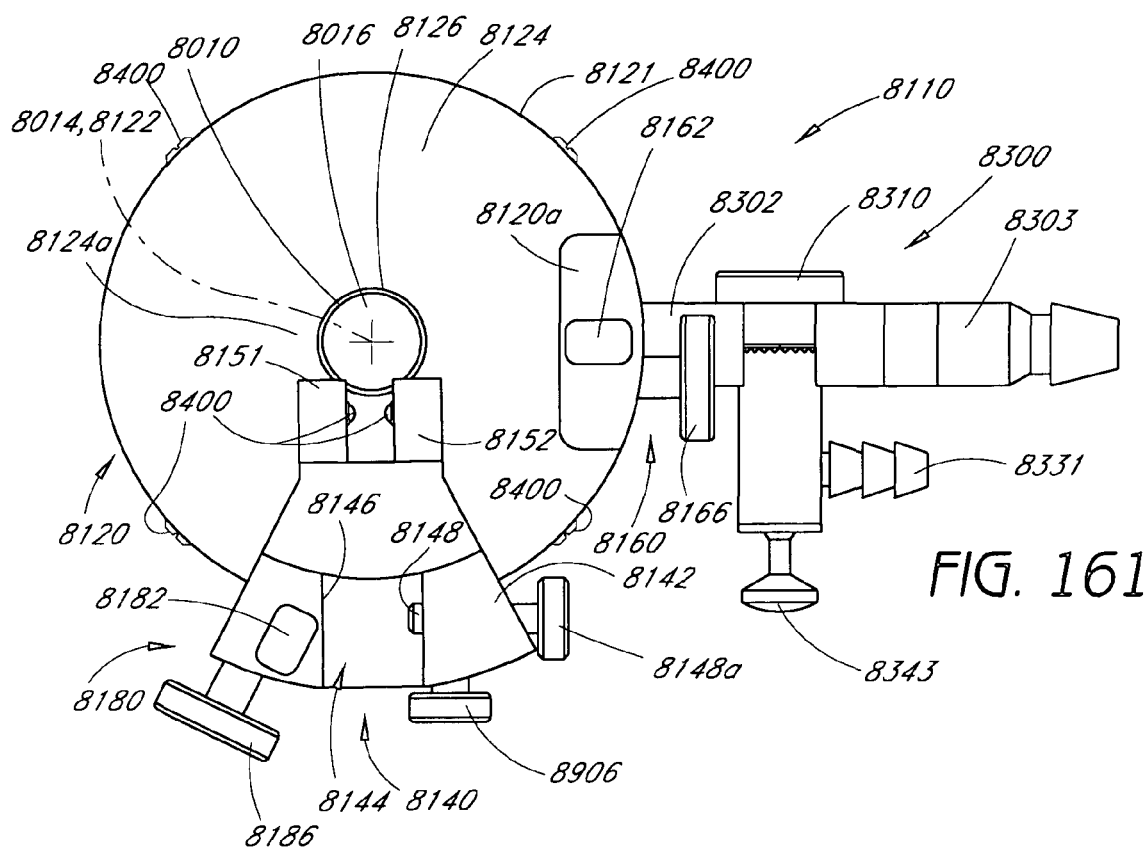

FIG. 161 is a schematic view taken along line 161-161 in FIG. 156.

Figure 162:
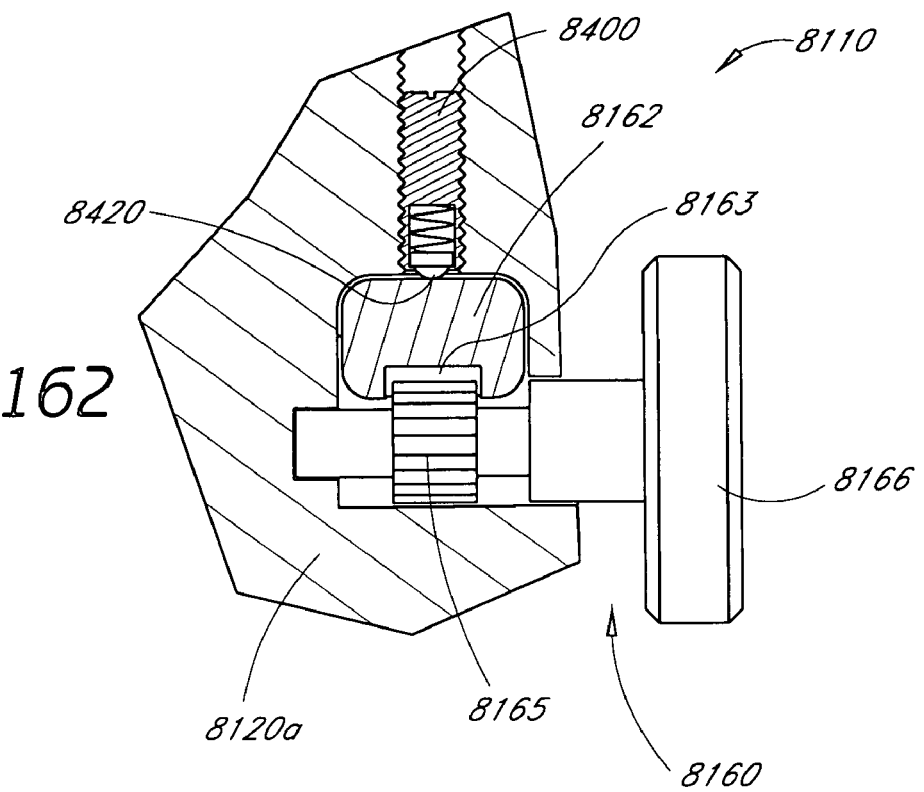

FIG. 162 is a schematic view taken along line 162-162 in FIG. 156 showing part of the support apparatus of FIG. 156.

Figure 163:
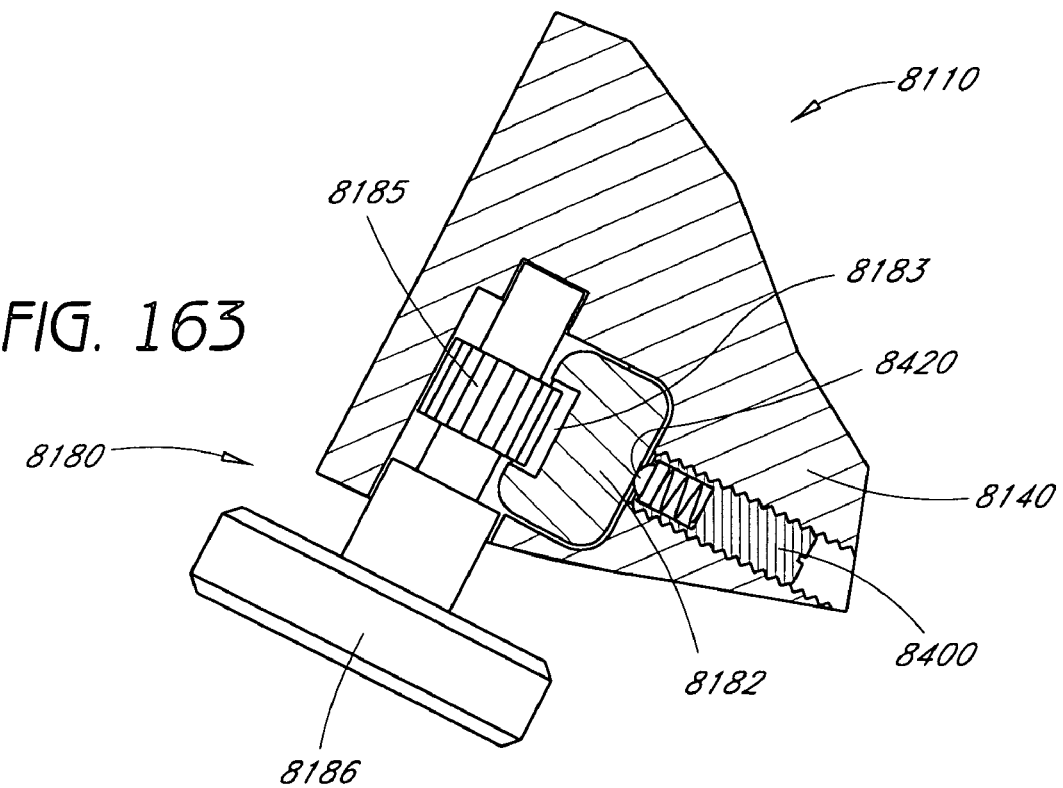

FIG. 163 is a schematic view taken along line 163-163 in FIG. 156 showing part of the support apparatus of FIG. 156.

Figure 164:
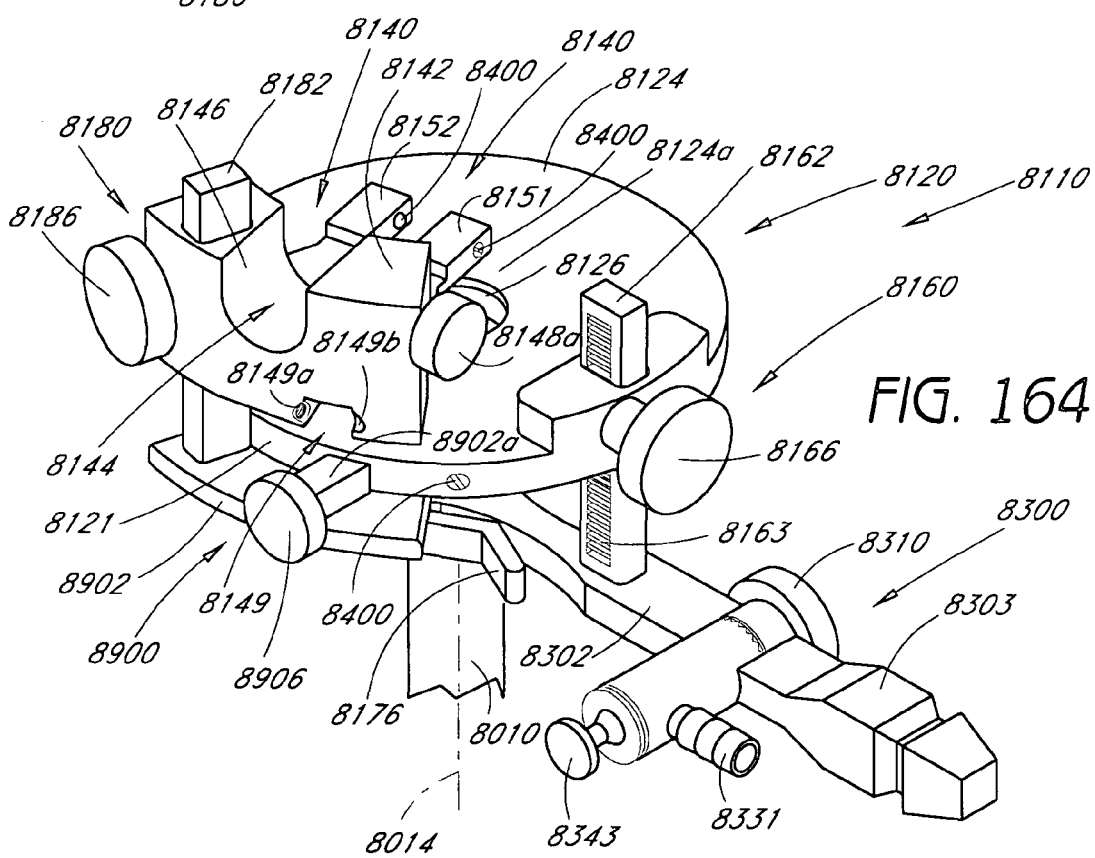

FIG. 164 is a perspective view of the support apparatus of FIG. 156.

Figure 165:
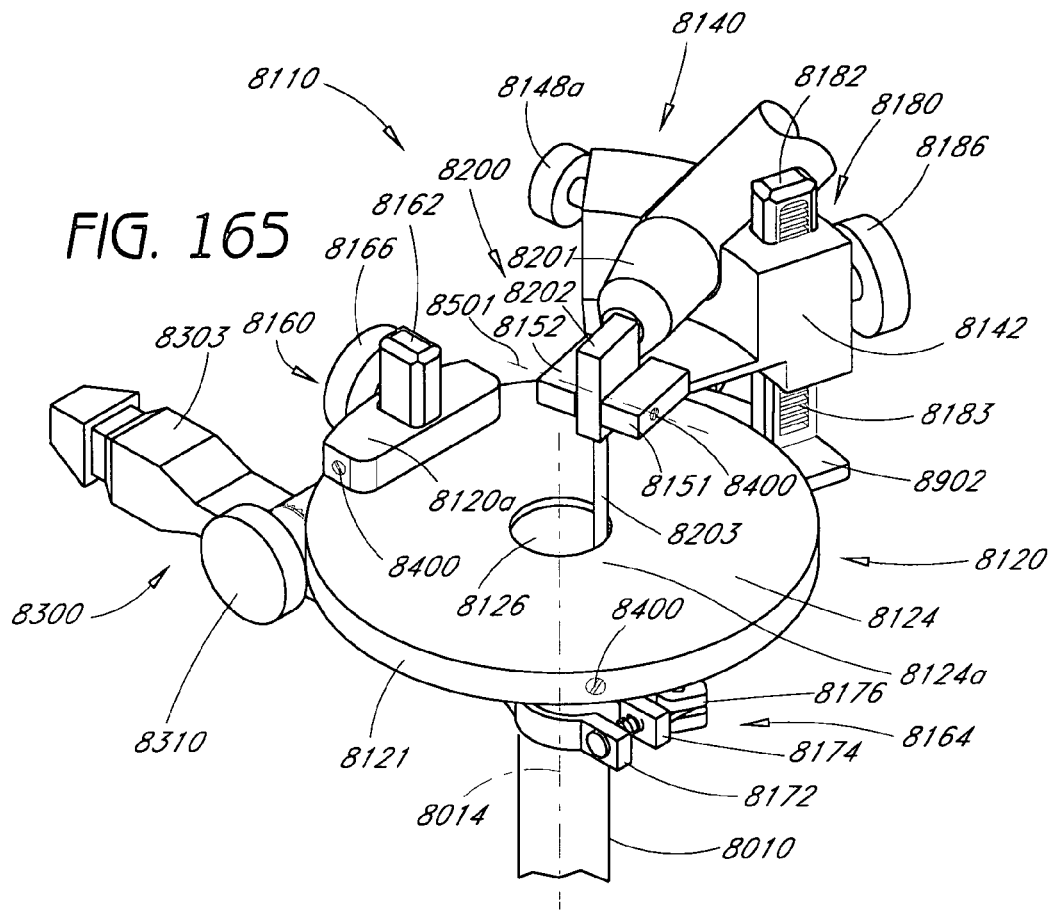

FIG. 165 is a perspective view of the support apparatus of FIG. 156 looking at the support apparatus from an angle different than FIG. 163.

Figure 166:
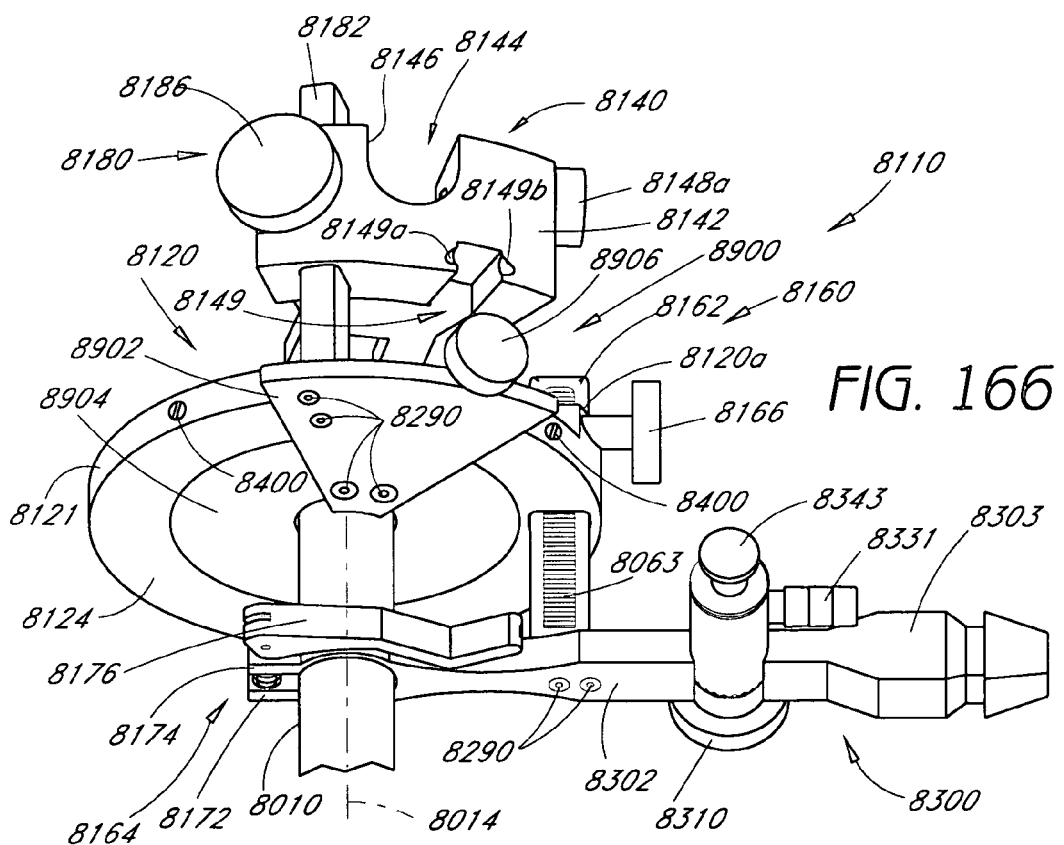

FIG. 166 is a perspective view of the support apparatus of FIG. 156 looking at the support apparatus from an angle different than FIGS. 164 and 165.

Figure 167:
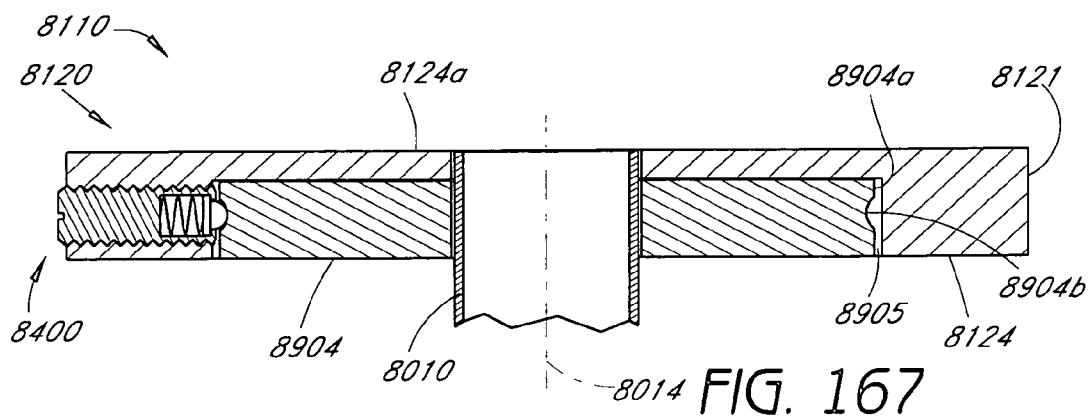

FIG. 167 is a sectional view taken approximately along line 167-167 of FIG. 159.

Figure 168:
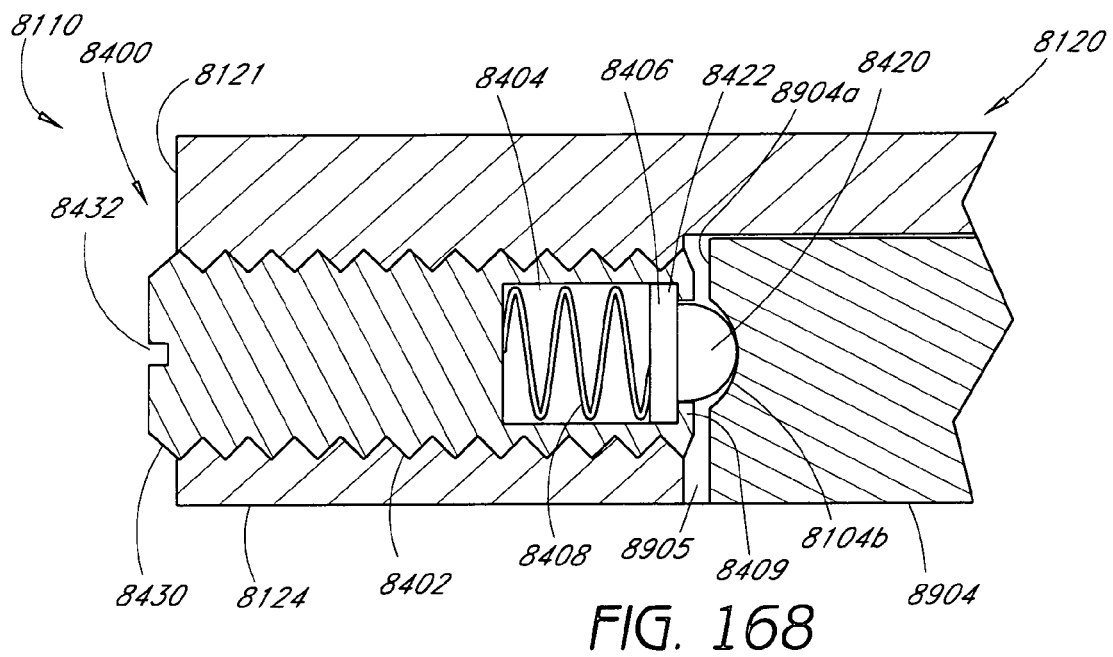

FIG. 168 is an enlarged view of a part of FIG. 167.

Figure 169:
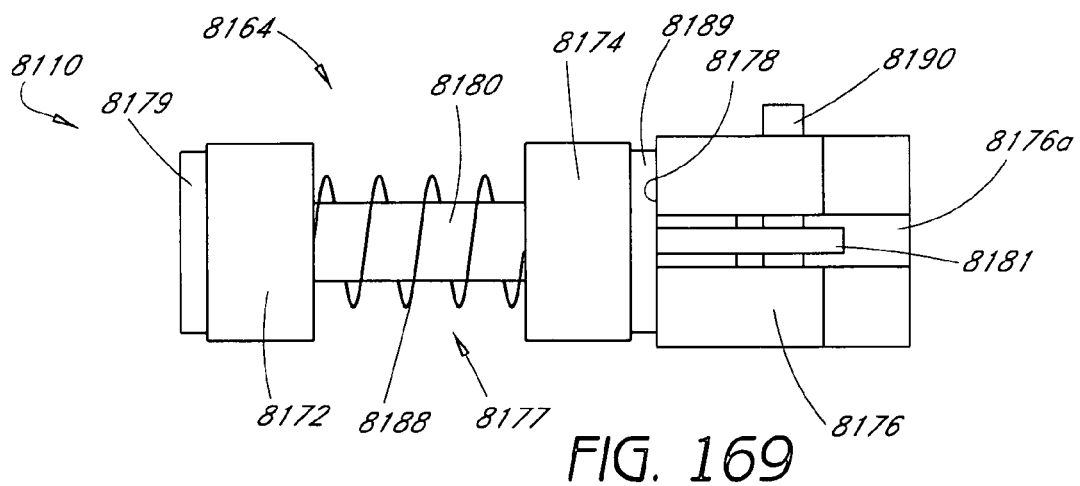

FIG. 169 is a schematic view taken along line 169-169 in FIG. 160 with parts removed.

FIG. 170 is a view further illustrating parts shown in FIG. 160.

FIG. 171 is a view taken approximately along line 171-171 of FIG. 170.

FIG. 172 is a schematic view showing the support apparatus with an associated known mechanical arm.

Figure 173:
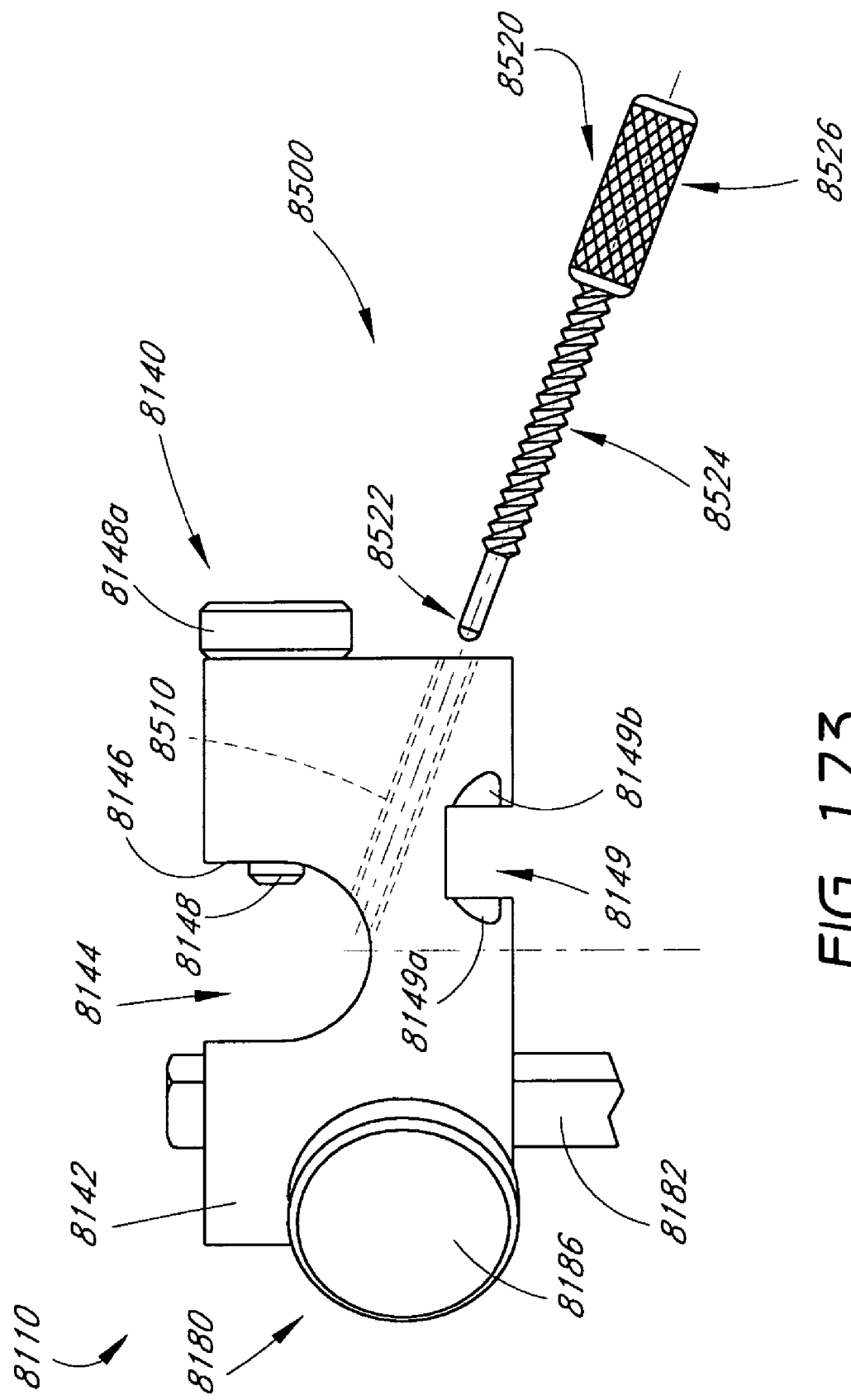

FIG. 173 is a schematic view of another feature of part of the support apparatus of FIG. 156.

Figure 174:
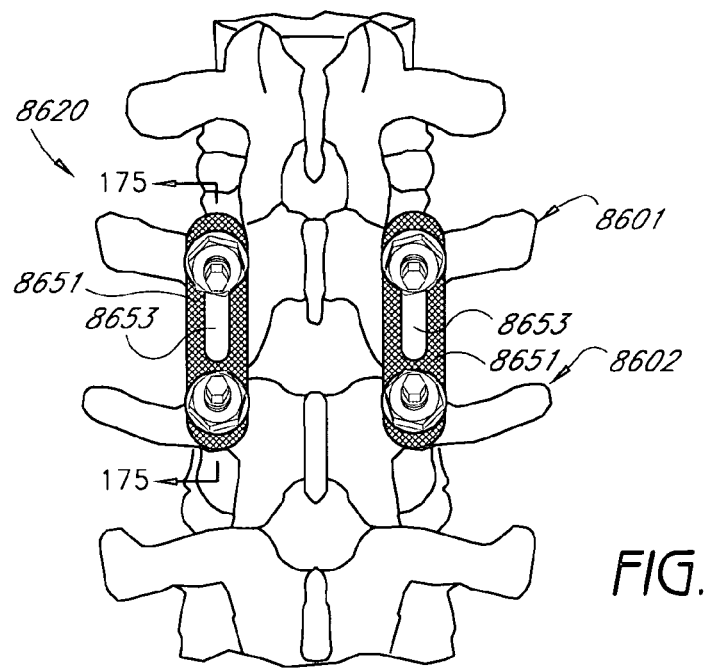

FIG. 174 is a schematic view of a fixation assembly attached to vertebrae of a patient.

Figure 175:
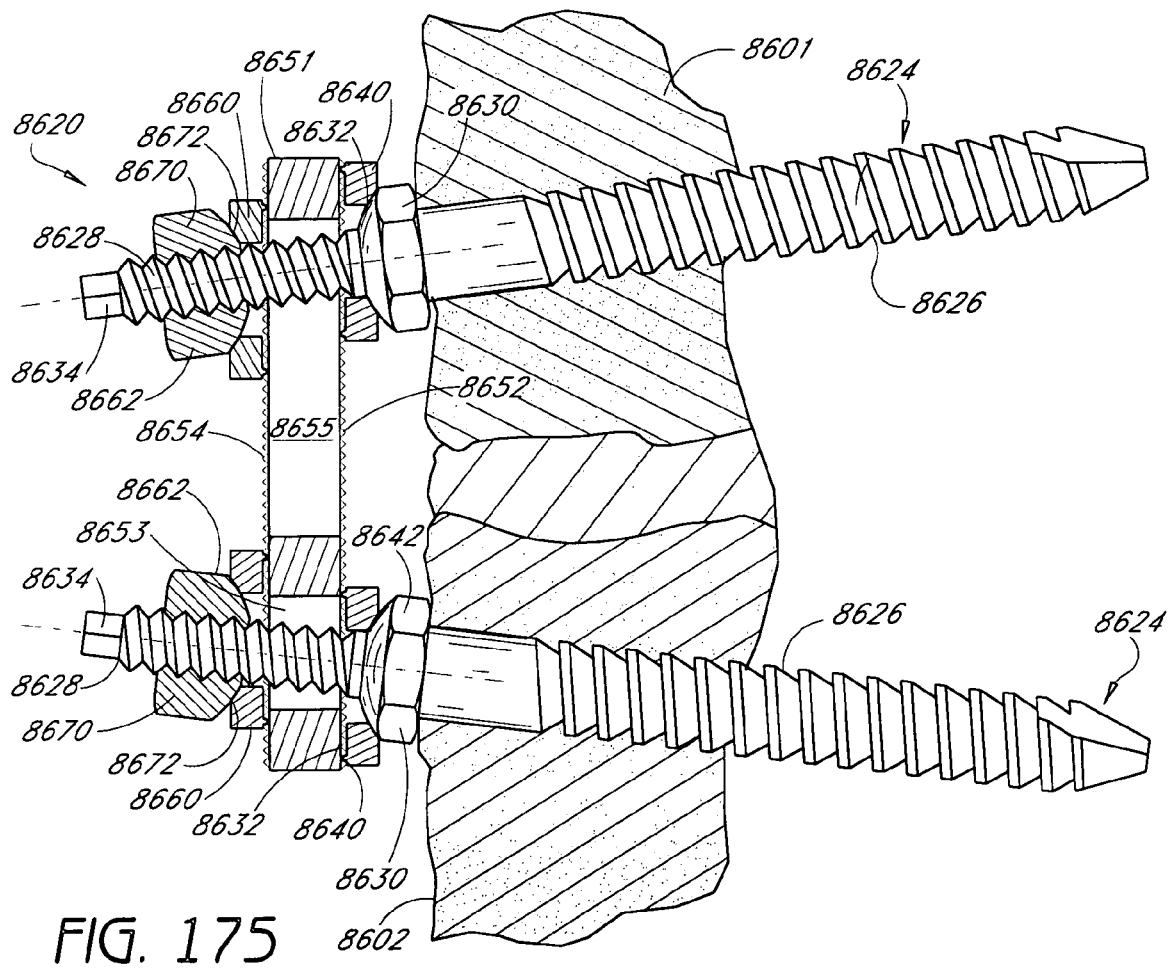

FIG. 175 is a schematic view taken along line 175-175 of FIG. 174.

FIG. 176 is an exploded schematic view of part of the assembly of FIG. 174.

FIG. 177 is a schematic view of another fixation assembly attached to vertebrae of a patient.

FIG. 178 is a schematic view taken along line 178-178 of FIG. 177.

FIG. 179 is an exploded schematic view of part of the assembly of FIG. 177.

Figures 180, 181:
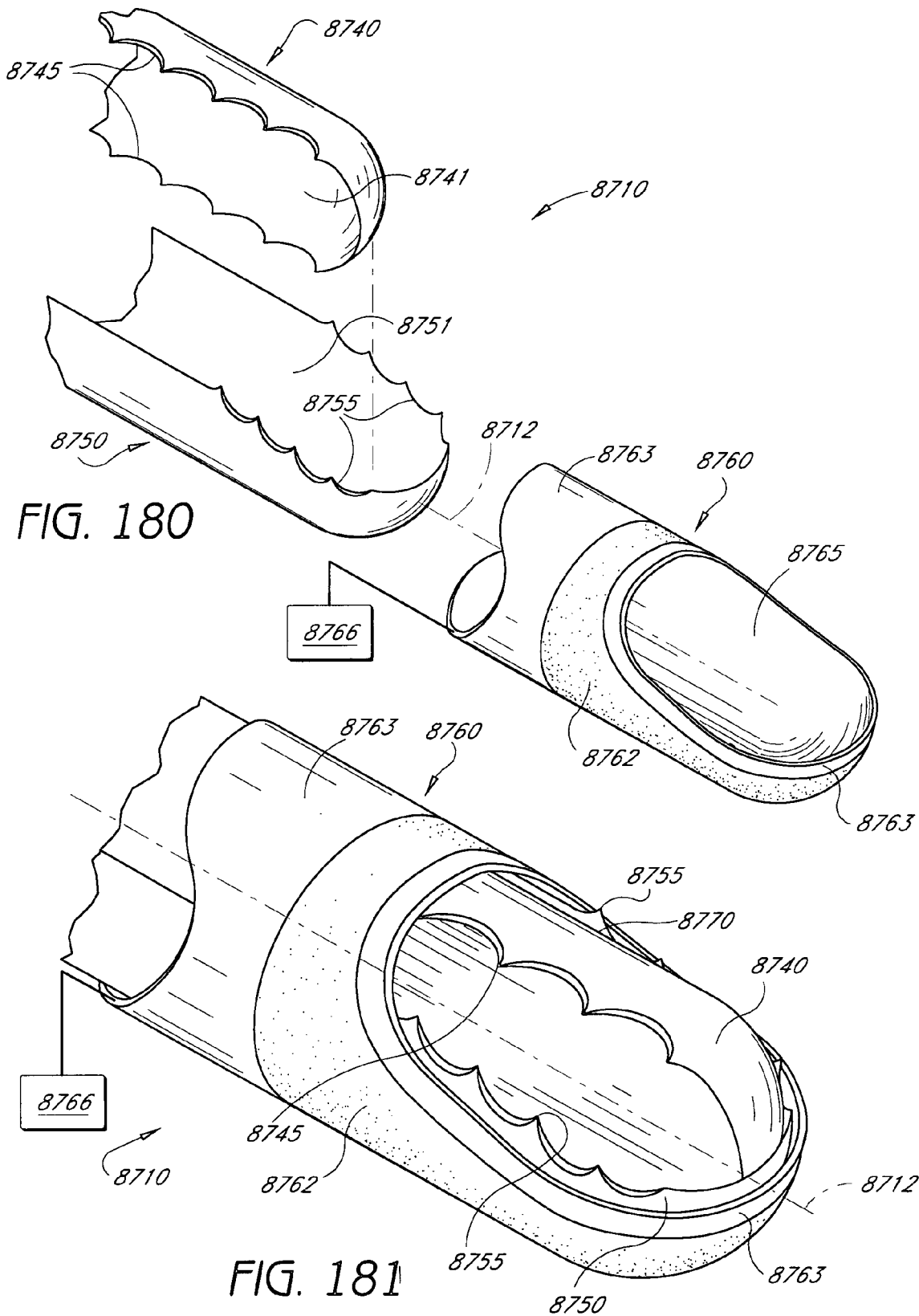

FIG. 180 is an exploded view of part of a cutting tool according to another embodiment.

FIG. 181 is an assembled view of part of the cutting tool of FIG. 180.

Figure 182:
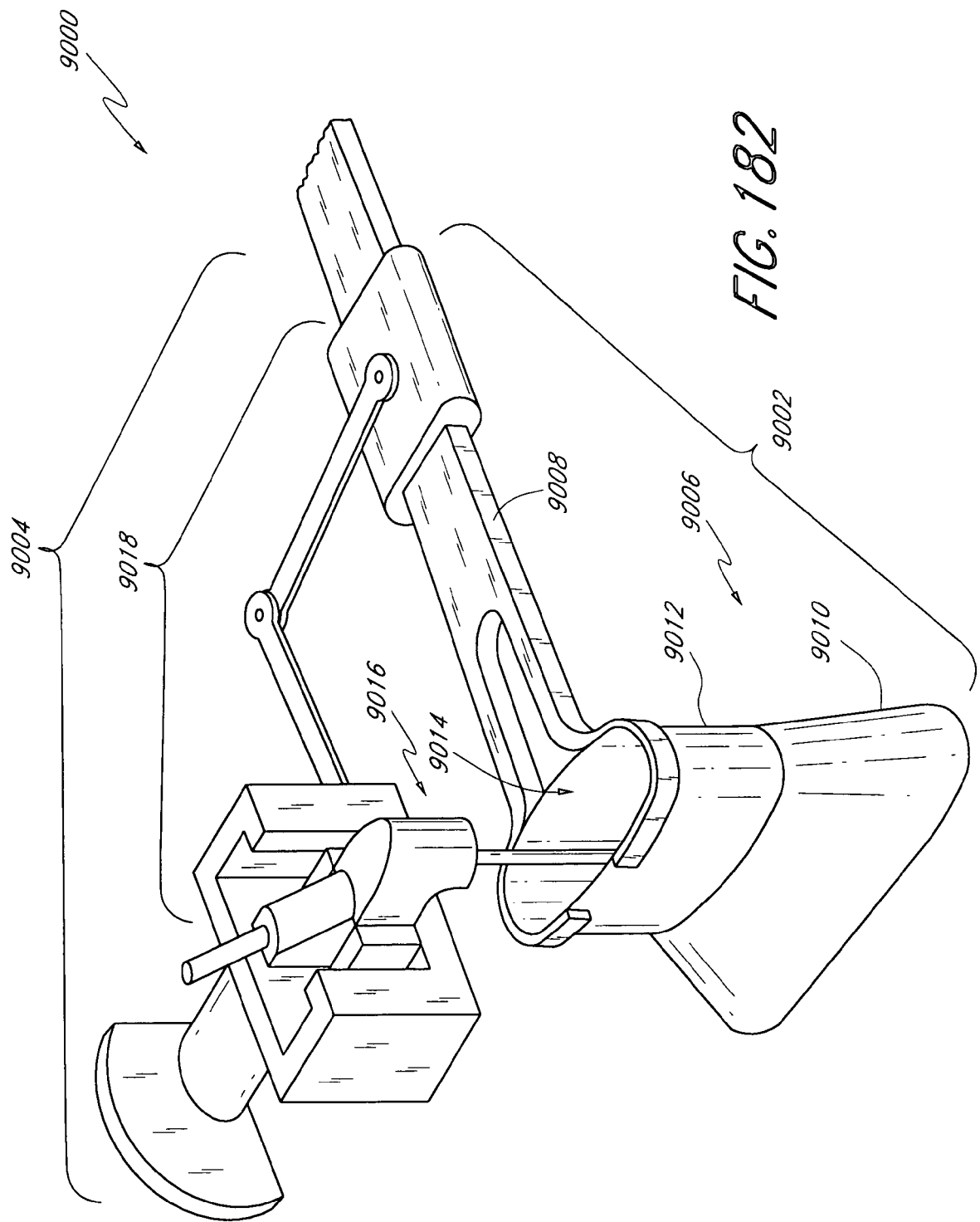

FIG. 182 is a perspective view of one embodiment of a surgical assembly.

Figure 183:
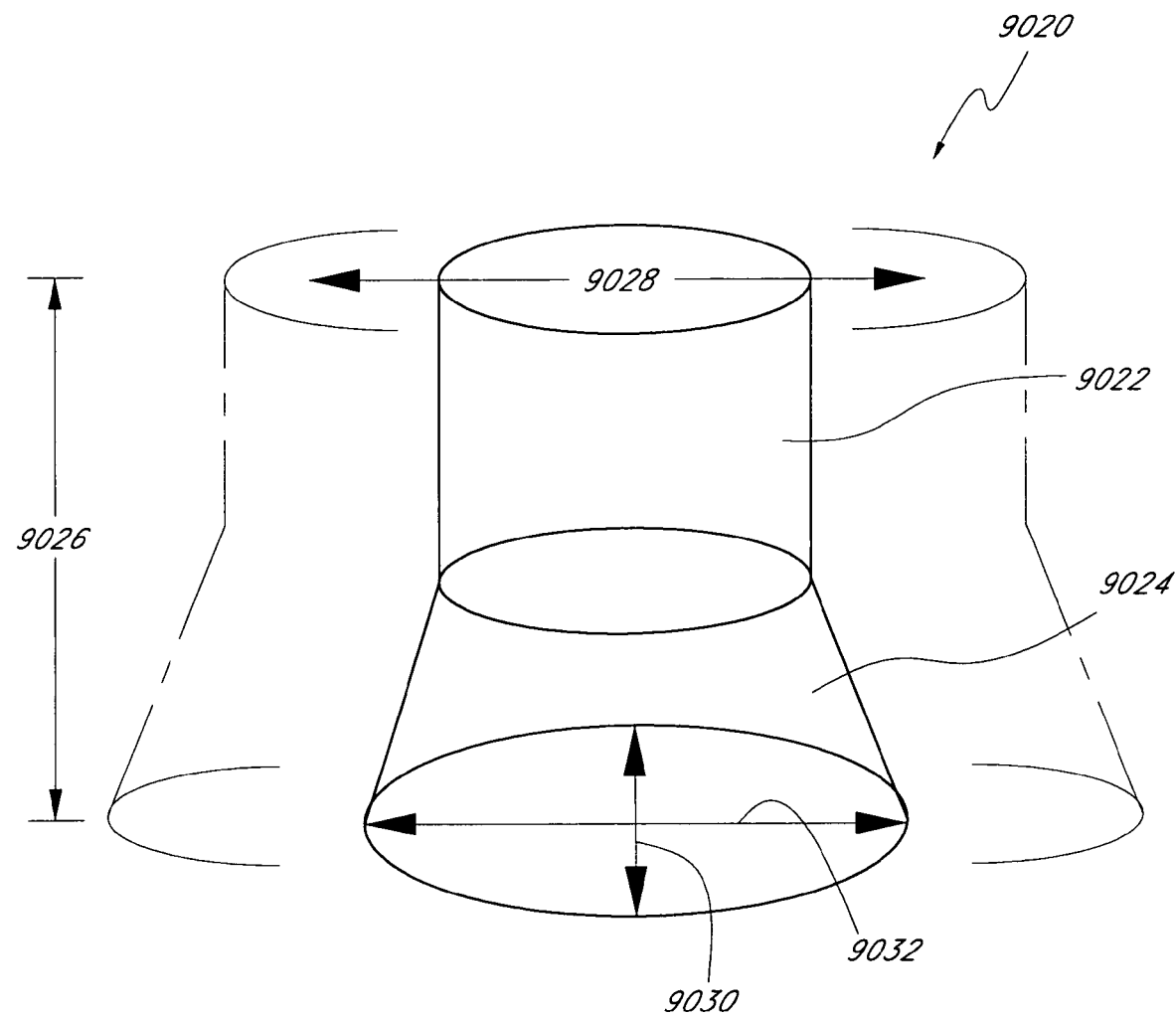

FIG. 183 is a schematic view of an expandable access device in a contracted state and in an expanded state (in phantom).

Figure 184:
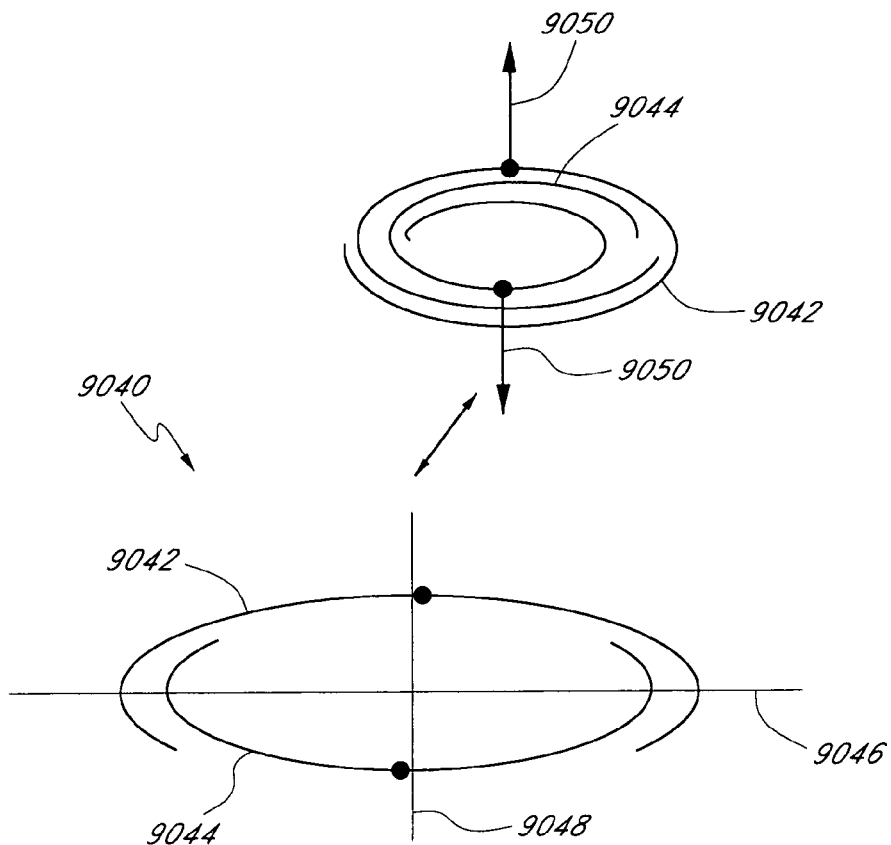

FIG. 184 is a bottom view of a distal portion of one embodiment of an access device illustrating a first overlapping arrangement.

Figure 185:
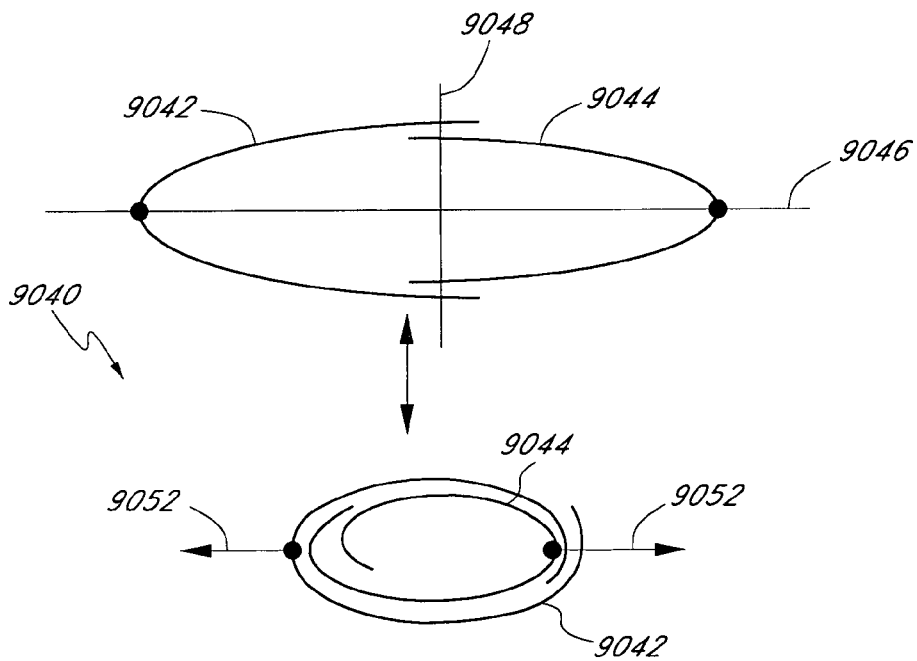

FIG. 185 is a bottom view of a distal portion of another embodiment of an access device illustrating a second overlapping arrangement.

Figure 186:
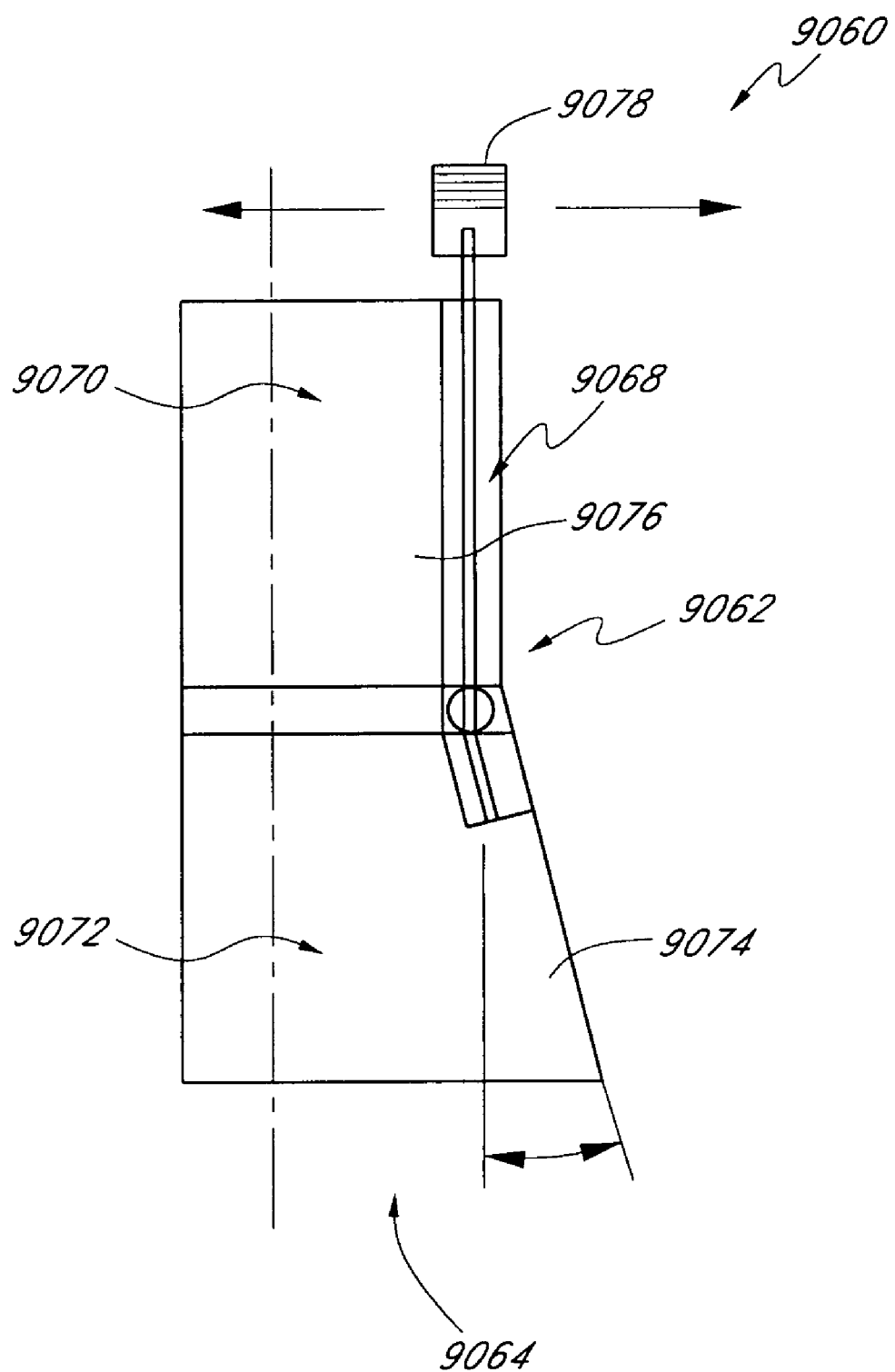

FIG. 186 is a schematic view of another embodiment of an expandable access device having an expansion mechanism.

FIG. 187 is a plan view of a proximal portion of an access device, the distal portion shown schematically.

FIG. 188 is a perspective view of the proximal portion of the access device of FIG. 187.

FIG. 189 schematically illustrates one approach to expanding or reducing the cross-sectional size of the proximal portion of the access device of FIG. 187.

Figure 190:
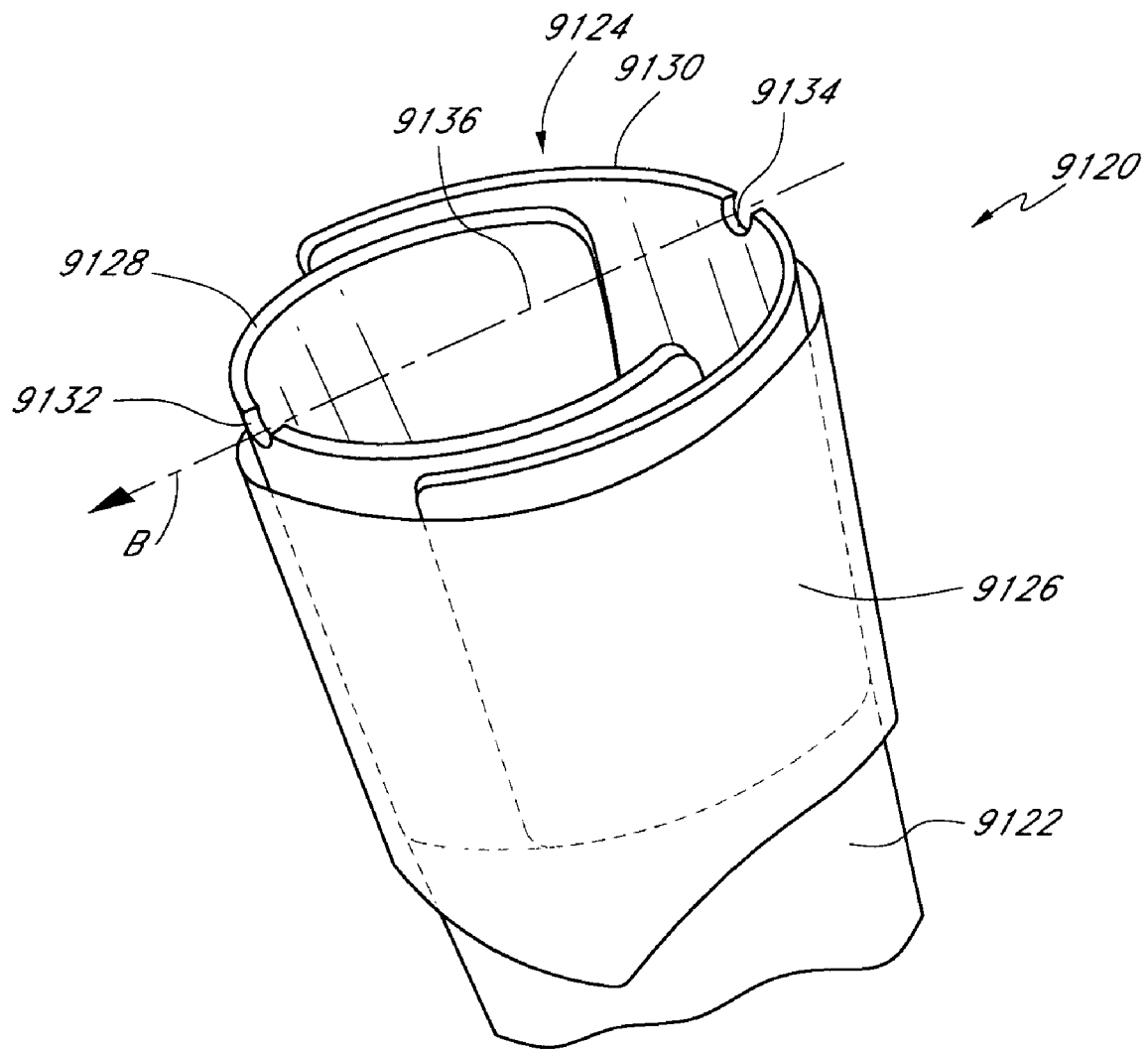

FIG. 190 is a perspective view of one embodiment of an access assembly, showing a proximal portion thereof.

Figure 191:
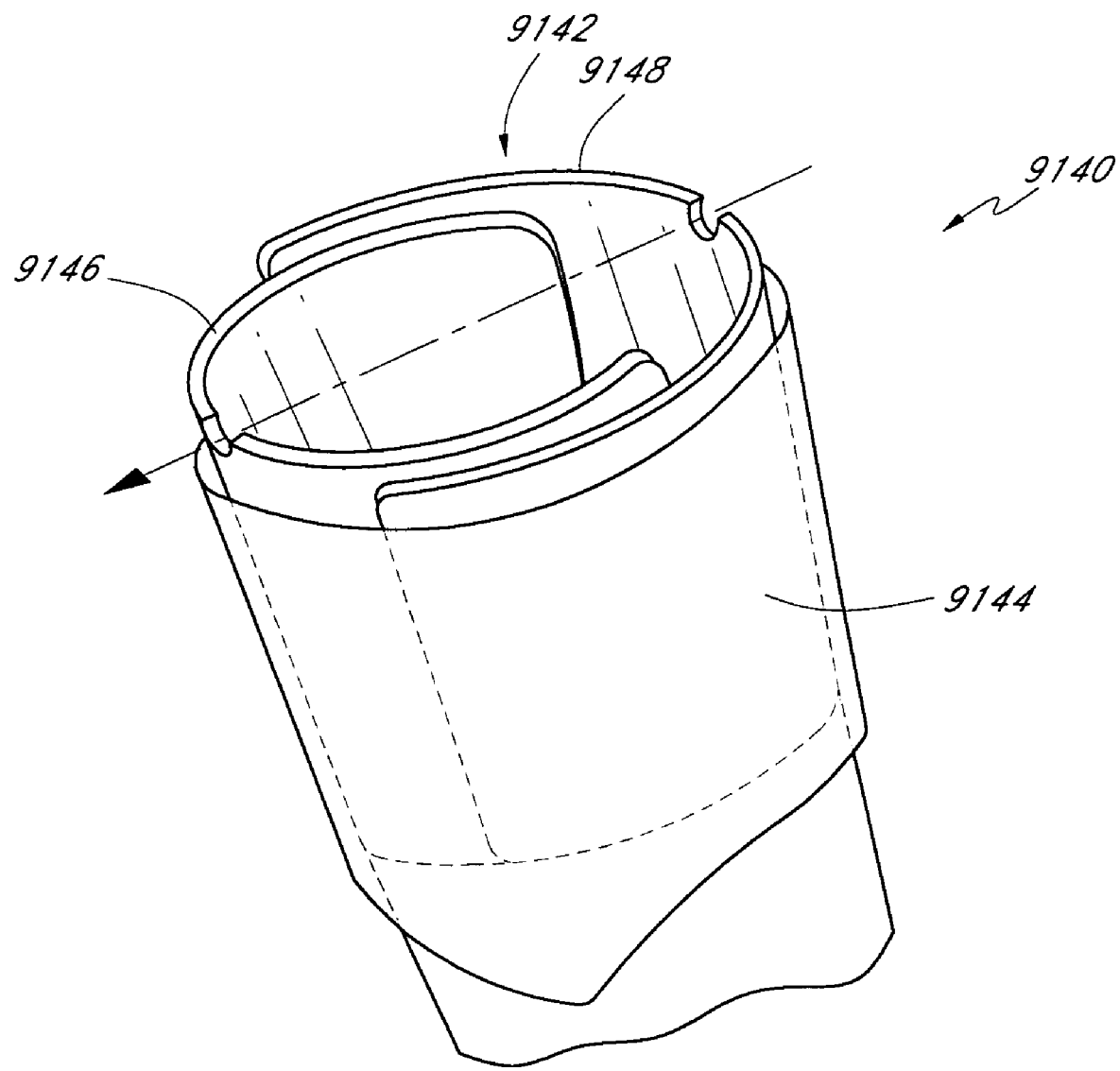

FIG. 191 is a perspective view of another embodiment of an access assembly, showing a proximal portion thereof with a stretchable cover.

Figure 192:
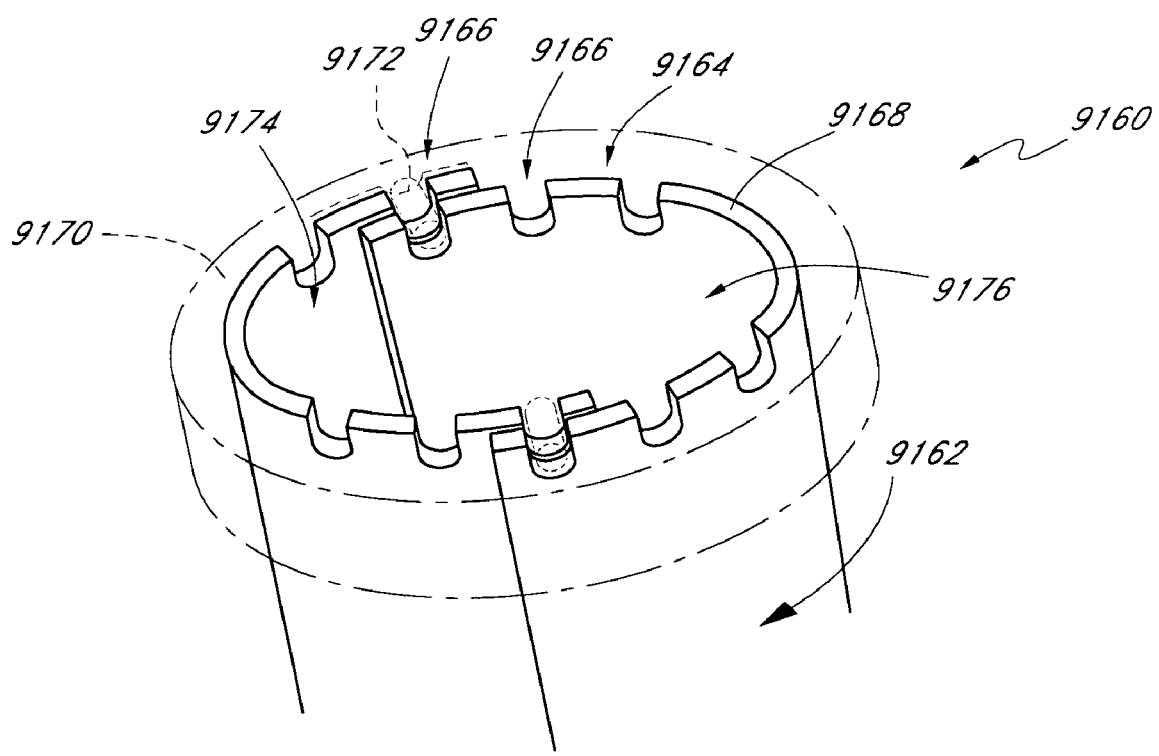

FIG. 192 is a perspective view of a proximal end of a proximal portion of one embodiment of an access device, the proximal end having a plurality of notches, with a portion of an access device mounting fixture shown in phantom.

FIG. 193 is a perspective proximal end view of an access device having a pivot rivet.

FIG. 194 is a perspective view of a proximal portion of one embodiment of an access device having a ratchet arrangement.

FIG. 195 is a partial top schematic view of the access device of FIG. 194.

FIG. 196 is a perspective view of another embodiment of an access device, which includes an expandable proximal portion and an expandable distal portion.

FIG. 197 is a plan view of one variation of the access device of FIG. 196, illustrating a first configuration for inserting the access device into a patient.

FIG. 198 is a plan view of another variation of the access device of FIG. 196, which has actuating rods located on the proximal portion.

FIG. 199 illustrates another embodiment of an access device in a low profile configuration, having an expandable distal portion with deployment teeth to fix the extent of the expansion of the distal portion.

FIG. 200 is a side view of the access device of FIG. 199 in an expanded configuration.

FIG. 201 includes a plurality of views illustrating the expansion of the access device of FIG. 199.

Figure 202:
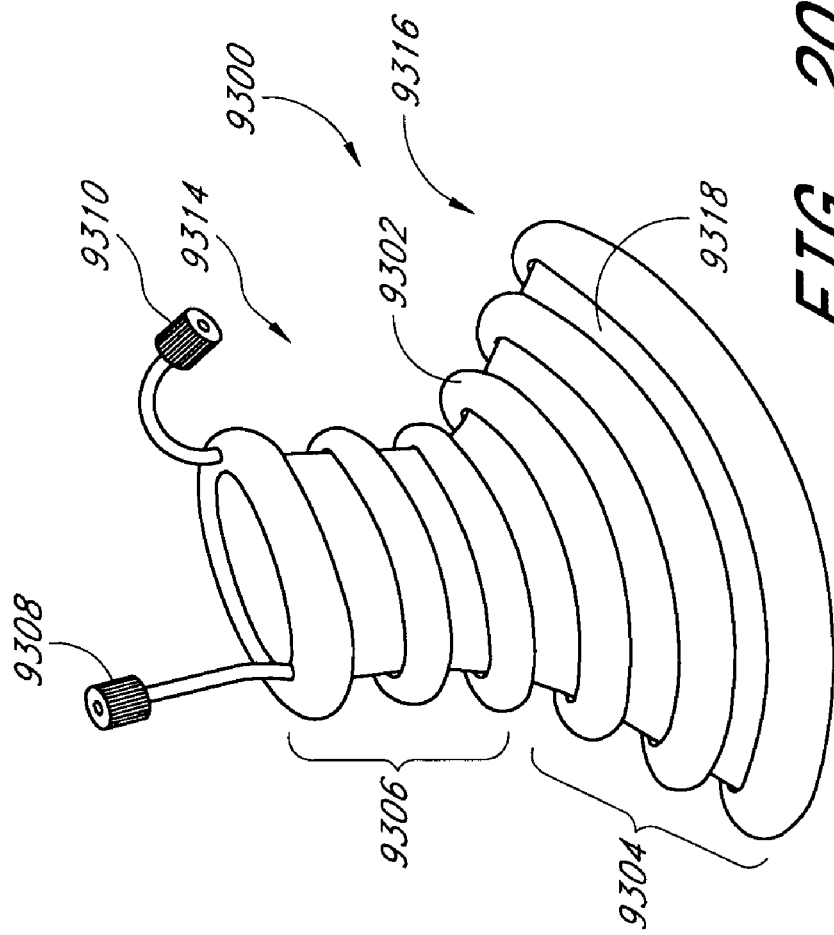

FIG. 202 illustrates one embodiment of an access device having an inflatable portion.

Figure 203:
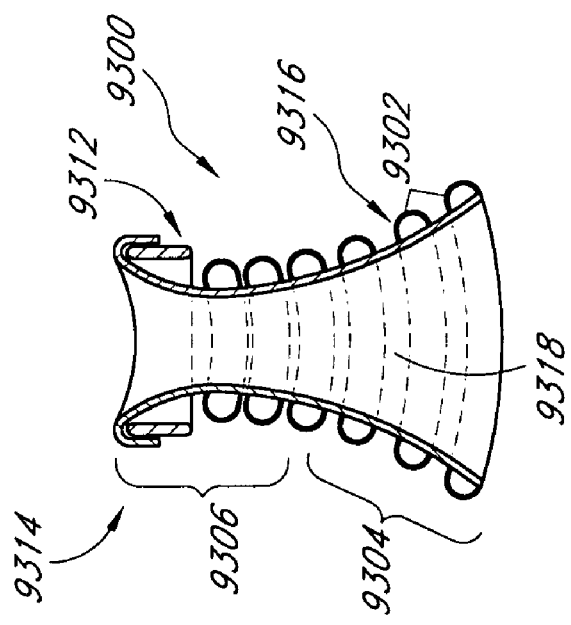

FIG. 203 is a cross section view of the access device of FIG. 202.

Figure 204:
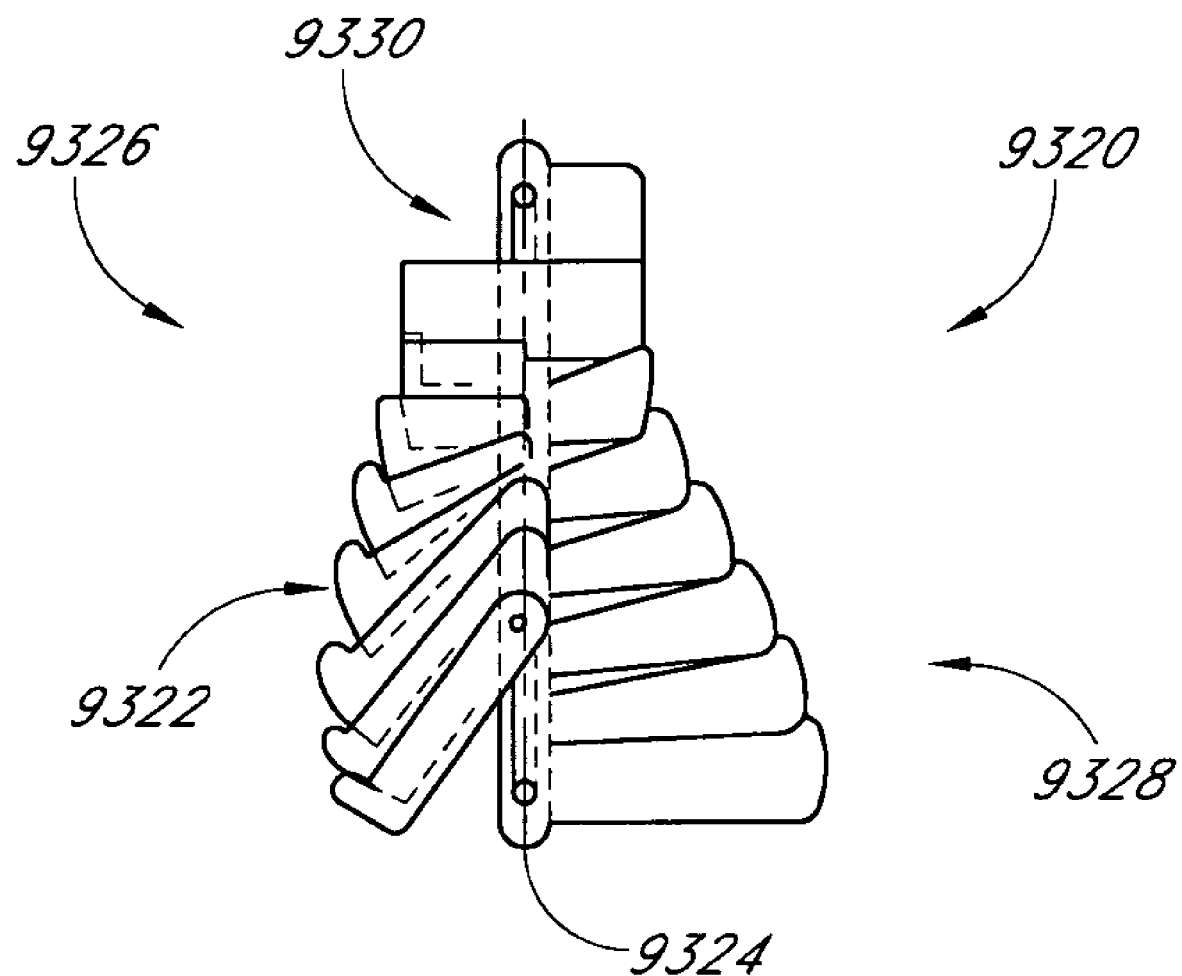

FIG. 204 is a plan view of another embodiment of an access device with interleaved semi-circular bands that can pivot in a track.

Figure 205:
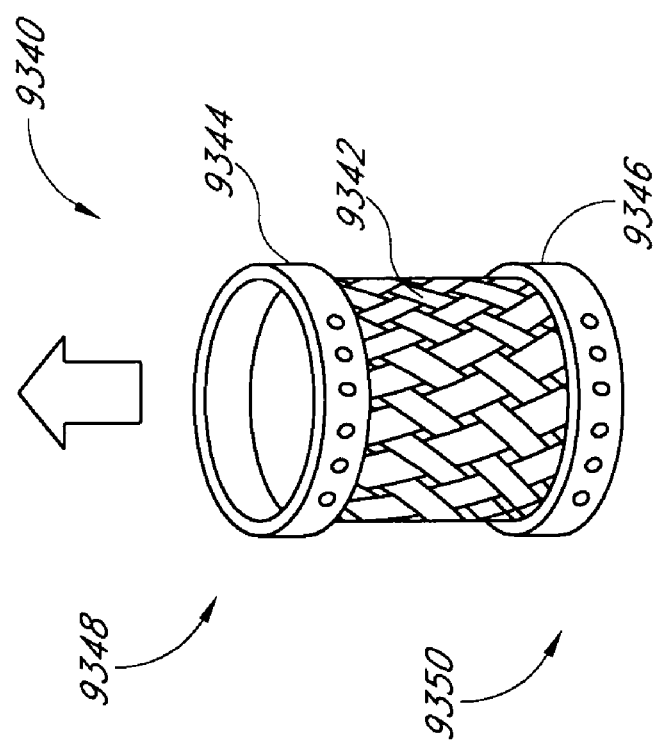

FIG. 205 is another embodiment of an access device that has a thin stainless steel weave and an elastomeric overmold, the access device being expandable upon longitudinal compression.

Figure 206:
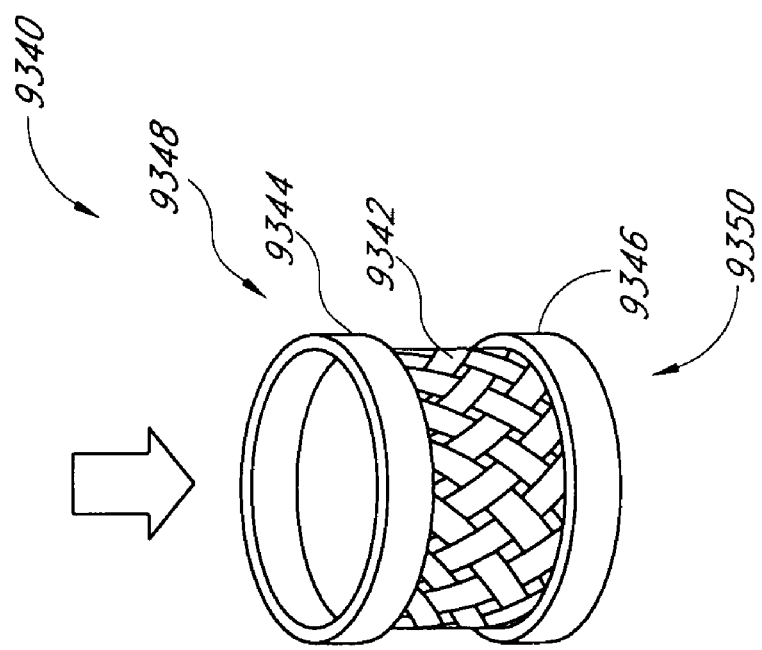

FIG. 206 is a side view of the access device of FIG. 205 in the expanded configuration.

Figure 207:
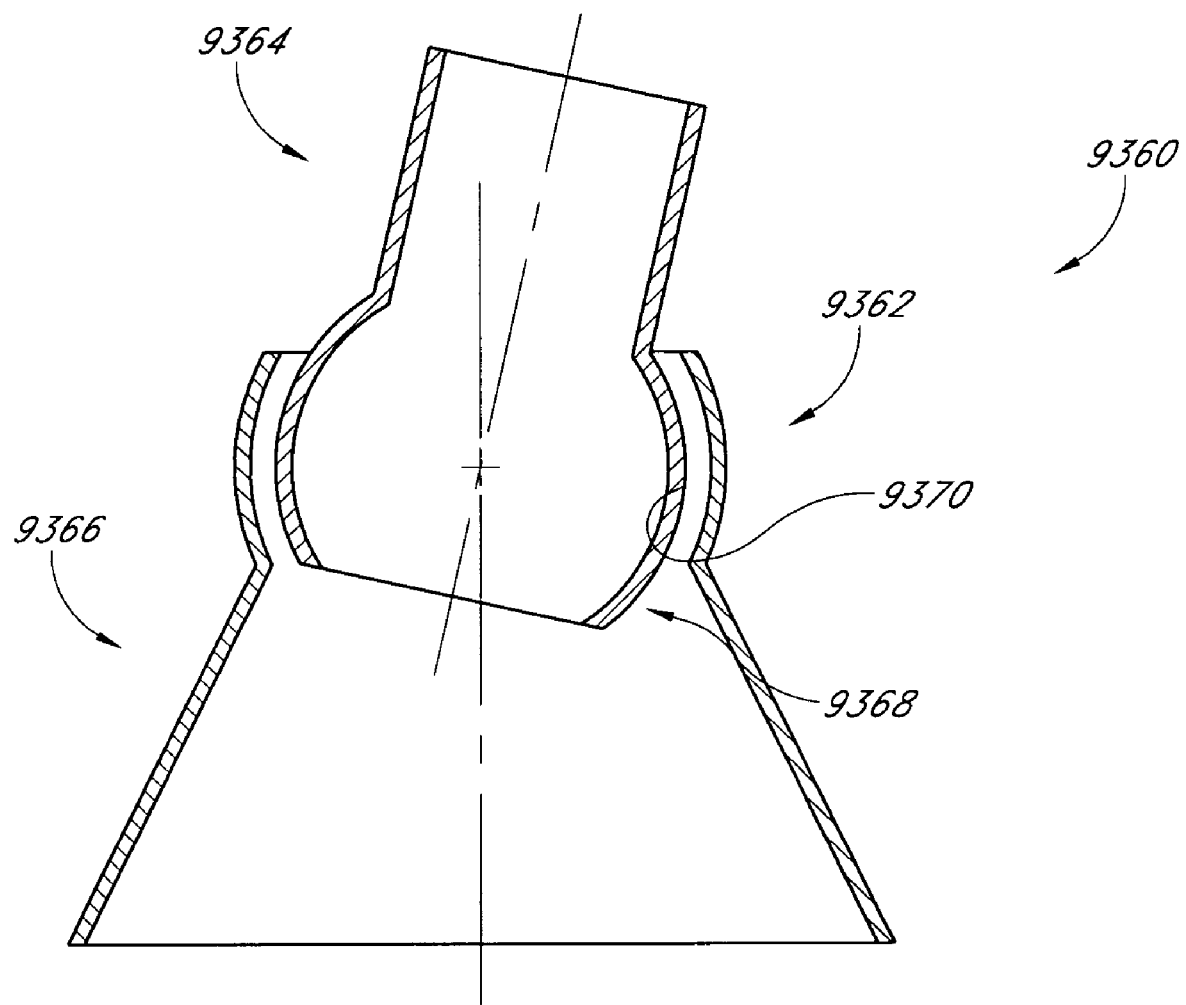

FIG. 207 is a cross-sectional view of another embodiment of an access device having a partial ball joint located between a proximal and a distal portion.

Figure 208:
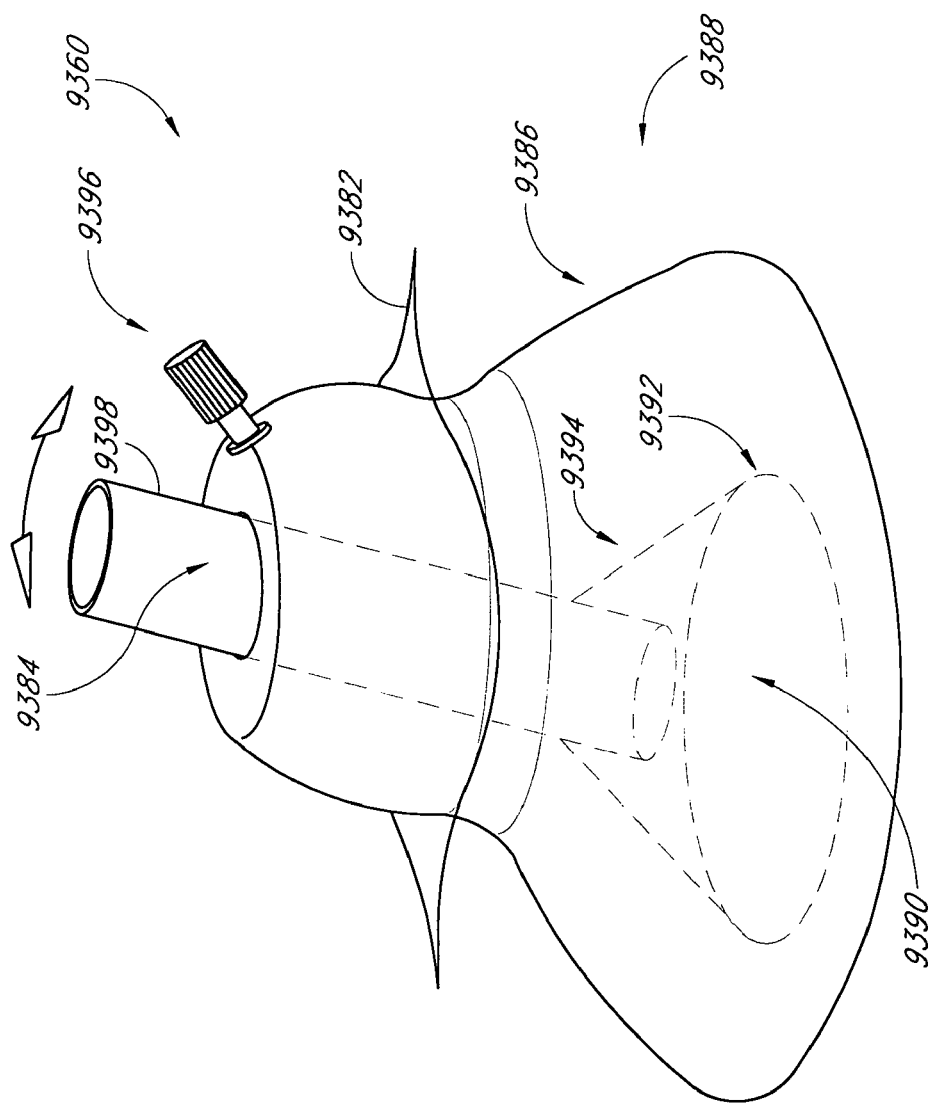

FIG. 208 is a schematic view of another embodiment of an inflatable access device that is shown applied across a patient's skin, the access device having a positionable passageway.

Figure 209:
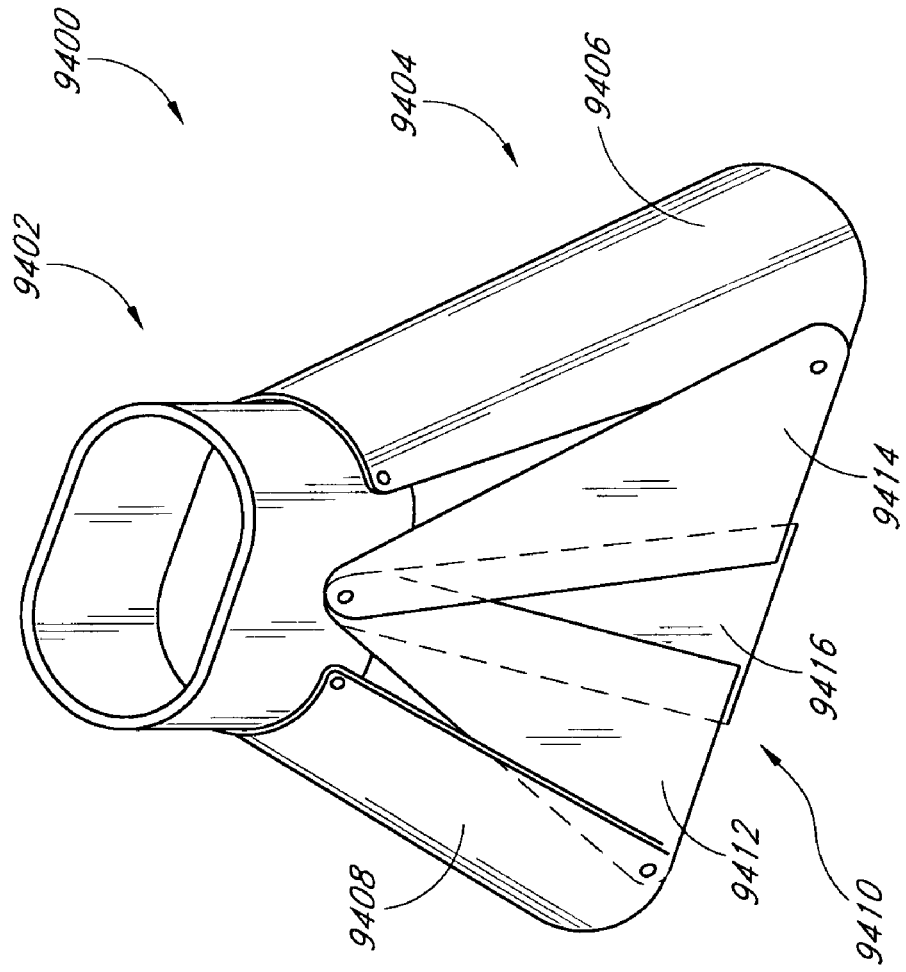

FIG. 209 is a perspective view of another embodiment of an access device having an oval proximal end and three leaves.

Figure 210:
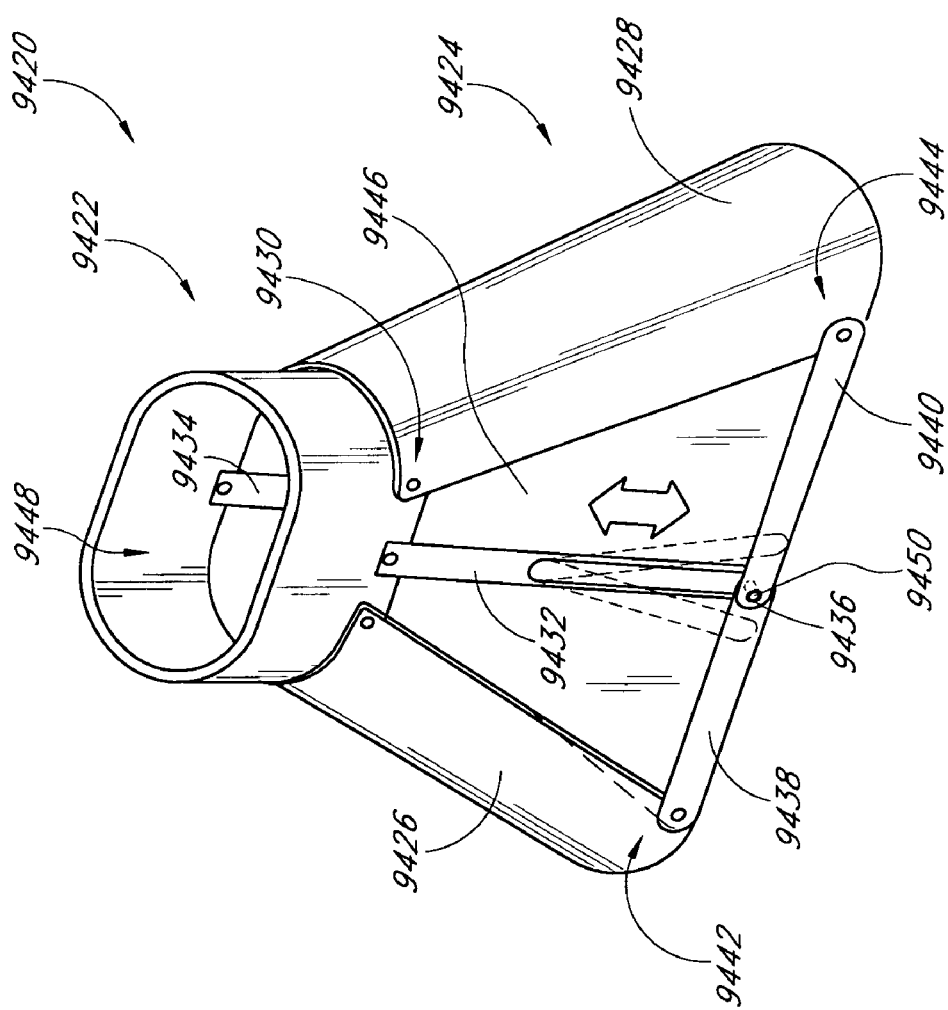

FIG. 210 is a perspective view of another embodiment of an access device having a flexible mesh, the access device being expandable.

Figure 211:
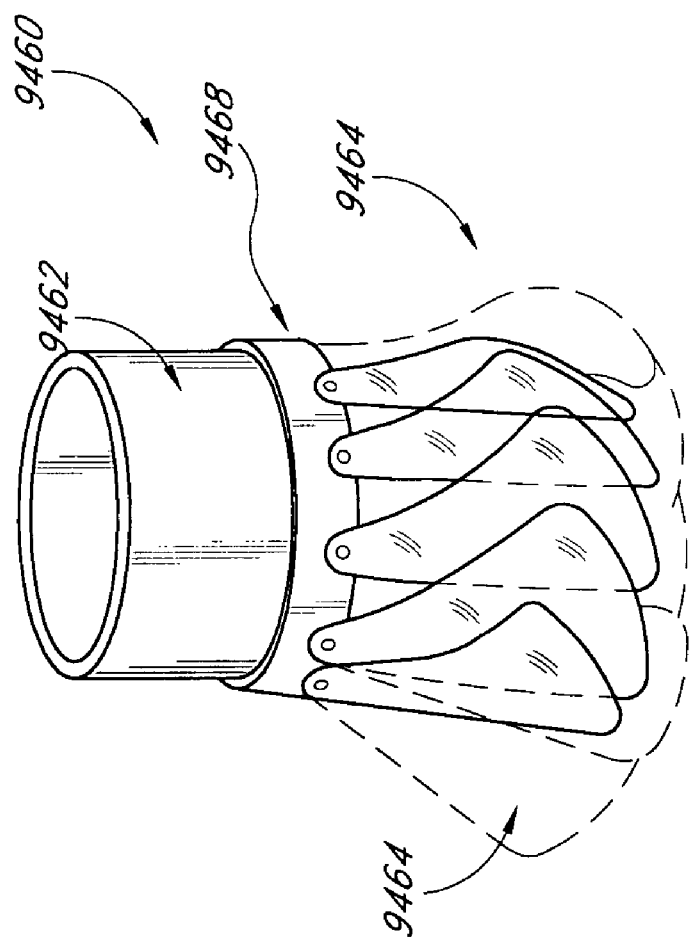

FIG. 211 is a perspective view of an access device having a curvilinear proximal portion (e.g., round or oval in transverse cross-section), a distal portion including elongate elements that fan-out to an enlarged distal end, and an intermediate portion located between the proximal end and the distal end.

Figure 212:
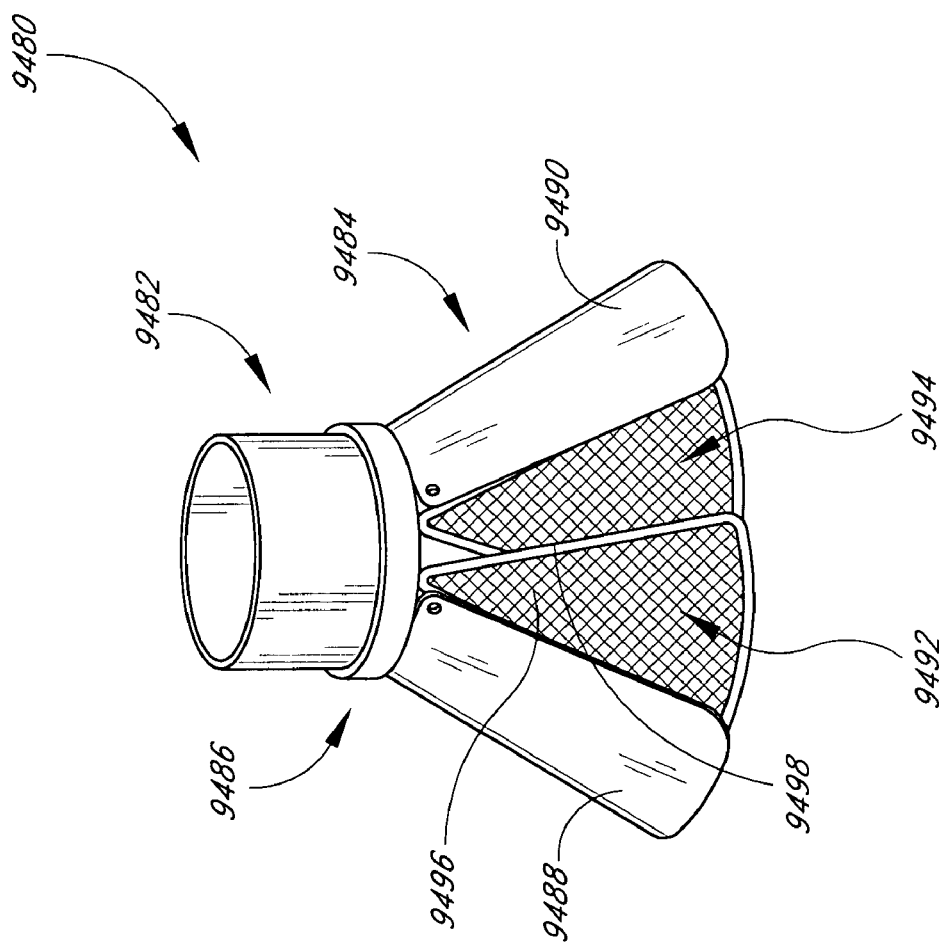

FIG. 212 is a perspective view of an access device having an expandable distal portion including elongate members with mesh material and a movable proximal portion, shown in the expanded condition.

Figure 213:
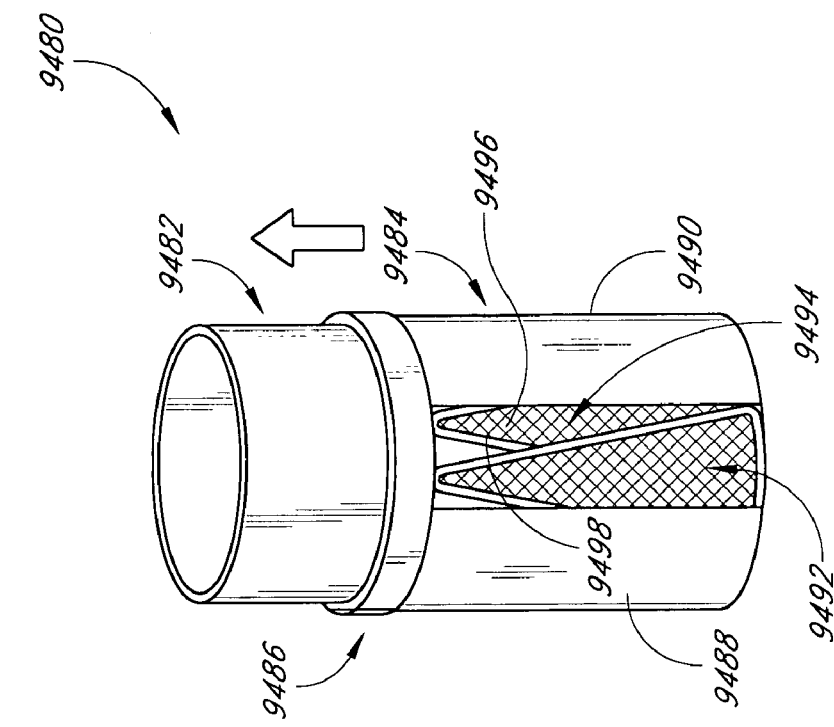

FIG. 213 is a perspective view of the access device of FIG. 212, shown in a low profile configuration.

Figure 214:
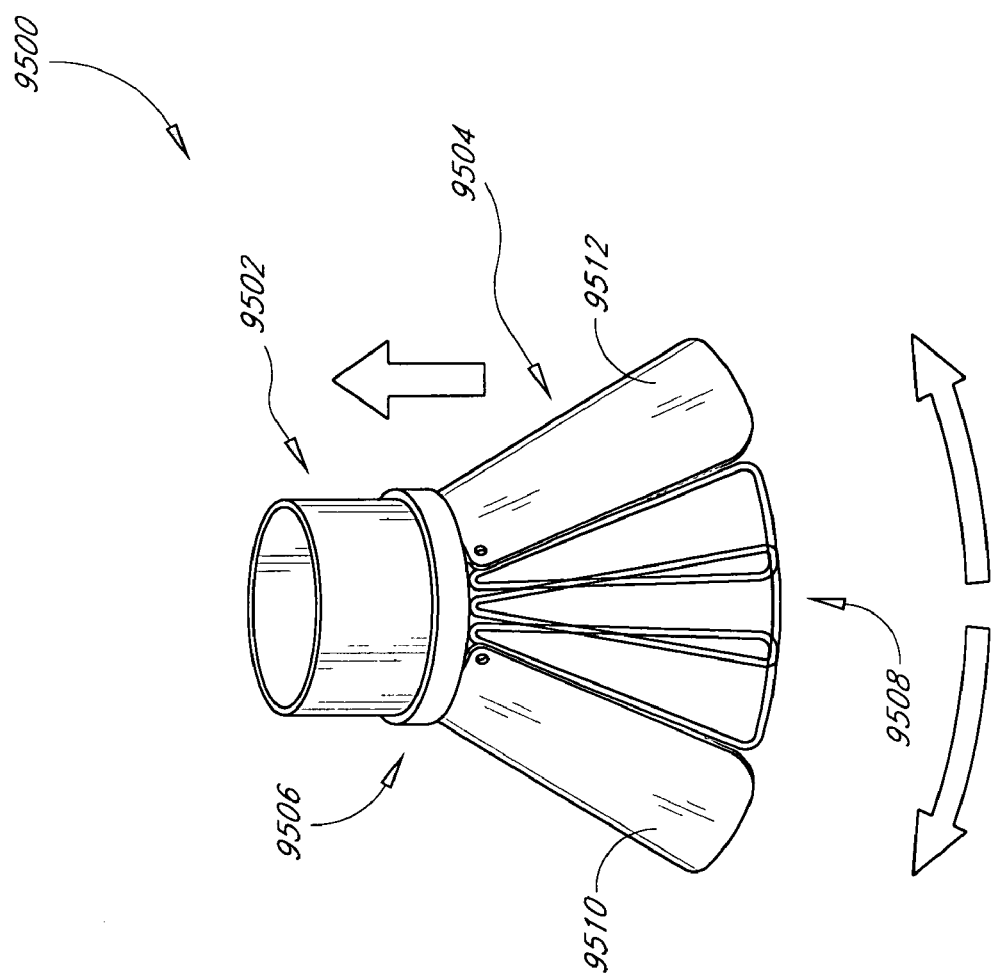

FIG. 214 is a perspective view of an access device having an expandable distal portion including elongate members made of wire and a movable proximal portion, shown in the expanded condition.

Figure 215:
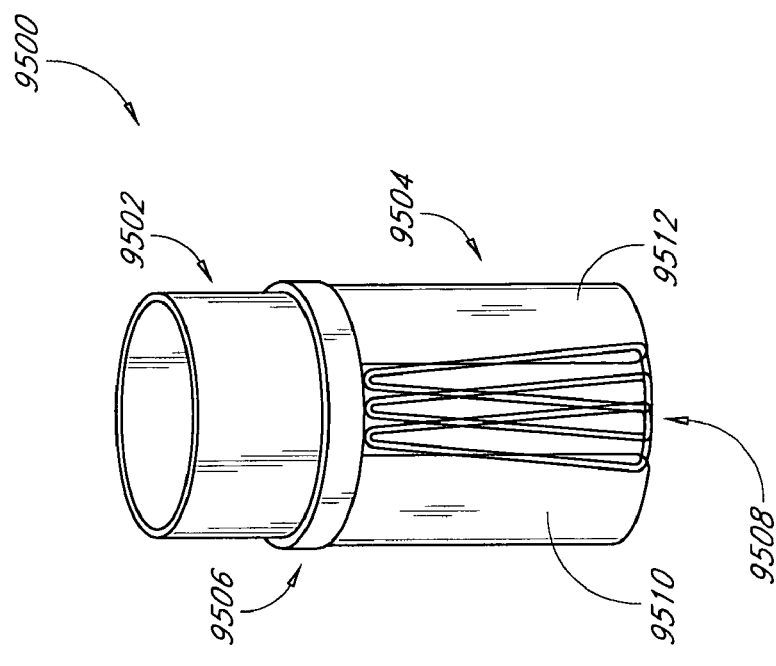

FIG. 215 is a perspective view of the access device of FIG. 214, shown in a low profile configuration.

FIG. 216 is an exploded perspective view of an access device having an expandable skirt connected to a collar at the proximal end at a pivot point.

FIG. 217 is a side view of a skirt portion of the access device of FIG. 216.

FIG. 218 is a side view of the access device of FIG. 216, in a contacted position.

FIG. 219 is a side view of the access device of FIG. 216, in an expanded position.

Figure 220:
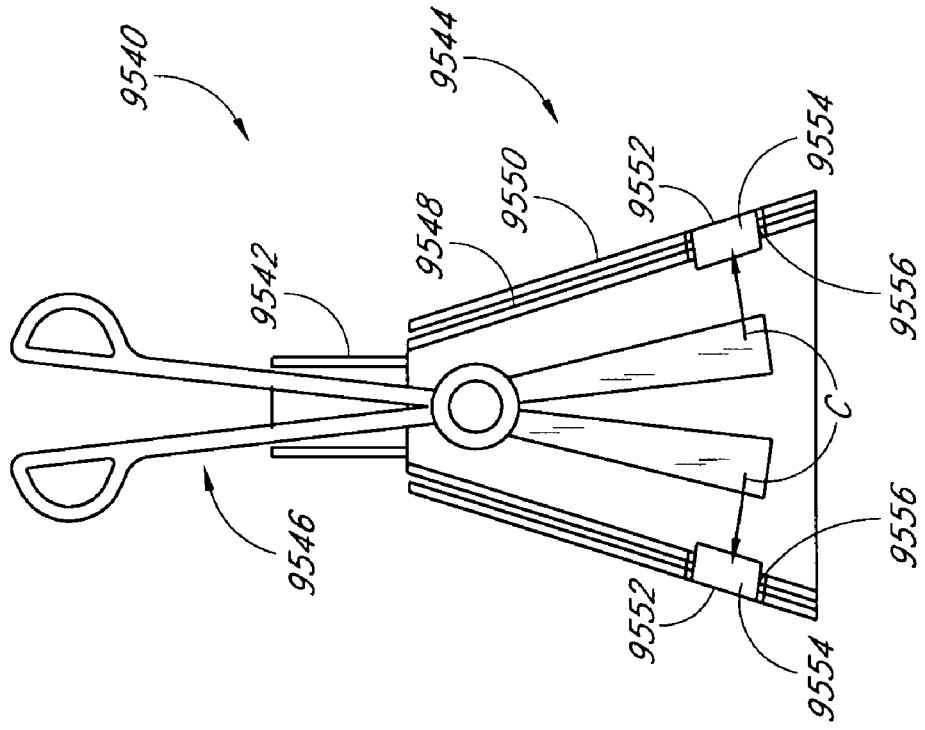

FIG. 220 is a cross-sectional view of one embodiment of an access device with an expander tool inserted therein.

Figure 221:
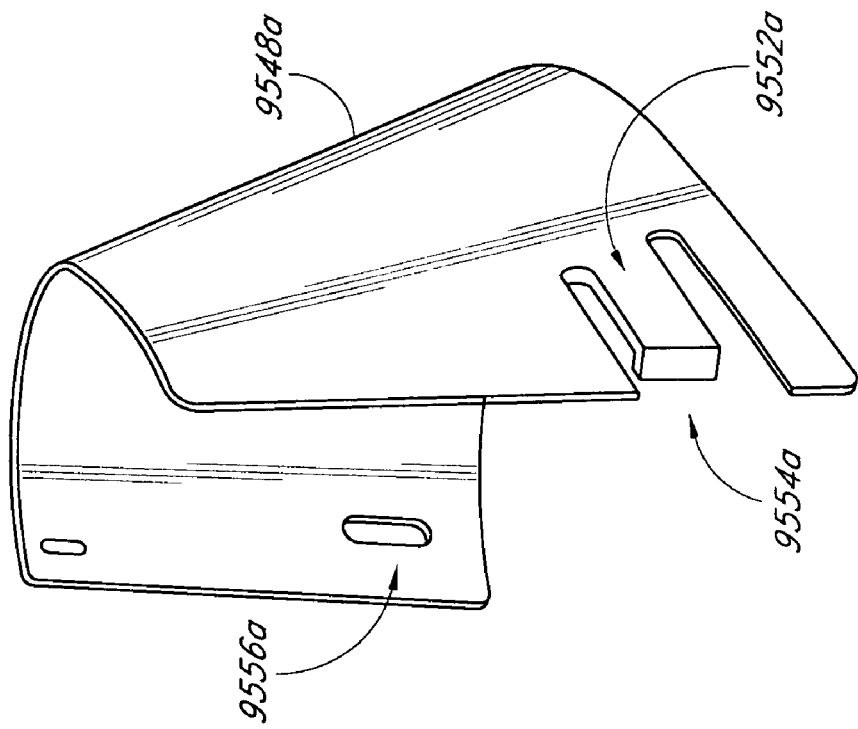

FIG. 221 is a perspective view of one embodiment of a longitudinally extending side of a distal portion of one embodiment of an access device.

FIG. 222 is a cross-sectional view of a portion of an access device with a deployment mechanism, the deployment mechanism in the un-deployed position.

FIG. 223 is a cross-sectional view of the access device of FIG. 222, the deployment mechanism being in a deployed position.

FIG. 224 is an exploded view of a portion of the access device of FIG. 222.

FIG. 225 is a perspective view of another embodiment of an access device having a distal portion with an inserted configuration, wherein the distal portion is capable of being locked in the inserted configuration.

FIG. 226 is a cross-sectional view of access device of FIG. 225 taken along section plane 226-226 illustrating one embodiment of a lock.

FIG. 227 is a partial distal-end view of an access device similar to the access device illustrated in FIG. 225, showing another embodiment of a lock.

FIG. 228 is a partial distal-end view of an access device similar to the access device illustrated in FIG. 225, showing another embodiment of a lock.

FIG. 229 is a perspective view of one access device embodiment having locking features.

FIG. 230 is a perspective view of another access device embodiment having locking features.

FIG. 231 is a cross section view of a locking element of FIG. 230.

FIG. 232 is a perspective view of a retractor with expandable locking blades and an expandable shroud, shown in a tubular configuration for insertion over a dilator.

FIG. 233 is a perspective view of the retractor of FIG. 232, showing components in hidden lines in a partially expanded condition.

FIG. 234 is a perspective view of the retractor of FIG. 232, showing components in hidden lines in a fully expanded condition.

Figure 234A:
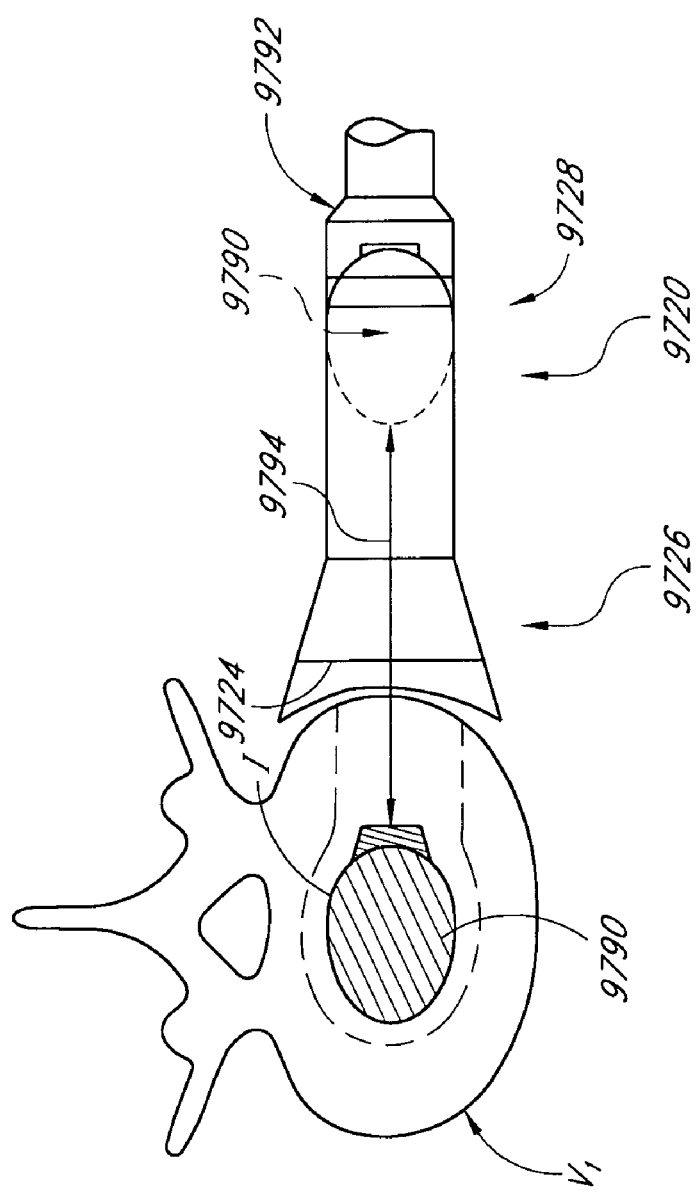

FIG. 234A is a schematic view illustrating one method of inserting a spinal implant into an interbody space through the retractor of FIG. 232.

Figure 235:
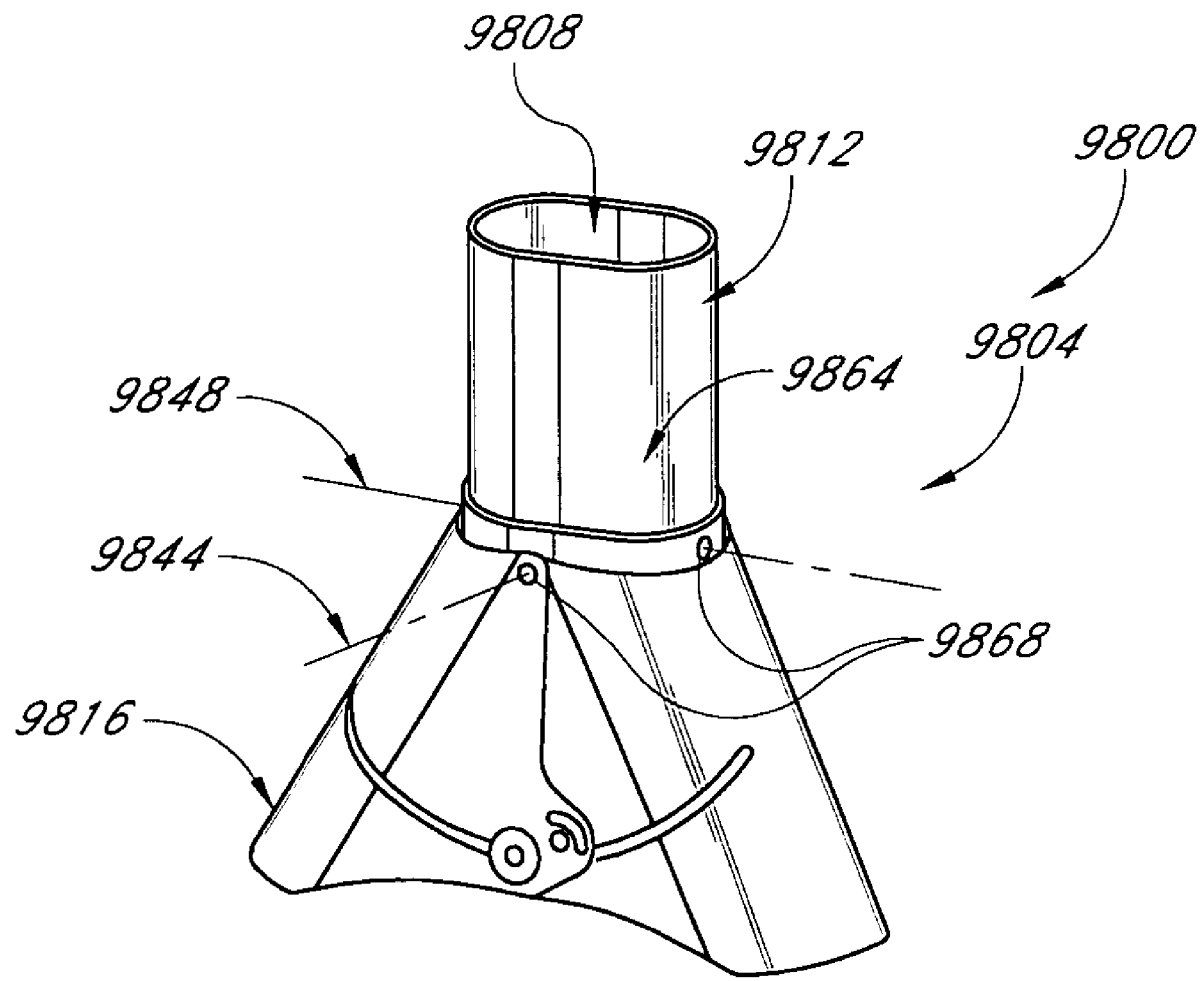

FIG. 235 is a perspective view of another access device embodiment, with an expandable locking distal portion and an oblong shaped proximal portion with a multi-pivot configuration, shown in an expanded locked position.

FIG. 236 is an exploded perspective view of the access device of FIG. 235, showing pivot components of the access device.

FIG. 237 is a front view of the access device of FIG. 235.

FIG. 238 is a side view of the access device of FIG. 235, showing the proximal portion in a pivoted position.

FIG. 239 is a top view of the access device of FIG. 235.

FIG. 240 is a perspective view of an obturator and an access device according to one embodiment, with the access device positioned on the obturator for insertion into a patient.

FIG. 241 is a side view of the obturator of FIG. 240.

Figures 242, 243:
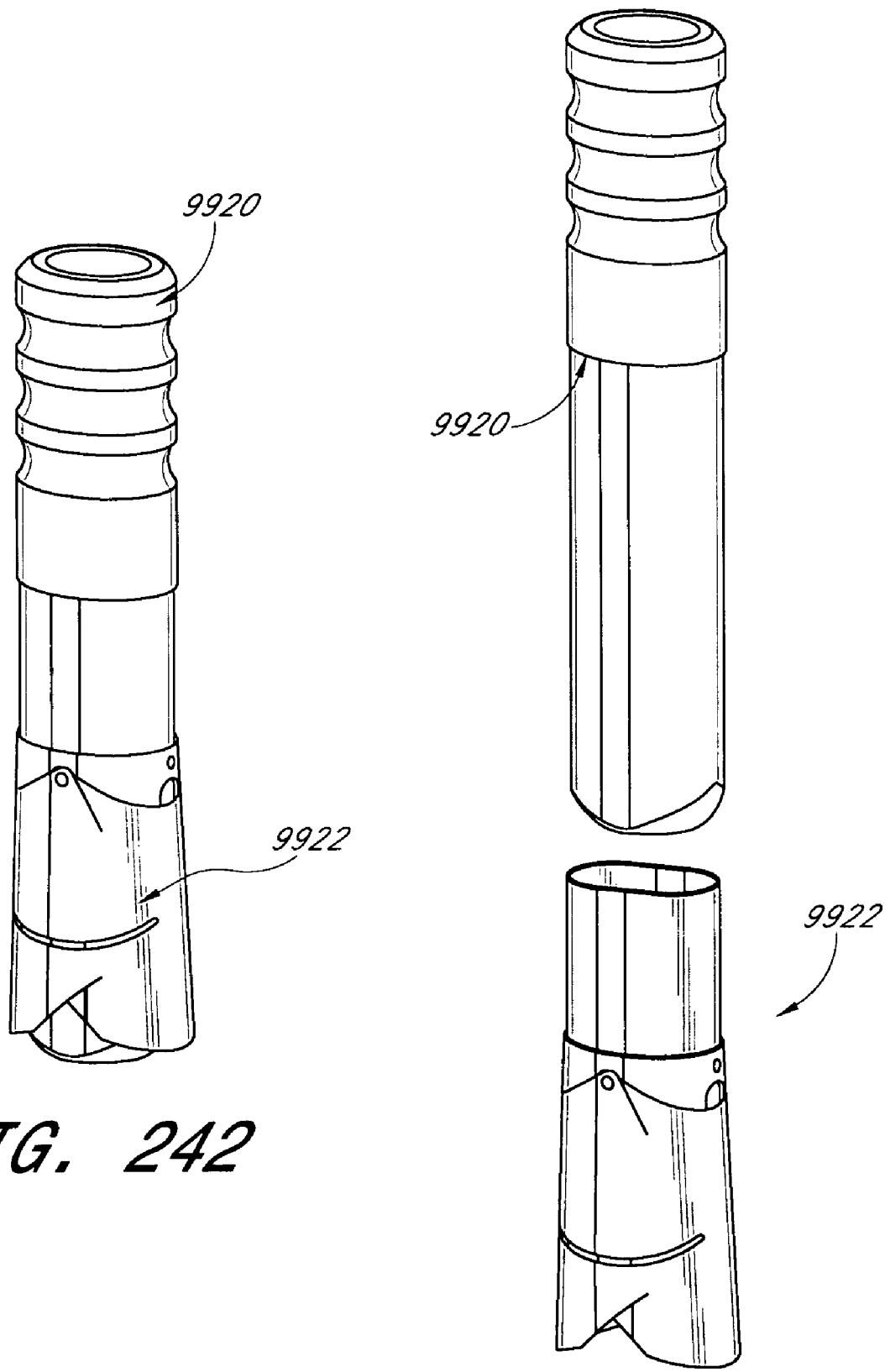

FIG. 242 is a perspective view of an oblong shaped obturator and an access device according to one embodiment, with the access device positioned on the obturator for insertion into a patient.

FIG. 243 is a perspective view of the obturator and access device of FIG. 242.

Figure 244:
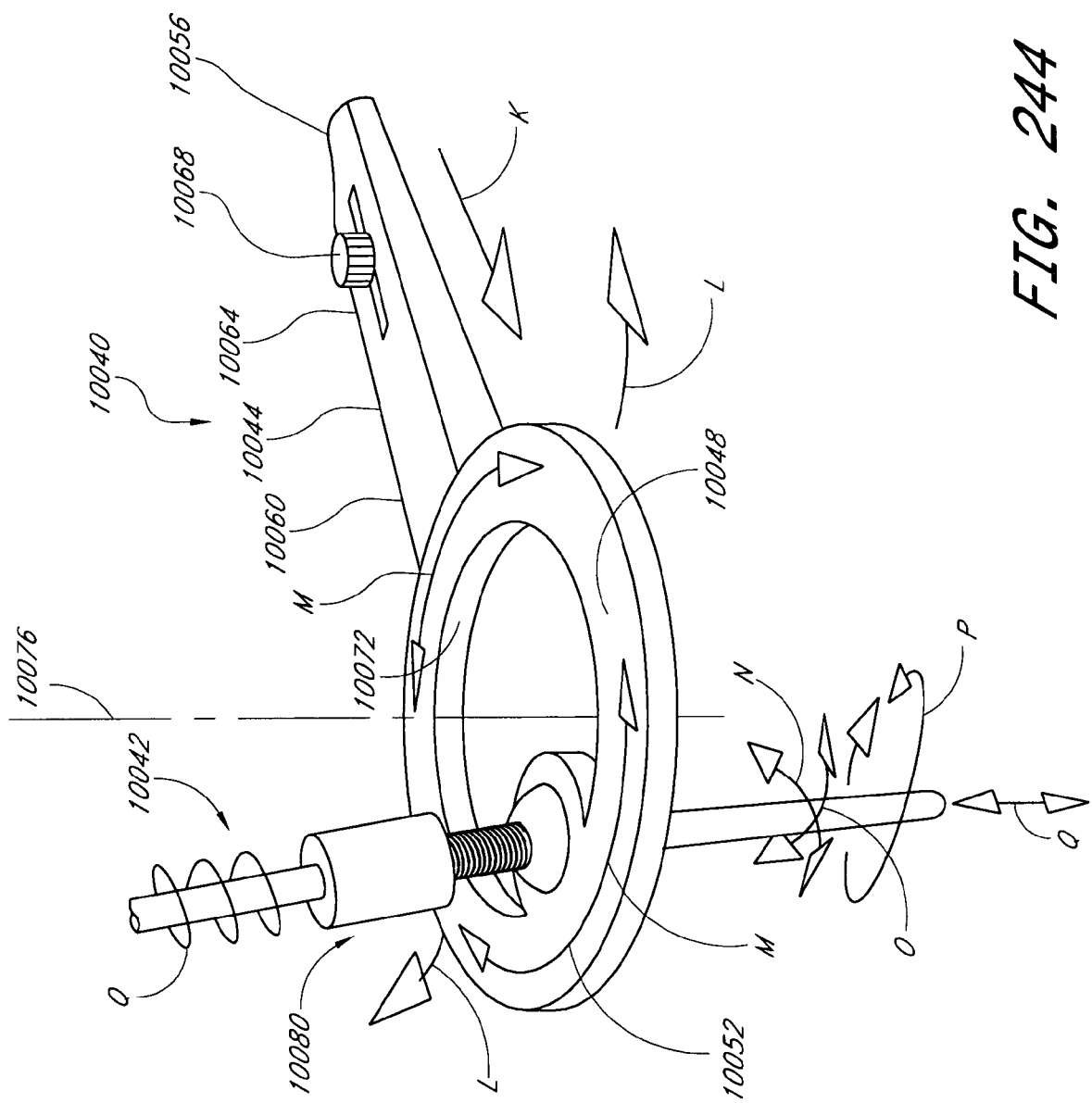

FIG. 244 is a perspective view of one embodiment of a viewing element mounting fixture for adjustably coupling a viewing element to an access device mounting fixture.

Figure 245:
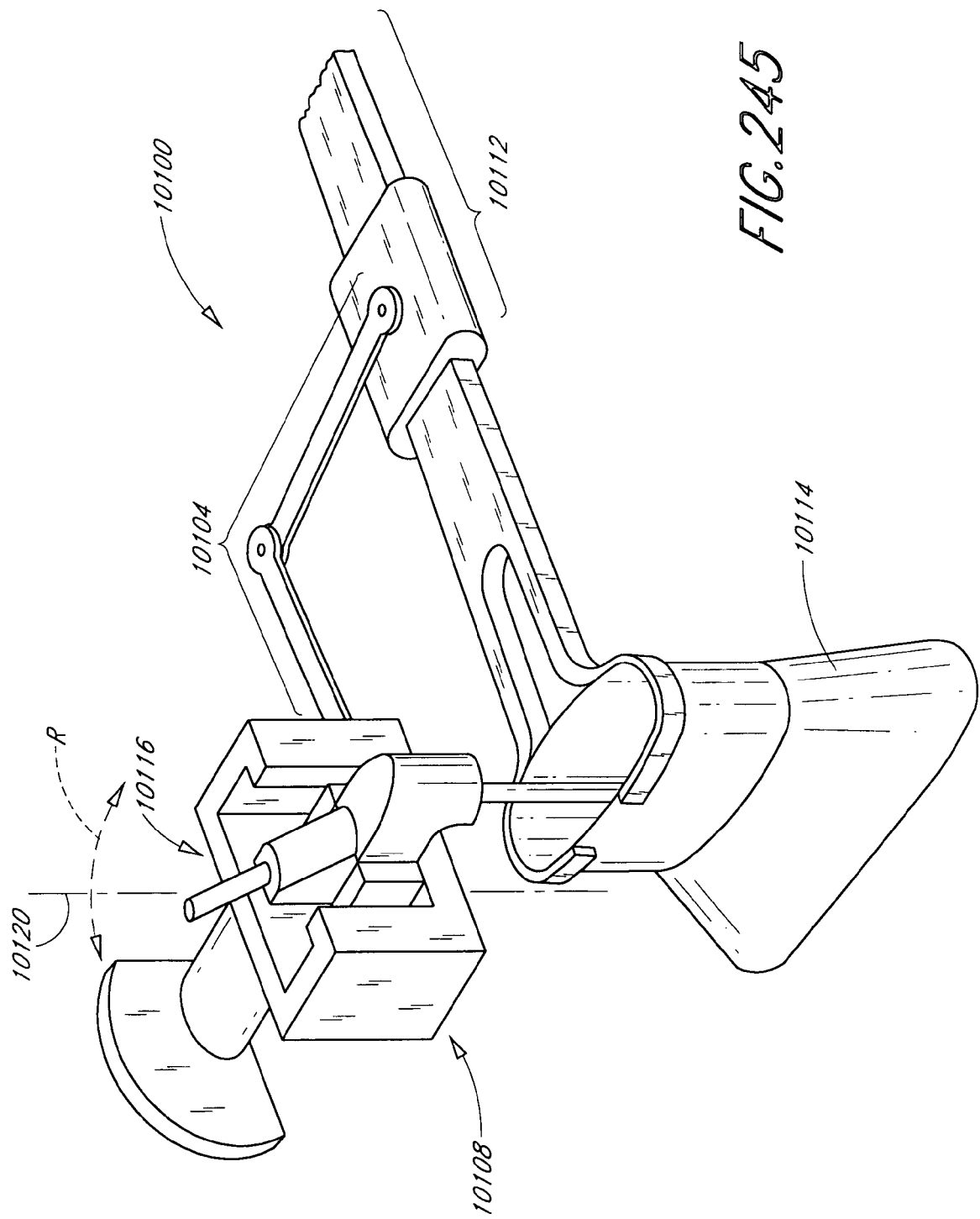

FIG. 245 is a perspective view of another embodiment of a surgical assembly.

Figure 246:
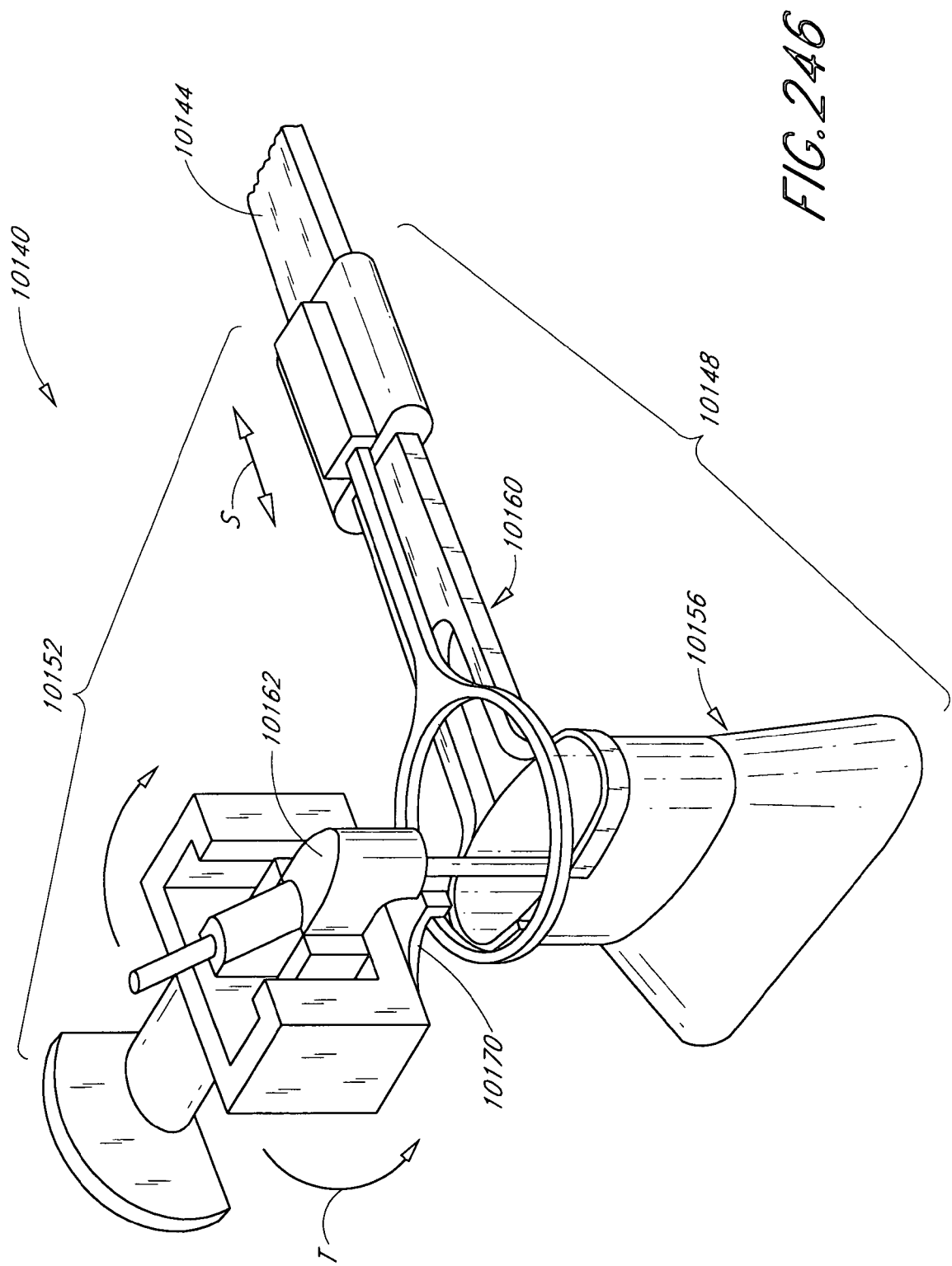

FIG. 246 is a perspective view of another embodiment of a surgical assembly.

Figure 247:
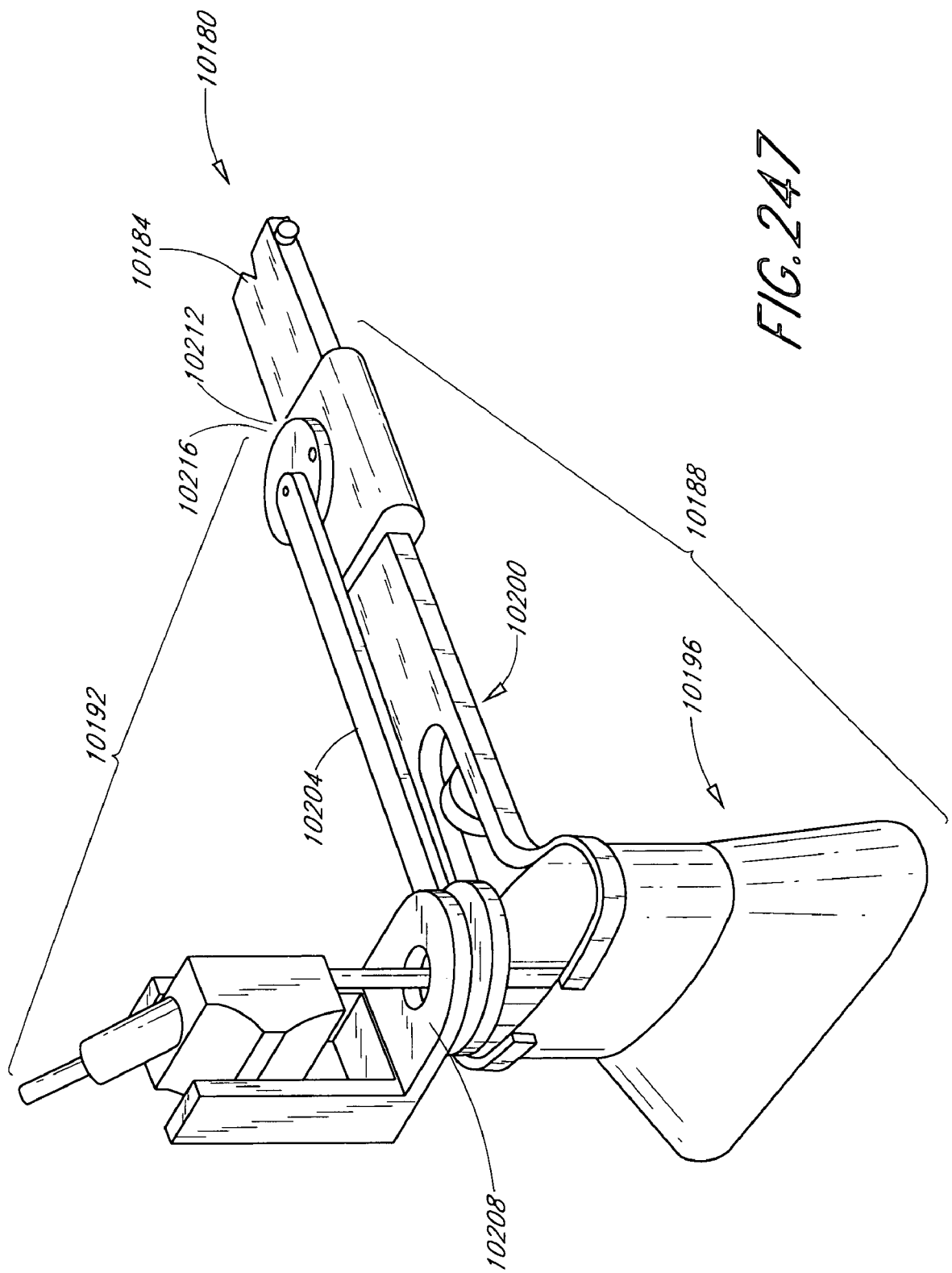

FIG. 247 is a perspective view of another embodiment of a surgical assembly.

Figure 248:
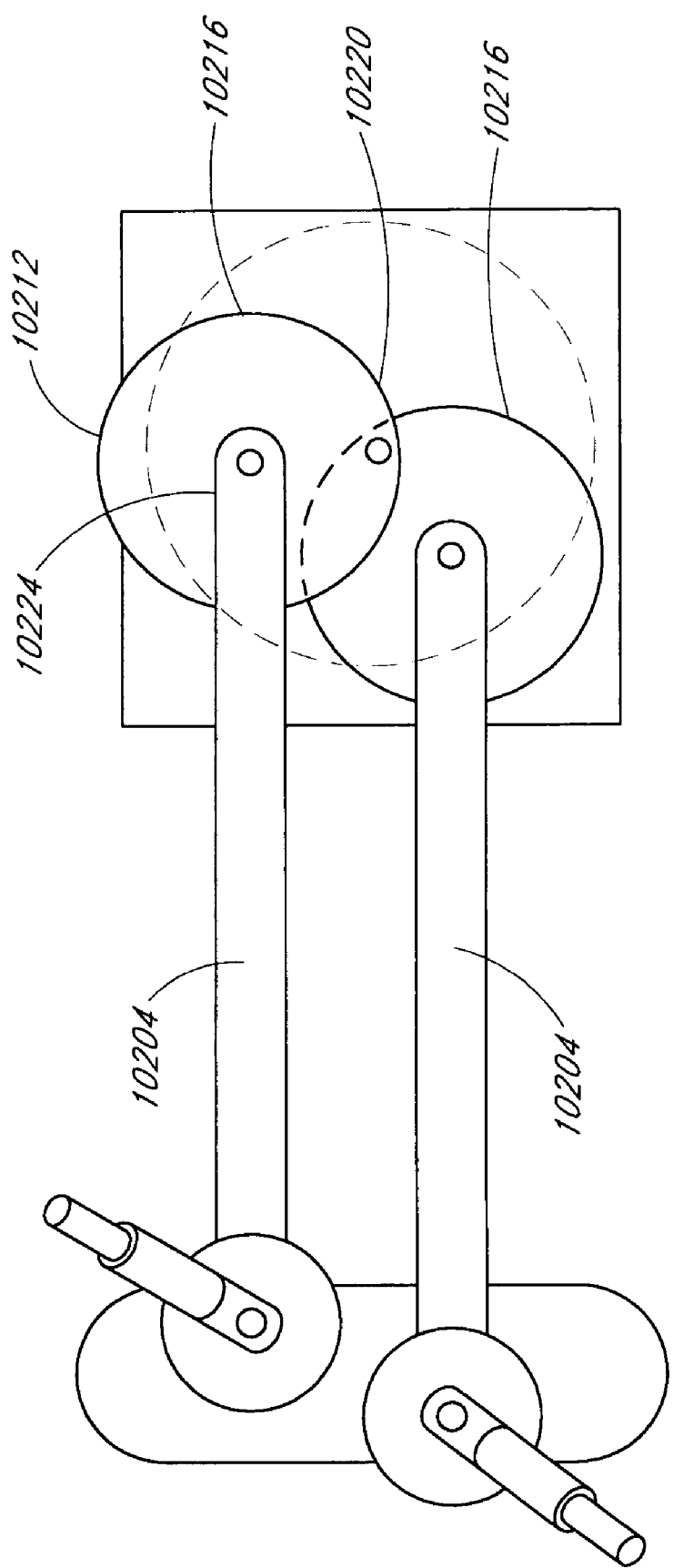

FIG. 248 is a top view of a portion of the surgical assembly of FIG. 247 illustrating two positions in which a viewing element thereof may be positioned.

FIG. 249 is a perspective view of another embodiment of a viewing assembly for adjustably coupling a viewing element to an access device mounting fixture.

FIG. 250 is a schematic view of a ratchet arrangement for expansion and un-expansion of a portion of a surgical assembly (e.g., an access device mounting fixture, an access device proximal end, or an access device distal end).

FIG. 251 is a schematic top view of the ratchet arrangement of FIG. 250.

FIG. 252 is a perspective view of a viewing element mount including a clamp and a slot.

FIG. 253 is a cross section side view of the viewing element mount of FIG. 252.

Figure 254:
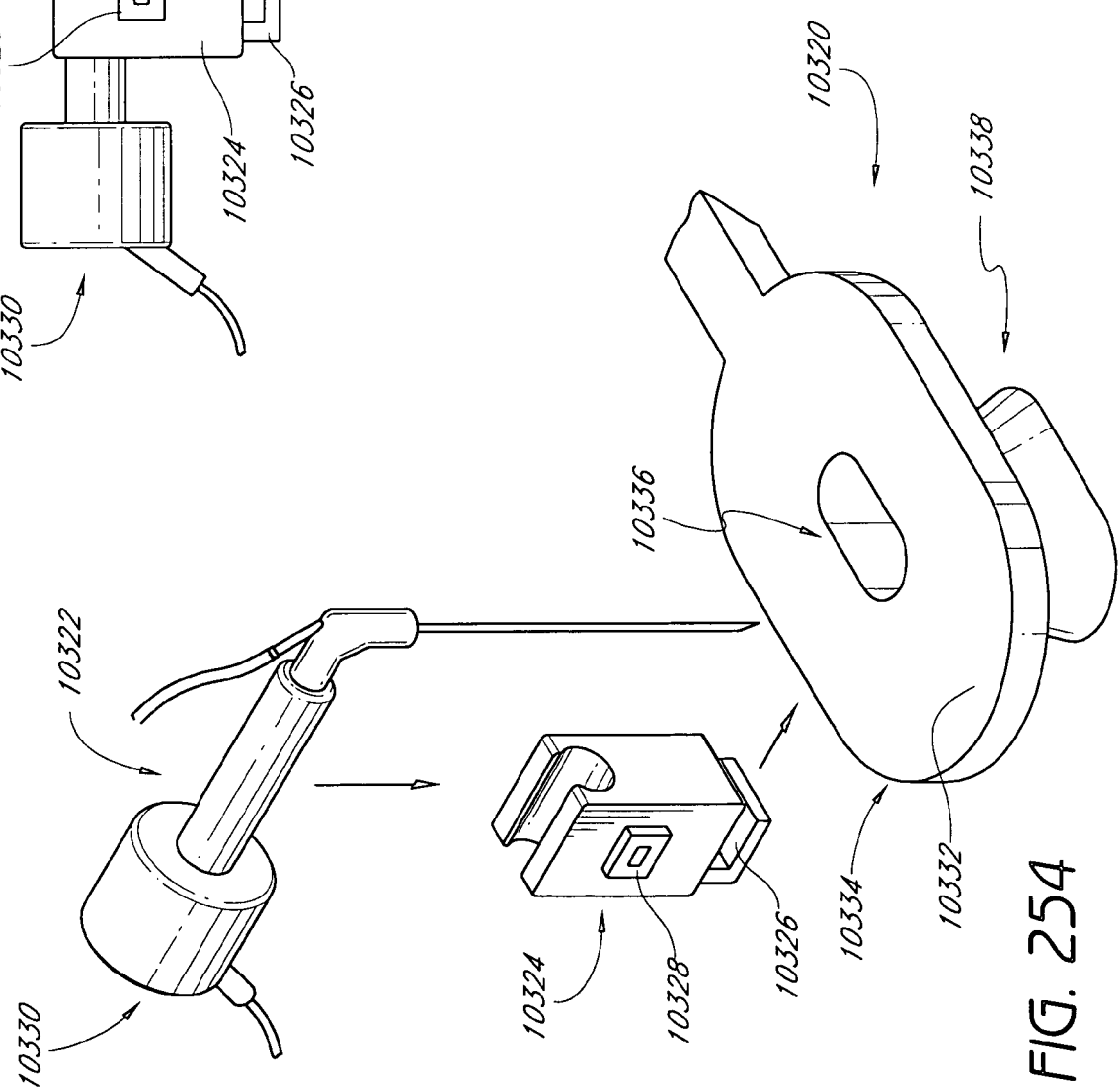

FIG. 254 is a perspective view of a viewing element mount including a C-clamp.

Figure 255:
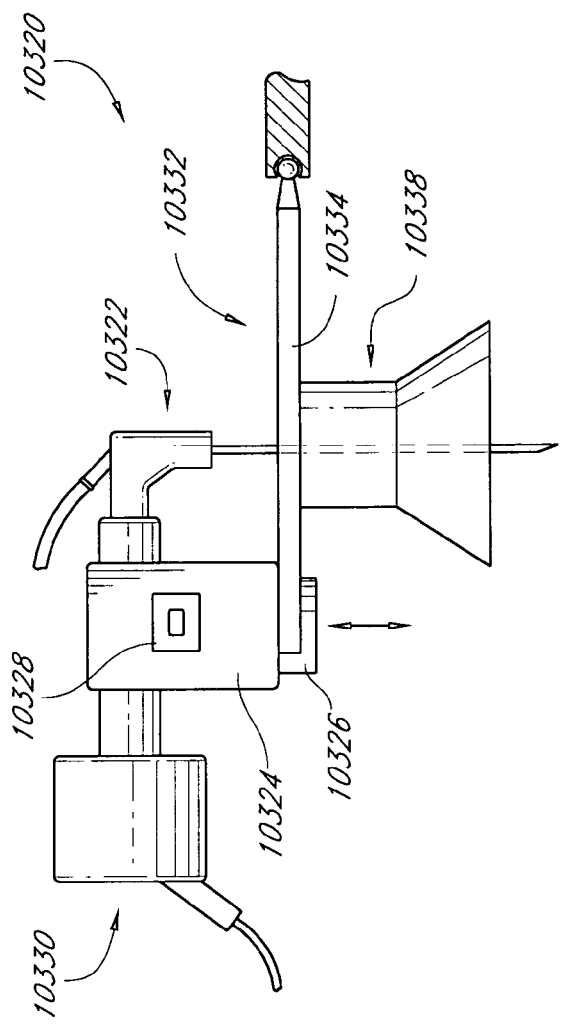

FIG. 255 is a side view of the viewing element mount of FIG. 254.

Figure 256:
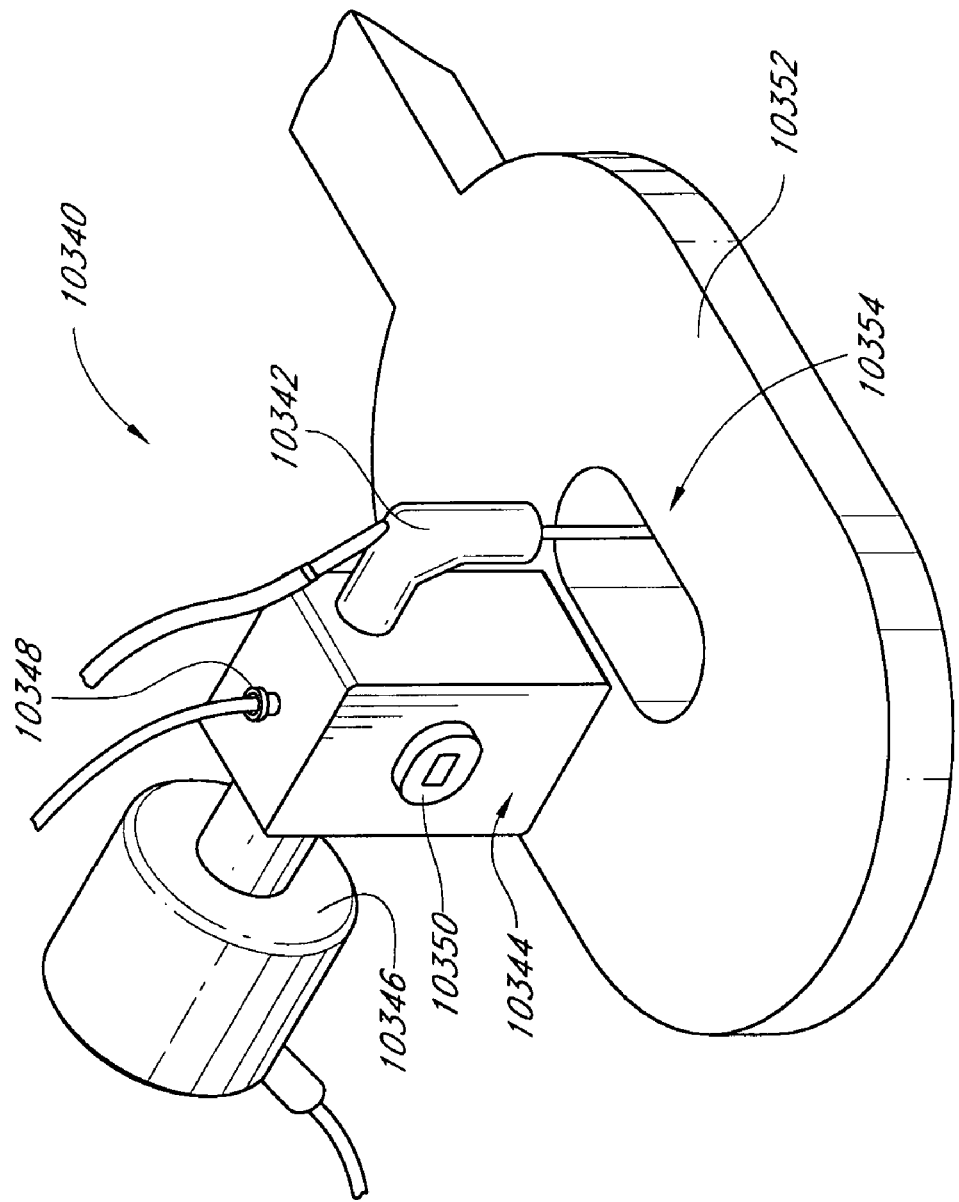

FIG. 256 is a perspective view of a viewing element mount using a vacuum source to position the mount on a mount support.

Figure 257:
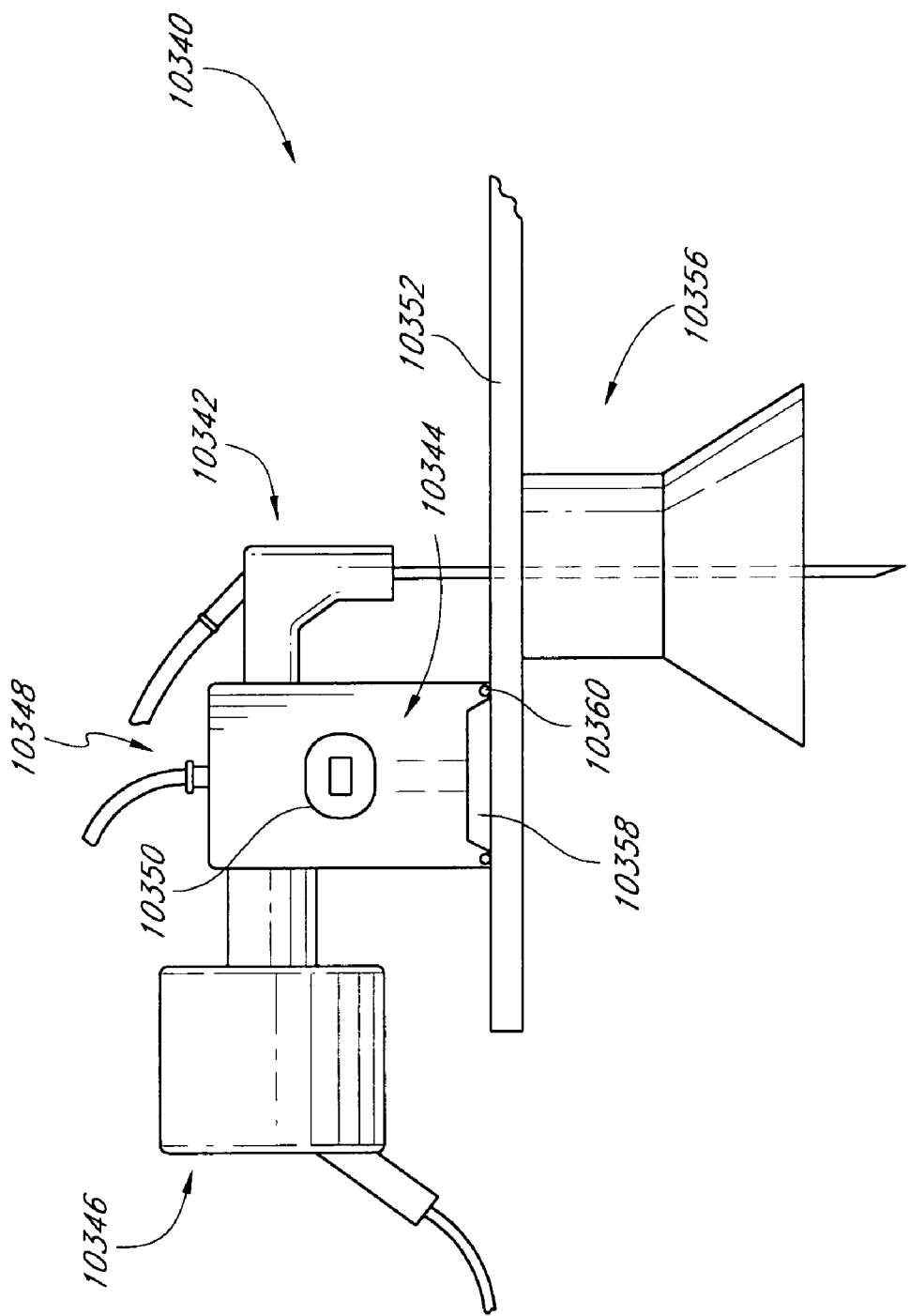

FIG. 257 is a side view of the viewing element mount in FIG. 256.

Figure 258:
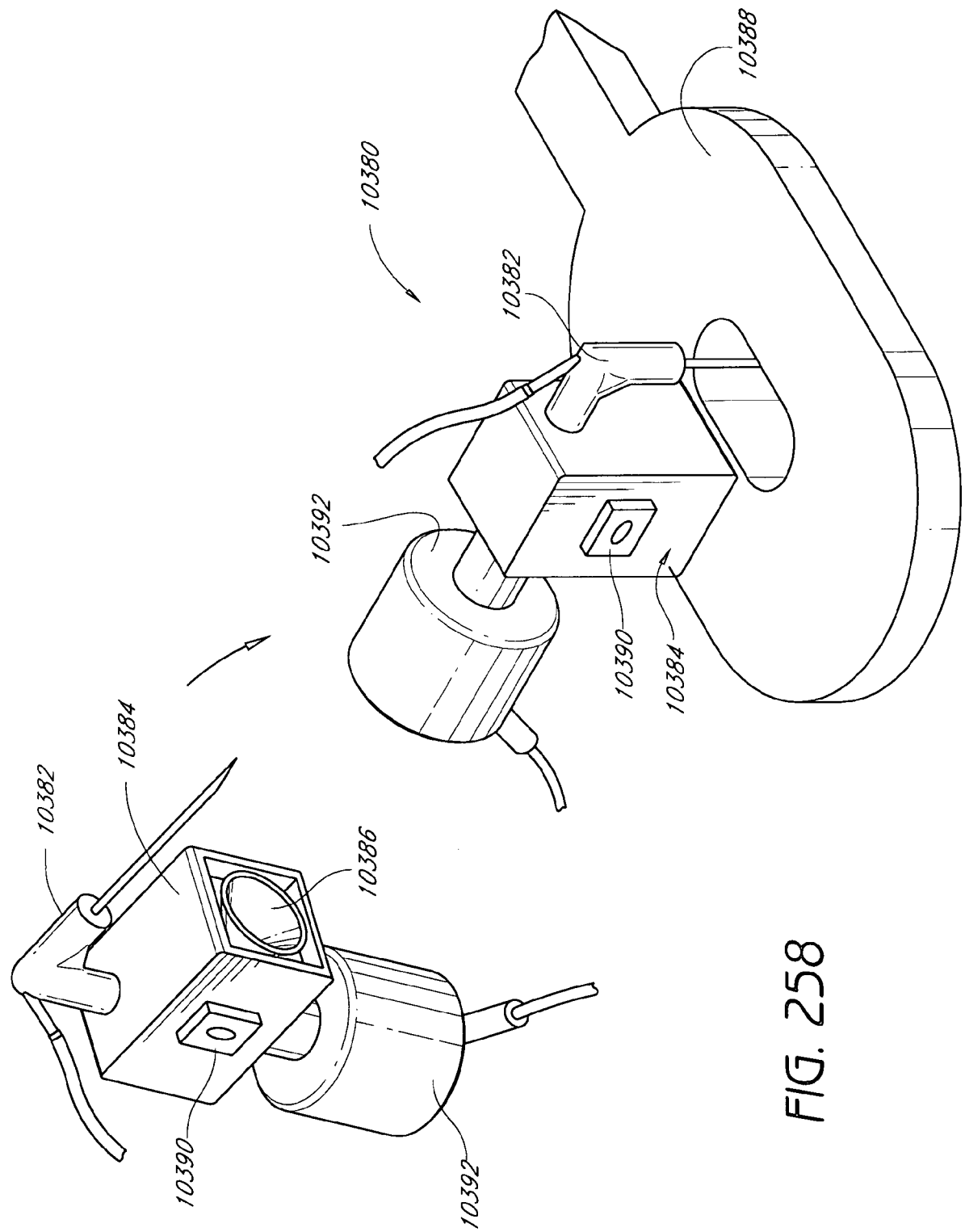

FIG. 258 is a perspective view of a viewing element mount having a suction cup for positioning the mount on a support.

Figures 259, 260:
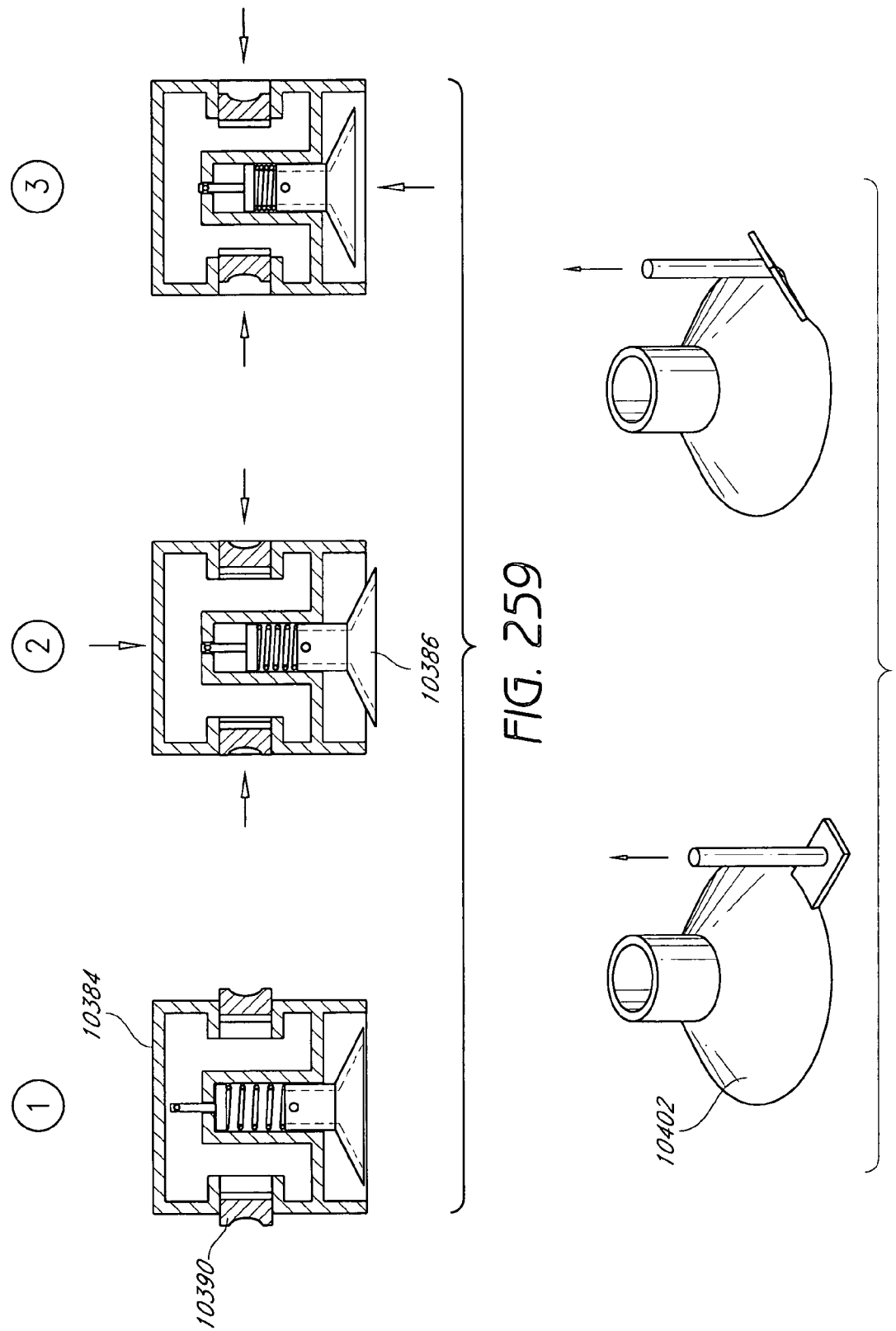

FIG. 259 is a schematic view showing various stages of suction for the viewing element mount of FIG. 258.

FIG. 260 is a schematic view of a suction mechanism for a viewing element mount.

Figure 261:
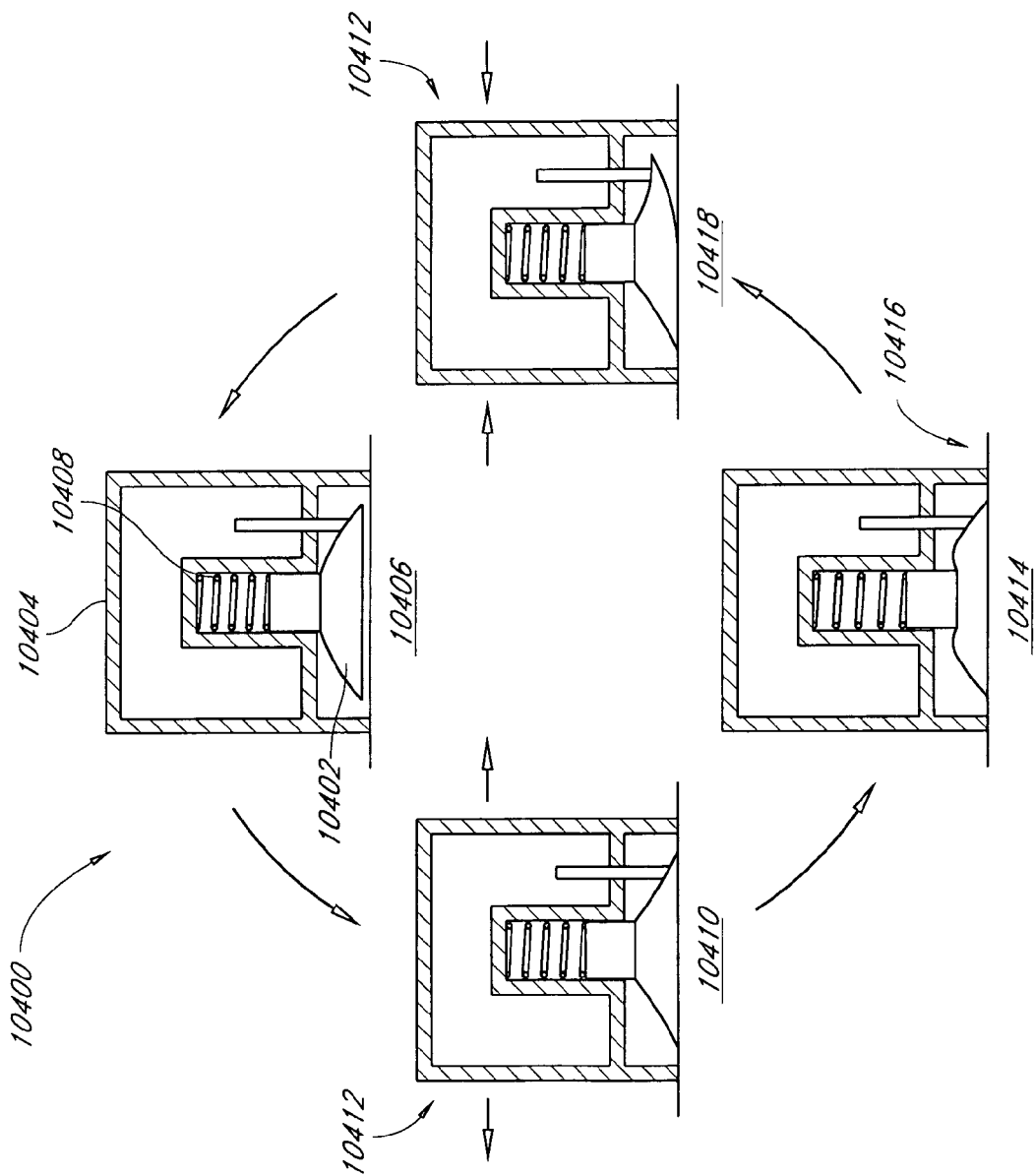

FIG. 261 is a schematic view showing various stages of suction for the suction mechanism of FIG. 260.

Figure 262:
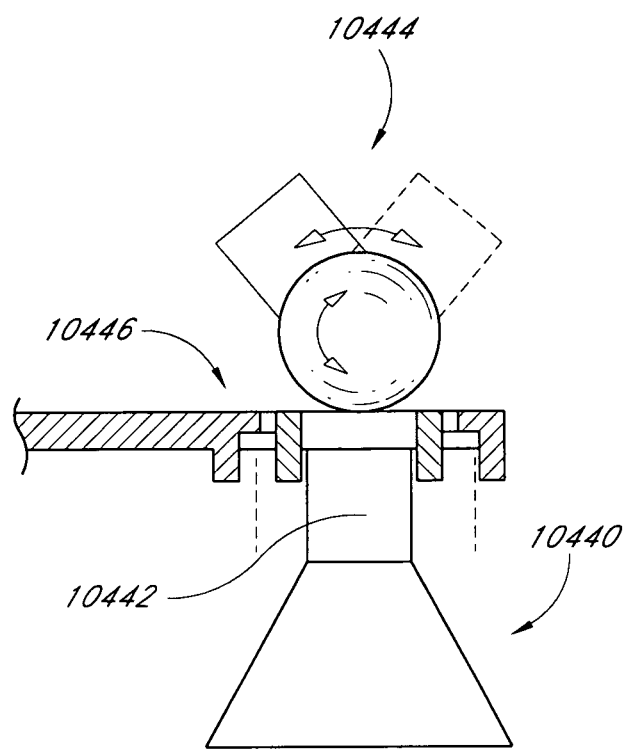

FIG. 262 is one embodiment of a surgical assembly having a view element mounting fixture including a ball joint.

FIG. 263 is a perspective view of another embodiment a viewing assembly for adjustably coupling a viewing element to an access device mounting fixture.

Figure 264:
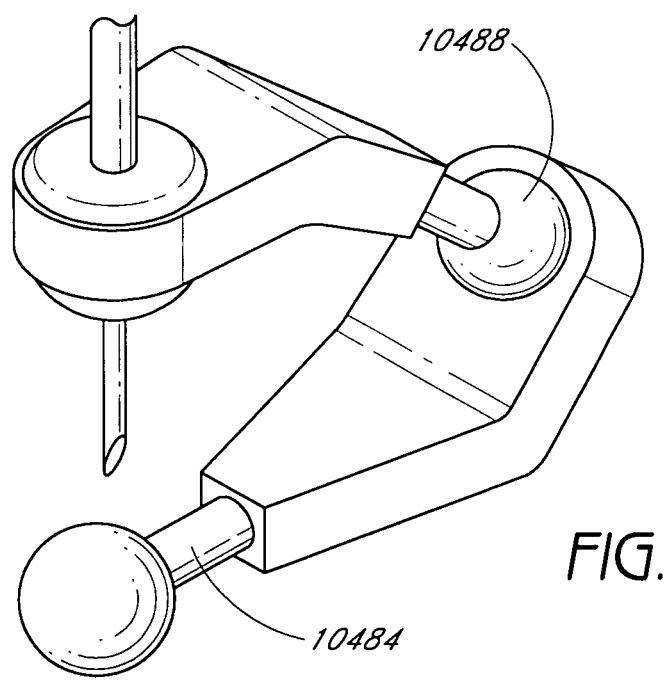

FIG. 264 is a perspective view of another embodiment of a viewing element mounting fixture for adjustably coupling a viewing element to an access device mounting fixture.

FIG. 265 is a perspective view of one embodiment of a clamp for fixing the position of a viewing element.

FIG. 266 is a partial cross sectional view of the clamp of FIG. 265.

FIG. 267 is a top view of one embodiment of an access device mounting fixture for adjustably supporting an access device.

FIG. 268 is a perspective view of another embodiment of an access device mounting fixture for adjustably supporting an access device.

FIG. 269 is a detail view of a portion of the access device mounting fixture of FIG. 268.

Figure 270:
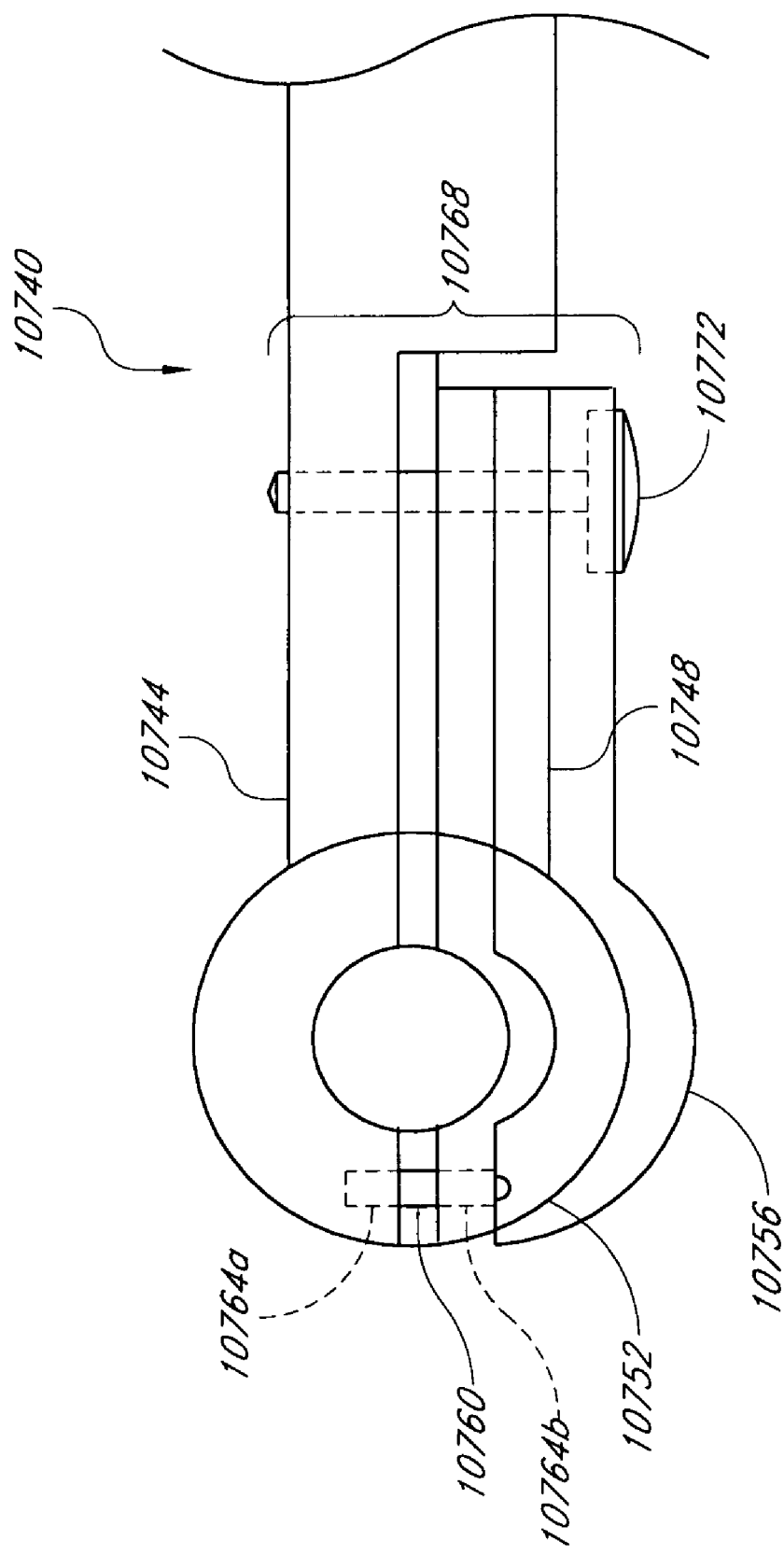

FIG. 270 is a top plan view of another embodiment of an access device mounting fixture.

FIG. 271 is a perspective view of one embodiment of a viewing element mounting fixture for adjustably coupling a viewing element to an access device mounting fixture.

FIG. 272 is a schematic view of a viewing element of FIG. 271.

FIG. 273 is a perspective view of one embodiment of a viewing element mounting fixture having a C linkage.

FIG. 274 is another embodiment of a viewing element mounting fixture having a coiled spring arrangement.

FIG. 275 is a perspective view of another embodiment of a viewing element mounting fixture with a viewing element pivot mount and a visualization window.

FIG. 276 is a perspective view of another embodiment of a viewing element mounting fixture.

FIG. 277 is a schematic view of the freedom of rotation for the viewing element of FIG. 276.

Figure 278:
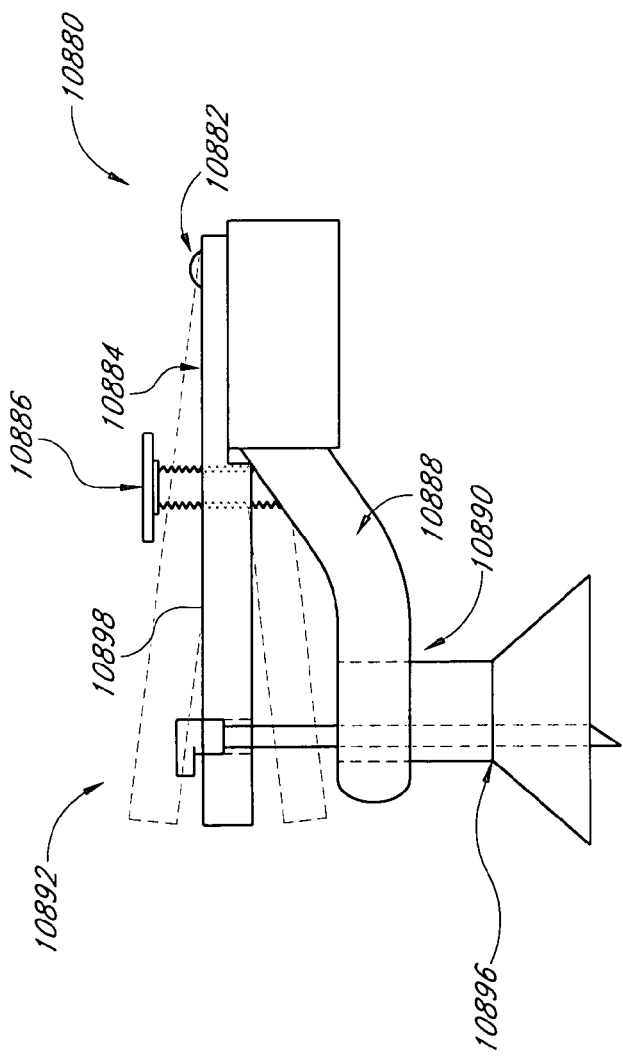

FIG. 278 is a schematic side view of the viewing element mounting fixture of FIG. 276.

Figure 279:
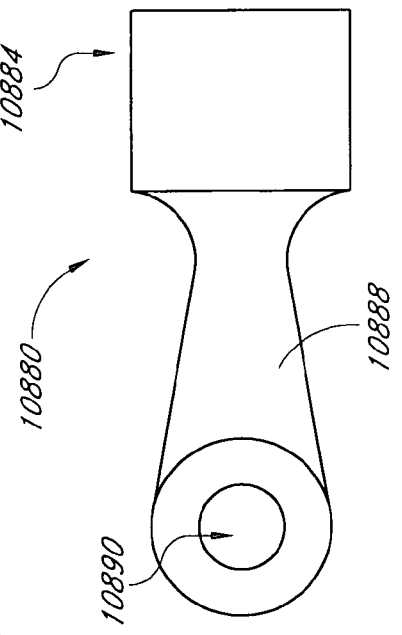

FIG. 279 is a schematic top view of the viewing element mounting fixture of FIG. 276.

Figure 280:
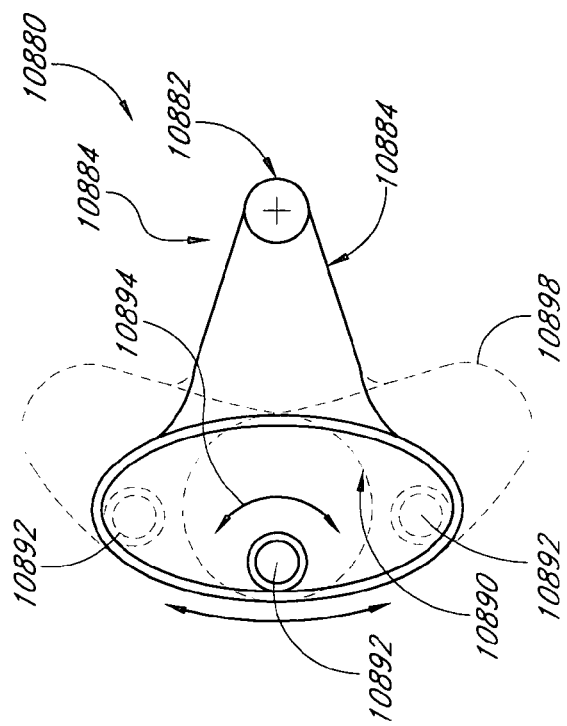

FIG. 280 is a schematic view of the pivot range and positionability of the viewing element of FIG. 276.

Figure 281:
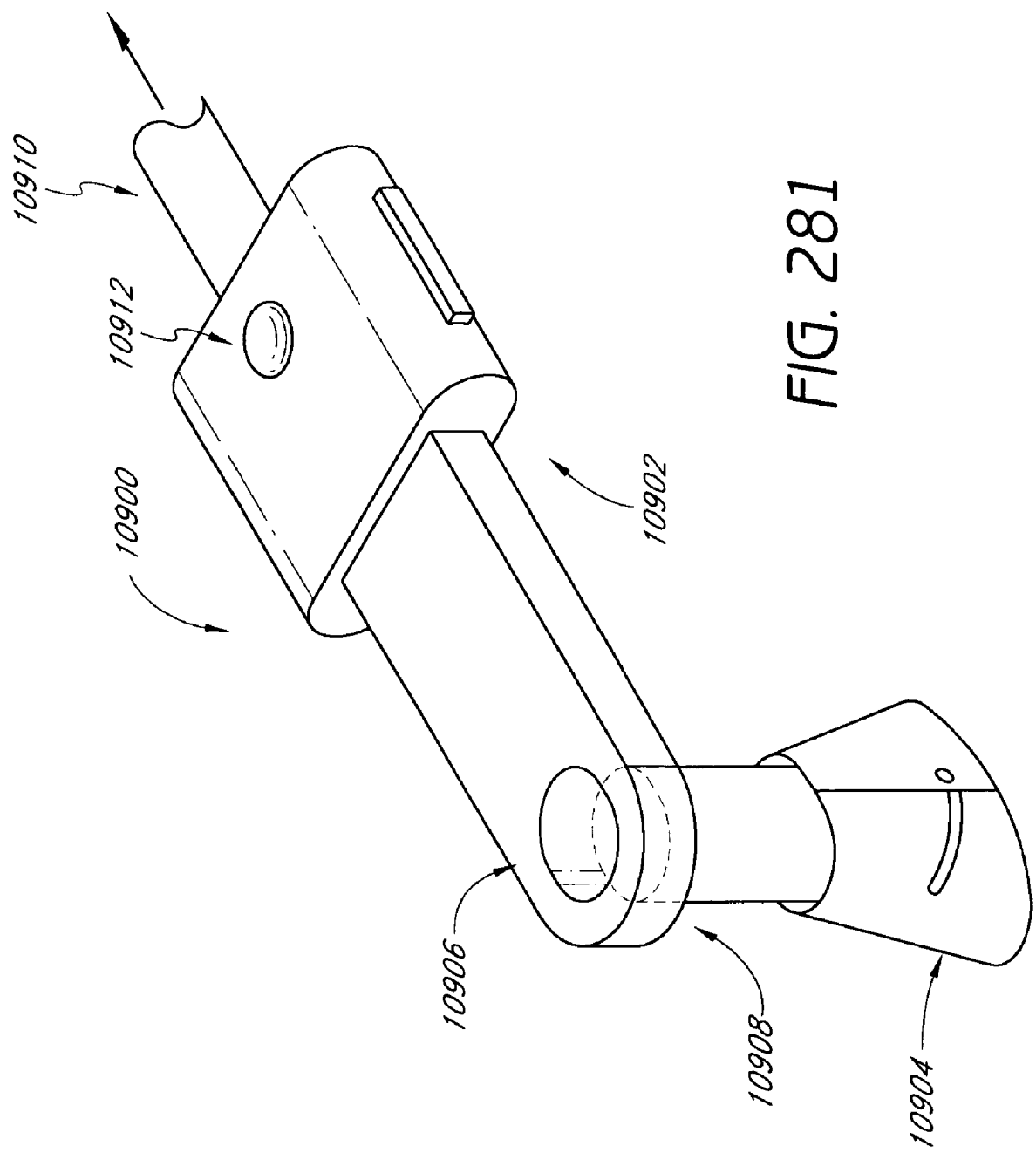

FIG. 281 is a perspective view of another embodiment of an access device mounting fixture.

FIG. 282 is a schematic top view of the access device mounting fixture of FIG. 281.

FIG. 283 is a schematic side view of the access device mounting fixture of FIG. 281 coupled with an access device.

Figure 284:
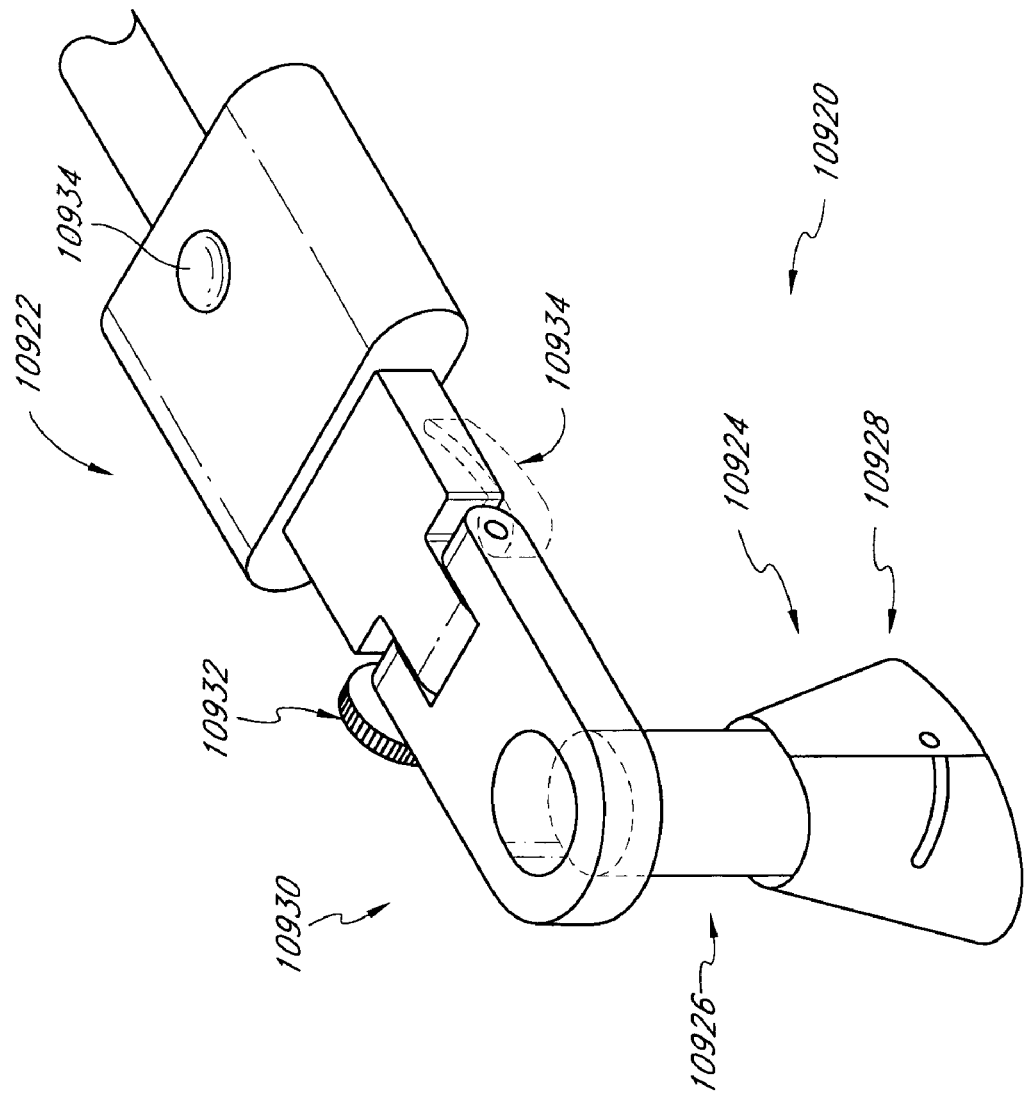

FIG. 284 is a perspective view of a surgical assembly having a thumb-wheel lock and/or a cam lever lock.

Throughout the figures, the same reference numerals and characters, unless otherwise stated, are used to denote like features, elements, components or portions of the illustrated embodiments. Moreover, while the subject matter of this application will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF THE PREFERRED EMBODIMENTS

As should be understood in view of the following detailed description, this application is primarily directed to, though not necessarily limited to, apparatuses and methods for treating the spine of a patient through an access device. More particularly, the systems described below provide access to surgical locations at or near the spine and provide a variety of tools useful in performing treatment of the spine. Also, the systems described herein enable a surgeon to perform a wide variety of methods as described herein.

I. Systems for Performing Procedures at a Surgical Location

Various embodiments of apparatuses and procedures described herein will be discussed in terms of minimally invasive procedures and apparatuses, e.g., of endoscopic apparatuses and procedures. However, many aspects of the present invention may find use in conventional, open, and mini-open procedures. As used herein, the term "proximal," as is traditional, refers to the end portion of the apparatus that is closest to the operator, while the term "distal" refers to the end portion that is farthest from the operator.

Figure 1:
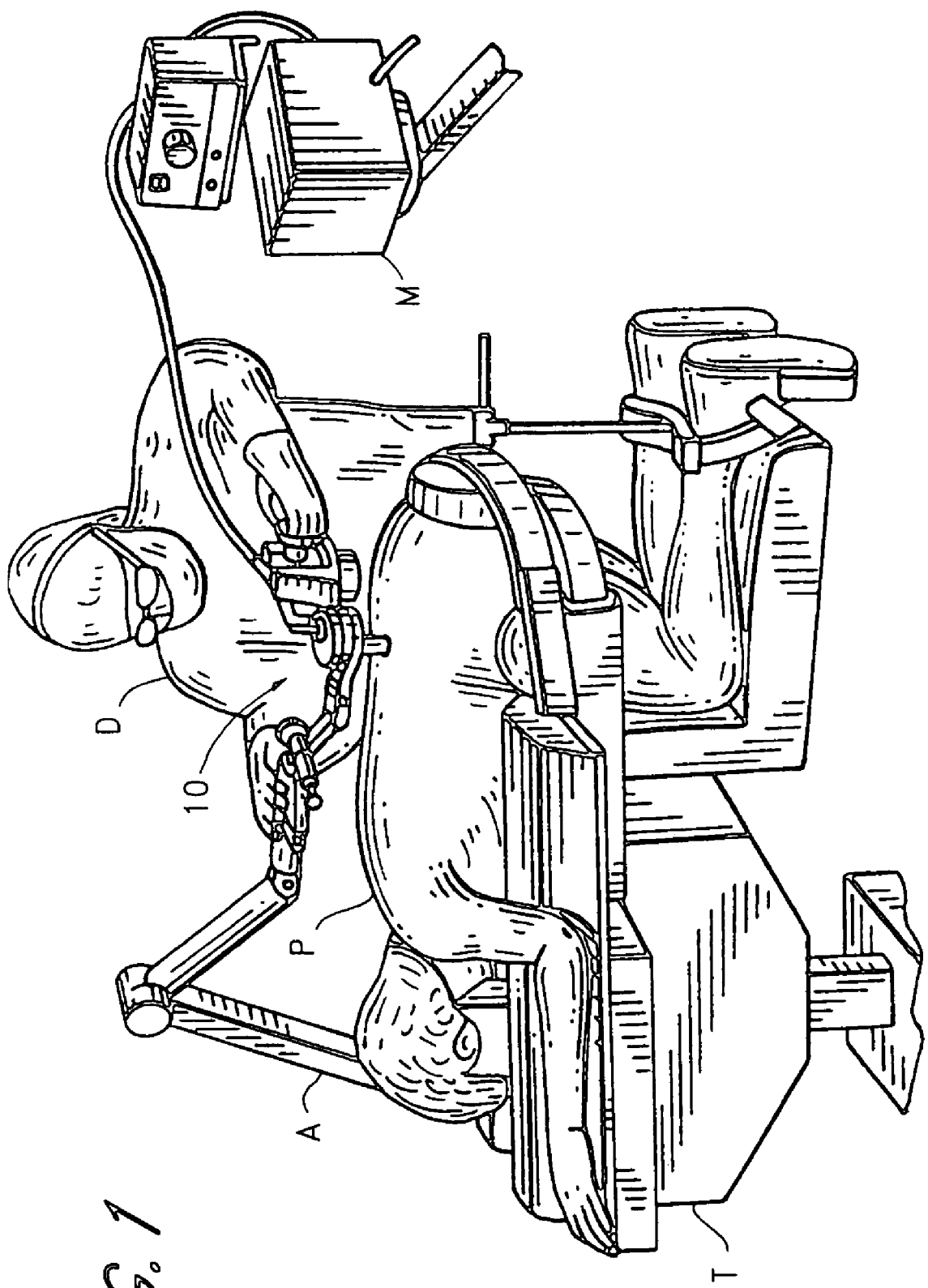
FIG. 1 is a perspective view of one embodiment of a surgical system and one embodiment of a method for treating the spine of a patient.

FIG. 1 shows one embodiment of a surgical system 10 that can be used to perform a variety of methods or procedures. In one embodiment, as discussed more fully below, the patient P is placed in the prone position on operating table T, taking care that the abdomen is not compressed and physiological lordosis is preserved. The physician D is able to access the surgical site and perform the surgical procedure with the components of the system 10, which will be described in greater detail herein. The system 10 may be supported, in part, by a mechanical support arm A, such as the type generally disclosed in U.S. Pat. No. 4,863,133, which is hereby incorporated by reference herein in its entirety. One mechanical arm of this type is manufactured by Leonard Medical, Inc., 1464 Holcomb Road, Huntington Valley, Pa., 19006.

Visualization of the surgical site may be achieved in any suitable manner, e.g., by use of a viewing element, such as an endoscope, a camera, loupes, a microscope, direct visualization, or any other suitable viewing element, or a combination of the foregoing. In one embodiment, the viewing element provides a video signal representing images, such as images of the surgical site, to a monitor M. The viewing element may be an endoscope and camera that captures images to be displayed on the monitor M whereby the physician D is able to view the surgical site as the procedure is being performed. The endoscope and camera will be described in greater detail herein.

The systems are described herein in connection with minimally invasive postero-lateral spinal surgery. One such procedure is a two level postero-lateral fixation and fusion of the spine involving the L4, L5, and S1 vertebrae. In the drawings, the vertebrae will generally be denoted by reference letter V. The usefulness of the apparatuses and procedures is neither restricted to the postero-lateral approach nor to the L4, L5, and S1 vertebrae. The apparatuses and procedures may be used in other anatomical approaches and with other vertebra (e) within the cervical, thoracic, and lumbar regions of the spine. The procedures may be directed toward surgery involving one or more vertebral levels. Some embodiments are useful for anterior and/or lateral procedures. Moreover, it is believed that embodiments of the invention are also particularly useful where any body structures must be accessed beneath the skin and muscle tissue of the patient, and/or where it is desirable to provide sufficient space and visibility in order to manipulate surgical instruments and treat the underlying body structures. For example, certain features or instrumentation described herein are particularly useful for minimally invasive procedures, e.g., arthroscopic procedures. As discussed more fully below, one embodiment of an apparatus described herein provides an access device that has an expandable distal portion. In addition to providing greater access to a surgical site than would be provided with device having a constant cross-section, the expandable distal portion prevents or substantially prevents the access device, or instruments extended therethrough to the surgical site, from dislodging or popping out of the operative site.

In one embodiment, the system 10 includes an access device that provides an internal passage for surgical instruments to be inserted through the skin and muscle tissue of the patient P to the surgical site. The term "access device" is used in its ordinary sense to mean a device that can provide access and is a broad term and it includes structures having an elongated dimension and defining a passage, e.g., a cannula or a conduit. The access device is configured to be inserted through the skin of the patient to provide access during a surgical procedure to a surgical location within a patient, e.g., a spinal location. The term "surgical location" is used in its ordinary sense (i.e. a location where a surgical procedure is performed) and is a broad term and it includes locations subject to or affected by a surgery. The term "spinal location" is used in its ordinary sense (i.e. a location at or near a spine) and is a broad term and it includes locations adjacent to or associated with a spine that may be sites for surgical spinal procedures. The access device also can retract tissue to provide greater access to the surgical location.

The access device preferably has a wall portion defining a reduced profile configuration for initial percutaneous insertion into the patient. This wall portion may have any suitable arrangement. In one embodiment, discussed in more detail below, the wall portion has a generally tubular configuration that may be passed over a dilator that has been inserted into the patient to atraumatically enlarge an opening sufficiently large to receive the access device therein.

The wall portion of the access device preferably can be subsequently expanded to an enlarged configuration, by moving against the surrounding muscle tissue to at least partially define an enlarged surgical space in which the surgical procedures will be performed. In a sense, it acts as its own dilator. The access device may also be thought of as a retractor, and may be referred to herein as such. Both the distal and proximal portion may be expanded, as discussed further below. However, the distal portion preferably expands to a greater extent than the proximal portion, because the surgical procedures are to be performed at the surgical site, which is adjacent the distal portion when the access device is inserted into the patient.

While in the reduced profile configuration, the access device preferably defines a first unexpanded configuration. Thereafter, the access device can enlarge the surgical space defined thereby by engaging the tissue surrounding the access device and displacing the tissue outwardly as the access device expands. The access device preferably is sufficiently rigid to displace such tissue during the expansion thereof. The access device may be resiliently biased to expand from the reduced profile configuration to the enlarged configuration. In addition, the access device may also be manually expanded by an expander device with or without one or more surgical instruments inserted therein, as will be described below. The surgical site preferably is at least partially defined by the expanded access device itself. During expansion, the access device can move from a first overlapping configuration to a second overlapping configuration.

In some embodiments, the proximal and distal portions are separate components that may be coupled together in a suitable fashion. For example, the distal end portion of the access device may be configured for relative movement with respect to the proximal end portion in order to allow the physician to position the distal end portion at a desired location. This relative movement also provides the advantage that the proximal portion of the access device nearest the physician D may remain substantially stable during such distal movement. In one embodiment, the distal portion is a separate component that is pivotally or movably coupled with the proximal portion. In another embodiment, the distal portion is flexible or resilient in order to permit such relative movement.

A. Systems and Devices for Establishing Access

1. Access Devices

One embodiment of an access device is illustrated in FIGS. 2-6 and designated by reference number 20. In one embodiment, the access device 20 includes a proximal wall portion 22 that has a tubular configuration, and a distal wall portion that has an expandable skirt portion 24. The skirt portion 24 preferably is enlargeable from a reduced profile configuration having an initial dimension 26 (illustrated in FIG. 2) and corresponding cross-sectional area, to an enlarged configuration having a second dimension 28 (illustrated in FIG. 4) and corresponding cross-sectional area. In one embodiment, the skirt portion 24 is coupled with the proximal wall portion 22 with a rivet 30, pin, or similar connecting device to permit movement of the skirt portion 24 relative to the proximal wall portion 22.

Figure 4:
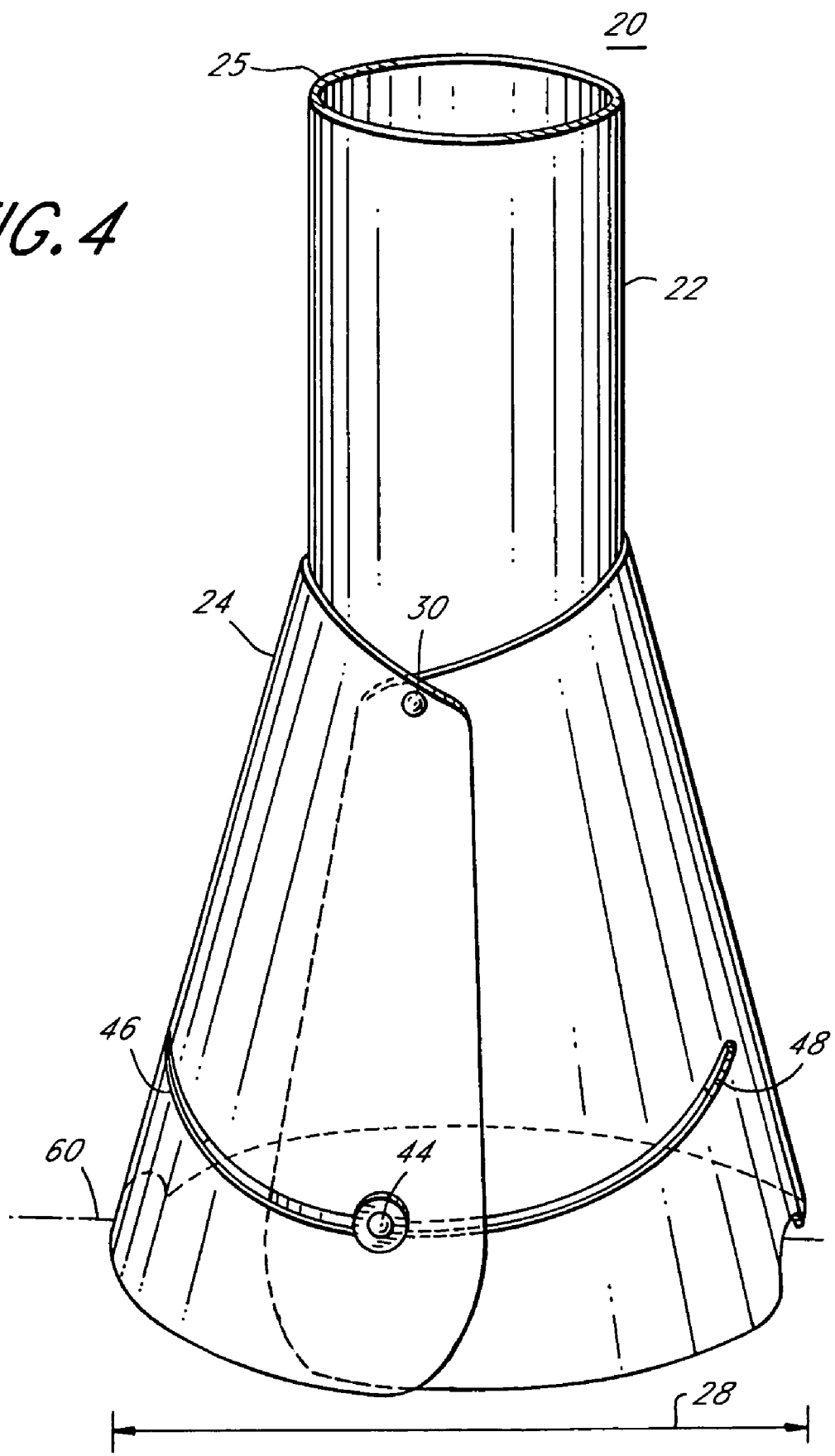
FIG. 4 is a perspective view of the access device of FIG. 2 in a second enlarged configuration.
Figure 6:
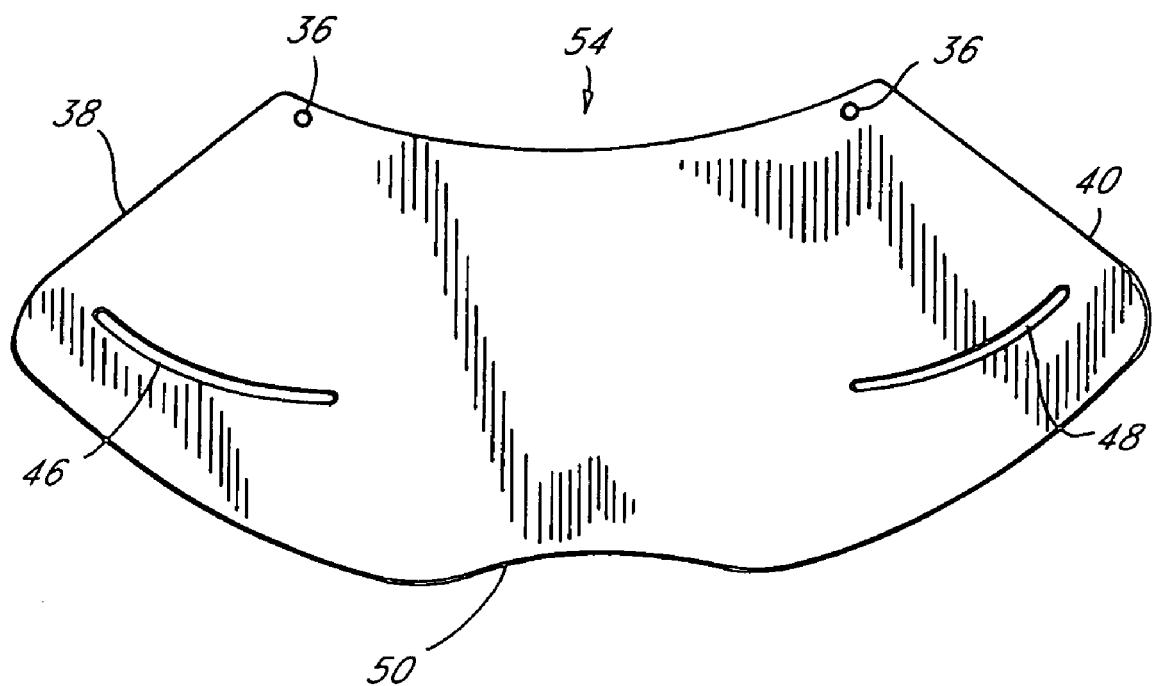
FIG. 6 is a view of another embodiment of a skirt portion of an access device.

In the illustrated embodiment, the skirt portion 24 is manufactured from a resilient material, such as stainless steel. The skirt portion 24 preferably is manufactured so that it normally assumes an expanded configuration as illustrated in FIG. 4. With reference to FIG. 3, the skirt portion 24 may assume an intermediate dimension 34 and corresponding cross-sectional area, which is greater than the initial dimension 26 of the reduced profile configuration of FIG. 2, and smaller than the dimension 28 of the enlarged configuration of FIG. 4. The skirt portion 24 may assume the intermediate configuration of FIG. 3 when deployed in the patient in response to the force of the tissue acting on the skirt portion 24. The intermediate dimension 34 can depend upon several factors, such as the rigidity of the skirt portion 24, the surrounding tissue, and whether such surrounding tissue has relaxed or tightened during the course of the procedure. An outer sleeve 32 (illustrated in dashed line in FIG. 2) may be provided. Preferably, the outer sleeve surrounds the access device 20 and maintains the skirt portion 24 in the reduced profile configuration prior to insertion into the patient. The outer sleeve 32 may be made of plastic. Where provided, the outer sleeve 32 preferably is configured to be easily deployed. For example, a release device may be provided that releases or removes the outer sleeve 32 upon being operated by the user. In one embodiment, a braided polyester suture is embedded within the sleeve 32, aligned substantially along the longitudinal axis thereof. In use, when the suture is withdrawn, the outer sleeve 32 is torn, allowing the access device 20 to resiliently expand from the reduced profile configuration of FIG. 2 to the expanded configurations of FIGS. 3-4. While in the reduced profile configuration of FIG. 2, the skirt portion 24 defines a first overlapping configuration 33, as illustrated by the dashed line. As the skirt portion 24 resiliently expands, the skirt portion 24 assumes the expanded configuration, as illustrated in FIGS. 3-4.

The skirt portion 24 preferably is sufficiently rigid that it is capable of displacing the tissue surrounding the skirt portion 24 as it expands. Depending upon the resistance exerted by surrounding tissue, the skirt portion 24 preferably is sufficiently rigid to provide some resistance against the tissue to remain in the configurations of FIGS. 3-4. Moreover, the expanded configuration of the skirt portion 24 is at least partially supported by the body tissue of the patient. The rigidity of the skirt portion 24 and the greater expansion at the distal portion preferably creates a stable configuration that is at least temporarily stationary in the patient. This arrangement preferably frees the physician from the need to actively support the access device 20, e.g., prior to adding an endoscope mount platform 300 and a support arm 400 (see FIGS. 21-22).

Figure 5:
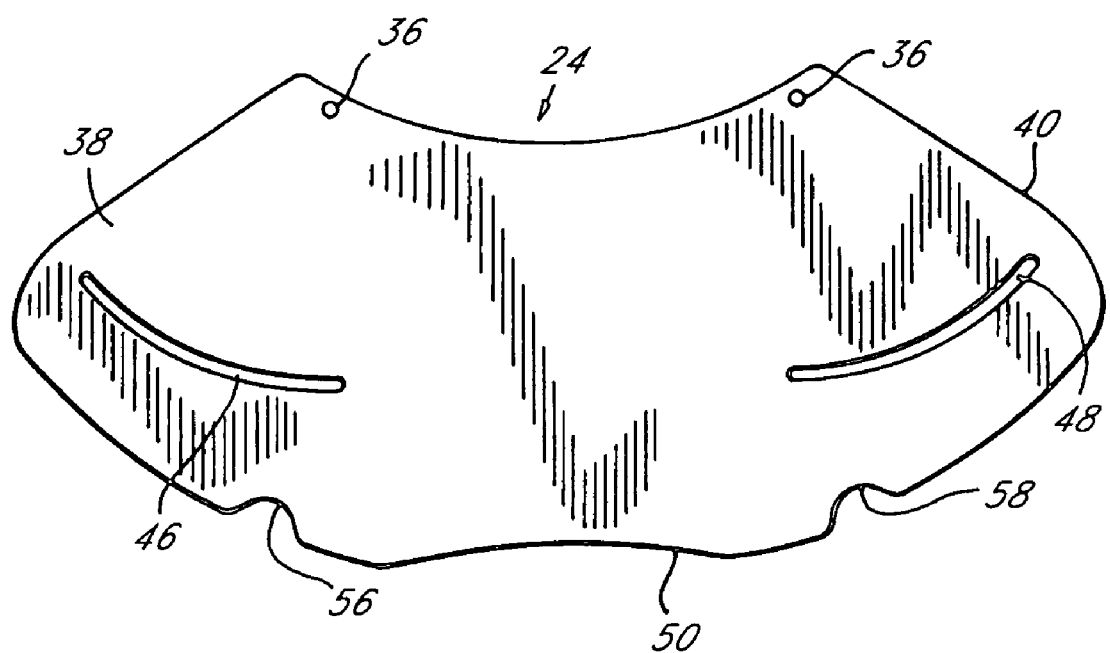
FIG. 5 is a view of one embodiment of a skirt portion of an access device.

One embodiment of the skirt portion 24 of the access device 20 is illustrated in an initial flattened configuration in FIG. 5. The skirt portion 24 may be manufactured from a sheet of stainless steel having a thickness of about 0.007 inches (0.178 mm). In various embodiments, the dimension 28 of the skirt portion 24 is about equal to or greater than 50 mm, is about equal to or greater than 60 mm, is about equal to or greater than 70 mm, is about equal to or greater than 80 mm, or is any other suitable size, when the skirt portion 24 is in the enlarged configuration. In one embodiment, the dimension 28 is about 63 mm, when the skirt portion 24 is in the enlarged configuration. The unrestricted shape of the skirt portion 24 is a circular shape in one embodiment and is an oblong shape in another embodiment. In another embodiment, the skirt portion 24 has an oval shape, wherein the dimension 28 defines a longer dimension of the skirt portion 24 and would be about 85 mm. In another embodiment, the skirt portion 24 has an oval shape and the dimension 28 defines a longer dimension of the skirt portion 24 of about 63 mm. An increased thickness, e.g., about 0.010 inches (0.254 mm), may be used in connection with skirt portions having a larger diameter, such as about 65 mm. Other materials, such as nitinol or plastics having similar properties, may also be useful.

As discussed above, the skirt portion 24 preferably is coupled with the proximal wall portion 22 with a pivotal connection, such as rivet 30. A pair of rivet holes 36 can be provided in the skirt portion 24 to receive the rivet 30. The skirt portion 24 also has two free ends 38 and 40 in one embodiment that are secured by a slidable connection, such as a second rivet 44 (not shown in FIG. 5, illustrated in FIGS. 2-4). A pair of complementary slots 46 and 48 preferably are defined in the skirt portion 24 adjacent the free ends 38 and 40. The rivet 44 is permitted to move freely within the slots 46 and 48. This slot and rivet configuration allows the skirt portion 24 to move between the reduced profile configuration of FIG. 2 and the enlarged or expanded configurations of FIGS. 3-4. The use of a pair of slots 46 and 48 reduces the risk of the "button-holing" of the rivet 44, e.g., a situation in which the opening of the slot becomes distorted and enlarged such that the rivet may slide out of the slot, and cause failure of the device. The likelihood of such occurrence is reduced in skirt portion 24 because each of the slots 46 and 48 in the double slot configuration has a relatively shorter length than a single slot configuration. Being shorter, the slots 46, 48 are less likely to be distorted to the extent that a rivet may slide out of position. In addition, the configuration of rivet 44 and slots 46 and 48 permits a smoother operation of enlarging and reducing the skirt portion 24, and allows the skirt portion 24 to expand to span three or more vertebrae, e.g., L4, L5, and S1. This arrangement enables multi-level procedures, such as multilevel fixation procedures alone or in combination with a variety of other procedures, as discussed below. Other embodiments include a single slot rather than the slots 46, 48, or more than two slots.

An additional feature of the skirt portion 24 is the provision of a shallow concave profile 50 defined along the distal edge of the skirt portion 24, which allows for improved placement of the skirt portion 24 with respect to the body structures and the surgical instruments defined herein. In one embodiment, a pair of small scalloped or notched portions 56 and 58 are provided, as illustrated in FIG. 5. When the skirt portion 24 is assembled, the notched portions 56 and 58 are generally across from each other. When the skirt portion 24 is applied to a patient, the notched portions 56, 58 are oriented in the cephcaudal direction (indicated by a dashed line 60 in FIG. 4). In this arrangement, instruments and implants, such as an elongated member 650 used in a fixation procedure (described in detail below), may extend beyond the area enclosed by the skirt portion 24 without moving or raising the skirt portion 24, e.g., by allowing the elongated member 650 (or other implant or instrument) to pass under the skirt portion 24. The notched portions 56, 58 also enable the elongated member 650 (or other implant or instrument) to extend beyond the portion of the surgical space defined within the outline of the distal end of the skirt portion 24. The notched portions 56, 58 are optional, as illustrated in connection with another embodiment of an access device 54, illustrated in FIG. 6, and may be eliminated if, for example, the physician deems the notches to be unnecessary for the procedures to be performed. For example, in some fixation procedures such extended access is not needed, as discussed more fully below. As illustrated in FIG. 4, the skirt portion 24 may be expanded to a substantially conical configuration having a substantially circular or elliptical profile.

Furthermore, it is contemplated that the skirt portion 24 of the access device 20 can include a stop that retains the skirt portion in an expanded configuration, as shown in U.S. patent application Ser. No. 10/361,887, filed Feb. 10, 2003, now U.S. Application Patent Publication No. US2003/153927 A1, which is hereby incorporated by reference in its entirety herein.

In another embodiment, features may be provided on the skirt portion 24 which facilitate the bending of the skirt portion at several locations to provide a pre-formed enlarged configuration. For example, another embodiment of an access device 70, illustrated in FIGS. 7-9, provides a skirt portion 74 that has four sections 76a, 76b, 76c, 76d having a reduced thickness. For a skirt portion 74 having a thickness 78 of about 0.007 inches (0.178 mm), reduced thickness sections 76a, 76b, 76c, 76d may have a thickness 80 of about 0.002-0.004 inches (0.102 mm) (FIG. 8). The reduced thickness sections 76a, 76b, 76c, 76d may have a width 82 of about 1-5 mm. The thickness 78 of the skirt portion 74 may be reduced by milling or grinding, as is known in the art. When the skirt portion 74 is opened, it moves toward a substantially rectangular configuration, as shown in FIG. 9, subject to the resisting forces of the body tissue. In another embodiment (not shown), a skirt portion may be provided with two reduced thickness sections (rather than the four reduced thickness sections of skirt 74) which would produce an oblong, substantially "football"-shaped access area.

FIGS. 10-12 show another embodiment of an access device 80. The access device 80 has a skirt portion 84 with a plurality of perforations 86. The perforations 86 advantageously increase the flexibility at selected locations. The size and number of perforations 86 may vary depending upon the desired flexibility and durability. In another embodiment, the skirt portion 84 may be scored or otherwise provided with a groove or rib in order to facilitate the bending of the skirt portion at the desired location.

Figure 13:
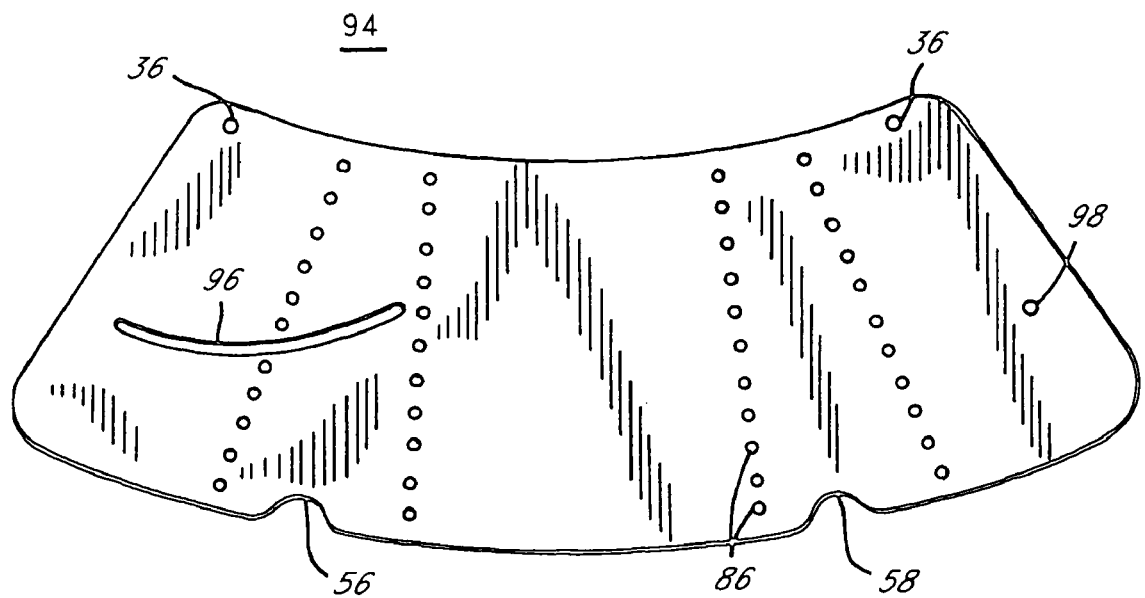
FIG. 13 is a view of a portion of another embodiment of the access device.
Figure 14:
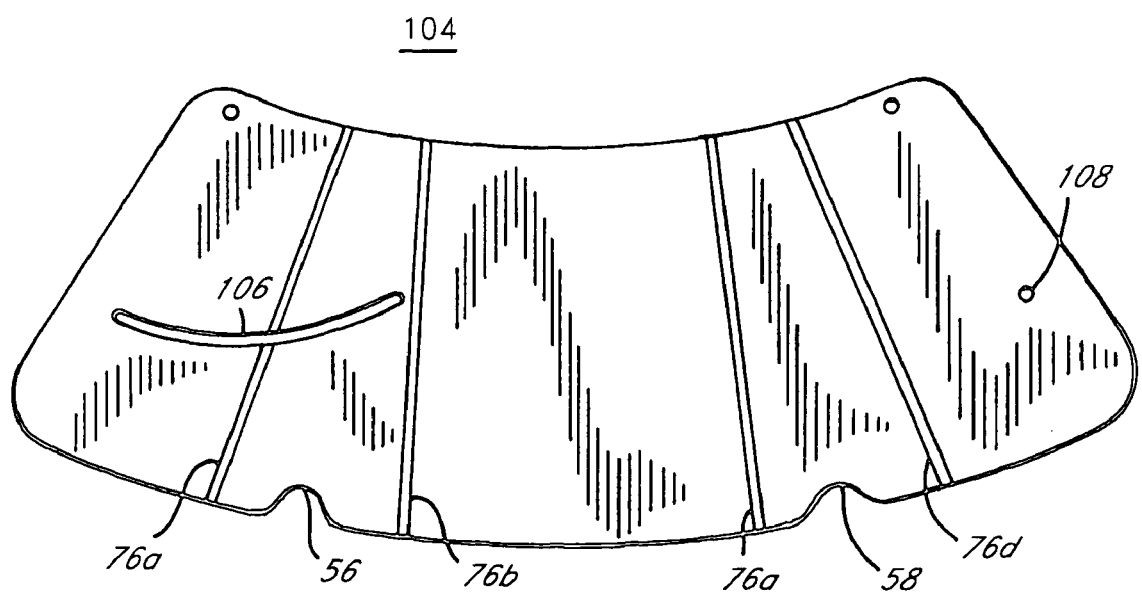
FIG. 14 is a view of a portion of another embodiment of the access device.

FIG. 13 illustrates another embodiment of an access device that has a skirt portion 94 having one slot 96 and an aperture 98. A rivet (not shown) is stationary with respect to the aperture 98 and slides within the slot 96. FIG. 14 illustrates another embodiment of an access device that has a skirt portion 104 that includes an aperture 108. The apertures 108 receives a rivet (not shown) that slides within elongated slot 106.

Another embodiment of an access device comprises an elongate body defining a passage and having a proximal end and a distal end. The elongate body has a proximal portion and a distal portion. The proximal portion has an oblong or generally oval shaped cross section in one embodiment. The term "oblong" is used in its ordinary sense (i.e., having an elongated form) and is a broad term and it includes a structure having a dimension, especially one of two perpendicular dimensions, such as, for example, width or length, that is greater than another and includes shapes such as rectangles, ovals, ellipses, triangles, diamonds, trapezoids, parabolas, and other elongated shapes having straight or curved sides. The term "oval" is used in its ordinary sense (i.e., egg like or elliptical) and is a broad term and includes oblong shapes having curved portions.

The proximal portion comprises an oblong, generally oval shaped cross section over the elongated portion. It will be apparent to those of skill in the art that the cross section can be of any suitable oblong shape. The proximal portion can be any desired size. The proximal portion can have a cross-sectional area that varies from one end of the proximal portion to another end. For example, the cross-sectional area of the proximal portion can increase or decrease along the length of the proximal portion. Alternatively, the proximal portion can have a constant cross section over its length. Preferably, the proximal portion is sized to provide sufficient space for inserting multiple surgical instruments through the elongate body to the surgical location. The distal portion preferably is expandable and may comprise first and second overlapping skirt members. The degree of expansion of the distal portion is determined by an amount of overlap between the first skirt member and the second skirt member in one embodiment.

The elongate body of the access device has a first location distal of a second location. The elongate body preferably is capable of having a configuration when inserted within the patient wherein the cross-sectional area of the passage at the first location is greater than the cross-sectional area of the passage at the second location. The passage preferably is capable of having an oblong shaped cross section between the second location and the proximal end. In some embodiments the passage preferably is capable of having a generally elliptical cross section between the second location and the proximal end. Additionally, the passage preferably is capable of having a non-circular cross section between the second location and the proximal end. Additionally, in some embodiments, the cross section of the passage can be symmetrical about a first axis and a second axis, the first axis being generally normal to the second axis. Other embodiments having an oblong cross-section are discussed below in connection with FIGS. 67-73B.

Further details and features pertaining to access devices and systems are described in U.S. Pat. No. 6,652,553, application Ser. No. 10/361,887, filed Feb. 10, 2003, application Ser. No. 10/280,489, filed Oct. 25, 2002, and application Ser. No. 10/678,744 filed Oct. 2, 2003, which are incorporated by reference in their entireties herein.

2. Dilators and Expander Devices

According to one embodiment of a procedure, an early stage involves determining a point in the skin of the patient at which to insert the access device 20. The access point preferably corresponds to a posterior-lateral aspect of the spine. Manual palpation and Anterior-Posterior (AP) fluoroscopy may be used to determine preferred or optimal locations for forming an incision in the skin of the patient. In one application, the access device 20 preferably is placed midway (in the cephcaudal direction) between the L4 through S1 vertebrae, centrally about 4-7 cm from the midline of the spine.

After the above-described location is determined, an incision is made at the location. A guide wire (not shown) is introduced under fluoroscopic guidance through the skin, fascia, and muscle to the approximate surgical site. A series of dilators is used to sequentially expand the incision to the desired width, about 23 mm in one procedure, preferably minimizing damage to the structure of surrounding tissue and muscles. A first dilator can be placed over the guide wire to expand the opening. The guide wire may then be removed. A second dilator, slightly larger than the first dilator, is placed over the first dilator to expand the opening further. Once the second dilator is in place, the first dilator may be removed. This process of (1) introducing a next-larger-sized dilator coaxially over the previous dilator and (2) optionally removing the previous dilator(s) when the next-larger-sized dilator is in place continues until an opening of the desired size is created in the skin, muscle, and subcutaneous tissue. According to one application, the desired opening size is about 23 mm. (Other dimensions of the opening, e.g., about 20 mm, about 27 mm, about 30 mm, etc., are also useful with this apparatus in connection with spinal surgery, and still other dimensions are contemplated.)

Figure 15:
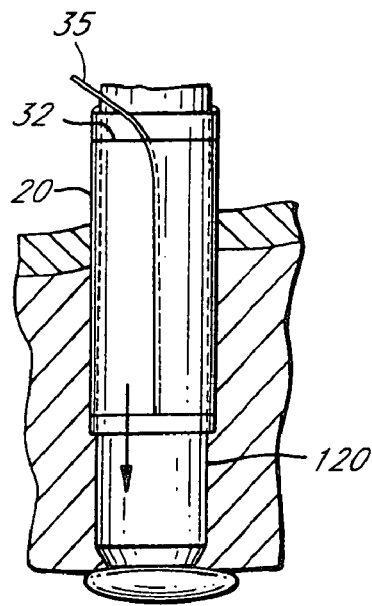
FIG. 15 is a sectional view illustrating one embodiment of a stage of one embodiment of a method for treating the spine of a patient.

FIG. 15 shows that following placement of a dilator 120, which is the largest dilator in the above-described dilation process, the access device 20 is introduced in its reduced profile configuration and positioned over the dilator 120. The dilator 120 is subsequently removed from the patient, and the access device 20 remains in position.

Once positioned in the patient, the access device 20 may be enlarged to provide a passage for the insertion of various surgical instruments and to provide an enlarged space for performing the procedures described herein. As described above, the access device may achieve the enlargement in several ways. In one embodiment, a distal portion of the access device may be enlarged, and a proximal portion may maintain a constant diameter. The relative lengths of the proximal portion 22 and the skirt portion 24 may be adjusted to vary the overall expansion of the access device 20. Alternatively, such expansion may extend along the entire length of the access device 20. In one application, the access device 20 may be expanded by removing a suture 35 and tearing the outer sleeve 32 surrounding the access device 20, and subsequently allowing the skirt portion 24 to resiliently expand towards its fully expanded configuration as (illustrated in FIG. 4) to create an enlarged surgical space from the L4 to the S1 vertebrae. The resisting force exerted on the skirt portion 24 may result in the skirt portion 24 assuming the intermediate configuration illustrated in FIG. 3. Under many circumstances, the space created by the skirt portion 24 in the intermediate configuration is a sufficiently large working space to perform the procedure described herein. Once the skirt portion 24 has expanded, the rigidity and resilient characteristics of the skirt portion 24 preferably allow the access device 20 to resist closing to the reduced profile configuration of FIG. 2 and to at least temporarily resist being expelled from the incision. These characteristics create a stable configuration for the access device 20 to remain in position in the body, supported by the surrounding tissue. It is understood that additional support may be needed, especially if an endoscope is added.

According to one embodiment of a procedure, the access device 20 may be further enlarged at the skirt portion 24 using an expander apparatus to create a surgical access space. An expander apparatus useful for enlarging the access device has a reduced profile configuration and an enlarged configuration. The expander apparatus is inserted into the access device in the reduced profile configuration, and subsequently expanded to the enlarged configuration. The expansion of the expander apparatus also causes the access device to be expanded to the enlarged configuration. In some embodiments, the expander apparatus may increase the diameter of the access device along substantially its entire length in a generally conical configuration. In other embodiments, the expander apparatus expands only a distal portion of the access device, allowing a proximal portion to maintain a relatively constant diameter.

In addition to expanding the access device, in some embodiments the expander apparatus may also be used to position the distal portion of the access device at the desired location for the surgical procedure. The expander can engage an interior wall of the access device to move the access device to the desired location. For embodiments in which the distal portion of the access device is relatively movable with respect to the proximal portion, the expander apparatus is useful to position the distal portion without substantially disturbing the proximal portion.

Figure 17:
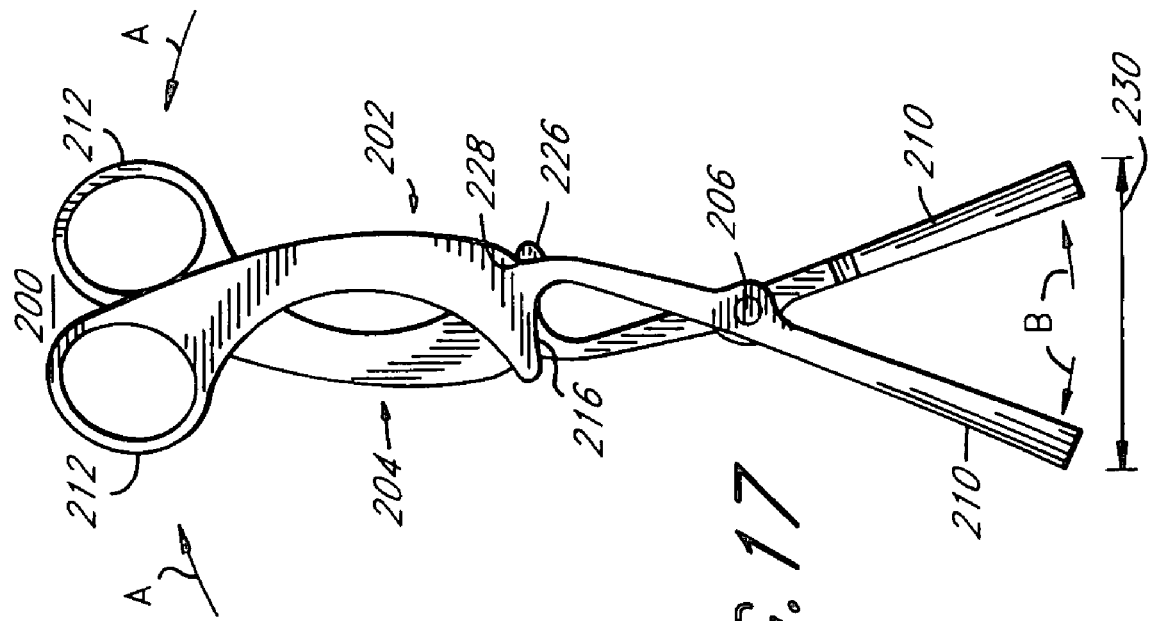
FIG. 17 is a side view of the expander apparatus of FIG. 16 in an expanded configuration.
Figure 16:
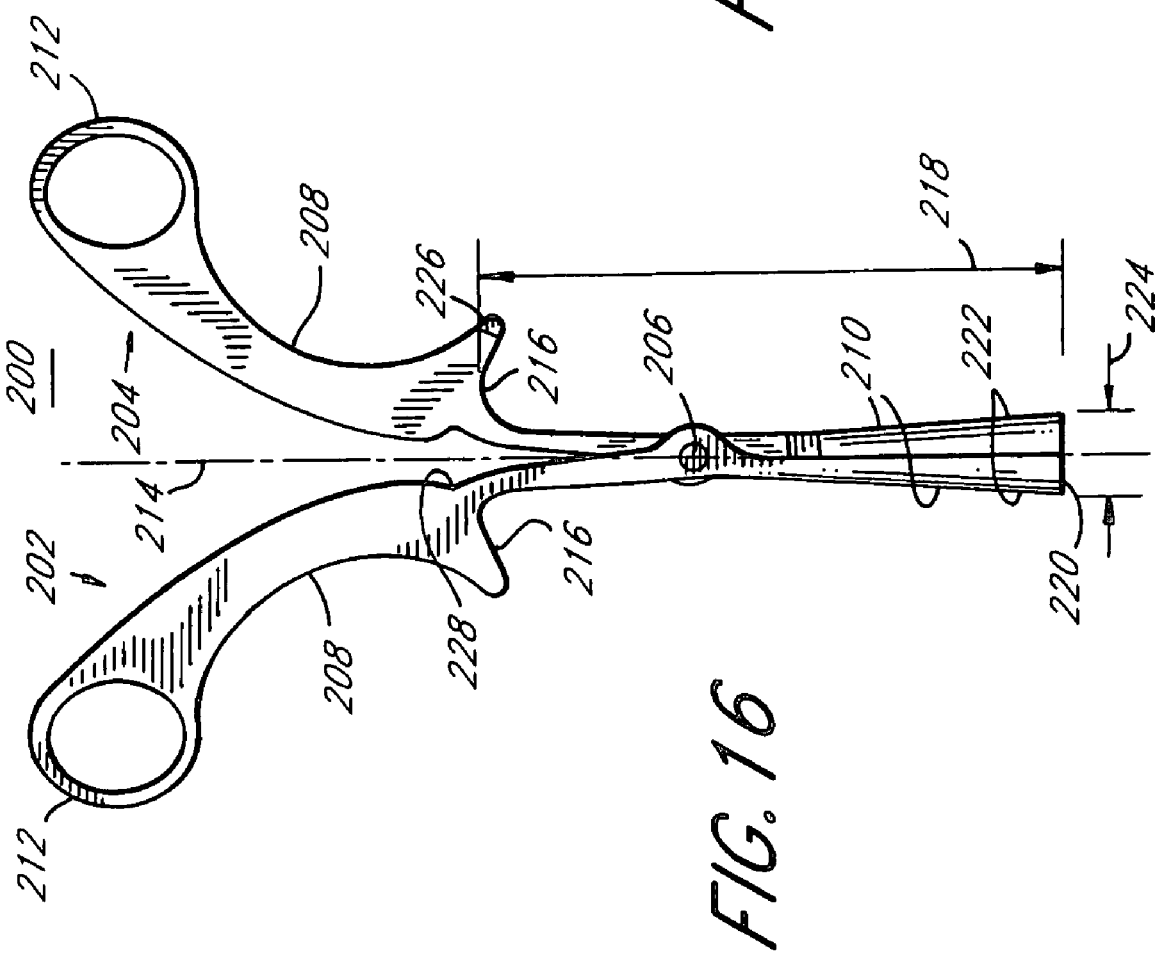
FIG. 16 is a side view of one embodiment of an expander apparatus in a reduced profile configuration.
Figure 20:
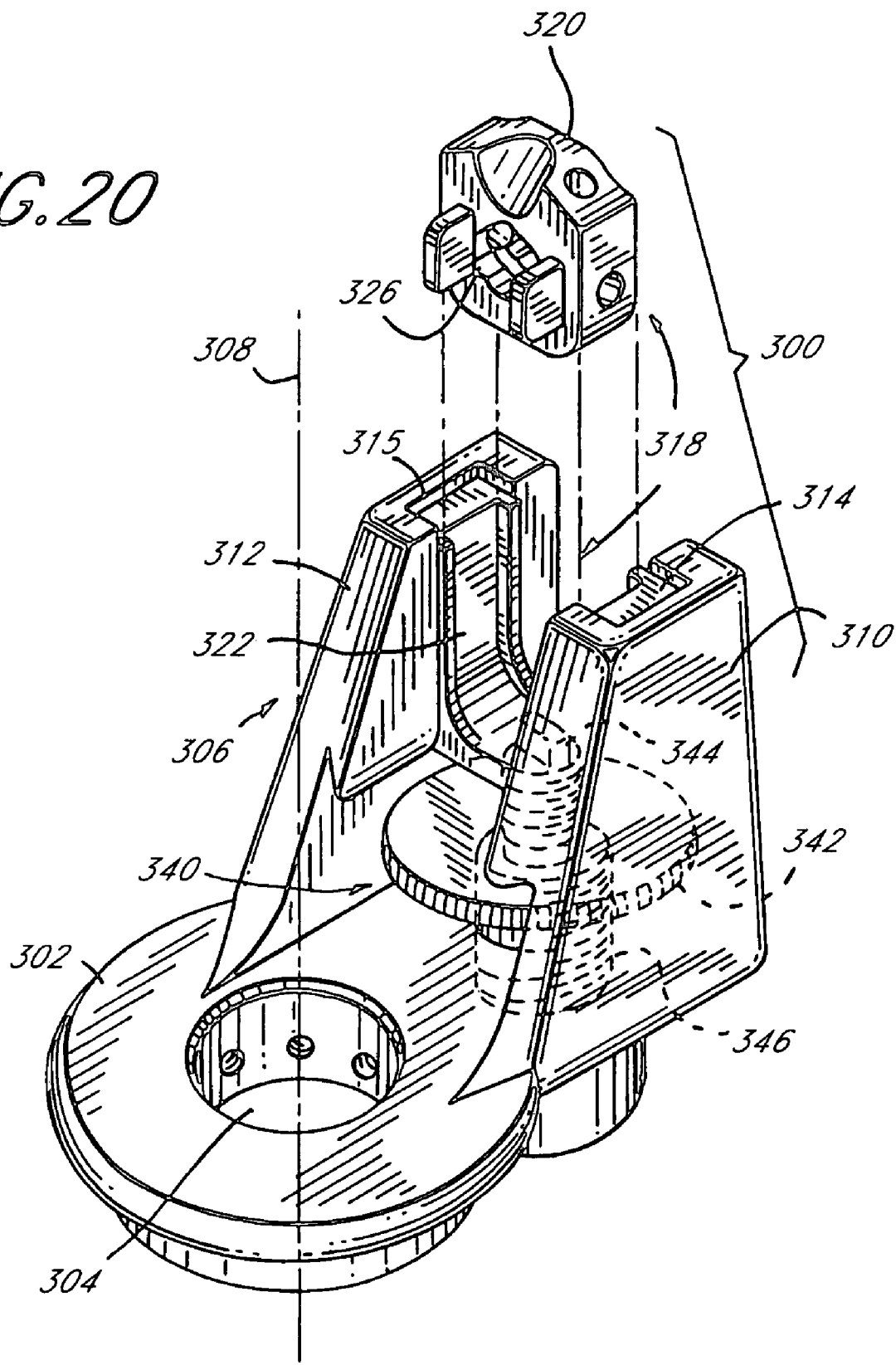
FIG. 20 is an exploded perspective view of one embodiment of an endoscope mount platform.

In some procedures, an expander apparatus is used to further expand the skirt portion 24 towards the enlarged configuration (illustrated in FIG. 4). The expander apparatus is inserted into the access device, and typically has two or more members that are movable to engage the interior wall of the skirt portion 24 and apply a force sufficient to further expand the skirt portion 24. FIGS. 16 and 17 show one embodiment of an expander apparatus 200 that has a first component 202 and a second component 204. The first component 202 and the second component 204 of the expander apparatus 200 are arranged in a tongs-like configuration and are pivotable about a pin 206. The first and second components 202 and 204 can be constructed of steel having a thickness of about 9.7 mm. Each of the first and second components 202 and 204 has a proximal handle portion 208 and a distal expander portion 210. Each proximal handle portion 208 has a finger grip 212 that may extend transversely from an axis, e.g., a longitudinal axis 214, of the apparatus 200. The proximal handle portion 208 may further include a stop element, such as flange 216, that extends transversely from the longitudinal axis 214. The flange 216 preferably is dimensioned to engage the proximal end 25 of the access device 20 when the apparatus 200 is inserted a predetermined depth. This arrangement provides a visual and tactile indication of the proper depth for inserting the expander apparatus 200. In one embodiment, a dimension 218 from the flange 216 to the distal tip 220 is about 106 mm. The dimension 218 is determined by the length of the access device 20, which in turn is a function of the depth of the body structures beneath the skin surface at which the surgical procedure is to be performed. The distal portions 210 are each provided with an outer surface 222 for engaging the inside wall of the skirt portion 24. The outer surface 222 is a frusto-conical surface in one embodiment. The expander apparatus 200 has an unexpanded distal width 224 at the distal tip 220 that is about 18.5 mm in one embodiment.

In use, the finger grips 212 are approximated towards one another, as indicated by arrows A in FIG. 17, which causes the distal portions 210 to move to the enlarged configuration, as indicated by arrows B. The components 202 and 204 are also provided with a cooperating tab 226 and shoulder portion 228 which are configured for mutual engagement when the distal portions 210 are in the expanded configuration. In the illustrated embodiment, the expander apparatus 200 has an expanded distal width 230 that extends between the distal portions 210. The expanded distal width 230 can be about 65 mm or less, about as large as 83 mm or less, or any other suitable width. The tab 226 and shoulder portion 228 together limit the expansion of the expander apparatus 200 to prevent expansion of the skirt portion 24 of the access device 20 beyond its designed dimension, and to minimize trauma to the underlying tissue. Further features related to the expander apparatus are described in U.S. Pat. No. 6,652,553, issued Nov. 25, 2003, which is incorporated by reference in its entirety herein.

When the access device 20 is inserted into the patient and the outer sleeve 32 is removed, the skirt portion 24 expands to a point where the outward resilient expansion of the skirt portion 24 is balanced by the force of the surrounding tissue. The surgical space defined by the access device 20 may be sufficient to perform any of a number of surgical procedures or combination of surgical procedures described herein. However, if it is desired to expand the access device 20 further, the expander apparatus 200, or a similar device, may be inserted into the access device 20 in the reduced profile configuration until the shoulder portions 216 are in approximation with the proximal end 25 of the skirt portion 24 of the access device 20, as shown in FIG. 18.

Figure 18:
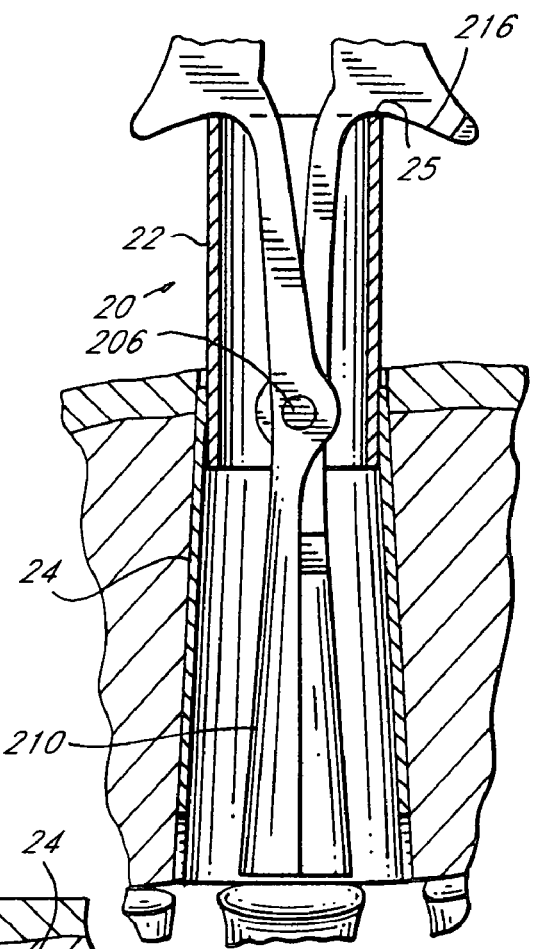
FIG. 18 is a sectional view of the expander apparatus of FIGS. 16-17 inserted into the access device of FIG. 2, which has been inserted into a patient.
Figure 19:
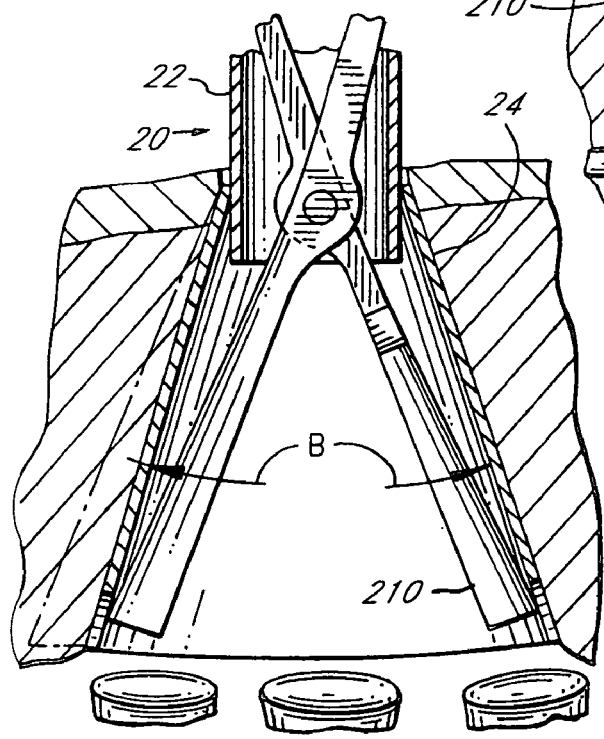
FIG. 19 is a sectional view of the expander apparatus of FIGS. 16-17 inserted into the access device of FIG. 2 and expanded to the expanded configuration to retract tissue.

FIG. 18 shows the expander apparatus 200 inserted in the access device 20 in the reduced profiled configuration. Expansion of the expander apparatus 200 is achieved by approximating the handle portions 212 (not shown in FIG. 18), which causes the distal portions 210 of the expander apparatus 200 to move to a spaced apart configuration. As the distal portions 210 move apart and contact the inner wall of the skirt portion 24, the rivet 44 is allowed to slide within the slots 46 and 48 of the skirt portion 24, thus permitting the skirt portion 24 to expand. When the distal portions 210 reach the maximum expansion of the skirt portion 24 (illustrated by a dashed line in FIG. 19), the tab 226 and shoulder portion 228 of the expander apparatus 200 come into engagement to prevent further expansion of the tongs-like portions (as illustrated in FIG. 17). Alternatively, the access device 20 may be expanded with another device that can selectively have a reduced profile configuration and an expanded configuration, e.g., a balloon or similar device.

An optional step in the procedure is to adjust the location of the distal portion of the access device 20 relative to the body structures to be operated on. For example, the expander apparatus 200 may also be used to engage the inner wall of the skirt portion 24 of the access device 20 in order to move the skirt portion 24 of the access device 20 to the desired location. For an embodiment in which the skirt portion 24 of the access device 20 is relatively movable relative to the proximal portion, e.g. by use of the rivet 30, the expander apparatus 200 is useful to position the skirt portion 24 without substantially disturbing the proximal portion 22 or the tissues closer to the skin surface of the patient. As will be described below, the ability to move the distal end portion, e.g., the skirt portion 24, without disturbing the proximal portion is especially beneficial when an additional apparatus is coupled with the proximal portion of the access device, as described below.

B. Systems and Devices for Stabilization and Visualization

Some procedures can be conducted through the access device 20 without any additional peripheral components being connected thereto. In other procedures it may be beneficial to provide at least one of a support device and a viewing element. As discussed more fully below, support devices can be advantageously employed to provide support to peripheral equipment and to surgical tools of various types. Various embodiments of support devices and viewing elements are discussed herein below.

1. Support Devices

One type of support device that can be coupled with the access device 20 is a device that supports a viewing element. In one embodiment, an endoscope mount platform 300 and indexing arm 400 support an endoscope 500 on the proximal end 25 of the access device 20 for remotely viewing the surgical procedure, as illustrated in FIGS. 20-23. The endoscope mount platform 300 may also provide several other functions during the surgical procedure. The endoscope mount platform 300 preferably includes a base 302 that extends laterally from a central opening 304 in a generally ring-shaped configuration. In one application, the physician views the procedure primarily by observing a monitor, when inserting surgical instruments into the central opening 304. The base 302 advantageously enables the physician by providing a visual indicator (in that it may be observable in the physician's peripheral vision) as well as tactile feedback as instruments are lowered towards the central opening 304 and into the access device 20.

The endoscope mount platform 300 preferably has a guide portion 306 at a location off-set from the central opening 304 that extends substantially parallel to a longitudinal axis 308. The base 302 can be molded as one piece with the guide portion 306. The base 302 and guide portion 306 may be constructed with a suitable polymer, such as, for example, polyetheretherketone (PEEK).

The guide portion 306 includes a first upright member 310 that extends upward from the base 302 and a second upright member 312 that extends upward from the base 302. In one embodiment, the upright members 310, 312 each have a respective vertical groove 314 and 315 that can slidably receive an endoscopic mount assembly 318.

Figure 25:
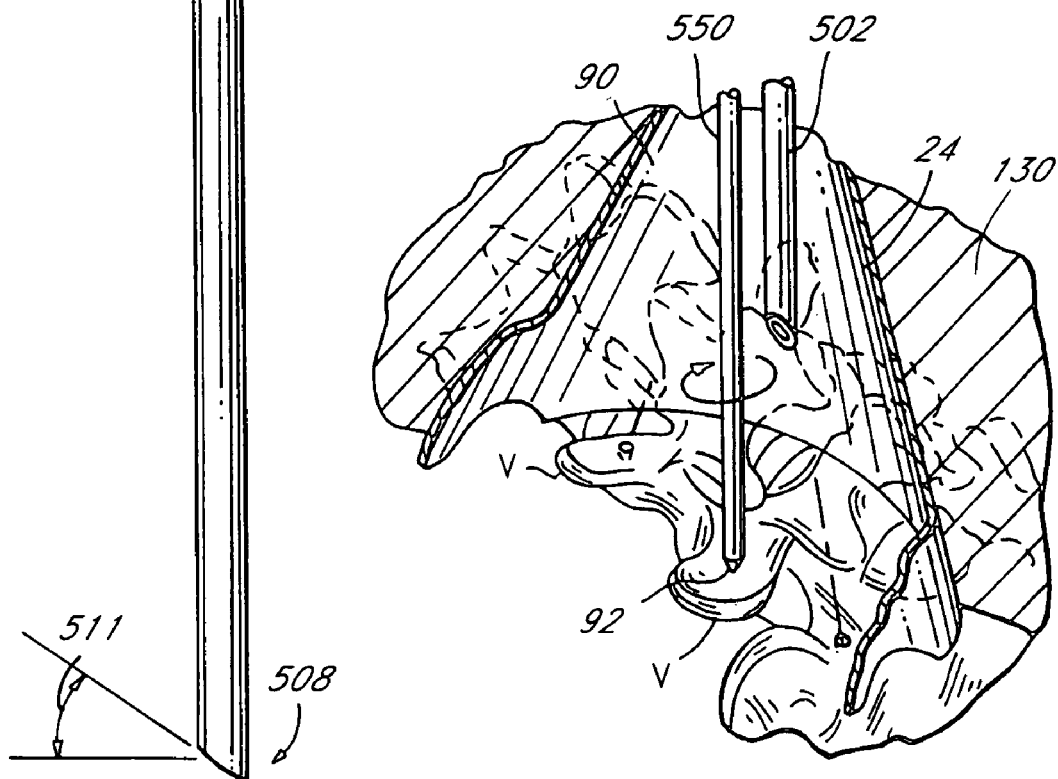
FIG. 25 is a partial sectional view of one embodiment of a stage of one embodiment of a method for treating the spine of a patient.

The endoscope 500 (not shown in FIG. 20) can be movably mounted to the endoscope mount platform 300 with the endoscope mount assembly 318 in one embodiment. The endoscope mount assembly 318 includes an endoscope mount 320 and a saddle unit 322. The saddle unit 322 is slidably mounted within the grooves 314 and 315 in the upright members 310 and 312. The endoscope mount 320 receives the endoscope 500 through a bore 326 which passes through the endoscope mount 320. Part of the endoscope 500 may extend through the access device 20 substantially parallel to longitudinal axis 308 into the patient's body 130, as shown in FIG. 25.

The endoscope mount 320 is removably positioned in a recess 328 defined in the substantially "U"-shaped saddle unit 322. In one embodiment, the saddle unit 322 is selectively movable in a direction parallel to the longitudinal axis 308 in order to position the endoscope 500 at the desired height within the access device 20. The movement of the endoscope 500 by way of the saddle unit 322 also advantageously enables the physician to increase visualization of a particular portion of the surgical space defined by the access device, e.g., by way of a zoom feature, as required for a given procedure or a step of a procedure.

In one embodiment, an elevation adjustment mechanism 340, which may be a screw mechanism, is positioned on the base 302 between the upright members 310 and 312. The elevation adjustment mechanism 340 can be used to selectively move a viewing element, e.g., the endoscope 500 by way of the saddle unit 322. In one embodiment, the elevation adjustment mechanism 340 comprises a thumb wheel 342 and a spindle 344. The thumb wheel 343 is rotatably mounted in a bore in the base 302. The thumb wheel 342 has an external thread 346 received in a cooperating thread in the base 302. The spindle 344 is mounted for movement substantially parallel to the central axis 308. The spindle 344 preferably has a first end received in a rectangular opening in the saddle unit 322, which inhibits rotational movement of the spindle 344. The second end of the spindle 344 has an external thread that cooperates with an internal thread formed in a bore within the thumb wheel 342. Rotation of the thumb wheel 342 relative to the spindle 344 causes relative axial movement of the spindle unit 344 along with the saddle unit 322. Further details and features related to endoscope mount platforms are described in U.S. Pat. Nos. 6,361,488, issued Mar. 26, 2002; 6,530,880, issued Mar. 11, 2003, and U.S. patent application Ser. No. 09/940,402, filed Aug. 27, 2001, published as Publication No. 2003/0040656 on Feb. 27, 2003, which are incorporated by reference in their entireties herein.

Figure 21:
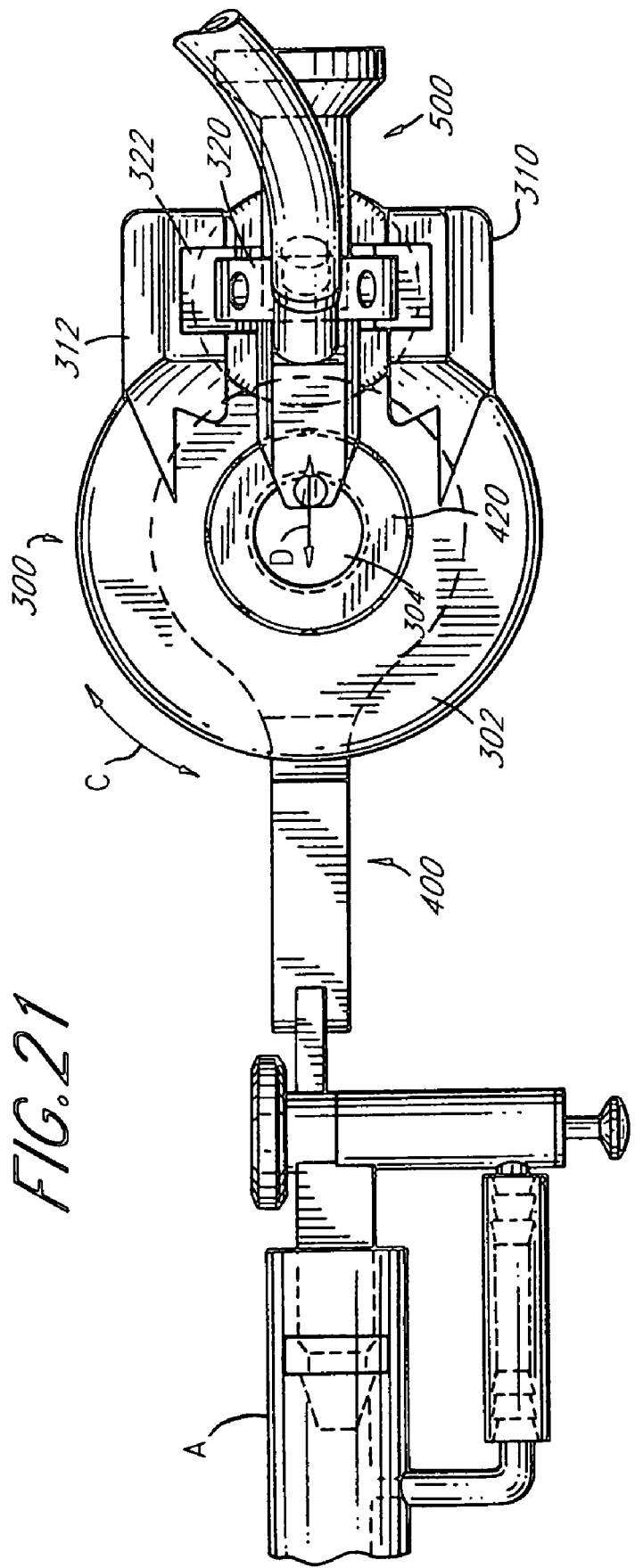
FIG. 21 is a top view of the endoscope mount platform of FIG. 20 coupled with one embodiment of an indexing arm and one embodiment of an endoscope.

FIGS. 21-23 show that the endoscope mount platform 300 is mountable to the support arm 400 in one embodiment. The support arm 400, in turn, preferably is mountable to a mechanical support, such as mechanical support arm A, discussed above in connection with FIG. 1. The support arm 400 preferably rests on, or is otherwise coupled with, the proximal end 25 of the access device 20. In one embodiment, the support arm 400 is coupled with an indexing collar 420, which is configured to be received in the central opening 304 of the base 302 of endoscope mount platform 300. The indexing collar 420 is substantially toroidal in section and has an outer peripheral wall surface 422, an inner wall surface 424, and a wall thickness 426 that is the distance between the wall surfaces 422, 424. The indexing collar 420 further includes a flange 428, which supports the indexing collar 420 on the support arm 400.

In one embodiment, a plurality of collars 420 may be provided to make the surgical system 10 modular in that different access devices 20 may be used with a single endoscope mount platform 300. For example, access devices 20 of different dimensions may be supported by providing indexing collars 420 to accommodate each access device size while using a single endoscope mount platform 300. The central opening 304 of the endoscope mount platform 300 can have a constant dimension, e.g., a diameter of about 32.6 mm. An appropriate indexing collar 420 is selected, e.g., one that is appropriately sized to support a selected access device 20. Thus, the outer wall 422 and the outer diameter 430 are unchanged between different indexing collars 420, although the inner wall 424 and the inner diameter 432 vary to accommodate differently sized access devices 20.

The indexing collar 420 can be positioned at or rested on the proximal portion of the access device 20 to allow angular movement of the endoscope mount platform 300 with respect thereto about the longitudinal axis 308 (as indicated by an arrow C in FIG. 21). The outer wall 422 of the index collar 420 includes a plurality of hemispherical recesses 450 that can receive one or more ball plungers 350 on the endoscope mount platform 300 (indicated in dashed line). This arrangement permits the endoscope mount platform 300, along with the endoscope 500, to be fixed in a plurality of discrete angular positions. Further details and features related to support arms and indexing collars are described in U.S. Pat. No. 6,361,488, issued Mar. 26, 2002, U.S. Pat. No. 6,530,880 issued Mar. 11, 2003, and application Ser. No. 09/940,402 filed Aug. 27, 2001, published as Publication No. 2003/0040656 on Feb. 27, 2003, which are incorporated by reference in their entireties herein.

2. Viewing Elements

As discussed above, a variety of viewing elements and visualization techniques are embodied in variations of the surgical system 10. One viewing element that is provided in one embodiment is an endoscope.

Figure 24:
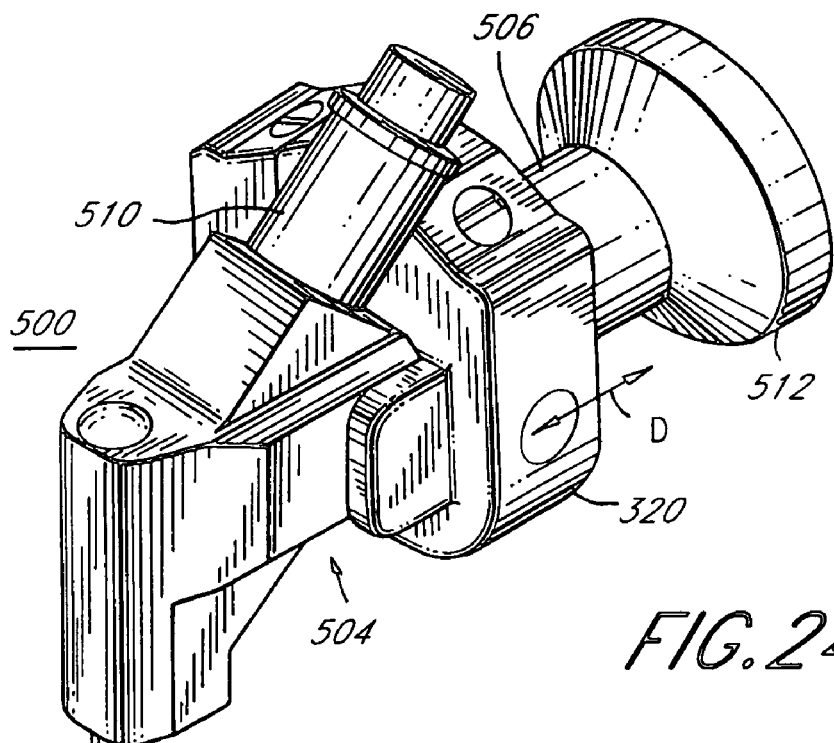
FIG. 24 is a perspective view of one embodiment of an endoscope.

FIG. 24 shows one embodiment of the endoscope 500 that has an elongated configuration that extends into the access device 20 in order to enable viewing of the surgical site. In particular, the endoscope 500 has an elongated rod portion 502 and a body portion 504. The rod portion 502 extends generally perpendicularly from the body portion 504. In one embodiment, the rod portion 502 of endoscope 500 has a diameter of about 4 mm and a length of about 106 mm. Body portion 504 may define a tubular portion 506 configured to be slidably received in the bore 326 of endoscope mount 320 as indicated by an arrow D. The slidable mounting of the endoscope 500 on the endoscope mount platform 300 permits the endoscope 500 to adjust to access device configurations that have different diameters. Additional mobility of the endoscope 500 in viewing the surgical site may be provided by rotating the endoscope mount platform 300 about the central axis 308 (as indicated by arrow C in FIG. 21).

The rod portion 502 supports an optical portion (not shown) at a distal end 508 thereof. In one embodiment, the rod portion 502 defines a field of view of about 105 degrees and a direction of view 511 of about 25-30 degrees. An eyepiece 512 preferably is positioned at an end portion of the body portion 504. A suitable camera (not shown) preferably is attached to the endoscope 500 adjacent the eyepiece 512 with a standard coupler unit. A light post 510 can supply illumination to the surgical site at the distal end portion 508. A preferred camera for use in the system and procedures described herein is a three chip unit that provides greater resolution to the viewed image than a single chip device.

C. Apparatuses and Methods for Performing Spinal Procedures

The surgical assembly 10 described above can be deployed to perform a wide variety of surgical procedures on the spine. In many cases, the procedures are facilitated by inserting the access device and configuring it to provide greater access to a surgical location, as discussed above and by coupling the support arm 400 and the endoscope mount platform 300 with the proximal portion, e.g., on the proximal end 25, of the access device 20 (FIGS. 1 and 22). As discussed above, visualization of the surgical location is enhanced by mounting a viewing element, such as the endoscope 500, on the endoscope mount platform 300. Having established increased access to and visualization of the surgical location, a number of procedures may be effectively performed.

Generally, the procedures involve inserting one or more surgical instruments into the access device 20 to manipulate or act on the body structures that are located at least partially within the operative space defined by the expanded portion of the access device 20. FIG. 25 shows that in one method, the skirt portion 24 of access device 20 at least partially defines a surgical site or operative space 90 in which the surgical procedures described herein may be performed. Depending upon the overlap of the skirt portion, the skirt portion may define a surface which is continuous about the perimeter or which is discontinuous, having one or more gaps where the material of the skirt portion does not overlap.

One procedure performable through the access device 20, described in greater detail below, is a two-level spinal fusion and fixation. Surgical instruments inserted into the access device may be used for debridement and decortication. In particular, the soft tissue, such as fat and muscle, covering the vertebrae may be removed in order to allow the physician to visually identify the various "landmarks," or vertebral structures, which enable the physician to determine the location for attaching a fastener, such as a fastener 600, discussed below, or other procedures, as will be described herein. Enabling visual identification of the vertebral structures enables the physician to perform the procedure while viewing the surgical area through the endoscope, microscope, loupes, or other viewing element, or in a conventional, open manner.

Tissue debridement and decortication of bone are completed using one or more of a debrider blade, a bipolar sheath, a high speed burr, and any other conventional manual instrument. The debrider blades are used to excise, remove and aspirate the soft tissue. The bipolar sheath is used to achieve hemostasis through spot and bulk tissue coagulation. Additional features of debrider blades and bipolar sheaths are described in U.S. Pat. No. 6,193,715, assigned to Medical Scientific, Inc., which is incorporated by reference in its entirety herein. The high speed burr and conventional manual instruments are also used to continue to expose the structure of the vertebrae.

1. Fixation Systems and Devices

Having increased visualization of the pertinent anatomical structure, various procedures may be carried out on the structures. In one procedure, one or more fasteners are attached to adjacent vertebrae V. As discussed in more detail below, the fasteners can be used to provide temporary or permanent fixation and to provide dynamic stabilization of the vertebrae V. These procedures may combined with other procedures, such as procedures employing other types of implant, e.g., procedures employing fusion devices, prosthetic disc components, or other suitable implants. In some procedures, fasteners are attached to the vertebrae before or after fusion devices are inserted between the vertebrae V. Fusion systems and devices are discussed further below.

In one application, the desired location and orientation of the fastener is determined before the fastener is applied to the vertebra. The desired location and orientation of the fastener may be determined in any suitable manner. For example, the pedicle entry point of the L5 vertebrae may be located by identifying visual landmarks alone or in combination with lateral and A/P fluoroscopy, as is known in the art. With continued reference to FIG. 25, an entry point 92 into the vertebra V is prepared. In procedure, the entry point 92 may be prepared with an awl 550. The entry point 92 corresponds to the pedicle in one procedure. The entry point 92 may be prepared in any suitable manner, e.g., employing a bone probe, a tap, and a sounder to create and verify the integrity of the prepared vertebra. The sounder, as is known in the art, determines whether the hole that is made is surrounded by bone on all sides, and can be used to confirm that there has been no perforation of the pedicle wall.

After the hole in the pedicle beneath the entry point 92 is prepared, a fastener may be advanced into the hole. Prior to advancing the fastener, or at any other point during the procedure, it may be desirable to adjust the location of the distal portion of the access device 20. The distal portion of the access device 20 may be adjusted by inserting the expander apparatus 200 into the access device 20, expanding the distal portions 210, and contacting the inner wall of the skirt portion 24 to move the skirt portion 24 to the desired location. This step may be performed while the endoscope 500 is positioned within the access device 20, and without substantially disturbing the location of the proximal portion of the access device 20 to which the endoscope mount platform 300 may be attached.

FIGS. 26-27 illustrate one embodiment of a fastener 600 that is particularly applicable in procedures involving fixation. The fastener 600 preferably includes a screw portion 602, a housing 604, a spacer member 606, a biasing member 608, and a clamping member, such as a cap screw 610. The screw portion 602 has a distal threaded portion 612 and a proximal, substantially spherical joint portion 614. The threaded portion 612 is inserted into the hole that extends away from the entry point 92 into the vertebrae, as will be described below. The substantially spherical joint portion 614 is received in a substantially annular, partly spherical recess 616 in the housing 604 in a ball and socket joint relationship (see also FIG. 29).

As illustrated in FIG. 27, the fastener 600 is assembled by inserting the screw portion 602 into a bore in a passage 618 in the housing 604 until the joint portion 614 engages the annular recess 616. The screw portion 602 is retained in the housing 604 by the spacer member 606 and by the biasing member 608. The biasing member 608 provides a biasing force to drive the spacer member 606 into frictional engagement with the joint portion 614 of the screw member 602 and the annular recess 616 of the housing 604. The biasing provided by the biasing member 602 frictionally maintains the relative positions of the housing 604 with respect to the screw portion 602. The biasing member 608 preferably is selected such that biasing force prevents unrestricted movement of the housing 604 relative to the screw portion 602. However, in some embodiments the biasing force is insufficient to resist the application of force by a physician to move the housing 604 relative to the screw portion 602. In other words, this biasing force is strong enough maintain the housing 604 stationary relative to the screw portion 602, but this force may be overcome by the physician to reorient the housing 604 with respect to the screw member 602, as will be described below.

In the illustrated embodiment, the biasing member 608 is a resilient ring having a gap 620, which permits the biasing member 608 to radially contract and expand. FIG. 27(*a*) illustrates that the biasing member 608 may have an arched shape, when viewed end-on. The arched shape of the spring member 608 provides the biasing force, as will be described below. The spacer member 606 and the biasing member 608 are inserted into the housing 604 by radially compressing the biasing member into an annular groove 622 in the spacer member 606. The spacer member 606 and the biasing member 608 are slid into the passage 618 until the distal surface of the spacer member 606 engages the joint portion 614 of the screw portion 602, and the biasing member 608 expands radially into the annular groove 622 in the housing 604. The annular groove 622 in the housing 604 has a dimension 623 that is smaller than the uncompressed height of the arched shape of the biasing member 608. When the biasing member 608 is inserted in the annular groove 620, the biasing member 608 is flattened against its normal bias, thereby exerting the biasing force to the spacer member 606. It is understood that similar biasing members, such as coiled springs, belleville washers, or the like may be used to supply the biasing force described herein.

The spacer member 606 is provided with a longitudinal bore 626, which provides access to a hexagonal recess 628 in the proximal end of the joint portion 614 of the screw member 602. The proximal portion of the housing 604 includes a pair of upright members 630 and 631 that are separated by substantially "U"-shaped grooves 632. A recess for receiving elongated member 650 is defined by the pair of grooves 632 between upright members 630 and 631. Elongated member 650 preferably is configured to be placed distally into the housing 604 in an orientation substantially transverse to the longitudinal axis of the housing 604, as will be described below. The inner walls of he upright members 630 and 631 are provided with threads 634 for attachment of the cap screw 610 by threads 613 therein.

Additional features of the fastener 600 are also described in U.S. patent application Ser. No. 10/075,668, filed Feb. 13, 2002, published as U.S. application Publication No. 2003/0153911A1 on Aug. 14, 2003, and application Ser. No. 10/087,489, filed Mar. 1, 2002, published as U.S. application Publication No. 2003/0167058A1 on Sep. 4, 2003, which are incorporated by reference in their entireties herein.

Figure 28:
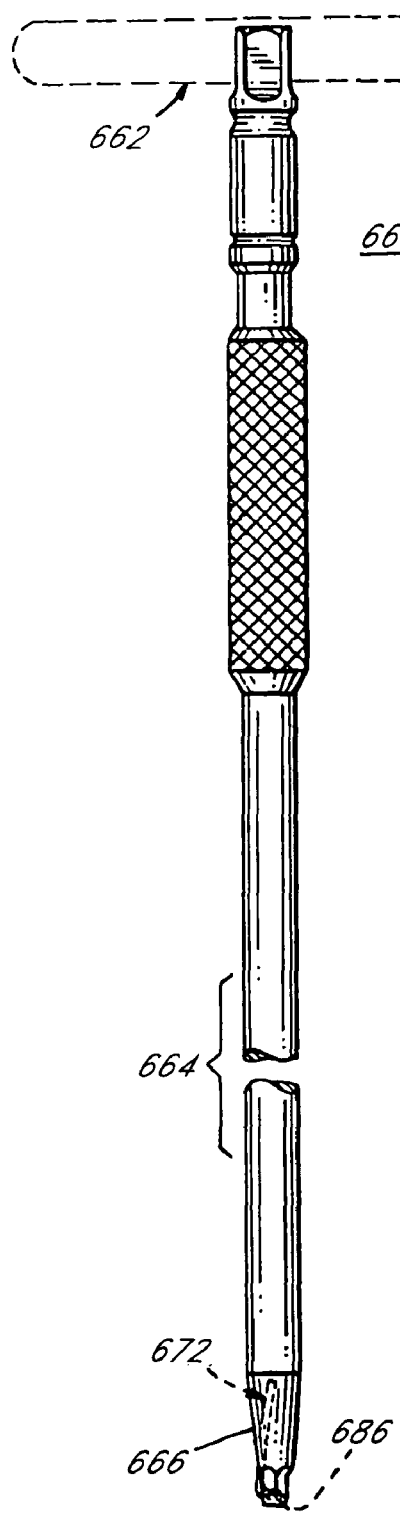
FIG. 28 is a perspective view of one embodiment of a surgical instrument.

According to one application, the fastener 600 is inserted into the access device 20 and guided to the prepared hole at the entry point 92 in the vertebrae. The fastener 600 preferably is simultaneously supported and advanced into the hole so that the fastener 600 is secured in the in the hole beneath the entry point 92. In the illustrated embodiment the fastener 600 is supported and attached to the bone by an endoscopic screwdriver apparatus 660, illustrated in FIGS. 28-29. The screwdriver 660 includes a proximal handle portion 662 (illustrated in dashed line), an elongated body portion 664, and a distal tool portion 666.

Figure 29:
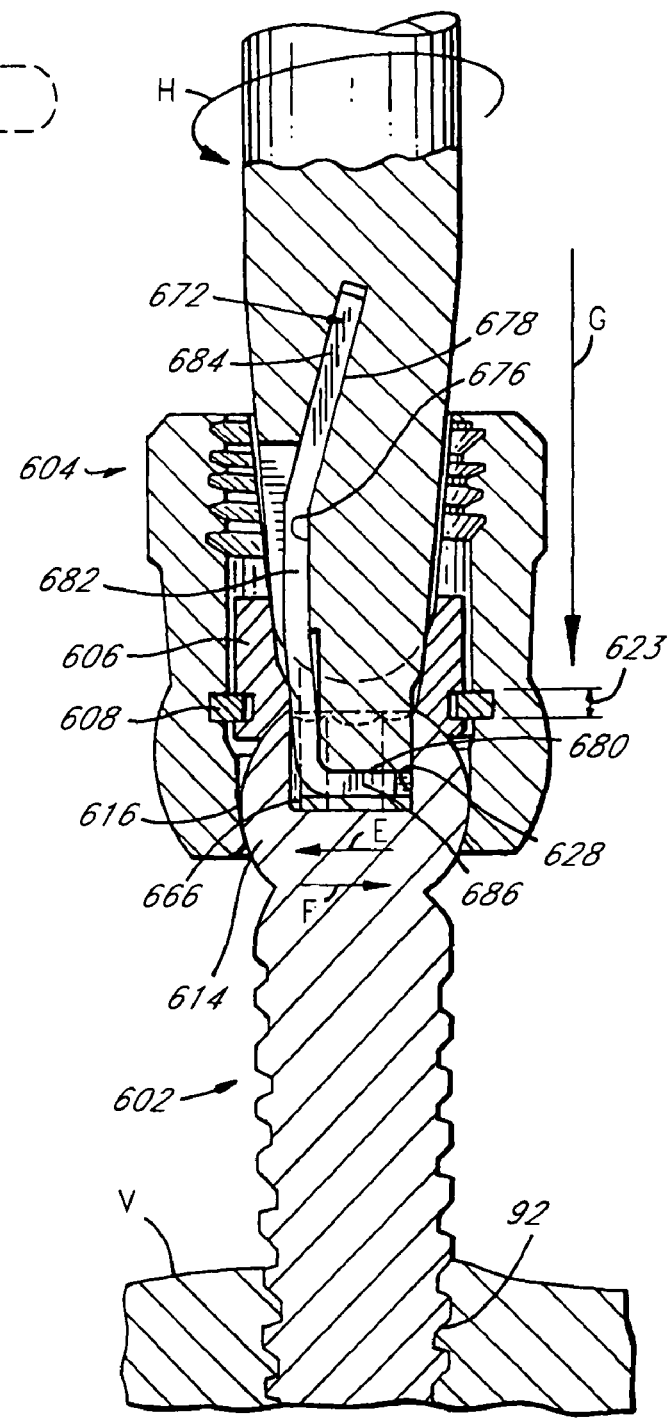
FIG. 29 is an enlarged sectional view of the fastener of FIGS. 26-27 coupled with the surgical instrument of FIG. 28, illustrating one embodiment of a stage of one embodiment of a method for treating the spine of a patient.

The distal tool portion 666, as illustrated in greater detail in FIG. 29 includes a substantially hexagonal outer periphery that is received in the substantially hexagonal recess 628 in the joint portion 614 of the screw member 602. A spring member at the distal tool portion 666 releasably engages the hexagonal recess 628 of the screw member 602 to support the fastener 600 during insertion and tightening. In the illustrated embodiment, a spring member 672 is configured to engage the side wall of the recess 628. More particularly, a channel or a groove is provided in the tip portion 666 for receiving the spring member 672. The channel or groove includes a medial longitudinal notch portion 676, a proximal, angled channel portion 678, and a distal substantially transverse channel portion 680. The spring member 672 is preferably manufactured from stainless steel and has a medial portion 682, proximal portion 684, and a transverse distal portion 686. The medial portion 682 is partially received in the longitudinal notch portion 676. The proximal portion 684 preferably is angled with respect to the medial portion 682 and is fixedly received in the angled channel portion 678. The transverse distal portion 686 preferably is slidably received in the transverse channel 680. The medial portion 682 of the spring member 672 is partially exposed from the distal tip portion 666 and normally is biased in a transverse outward direction with respect to the longitudinal axis (indicated by arrow E), in order to supply bearing force against the wall of the recess 628. Alternatively, the distal tip portion of the screwdriver may be magnetized in order to hold the screw portion 602. Similarly, the distal tip portion may include a ball bearing or similar member which is normally biased in a radially outward direction to engage the interior wall of the recess 628 to secure the fastener 600 to the screwdriver distal tip 666. Other means may be provided for temporarily but securely coupling the fastener 600 with the screwdriver distal tip 666.

The insertion of the fastener 600 into the prepared hole that extends into the vertebrae from the entry point 92 may be achieved by insertion of screwdriver 660 into access device 20 (indicated by arrow G). This procedure may be visualized by the use of the endoscope 500 in conjunction with fluoroscopy, or by way of any other suitable viewing element. The screw portion 602 is threadedly advanced by the endoscopic screwdriver 660 into the prepared hole that extends beneath the entry point 92 (indicated by arrow H). The endoscopic screwdriver 660 is subsequently separated from the fastener 600, by applying a force in the proximal direction, and thereby releasing the distal tip portion 666 from the hexagonal recess 628 (e.g., causing the transverse distal portion 686 of the spring member 672 to slide within the transverse recess 680 against the bias, indicated by arrow F), and removing the screwdriver 660 from the access device 20. An alternative method may use a guidewire, which is fixed in the hole beneath the entry point 92, and a cannulated screw which has an internal lumen and is guided over the guidewire into the hole beneath the entry point 92. Where a guidewire system is used, the screwdriver also would be cannulated so that the screwdriver would fit over the guidewire.

For a two-level fixation, it may be necessary to prepare several holes and attach several fasteners 600. Preferably, the access device 20 is sized to provide simultaneous access to all vertebrae in which the surgical procedure is being performed. In some cases, however, additional enlargement or repositioning of the distal portion of the access device 20 may be helpful in providing sufficient access to the outer vertebrae, e.g., the L4 and S1 vertebrae. In the illustrated embodiment, the expander apparatus 200 may be repeatedly inserted into the access device 20 and expanded in order to further open or to position the skirt portion 24. In one procedure, additional fasteners are inserted in the L4 and S1 vertebrae in a similar fashion as the fastener 600 inserted into the L5 vertebra as described above. (When discussed individually or collectively, a fastener and/or its individual components will be referred to by the reference number, e.g., fastener 600, housing 604, and all fasteners 600. However, when several fasteners and/or their components are discussed in relation to one another, an alphabetic subscript will be used, e.g., fastener 600a is moved towards fastener 600b.)

In one application, after the fasteners 600 are advanced into the vertebrae, the housing portions 604 of the fasteners 600 are substantially aligned such that their upright portions 630 and 631 face upward, and the notches 632 are substantially aligned to receive the elongated member 650 therein. The frictional mounting of the housing 604 to the screw member 602, described above, allows the housing 604 to be temporarily positioned until a subsequent tightening step is performed, described below.

Positioning of the housing portions 604 may be performed by the use of an elongated surgical instrument capable of contacting and moving the housing portion to the desired orientation. One such instrument for positioning the housings 604 is a grasper apparatus 700, illustrated in FIG. 30. The grasper apparatus 700 includes a proximal handle portion 702, an elongated body portion 704, and distal nose portion 706. The distal nose portion 706 includes a pair of grasping jaws 708a and 708b, which are pivotable about pin 710 by actuation of the proximal handle portion 702. The grasping jaws 708a and 708b are illustrated in the closed position in FIG. 30. Pivoting the movable handle 714 towards stationary handle 712 causes longitudinal movement of actuator 716, which in turn pivots the jaw 708b towards an open position (illustrated in dashed line). The biasing members 718 and 720 are provided to return the handles 712 and 714 to the open position and bias the jaws 708a and 708b to the closed position.

In one application, the elongated member 650 is inserted into the access device 20. In one application, the elongated member 650 is manufactured from a biocompatible material and is sufficiently strong to maintain the position of the vertebrae, or other body structures, coupled by the elongate member 650 with little or no relative motion therebetween. In one embodiment, the elongated members 650 are manufactured from Titanium 6/4 or titanium alloy. The elongated member 650 also may be manufactured from stainless steel or any other suitable material. The transverse shape, width (e.g., radii), and lengths of the elongated members 650 are selected by the physician to provide the best fit for the positioning of the screw heads. Such selection may be performed by placing the elongated member 650 on the skin of the patient overlying the location of the fasteners and viewed fluoroscopically. For example, a 70 mm preformed rod having a 3.5" bend radius may be selected for the spinal fixation.

Figure 30:
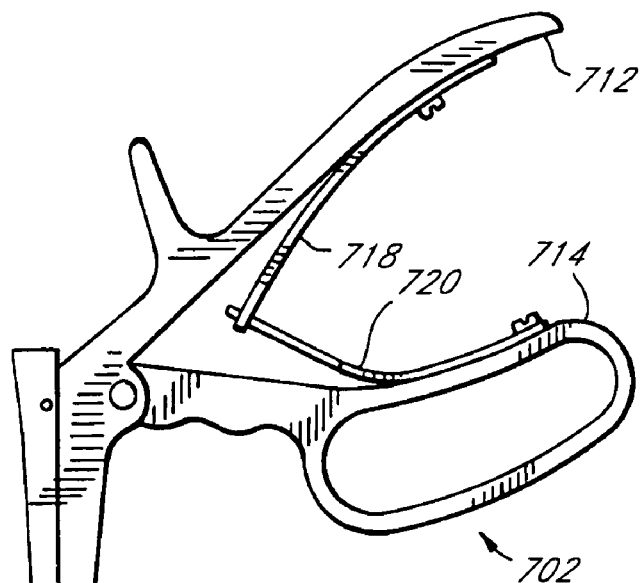
FIG. 30 is side view of one embodiment of another surgical instrument.

In one application, the elongated member 650 is fixed to each of the fasteners 600, and more particularly, to the housings 604 of each fastener 600. The grasper apparatus 700, described above, is also particularly useful for inserting the elongated member 650 into the access device 20 and positioning it with respect to each housing 604. As illustrated in FIG. 30, the jaws 708a and 708b of the grasper apparatus 700 each has shaped (e.g., curved) contact portions 722a and 722b for contacting and holding the outer surface of the elongated member 650.

Figure 31:
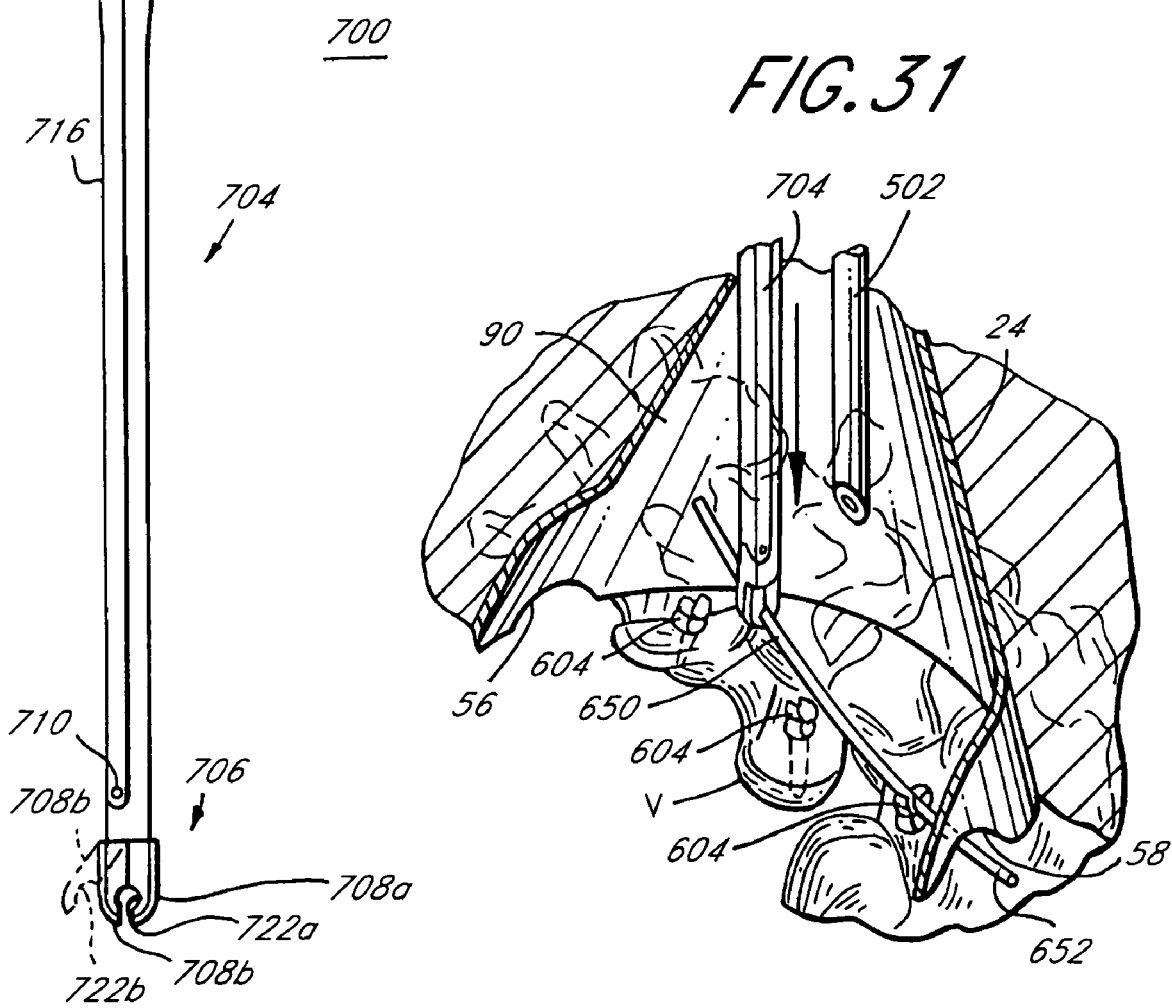
FIG. 31 is a partial sectional view of one embodiment of a stage of one embodiment of a method for treating the spine of a patient.

As illustrated in FIG. 31, the grasper apparatus 700 may be used to insert the elongated member 650 into the operative space 90 defined at least partially by the skirt portion 24 of the access device 20. In some embodiments, the cut-out portions 56 and 58 provided in the skirt portion 24 assist in the process of installing the elongated member 650 with respect to the housings 604. The cut-out portions 56 and 58 allow an end portion 652 of the elongated member 650 to extend beyond the operative space without raising or repositioning the skirt portion 24. The elongated member 650 is positioned within the recesses in each housing 604 defined by grooves 632 disposed between upright members 630 and 631. The elongated member 650 is positioned in an orientation substantially transverse to the longitudinal axis of each housing 604.

Further positioning of the elongated member 650 may be performed by guide apparatus 800, illustrated in FIG. 32. Guide apparatus 800 is useful in cooperation with an endoscopic screwdriver, such as endoscopic screwdriver 660 (illustrated in FIG. 28), in order to position the elongated member 650, and to introduce and tighten the cap screw 610, described above and illustrated in FIG. 27. Tightening of the cap screw 610 with respect to the housing 604 fixes the orientation of the housing 604 with respect to the screw portion 602 and fixes the position of the elongated member 650 with respect to the housings 604.

In the illustrated embodiment, the guide apparatus 800 has a proximal handle portion 802, an elongated body portion 804, and a distal tool portion 806. The elongated body portion 804 defines a central bore 808 (illustrated in dashed line) along its longitudinal axis 810. The central bore 808 is sized and configured to receive the endoscopic screwdriver 660 and cap screw 610 therethrough. In the exemplary embodiment, the diameter of the central bore 808 of the elongated body portion 804 is about 0.384-0.388 inches (9.75-9.86 mm) in diameter, and the external diameter of the endoscopic screwdriver 660 (FIG. 28) is about 0.25 inches (6.35 mm). The proximal handle portion 802 extends transverse to the longitudinal axis 810, which allows the physician to adjust the guide apparatus 800 without interfering with the operation of the screwdriver 660.

The distal portion 806 of the apparatus includes several shaped cut out portions 814 which assist in positioning the elongated member 650. As illustrated in FIG. 33, the cut out portions 814 are sized and configured to engage the surface of elongated member 650 and move the elongated member 650 from an initial location (illustrated in dashed line) to a desired location. In the illustrated embodiment, the cut out portions 814 are semicircular, to match the round elongated member 650. However, other shaped cut out portions may be provided to match other shaped elongated members.

As illustrated in FIG. 34, the guide apparatus 800 is used in cooperation with the endoscopic screwdriver 660 to attach the cap screw 610. The distal end of the body portion 804 includes a pair of elongated openings 816. The openings 816 provide a window to enable the physician to endoscopically view the cap screw 610 retained at the distal tip 666 of the endoscopic screw driver 660. Fewer or more than two openings can be provided and the openings 816 need not be elongated.

The guide apparatus 800 and the endoscopic screwdriver 660 cooperate as follows in one application. The guide apparatus 800 is configured to be positioned in a surrounding configuration with the screwdriver 600. In the illustrated embodiment, the body portion 804 is configured for coaxial placement about the screwdriver 660 in order to distribute the contact force of the guide apparatus 800 on the elongated member 650. The distal portion 806 of the guide apparatus 800 may bear down on the elongated member 650 to seat the elongated member 650 in the notches 632 in the housing 604. The "distributed" force of the guide apparatus 800 may contact the elongated member 650 on at least one or more locations. In addition, the diameter of central bore 808 is selected to be marginally larger than the exterior diameter of cap screw 610, such that the cap screw 610 may freely slide down the central bore 808, while maintaining the orientation shown in FIG. 34. This configuration allows the physician to have effective control of the placement of the cap screw 610 into the housing 604. The cap screw 610 is releasably attached to the endoscopic screwdriver 660 by means of spring member 672 engaged to the interior wall of hexagonal recess 611 as it is inserted within the bore 808 of the body portion 804 of guide apparatus 800. The cap screw 610 is attached to the housing 604 by engaging the threads 615 of the cap screw 610 with the threads 634 of the housing.

Figure 35:
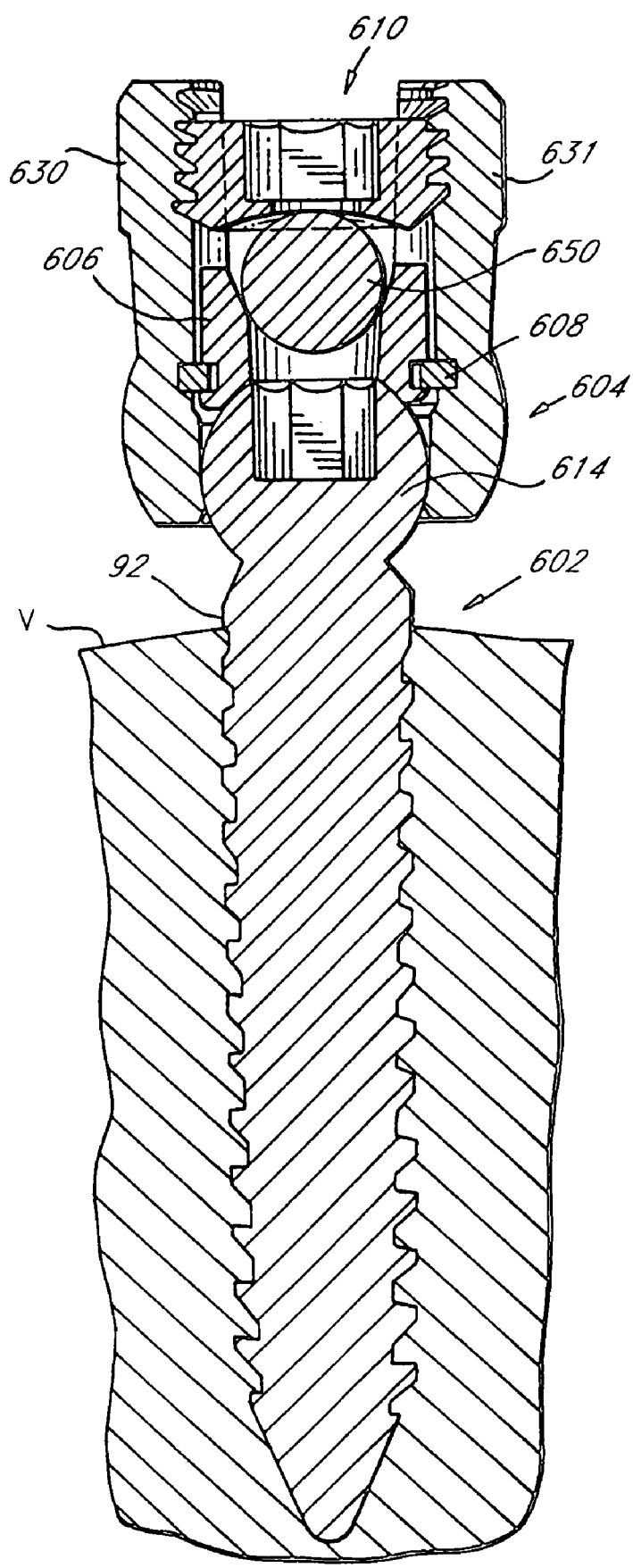
FIG. 35 is an enlarged sectional similar to FIG. 34, illustrating one embodiment of a stage of one embodiment of a method for treating the spine of a patient.

As illustrated in FIG. 35, tightening of the cap screw 610 fixes the assembly of the housing 604 with respect to the elongated member 650. In particular, the distal surface of the cap screw 610 provides a distal force against the elongated member 650, which in turn drives the spacer member 606 against the joint portion 614 of the screw portion 602, which is fixed with respect to the housing 604.

If locations of the vertebrae are considered acceptable by the physician, then the fixation procedure is substantially complete once the cap screws 610 have been attached to the respective housings 604, and tightened to provide a fixed structure as between the elongated member 650 and the various fasteners 600. However, if compression or distraction of the vertebrae with respect to one another is required additional apparatus would be used to shift the vertebrae prior to final tightening all of the cap screws 610.

In the illustrated embodiment, this step is performed with a surgical instrument, such as a compressor-distracter instrument 900, illustrated in FIG. 36, which is useful to relatively position bone structures in the cephcaudal direction and to fix their position with respect to one another. Thus, the compressor-distracter instrument 900 has the capability to engage two fasteners 600 and to space them apart while simultaneously tightening one of the fasteners to fix the spacing between the two vertebrae, or other bone structures. Moreover, the compressor-distracter instrument 900 may also be used to move two fasteners 600, and the vertebrae attached thereto into closer approximation and fix the spacing therebetween.

The distal tool portion 902 of one embodiment of the compressor-distracter instrument 900 is illustrated in FIG. 36. The distal tool portion 902 includes a driver portion 904 and a spacing member 906. The driver portion 904 has a distal end portion 908 with a plurality of wrenching flats configured to engage the recess 611 in the proximal face of the cap screw 610, and to apply torque to the cap screw. The driver portion 904 is rotatable about the longitudinal axis (indicated by arrow M) to rotate the cap screw 610 relative to the fastener 600. Accordingly, the driver portion 904 can be rotated to loosen the cap screw 610 on the fastener 600 and permit movement of the elongated member 650 connected with the vertebra relative to the fastener 600 connected with the vertebra. The cap screw 610 can also be rotated in order to tighten the cap screw 610 and clamp the elongated member 650 to the fastener 600.

The distal tool portion 902 may also include a spacing member, such as spacing member 906, which engages an adjacent fastener 600b while driver member 904 is engaged with the housing 604a to move the fastener 600b with respect to the fastener 600a. In the exemplary embodiment, spacing member 906 comprises a jaw portion that is pivotably mounted to move between a first position adjacent the driver portion and a second position spaced from the driver portion, as shown in FIG. 36. The distal tip 910 of the spacing member 906 is movable relative to the driver portion 904 in a direction extending transverse to the longitudinal axis. (Further details and features related to compressor-distracter apparatuses are described in U.S. application Ser. No. 10/178,875, filed Jun. 24, 2002, entitled "SURGICAL INSTRUMENT FOR MOVING VERTEBRAE," published as U.S. patent application Publication No. 2003/0236529A1 on Dec. 25, 2003, which is incorporated by reference in its entirety herein. Also, further details and features related to other apparatuses for manipulating implants and bone segments (e.g., vertebrae) to which implants are coupled are described in U.S. Pat. No. 6,648,888, issued Nov. 18, 2003, entitled "SURGICAL INSTRUMENT FOR MOVING VERTEBRAE.")

As illustrated in FIG. 36, the spacer member 906 can be opened with respect to the driver portion 904 to space the vertebrae farther apart (as indicated by arrow N). The distal portion 910 of the spacer member 906 engages the housing 604b of fastener 600b and moves fastener 600b further apart from fastener 600a to distract the vertebrae. Where the vertebrae are to be moved closer together, e.g. compressed, the spacer member 906 is closed with respect to the driver portion 904 (arrow P), as illustrated in FIG. 37. The distal portion 910 of the spacer member 906 engages the housing 604b of the fastener 600b and moves the fastener 600b towards the fastener 600a. When the spacing of the vertebrae is acceptable to the physician, the cap screw 610a is tightened by the driver member 904, thereby fixing the relationship of the housing 604a with respect to the elongated member 650, and thereby fixing the position of the vertebrae, or other bone structures, with respect to one another. In one application, once the elongated member 650 is fixed with respect to the fasteners 600, the fixation portion of the procedure is substantially complete.

2. Fusion Systems and Devices

Although fixation may provide sufficient stabilization, in some cases it is also desirable to provide additional stabilization. For example, where one or more discs has degraded to the point that it needs to be replaced, it may be desirable to position an implant, e.g., a fusion device, a prosthetic disc, a disc nucleus, etc., in the intervertebral space formerly occupied by the disc.

Figure 48:
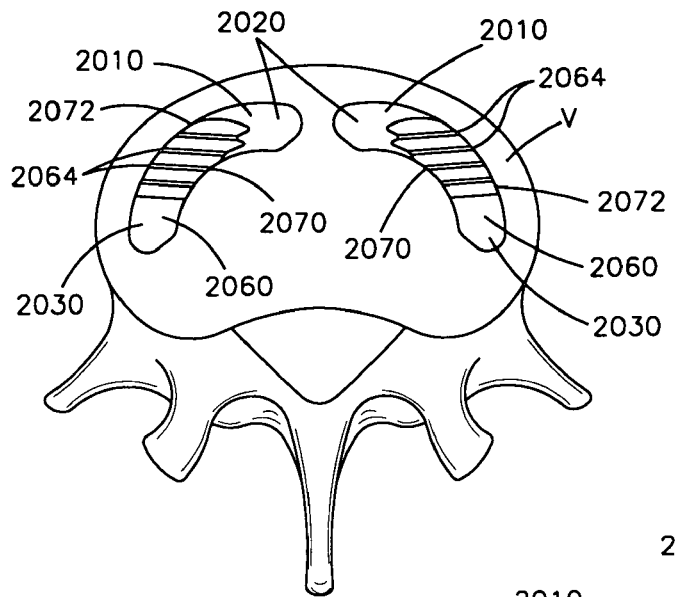
FIG. 48 is a view showing a pair of the spinal implants of FIG. 38 in first relative positions between adjacent vertebrae.
Figure 49:
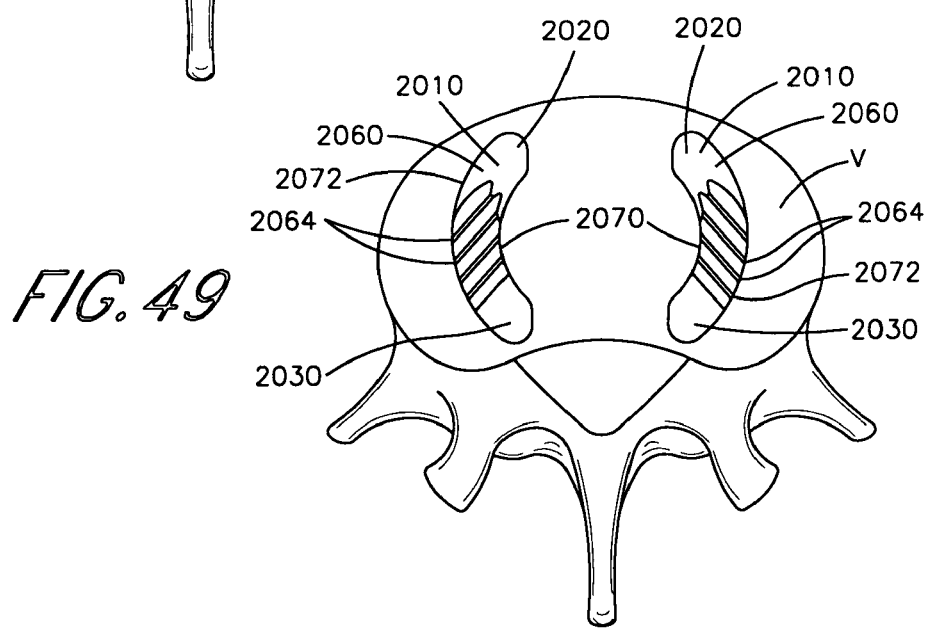
FIG. 49 is a view showing a pair of the spinal implants of FIG. 38 in second relative positions between adjacent vertebrae.

In one application, a fusion device is inserted between adjacent vertebrae V. Portions of the fusion procedure can be performed before, during, or after portions of the fixation procedure. FIGS. 38-42 illustrate one embodiment of a fusion device, referred to herein as a spinal implant 2010, that is inserted between adjacent vertebrae. The spinal implant 2010 preferably is placed between adjacent vertebrae to provide sufficient support to allow fusion of the adjacent vertebrae, as shown in FIGS. 48-49. The spinal implants 2010 are preferably made from an allograft material, though other materials could also be used, including autograft, xenograft, or some non-biologic biocompatible material, such as titanium or stainless steel. Also, where non-biologic materials are used, the implant 2010 may be configured as a cage or other suitable configuration.

Figure 41:
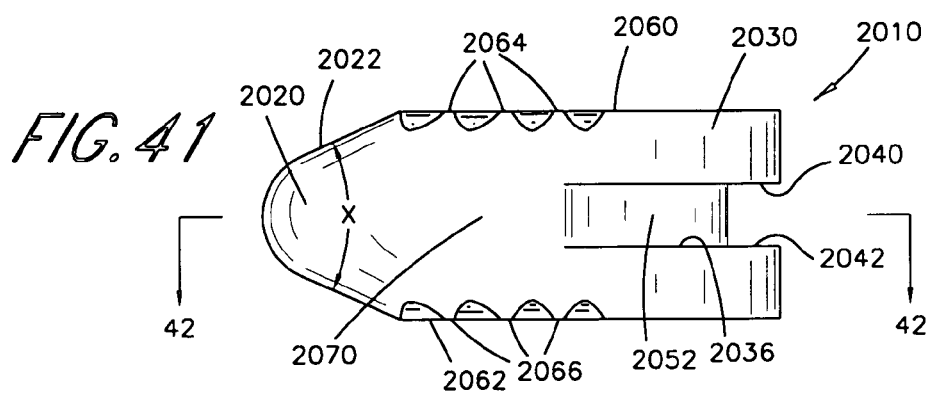
FIG. 41 is a side view of the spinal implant of FIG. 38 showing the first side surface.
Figure 42:
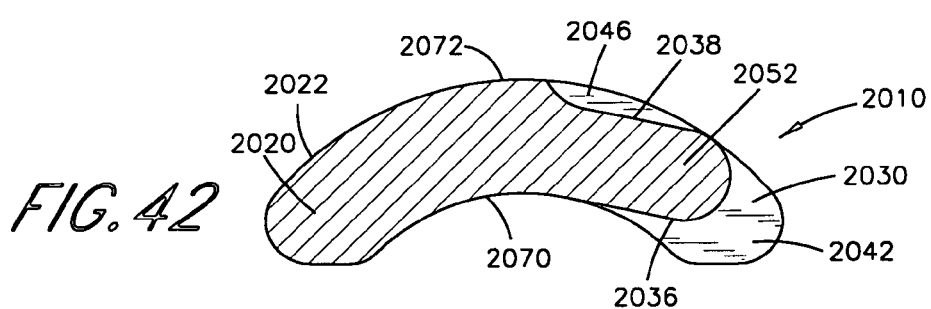
FIG. 42 is a cross-sectional view of the spinal implant taken along the line 42-42 in FIG. 41.

The spinal implant 2010 (FIGS. 38-42) has a first end 2020 for insertion between adjacent vertebrae V. The first end 2020 has a tapered surface 2022 to facilitate insertion of the implant between adjacent vertebrae V. The surface 2022 defines an angle X of approximately 45° as shown in FIG. 41.

Figure 51:
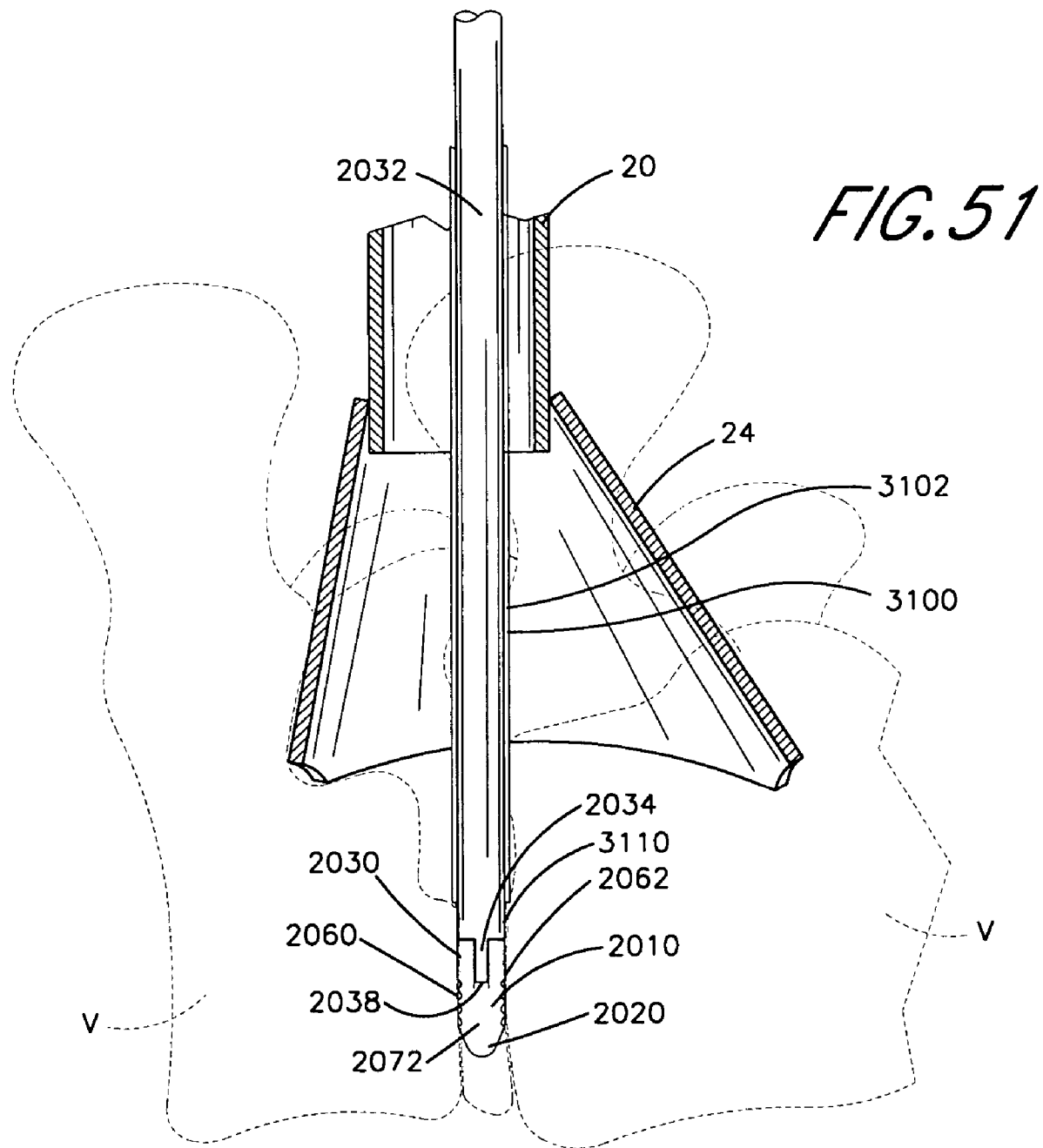
FIG. 51 is a view showing a spinal implant being inserted between the adjacent vertebrae according to another embodiment.
Figure 52:
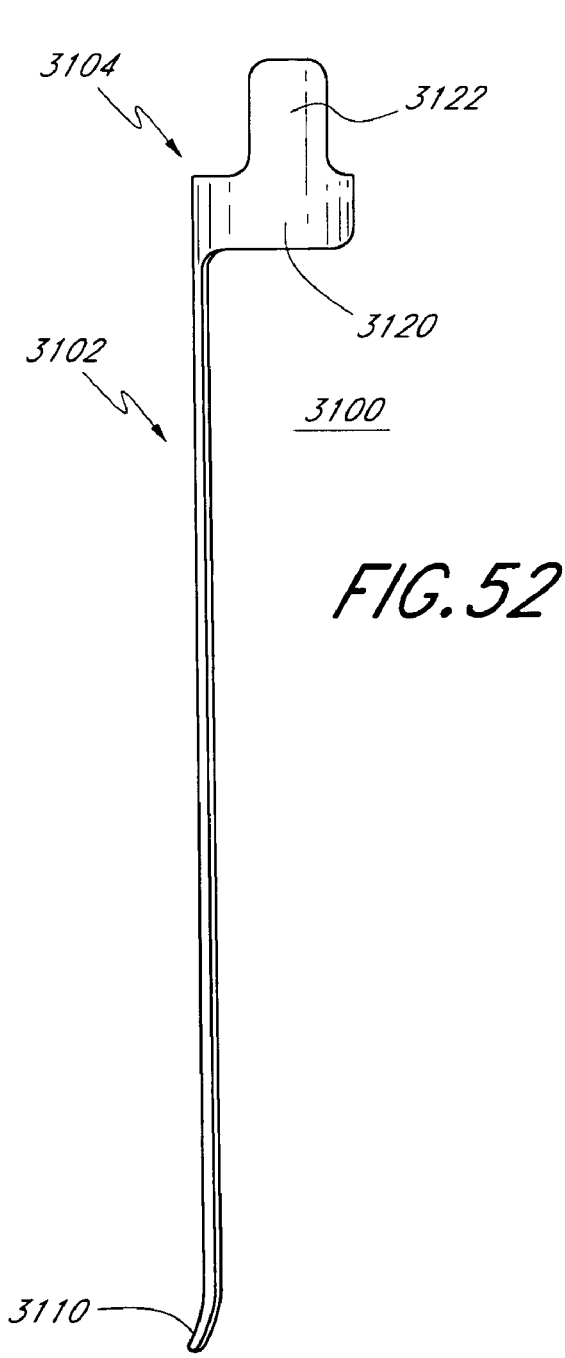
FIG. 52 is a side view of an apparatus according to another embodiment.
Figure 53:
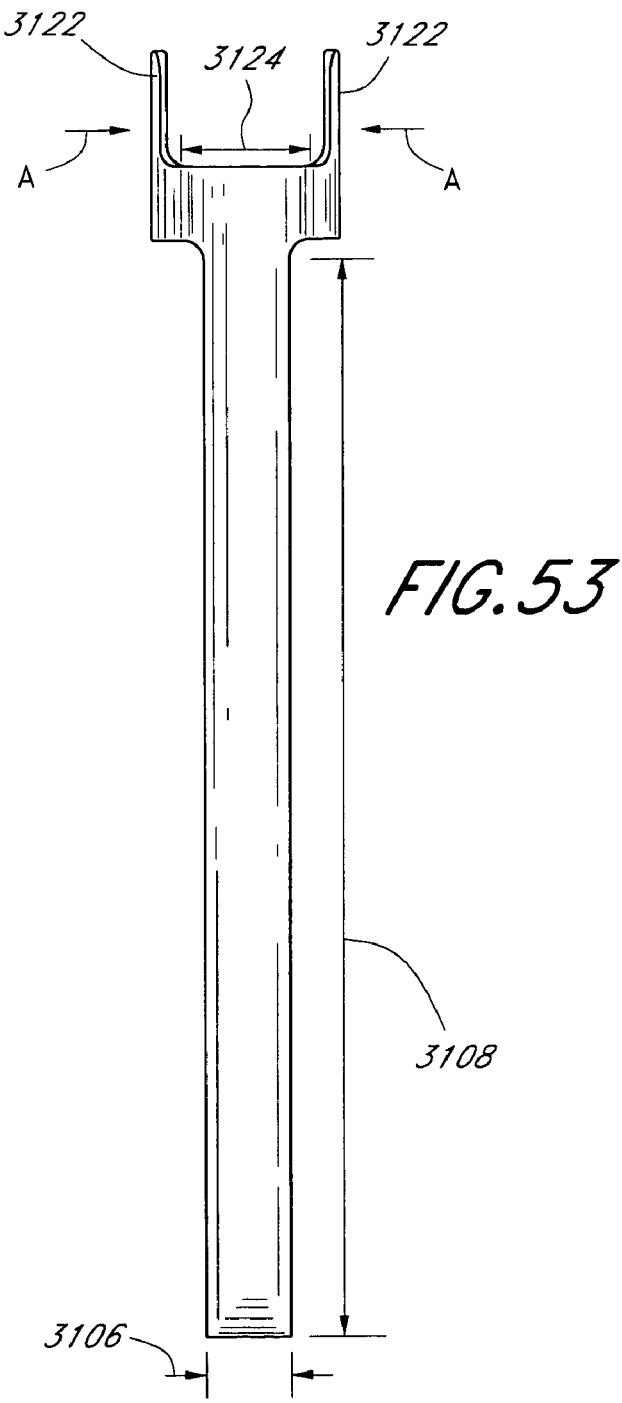
FIG. 53 is a front view of the apparatus of FIG. 52.
Figure 54:
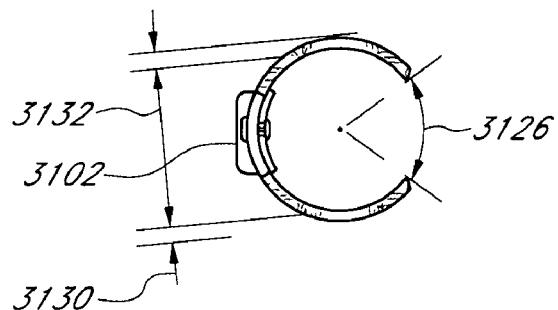
FIG. 54 is a top view of the apparatus of FIG. 52.
Figure 56:
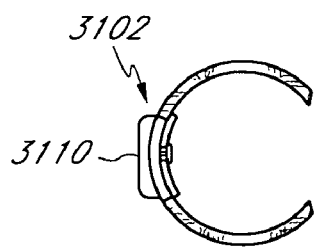
FIG. 56 is a bottom view of the apparatus of FIG. 52.
Figure 55:
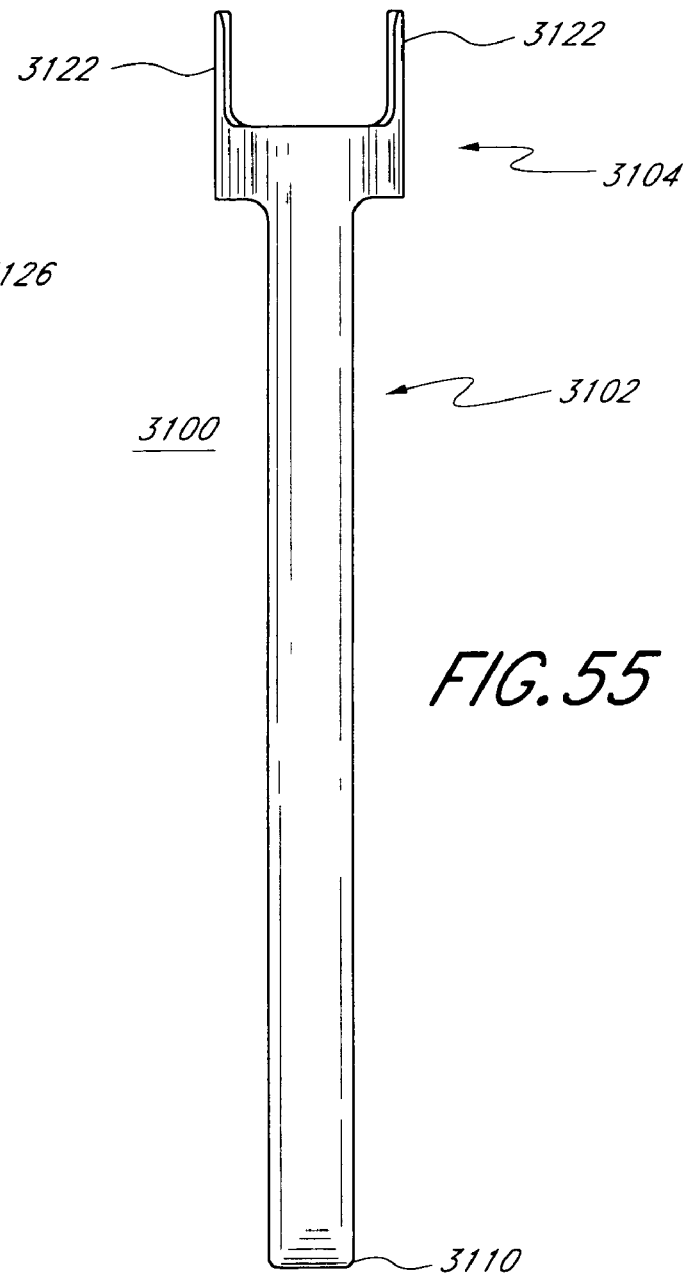
FIG. 55 is a back view of the apparatus of FIG. 52.

The spinal implant 2010 (FIGS. 38-39) has a second end 2030 that is engageable with a tool 2032 (FIG. 51) for inserting the implant between the adjacent vertebrae V. The tool 2032 has a pair of projections 2034, one of which is shown in FIG. 51, that extend into recesses 2036 and 2038 in the end 2030 of the implant 2010. The recesses 2036 and 2038 (FIGS. 38-39) extend from the second end 2030 toward the first end 2020. The recess 2036 (FIG. 41) is defined by an upper surface 2040 and a lower surface 2042 extending generally parallel to the upper surface 2040. The recess 2038 (FIG. 39) has a lower surface 2046 and an upper surface 2048. The upper surface 2048 extends generally parallel to the lower surface 2046.

The recesses 2036 and 2038 define a gripping portion 2052. The projections 2034 on the tool 2032 extend into the recesses 2036 and 2038 and grip the gripping portion 2052. The projections 2034 engage the upper and lower surfaces 2040 and 2042 of the recess 2036 and the upper and lower surfaces 2046 and 2048 of the recess 2038. Accordingly, the tool 2032 can grip the implant 2010 for inserting the implant between the adjacent vertebrae V.

Figures 38, 39:
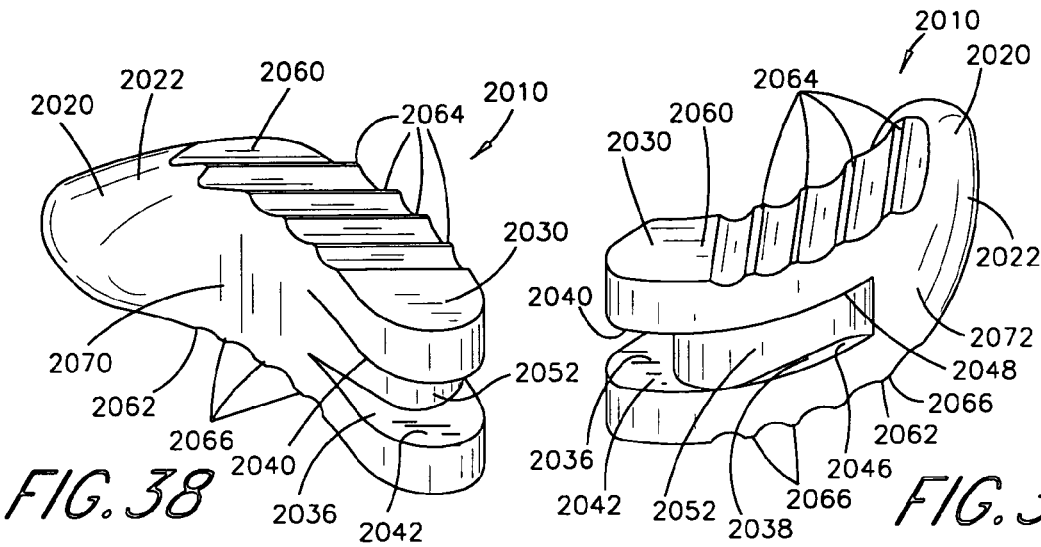
FIG. 38 is a perspective view of a spinal implant or fusion device constructed according to another embodiment showing a first side surface of the spinal implant.
FIG. 39 is a perspective view of the spinal implant of FIG. 38 showing a second side surface of the spinal implant.
Figure 40:
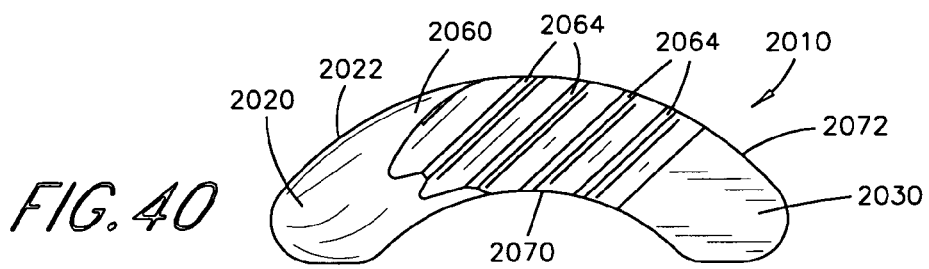
FIG. 40 is a plan view of the spinal implant of FIG. 38 showing an upper surface of the spinal implant.

As viewed in FIGS. 38-41, the implant 2010 has an upper surface 2060 for engaging the upper vertebra V. The implant 2010 has a lower surface 2062, as viewed in FIGS. 38-41, for engaging the lower vertebra V. The upper and lower surfaces 2060 and 2062 extend from the first end 2020 to the second end 2030 of the implant 2010 and parallel to the upper and lower surfaces 2040, 2042, 2046, and 2048 of the recesses 2036 and 2038. The upper surface 2060 has teeth 2064 for engaging the upper vertebra V. The lower surface 2062 has teeth 2066 for engaging the lower vertebra V. Although FIGS. 38-39 show four teeth 2064 and four teeth 2066, it is contemplated that any number of teeth could be used.

A first side surface 2070 and a second side surface 2072 extend between the upper and lower surfaces 2060 and 2062. The first side surface 2070 extends along a first arc from the first end 2022 of the implant 2010 to the second end 2030. The second side surface 2072 extends along a second arc from the first end 2022 to the second end 2030. The first and second side surfaces 2070 and 2072 are concentric and define portions of concentric circles. The teeth 2064 and 2066 extend parallel to each other and extend between the side surfaces 2070 and 2072 and along secant lines of the concentric circles defined by the side surfaces.

The implant 2010 preferably is formed by harvesting allograft material from a femur, as known in the art. The femur is axially cut to form cylindrical pieces of allograft material. The cylindrical pieces are then cut in half to form semi-cylindrical pieces of allograft material. The semi-cylindrical pieces of allograft material are machined into the spinal implants 2010.

A pair of spinal implants 2010 may be placed bilaterally between the adjacent vertebrae V. The access device 20 is positioned in the patient's body adjacent the vertebrae V. The skirt portion 24 of the access device 20 preferably is in a radially expanded condition to provide a working space adjacent the vertebrae V as described above. Disc material between the vertebrae V can be removed using instruments such as kerrisons, rongeurs, or curettes. A microdebrider may also be utilized to remove the disc material. An osteotome, curettes, and scrapers can be used to prepare end plates of the vertebrae V for fusion. Preferably, an annulus of the disc is left between the vertebrae V.

Distracters can be used to sequentially distract the disc space until the desired distance between the vertebrae V is achieved. The fusion device or implant 2010 is placed between the vertebrae V using the tool 2032. The first end 2020 of the implant 2010 is inserted first between the vertebrae V. The implant 2010 is pushed between the vertebrae V until the end 2030 of the implant is between the vertebrae. A second spinal implant 2010 is inserted on the ipsilateral side using the same procedure.

A shield apparatus 3100 with an elongated portion 3102 may be used to facilitate insertion of the implants 2010 between the vertebrae V. A distal portion 3110 of the apparatus 3100 may be placed in an annulotomy. The implant 2010 is inserted with the side surface 2170 facing the elongated portion 3102 so that the apparatus 3100 can act as a "shoe horn" to facilitate or guide insertion of the implants 2010 between the vertebrae.

The implants 2010 may be inserted between the vertebrae V with the first ends 2020 located adjacent each other and the second ends 2030 spaced apart from each other, as shown in FIG. 48. The implants 2010 may also be inserted between the vertebrae V with the first ends 2020 of the implants 2010 spaced apart approximately the same distance that the second ends 2030 are spaced apart. It is contemplated that the implants 2010 may be inserted in any desired position between the vertebrae V. It is also contemplated that in some embodiments only one implant 2010 may be inserted between the vertebrae V. Furthermore, it is contemplated that the implants 2010 may be inserted between vertebrae using an open procedure.

Figure 50:
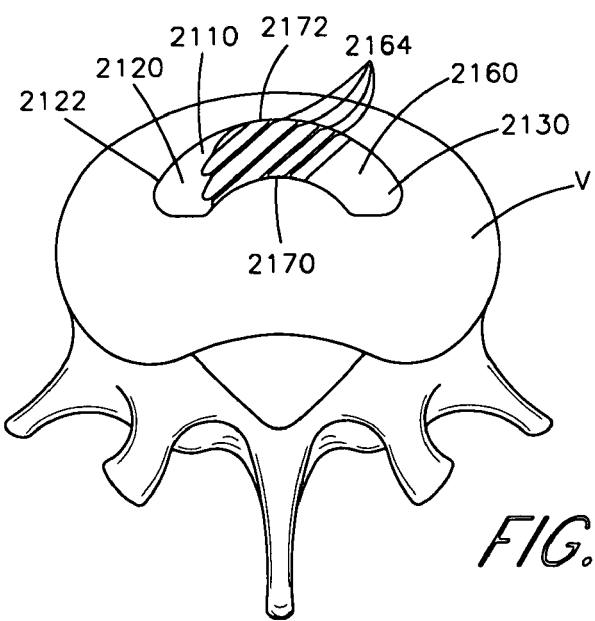
FIG. 50 is a view showing the spinal implant of FIG. 43 between adjacent vertebrae.

Another embodiment of a fusion device or spinal implant 2110 is illustrated in FIGS. 43-47. The spinal implant 2110 is substantially similar to the embodiment disclosed in FIGS. 38-42. The implant 2110 is placed between the adjacent vertebrae V to provide sufficient support to allow fusion of the adjacent vertebrae, as shown in FIG. 50. The spinal implant 2110 is preferably made from an allograft material, though the materials described above in connection with the spinal implant 2010 may also be used. Also, as with the implant 2010, the implant 2110 may be formed as a cage or other suitable configuration.

Figure 65:
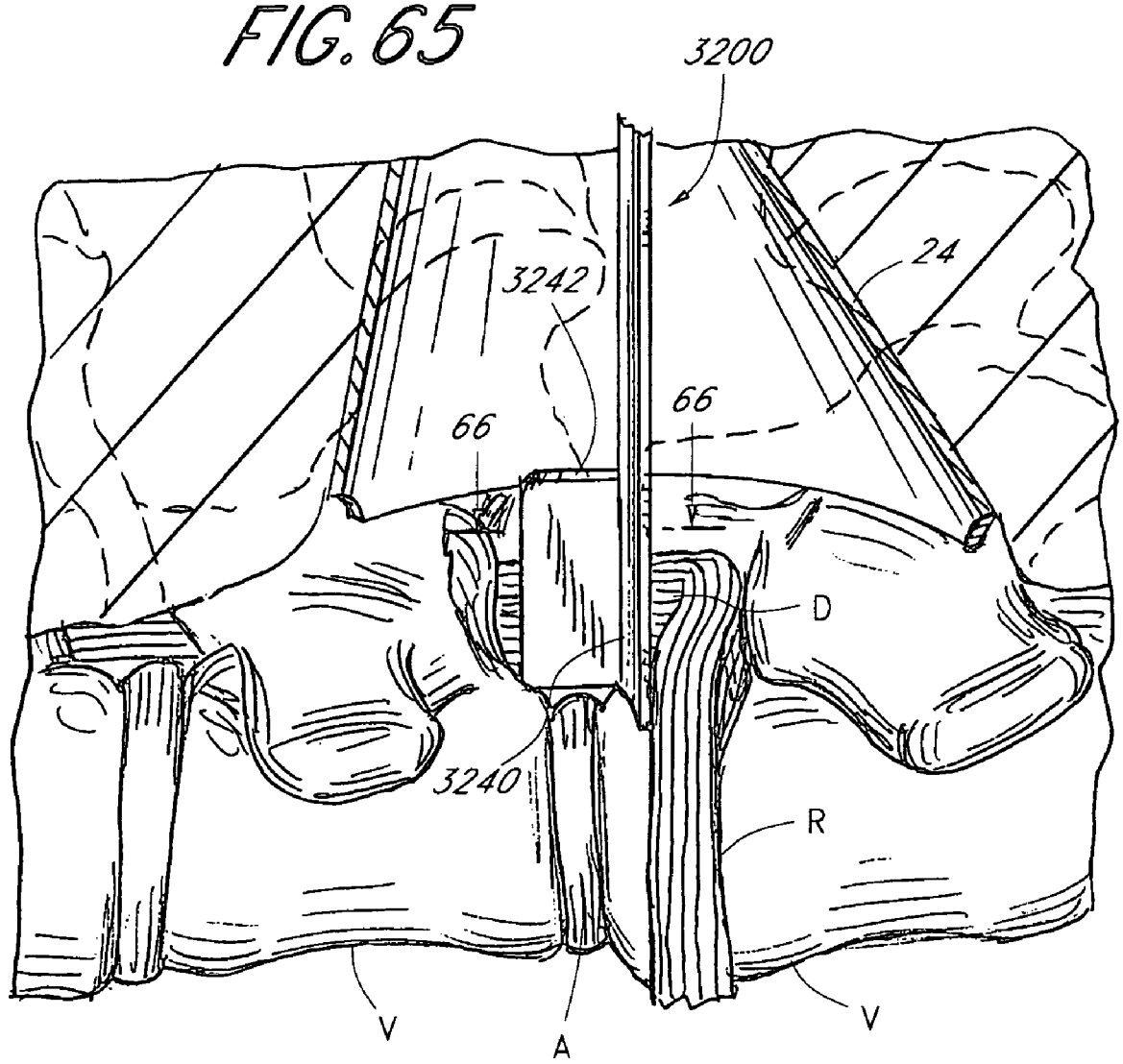
FIG. 65 is a sectional view, similar to FIG. 57, of the apparatus of FIG. 63, used in conjunction with additional structure in a patient.

The spinal implant 2110 (FIGS. 43-47) has a first end 2120 for insertion between the adjacent vertebrae V. The first end 2120 has a tapered surface 2122 to facilitate insertion of the implant between the adjacent vertebrae V. The surface 2122 defines an angle Y of approximately 45° as shown in FIG. 65.

The spinal implant 2110 (FIGS. 43-44) has a second end 2130 that is engageable with the projections 2034 on the tool 2032 for inserting the implant between the adjacent vertebrae V. The projections 2034 extend into recesses 2136 and 2138 in the end 2130 of the implant 2110. The recesses 2136 and 2138 extend from the second end 2130 toward the first end 2120. The recess 2136 (FIGS. 43 and 46) is defined by an upper surface 2140 and a lower surface 2142 extending generally parallel to the upper surface 2140. The recess 2138 (FIG. 44) has a lower surface 2146 and an upper surface 2148 extending generally parallel to the lower surface 2146.

The recesses 2136 and 2138 define a gripping portion 2152. The projections 2034 on the tool 2032 extend into the recesses 2136 and 2138 and grip the gripping portion 2152. The projections 2034 engage the upper and lower surfaces 2140 and 2142 of the recess 2136 and the upper and lower surfaces 2146 and 2148 of the recess 2138. Accordingly, the tool 2032 can grip the implant 2110 for inserting the implant between the adjacent vertebrae V.

Figures 43, 44:
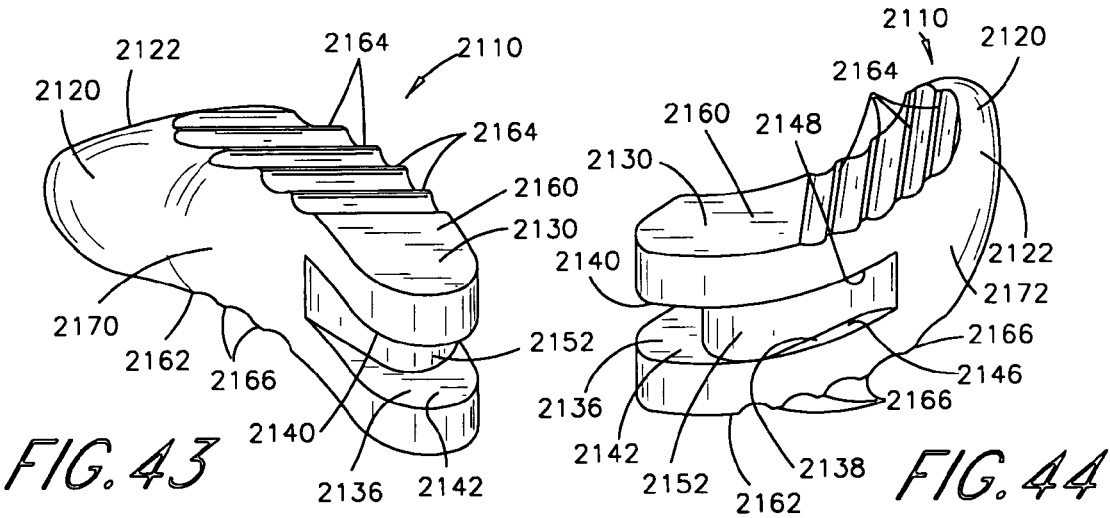
FIG. 43 is a perspective view of another embodiment of a spinal implant constructed according to another embodiment showing a first side surface of the spinal implant.
FIG. 44 is a perspective view of the spinal implant of FIG. 43 showing a second side surface of the spinal implant.
Figure 45:
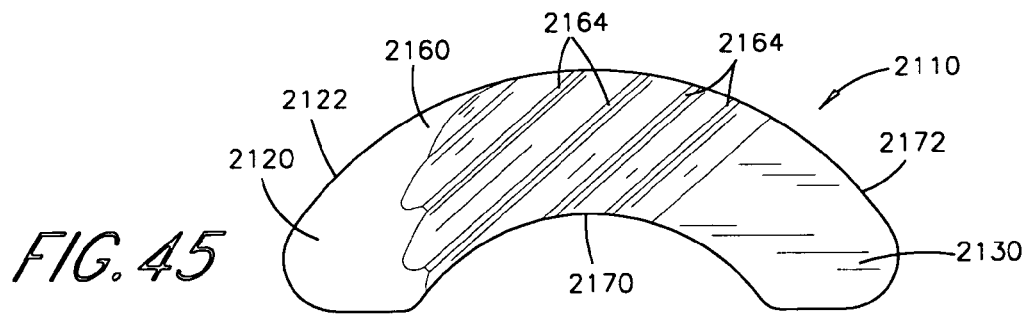
FIG. 45 is a plan view of the spinal implant of FIG. 43 showing an upper surface of the spinal implant.
Figure 46:
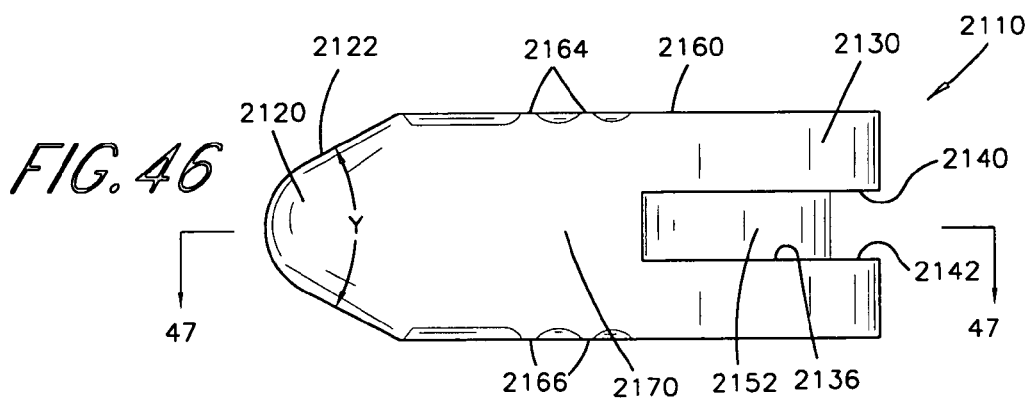
FIG. 46 is a side view of the spinal implant of FIG. 43 showing the first side surface.
Figure 47:
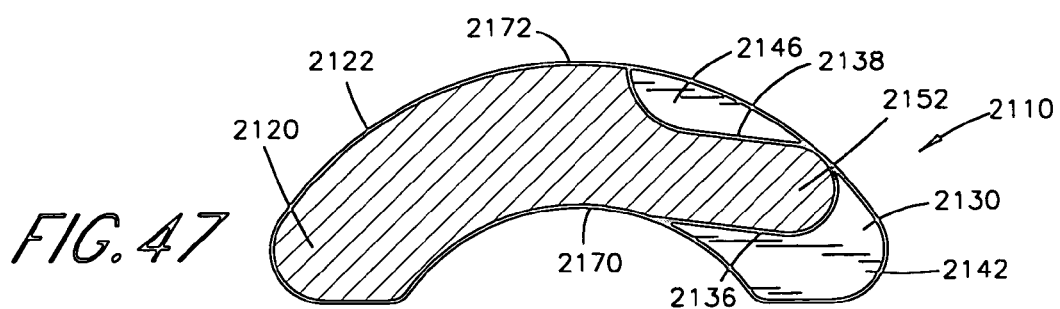
FIG. 47 is a cross-sectional view of the spinal implant taken along the line 47-47 in FIG. 46.

As viewed in FIGS. 43-46, the implant 2110 has an upper surface 2160 for engaging the upper vertebra V. The implant 2110 has a lower surface 2162, as viewed in FIGS. 43-46, for engaging the lower vertebra V. The upper and lower surfaces 2160 and 2162 extend from the first end 2120 to the second end 2130 of the implant 2110 and parallel to the upper and lower surfaces 2140, 2142, 2146, and 2148 of the recesses 2136 and 2138. The upper surface 2160 has teeth 2164 for engaging the upper vertebra V. The lower surface 2162 has teeth 2166 for engaging the lower vertebra V. Although FIG. 44 shows four teeth 2164 and four teeth 2166, it is contemplated that any number of teeth could be used.

A first side surface 2170 and a second side surface 2172 extend between the upper and lower surfaces 2160 and 2162. The first side surface 2170 extends along a first arc from the first end 2122 of the implant 2110 to the second end 2130. The second side surface 2172 extends along a second arc from the first end 2120 to the second end 2130. The first and second side surfaces 2170 and 2172 are concentric and define portions of concentric circles. The teeth 2164 and 2166 extend parallel to each other and between the side surfaces 2170 and 2172 along secant lines of the concentric circles defined by the side surfaces.

The implant 2110 preferably is formed by harvesting allograft material from a femur, as is known in the art. The femur is axially cut to form cylindrical pieces of allograft material. The cylindrical pieces are then cut in half to form semi-cylindrical pieces of allograft material. The semi-cylindrical pieces of allograft material are machined into the spinal implants 2110.

A spinal implant 2110 is placed unilaterally between the adjacent vertebrae V. The access device 20 is positioned in the patient's body adjacent the vertebrae V. The skirt portion 24 of the access device 20 preferably is in a radially expanded condition to provide a working space adjacent the vertebrae V as described above. Disc material between the vertebrae V can be removed using instruments such as kerrisons, rongeurs, or curettes. A microdebrider may also be utilized to remove the disc material. An osteotome, curettes, and scrapers can be used to prepare end plates of the vertebrae V for fusion. Preferably, an annulus of the disc is left between the vertebrae V.

Distracters are used to sequentially distract the disc space until the desired distance between the vertebrae V is achieved. The implant 2110 is placed between the vertebrae V using the tool 2032. It is contemplated that the apparatus 3100 could be used also. The first end 2120 of the implant 2110 is inserted first between the vertebrae V. The implant 2110 is pushed between the vertebrae V until the end 2130 of the implant is between the vertebrae. It is contemplated that the implant 2110 may be inserted in any desired position between the vertebrae V. It is also contemplated that in some embodiments more than one implant 2110 may be inserted between the vertebrae.

The apparatus or shield 3100 for use in placing the fusion devices or spinal implants between the vertebrae is illustrated in FIGS. 52-56. The apparatus 3100 preferably includes an elongated body portion 3102, which protects the nerve root or dura, and a mounting portion 3104, which allows for the surgeon to releasably mount the apparatus 3100 to the access device 20. Consequently, the surgeon is able to perform the surgical procedures without requiring the surgeon or an assistant to continue to support the apparatus 3100 throughout the procedure, and without reducing the field of view.

The apparatus 3100 may be manufactured from a biocompatible material such as, for example, stainless steel. In the illustrated embodiment, apparatus 3100 is manufactured from stainless steel having a thickness of about 0.02 inches (0.508 mm) to about 0.036 inches (0.914 mm). The elongated body portion 3102 has dimensions that correspond to the depth in the body in which the procedure is being performed, and to the size of the body structure that is to be shielded by elongated body portion 3102. In the exemplary embodiment, the elongated body portion 3102 has a width 3106 of about 0.346 inches (8.79 mm) and a length of about 5.06 inches (128.5 mm) (FIG. 53), although other dimensions would be appropriate for spinal surgical procedures performed at different locations, or for surgical procedures involving different body structures. The distal tip portion 3110 of the apparatus 3100 may have a slightly curved "bell mouth" configuration which allows for atraumatic contact with a body structure, such as a nerve. It is contemplated that the elongated body portion may have any desired shape.

The mounting portion 3104 preferably allows the apparatus 3100 to be secured to a support structure in any number of ways. In the exemplary embodiment, mounting portion 3104 may include a ring portion. With reference to FIGS. 52-56, ring portion 3120 has a substantially ring-shaped configuration with an opening 3124, which defines an angle 3126 of about 90 degrees of the total circumference of the ring portion 3120. As will be described in greater detail below, the angle 3126 is a nominal value, because the ring portion 3104 is resilient, which permits the opening 3124 to change size during the mounting process.

In the illustrated embodiment, the mounting portion 3104 has a substantially cylindrical configuration in order to be mounted within the interior lumen of the access device 20, as will be described below. The ring portion 3104 has an exterior dimension 3130 of about 0.79 inches (20.1 mm), and an interior dimension 3132 of about 0.76 inches (19.3 mm). It is understood that the dimensions of the ring portion 3104 can be different, such as, for example, where the access device 20 has a different interior dimension. Moreover, the cylindrical shape of the ring portion 3104 can change, such as, for example, where the apparatus 3100 is used with a support member having a differently shaped internal lumen.

Finger grip portions 3122 preferably extend from the mounting portion 3104 and allow the surgeon to apply an inwardly directed force (as indicated by arrows A) to the ring portion 3120. The resilient characteristics of the ring portion 3120 allow the material to deflect thereby reducing the exterior dimension 3130 and reducing the spacing 3124. Releasing the finger grip portions 3122 allows the ring portion to move towards its undeflected condition, thereby engaging the interior wall of the access device 20.

The elongated body portion 3102 and the mounting portion 3104 may be manufactured from a single component, such as a sheet of stainless steel, and the mounting portion 3104 may be subsequently formed into a substantially cylindrical shape. In another embodiment, the mounting portion 3104 may be manufactured as a separate component and coupled with the elongated body portion, by techniques such as, for example, welding and/or securement by fasteners, such as rivets.

The access device 20 serves as a stable mounting structure for apparatus 3100. In particular, mounting portion 3104 is releasably mounted to the interior wall of proximal wall portion 22 of access device 20. Elongated body portion 3102 extends distally into the operative site to protect the desired body structure, such as the nerve, as will be described below.

Figure 58:
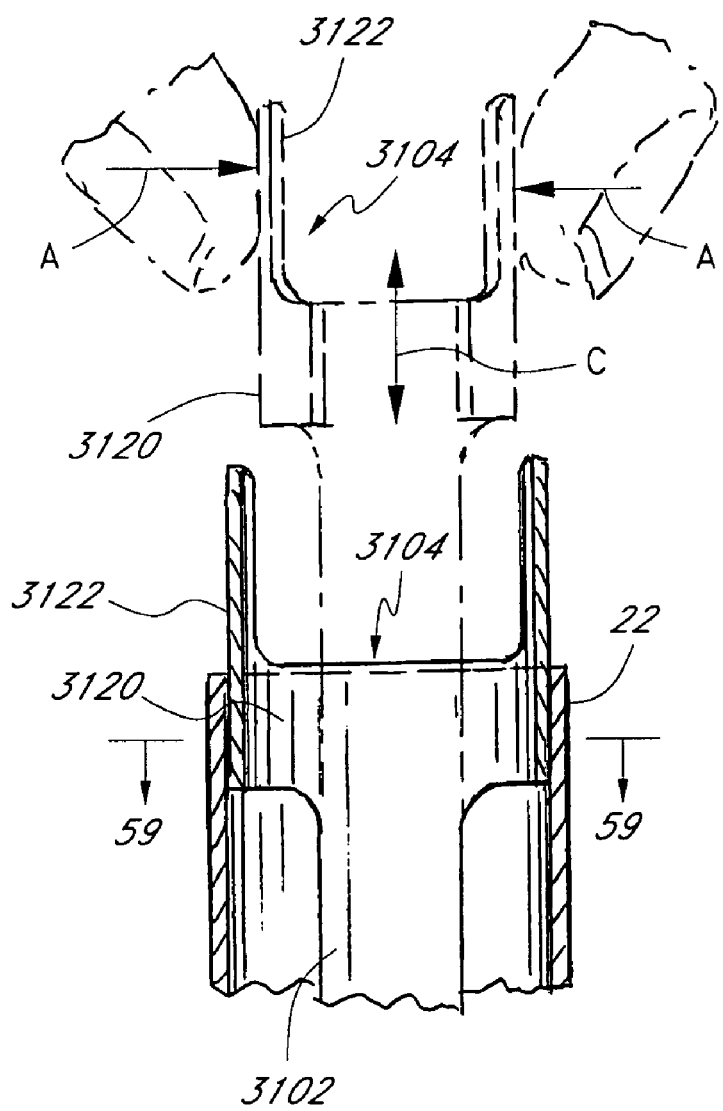
FIG. 58 is a longitudinal sectional view of the apparatus of FIG. 57 taken from line 58-58 of FIG. 57.
Figure 59:
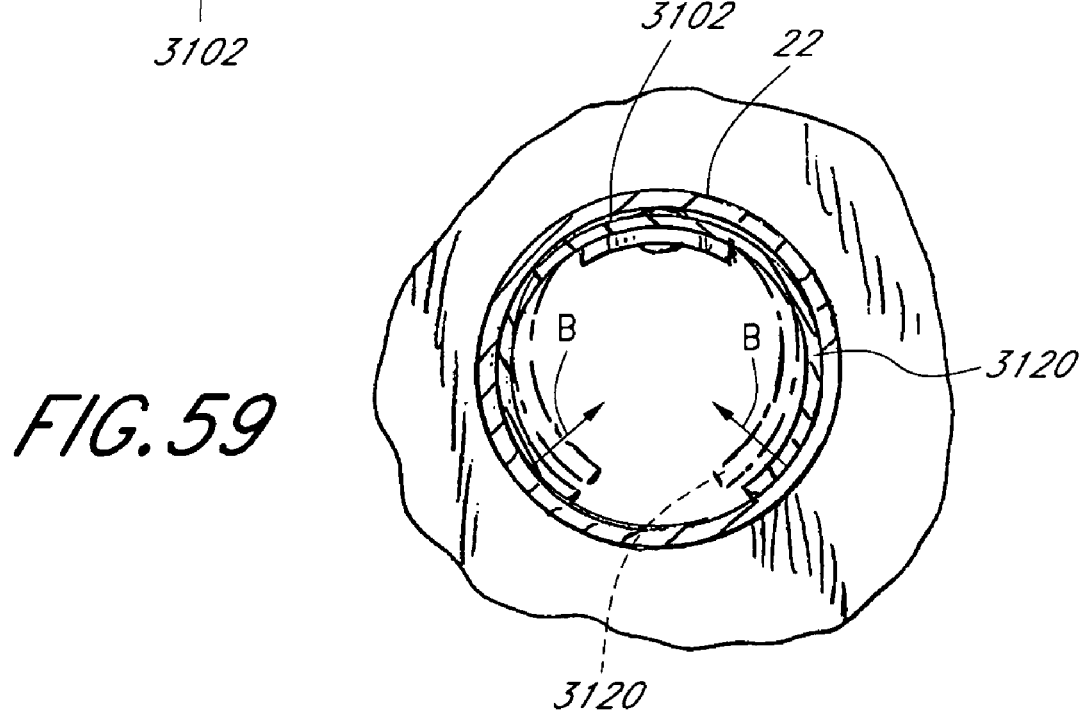
FIG. 59 is a transverse sectional view of the apparatus of FIG. 58 taken from line 59-59 of FIG. 58.

To install the apparatus 3100 within the interior passage of the proximal wall portion 22, the surgeon may apply an inwardly directed force on the ring portion 3120, thereby causing the ring portion to resiliently deform, as illustrated by dashed line and arrows B in FIG. 59. The surgeon subsequently inserts the apparatus 3100 into the interior lumen of the proximal wall portion 22 (as indicated by arrow C) to the position of ring portion 3104 illustrated in solid line in FIG. 58. When the surgeon releases the finger grip portions 3122, the ring portion 3120 resiliently moves towards its undeflected configuration, thereby engaging the interior lumen of the proximal wall portion 22. Advantages of some embodiments include that the mounting portion 3104 is easily removed and/or moved with respect to the access device 20 without disturbing the position of the access device 20 or any other instrumentation.

Figure 57:
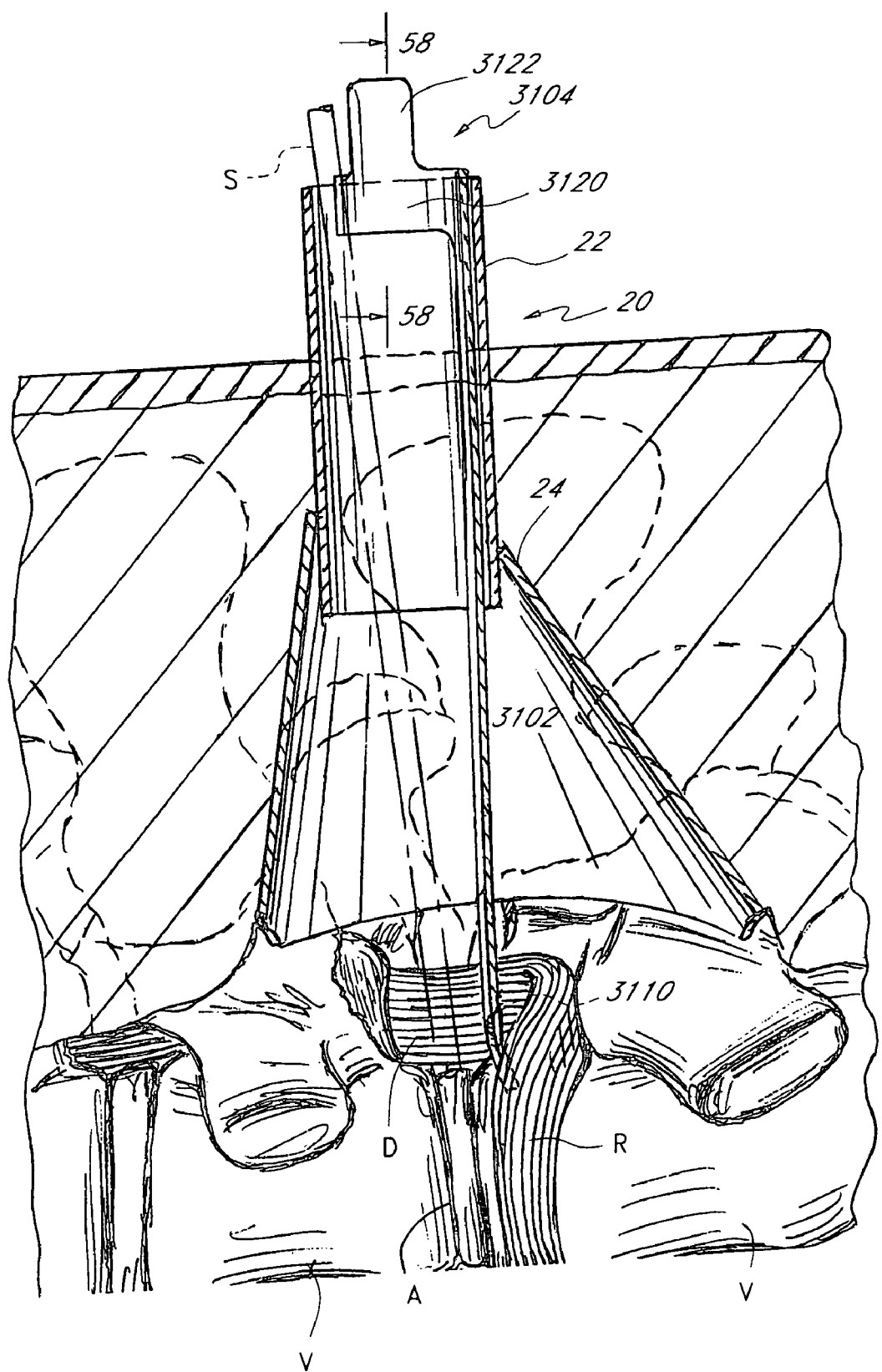
FIG. 57 is a sectional view of the apparatus of FIG. 52, used in conjunction with additional structure in a patient.

As illustrated in FIG. 57, the configuration of the mounting portion 3104 and the elongated body portion 3102 allow the elongated body portion to occupy a small space along the periphery of the proximal wall portion 3122. This allows the apparatus to protect the desired body structure without blocking access for the insertion of other surgical instrumentation, and without blocking visibility by the surgeon during the procedure.

The mounting portion 3104 is one exemplary configuration for mounting the apparatus 3100 to the support structure. It is contemplated that the apparatus 3100 may be mounted within the access device 20 in any suitable manner.

When in position, the distal end portion 3110 covers the exiting nerve root R, while exposing the disc annulus A (See FIG. 57). As discussed above, the debridement and decortication of tissue covering the vertebrae, as well as a facetectomy and/or laminectomy if indicated, are preferably performed prior to the insertion of apparatus 3100 into the surgical space. Accordingly, in some embodiments, there is no need to displace or retract tissue, and apparatus 3100 merely covers the nerve root and does not substantially displace the nerve root or any other body tissue. It is understood that the term "cover" as used herein refers to apparatus 3100 being adjacent to the body structure, or in contact with the body structure without applying significant tension or displacement force to the body structure.

Additional surgical instrumentation S may be inserted into the access device to perform procedures on the surrounding tissue. For example, an annulotomy may be performed using a long handled knife and kerrisons. A discectomy may be completed by using curettes and rongeurs. Removal of osteophytes which may have accumulated between the vertebrae may be performed using osteotomes and chisels.

Figure 60:
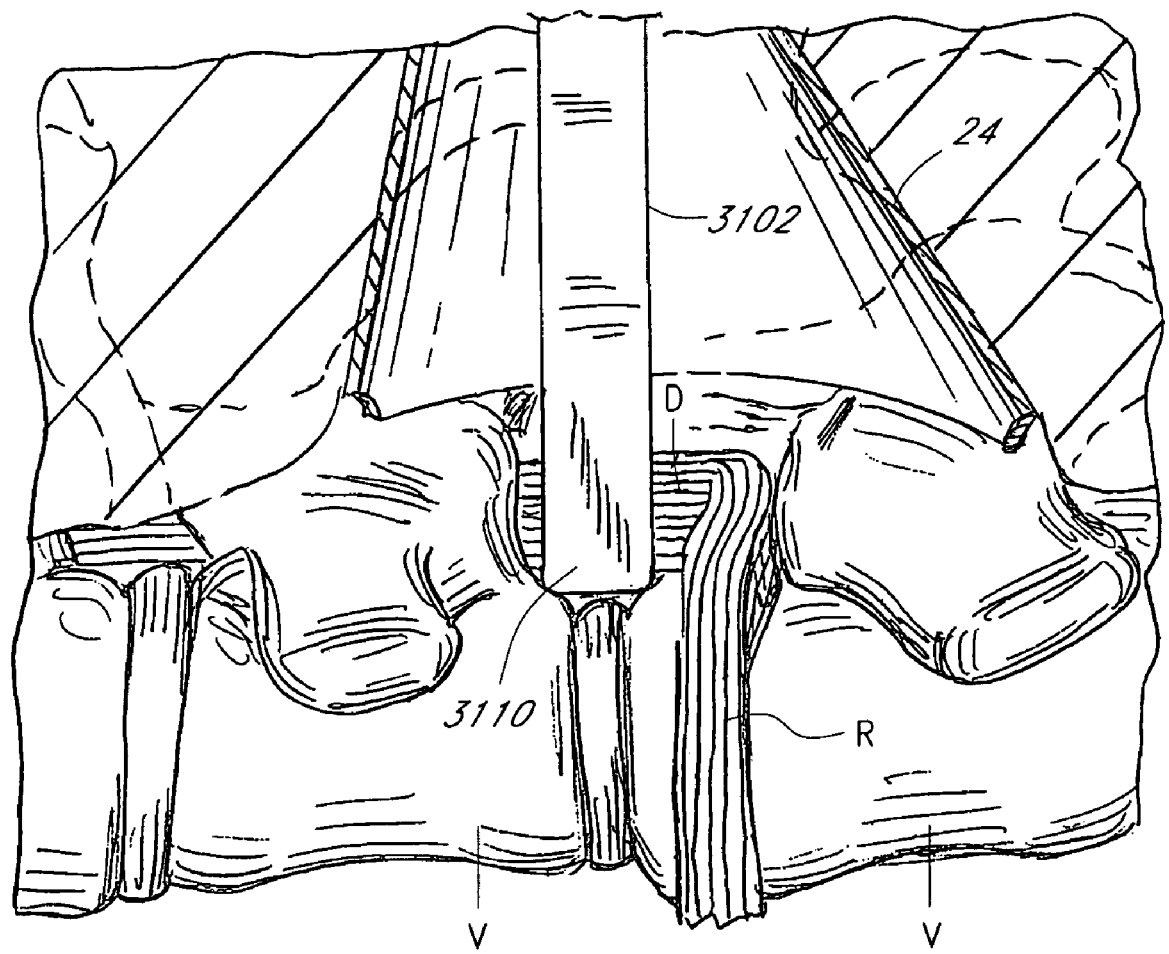
FIG. 60 is a sectional view, similar to FIG. 57, illustrating an alternative position of the apparatus of FIG. 52.

As illustrated in FIG. 60, the elongated body portion 3102 preferably is rotated to protect the spinal cord, or dura D, during the above procedures. The surgeon may change the position of the apparatus 3100 by approximating the finger grips 3122 to release the ring portion from engagement with the inner wall of the proximal wall portion 20, and then re-position the apparatus 3100 without disturbing the access device 20 (as shown in FIG. 58).

Figure 61:
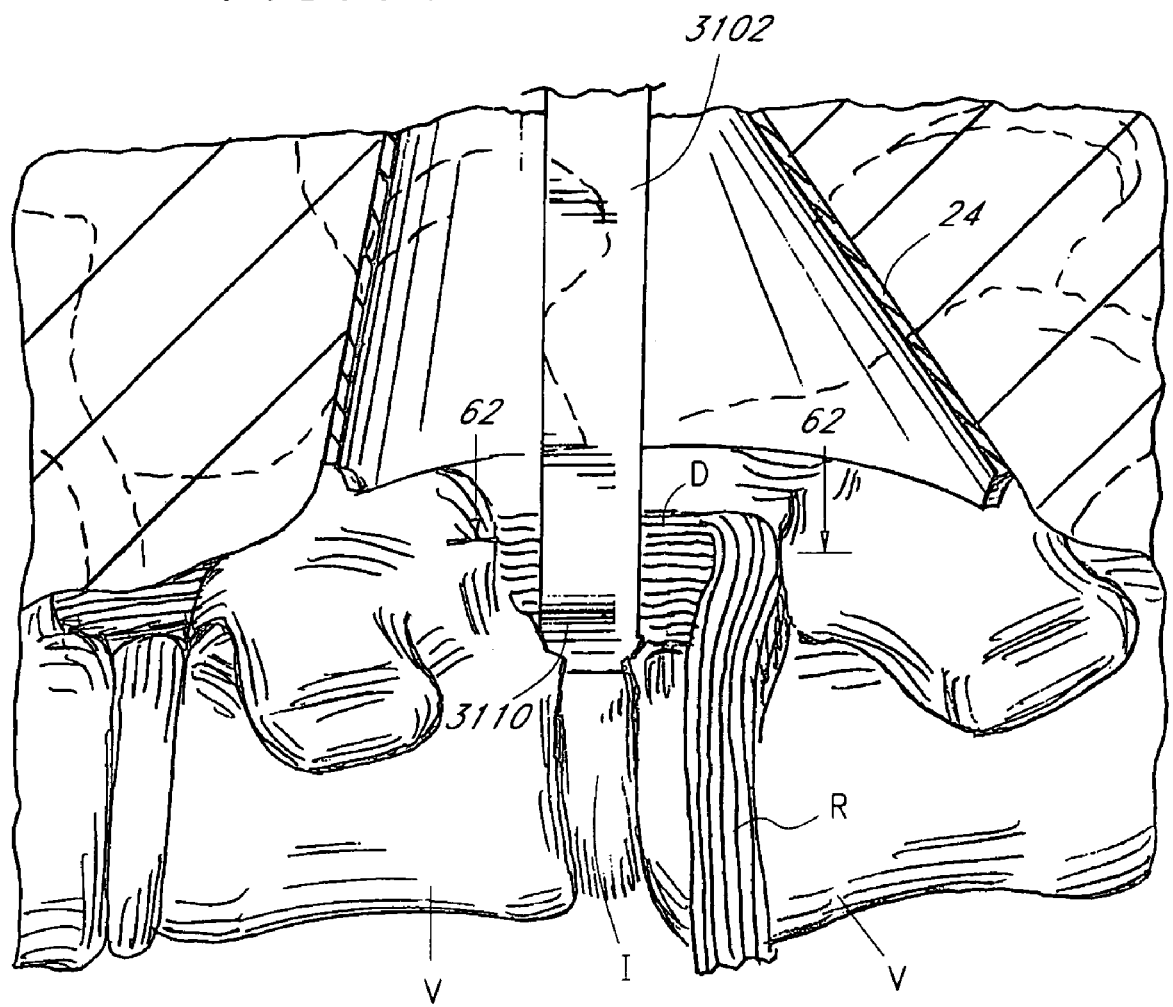
FIG. 61 is a sectional view, similar to FIG. 57, illustrating another alternative position of the apparatus of FIG. 52.
Figure 62:
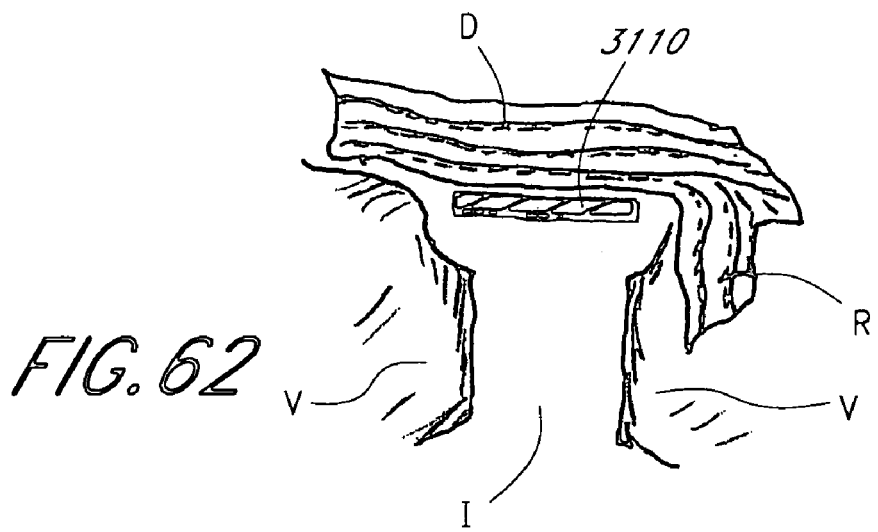
FIG. 62 is a transverse sectional view of the apparatus of FIG. 61, taken along lines 62-62 of FIG. 61.

During certain surgical procedures, it may be useful to introduce crushed bone fragments or the fusion devices 2010 or 2110 to promote bone fusion. As illustrated in FIGS. 61-62, apparatus 3100 is useful to direct the implants into the space I between adjacent vertebrae V. As shown in the figures, the distal portion 3110 of the elongated body portion 3102 is partially inserted into the space I. The distal end portion 3110, is positioned between adjacent vertebrae V, and creates a partially enclosed space for receiving the implants or other material therein.

Figure 63:
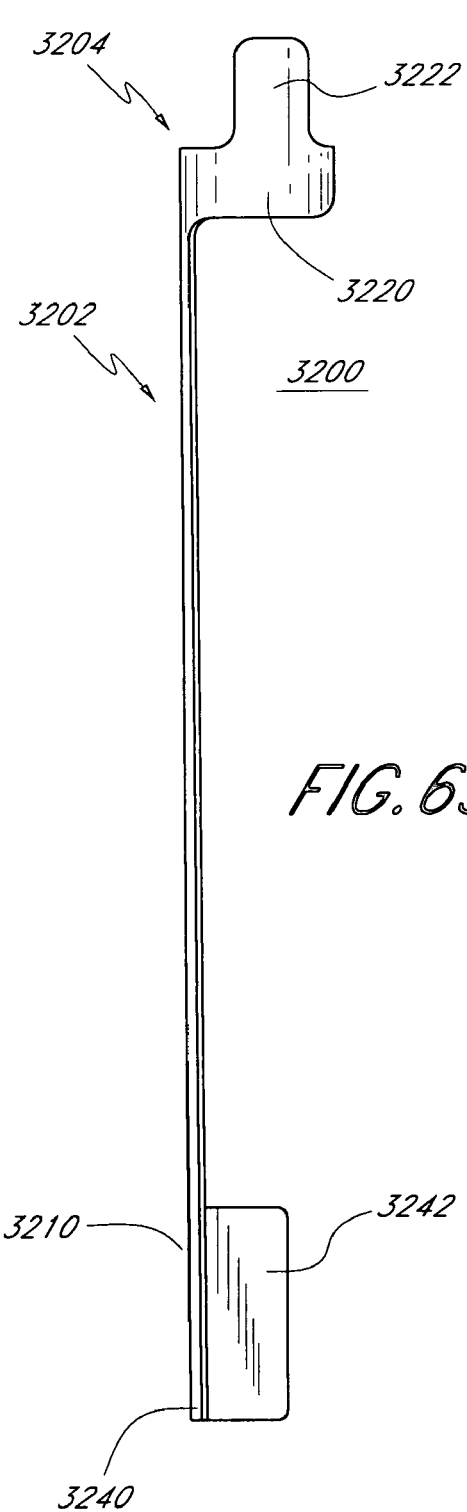
FIG. 63 is a side view, similar to FIG. 52, of another apparatus.
Figure 64:
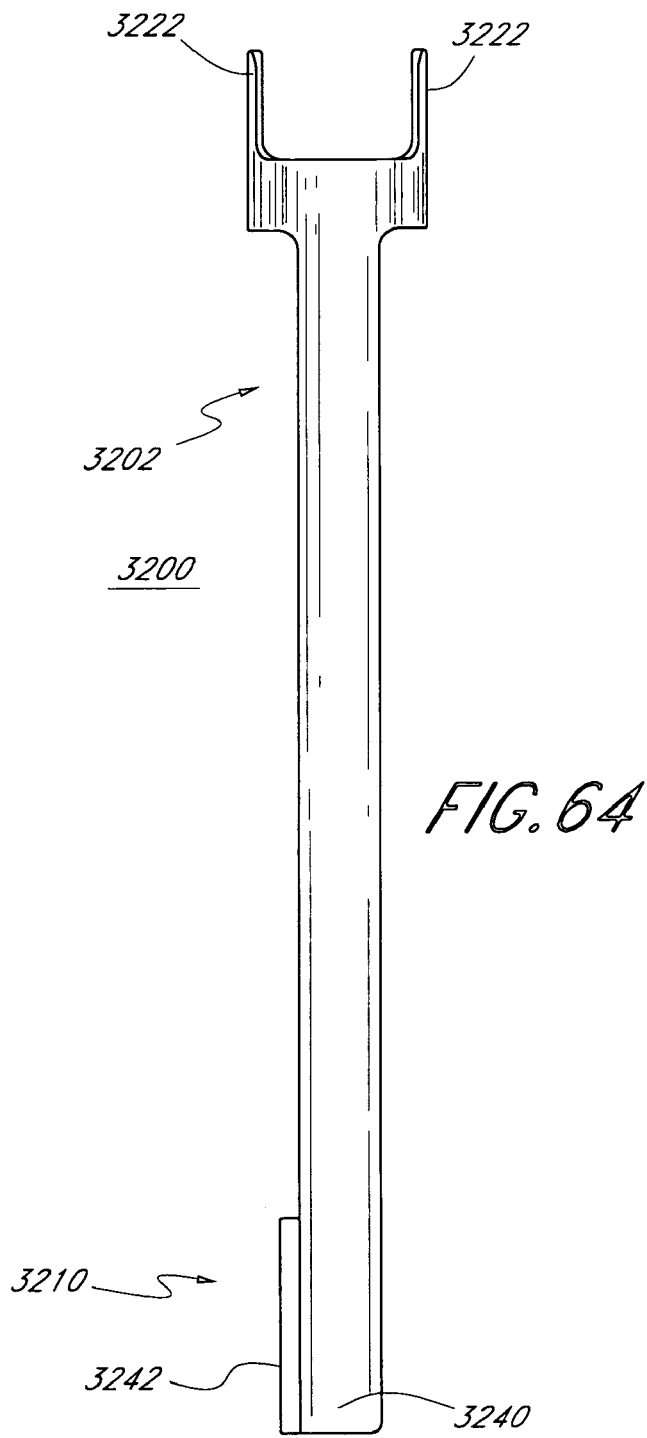
FIG. 64 is a front view, similar to FIG. 55, of the embodiment of FIG. 63.

Another embodiment of the apparatus or shield is illustrated in FIGS. 63-64, and designated apparatus 3200. Apparatus 3200 is substantially identical to apparatus 3100, described above, with the following differences noted herein. In particular, distal end portion 3210 includes a pair of surfaces 3240 and 3242. Surface 3240 is an extension of elongated shield portion 3202, and surface 3242 extends at an angle with respect to surface 3240. In the exemplary embodiment, surfaces 3240 and 3242 defined an angle of about 90 degrees between them. Alternatively another angle between surfaces 3240 and 3242 may be defined as indicated by the body structures to be protected.

Figure 66:
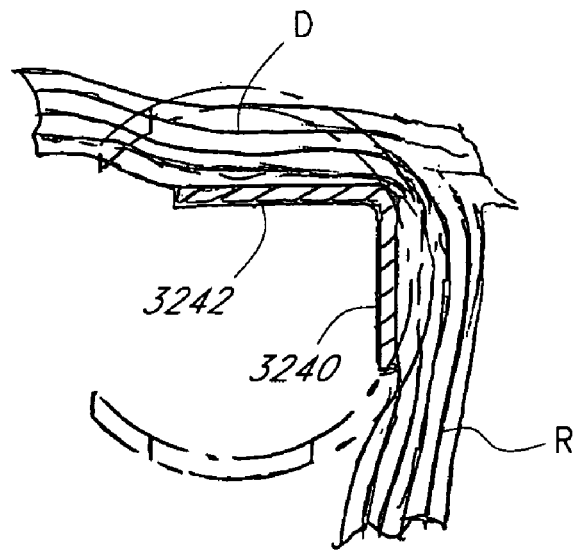
FIG. 66 is a transverse sectional view of the apparatus of FIG. 63, taken along lines 66-66 of FIG. 65.

Distal end portion 3210 allows the apparatus to provide simultaneous shielding of both the dura D and the nerve root R. In FIGS. 65-66, surface 3242 shields the dura D, and surface 3240 shields the nerve root R. It is understood that surfaces 3240 and 3242 may be interchanged with respect to which tissue they protect during the surgical procedure.

According to the exemplary embodiment, once the fusion and fixation portions of the procedure have been performed, the procedure is substantially complete. The surgical instrumentation, such as the endoscope 500 can be withdrawn from the surgical site. The access device 20 is also withdrawn from the site. The muscle and fascia typically close as the access device 20 is withdrawn through the dilated tissues in the reduced profile configuration. The fascia and skin incisions are closed in the typical manner, with sutures, etc. The procedure described above may be repeated for the other lateral side of the same vertebrae, if indicated.

II. Surgical Procedures that May be Performed with the Systems Described Herein As discussed above, the systems disclosed herein provide access to a surgical location at or near the spine of a patient to enable procedures on the spine. These procedures can be applied to one or more vertebral levels, as discussed above. Additional procedures and combinations of procedures that may be performed using the systems described herein are discussed below. In various forms, these procedures involve an anterior lumbar interbody fusion, a minimally invasive lumbar interbody fusion, and other procedures particularly enabled by the access devices and systems described above.

A. Procedures Involving Anterior Lumbar Interbody Fusion

The access devices and systems described herein are amenable to a variety of procedures that may be combined with an anterior lumbar interbody fusion (referred to herein as an "ALIF").

In one embodiment of a first method, three adjacent vertebrae, such as the L4, the L5, and the S1 vertebrae of the spine, are treated by first performing an ALIF procedure. Such a procedure may be performed in a convention manner. The ALIF involves exposing a portion of the spine, in particular the vertebrae and discs located in the interbody spaces, i.e., the spaces between adjacent vertebrae. Any suitable technique for exposing the interbody spaces may be employed, e.g., an open, mini-open, or minimally invasive procedure. In one embodiment, the interbody spaces between the L4, L5, and S1 vertebrae are exposed to the surgeon. Once exposed, the surgeon may prepare the interbody space, if needed, in any suitable manner. For example, some or all of the disc may be removed from the interbody space and the height of the interbody space may be increased or decreased. The interbody space between the L4 and the L5 vertebrae may be exposed separately from the interbody space between the L5 and S1 vertebrae or they may be generally simultaneously exposed and prepared.

After the interbody space has been exposed and prepared, a suitable fusion procedure may be performed. For example, in one example fusion procedure, one or more fusion devices may be placed in the interbody space. Any suitable fusion device may be used, e.g., a fusion cage, a femoral ring, or another suitable implant. Various embodiments of implants and techniques and tools for the insertion of implants are described in U.S. application Ser. No. 10/280,489, filed Oct. 25, 2002, which has been published as Publication No. 2003/0073998 on Apr. 17, 2003, which is hereby incorporated by reference herein in its entirety. In one variation, one or more fusion cages may be placed in an interbody space, e.g., between the L4 and L5 vertebrae, between the L5 and S1 vertebrae, or between the L4 and L5 vertebrae and between the L5 and S1 vertebrae. In another variation, one or more femoral rings may be substituted for one or more of the fusion cages and placed between the L4 and L5 vertebrae and/or between the L5 and S1 vertebrae. In another variation, one or more fusion devices are combined with a bone growth substance, e.g., bone chips, to enhance bone growth in the interbody space(s).

After anterior placement of the fusion device, an access device is inserted into the patient to provide access to a spinal location, as described above. A variety of anatomical approaches may be used to provide access to a spinal location using the access device 20. The access device preferably is inserted generally posteriorly. As used herein the phrase "generally posteriorly" is used in its ordinary sense and is a broad term that refers to a variety of surgical approaches to the spine that may be provided from the posterior side, i.e., the back, of the patient, and includes, but is not limited to, posterior, postero-lateral, and transforaminal approaches. Any of the access devices described or incorporated herein, such as the access device 20, could be used.

The distal end of the access device may be placed at the desired surgical location, e.g., adjacent the spine of the patient with a central region of the access device over a first vertebrae. In one procedure, the distal end of the access device is inserted until it contacts at least a portion of at least one of the vertebrae being treated or at least a portion of the spine. In another procedure, the distal end of the access device is inserted until it contacts a portion of the spine and then is withdrawn a small amount to provide a selected gap between the spine and the access device. In other procedures, the access device may be inserted a selected amount, but not far enough to contact the vertebrae being treated, the portion of the vertebrae being treated, or the spine.

The access device may be configured, as described above, to provide increased access to the surgical location. The access device can have a first configuration for insertion to the surgical location over the first vertebra and a second configuration wherein increased access is provided to the adjacent vertebrae. The first configuration may provide a first cross-sectional area at a distal portion thereof. The second configuration may provide a second cross-sectional area at the distal portion thereof. The second cross-sectional area preferably is enlarged compared to the first cross-sectional area. In some embodiments, the access device may be expanded from the first configuration to the second configuration to provide access to the adjacent vertebrae above and below the first vertebra.

When it is desired to treat the L4, L5, and S1 vertebrae, the access device may be inserted over the L5 vertebrae and then expanded to provide increased access to the L4 and S1 vertebrae. In one embodiment, the access device can be expanded to an oblong shaped configuration wherein the access device provides a first dimension of about 63 mm, and a second dimension perpendicular to the first dimension of about 24 mm. In another embodiment, the access device can be expanded to provide a first dimension of about 63 mm, and a second dimension perpendicular to the first dimension of about 27 mm. These dimensions provide a surgical space that is large enough to provide access to at least three adjacent vertebrae without exposing excessive amounts of adjacent tissue that is not required to be exposed for the procedures being performed. Other dimensions and configurations are possible that would provide the needed access for procedures involving three adjacent vertebrae.

When the access device is in the second configuration, fixation of the three vertebrae may be performed. As discussed above, fixation is a procedure that involves providing a generally rigid connection between at least two vertebrae. Any of the fixation procedures discussed above could be used in this method, as could other fixation procedures. One fixation procedure that could be used is discussed above in connection with FIG. 36 wherein the fasteners 600*a*, 600*b*, and 600*c* are advanced through the access device 20 to three adjacent vertebrae and are attached to the vertebrae. The three fasteners 600*a*, 600*b*, and 600*c* are interconnected by the elongated member 650. The three fasteners 600*a*, 600*b*, and 600*c* and the elongate member 650 comprise a first fixation assembly. A second fixation assembly may be applied to the patient on the opposite side of the spine, i.e., about the same location on the opposite side of the medial line of the spine. Other fixation procedures could be applied, e.g., including two fasteners that coupled with the L4 and the S1 vertebrae and an elongate member interconnecting these vertebrae.

One variation of the first method provides one level of fixation on the anterior side of the patient, e.g., when the fusion device is placed in the interbody space. For example, fixation of the L5 and S1 vertebrae could be provided on the anterior side of the spine, in addition to the other procedures set forth above (e.g., a two level postero-lateral fixation). Also, fixation of the L4 and L5 vertebrae could be provided on the anterior side of the spine, in addition to the other procedures set forth above (e.g., a two level postero-lateral fixation).

In a second method, substantially the same steps as set forth above in connection with the first method would be performed. In addition, after the access device is inserted, a decompression procedure is performed through the access device. A decompression procedure is one where unwanted bone is removed from one or more vertebrae. Unwanted bone can include stenotic bone growth, which can cause impingement on the existing nerve roots or spinal cord. Decompression procedures that may be performed include laminectomy, which is the removal of a portion of a lamina(e), and facetectomy, which is the removal of a portion of one or more facets. In one variation of this method, decompression includes both a facetectomy and a laminectomy. Any suitable tool may be used to perform decompression. One tool that is particularly useful is a kerrison.

In a third method, substantially the same steps as set forth above in connection with the first method would be performed. That is, an ALIF procedure is performed in combination with a fixation procedure. In addition, a fusion procedure may be performed through the access device which may have been placed generally posteriorly, e.g., postero-laterally, tranforaminally or posteriorly, whereby bone growth is promoted between the vertebrae and the fixation assembly, including at least one of the fasteners 600*a*, 600*b*, 600*c* and/or the elongate element 650. This procedure is also referred to herein as an "external fusion" procedure.

One example of an external fusion procedure that may be performed involves placement of a substance through the access device intended to encourage bone growth in and around the fixation assembly. Thus, fusion may be enhanced by placing a bone growth substance adjacent any of the fasteners 600*a*, 600*b*, 600*c* and/or the elongate member 650. The bone growth substance may take any suitable form, e.g., small bone chips taken from the patient (e.g., autograft), from another donor source (e.g., allograft or xenograft), and orthobiologics.

After the bone growth substance is applied to the fixation assembly, the access device is removed. Absent the retracting force provided by the access device, the patient's tissue generally collapses onto the bone growth substance. The tissue will thereby maintain the position of the bone growth substance adjacent to the fixation assembly. The presence of the bone growth substance can cause bone to bridge across from the vertebra(e) to one or more components of the fixation assembly.

In a fourth method, substantially the same steps as set forth above in connection with the second method would be performed. That is, an ALIF procedure is performed anteriorly, and a decompression procedure and a fixation procedure are performed through the access device which may be placed generally posteriorly, e.g., postero-laterally, tranforaminally, or posteriorly. In addition, bone growth substance is placed in and around a fixation assembly through the access device, as discussed above in connection with the third method. The bone growth substance encourages bone to bridge across from the vertebrae to the fixation assembly.

In a fifth method, an ALIF procedure is performed, as discussed above in connection with the second method. After one or more fusion devices is placed in the interbody space, access is provided by way of the access device, as discussed above, from any suitable anatomical approach, e.g., a generally posterior approach. Preferably, a postero-lateral approach is provided. After access has been provided, a bone growth substance, such as those discussed above in connection with the third method, is delivered through the access device. The bone growth substance is placed adjacent an interbody space, e.g., the space between the L4 and the L5 vertebrae and/or between the L5 and the S1 vertebrae. The bone growth substance encourages fusion of the adjacent vertebrae, e.g., L4 to L5 and/or L5 to S1, by stimulating or enhancing the growth of bone between adjacent vertebrae, as discussed above.

In a sixth method, substantially the same steps described in connection with the first method are performed, except that the fixation procedure is optional. In one variation of the sixth method, the fixation procedure is not performed. However, after the access device is inserted, a bone growth substance is placed in and around one or more interbody spaces through the access device. Where the sixth method involves a two level procedure, the bone growth substance can be placed adjacent the interbody space between the L4 and the L5 vertebra and/or between the L5 and the S1 vertebra. Thus, bone growth may occur in the interbody space and adjacent the interbody space between the vertebrae.

The foregoing discussion illustrates that an ALIF procedure can be combined with a variety of procedures that can be performed through an access device disclosed herein. In addition, though not expressly set forth herein, any combination of the procedures discussed above, and any other suitable known procedure, may also be combined and performed through the access devices described herein, as should be understood by one skilled in the art.

B. Spine Procedures Providing Minimally Invasive Lumbar Interbody Fusion

Another category of procedures that may be performed with the access devices and systems described above involves a minimally invasive lumbar interbody fusion (referred to herein as a "MILIF"). MILIF procedures are particularly advantageous because they permit the surgeon to perform a wide variety of therapeutic procedures without requiring fusion by way of an anterior approach, as is required in an ALIF. This provides a first advantage of allowing the surgeon to perform all procedures from the same side of the patient and also possibly from the same approach. Also, the access devices and systems disclosed herein provide the further advantage of enabling two level procedures, and many other related procedures, to be performed by way of a single percutaneous access. These and other advantages are explained more fully below.

In a first MILIF method, a two level postero-lateral fixation of the spine involving three adjacent vertebrae, such as the L4, L5, and S1 vertebrae, is provided. Analogous one level procedures and two level procedures involving any other three vertebrae also may be provided. In addition, the access devices and systems described herein could be used or modified to accommodate other multi-level procedures, such as a three level procedure. The surgeon inserts an access device such as described herein to a surgical location near the spine. As discussed above, the access devices are capable of a wide variety of anatomical approaches. In this procedure, a postero-lateral approach is preferred. Once the access device is inserted to a location adjacent the spine, as discussed above, it may be configured, e.g., expanded, as discussed above, to a configuration wherein sufficient access is provided to the surgical location.

Any suitable fusion process may then be performed. For example, an implant may be advanced through the access device into the interbody space in order to maintain disc height and allow bone growth therein, e.g., as in a fusion procedure. In order to ease insertion of the implant, it may be beneficial to prepare the interbody space. Interbody space preparation may involve removal of tissue or adjusting the height of the interbody space through the access device, such as in a distraction procedure. Once the interbody space is prepared, a suitable implant may be advanced through the access device into the interbody space, taking care to protect surrounding tissues. Various embodiments of implants and techniques and tools for their insertion are described in U.S. application Ser. No. 10/280,489, incorporated by reference herein. In general, the implant preferably is an allograft strut that is configured to maintain disc height and allow bone growth in the interbody space.

In addition to providing a suitable fusion, the first method provides fixation of the vertebrae. The fixation procedure may take any suitable form, e.g., any of the fixation procedures similar to those disclosed above. In particular, when the access device is in the expanded or enlarged configuration, fixation of the three adjacent vertebrae may be performed. One fixation procedure that could be used is discussed above in connection with FIG. 36 wherein the fasteners 600a, 600b, and 600c are advanced through the access device 20 to three adjacent vertebrae and are attached to the vertebrae. The three fasteners 600a, 600b, and 600c are interconnected by way of the elongated member 650. As discussed above, a second fixation assembly may be applied to the patient on the opposite side of the spine, e.g., about the same location on the opposite side of the medial line of the spine.

In a second MILIF method, substantially the same procedures set forth above in connection with the first MILIF method are performed. In addition, a suitable decompression procedure may be performed, as needed. As discussed above, decompression involves removal of unwanted bone by way of a suitable decompression technique that may be performed through the access device. In one embodiment, decompression is performed through the access device after the access device has been expanded. As discussed above, suitable decompression techniques include a laminectomy, a facetectomy, or any other similar procedure. Decompression for the L4, the L5, and/or the S1 vertebrae may be needed and can be performed through the access devices described herein without requiring the access device to be moved from one position to another.

In a third MILIF method, substantially the same procedures set forth above in connection with the first MILIF method are performed. In addition, a further fusion procedure, e.g., a fusion procedure external to the interbody space, is provided. The external fusion procedure is performed adjacent to the interbody space wherein bone growth may be promoted in the proximity of the fixation assembly, e.g., above the postero-lateral boney elements of the spine, such as the facet joints and the transverse processes. In one embodiment, when the fixation assembly comprising the fasteners 600a, 600b, 600c and/or the elongate element 650 has been applied to three adjacent vertebrae, a substance is applied through the access device to one or more components of the fixation assembly to maintain or enhance the formation and/ or growth of bone in the proximity of the fixation assembly. For example, a bone growth substance may be placed adjacent any of the fasteners 600a, 600b, 600c and/or the elongate member 650. Bone growth substance may take any suitable form, e.g., small bone chips taken from the patient (e.g., autograft), from another donor source (e.g., allograft or xenograft), and orthobiologics.

After the bone growth substance is applied to the fixation assembly, the access device is removed. Absent the retracting force provided by the access device, the patient's tissue generally collapses onto the bone growth substance. The tissue will thereby maintain the position of the bone growth substance adjacent to the fixation assembly. The presence of the bone growth substance advantageously causes bone to grow between the vertebrae and the fixation assembly to form a bridge therebetween.

A fourth MILIF method involves substantially the same procedures performed in connection with the third MILIF method. In particular, one or more implants are positioned in the interbody spaces through an access device, a fixation procedure is performed through the access device, and a further fusion procedure is performed wherein bone growth substance is positioned adjacent the interbody space through the access device. In addition, a decompression procedure is performed through the access device that may include a facetectomy and/or a laminectomy.

A fifth MILIF method involves substantially the same procedures performed in connection with the first MILIF method, except that the fixation is optional. In one embodiment, the fixation is not performed. In addition, a further fusion procedure is performed through the access device wherein bone growth substance is positioned adjacent the interbody space, as discussed above.

A sixth MILIF method is substantially the same as the fifth MILIF method, except that a further fusion procedure is performed through the access device. In particular, an implant is positioned in the interbody space through an access device, a decompression procedure is performed through the access device, and a further fusion procedure is performed whereby bone growth substance is placed adjacent the interbody space through the access device. As discussed above, the decompression procedure may include a facetectomy, a laminectomy, and any other suitable procedure. As with any of the methods described herein, the procedures that make up the sixth MILIF method may be performed in any suitable order. Preferably the decompression procedure is performed before the external fusion procedure.

The foregoing discussion illustrates that a MILIF procedure can include a variety of procedures that can be performed through an access device described herein. In addition, though not expressly set forth herein, any combination of the procedures discussed above, and any other suitable known procedures, may also be combined, as should be understood by one skilled in the art.

C. Other Multi-level Procedures

While the foregoing procedures have involved interbody fusion, the access devices and systems described herein can be employed in a variety of single level and multi-level procedures (e.g., more than two levels) that do not involve an interbody fusion. For example, a discectomy can be performed through the access devices described herein without implanting an interbody fusion device thereafter, e.g., to remove a herniation. In another embodiment, a discectomy can be performed in more than one interbody space without inserting an interbody fusion device into each interbody space, e.g., to remove multiple herniations. In another embodiment, a single or multi-level decompression procedure can be performed to remove unwanted bone growth.

It will be understood that the foregoing is only illustrative of the principles of the invention, and that various modifications, alterations, and combinations can be made by those skilled in the art without departing from the scope and spirit of the invention. Some additional features and embodiments are described below.

Figure 67:
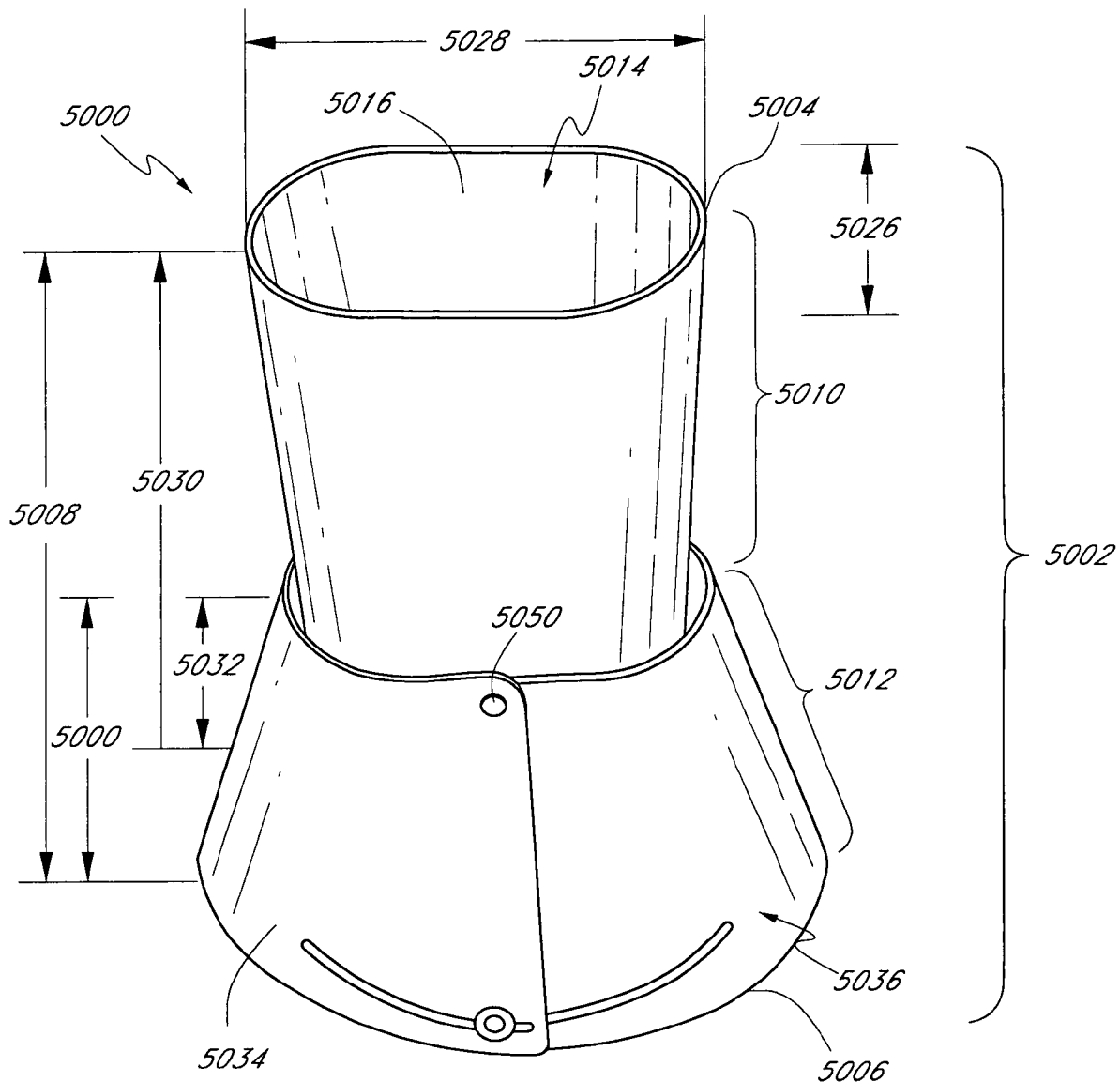
FIG. 67 is a perspective view of an access device according to another embodiment.
Figure 68:
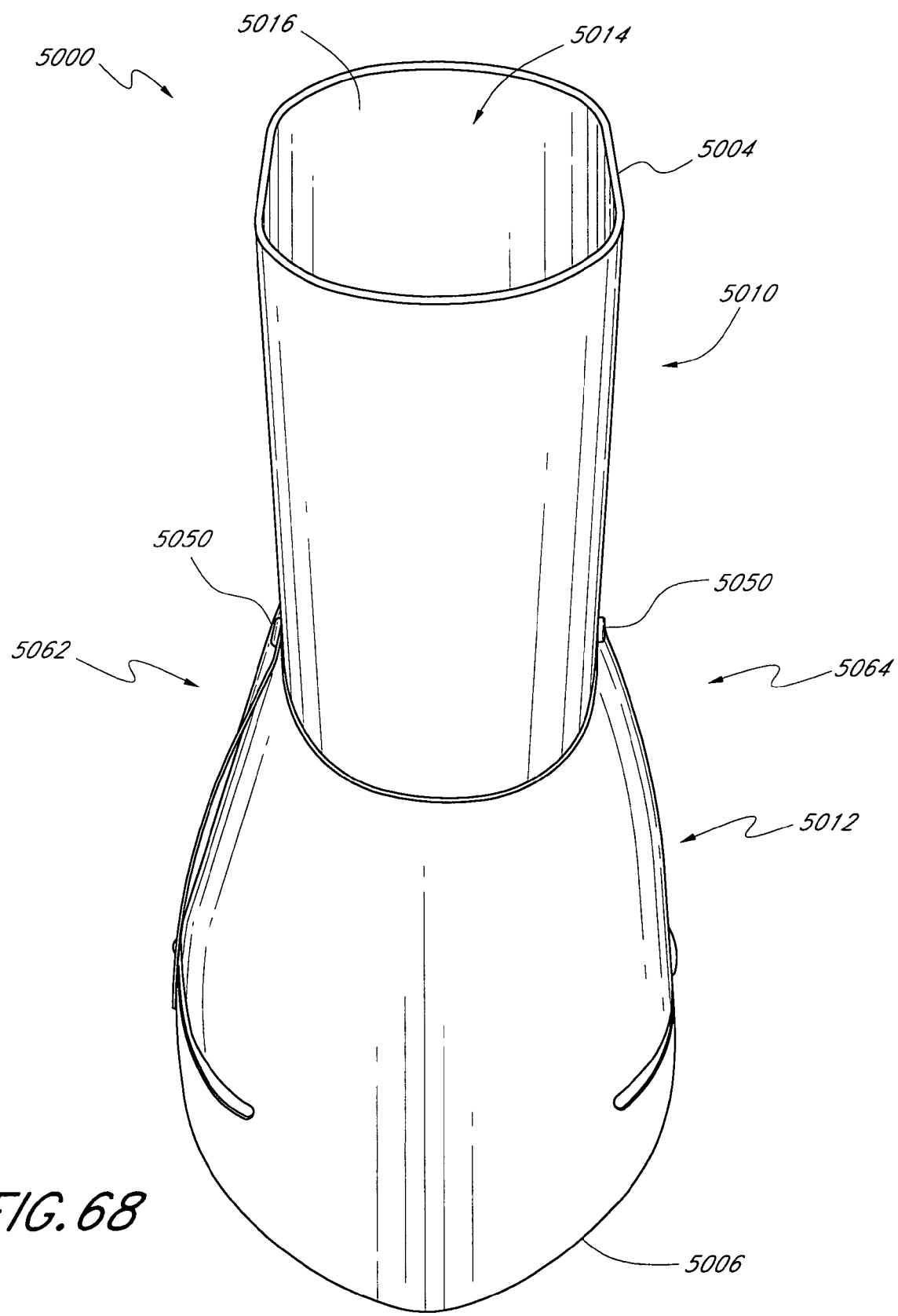
FIG. 68 is a side perspective view of the access device of FIG. 67.

III. Additional Features and Embodiments of Systems and Methods for Performing Surgical Procedures FIGS. 67-75 illustrate various embodiments of another access device designated by reference number 5000. The term "access device" is used in its ordinary sense to mean a device that can provide access and is a broad term and it includes structures having an elongated dimension and defining a passage, e.g., a cannula or a conduit. With reference to FIGS. 67 and 68, the access device 5000 is configured to be inserted through the skin of the patient to provide access during a surgical procedure to a surgical location within a patient, e.g., a spinal location. The term "surgical location" is used in its ordinary sense (i.e. a location where a surgical procedure is performed) and is a broad term and it includes locations subject to or affected by a surgery. The term "spinal location" is used in its ordinary sense (i.e. a location at or near a spine) and is a broad term and it includes locations adjacent to or associated with a spine that may be sites for surgical spinal procedures. The access device 5000 also can retract tissue to provide greater access to the surgical location.

The access device 5000 has an elongate body 5002 that has a proximal end 5004 and a distal end 5006. With reference to FIGS. 67 and 68, the elongate body 5002 has a length 5008 between the proximal end 5004 and the distal end 5006. The length 5008 is selected such that when the access device 5000 is applied to a patient during a surgical procedure, the distal end 5006 can be positioned inside the patient adjacent the spinal location. When so applied, the proximal end 5004 is preferably outside the patient at a suitable height, as discussed more fully below.

In one embodiment, the elongate body 5002 comprises a proximal portion 5010 and a distal portion 5012. The proximal portion 5010 has an oblong or generally oval shaped cross section in one embodiment. The term "oblong" is used in its ordinary sense (i.e., having an elongated form) and is a broad term and it includes a structure having a dimension, especially one of two perpendicular dimensions, such as, for example, width or length, that is greater than another and includes shapes such as rectangles, ovals, ellipses, triangles, diamonds, trapezoids, parabolas, and other elongated shapes having straight or curved sides. The term "oval" is used in its ordinary sense (i.e., egg like or elliptical) and is a broad term and includes oblong shapes having curved portions.

The distal portion 5012 is expandable in one embodiment. At least one passage 5014 extends through the elongate body 5002 between the proximal end 5004 and the distal end 5006, e.g., through the proximal and distal portions 5010, 5012. The passage 5014 is defined by a smooth metal inner surface 5016 that extends substantially entirely around the perimeter of the passage 5014 between the proximal and distal ends 5004, 5006 in one embodiment. The inner surfaces 5016 can take other forms, e.g., employing other materials, different but generally constant smoothness, and/or varying degrees of smoothness.

Figure 71:
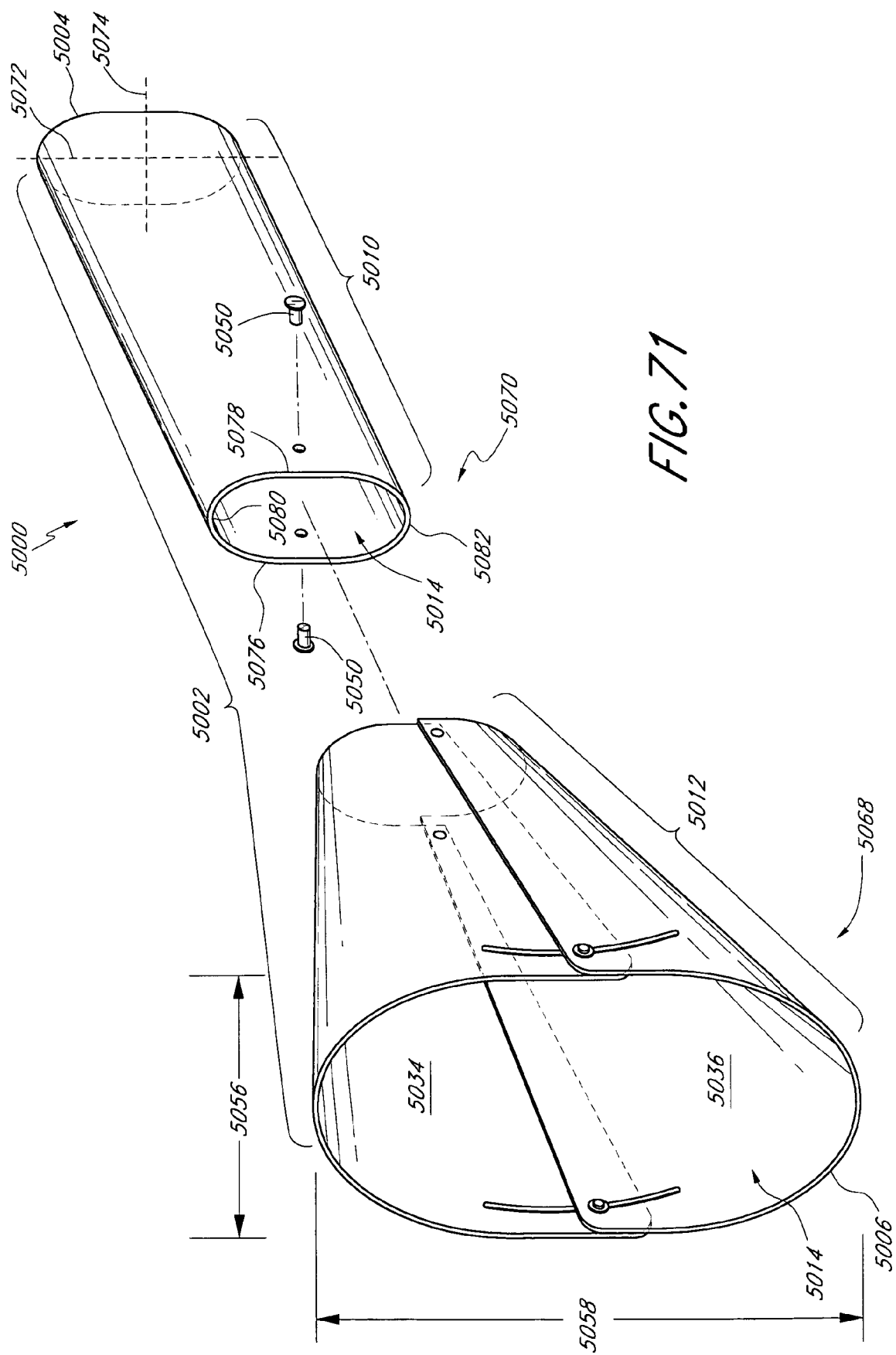
FIG. 71 is an exploded perspective view of the access device of FIG. 67 in an expanded configuration with some portions shown in hidden line.
Figure 72:
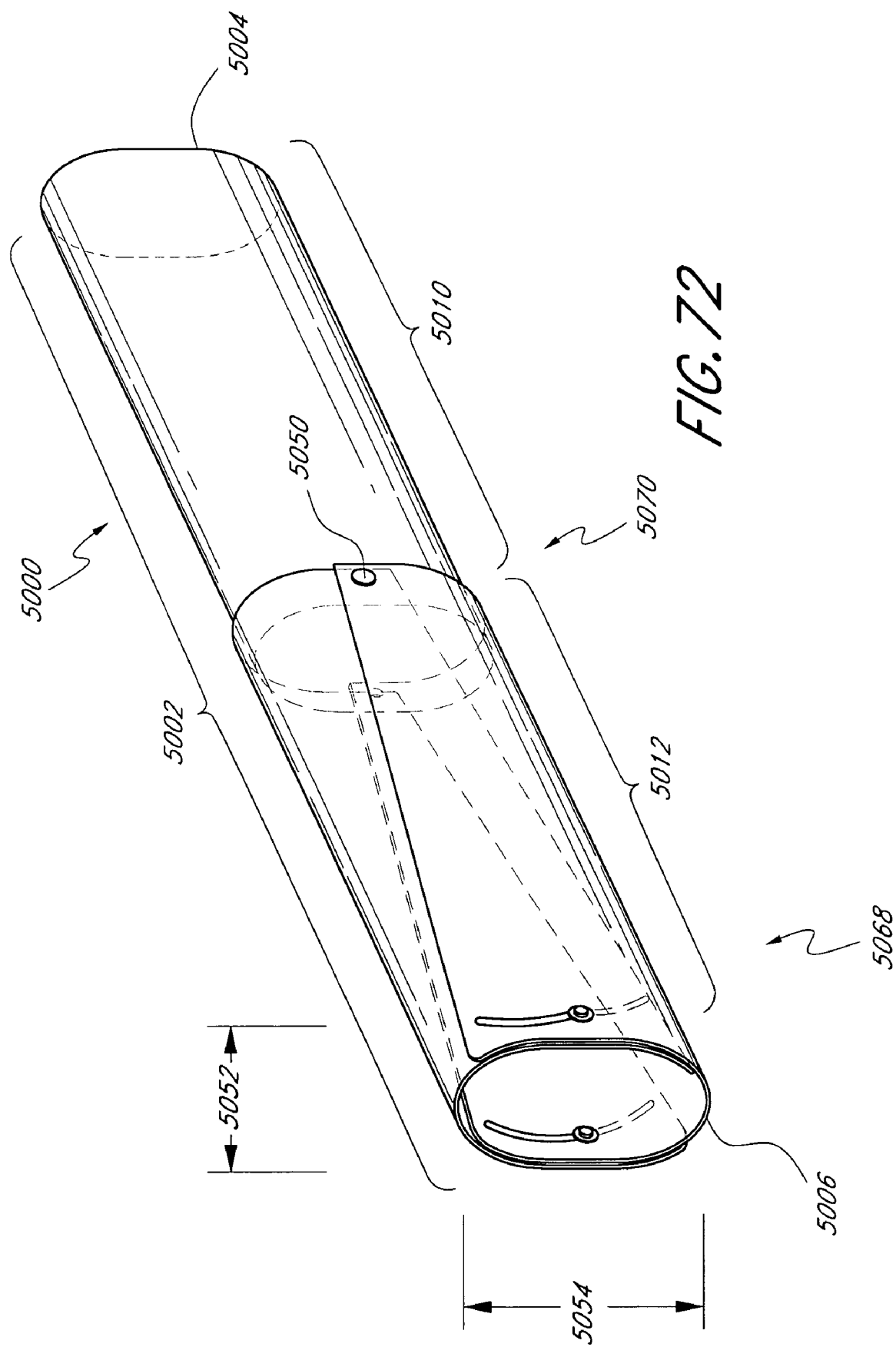
FIG. 72 is a perspective view of the access device of FIG. 67 in a contracted configuration with some portions shown in hidden line.

In one embodiment, the elongate body 5002 is expandable from a first configuration, shown in FIG. 72, to a second configuration, shown in FIG. 71. In one embodiment, the elongate body 5002 is movable from the first configuration to the second configuration when inserted within the patient, as discussed above. In the first configuration, the access device 5000 is configured, e.g., sized, for insertion into the patient. As discussed more fully below, in one embodiment, the passage 5014 has a relatively small transverse cross-sectional area at the distal end 5006 of the first configuration of the access device 5000. For example, the passage 5014 can have a cross-sectional area about equal to the cross-sectional area of the proximal end 5004, or less.

In the second configuration, the cross-sectional area of the passage 5014 at the distal end 5006 is greater than the cross-sectional area of the passage 5014 at the proximal end 5004 in one embodiment. The second configuration is particularly well suited for performing surgical procedures in the vicinity of a spinal location. Other configurations and arrangements of the access device 5000 are discussed herein below.

As shown in FIGS. 67 and 68, in one embodiment, the proximal portion 5010 and the distal portion 5012 are discrete, i.e., separate members. In other embodiments, the proximal and distal portions 5010, 5012 are a unitary member. In the illustrated embodiment, the proximal portion 5010 comprises an oblong, generally oval shaped cross section over the elongated portion. It will be apparent to those of skill in the art that the cross section can be of any suitable oblong shape. The proximal portion 5010 can be any desired size. The proximal portion 5010 can have a cross-sectional area that varies from one end of the proximal portion 5010 to another end. For example, the cross-sectional area of the proximal portion 5010 can increase or decrease along the length of the proximal portion 5010. Preferably, the proximal portion 5010 is sized to provide sufficient space for inserting multiple surgical instruments through the elongate body 5002 to the surgical location. In one embodiment, the cross-sectional area of the proximal portion 5010 can have a generally elliptical shape. In some embodiments, the generally elliptical shape can include generally straight side portions.

Figure 70:
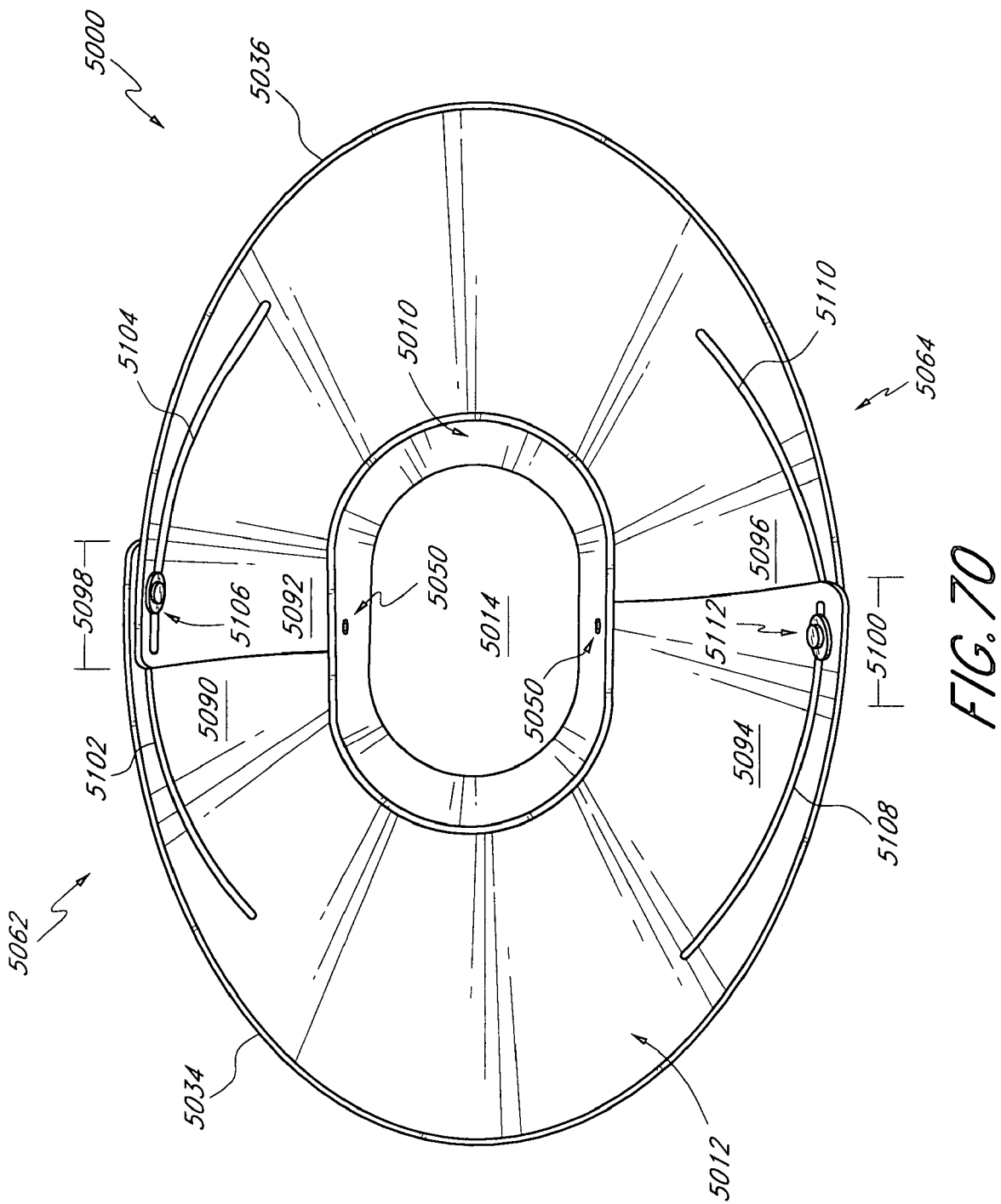
FIG. 70 is an end view of the access device of FIG. 67.

As shown in FIG. 67, the generally oval shaped cross section of the proximal portion 5010 in one embodiment has a first dimension 5026 of about 24 mm and a second dimension 5028 of about 35 mm. The first and second dimensions 5026, 5028 could range from at least about 10 mm up to about 70 mm or more. The proximal portion 5010 in one embodiment has a third dimension 5030 of about 50 mm, but the third dimension 5030 could range from about 10 mm up to about 180 mm or more. In one embodiment, the proximal portion 5010 extends distally at least partially into the distal portion 5012 of the device 5000, as shown in FIG. 70. In FIG. 67, the proximal portion 5010 extends a distance 5032 of about 10 mm into the distal portion 5012. The proximal portion 5010 can extend a distance 5032 of between about 5 mm and about 20 mm into the distal portion 5012 in some embodiments. The exposed portion of the proximal portion 5010 (e.g., the portion thereof that extends proximally of the distal portion 5012) can be of any suitable height. Additionally, the distance 5032 that the proximal portion 5010 extends into the distal portion 5012 can be increased or decreased, as desired.

As shown in FIGS. 67 and 68, the proximal portion 5010 is coupled with the distal portion 5012, e.g., with one or more couplers 5050. The proximal and distal portions 5010, 5012 are coupled on a first lateral side 5062 and on a second lateral side 5064 with the couplers 5050 in one embodiment. When applied to a patient in a posterolateral procedure, either of the first or second lateral sides 5062, 5064 can be a medial side of the access device 5000, i.e., can be the side nearest to the patient's spine. The couplers 5050 can be any suitable coupling devices, such as, for example, rivet attachments. In one embodiment, the couplers 5050 are located on a central transverse plane of the access device 5000.

Figure 69:
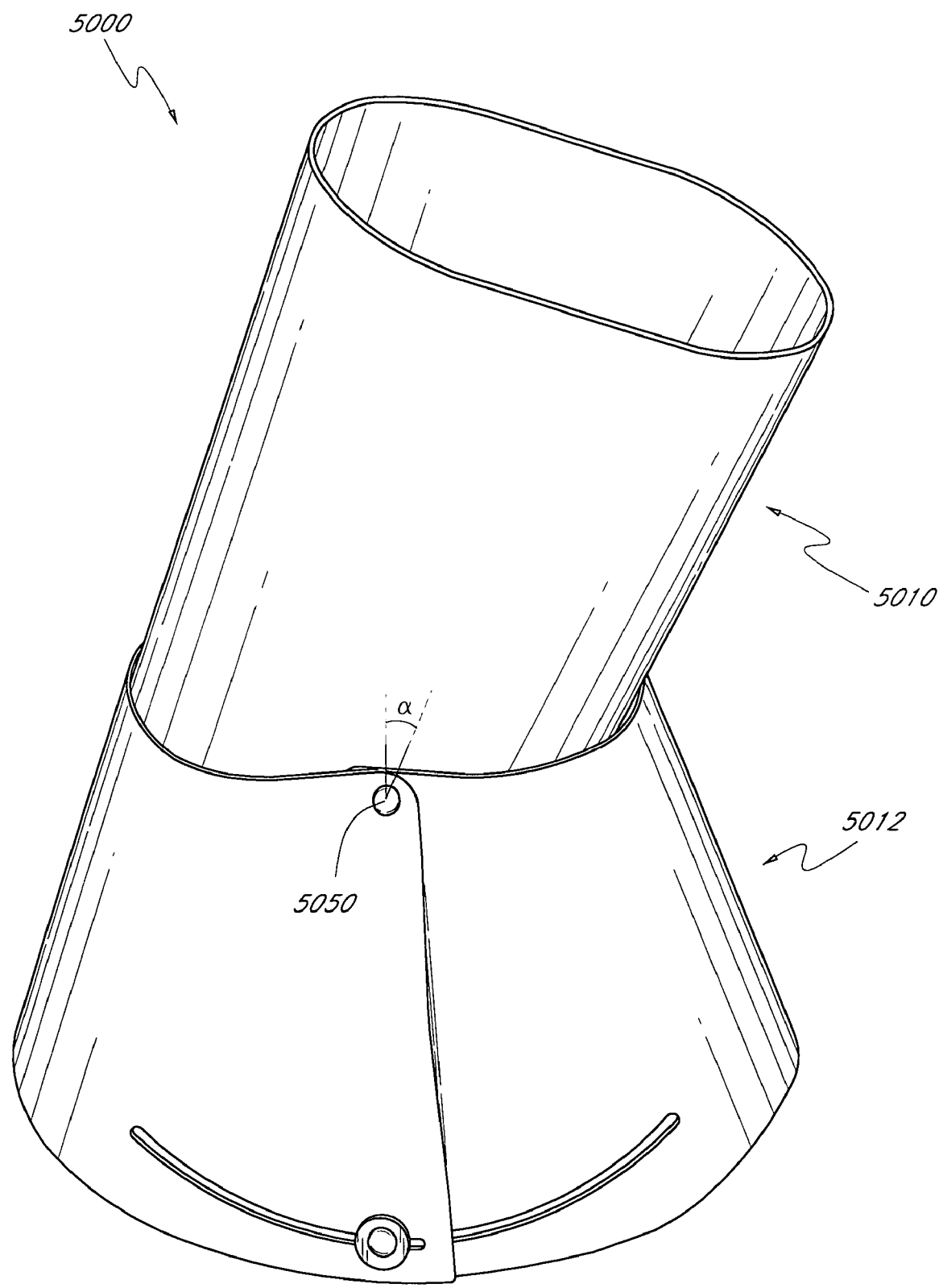
FIG. 69 is a perspective view of the access device of FIG. 67 in a pivoted configuration.

The couplers 5050 preferably allow for at least one of rotation and pivotal movement of the proximal portion 5010 relative the distal portion 5012. A portion of the range of rotation and pivotal movement of the proximal portion 5010 relative the distal portion 5012 can be seen by comparing the position of the proximal portion 5010 in FIG. 67 to the position thereof in FIG. 69. In FIG. 69, the proximal portion 5010 is seen at an angle $\alpha$ of about 20 degrees with respect to a transverse plane extending vertically through the couplers. One skilled in the art will appreciate that rotating or pivoting the proximal portion 5010 to the angle $\alpha$ permits enhanced visualization of and access to a different portion of the spinal location accessible through the access device 5000 than would be visualized and accessible at a different angle. Depending on the size of the distal portion 5012, the angle $\alpha$ can be greater than, or less than, 20 degrees. Preferably, the angle $\alpha$ is between about 10 and about 40 degrees.

The pivotable proximal portion 5010 allows for better access to the surgical location and increased control of surgical instruments. Additionally, the generally oval shape of the proximal portion 5010 has increased the cross-sectional area available for a variety of procedures, some of which may require or benefit from more proximal end exposure. Embodiments having a generally oval shape can also be employed advantageously in procedures such as the lateral or posterolateral placement of artificial disks, as well as other developing procedures.

As discussed above, the distal portion 5012 is expandable in one embodiment. As shown in FIG. 70, the degree of expansion of the distal portion 5012 is determined by an amount of overlap between a first skirt member 5034 and a second skirt member 5036 in one embodiment. In particular, the first skirt member 5034 has a first overlapping portion 5090 on the first lateral side 5062 and the second skirt member 5036 has a second overlapping portion 5092 on the first lateral side 5062. The first skirt member 5034 has a third overlapping portion 5094 on the second lateral side 5064 and the second skirt member 5036 has a fourth overlapping portion 5096 on the second lateral side 5064. The first and second overlapping portions 5090, 5092 overlap to define a first overlap area 5098. The third and fourth overlapping portions 5094, 5096 overlap to define a second overlap area 5100. The extents of the first and second overlap areas 5098, 5100 preferably are reduced when the distal portion 5012 is in the second configuration. The extents of the first and second overlap areas 5098, 5100 preferably are increased when the distal portion 5012 is in the first configuration.

The distal portion 5012 preferably is manufactured from a rigid material, such as stainless steel. The distal portion 5012 of the access device 5000 can be manufactured from a sheet of stainless steel having a thickness of between about 0.003-0.010 inches (0.076-0.254 mm). In some embodiments, the thickness is about 0.007 inches (0.178 mm). Nitinol, plastics, and other suitable materials can also be used.

In some embodiments, the distal portion 5012 can be manufactured so that it normally assumes an expanded configuration. Additionally, the distal portion 5012 can assume an intermediate configuration and corresponding cross-sectional area, which has greater dimensions than the first configuration, and smaller dimensions than the second configuration. Alternatively, an expander apparatus, similar to those previously discussed herein, can be used to expand the distal portion 5012 a suitable amount.

The skirt members 5034, 5036 preferably are slidably coupled together. In one embodiment, the first and second skirt members 5034, 5036 are slidably coupled with each other with at least one guide member disposed in at least one slot defined in each of the skirt members 5034, 5036. In particular, a first slot 5102 is formed in the first overlapping portion 5090 of the first skirt member 5034 and a second slot 5104 is formed in the second overlapping portion 5092 of the second skirt member 5036 on the first lateral side 5062 of the access device 5000. A guide member 5106 extends through the first and second slots 5102, 5104 and is translatable therein. Similarly, a third slot 5108 is formed in the third overlapping portion 5094 of the first skirt member 5034 and a fourth slot 5110 is formed in the fourth overlapping portion 5096 of the second skirt member 5036 on the second lateral side 5064 of the access device 5000. A guide member 5112 extends through the third and fourth slots 5108, 5110 and is translatable therein.

Any suitable mechanism for slidably coupling the skirt members 5034, 5036 can be used. In the illustrated embodiment, two floating rivets are used as guide members 5106, 5112. In another embodiment, one or more of the slots 5102, 5104, 5108, 5110 can include a locking or ratcheting mechanism (not shown). Locking mechanism is used in its ordinary sense (i.e. a mechanism to maintain relative positions of members) and is a broad term and it includes structures having detent arrangements, notches, and grooves. Some additional examples of locking mechanisms are disclosed in U.S. patent application Ser. No. 10/361,887, filed Feb. 10, 2003, entitled "Structure for Receiving Surgical Instruments," published as application publication No. US2003/0153927 on Aug. 14, 2003, which is hereby incorporated by reference herein in its entirety.

With reference to FIGS. 67-72, as discussed above, the skirt members 5034, 5036 preferably pivot about couplers 5050 joining the proximal portion 5010 with the distal portion 5012. The distal portion 5012 preferably pivots on an axis perpendicular to the longitudinal axis of the access device 5000. This arrangement is particularly useful for providing surgical access to anatomical features generally located and oriented along the Cephalad-Caudal direction.

As discussed above, the access device 5000 can be expanded from the first configuration to the second configuration by way of the movement of the first skirt member 5034 relative to the second skirt member 5036. In the illustrated embodiment, the distal portion 5012 is generally oval shaped both in the first configuration, when the device 5000 is generally contracted, and in the second configuration, when the device 5000 is generally expanded. However, the distal portion 5012 may be configured to transition from a generally circular cross-section distal end (or other convenient shape) in the first configuration to a generally oval cross-section distal end in the second configuration.

As best seen in FIG. 72, the distal portion 5012 preferably has a first dimension 5052 in the first configuration of approximately 24 mm and a second dimension 5054 of approximately 35 mm. As best seen in FIG. 71, the distal portion 5012 preferably has a first dimension 5056 of approximately 45 mm and a second dimension 5058 of approximately 70 mm in the second configuration. Accordingly, in one embodiment in the expanded configuration the distal portion 5012 opens distally to approximately 45 mm by 70 mm. The distal portion 5012 can be arranged to open more or less, as needed or desired. For example, the distal portion 5012 can take on an oval shape wherein the second dimension 5058 is longer than 70 mm, e.g., about 85 mm or more. Alternatively, the distal portion 5012 can have a shape wherein the second dimension 5058 is shorter than 70 mm, e.g., about 45 mm or less. Similarly, in some embodiments the first dimension 5052 can be longer or shorter than 45 mm, e.g., about 35 mm or about 55 mm. As shown in FIG. 67, the distal portion 5012 has a height 5060 that is approximately 45 mm. However, one skilled in the art should recognize that the height 5060 of the distal portion 5012 can be any suitable height. The height 5060 preferably is within the range of about 20 mm to about 150 mm. Access devices having relatively shorter skirt heights 5060 may be advantageous for use with patients having relatively less muscle tissue near the surgical location and generally require smaller incisions. Access devices having relatively longer skirt height 5060 may be advantageous for use with patients having relatively more muscle tissue near the surgical location, and may provide greater access.

The distal portion 5012 preferably is sufficiently rigid that it is capable of displacing surrounding tissue as the distal portion 5012 expands. Depending upon the resistance exerted by the surrounding tissue, the distal portion 5012 is sufficiently rigid to provide some resistance against the tissue to remain in the second, expanded configuration. Moreover, the second configuration is at least partially supported by the body tissue of the patient. The displaced tissue tends to provide pressure distally on the distal portion 5012 to at least partially support the access device 5000 in the second configuration. The rigidity of the distal portion 5012 and the greater expansion at the distal end 5006 creates a stable configuration that is at least temporarily stationary in the patient, which at least temporarily frees the physician from the need to actively support the elongate body 5002.

Another advantageous aspect of the access device 5000 is illustrated with reference to FIGS. 71 and 72. In particular, the elongate body 5002 has a first location 5068 and a second location 5070. The first location 5068 is distal of the second location 5070. The elongate body 5002 is capable of having a configuration when inserted within the patient wherein the cross-sectional area of the passage 5014 at the first location 5068 is greater than the cross-sectional area of the passage 5014 at the second location 5070. The passage 5014 is capable of having an oblong shaped cross section between the second location 5070 and the proximal end 5004.

In some embodiments the passage 5014 preferably is capable of having a generally elliptical cross section between the second location 5070 and the proximal end 5004. Additionally, the passage 5014 preferably is capable of having a non-circular cross section between the second location 5070 and the proximal end 5004. Additionally, in some embodiments, the cross section of the passage 5014 can be symmetrical about a first axis 5072 and a second axis 5074, the first axis 5072 being generally normal to the second axis 5074.

As shown in FIG. 71, the configuration of the elongate body 5002 between the first location 5068 and the second location 5070 is generally conical, when the elongate body 5002 is expanded within the patient. The term "conical" is used in its ordinary sense (i.e. a surface formed by line segments joining every point of the boundary of a closed base to a common vertex) and is a broad term and it includes structures having a generally oblong, or oval, cross section, as well as structures having a surface that extends only partially toward a vertex. In some embodiments, the first location 5068 can be near a distal end 5006 of the elongate body 5002, and the second location 5070 can be near a proximal end 5004 of the elongate body 5002.

In the illustrated embodiment, the elongate body 5002 has an oblong shaped cross section near its proximal end 5004 at least when the elongate body 5002 is in the second configuration. In some embodiments, the elongate body 5002 has an oblong shaped cross section along substantially the entire length between the proximal end 5004 and the second location 5070.

Additionally, in some embodiments the passage 5014 can have a generally oval shaped cross section between the second location 5070 and the proximal end 5004. The elongate body preferably has a generally oval shaped cross section at its proximal end 5004 at least when the elongate body 5002 is in the second configuration. The elongate body 5002 can have a generally oval shaped cross section along substantially the entire length between the proximal end 5004 and the second location 5070. The passage 5014 can also have a cross section between the second location 5070 and the proximal end 5004 where the cross section is defined by first and second generally parallel opposing side portions 5076, 5078 and first and second generally arcuate opposing side portions 5080, 5082.

Figure 73:
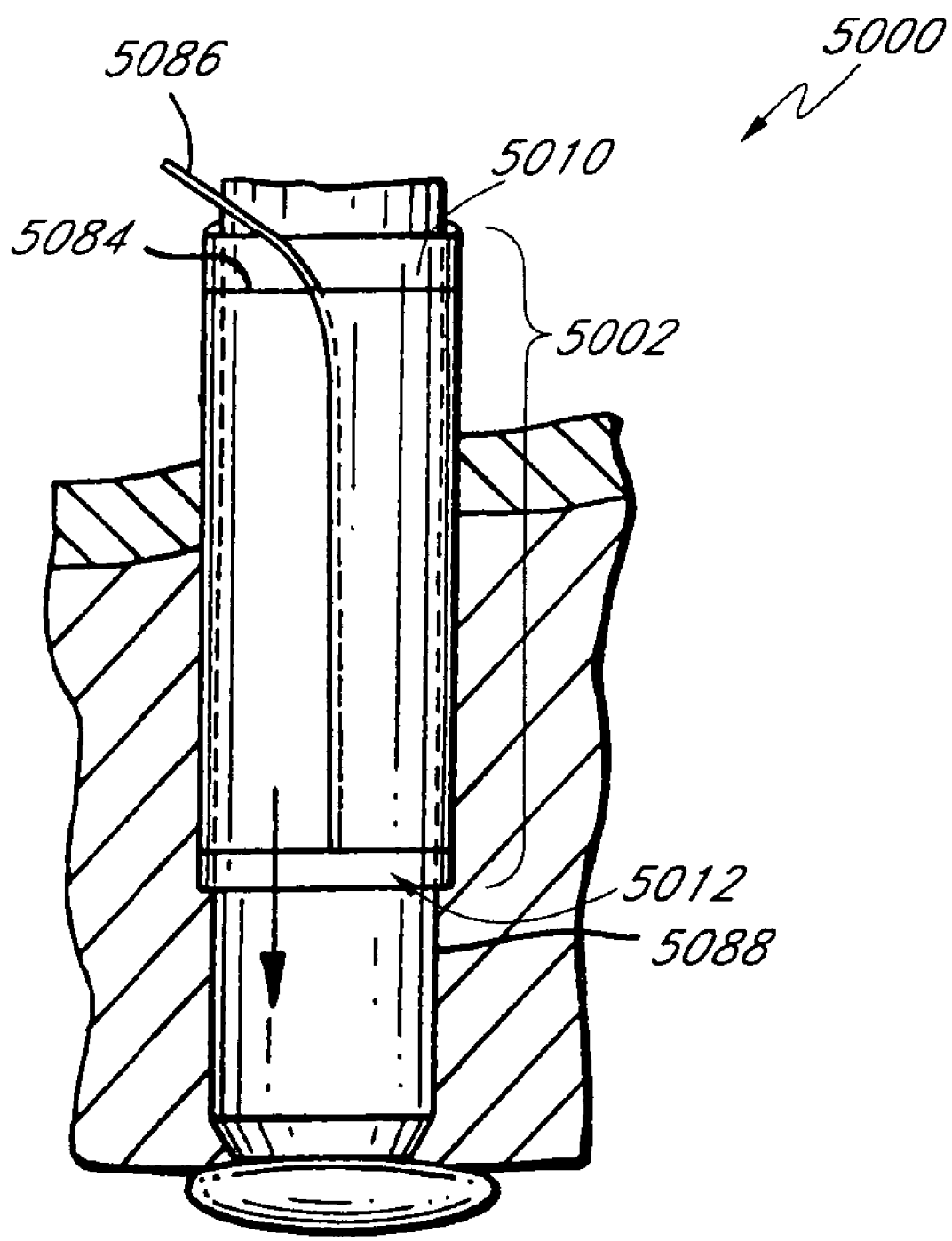
FIG. 73 is a partial sectional view of the access device of FIG. 67 in an early stage of a procedure.

In some embodiments, it is useful to provide a structure to maintain the access device 5000 in an un-expanded state until expansion of the device is desired. As shown in FIG. 73, in one embodiment an outer sleeve 5084, e.g., a plastic sleeve, is provided which surrounds the access device 5000 and maintains the distal portion 5012 in the first configuration. The outer sleeve 5084 can be produced to function as previously described herein with reference to other embodiments. For example, the outer sleeve 5084 can have a braided polyester suture 5086 embedded within it, aligned substantially along the longitudinal axis thereof, such that when the suture 5086 is withdrawn, the sleeve 5084 is torn, which allows the access device 5000 to expand, either resiliently or mechanically, from the first configuration to the second configuration.

In a method for accessing a surgical location within a patient an access device, such as the access device 5000, is provided. As stated above, the elongate body 5002 is capable of having a first configuration sized for insertion into the patient. The elongate body 5002 is capable of having a second configuration when expanded within the patient. In the second configuration, the cross-sectional area of the passage 5014 at a first location 5068 is greater than the cross-sectional area of the passage 5014 at a second location 5070. The first location 5068 is distal to the second location 5070. The passage 5014 is capable of having an oblong shaped cross section between the second location 5070 and the proximal end 5004. The method comprises inserting the access device 5000, in the first configuration, into the patient to the surgical location and expanding the device to the second configuration.

The access device 5000 is inserted to a spinal location in some methods. As shown in FIG. 73, an oblong shaped dilator 5088 preferably is inserted into the patient prior to insertion of the access device 5000. In some applications, the access device 5000 may be inserted laterally to the spinal location. In other applications, the device 5000 is inserted posterolaterally to the spinal location. In some applications, the device 5000 is inserted anteriorly to the spinal location. The device 5000 preferably can be expanded in a cephalad-caudal direction at a spinal location.

With reference to FIG. 73, an early stage in one method involves determining an access point in the skin of the patient to insert the access device 5000. An incision is made at the determined location. In some cases, the incision is approximately 1" to 2" long. A guide wire (not shown) is introduced under fluoroscopic guidance through the incision and past the skin, fascia, and muscle to the approximate surgical site. A series of oblong, or generally oval shaped, dilators is used to sequentially expand the incision to the desired widths, about 24 mm by 35 mm for the illustrated embodiment, without damaging the structure of surrounding tissue and muscles. In one technique, a first oblong dilator is placed over the guide wire, which expands the opening. The guide wire is then subsequently removed. A second oblong dilator that is slightly larger than the first dilator is placed over the first dilator, which expands the opening further. Once the second dilator is in place, the first dilator is subsequently removed. This process of (1) introducing a next-larger-sized dilator coaxially over the previous dilator and (2) subsequently removing the previous dilator when the next-larger-sized dilator is in place continues until an opening of the desired size is created in the skin, muscle, and subcutaneous tissue. For the illustrated embodiment, these dimensions are about 24 mm by about 35 mm. (Other dimensions for the openings that are useful with some embodiments in connection with spinal surgery range from about 20 mm to about 50 mm, and still other dimensions are contemplated.) In other techniques, a series of dilators having circular (or other shaped) cross-sections are used to partially dilate the opening. Then, a final dilator having a circular inner diameter and an oblong or generally oval shaped outer perimeter can be used to further dilate the opening.

As illustrated in FIG. 73, following placement of the largest oblong, or generally oval shaped dilator 5088, the access device 5000, in the first configuration, is introduced and positioned in a surrounding relationship over the dilator 5088. The dilator 5088 is subsequently removed from the patient, and the access device 5000 is allowed to remain in position.

Once the access device 5000 is positioned in the patient, it can be enlarged to provide a passage 5014 for the insertion of various surgical instrumentation and an enlarged space for performing the procedures described herein. As described above, the elongate body 5002 can accommodate the enlargement in several ways. In the illustrated embodiment, the distal portion 5012 of the device 5000 can be enlarged, and the proximal portion 5010 can maintain an oblong shape. The relative lengths of the proximal portion 5010 and the distal portion 5012 can be adjusted to vary the overall expansion of the access device 5000. Alternatively, in some embodiments expansion can extend along the entire length of the elongate body 5002.

In the illustrated embodiment, the access device 5000 can be expanded by removing the suture 5086 and tearing the sleeve 5084 surrounding the access device 5000, and subsequently expanding the distal portion 5012 mechanically, or allowing the distal portion 5012 to resiliently expand towards the expanded configuration, to create an enlarged surgical space. In some embodiments, the enlarged surgical space extends from the L4 to the S1 vertebrae.

The access device 5000 can be enlarged at its distal portion 5012 using an expander apparatus to create a surgical access space. An expander apparatus useful for enlarging the elongate body 5002 has a reduced profile configuration and an enlarged configuration. Additionally, the expander apparatus can have an oblong, or generally oval shape. The expander apparatus is inserted into the elongate body 5002 in the reduced profile configuration, and subsequently expanded to the enlarged configuration. The expansion of the expander apparatus also causes the elongate body 5002 to be expanded to the enlarged configuration. In some embodiments, the expander apparatus can increase the cross-sectional area of the elongate body 5002 along substantially its entire length. In other embodiments, the expander apparatus expands only a distal portion 5012 of the elongate body 5002, allowing a proximal portion 5010 to maintain a constant oblong, or generally oval shape. Other expander apparatus are disclosed in U.S. patent application Ser. No. 10/665,754, entitled "Surgical Tool for Use in Expanding a Cannula", filed on Sep. 19, 2003.

In addition to expanding the elongate member 5002, the expander apparatus can also be used to position the distal portion 5012 of the elongate member 5002 at the desired location for the surgical procedure in a manner similar to that described previously with reference to another embodiment.

Once the distal portion 5012 has expanded, the rigidity and resilient characteristics of the distal portion 5012 allow the elongate body 5002 to resist closing to the first configuration and to at least temporarily resist being expelled from the incision. These characteristics create a stable configuration for the elongate body 5002 to remain in position in the body, supported by the surrounding tissue.

The access device 5000, like the other access devices described herein, has a wide variety of applications wherein the passage 5014 provides access to one or more surgical instruments for performing a surgical procedure. In one application, the passage 5014 provides access to perform a two level posterolateral fixation of the spine involving the L4, L5 and S1 vertebrae. The access devices 5000 can be used to deliver a wide variety of fixation elements, including rigid, semi-rigid, or dynamic fixation elements. The access devices are not limited to the posterolateral approach nor to the L4, L5 and S1 vertebrae. The access devices may be applied in other anatomical approaches and with other vertebrae within the cervical, thoracic and lumbar spine. The access devices can be applied in procedures involving one or more vertebral levels and in anterior and lateral procedures. Further procedures in which the access devices described herein can be applied include procedures involving orthobiologics, bone morphogenetic proteins, and blood concentrators. The access devices can also be used with procedures involving prosthetics, such as disc nucleus replacement, facet joint replacement, or total disc replacement. The access devices can also be applied in procedures involving vertebroplasty, where a crushed vertebra is brought back to its normal height.

The access devices described herein also can be used in connection with interbody fusion, and fusion of the facets and transverse processes. Some of the fusion procedures that can be performed via the access devices described herein employ allograft struts, bone filling material (e.g., autograft, allograft or synthetic bone filling material), and cages and/or spacers. The cages and the spacers can be made of metal, a polymeric material, a composite material, or any other suitable material. The struts, cages, and spacers are used in the interbody space while the bone filling material can be used both interbody and posterolaterally. Any of the foregoing or other fusion procedures can be used in combination with the orthobiologics and can be performed via the access devices described herein.

Some examples of uses of the access devices described in other procedures and processes, as well as further modifications and assemblies, are disclosed in U.S. patent application Ser. No. 10/845,389, filed May 13, 2004, entitled "Access Device For Minimally Invasive Surgery," and in U.S. patent application Ser. No. 10/658,736, filed Sep. 9, 2003 which are hereby incorporated by reference herein in their entireties.

Figure 74:
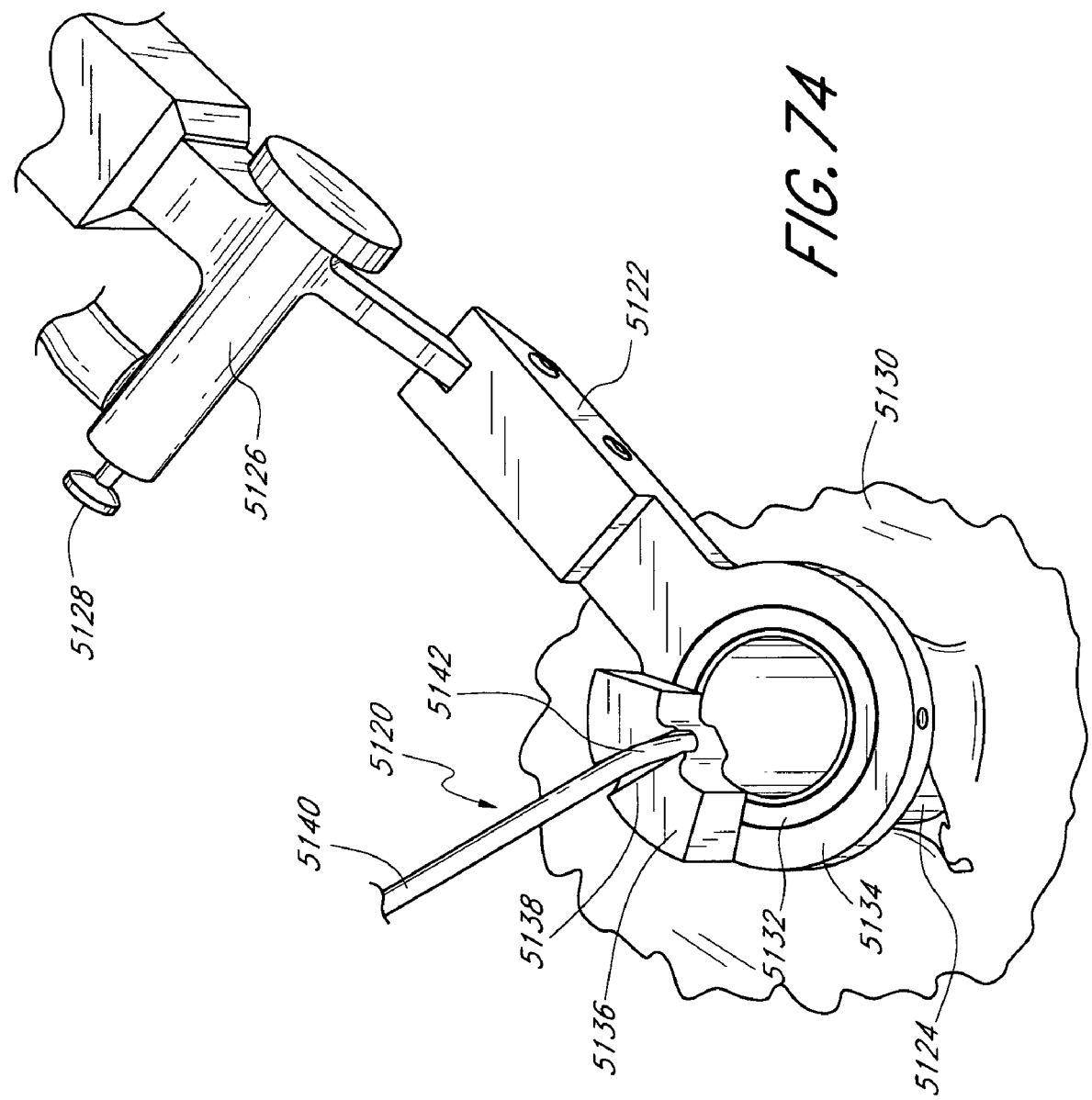
FIG. 74 is a perspective view of a portion of one embodiment of a surgical system that includes an access device, a support arm, and a lighting element shown applied to a patient.
Figure 75:
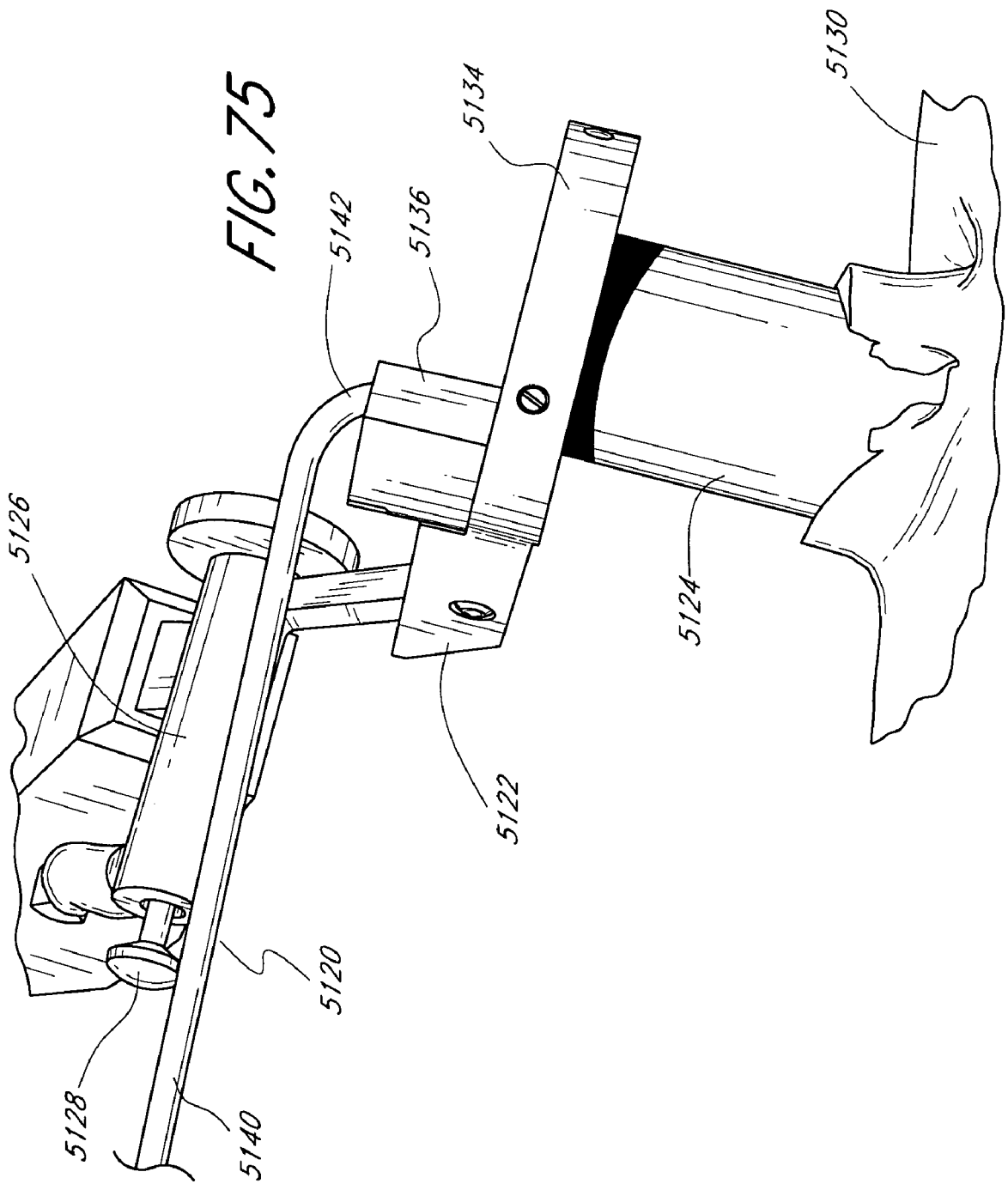
FIG. 75 is a perspective side view of the surgical system of FIG. 74 shown applied to a patient.
Figure 76:
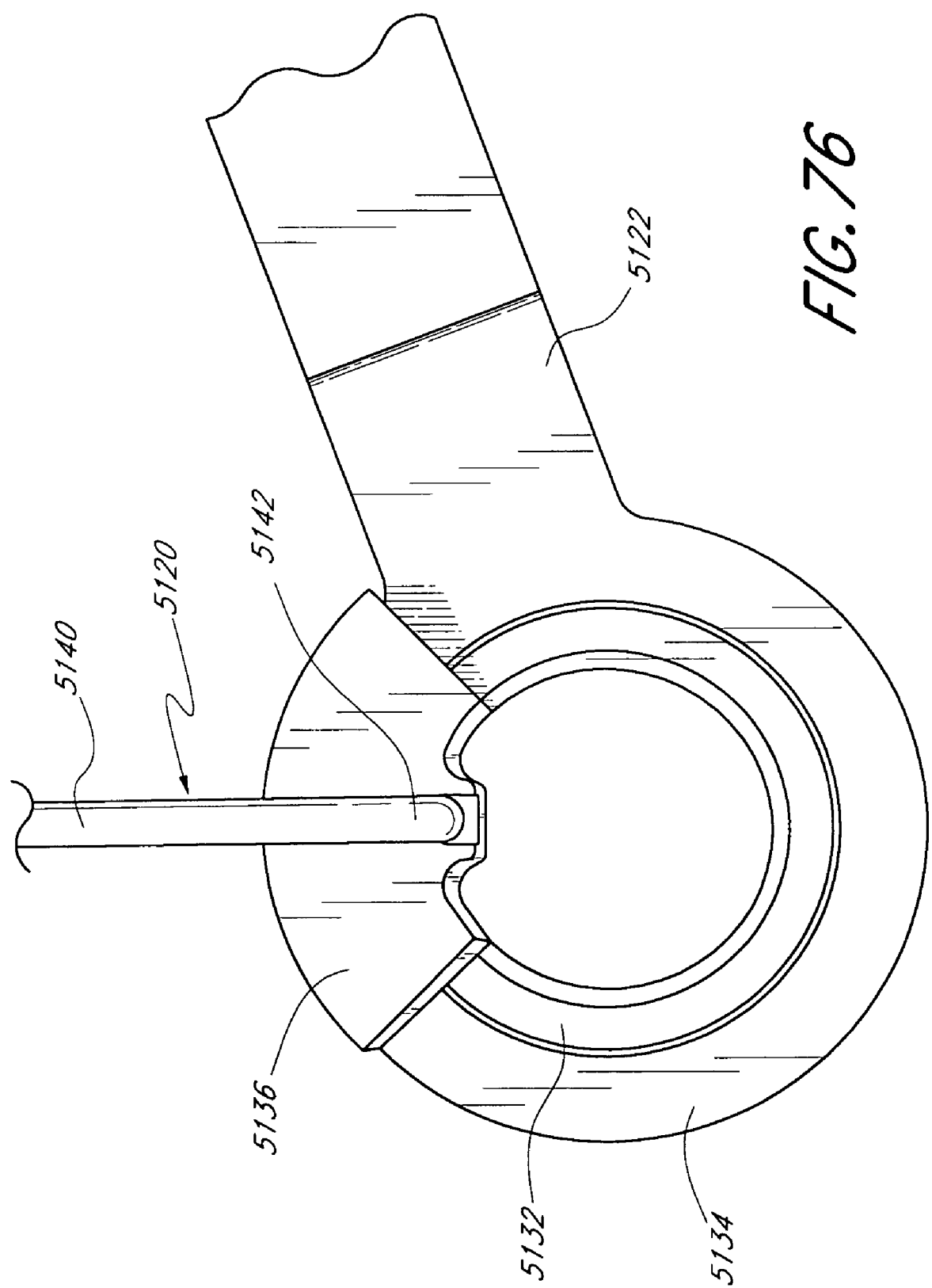
FIG. 76 is a top view of the surgical system of FIG. 74.

FIGS. 74-79 illustrate embodiments having lighting elements. FIGS. 74-76 illustrate one embodiment of a lighting element 5120 coupled with a support arm 5122 compatible with an access device 5124 having a proximal portion with a generally circular cross section. In other embodiments, support arms can be configured to be coupled with access devices having proximal portions with generally oblong or oval cross sections.

The support arm 5122 preferably is coupled with the access device 5124 to provide support for the access device 5124 during a procedure. As shown in FIGS. 74 and 75, the support arm 5122 comprises a pneumatic element 5126 for maintaining the support arm 5122 in a desired position. Depressing a button 5128 coupled with a valve of the pneumatic element 5126 releases pressure and allows the support arm 5122 and access device 5124 to be moved relative the patient 5130. Releasing the button 5128 of the pneumatic element 5126 increases pressure and maintains the access device 5124 and support arm 5122 in the desired position. The support arm 5122, as shown, is configured for use with a mechanical arm using suction, or a vacuum to maintain the access device in a desired location. One of skill in the art will recognize that various other support arms and mechanical arms can be used. For example, commercially available mechanical arms having clamping mechanisms can be used as well as suction or pressure based arms.

As shown in FIGS. 74-76, the support arm 5122 can comprise an inner ring portion 5132 and an outer ring portion 5134 for surrounding the access device 5124 at its proximal end. In the illustrated embodiment, the inner and outer ring portions 5132, 5134 are fixed relative each other. In other embodiments the inner and outer ring portions 5132, 5134 can move relative each other. The support arm 5122 preferably comprises a lighting element support portion 5136. In the illustrated embodiment, the lighting element support portion 5136 extends above upper surfaces of the inner and outer ring portions 5132, 5134. The lighting element support portion 5136 can extend from the inner ring portion 5132, the outer ring portion 5134, or both. The lighting element support portion 5136 can have a notch or groove 5138 for receiving and supporting the lighting element 5120. Additionally, the lighting element support portion 5136 can have one or more prongs extending at least partially over the lighting element 5120 to hold it in place.

In the illustrated embodiment, the lighting element 5120 has an elongated proximal portion 5140 and a curved distal portion 5142. The proximal portion 5140 of the lighting element 5120 preferably is coupled with a light source (not shown). The curved distal portion of the lighting element 5120 in one embodiment extends only a short distance into the access device and is configured to direct light from the light source down into the access device 5124. In another embodiment, the lighting element 5120 can be provided such that it does not extend into the access device. In such an embodiment, the right portions 5132 and 5134 only partially surround the proximal end of the access device 5124. Providing a lighting element 5120 for use with the access device 5124 preferably allows a user to see down into the access device 5124 to view a surgical location. Accordingly, use of a lighting element 5120 can, in some cases, enable the user to perform a procedure, in whole or in part, without the use of an endoscope. In one embodiment, the lighting element 5120 enables a surgeon to perform the procedure with the use of microscopes or loupes.

Figure 77:
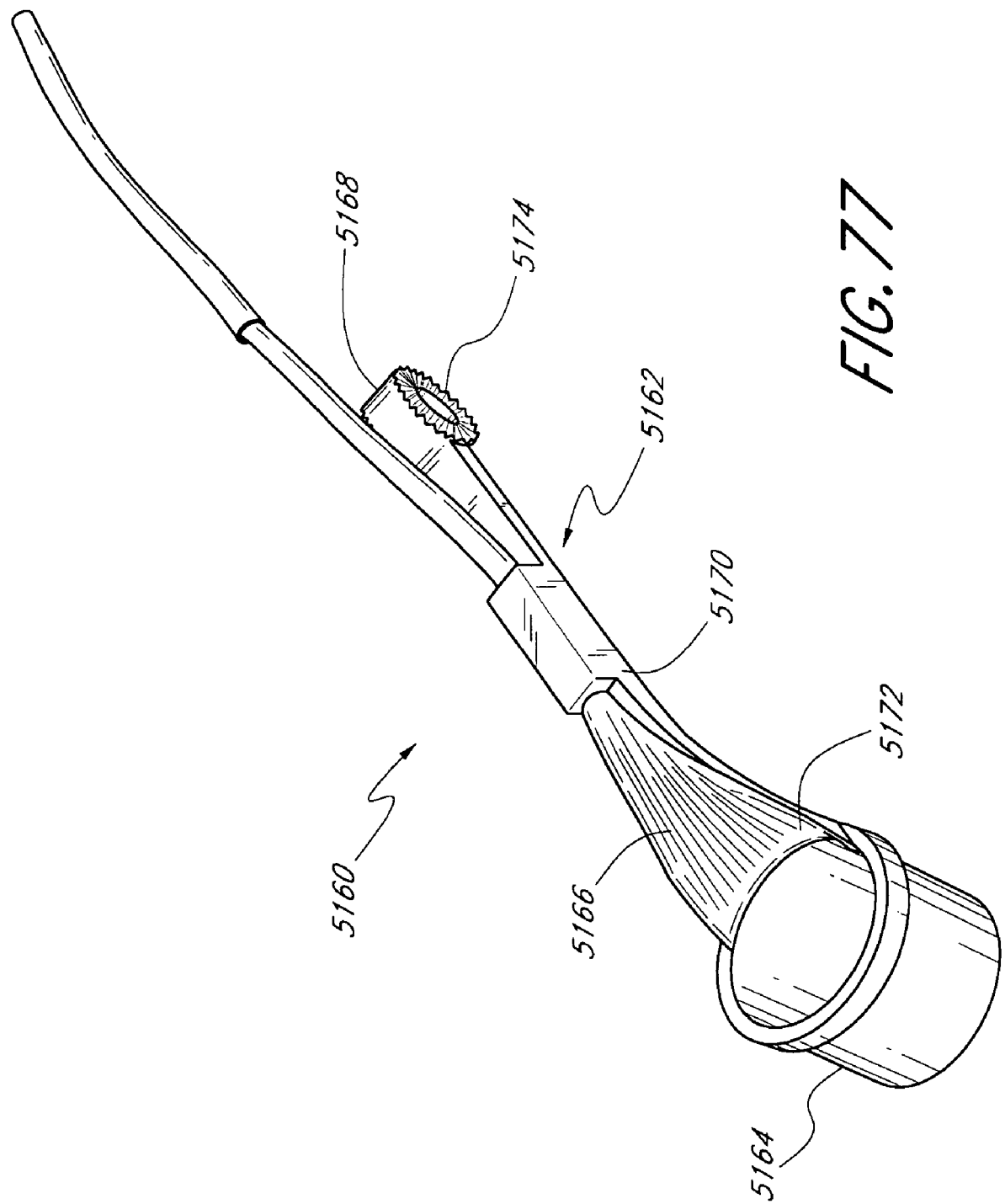
FIG. 77 is a perspective view of one embodiment of a lighting element.

FIGS. 74-79 illustrate other embodiments of lighting elements. As shown in FIG. 77, a lighting element 5160 comprises a support member 5162, an access device insert 5164, and fiber optic elements 5166. The support member 5162 has a proximal end 5168, a central portion 5170, and a distal end 5172. The proximal end 5168 preferably has a coupling portion 5174 for coupling the support member 5162 to a support arm or other support system (not shown). The central portion 5170 preferably is coupled with the fiber optic elements 5166 to provide support there to. The distal end 5172 preferably is coupled with the access device insert 5164.

In the illustrated embodiment, the access device insert 5164 is configured to be inserted in an access device having a proximal portion with a generally circular cross section. The access device insert 5164 is coupled with the fiber optic elements 5166. The fiber optic elements 5166 extend down into the access device insert 5164 so that the ends of the fiber optic elements 5166 can direct light down inside an access device along side portions thereof.

FIGS. 78 and 79 illustrate other embodiments of lighting elements similar to the embodiment described with reference to FIG. 77. Components of the lighting elements shown in FIGS. 108 and 109 that were described with reference to FIG. 77 are given the same reference numerals that were used in FIG. 77, except that an "a" is added in FIG. 78 and a "b" is added in FIG. 79. As shown in FIGS. 78 and 79, access device inserts 5164*a*, 5164*b* are configured to be inserted into access devices having proximal portions with generally oblong, or oval, cross sections. As shown in FIG. 78, the access device insert 5164*a* has a generally oblong or oval shaped cross section. The access device insert 5164*a* is coupled with the fiber optic elements 5166*a* along a longer side surface of the access device insert 5164*a*. As shown in FIG. 79, the access device insert 5164*b* has a generally oblong or oval shaped cross section. The access device insert 5164*b* is coupled with the fiber optic elements 5166*b* along a shorter side surface of the access device insert 5164*b*. Use of an illumination element with an expandable access device having an oblong shaped proximal section, in some cases, allows a doctor to perform procedures that would be difficult to perform using an endoscope. Increased visualization of the surgical location through the access device can simplify some procedures. For example, decompression of the contra-lateral side can be achieved more easily in some cases without the use of an endoscope.

Figure 80:
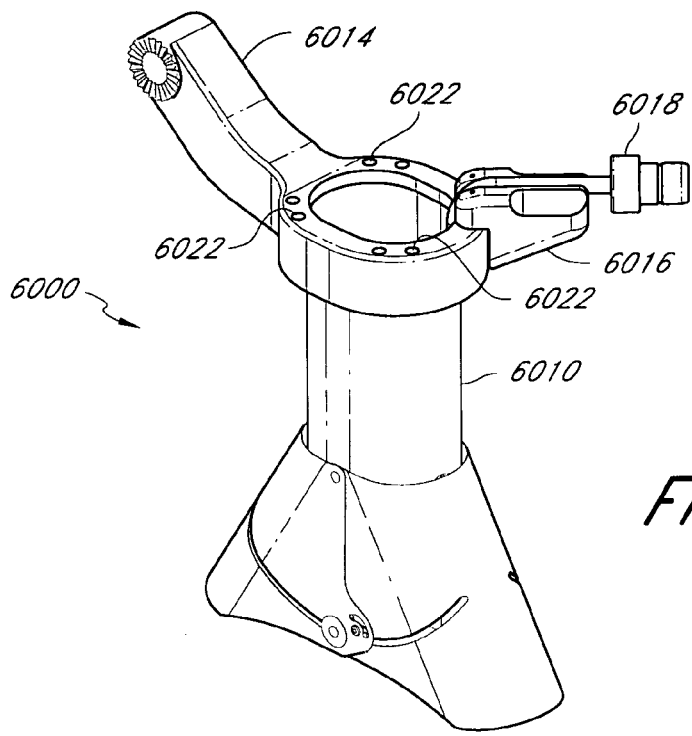
FIG. 80 is a perspective view of an access assembly.
Figure 81:
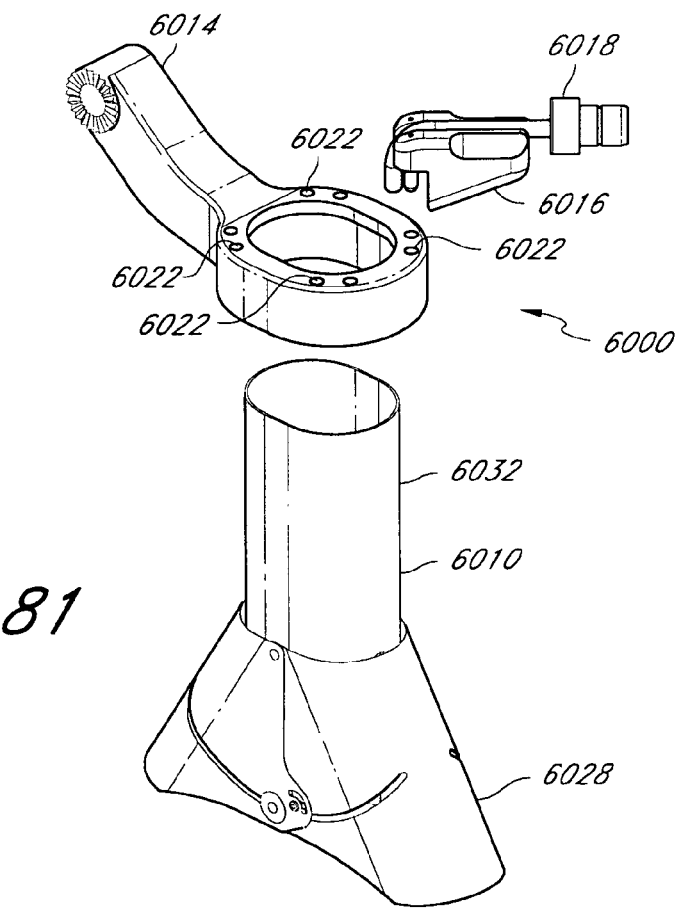
FIG. 81 is an exploded perspective view of the access assembly of FIG. 80.

FIGS. 80 and 81 show an access assembly 6000 that can be incorporated into a surgical system, such as the system 10. The access assembly 6000 includes an access device or retractor 6010 coupled with a mount fixture 6014. The mount fixture 6014 may be coupled with a support arm, such as those discussed above. The access device 6010 preferably is provided with an oblong transverse cross-section near the proximal end thereof, which can be coupled with the mount fixture 6014. More preferably, the access device 6010 can be provided with an oval transverse cross-section in some embodiments. The cross section can be generally elliptical in some embodiments. The oblong shaped cross-section of the access device 6010 is particularly beneficial for surgical procedures (such as two level pedicle screw fixation) that are performed at an elongated surgical field. Also coupled with the mount fixture 6014 is a guide fixture 6016. In one embodiment, the guide fixture 6016 is configured to be coupled with a viewing element 6018, such as any of those discussed herein, or any other suitable viewing element.

The mount fixture 6014 and the guide fixture 6016 advantageously are configured to introduce the viewing element 6018 into the access device 6010 at discrete locations. In the illustrated embodiment, the mount fixture 6014 and the guide fixture 6016 are configured to enable a viewing element to be positioned at four discrete locations that are located at opposite corners of the elongated mount fixture 6014. In the illustrated embodiment, a plurality of holes 6022 (e.g., two holes) is provided at each of four corners on the top surface of the mount fixture 6014. Each of the holes 6022 is configured to receive a pin that extends from the lower surface of the guide fixture 6016. The engagement of the pins in the holes 6022 is such that the guide fixture 6016 is securely coupled with the mount fixture 6014 so that the guide fixture 6016 will not be dislodged inadvertently during a procedure. However, the engagement of the pins in the holes 6022 also is such that a user of the access assembly 6000 can disengage the guide fixture 6016 and the viewing element 6018 and reposition it at any of the other discrete locations during a procedure. Although the coupling of the mount fixture 6014 and the guide fixture 6016 is illustrated as a two hole-two pin arrangement, other arrangements are possible and contemplated. For example, more or less than two holes and pins, couplers of other shapes (e.g., pins and holes of different shapes, tongues and slots, etc.), and clamp devices could be used in place of or in combination with the illustrated two hole-two pin arrangement.

Figure 82:
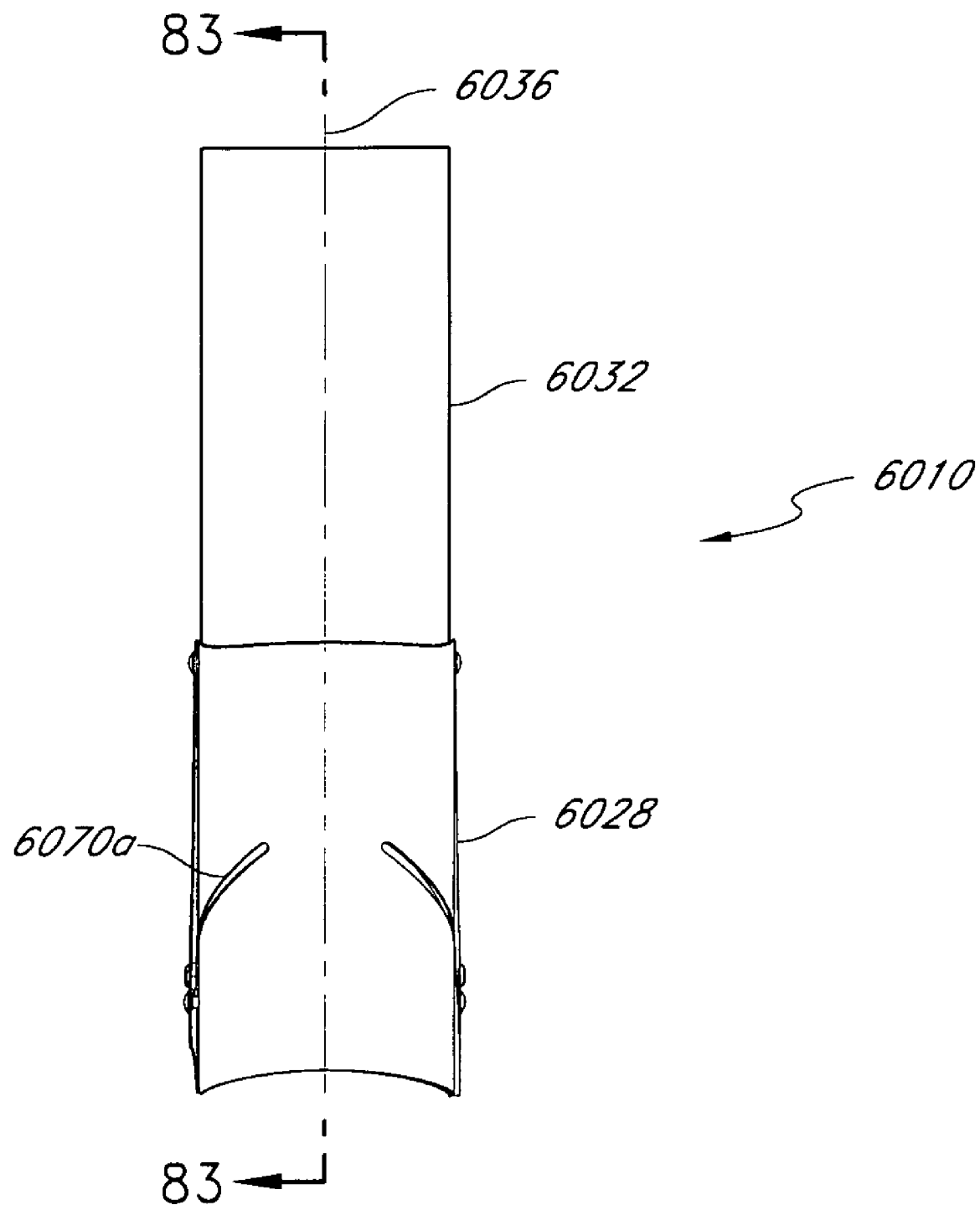
FIG. 82 is a side view of an access device of the access assembly of FIG. 80, the access device having a lock to maintain a state of expansion thereof.

FIG. 82 shows one embodiment of the access device 6010 that is similar to those hereinbefore described, except as set forth below. The access device 6010 has an elongate body with a distal portion 6028 and a proximal portion 6032. Each of the distal and proximal portions 6028, 6032 defines a portion of a passage that extends through the access device 6010. In some embodiments, the distal portion 6028 of the access device 6010 is shorter compared to the distal portion of some of the other access devices described herein. In particular, the distal portion 6028 is configured such that when the access device 6010 is applied to the patient, the distal portion 6028 is completely or substantially completely beneath the skin, as discussed below. This arrangement is advantageous in that the access device 6010 does not need to further dilate the incision at the skin.

Although the illustrated embodiment of the access device 6010 has two discrete portions that are coupled in a suitable manner, other access devices embodying features discussed herein can be configured without multiple, discrete portions. Both the proximal and distal portions preferably are made from a rigid, radiolucent material that is visible under fluoroscopy. The distal and proximal portions 6028, 6032 preferably both have sufficient strength or stiffness to retract tissue, though the strength or stiffness of the proximal and distal portions need not be the same. Examples of materials that may be used and other features that can be incorporated into the access device 6010 are discussed above and in the patents and applications incorporated by reference herein.

The proximal portion 6032 preferably is elongated and has a length along a longitudinal axis 6036 that is selected based upon the anatomy (e.g., the portion of the spine) being treated. The length of the proximal portion 6032, and other aspects of the access device 6010, also can be based in part on the individual patient's anatomy, e.g., on the amount of tissue between the skin and the surgical location, which varies across the patient population.

As discussed above, the configuration of at least a portion of the proximal portion 6032 is elongated in at least one direction in a plane perpendicular to the axis 6036. One advantageous arrangement of the proximal portion 6032 provides an oblong transverse cross-section. Another advantageous arrangement provides an oval transverse cross-section. The configuration of the proximal portion 6032 is illustrated in FIGS. 85-86A, which show that the transverse cross-section of the proximal portion 6032 is elongated along a line 6040. As will be discussed in more detail below, the line 6040 extends along the main axis of expansion of the access device 6010.

There are several advantages to configuring the proximal portion 6032 with an oblong transverse cross-section. Many bone and joint procedures, particularly spine procedures, are performed at elongated surgical fields. For example, multi-level procedures may be much more convenient for the surgeon and beneficial for the patient if access can be provided to at least a portion of three or more adjacent vertebrae. While symmetrical access could be provided to three or more adjacent vertebrae, much non-adjacent tissue (i.e., tissue not in the immediate vicinity of the structures being treated) would be disrupted, causing greater trauma to treat the patient than necessary. This additional trauma approaches that of open surgery as the length of the surgical field increases. In contrast, the use of an oblong transverse cross-section proximal portion 6032 and access device 6010 lessens, if not minimizes, the amount of non-adjacent tissue that is disrupted. Oblong access from a posterior or posterolateral approach is particularly advantageous in that it provides access to anatomy for a wide variety or procedures, e.g., those that affect the pedicles.

The distal portion 6028 also extends along the longitudinal axis 6036 and comprises a first overlapping portion 6050 and a second overlapping portion 6054. The first overlapping portion 6050 extends between a proximal end 6058 and a distal end 6062 of the distal portion 6028. The second overlapping portion 6054 extends between the proximal end 6058 and the distal end 6062 of the distal portion 6028. The overlapping portions 6050, 6054 overlap each other to create an enclosed space 6066 therebetween. In one embodiment, each of the overlapping portions 6050, 6054 extends along the axis 6036 when the overlapping portions are coupled with the proximal portion 6032 and is formed from a thin, rigid material (such as sheet metal) that is curled into a generally U-shaped structure.

The first and second overlapping portions 6050, 6054 are coupled in a manner that permits expansion of the distal portion 6028 at the distal end 6062. The advantages of being able to expand the distal portion are discussed above. The first and second overlapping portions 6050, 6054 also are configured to be selectively locked or unlocked in one or more states of expansion or contraction. Further advantages of the locking aspect of the first and second overlapping portions 6050, 6054 are discussed below.

In one embodiment, the distal portion 6028 has a slot and guide member arrangement that enables expansion of the distal portion 6028. Corresponding arcuate slots 6070*a*, 6070*b* are formed in the first overlapping portion 6050 and the second overlapping portion 6054, respectively. In one embodiment, a guide member, such as a sliding rivet 6074, extends through the corresponding slots 6070*a*, 6070*b* thereby coupling the slots. The slots 6070*a*, 6070*b* and the rivet 6074 enable the distal portion 6028 to be expanded by allowing the rivet 6074 to slide along the slots as the overlapping portions 6050, 6054 move away from or toward each other. In the illustrated embodiment, a second pair of slots and a corresponding guide member (e.g., a rivet) are provided on the opposite side of the access device 6010 from the slots 6070*a*, 6070*b* and the rivet 6074. Thus, two rivets 6074 are provided in corresponding pairs of slots adjacent each edge of the overlapping sections 6050, 6054. This arrangement enables generally linear expansion of the distal portion 6028 along and parallel to a vertical plane extending along the long dimension of the proximal portion 6032 and containing the line 6040. Another arrangement provides one or more slots on only one side of the access device 6010, which would provide a more multi-directional expansion (e.g., both cephalad-caudad and medial-lateral) near the distal end 6062 of the distal portion 6028.

The distal portion 6028 is configured to be actuatable from a non-expanded configuration to an expanded configuration. The non-expanded configuration is said to be "low-profile" in that the transverse cross-section of the distal portion 6028, particularly at the distal end 6062, is relatively small. The access device 6010, like the other access devices described herein, is configured to be inserted over a dilating structure, such as a dilator or an obturator. One suitable dilator is described below in connection with FIGS. 120-122. Providing a low-profile distal end 6062 in the non-expanded configuration enables a generally smaller dilating structure to be used, reducing the amount of trauma to the patient during insertion. In one embodiment the distal portion 6028 has an oblong cross-section similar to that of the proximal portion 6032 when the distal portion 6028 is in a low profile configuration. The transverse cross-section of the distal portion 6028 in the low profile configuration need not be constant from the distal end 6058 to the proximal end 6062 thereof. For example, in one embodiment the transverse cross-section of the distal portion 6028 transitions from generally circular near the distal end 6058 to generally oblong near the proximal end 6062 (e.g., generally matching the transverse cross-section of the proximal portion 6062 at the distal end thereof). The distal portion 6028 may also be arranged to transition from a circular cross-section configuration to a non-circular cross-section configuration.

The distal portion 6028 also is provided with a lock 6090 that enables a user to selectively lock the distal portion 6028 into one or more states of expansion. The lock 6090 can take many forms. In one embodiment, the lock 6090 includes a slot 6094 and an L-shaped flange 6098 that can be moved (e.g., rotated) into and out of the slot 6094.

In one embodiment, the slot 6094 extends generally perpendicularly from the slot 6070*a* and the slot 6094 has a first side 6094*a* and a second side 6094*b*. Each of the first and second sides 6094*a*, 6094*b* of the slot 6094 restrains relative movement of the overlapping portions 6050, 6054 to selectively limit expansion or un-expansion of the distal portion 6028 when the lock 6090 is engaged.

In one embodiment, the L-shaped flange 6098 includes an elongated planar portion 6502 and a lock tab 6506. The elongated portion 6502 preferably is relatively thin so that it may reside between the overlapping portions 6050, 6054. In one embodiment, the elongated portion 6502 is rotatably coupled (e.g., with a pin or a portion of a rivet, e.g., a half-rivet) with the overlapping portion 6054 near one edge thereof. The elongate portion 6502 is thereby enabled to swing about an arc. In one embodiment, the lock tab 6506 extends generally perpendicularly from the end of the elongated portion 6502 that is opposite the rotatably coupled end. The length of the lock tab 6506 is greater than the thickness of the first overlapping portion 6050. In one embodiment, the lock tab 6506 extends far enough beyond the first overlapping portion 6050 into the area defined within the access device 6010 to enable a user to engage and manipulate the lock tab 6506 in the enclosed space 6066. Where the access device 6010 is to be inserted over a dilating structure, the lock tab 6506 preferably is configured to not interfere with the dilating structure. For example, the lock tab 6506 can be made short enough so that the lock tab 6506 does not extend far enough into the enclosed space 6066 defined inside the access device 6010 to interfere with the dilating structure. Any suitable tool may be used to articulate the lock 6090, e.g., by engaging and manipulating the lock tab 6506. For example, a tool that is long enough to extend from a location proximal of the proximal end of the proximal portion 6032 to the location of the lock 6090 could be used. A number of conventional tools can be configured in this manner, including a cobb elevator, a penfield, and a nerve hook.

In one application, the access device 6010 is used to provide minimally invasive access to the spine for a spinal procedure, such as a one-level or a multi-level procedure. The patient is positioned prone on a radiolucent table and draped for posterior spinal surgery. The location of the spine anatomy to be treated is identified, e.g., via fluoroscopy. In one technique, the location of adjacent pedicles on one side of the mid-line of the spine are identified. Thereafter, an incision is made through the skin above the adjacent pedicles. In one technique, an incision of about 30-40 mm in length is made between two adjacent pedicles where a single level procedure (one involving two adjacent vertebrae) is to be performed. In another technique where a two-level procedure (one involving three vertebrae) is to be performed, an incision of 40-50 mm in length is made. As discussed above, in some embodiments, the access device 6010 is configured to be applied such that the distal portion 6028 is completely or substantially completely submerged beneath the skin. In one technique, an incision of about 30 mm is made in the skin so that an access device configured to be applied in this manner may be applied to the patient. In some embodiments of the access devices described herein, a proximal portion thereof is configured to be expandable. In some techniques for applying access devices with expandable proximal portions, a larger incision may be made to accommodate all or substantially all of the expansion of the proximal portion.

Thereafter a dilating structure, such as a series of dilators or an obturator, is inserted into the incision to enlarge the incision. It may be desirable to use round or oblong dilators. Preferably the last dilator has an outer profile that matches the un-expanded inner profile of the access device 6010. In one technique for a single level procedure, a 5 mm dilator is first inserted through the skin near the center of the skin incision and is docked on the lateral aspect of the superior facet. In a two-level procedure, a 5 mm dilator is first advanced through the skin near the center of the incision and is docked on the mamillo-accessory ridge of the middle pedicle. Placement of the 5 mm dilator may be verified by fluoroscopy. Subsequently, progressively larger dilators are inserted over each other. After a larger dilator is inserted, the next-smaller dilator is normally removed. One or more of the dilators, a cobb device, or even one of the surgeon's fingers may also be used to probe and to dissect soft tissue to ease expansion of the access device 6010, as discussed below. Placement of the final dilator may be verified by fluoroscopy. Other procedures employ similar dilating techniques by initially approaching other anatomical features on or near the spine.

Thereafter, the access device 6010 is advanced to the anatomy to be treated. As discussed above, a sleeve deployable by a string may be employed to maintain the access device 6010 in the low-profile configuration (e.g., in the un-expanded state) until the access device is in place. Various embodiments of the sleeve and string are discussed herein, e.g., in connection with FIGS. 123-124. In one technique, the assembly of the access device 6010, the sleeve, and the string is inserted into the incision and positioned so that the string faces the mid-line of the spine. Thereafter the string is withdrawn, releasing the sleeve from the access device 6010. In particular, in one technique, the string is pulled from near the proximal end of the access device 6010. This action causes the sleeve to be torn along a line extending proximally from the distal end of the sleeve. The sleeve may be partially or completely torn from distal to proximal, releasing at least the distal end of the access device 6010 for expansion. After the sleeve is released from the access device 6010, the access device 6010 is free to expand and to be expanded.

Figure 83:
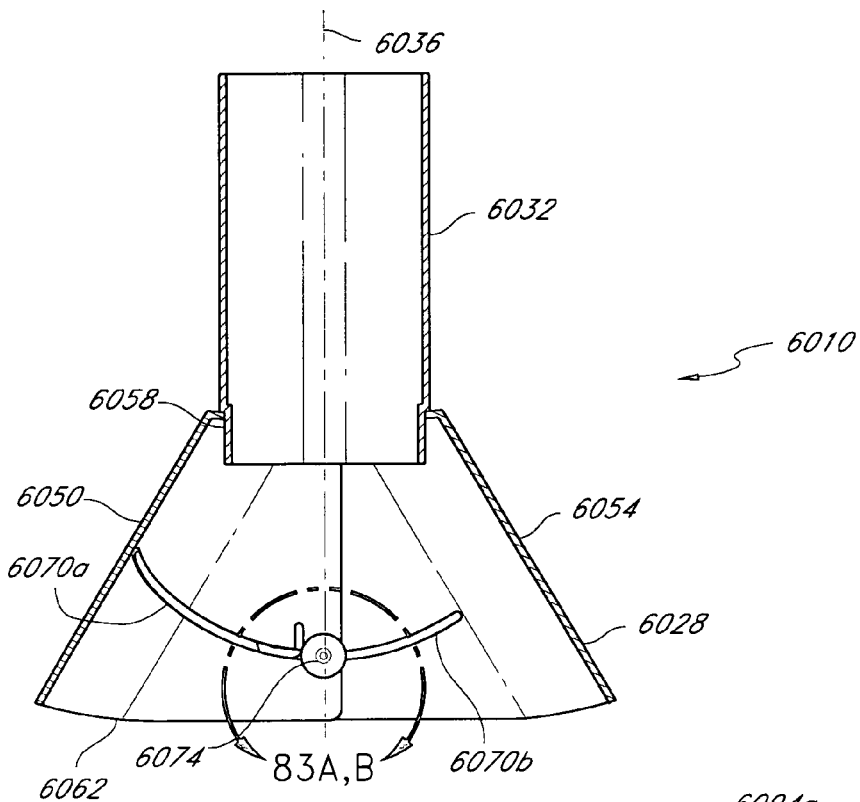
FIG. 83 is a cross-sectional view of the access device of FIG. 82 taken along section plane 83-83.
Figure 83A:
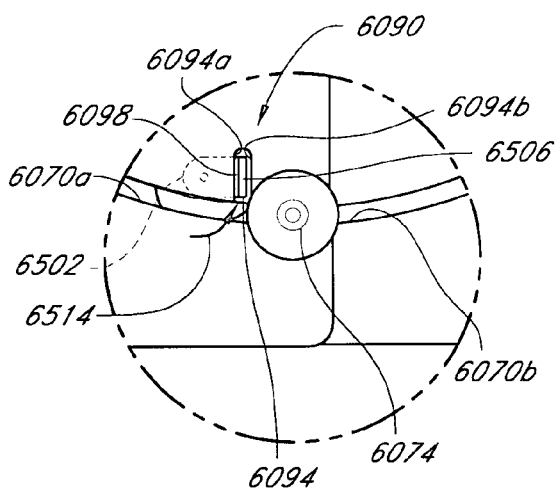
FIG. 83A is a detail view of one embodiment of a lock to maintain a state of expansion of an access device, the lock shown in the locked position.
Figure 83B:
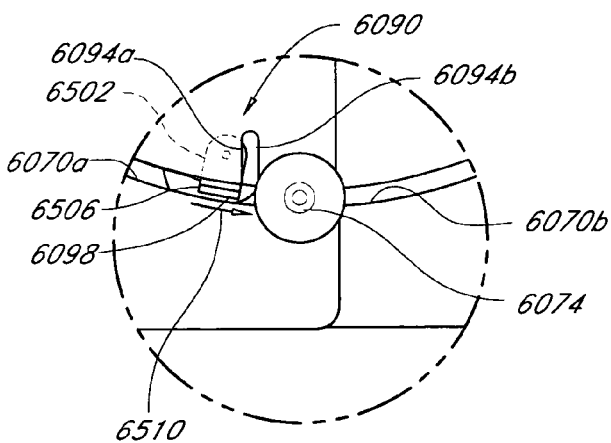
FIG. 83B is a detail of the lock of FIG. 83A, the lock shown in the unlocked position.

FIG. 83B shows that prior to and during expansion of the access device 6010, the L-shaped flange 6098 is positioned so that the lock tab 6506 is located in the arcuate slot 6070*a*. The lock tab 6506 has a thickness that is less than the proximal to distal width of the slot 6070*a* so that the lock tab 6506 can translate along the slot 6070*a* between positions corresponding to the un-expanded and expanded configurations of the access device 6010. The access device 6010 may resiliently expand with the lock tab 6095 in the slot 6070*a*. Further expansion of the access device 6010 may be achieved by inserting and articulating an expander tool, such as the expander tool 200 discussed above. The expansion and location of the access device 6010 may be confirmed by fluoroscopy.

After the access device 6010 has been fully expanded, the lock 6090 may be articulated to lock the access device 6010 in the expanded configuration. In particular, the lock tab 6098 may be positioned in the slot 6094. As discussed above, the lock tab 6098 is pivotable at the end opposite the lock tab 6506. In one procedure, the user grasps and rotates the lock tab 6506 from the expansion position in the slot 6070*a* to the locked position in the slot 6094. As discussed above, the lock 6090 may be manipulated in any convenient manner, e.g., by any suitable tool, as discussed above. FIG. 83B shows an arrow 6510 that indicates the rotation of the lock tab 6098 to the locked position. When in the locked position, the lock tab 6098 may engage one of the sides 6094*a*, 6094*b* of the slot 6094 to prevent either inadvertent further expansion or un-expansion of the access device 6010.

In one variation, another slot analogous to the slot 6094 is provided at the opposite end of the arcuate slot 6070*a* to enable the access device 6010 to be locked in the un-expanded configuration. This arrangement and variations thereof may substitute for the sleeve and string arrangement, discussed above.

After the access device 6010 is locked in position, various procedures may be performed on the spine (or other joint or bone segment). As discussed above, these procedures may be performed with much less trauma than that associated with open surgery. After the procedures are complete, the access device 6010 may be un-expanded by articulating the lock 6090 from the locked position to the unlocked position, e.g., by moving the lock tab 6098 from the slot 6094 to the slot 6070*a*, wherein it is free to translate. FIG. 83A shows an arrow 6514 that indicates the rotation of the lock tab 6098 to the unlocked position.

Figure 84:
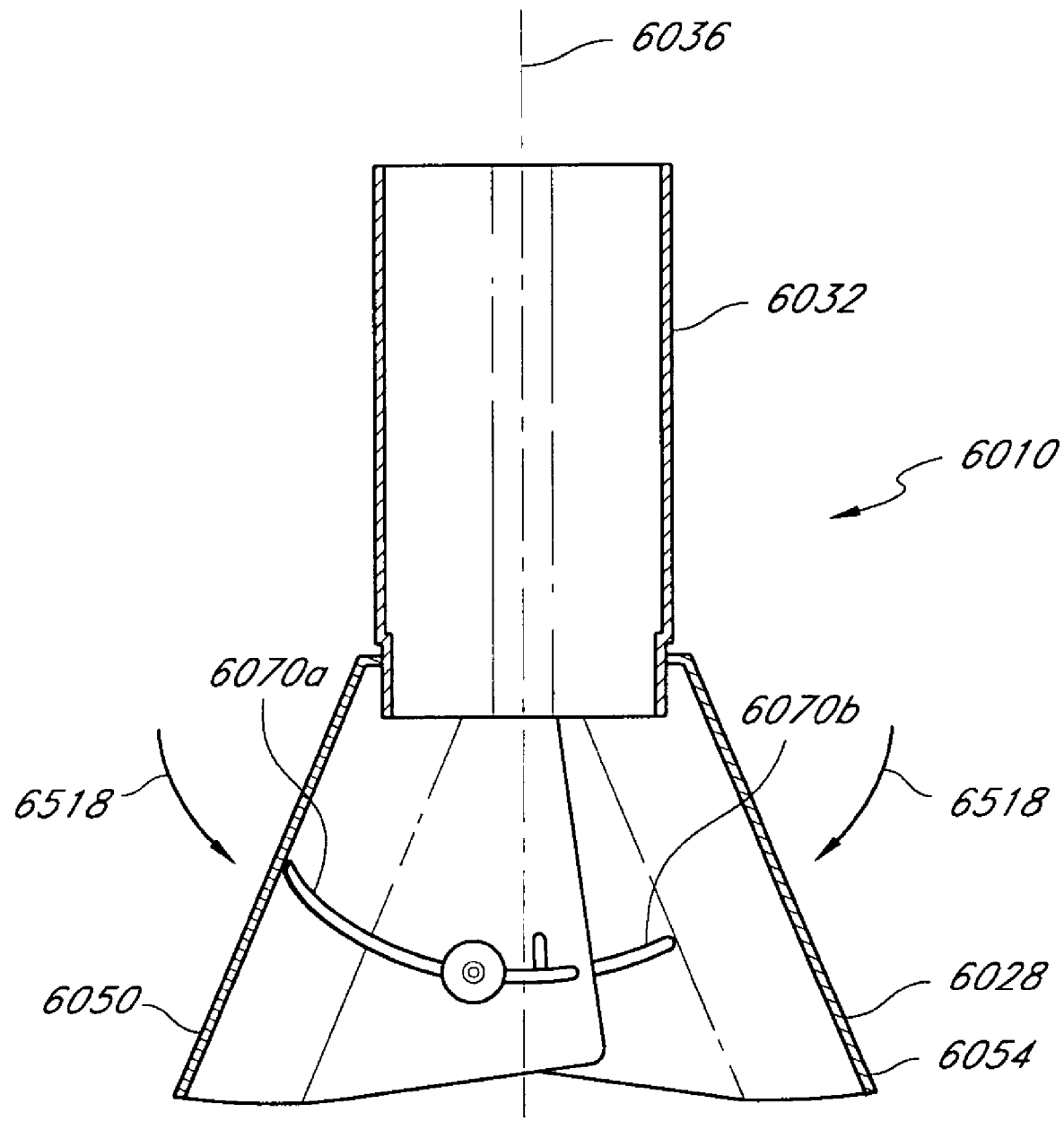
FIG. 84 is a cross-section view similar to that of FIG. 83 with the lock device in the unlocked position during the un-expansion of the access device.

FIG. 84 shows an arrow 6518 that indicates un-expansion of the access device 6010 after the procedure is complete.

FIGS. 87-150 illustrate and describe systems, devices, components, and methods according to some additional embodiments. Details shown or described in FIGS. 87-150 are merely representative of some preferred embodiments and are not intended to limit other embodiments. Some of the systems, devices, components, and methods shown are similar to those described above or in the documents incorporated by reference herein. Additional features and advantages of the illustrated embodiments will be apparent to those of ordinary skill in the art in view of the disclosure herein.

FIGS. 87-122 illustrate instrumentation, systems, devices, components, and methods according to some embodiments. FIGS. 87-122 illustrate portions of support arms, light post mounts, visualization mounts, light posts, visualization elements, indexing collar assemblies, and dilators, according to some embodiments. These devices and components can cooperate with access devices in access systems, such as those described and shown herein to facilitate various surgical procedures.

FIGS. 87-119 illustrate portions of a visualization assembly 7000. The visualization assembly 7000 preferably is configured to be coupled with a proximal portion of an access device. In the illustrated embodiment, the visualization assembly 7000 is configured to be coupled with an access device having a proximal portion with an oval shaped cross-sectional area. In other embodiments, the visualization assembly 7000 can be configured to be coupled with a proximal portion of an access device having any other oblong shaped or circular shaped (as suggested in FIG. 102) cross-sectional area. In one embodiment, the visualization assembly 7000 is configured to be coupled with an access device having a proximal portion that has a generally oval shaped opening that is about 24 mm wide and about 30 mm long. In another embodiment, the visualization assembly can be configured to be coupled with an access device having a proximal portion with a generally oval shaped opening that is about 24 mm wide and about 35 mm long.

FIGS. 87 and 88 show a visualization assembly 7000 that is similar to the other visualization assemblies described herein, except as set forth below. With reference to FIGS. 87 and 88, the visualization assembly 7000 has a light post mount 7002. In other embodiments, other suitable visualization element mounts can be used. The light post mount 7002 has a distal portion 7004 and a proximal portion 7006. The distal portion 7004 has a generally oval shaped mounting portion 7008. In other embodiments, the distal portion 7004 can have any other oblong shaped or circular shaped mounting portion 7008. A light post assembly 7010 (see FIGS. 98-99) preferably can be supported on a mounting portion 7008 of the light post mount 7002. The mounting portion 7008 has an outside surface 7012 and an inside surface 7014. The inside surface 7014 preferably defines an oblong shaped opening 7016 to provide access to a passage of an access device. In the illustrated embodiment, the inside surface 7014 defines a generally oval shaped opening 7016.

FIGS. 89-94 show a viewing element support mount that is similar to the other viewing element support mounts described herein, except as set forth below. With reference to FIGS. 89-94, the light post mount 7002 has a ledge 7018 on the inside surface 7014 of the light post mount 7002. The ledge 7018 preferably is configured so that the light post mount 7002 can rest on a top surface, a top edge, or an end of a proximal portion of an access device. The inside surface 7014 of the light post mount 7002, below the ledge 7018, can extend over a proximal portion of an access device. The mounting portion 7008 preferably has openings 7020, such as, for example, holes or slots, defined in the wall of the mounting portion 7008 for supporting the light post assembly 7010 or other visualization tool. As shown in the illustrated embodiment, the mounting portion 7008 preferably is configured to receive the light post assembly 7010 at a plurality of locations or positions.

Figure 89:
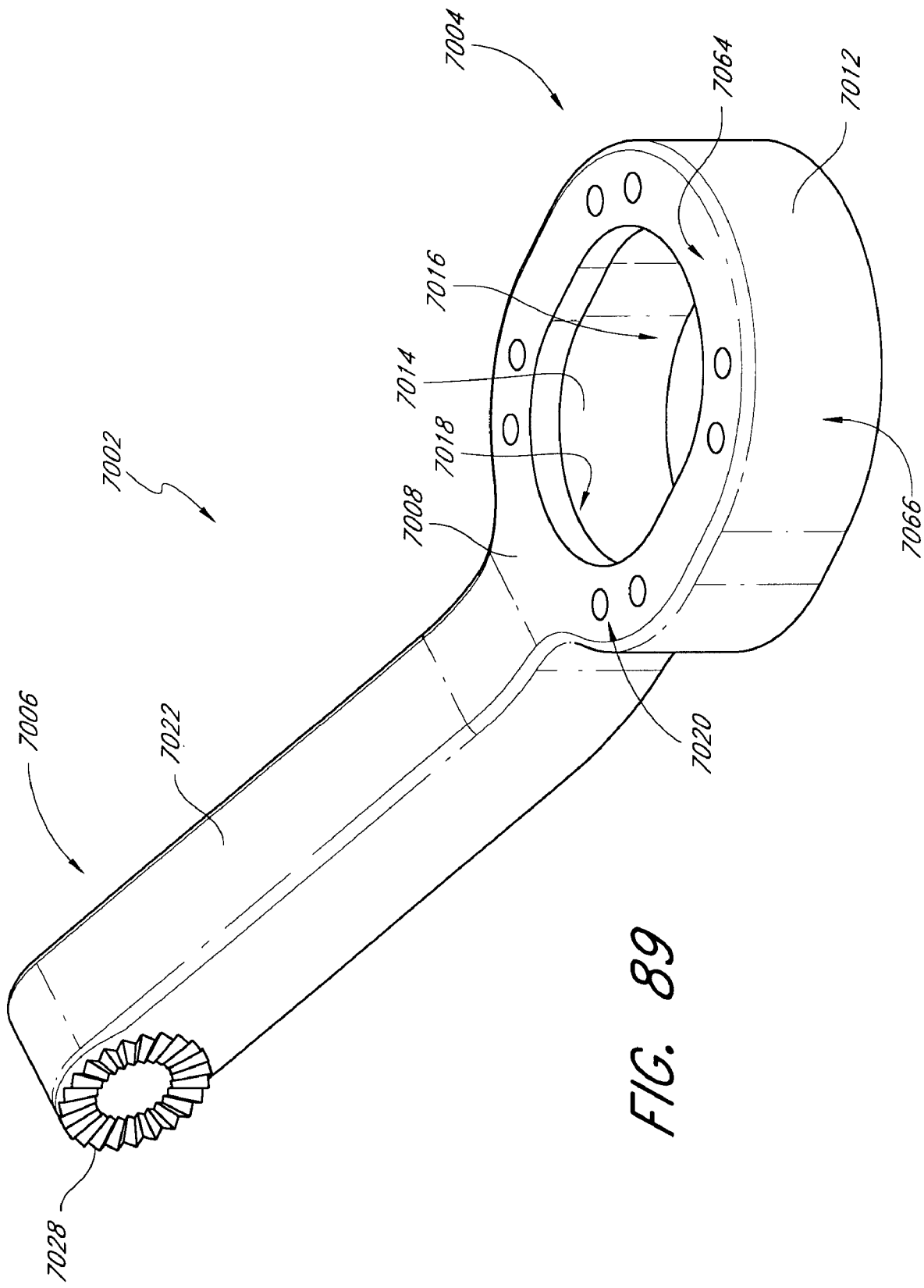
FIG. 89 is a perspective view of the light post mount or visualization mount of FIG. 87.

The light post mount 7002 has a support arm 7022 extending proximally from the mounting portion 7008. With reference to FIGS. 87 and 88, the support arm 7022 preferably is coupled with an arm extension assembly 7024 via an arm locking screw 7026. With reference to FIG. 89, the light post mount 7002 has a spline ring 7028 at a proximal portion 7006 of the support arm 7022. The spline ring 7028 preferably is configured for coupling the light post mount 7002 with the arm extension assembly 7024 via the arm locking screw 7026.

Figure 97:
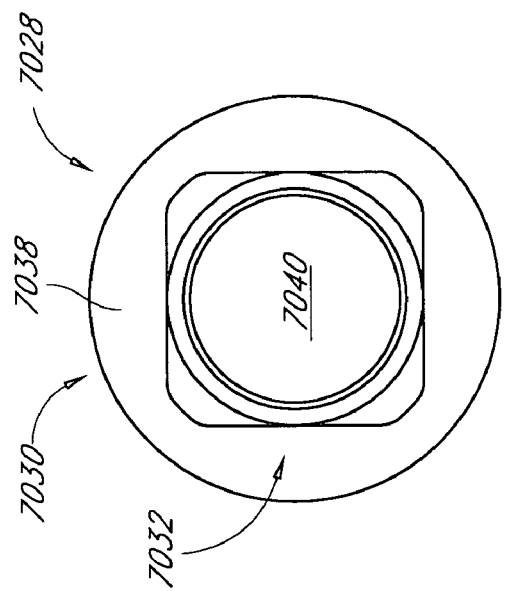
FIG. 97 is another end view of the spline ring of FIG. 95.
Figure 96:
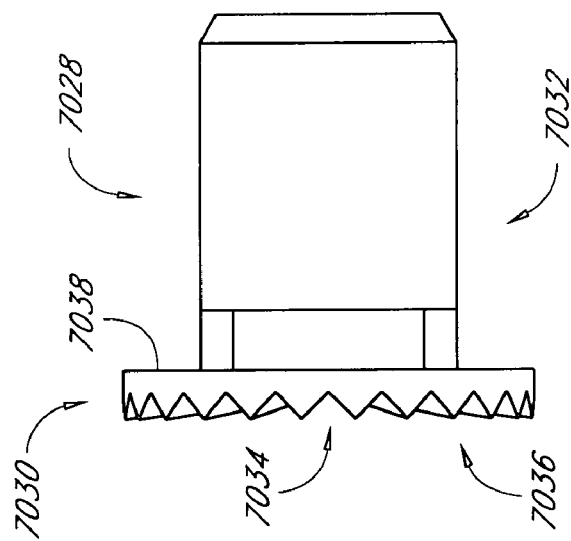
FIG. 96 is a side view of the spline ring of FIG. 95.
Figure 95:
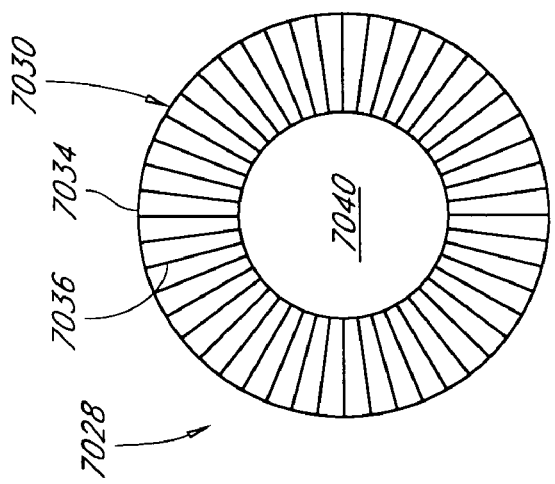
FIG. 95 is an end view showing a spline surface of a spline ring for the light post mount or visualization mount of FIG. 89.
Figure 100:
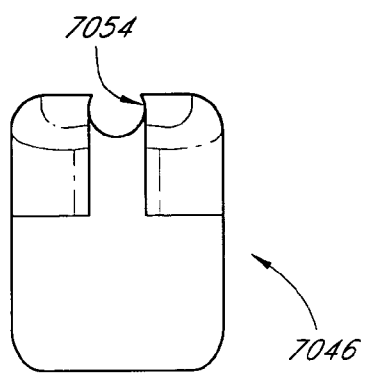
FIG. 100 is a front view of a light post mount block or visualization element mount block, according to one embodiment.
Figure 101:
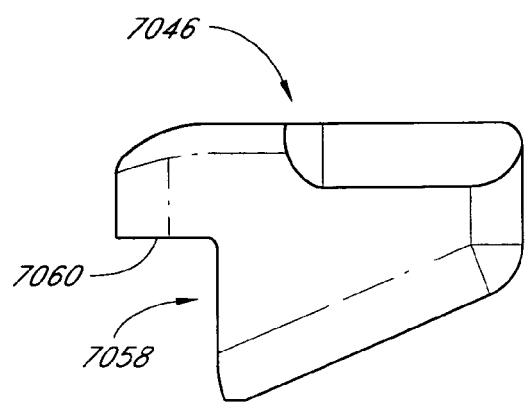
FIG. 101 is a side view of the light post mount block or visualization element mount block of FIG. 100.
Figure 102:
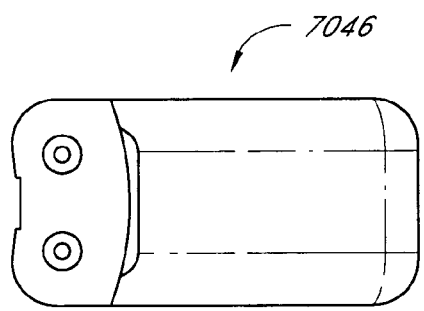
FIG. 102 is a top view of the light post mount block or visualization element mount block of FIG. 100.
Figure 103:
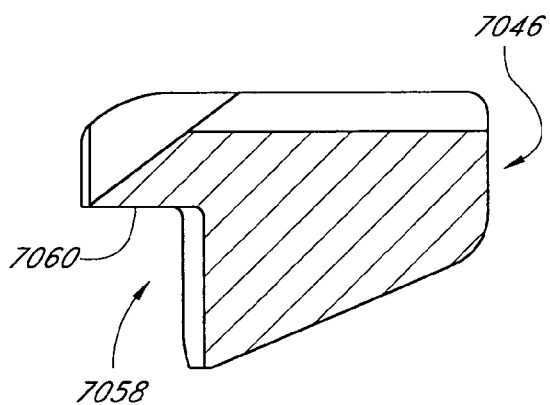
FIG. 103 is a side cross section view of the light post mount block or visualization element mount block of FIG. 100.
Figure 104:
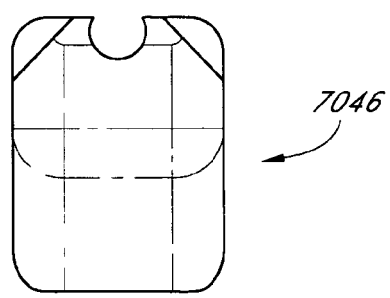
FIG. 104 is a back view of the light post mount block or visualization element mount block of FIG. 100.
Figure 105:
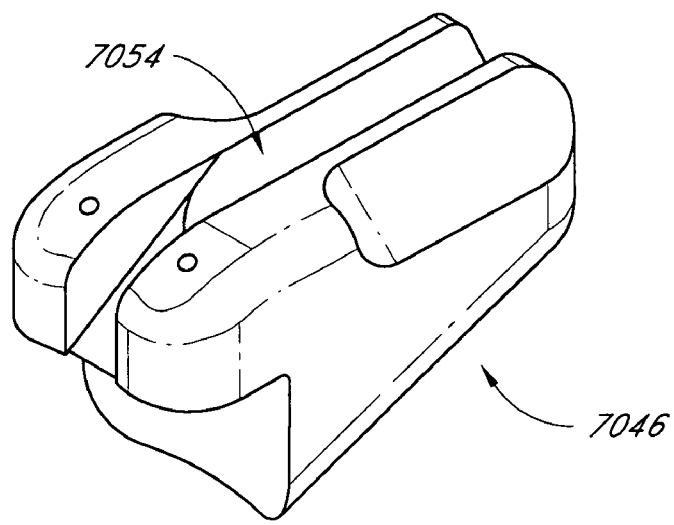
FIG. 105 is a top perspective view of the light post mount block or visualization element mount block of FIG. 100.
Figure 106:
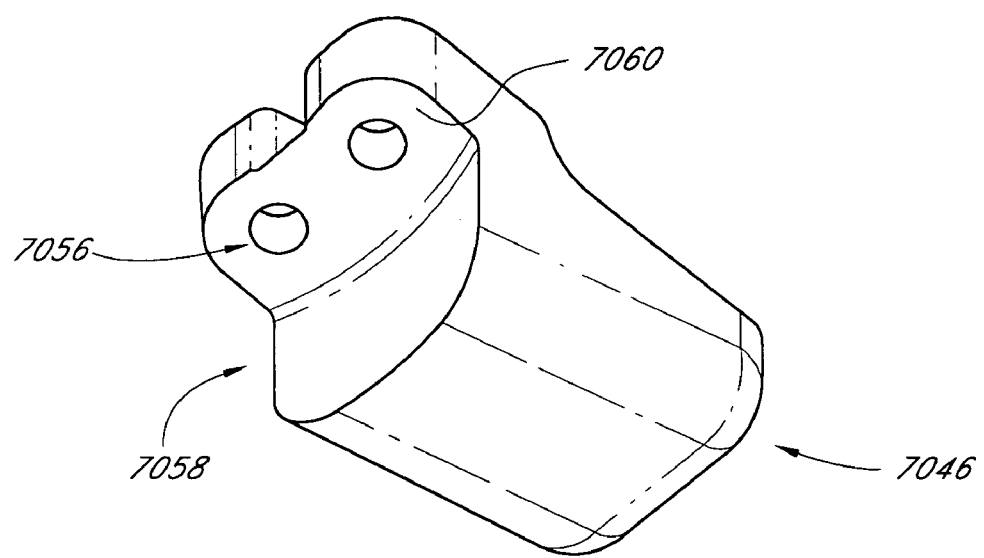
FIG. 106 is a bottom perspective view of the light post mount block or visualization element mount block of FIG. 100.

With reference to FIGS. 95-97, the spline ring 7028 has a spline portion 7030 and an anchor portion 7032. The spline portion 7030 preferably comprises a plurality of notches 7034 formed in a first surface 7036 of the spline portion 7030 to interface with the arm extension assembly 7024 via the arm locking screw 7026. The anchor portion 7032 of the spline ring 7028 extends from a second surface 7038 of the spline portion 7030 generally opposite the spline surface 7036. The anchor portion 7032 and spline portion 7030 define an opening 7040 extending through the spline ring 7028. The anchor portion 7032 can be inserted into an opening 7042 (see FIGS. 90 and 93) in the light post mount 7002 and preferably is secured therein using an epoxy.

FIGS. 98-99 show a viewing element that is similar to the other viewing elements described herein, except as set forth below. With reference to FIGS. 98-99, a light post assembly 7010 preferably comprises a light tube 7044, a light post mount block 7046, and one or more locator pins 7048. The light post assembly 7010 preferably is configured to be coupled with the light post support mount 7002. The light post assembly 7010 has a coupler 7050 for connecting the light post assembly 7010 to a light source (not shown). The light tube 7044 preferably is angled to direct light down into a channel or passage of an access device when the light post assembly 7010 is supported on the light post support mount 7002. The light tube 7044 in the illustrated embodiment is about 3 mm in diameter and about 15 mm long. A longer light tube 7044 may be used where it is desired to locate the end 7052 of the light tube 7044 farther distally in an access device.

Figure 107:
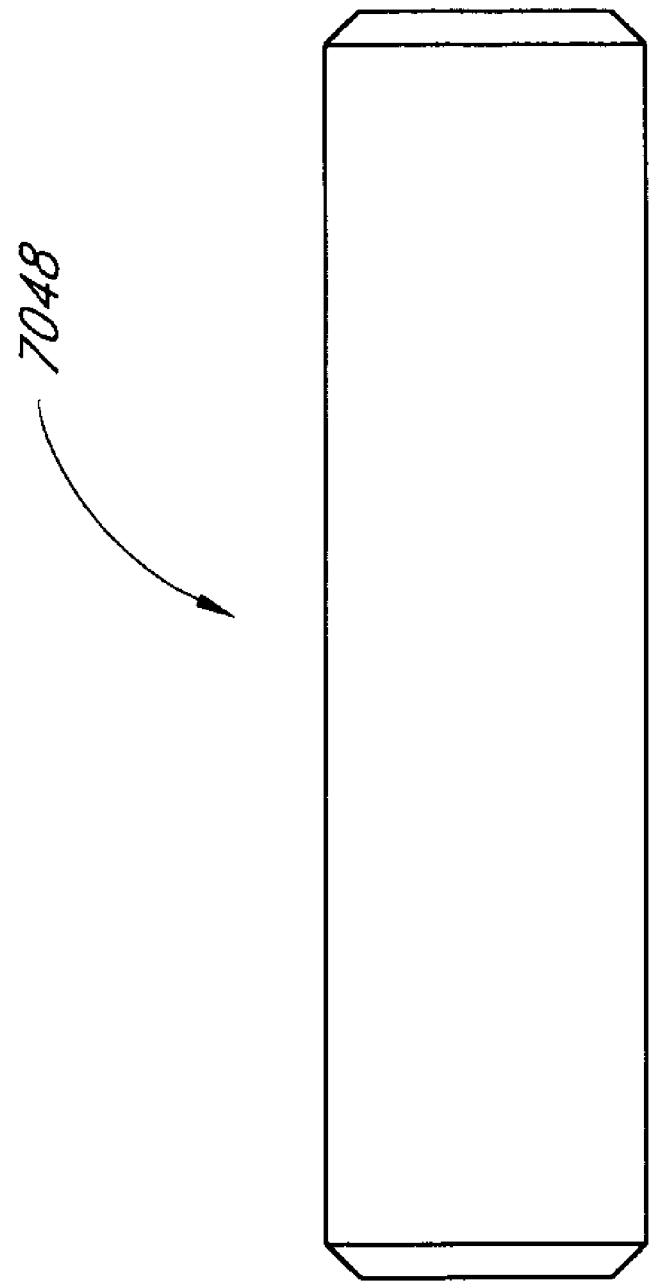
FIG. 107 illustrates a pin configured to be coupled with the light post mount block or visualization element mount block of FIG. 100.
Figure 110:
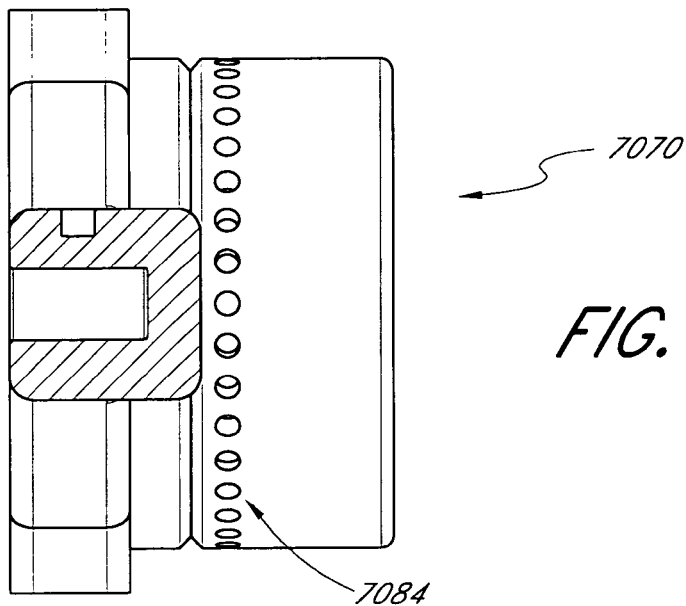
FIG. 110 is an end cross section view of the indexing collar of FIG. 108.
Figure 111:
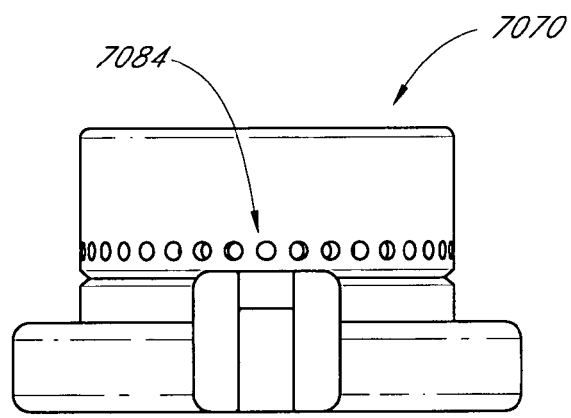
FIG. 111 is an end view of the indexing collar of FIG. 108.
Figure 112:
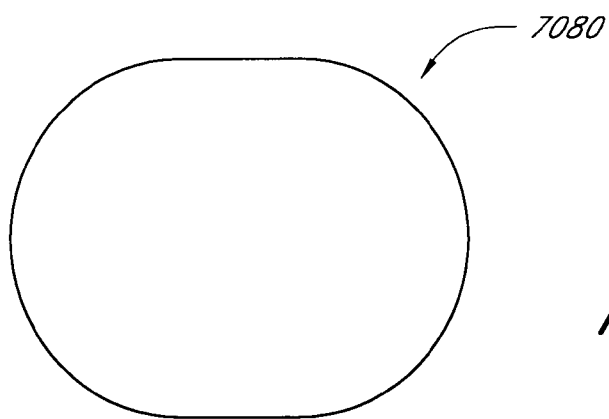
FIG. 112 is a schematic view of a passage of the indexing collar of FIG. 108.
Figure 113:
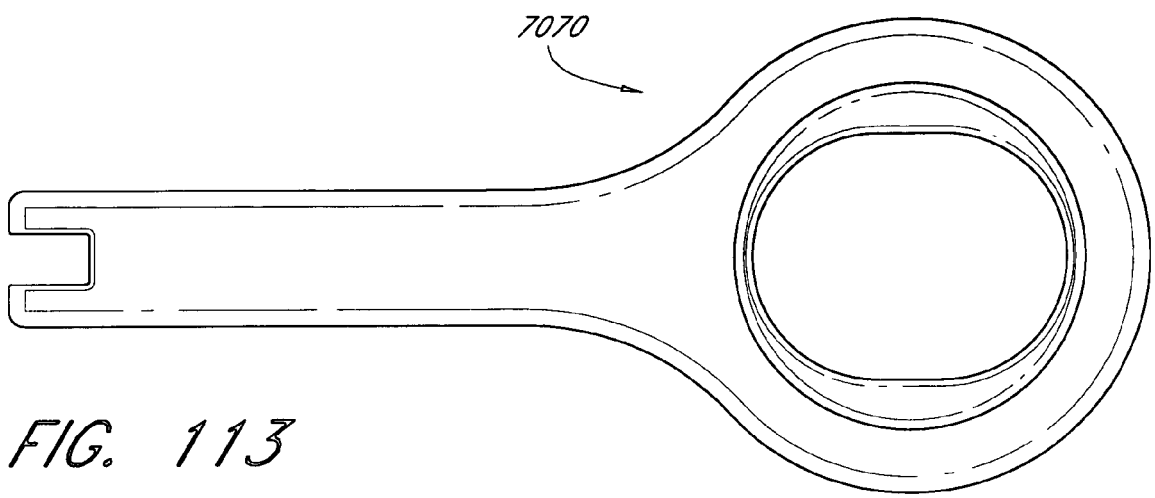
FIG. 113 is a top view of the indexing collar of FIG. 108.
Figure 114:
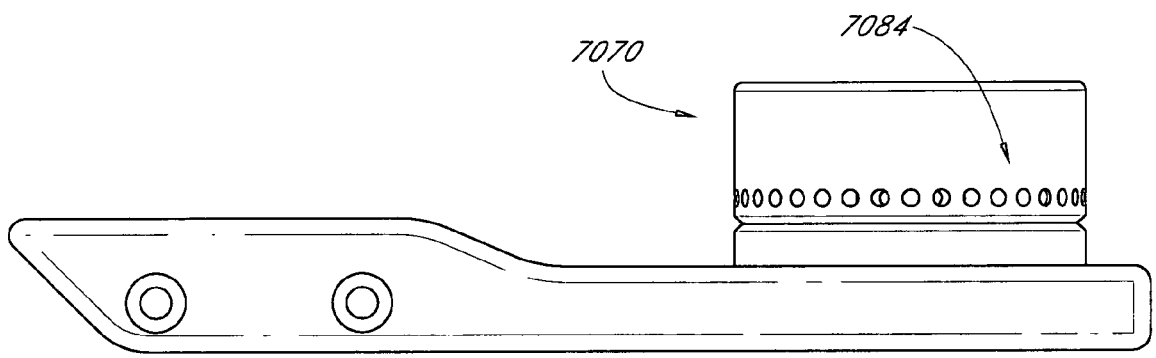
FIG. 114 is a side view of the indexing collar of FIG. 108.
Figure 115:
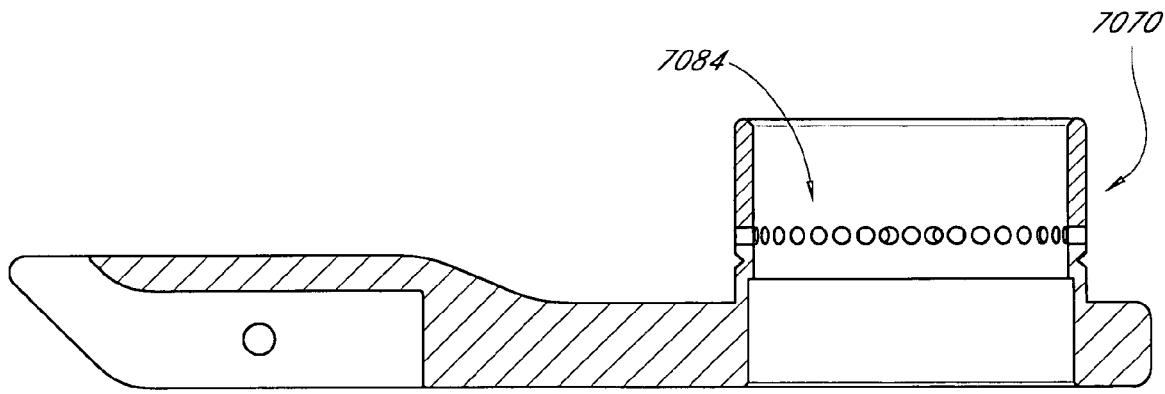
FIG. 115 is a side cross section view of the indexing collar of FIG. 108.
Figure 116:
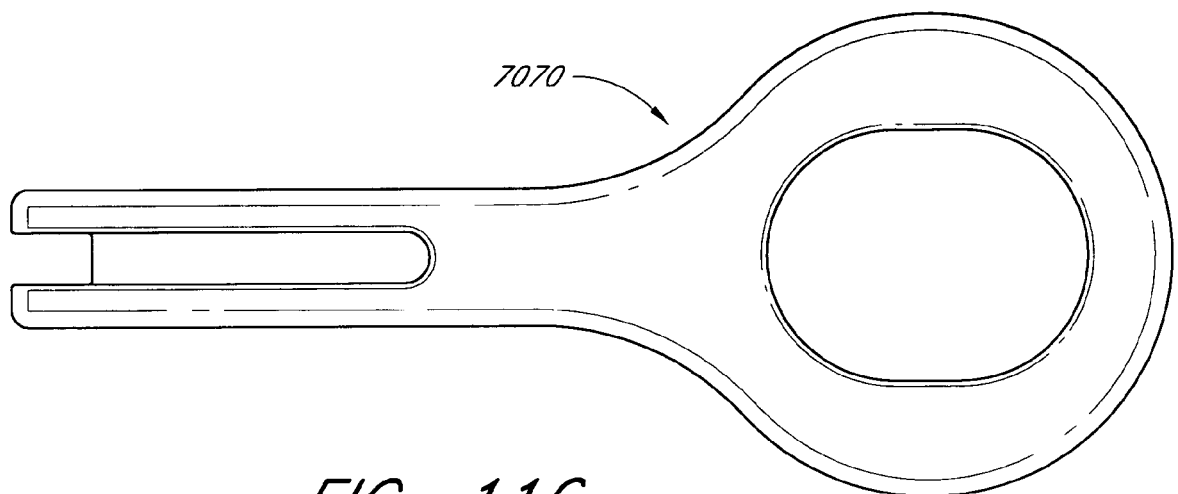
Figure 117:
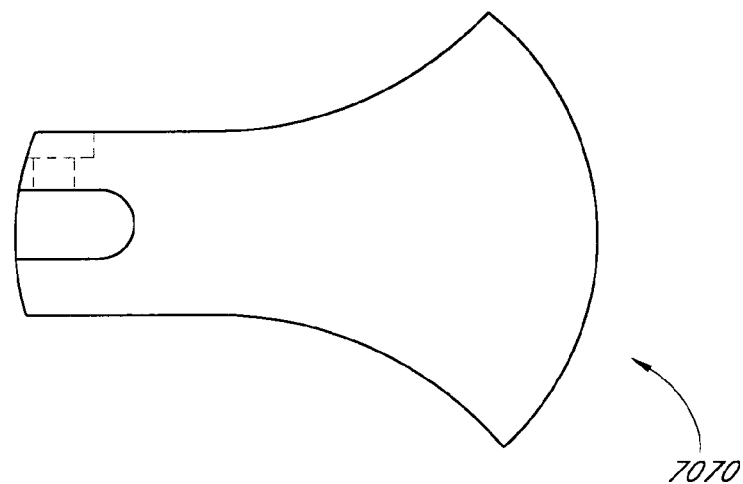
Figure 118:
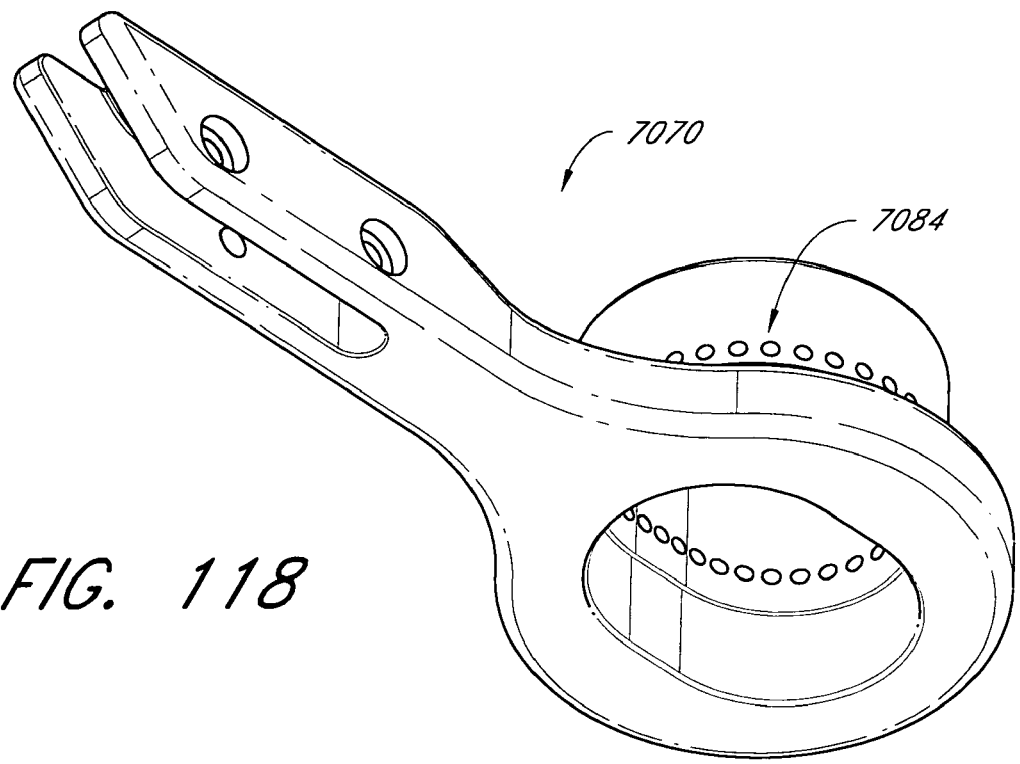

FIGS. 100-106 show a viewing element support block that is similar to the other viewing element support blocks described herein, except as set forth below. With reference to FIGS. 100-106, the light post mount block 7046 is configured to receive and support the light tube 7044, or other viewing element. In one embodiment, the light post mount block 7046 has an upper surface 7054 that is contoured for receiving the light tube 7044. The light post mount block 7046 can have one or more openings 7056 for receiving one or more locator pins 7048. The light post mount block 7046 has a notched portion 7058 including a first surface 7060 for contacting a top surface 7064 (see FIG. 89) of the light post mount 7002 and a second surface 7062 for contacting a side surface 7066 of the light post mount 7002. FIG. 107 shows one embodiment of a locator pin 7048. The locator pin 7048 is generally cylindrical, though other shapes may be used in some embodiments. The locator pin 7048 can be coupled with the light post mount block 7046 to retain the light post mount assembly 7010 in a desired location on the light post mount 7002.

FIGS. 108-109 show an indexing collar assembly that is similar to the other indexing collar assemblies described herein, except as set forth below. With reference to FIGS. 108-109, one embodiment of an indexing collar assembly 7068 comprises an indexing collar 7070, as shown in more detail in FIGS. 110-119. The indexing collar assembly 7068 also preferably comprises a support arm 7072 or clamp arm, an arm extension assembly 7074, and an arm locking screw 7076. In the illustrated embodiment, the indexing collar 7070 is configured to be coupled with an access device having a proximal portion with a generally oval shaped cross-sectional area. In other embodiments, the indexing collar 7070 can be configured to be coupled with an access device having any other oblong shaped cross-sectional area. In one embodiment, the indexing collar 7070 is configured to be coupled with an access device having a proximal portion that has a generally oval shaped opening that is about 24 mm wide and about 30 mm long. In another embodiment, the indexing collar 7070 is configured to be coupled with an access device having a proximal portion with a generally oval shaped opening that is about 24 mm wide and about 35 mm long.

Figure 119:
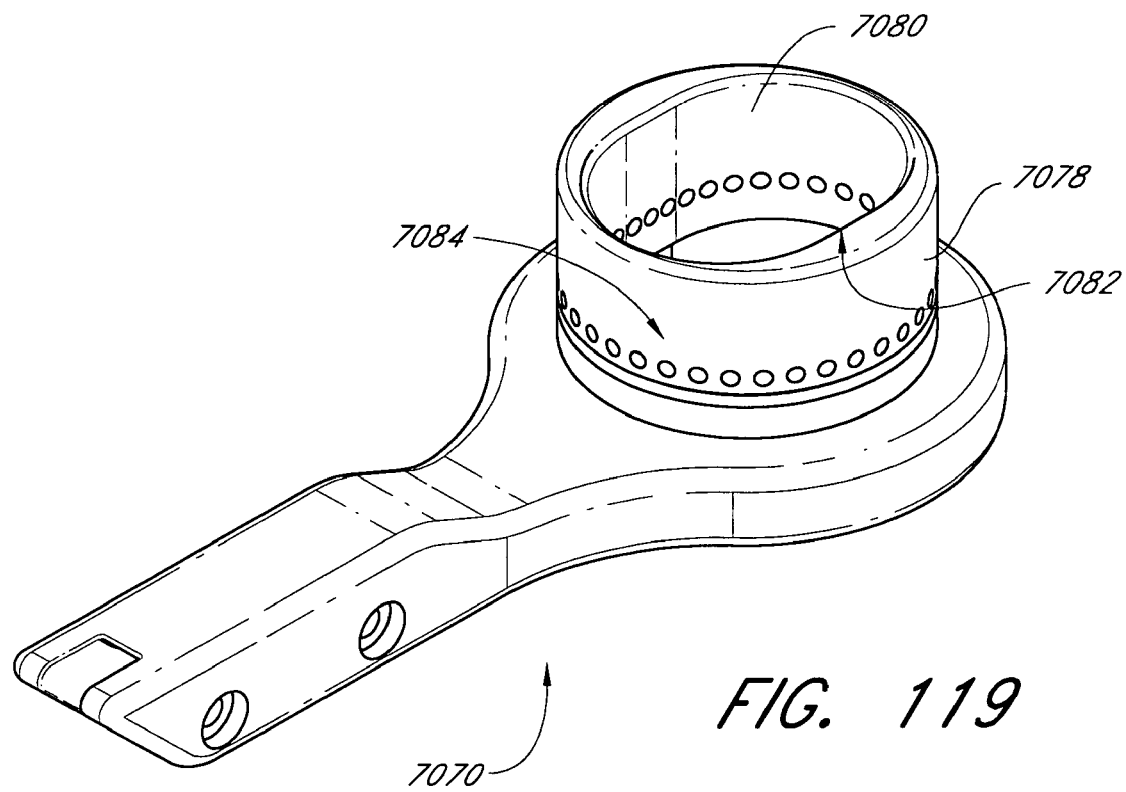

FIGS. 108-119 show an indexing collar that is similar to the other indexing collars described herein, except as set forth below. With reference to FIGS. 108-119, in one embodiment, the support arm 7072 is coupled with an indexing collar 7070, which can be configured to be received in a central opening of a base of an endoscope mount platform or other viewing element mount platform, such as shown in FIGS. 20-23. The indexing collar 7070 has an outer peripheral wall surface 7078, an inner wall surface 7080, and a wall thickness 7082 that is the distance between the wall surfaces. With reference to FIG. 119, the outer peripheral wall surface 7078 has a generally constant diameter. The inner wall surface 7080 preferably has a variable diameter resulting in a generally oval shaped cross-sectional area defined by the inner wall surface 7080. In other embodiments, the inner wall surface 7080 can define any other oblong shaped cross-sectional area. Accordingly, the wall thickness 7082 varies between the outer peripheral wall surface 7078 and the inner wall surface 7080.

In one embodiment, access devices of different shapes and dimensions can be supported by providing indexing collars to accommodate each access device size while using a single endoscope mount platform. The central opening of the endoscope mount platform can have a constant dimension, e.g., a diameter of about 1.28 inches (32.5 mm). An appropriate indexing collar is selected, e.g., one that is appropriately sized to support a selected access device. Thus, the outer wall and the outer diameter preferably are unchanged between different indexing collars, although the inner wall and the inner diameters of the oval shape can vary to accommodate differently sized access devices.

The indexing collar 7070 can be positioned at or rested on a proximal portion of an access device to allow angular movement of the endoscope mount platform, or other viewing element mount platform, with respect thereto about the longitudinal axis. In one embodiment, the outer wall of the indexing collar 7070 includes a plurality of hemispherical recesses, or through holes 7084, that can receive one or more ball plungers on the endoscope mount platform. This arrangement permits the endoscope mount platform, along with an endoscope, or other viewing element, to be fixed in a plurality of discrete angular positions relative the indexing collar 7070.

Figure 120:
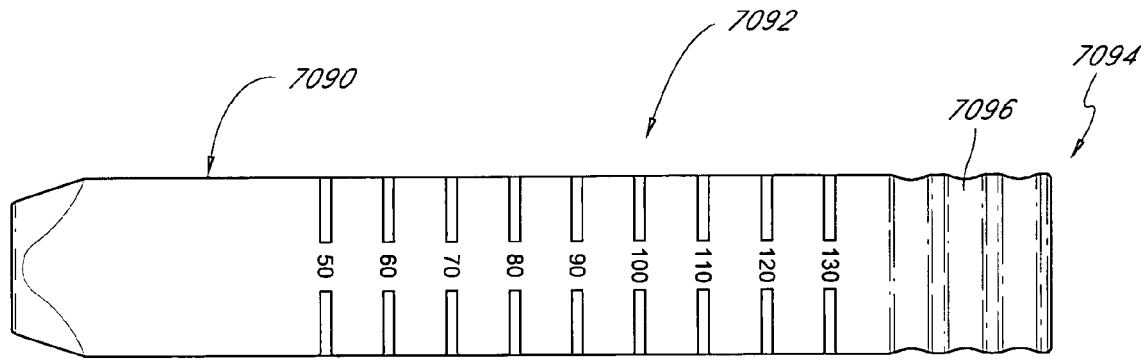
Figure 121:
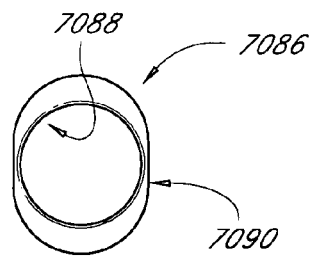
Figure 122:
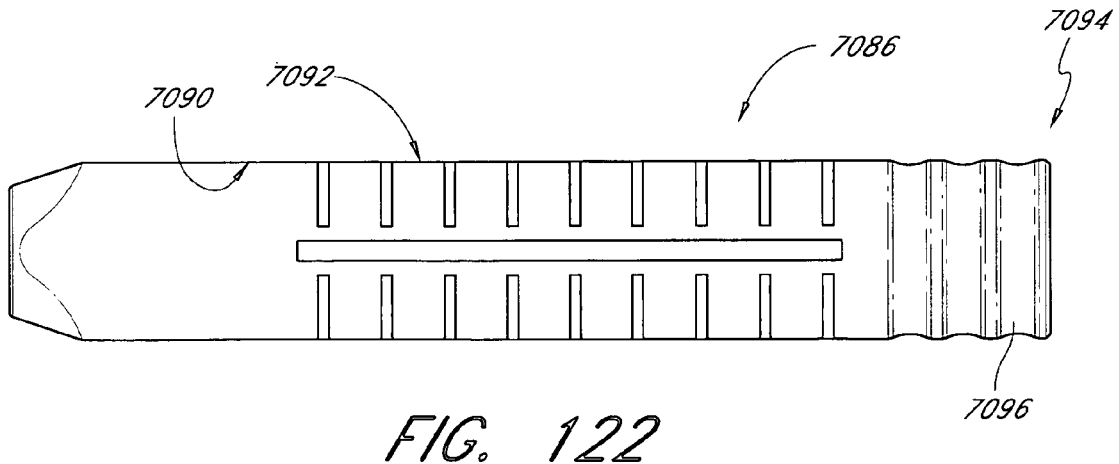

FIGS. 120-122 show a dilation element that is similar to the other dilation elements described herein, except as set forth below. FIGS. 120-122 illustrate one embodiment of a dilating structure or tool for use with an access device. As shown in the illustrated embodiment, a cannulated oval dilator 7086 can have an inner surface 7088 that has a generally circular cross section and an outer surface 7090 that has a generally oval shaped cross section. In other embodiments, the outer surface 7090 can have any other oblong shaped cross section. The outer surface 7090 preferably provides indications 7092 regarding instrument depth. In one embodiment, a proximal portion 7094 of the dilator 7086 comprises a gripping portion 7096 to facilitate handling and to aid in the insertion of the dilator 7086 into a patient. The gripping portion 7096 of the dilator 7086, in some embodiments, can have, for example, raised portions or a knurled surface. The dilator 7086 preferably has a tapered distal portion.

Figure 124:
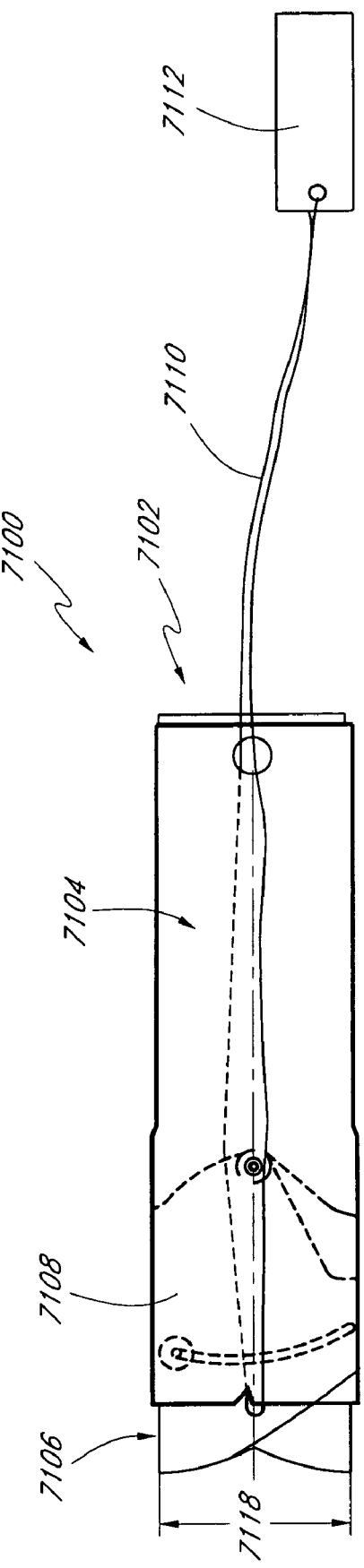

FIGS. 123-150 illustrate some embodiments of access devices, access assemblies, and portions of access devices. FIGS. 123-150 show access devices that are similar to the other access devices described herein, except as set forth below. With reference to FIGS. 123-124, one embodiment of an access device 7100 can be positioned in a low-profile configuration for insertion into a patient. As shown in FIGS. 123-124, the access device 7100 has a passage 7102 with a generally oval shaped cross section. In one embodiment, the cross section of a proximal portion 7104 of the passage 7102 preferably has a width of about 24 mm and a length of about 30 mm. The cross section of the passage 7102 at the distal portion 7106 of the access device 7100, in the low profile configuration, preferably has a width of about 24 mm and a length of about 30 mm. The access device 7100 can be held in a low profile position using a sleeve 7108 or a length of shrink tubing. A pull string 7110 and tab 7112 can be used to at least partially release the shrink tubing from the access device 7100.

FIGS. 125-126 show the access device 7100 in an expanded configuration. In the illustrated embodiment, the access device 7100 has a distal portion 7106 that expands to a cross section at or near the distal end having a width of about 24 mm and a length of about 50 mm. In other embodiments, the sizes and lengths associated with the access device 7100 can vary, as will be described further below. The length 7128 of the access device 7100 from the proximal end of the proximal portion 7104 to the distal end of the distal portion 7106 preferably is between about 2 inches (50.8 mm) and about 5 inches (127 mm). In some embodiments, the length 7128 of the access device 7100, e.g., about 60 mm, about 70 mm, about 80 mm, about 90 mm, about 100 mm, about 110, or more than any of the foregoing dimensions, preferably is selected based on the anatomy of the patient and/or the type of procedure to be performed.

With reference to FIGS. 125-129, the proximal portion 7106 of the access device 7100 includes a tube 7114. The distal portion 7106 of the access device 7100 has an expandable skirt portion 7116. The skirt portion 7116 preferably has a reduced profile configuration with an initial dimension 7118 and corresponding cross-sectional area. The skirt portion 7116 preferably is expandable to an enlarged configuration with a relatively larger dimension 7120 and corresponding cross-sectional area. In one embodiment, the skirt portion 7116 is coupled with the proximal portion 7104. A rivet 7122, pin, or similar connecting device can be used to couple the proximal and distal portions 7102, 7104. The rivet 7122 preferably permits movement of the skirt portion 7116 relative to the proximal portion 7104. The skirt portion 7116 is shown coupled with the proximal portion in FIG. 129.

In the illustrated embodiment, the skirt portion 7116 is manufactured from a resilient material, such as stainless steel. The skirt portion 7116 preferably is manufactured so that it normally assumes an expanded configuration. The skirt portion 7116 preferably is sufficiently rigid that it is capable of displacing the tissue surrounding the skirt portion 7116 as it expands. Depending upon the resistance exerted by surrounding tissue, the skirt portion 7116 preferably is sufficiently rigid to provide some resistance against the tissue to remain in the expanded configuration. In some embodiments, one feature of the skirt portion 7116 is the provision of a shallow concave profile 7124 defined along a distal edge of the skirt portion 7116, which allows for improved placement of the skirt portion 7116 with respect to body structures and surgical instruments. In some embodiments, one or more portions of the skirt portion 7116, e.g., along the distal edge, are formed to accommodate long implants or tools. For example, cut outs can be provided on opposite sides of the distal edge of the skirt portion 7116 to enable a fixation element to be at least partially extended out of the working space.

FIGS. 130-132 further illustrate the proximal portion 7104 of the access device 7100, according to one embodiment. The length 7126 of the proximal portion 7104 of the access device 7100 preferably is between about 1 inch (25.4 mm) and about 4 inches (101.6 mm) in one embodiment. The length 7104 of the proximal portion of the access device, e.g., about 27 mm, about 37 mm, about 47 mm, about 57 mm, about 67 mm, or about 77 mm, preferably is selected based on the anatomy of the patient and/or the type of procedure to be performed.

FIGS. 133-134 show distal skirt portions 7116 of the access device 7100 according to one embodiment. The size and shape of the skirt portion 7116 advantageously provides access to a surgical location when coupled with the proximal portion of the access device and placed in an expanded configuration. In other embodiments, skirt portions 7116 have different sizes and shapes. In some embodiments, the shape of the distal portion 7106 of the access device 7100 can provide an oval shaped access area when expanded. In other embodiments, the shape of the distal portion 7106 of the access device 7100 can provide any other oblong shaped access area when expanded. In some embodiments a locking mechanism 7130 is provided on the distal portion 7106 of the access device 7100 as will be described further below.

FIGS. 133-134 show right and left skirt portions 7148, 7150 in initial flattened configurations. FIG. 133 illustrates a right skirt portion 7148 for an access device 7100 with an oval shaped cross section having an expanded length 7120 of about 50 mm along the long axis. FIG. 134 illustrates a cooperating left skirt portion 7150 for the access device 7100. The skirt portions 7116 can be manufactured from sheets of stainless steel having a thickness of about 0.007 inches (0.178 mm). Other materials, such as nitinol or plastics having similar properties, may also be used. The skirt portions 7148, 7150 preferably each have a protruding portion 7132 along one of the sides for providing a locking feature, as will be described further below.

As discussed above, the skirt portions 7148, 7150 are coupled with the proximal portion 7104 with pivotal connections, such as rivets 7122. A first rivet hole 7134 and second rivet hole 7136 can be provided in each of the right and left skirt portions 7148, 7150 to receive the rivets 7122. In the illustrated embodiment, the right and left skirt portions 7148, 7150 each have first and second free ends 4138, 4140 that are secured by slidable connections, such as additional rivets 7142. In the illustrated embodiment, a first slot 7144 and a second slot 7146 are defined in the right skirt portion 7148 near the free ends 7138, 7140 respectively. In the illustrated embodiment, a first slot 7152 and a second slot 7154 are defined in the left skirt portion 7150 near the free ends 7138, 7140 respectively. With reference to FIGS. 133-134, in one embodiment, the first slots 7144, 7152 preferably are longer than the second slots 7146, 7154. The right and left skirt portions 7148, 7150 preferably are configured so that a rivet 7142 that is positioned within the longer slot 7144 in the right skirt portion 7148 is positioned in the shorter slot 7154 in the left skirt portion 7150. Similarly, a rivet 7142 that is positioned within the longer slot 7152 in the left skirt portion 7150 is positioned in the shorter slot 7146 in the right skirt portion 7148. The rivets 7142 are permitted to move freely within the slots 7144, 7154, 7152, 7146. This slot and rivet configuration allows the skirt portions 7148, 7150 to move between the reduced profile configuration of FIGS. 123-124 and the expanded configuration of FIGS. 125-129. The skirt portion 7116 preferably can expand to span up to three or more vertebrae, e.g., L4, L5, and S1. This arrangement enables multi-level procedures, such as multilevel fixation procedures alone or in combination with a variety of other procedures. One of the rivets 7142 coupling the left and right skirt portions 7148, 7150 together, along with a pair of washers 7156, is shown in FIG. 128.

In the illustrated embodiment, the access device 7100 has a locking mechanism 7130. The distal portion 7106 is provided with a lock that enables a user to selectively lock the distal portion 7106 into a state of expansion. In some embodiments, the user can lock the distal portion in a contracted configuration. In the illustrated embodiment, a first locking mechanism 7130 is provided on a first side of the access device 7100. A second locking mechanism preferably is provided on a second side of the access device 7100. The locking mechanism 7130 can take many forms. In one embodiment, the locking mechanism 7130 includes a first locking slot 7160, a second locking slot 7162, and a clip or locking element 7164 that can be moved (e.g., rotated, actuated, manipulated) to lock the access device 7100 in a desired configuration. In the illustrated embodiment, first and second locking slots 7160, 7168 are defined in the right skirt portion 7148 near the free ends 7138, 7140. In the illustrated embodiment, first and second locking slots 7166, 7162 are defined in the left skirt portion 7150 near the free ends 7138, 7140. With reference to FIGS. 133-134, the first locking slots 7160, 7166 preferably are longer than the second locking slots 7162, 7168. The longer slots 7160, 7166 preferably are curved or angled near an end of the slots. The shorter slots 7162, 7168 preferably are also curved. In one embodiment, each of the shorter slots 7162, 7168 generally forms an arc. The right skirt portion 7148 has an opening 7170 positioned near the shorter slot 7168. The left skirt portion 7150 has an opening 7172 positioned near the shorter slot 7162. The shorter curved slots 7162, 7168 preferably are formed on or near protruding portions 7132 of the skirts.

FIGS. 135-137 illustrate a locking clip or locking element 7164, according to one embodiment. With reference to FIGS. 135-137, a locking element 7164, e.g., a lock, a stop, a tab, a flange, a clip, or a hook, preferably is coupled with one or more of the left and right skirt portions 7148, 7150. In the illustrated embodiment, the locking element 7164 has a generally L-shaped configuration. The locking element 7164 preferably is movable, e.g., rotatable, articulable, manipulatable, or positionable, relative to one or more of the skirt portions 7148, 7150. As shown in FIGS. 135-137, the locking element has a base portion 7174, a tab portion 7176, and a disk portion 7178. The base portion 7174 preferably has a length of about 0.21 inches (5.33 mm) and a thickness of about 0.0155 inches (0.394 mm) in one embodiment. An opening 7180 is defined in the base portion 7174. The opening 7180 preferably is sized to receive a coupling member, such as, for example, a rivet 7182. In the illustrated embodiment, the opening 7180 preferably has a diameter of about 0.046 inches (1.17 mm). In some embodiments the opening 7180 can be located generally centrally on the base portion 7174. The disk portion 7178 preferably extends from a first surface 7184 of the base portion 7174. In the illustrated embodiment, the disk portion 7178 extends from the first surface 7184 a distance of about 0.0155 inches (0.394 mm) and has a diameter of about 0.04 inches (1.02 mm). The disk portion 7178 preferably is positioned near a first end of the base portion 7174. In some embodiments, the disk portion 7178 can be welded to the base portion 7174. In the illustrated embodiment, the tab portion 7176 is positioned generally normal to the base portion 7174 near a second end of the base portion 7174. The tab portion 7176 preferably extends about 0.055 inches (1.40 mm) from a second surface 7186 of the base portion 7174 and has a thickness of about 0.0155 inches (0.394 mm). In one embodiment, the locking element 7164 is made of stainless steel. In some embodiments, the locking element 7164 can be fabricated by machining or formed and welded.

With reference to FIGS. 125-127 and 133-134, in one embodiment, the locking mechanism 7130 comprises the right and left skirt portions 7148, 7150, the locking element 7164, one or more compression washers 7188 (See FIGS. 127 and 138) and a rivet 7182. The locking element 7164 preferably is coupled with the right skirt portion 7148 at the opening 7170 on or near the protruding portion 7132 of the skirt using the one or more compression washers 7188 and the rivet 7182. The locking element 7164 preferably is positioned between the right and left skirt members 7148, 7150 and oriented such that the first surface 7184 of the base portion 7174 of the locking element 7164 faces toward the right skirt portion 7148. The disk portion 7178 preferably is positioned to face toward the smaller arcuate slot 7168 on the protruding portion 7132 of the right skirt portion 7148. The locking element 7164 is sized and configured so that when the locking rivet 7182 is positioned in the opening 7180 of the locking element 7164 and also in the opening 7170 on the right skirt portion 7148, the disk portion 7178 of the locking element 7164 can be positioned so that it extends into the smaller arcuate slot 7168 on the right skirt portion 7148. In the illustrated embodiment, the disk portion 7178 is oriented such that the disk portion 7178 faces toward the outside of the access device 7100. The access device 7100 preferably is also configured so that when the sliding rivets 7142 coupling the right and left skirt portions 7148, 7150 are positioned within the appropriate slots, e.g., the rivet 7142 within slots 7144 and 7154, the tab end 7176 of the locking mechanism 7130 can extend toward, and be positioned within, the longer curved or angled slot 7166 on the left skirt portion 7150. In the illustrated embodiment, the tab portion 7176 extends toward the inside of the access device 7100. The locking element 7164 preferably is rotatably coupled with the right skirt portion 7148 at the opening 7170 with the one or more compression members 7188 and the rivet 7182, as shown in FIG. 127.

When the access device 7100 is in the closed position, or the low profile position, the locking element 7164 preferably is rotated so that the tab portion 7176 is positioned within the longer portion of the longer curved or angled slot 7166. In this configuration, the right and left skirt portions 7148, 7150 are free to slide past one another into the expanded configuration. When the access device 7100 is in the expanded configuration, the tab portion 7176 of the locking element 7164 can be rotated into the shorter curved or angled portion of the longer slot 7166. The locking element 7164 can be actuated, manipulated, or rotated using an instrument or in any other suitable manner to position the tab portion 7176 in the angled portion of the slot 7166. When the tab portion 7176 is engaged in the locked position, the sides of the curved or angled portion of the longer slot 7166 act to restrain the relative movement of the overlapping skirt portions 7148, 7150 to selectively limit expansion or un-expansion of the distal portion 7106 of the access device 7100. In some other embodiments, the relative sizes and configurations of the locking structures and mechanisms can vary.

In one application, the access device 7100 is used to provide minimally invasive access to the spine for a spinal procedure as described herein. The expansion and location of the access device 7100 may be confirmed by fluoroscopy. After the access device 7100 has been fully expanded, the lock can be articulated to lock or unlock the access device 7100.

FIGS. 139-150, illustrate another embodiment of an access device 7200. The structure and configuration of the access device shown in FIGS. 139-150 is similar to that described in connection with FIGS. 123-138, except as shown or noted below. Like reference numerals have been used to identify like features in the two embodiments, except that the reference numerals used with respect to FIGS. 139-150 will be in the "7200s" rather than the "7100s."

As shown in FIGS. 139-150, the access device 7200 has a passage 7202 with a generally oval shaped cross section. FIGS. 141-142 show the access device 7200 in an expanded configuration. In the illustrated embodiment, the access device 7200 has a distal portion 7206 that expands to a cross section having a width of about 24 mm and a length 7220 of about 80 mm. The sizes and lengths associated with the access device 7200 can vary. In some embodiments, a generally longer cross-sectional length provides increased access for performing some surgical procedures. FIGS. 149-150 show distal skirt portions 7216 of the access device 7200 according to one embodiment. The size and shape of the skirt portion 7216 advantageously provides increased access to a surgical location in an expanded configuration. In other embodiments, skirt portions 7216 have different sizes and shapes. In some embodiments, the shape of the distal portion 7206 of the access device 7200 can provide an oblong shaped access area when expanded. FIGS. 149-150, show right and left skirt portions 7248, 7250 in initial flattened configurations. In the illustrated embodiment, the skirt portions 7248, 7250 are configured to form an access device 7200 having an oval shaped cross section with an expanded length 7220 of about 80 mm along the long axis. In the illustrated embodiment, a locking mechanism 7230 generally similar to that described with respect to the embodiment shown in FIGS. 123-138 is provided.

FIGS. 151-181 illustrate surgical systems that may include a device for providing minimally invasive access at a surgical site and a variety of tools that can be used to perform various procedures at the surgical site. FIGS. 151-181 show surgical systems and components that are similar to the other surgical systems and components described herein, except as set forth below. Also disclosed are a number of components, e.g., implants, that may be applied to the spine at various spinal locations in connection with such procedures. A variety of advantageous combinations may be provided whereby features of these embodiments are combined with features of other embodiments described herein.

One embodiment of a surgical system described herein is particularly well suited for performing various methods for fixing the vertebrae of a patient at a surgical site. As discussed more fully herein, a surgical system can include an access device, such as an expandable cannula or conduit, an adjustable support for the access device, a variety of surgical instruments, a viewing device, a lighting element, a spinal implant or fusion device, and a vertebral fixation assembly. Many of these components, e.g., the instruments, viewing device, spinal implants, and fixation assembly components, preferably are configured to be inserted through the access device to the surgical site.

FIGS. 151-155 illustrate one suitable expandable cannula or conduit 8010 constructed for use in a method according to one embodiment. The cannula 8010 is a tubular structure 8012 centered on an axis 8014. The tubular structure 8012 defines a passage 8016 through the cannula 8010. Surgical instruments are inserted into the body during surgery through the passage 8016.

The tubular structure 8012 comprises a first tubular portion 8020 and a second tubular portion 8040 attached to the first tubular portion. The first tubular portion 8020 is preferably made of a length of stainless steel tubing, but could alternatively be made of another suitable material. The first tubular portion 8020 has a proximal end 8022 and a distal end 8024. Parallel cylindrical inner and outer surfaces 8026 and 8028, respectively, extend between the ends 8022, 8024 of the first tubular portion 8020. The inner surface 8026 defines a first passage portion 8030 of the passage 8016 through the cannula 8010. The first passage portion 8030 has a diameter D1 that is preferably in the range from 10 mm to 30 mm.

The second tubular portion 8040 of the tubular structure 8012 is attached to the distal end 8024 of the first tubular portion 8020. The second tubular portion 8040 is preferably made from stainless steel, but could alternatively be made from another suitable material.

As best seen in the rollout view of FIG. 154, the second tubular portion 8040 comprises an arcuate segment 8042 of sheet stock. The arcuate segment 8042 includes first and second arcuate edges 8044 and 8046, respectively, and first and second planar edges 8048 and 50, respectively. The first and second planar edges 8048 and 8050 are rolled in an overlapping manner to form the tubular configuration of the second tubular portion 8040.

When the second tubular portion 8040 has been rolled into its tubular configuration, the first and second arcuate edges 8044 and 8046 define oppositely disposed first and second ends 8060 and 8062 (FIGS. 151-152), respectively, of the second tubular portion. The first and second ends 8060 and 8062 are connected by a central portion 8064. The first end 8060 of the second tubular portion 8040 is attached to the distal end 8024 of the first tubular portion 8020 by a single fastener, such as a rivet 8066. The rivet 8066 extends through two aligned apertures 8068 (FIG. 154) at the first end 8060 of the second tubular portion 8040. The first end 8060 of the second tubular portion 8040 is pivotable about the rivet 8066.

The second tubular portion 8040 includes parallel inner and outer surfaces 8070 and 8072 (FIGS. 151-152), respectively, extending between the first and second ends 8060 and 8062. The inner surface 8070 defines a second passage portion 8074 of the passage 8016 through the cannula 8010 that extends as a continuation of the first passage portion 8030 in the first tubular portion 8020.

An arcuate slot 8080 is formed in the second tubular portion 8040 and extends between the inner and outer surfaces 8070 and 8072 of the second tubular portion. The arcuate slot 8080 extends along a curvilinear path in the central portion 8064 of the second tubular portion 8040 toward the second end 8060 of the second tubular portion. The arcuate slot 8080 has a first terminal end 8082 located in the central portion 8064 of the second tubular portion 8040. A second terminal end 8084 of the arcuate slot 8080 is located adjacent the intersection of the second arcuate edge 8046 and the first planar edge 8048 of the arcuate segment 8042.

A guide pin 8090 is attached to the inner surface 8070 of the second tubular portion 8040 adjacent the intersection of the second arcuate edge 8046 and the second planar edge 8050. In the tubular configuration of the second tubular portion 8040, the guide pin 8090 is located in the arcuate slot 8080 and is movable along the curvilinear path of the arcuate slot. A washer 8092 is secured to an inner end of the guide pin 8090 to retain the guide pin in the arcuate slot 8080.

The second tubular portion 8040 of the tubular structure 8012 is expandable from a contracted condition shown in FIG. 152 to an expanded condition shown in FIG. 151. In the contracted condition, the guide pin 8090 is located in the first terminal end 8082 of the arcuate slot 8080 in the second tubular portion 8040 and the second passage portion 8074 defined by the second tubular portion is cylindrical in shape. The second passage 8074 has a generally constant diameter D2 (FIGS. 152-153) that is approximately equal to the diameter D1 of the first tubular portion 8020. Thus, the cross-sectional area of the second passage portion 8074 at the second end 8062 of the second tubular portion 8040, which is function of the diameter D2, is approximately the same as the cross-sectional area at the first end 8060 of the second tubular portion and is approximately the same as the cross-sectional area of the first passage portion 8030 in the first tubular portion 8020.

In the expanded condition, the guide pin 8090 is located in the second terminal end 8084 of the arcuate slot 8080 in the second tubular portion 8040 and the second tubular portion has a conical configuration. At the second end 8062 of the second tubular portion 8040, the second passage portion 8074 has a diameter D3 (FIG. 153) that is larger than the diameter D2 of the second passage portion at the first end 8060. Preferably, the diameter D3 of the second passage portion 8074 at the second end 8062 of the second tubular portion is 40% to 80% greater than the diameter D1 of the second passage portion at the first end 8060. Thus, in the expanded condition, the cross-sectional area of the second passage portion 8074 at the second end 8062 of the second tubular portion 8040, which is function of the diameter D3, is 16% to 64% greater than the cross-sectional area of the second passage portion at the first end 8060 of the second tubular portion. In the expanded condition, the cross-sectional area of the second passage portion 8074 at the second end 8062 of the second tubular portion 8040 is large enough to overlie a major portion of at least two adjacent vertebrae.

The cannula 8010 includes an outer layer 8100 (FIG. 151) for maintaining the second tubular portion 8040 of the cannula in the contracted condition. It is contemplated that other suitable means for maintaining the second tubular portion 8040 in the contracted condition could be employed. In accordance with a preferred embodiment of the present invention, the outer layer 8100 comprises a section of plastic tubing 8102 which is heat shrunk over both the first and second tubular portions 8020 and 8040 to hold the second tubular portion in the contracted condition.

In addition, a loop of polyester string 8104 for tearing the heat shrunk tubing 8102 is wrapped around the heat shrunk tubing so that it extends both underneath and on top of the tubing. An outer end 8106 of the string 8104 extends beyond the tubing 8102.

FIG. 151 shows an actuatable device 8111 for expanding the second tubular portion 8040 from the contracted condition to the expanded condition. In accordance with a preferred embodiment, the actuatable device 8111 comprises a manually operated expansion tool 8112. The expansion tool 8112 resembles a common pair of scissors and has a pair of legs 8114 pivotally connected to one another. The expansion tool 8112 includes a frustoconical end section 8116 formed by a pair of frustoconical halves 8118. Each of the frustoconical halves 8118 extends from a respective one of the legs 8114 of the expansion tool 8112. It is contemplated that other suitable means for expanding the second tubular portion 8040 toward the expanded condition could be employed, such as an inflatable balloon (not shown).

During an endoscopic surgical procedure, the cannula 8010 is inserted into the body of a patient in the contracted condition. The outer end 8106 of the string 8104 is then manually pulled on by the surgeon. Pulling on the string 8104 tears the heat shrunk tubing 8102 most of the way along the heat shrunk tubing, which frees the second tubular portion 8040 for expansion. The heat shrunk tubing 8102, in its torn condition, remains attached or secured to the first tubular portion 8020.

Next, the expansion tool 8112 is inserted into the passage 8016 in the cannula 8010 until the frustoconical end section 8114 is located at the second end 8062 of the second tubular portion 8040. The legs 8114 of the expansion tool 8112 are manually separated, causing the frustoconical halves 8118 to separate also. As the halves 8118 separate, a radially outward directed force is exerted on the inner surface 8070 of the second tubular portion 8040 by the halves 8118, causing the second tubular portion to expand toward the expanded condition. Under the force of the expanding expansion tool 8112, the guide pin 8090 slides from the first terminal end 8082 of the arcuate slot 8080 to the second terminal end 8084 of the arcuate slot to permit the expansion of the second tubular portion 8040. The expansion tool 8112 can be rotated about the axis 8014 to ensure that the second tubular portion 8040 of the cannula 8010 is completely expanded to the expanded condition. The expansion tool 8112 is then collapsed and removed so that one or more surgical instruments (indicated schematically at 8021 in FIG. 155) and a viewing element can be received through the cannula 8010 and inserted into a patient's body 8130. The expandable second tubular portion 8040 of the cannula 8010 provides a significantly larger working area for the surgeon inside the body 8130 within the confines of the cannula.

The expanded tubular portion 8040 can dilate and locally retract and separate spinalis muscle and soft tissues from the vertebrae thereby creating an endoscopic operating field at the surgical site. This endoscopic operating field within the spinal muscles differs from arthroscopic, laparoscopic, or cystoscopic working spaces in that there is no physiologic space or defined tissue plane that can be insufflated with air or distended with fluid.

FIGS. 156-173 illustrate one suitable support apparatus for use in a method according to one embodiment. The support apparatus 8110 includes a first support 8120, a second support 8140, a first adjustment mechanism 8160, a second adjustment mechanism 8180, and a third adjustment mechanism 8900.

As viewed in FIGS. 159 and 165, the first support 8120 is associated with the cannula 8010 and has a circular perimeter 8121. The perimeter 8121 has a center 8122 located on the axis 8014. The first support 8120 comprises a circular platform, or disk 8124, which has a circular opening 8126 in the central area of the disk 8124 for receiving the proximal end 8022 of the cannula 8010. The circular opening 8126 has a center located on the axis 8014. The proximal end 8022 of the cannula 8010 can be easily inserted into and removed from the opening 8126. The disk 8124 has a projection portion 8120a, which is located adjacent the perimeter 8121 of the disk 8124. The disk 8124 has an upper circular surface area 8124a, which surrounds the opening 8126.

As viewed in FIG. 165, the second support 8140 supports a viewing device 8200 including a camera head 8201 and an endoscope 8202 with a rod and lens assembly 8203, herein referred to as a viewing element, extending down through the passage 8016 of the cannula 8010. With reference to FIGS. 165-166, the second support 8140 includes a body 8142 having an opening 8144 through which the viewing device 8200 extends and a clamp 8146 for clamping the viewing device 8200 to the body 8142 in the opening 8144. The clamp 8146 includes a threaded set screw 8148 for securing the viewing device 8200 to the body 8142. The set screw 8148 has a manually rotatable knob 8148a and a stem threaded into the body 8142. When rotated, the screw 8148 moves axially relative to the body 8142 to clamp or release the viewing device 8200 depending on the direction of rotation of the screw 8148.

The body 8142 of the second support 8140 further includes two extension arms 8151, 8152 (FIG. 158) for supporting the endoscope 8202. Each extension arm 8151, 8152 includes a threaded bore for receiving a resilient detent member, or ball plunger 8400.

As viewed in FIGS. 167-168, a ball plunger 8400 is illustrated at another location in the support apparatus 8110. Each ball plunger 8400, including those in the extension arms 8151, 8152, has an externally threaded tubular body 8402 with a cylindrical cavity 8404 located therein. The cavity 8404 houses a projection 8406 and a coiled spring 8408. The projections 8406 of the two ball plungers 8400 of the extension arms 8151, 8152 are spherical detent members 8420 in the form of balls (not shown). The spring 8408 urges each projection 8406 against a lip portion 8409 of the body 8402. The lip portion 8409 is located at one end of the cavity 8404. As shown in FIG. 168, the other ball plungers 8400 of the apparatus 8010 have projections 8406 with hemispherical extensions 8420 and shoulder portions 8422.

As viewed in FIG. 165, the endoscope 8202 has corresponding hemispherical recesses (not shown) for receiving the spherical detent members (balls) of the ball plungers 8400 which are located in extension arms 8151, 8152. The springs 8408 will compress in each ball plunger 8400 in each extension arm 8151, 8152 and the spherical detent members will move inward of each cavity 8404 and then spring back into the hemispherical recesses in the endoscope 8202, as the endoscope 8202 is inserted between the extension arms 8151, 8152. The entire viewing device 200 will thus be secured between the extension arms 8151, 8152, but may be removed by overcoming the force of the spherical detent members of each ball plunger 8400 in the extension arms 8151, 8152.

The ball plunger 8400 further includes a head portion 8430 with a slot 8432 for engaging a tool, such as a screwdriver. The ball plunger 8400 may be threadedly adjusted within the threaded bore of either extension arm 8151, 8152 to alter the distance that the spherical detent member 8420 projects away from the extension arms 8151, 8152 (toward each other). This distance, along with the stiffness of each spring 8408, will determine the holding force by which the endoscope 8202 is secured between the extension arms 8151, 8152.

The first adjustment mechanism 8160 provides for relative axial adjustment of the cannula 8010 and the first support 8120 along the axis 8014. The first adjustment mechanism 8160 includes a first toothed rack member 8162, a cannula gripper mechanism 8164 fixedly connected to the first rack member 8162, a first manually adjustable, rotatable knob 8166 rotatably carried by the projection portion 8120a of the first support 8120, and a first gear member 8165 (FIG. 162) rotatable by the first knob 8166 and in meshing engagement with the teeth 8163 of the first rack member 8162. The first support 8120 and, in particular, the projection portion 8120a, rotatably carries the first gear member 8165 (FIG. 162).

The first rack member 8162 is secured to slide axially within the first support 8120 and the projection portion 8120a by two ball plungers 8400 (FIG. 162). One ball plunger 8400 is tangentially threaded into a tapered, threaded bore (FIG. 157) in the perimeter 8121 of the first support 8120 and the other is tangentially threaded into a threaded bore in the projection portion 8120a. The hemispherical extensions 8420 thus frictionally engage a smooth portion (without teeth 8163) of the first rack member 8162 and bias the first rack member 8162 against the first support 8120 and the projection portion 8120a. This biasing also maintains the engagement of the first rack member 8162 and the first gear member 8165 (FIG. 162).

As viewed in FIGS. 160 and 169, the cannula gripper mechanism 8164 includes two gripper arms 8172, 8174 for clamping against the outer surface of the cannula 8010, and a gripper actuating lever 8176 for moving the arms 8172, 8174 into engagement with the outer surface of the cannula 8010 and for releasing the arms 8172, 8174 from engagement with the cannula 8010.

As viewed in FIG. 169, the cannula gripper mechanism 8164 further includes a support pin 8177, a coiled spring 8188, a washer 8189 with a bore (not shown), and a lock pin 8190. The support pin 8177 has a head 8179, a shaft 8180, and an elongate, or flat, end 8181 that can mate with the bore in the washer 8189. Other suitable structures could be used.

During assembly, the coiled spring 8188 is interposed between the arms 8172, 8174. The flat end 8181 of the support pin 8177 is inserted through a circular bore in the first clamp arm 8172, through the coil of the spring 8188, through a circular bore in the second arm 8174, and through the bore in the washer 8189. The flat end 8181 of the support pin 8177 is then inserted into a slot 8176a in the lever 8176. The lock pin 8190 is inserted through a bore in the lever 8176 and through a bore in the flat end 8181 of the support pin 8177 thereby securing the mechanism 8164 together and allowing the lever 8176 to rotate about the lock pin 8190. A camming surface 8178 on the lever 8176 adjacent the washer 8189 forces the arms 8172, 8174 together to grip the cannula 8010 as the lever 8176 is rotated clockwise (as viewed in FIG. 160). Counter-clockwise rotation of the lever 8176 allows the spring 8188 to force the arms 8172, 8174 apart and releases the cannula 8010 from the gripper mechanism 8164.

When the gripper mechanism 8164 is either gripping the cannula 8010 or released from the cannula 8010 and the knob 8166 is rotated, the disk 8124 and parts attached to the disk 8124 will move along the axis 8014 of the cannula 8010 relative to the cannula 8010. After the support apparatus 8110 is initially lined up with the cannula 8010, the viewing device 8200 may be positioned on the support apparatus 8110 and adjusted along the axis 8014 by rotation of knob 8166.

The second adjustment mechanism 8180 provides axial adjustment of the first and second supports 8120, 8140 relative to each other along the axis 8014. The second adjustment mechanism 8180 includes a second toothed rack member 8182 connected to the first support 8120, a second manually adjustable, rotatable knob 8186 rotatably carried by the body 8142 of the second support 8140, and a second toothed gear member 8185 (FIG. 163) rotatable by the second knob 8186 and in meshing engagement with the teeth 8183 of the second rack member 8182. The second support 8140, and in particular, the body 8142, rotatably carries the second gear member 8185 (FIG. 163).

The body 8142 of the second support 8140 may have a notch 8149 which can fit around part 8902a of the third adjustment mechanism 8900 and allow the lower surface of the body 8142 to completely abut the disk 8124 as the body 8142 is brought into an axial position adjacent the disk 8124.

The second rack member 8182 is secured to slide axially within the second support 8140 by a ball plunger 8400 (FIG. 163). The ball plunger 8400 is tangentially threaded into a threaded bore in the side of the notch 8149 of the second support 8140. The hemispherical extension 8420 thus frictionally engages a smooth portion (without teeth 8183) of the second rack member 8182 and biases the second rack member 8182 against the second support 8140. The biasing also maintains the engagement of the second rack member 8182 and the second gear member 8185. Both sides of the notch 8149 have tapered portions 8149a, 8149b for facilitating insertion of the ball plunger 8400 into the threaded bore of the notch 8149 of the second support 8140. Rotation of the knob 8186 causes the body 8142 and the viewing device 8200 attached thereto to move relative to the cannula 8010 and disk 8124 along the axis 8014.

The third adjustment mechanism 8900 provides arcuate, circumferential adjustment of the second support 8140 about the axis 8014 relative to the first support 8120. The third adjustment mechanism 8900 includes a wedge-shaped support member 8902 (FIG. 159) fixedly connecting the second rack member 8182 to a ring member 8904 that is rotatably supported by the first support 8120 and rotatable about the axis 8014 relative to the first support 8120 (FIG. 167).

The third adjustment mechanism 8900 further includes a third manually adjustable, rotatable knob 8906 that is part of a set screw. The set screw is rotatably threaded into a projection portion 8902a of the support member 8902 and is engageable with the circular perimeter 8121 of the disk 8124 of the first support 8120 to lock the support member 8902 in an arcuate position relative to the first support 8120 and the axis 8014.

As viewed in FIGS. 167-168, the ring member 8904 is supported within a cylindrical, open ended recess 8905 of the first support 8120. The recess 8905 is concentric about the axis 8014. The perimeter 8904a of the ring member 8904 has a groove 8904b for engaging a plurality of ball plungers 8400 (preferably four equally spaced apart) in the first support 8120. Each of these ball plungers 8400 is similar in construction. Each ball plunger 8400 is threaded radially into the perimeter 8121 of the first support 8120 to provide a hemispherical extension 8420 extending into the recess 8905 of the first support 8120.

The ring member 8904 thus is biasingly supported within the recess 8905 of the first support 8120 and can rotatably slide within the recess 8905 about the axis 8014. The ball plungers 8400 operatively support the ring member 8904 in the recess 8905 of the first support 8120. The ring member 8904, along with the second support 8140 and the second and third adjustment mechanisms 8180, 8900, can be easily removed from the recess 8905 for cleaning, maintenance, etc. of the parts by overcoming the force applied by the ball plungers 8400 to the ring member 8904. When the knob 8906 is rotated to disengage the perimeter 8121 of disk 8124, the body 8142 and parts connected thereto can be manually rotated about the axis 8014. This causes the viewing device 8200 to rotate about the axis 8014 of the cannula 8010 and enables the surgeon to view different parts of the surgical sight as desired.

As viewed in FIG. 166, the fixed connections of the first rack member 8162 to a support arm 8300, the second rack member 8182 to the wedge-shaped support member 8902, and the support member 8902 to the ring member 8904 may be made by one or more suitable metal fasteners 8290, such as rivets or bolts. The entire support apparatus 8110 can be constructed from metal or any other suitable material having sufficient mechanical strength and durability. Certain parts may be made from materials permitting X-rays and other techniques for viewing the surgical sight (i.e., radiolucent parts). Other parts may also be made from non-magnetic materials to reduce electromagnetic interference (i.e., electromagnetic insulating parts).

With reference to FIGS. 160 and 172, the gripper's arms 8172, 8174 are a part of the support arm 8300 for attaching the support apparatus 8110 to a mechanical robotic arm 8301. The support arm 8300 includes an arm portion 8302 that is formed integrally with the arms 8172, 8174. The arms 8172, 8174 are integrally constructed with the arm portion 8302.

The support arm 8300 also includes an arm portion 8303. The arm portion 8303 has an attaching structure 8304, including a groove 8305, which snaps into a socket in the mechanical arm 8301. Detents of any suitable type and designated 8306 in the mechanical arm 8301, hold the arm portion 8303 in position in the socket in the mechanical arm 8301. The detents 8306 may be controlled by external actuation levers (not shown) on the mechanical arm 8301 for manually releasing the arm portion 8303 from the mechanical arm 8301.

The arm portions 8302 and 8303 are pivotally connected to each other by a fastener 8310. The fastener 8310 extends through an opening 8311 in the arm portion 8302 and threads into a threaded opening 8312 in the arm portion 8303. When the fastener 8310 is released, the arm portions 8302, 8303 may pivot relative to each other about a pivot axis 8314. The pivot axis 8314 is centered on the axis of the fastener 8310 and the axis of the threaded opening 8312. When the fastener 8310 is tightly screwed into the threaded opening 8312, the arm portions 8302, 8303 are secured together against pivoting movement. When the fastener is released, the arm portions 8303, 8302 may pivot relative to each other about the axis 8314.

The end of the arm portion 8302, which is adjacent to the arm portion 8303, has a convex surface 8350, which is curved about the axis 8314. The arm portion 8303 has a concave surface 8351, which is also curved about the axis 8314. The surfaces 8350, 8351 move concentrically relative to each other when the arm portions 8303 and 8302 pivot relatively about the axis 8314.

The arm portion 8303 has a set of teeth 8320 which encircle the axis 8314 and which project axially toward a set of teeth 8321 on the arm portion 8302. The teeth 8321 project axially toward the teeth 8320. The teeth 8320 and the teeth 8321 mesh with each other and provide a locking action so that the arm portions 8302, 8303 are positively locked against relative movement about axis 8314 when the fastener 8310 is tightly screwed into the opening 8312. The teeth 8320, 8321 comprise a lock which blocks relative rotation of the arm portions 8302, 8303 about the axis 8314. When the fastener 8310 is loosened, the arm portions 8302, 8303 may be rotated relative to each other about the axis 8314, and thus, the arm portions 8302, 8303 may pivot relative to each other to adjust the position of the support apparatus 8110.

A cylindrical projection 8325 is welded to the arm portion 8303. Thus, the projection 8325 and arm portion 8303 are fixedly connected together. The projection 8325 is centered on the axis 8314 and contains a chamber 8328.

As viewed in FIG. 170, the chamber 8328 communicates with a fluid passage 8329 in a male fluid connector 8331. The male connector 8331 attaches to a male connector 8333 on the mechanical arm 8301 by means of a flexible hose 8392 so that the fluid passage 8329 communicates with a fluid passage in the mechanical arm 8301.

As viewed in FIG. 170, the chamber 8328 is closed at its upper end by a cap 8335. The cap 8335 has an opening 8336 centered on the axis 8314. The opening 8336 communicates with the chamber 8328. A manually movable internal valve member 8340 normally closes the opening and blocks the chamber 8328 from communicating with the ambient air surrounding the support arm 8300. The valve member 8340 is connected to a stem 8341, which is also centered on the axis 8314. The stem 8341 has a knob or button 8343 on its end that may be manually depressed to move the stem 8341 and valve member 8340 downward into the chamber 8328. When the stem 8341 and valve member 8340 are so moved, the chamber 8328 is in communication with the ambient air surrounding the device due to the unblocking of the opening 8336.

The mechanical arm 8301 includes relatively movable parts, which permit movement and adjustment of the support apparatus 8110 in a variety in planes, directions, and orientations. The mechanical arm 8301 permits easy movement when a vacuum is not applied to the arm 8301. When a vacuum is applied to the arm 8301, relative movement of the parts of the arm 8301 is resisted, and therefore adjustment of the support apparatus 8110 is difficult.

When the button 8343 is depressed, the chamber 8328 loses its vacuum and the pressure in the chamber 8328 increases toward ambient pressure. The passage 8329 communicates this pressure increase to the mechanical arm 8301, and thus the parts of the mechanical arm 8301 are free to move and allow for adjustment of the position of the support apparatus 8110 by the surgeon.

Accordingly, when the surgeon uses the support apparatus 8110, the support arm 8300 is snapped into the socket of the mechanical arm 8301 where it is held by the detent 8306. The surgeon may then depress the button 8343 and relatively move parts of the mechanical arm 8301, as well as the support apparatus 8110 into the position where the surgeon desires the support apparatus 8110 to be. This position may be where the opening 8126 in the disk 8124 is aligned with the proximal end 8016 of the cannula 8010 that has been positioned in the patient's body with the distal end 8024 of the cannula 8010 being located in an incision in the body of the patient. The viewing device 8200 may be mounted on the support apparatus 8110, and the surgeon may make adjustments prior to and during the surgical procedure as desired, as described above.

As viewed in FIG. 173, the support apparatus 8110 may include a second support with a fourth adjustment mechanism 8500 for rotating the viewing device 8200 about an axis 8501 (FIG. 165) defined by the ball plungers 8400 of the extension arms 8151, 8152 when set screw 8148 is not clamping the viewing device 8200 to the body 8142. The axis 8501 is offset from the axis 8014 of the cannula 8010 and perpendicular to the axis 8014 of the cannula 8010. Rotation of the viewing device 8200 about axis 8501 causes the endoscope 8200 and the rod and lens assembly 8203 to move perpendicular to the axis 8014 of the cannula 8010. This rotation will result in radial adjustment of the position of the rod and lens assembly 8203 in a radial direction transverse to the axis 8014.

The spring-loaded connections of the spherical detent members 8420 of the ball plungers 8400 and the hemispherical recesses of the endoscope 8202 allow rotation about the axis 8501 when the set screw 8148 is released from clamping engagement of the viewing device 8200.

The mechanism 8500 includes a threaded bore 8510 in the second support 8140 and an adjustable member 8520 for moving (vertically as viewed in the figures) a part of the viewing device 8200 about the axis 8501. The adjustable member 8520 has a rounded first end portion 8522, a threaded middle portion 8524, and a knurled second end portion 8526, or knob. The bore 8510 extends at an angle as shown in FIG. 173 from a lower portion of the second support 8140 up to the opening 8144 in the clamp 8146 of the second support 8140.

The adjustable member 8520 is rotated and threaded into the bore 8510 and may be rotated until the first end portion 8522 protrudes into the opening 8144 of the second support 8140. Accordingly, when the surgeon wishes to adjust the rod and lens assembly 8203 (within the surgical sight) about the axis 8501 and radially relative to the axis 8014 of the cannula 8010, the surgeon may loosen the connection of the set screw 8148 with the viewing device 8200 and rotate the adjustable member 8520 by manually rotating knob 8526 so that the first end portion 8522 vertically extends farther or less into the opening 8144. This adjustment will adjust the part of the viewing device 8200 engaged by the clamp 8146 along the axis 8014, rotate the viewing device 8200 about the axis 8501, and cause the lens 8203 at the surgical site to move transverse to the axis 8014 of the cannula 8010. This will expand the area of the surgical site that the surgeon may view. When the adjustment is complete, the surgeon may tighten the set screw 8148 and re-secure the viewing device 8200 to the second support 8140 of the support apparatus 8110.

The method of securing two vertebrae 8601, 8602 together according to one embodiment may include the insertion of a vertebral fixation assembly 8620 through the cannula 8010 and attachment of the vertebral fixation assembly 8620 to two vertebrae (such as the L4 and L5 vertebrae), as viewed in FIGS. 174-179. The fixation assembly 8620 may be of any suitable construction and is shown in FIG. 176 as including four identical attachment devices 8622. Each attachment device 8622 includes a threaded fastener 8624 or pedicle screw, placed in a vertebra 8601 or 8602, as viewed in FIGS. 175 and 178. The fastener 8624 has a first threaded portion 8626 with a first threaded diameter that threads into the vertebrae 8601, 8602 by screwing the fastener 8624 into the vertebrae. The fastener 8624 further includes a second threaded portion 8628 with a second threaded diameter that may be less than the first threaded diameter. The second threaded portion 8628 extends away from the vertebrae 8601, 8602.

A first hexagonal engagement surface 8630, intermediate the first and second threaded portions 8626, 8628, allows gripping of the fastener 8624 when the fastener is screwed into the vertebrae 8601, 8602. A first convex engagement surface 8632, adjacent the first hexagonal engagement surface 8630 and the second threaded portion 8628, projects away from the vertebrae 8601, 8602. A second hexagonal engagement surface 8634 projects away from the second threaded portion 8628 and allows further gripping of the fastener 8624.

Each attachment device 8622 further includes a first fixation washer 8640 (FIGS. 176 and 179) that engages the first convex engagement surface 8632. The first fixation washer 8640 includes a first concave engagement surface 8642 for abutting and slidingly engaging the first convex engagement surface 8632 of the fastener 8624.

The first fixation washer 8640 further includes spikes 8644, typically three, extending away from the vertebrae 8601, 8602. The spikes 8644 of the first fixation washer 8640 engage a lower knurled surface 8652 of a vertebral fixation element 8650 that in FIGS. 174-176 is a spine plate.

An upper knurled surface 8654 of the fixation element 8650 engages the spikes 8664 of a second fixation washer 8660 that is identical to the first fixation washer 8640, but inverted, as viewed in FIGS. 176 and 179. A second convex engagement surface 8672 of a threaded locking nut 8670 abuts and slidingly engages the second concave engagement surface 8662 of the second fixation washer 8660 when the locking nut 8670 is loosely threaded onto the second threaded portion 8628 of the fastener 8624.

The convex and concave engagement surfaces 8632, 8642, 8662, 8672 allow angular adjustment of the fixation elements 8650, before the locking nut 8670 is fully tightened, when the fasteners 8624 are not threaded into the vertebrae 8601, 8602 exactly parallel to each other, as shown exaggerated in FIG. 175. These surfaces may typically allow for up to a 12-degree offset of the axes of the two fasteners 8624.

One of two types of fixation elements 8650 may typically be used to secure the vertebrae 8601, 8602 together. The first type may be a spinal plate 8651 (FIG. 176) with two slots 8653, 8655 extending along the longitudinal axis 8657 of the spinal plate. The second threaded portion 8628 of one fastener 8624, screwed into one vertebra 8601, extends through one slot 8653 and the second threaded portion 8628 of another fastener 8624, screwed into another vertebra 8602, extends through the other larger slot 8655. Two of the spinal plates 8651, one on each side of the vertebrae 8601, 8602, are used to secure the two vertebrae together, as viewed in FIG. 174. The slots 8653, 8655 allow further transverse adjustment so that the same spinal plate 8651 may be used for different size patients.

A second type of fixation element 8650 may be two universal side blocks 8651*a* (FIG. 179), each with one slot 8653*a* extending along the longitudinal axis 8657*a* of each side block and a securement opening 8655*a* extending substantially perpendicularly to each slot 8653*a*, as viewed in FIG. 179. The second threaded portion 8628 of a fastener 8624, screwed into one vertebra 8601, extends through one slot 8653*a* and the second threaded portion 8628 of another fastener 8624, screwed into another vertebra 8602, extends through a slot 8653*a* in an identical side block 8651*a*. The side blocks 8651*a* further include lower and upper knurled surfaces 8652*a*, 8654*a* similar to the knurled surfaces 8652, 8654 of the spinal plate 8651.

This second type of fixation element 8650 further includes a rod 8658*a* extending from the opening 8655*a* in one side block 8651*a* to the opening 8655*a* in the other side block 8651*a*. Set screws 8659*a* secure the rod 8658*a* in each opening 8655*a* when the rod 8658*a* is positioned properly to secure the vertebrae 8601, 8602 together, as viewed in FIG. 177.

Four of the side blocks 8651*a*, one on each side of each vertebra 8601, 8602, and two rods 8658*a* are used to secure the two vertebrae together. The slots 8653*a* allow further transverse adjustment so that the same side block 8651*a* may be used for different size patients. The rods 8658*a* may also be cut to fit different sized patients.

The cannula 8010, support apparatus 8110, and vertebral fixation assembly 8620 described above may be used to perform an operation which secures two vertebrae 8601, 8602 together, such as the posterolateral fusion and screw placement described above. This type of operation traditionally results in much blood loss because of the open access to the spine required for its performance. Utilizing the cannula 8010 and support apparatus 8110 for placement of the fixation assembly 8620 at the surgical site and attachment of the fixation assembly 8620 to the vertebrae 8601, 8602 in a manner to be described results in a much less invasive procedure and significantly less blood loss.

According to one embodiment, a method of fixing the vertebrae 8601, 8602 of a patient together at two surgical sites includes two main procedures. In the first procedure, a first cannula 8010 is inserted into the body 8130 of the patient adjacent one side of the spinal column. A second cannula 8010 is inserted into the body 8130 of the patient adjacent the other side of the spinal column. The second tubular portions 8040 of both cannulae are expanded as described above thereby creating a substantially complete view of both sides of the two adjacent vertebrae 8601, 8602. In one embodiment, the two adjacent vertebrae 8601, 8602 are viewed by way of two endoscopes 8200 and one or more monitors.

Alternatively, instead of using two cannulae and two endoscopes simultaneously so that both sides of adjacent vertebrae may be worked on by the surgeon at the same time, only one side of the adjacent vertebrae may be worked on and then the other side of the adjacent vertebrae may be worked on. In this case, only one endoscope, one endoscope support 8110, and one monitor is required. Two cannulae would most probably be used, one for each side of the vertebrae.

In the second procedure, the vertebrae 8601, 8602 are accessed through the cannulae 8010. Four insertion openings are drilled, one in each side of each vertebra 8601, 8602, utilizing suitable instruments extending through the cannulae 8010. The fasteners 8624 are inserted through each cannula 8010 and are screwed one fastener 8624 into each insertion opening, thereby securing each fastener 8624 to a vertebra. The position of the vertebrae 8601, 8602 are checked to ensure that the vertebrae have maintained the proper position.

If necessary, the vertebrae 8601, 8602 are repositioned. Eight fixation washers 8640, 8660, four locking nuts 8670, and two fixation elements 8650 are moved through the cannulae 8010. Four fixation washers 8640 and the fixation elements 8650 are placed on the fasteners 8624. Each fastener 8624 is extended through one fixation washer and one slot in each fixation element 8650. The additional fixation washers 8660 are placed on the fasteners 8624. The locking nuts 8670 are threaded onto each fastener 8624 thereby fixing the fixation elements 8650 to the vertebrae 8601, 8602 and securing the vertebrae together in a natural and permanent position within the body. Also, bone graft may be moved through the cannulae 8010 and placed in and around the fixation element 8650 and fasteners 8624 to permit a posterior fusion across the bony elements of the vertebrae 8601, 8602.

If necessary, the disc between the vertebrae 8601, 8602 may be removed through the cannula; the area between the vertebrae cleaned and the vertebrae prepared for receiving a fusion cage or cages and/or disc replacement material. This would be done before inserting the fasteners 8624 or attaching the fixation elements 8650. The method may also include inserting, through the cannulae 8010, one or more appropriately sized fusion cages and positioning the fusion cage(s) appropriately relative to the vertebrae 8601, 8602; and inserting bone graft tissue through the cannulae 8010 and positioning the tissue in and around the fusion cage(s).

The fusion cage may be of any known construction. One typical fusion cage is a hollow rectangular cage that is inserted into grooves that are formed in facing bone surfaces of the vertebrae. Another type of fusion cage is a hollow cylindrical threaded cage which screws into position between the vertebrae. Any suitable fusion cage may be used.

The cannulae 8010 and the shrink wrap 8102 are then removed from the body and the incisions are suitably closed. After a time, vertebrae 8601, 8602 and bone graft will grow together across the fusion cage(s) and in and around the fixation elements 8650. The vertebrae 8601, 8602 will then no longer require the fixation assembly to maintain their position. The fixation elements 8650 and fasteners 8624 may then be removed. The removal procedure may utilize the same type of apparatus as was used in the first and second procedures (i.e., cannula, support apparatus, etc.).

The first and second cannulae 8010 may be shifted slightly in the incisions in the body 8130 to desired locations within the incisions at any time during the first and second procedures or the removal procedure. This is accomplished by changing the position of the support apparatus 8110 by manipulating the arm 8301.

The method described above may, and most probably does, involve removal of tissue from the surgical site through the cannula 8010. Muscle, fat, and bone may be removed through the cannula 8010 to provide a proper view of the vertebrae 8601, 8602 at the location to receive the fixation assembly 8620. Different tools may be used in the process of removing tissue. These tools may include a burr and/or tissue cutting blades that are inserted through the cannula 8010.

A preferred tissue cutting blade device 8710 is shown in FIGS. 180-181. The device 8710 has an axis 8712 and includes inner and outer cutting tubes 8740, 8750. Each of the inner and outer tubes 8740, 8750 has openings 8741, 8751 into their interiors. Cutting teeth 8745, 8755 are located on opposite sides of each opening 8741, 8751.

The inner tube 8740 rotates about the axis 8712 relative to the outer tube 8750 within the outer tube. The inner tube 8740 rotates in opposite directions a predetermined amount equal to one or more revolutions about the axis 8712, and then rotates in the opposite direction the same predetermined amount. Thus, the inner tube 8740 oscillates about the axis 8712. As the inner tube 8740 oscillates/rotates about the axis 8712, the cutting teeth 8745, 8755 on the inner and outer tubes 8740, 8750 cut tissue. Alternatively, the inner tube 8740 may rotate in one direction (clockwise or counterclockwise) within the outer tube.

During the cutting of tissue, a saline solution or the like may be forced through the annular space 8770 between the inner tube 8740 and the outer tube 8750 to the surgical site. Suction may be applied in the opening 8741 of the inner tube 8740 to remove the cut tissue and the saline solution from the surgical site.

A tubular sheath 8760 receives the inner and outer cutting tubes 8740, 8750. The sheath 8760 extends along the length of the cutting tubes 8740, 8750 and adjacent a distal end of the cutting tubes where the cutting teeth 8745, 8755 are located. The sheath 8760 is a stainless steel tube that is electrically insulated along its length from the patient's body and from the outer tube 8750. An electrical insulator 8763, such as a suitable polymer coating, is provided over the outside and inside surfaces of the sheath 8760. However, a selected area 8762 of the outside surface of the sheath 8760 adjacent the distal end of the cutting tubes 8740, 8750 is not coated with the insulator 8763. A portion 8765 of the distal end of the sheath 8760 is cut away so that the cutting teeth 8745, 8755 on the cutting tubes 8740, 8750 are not blocked by the sheath 8760 from cutting tissue.

An electric current from a current source 8766 is applied to the sheath 8760. The electric current flows through the sheath 8760 and to the selected uncoated area 8762 of the sheath. The current then flows through tissue and blood into the distal end of the outer cutting tube 8750 and back to the current source through the outer cutting tube to form a completed circuit.

The current flow through the electrically energized sheath 8760 and outer cutting tube 8750 serves to electrocoagulate blood in the cutting area at the surgical site. Electrocoagulation of blood is known and any other suitable electrocoagulation device may alternatively be used.

It is contemplated that viewing of the surgical site may be performed without using an endoscope. A microscope or glasses that magnify the site may be used. In fact, any suitable viewing device may be used. Also, the procedure discussed above mentions drilling the vertebrae. Any suitable alternative to drilling may be used such as using an awl or other instrument to form an opening to receive a fastener.

FIGS. 182-284 show other embodiments of surgical assemblies, access devices, viewing assemblies, and mounting assemblies. FIGS. 182-243 in particular illustrate additional embodiments of access devices. FIGS. 182-243 show access devices that are similar to the other access devices described herein, except as set forth below. FIGS. 244-284 show additional embodiments of viewing elements and mounting systems for access devices. FIGS. 244-284 show viewing elements and mounting systems that are similar to the other viewing elements and mounting systems described herein, except as set forth below.

FIG. 182 shows a surgical assembly 9000 that includes an access assembly 9002 and a viewing assembly 9004. The access assembly 9002 preferably includes an access device 9006 or retractor that is adjustably coupled with an access device mounting fixture 9008. In various embodiments described herein, the access device 9006 is an elongate body having a distal portion 9010 and a proximal portion 9012 defining a passage 9014 therethrough. Some embodiments of the adjustable coupling of the access device 9006 and the access device mounting fixture 9008 are discussed herein.

The viewing assembly 9004 preferably includes a viewing element 9016 coupled with a viewing element mounting fixture 9018. The viewing element mounting fixture 9018 preferably is adjustably coupled with the access device mounting fixture 9008. Some embodiments of the adjustable coupling of the viewing element mounting fixture 9018 and the access device mounting fixture 9008 are described herein.

Access devices can have any number of configurations. In some embodiments, access devices have expanding proximal portions and/or expanding distal portions. Expanding access devices can include different configurations and structures, for example, access devices can incorporate overlapping leaves, overlapping skirt portions, overlapping tubes, sleeve portions, doughnut shaped portions, umbrella shaped portions, weaved portions, pop-up loops or springs, conical springs, and telescoping arrangements, and other structures.

FIG. 183 is a schematic diagram illustrating possible expansion directions for an access device 9020. In the illustrated embodiment, the access device 9020 has a generally oval-shaped cross-section. The access device 9020 has a proximal portion 9022 and a distal portion 9024. In some embodiments, the access device 9022 can be expanded in the longitudinal direction 9026 increasing the overall length of the access device 9020. In some embodiments, the proximal portion 9022 can be expanded in a horizontal or transverse direction 9028. The distal portion 9024 of the access device 9020 in some embodiments can be expanded in the direction 9030 of the minor access and/or in the direction 9032 of the major access.

FIGS. 184-185 show distal portions of two access device embodiments and illustrate various overlapping arrangements. In some embodiments, a skirt portion 9042 at a distal part of the access device 9040 is overlapped relative another skirt portion 9044. The skirt portions 9042, 9044 in the expanded configuration can have a generally oblong shaped cross-section. In the illustrated embodiment, the skirt portions 9042, 9044 form a generally oval shaped cross-section. In the low profile configuration, the skirt portions 9042, 9044 generally can be overlapped in any suitable manner. In one embodiment, the skirt portions 9042, 9044 can be overlapped so that when expanded, the skirt portions 9042, 9044 at least partially overlap near a major access 9046 of the oval-shaped cross-section, as shown in FIG. 184. In another embodiment, the skirt portions 9042, 9044 can be overlapped so that when expanded, the skirt portions 9042, 9044 are positioned along a minor access 9048 of the oval shaped cross section, as shown in FIG. 185. FIGS. 184-185 also illustrate that in some embodiments, an access device is configured to expand by applying a force 9050 primarily along the minor axis 9048 or by applying a force 9052 primarily along the major axis 9046.

FIG. 186 is a schematic view of another embodiment of an expandable access device 9060 having an expansion mechanism 9062. In some embodiments, it is desirable to expand the access device 9060 using the expansion mechanism 9062 positioned generally outside a passage 9064 defined within the access device 9060. In other embodiments, the expansion mechanism 9062 can be positioned within the passage 9064 of the access device 9060. In the illustrated embodiment, a push/pull rod 9068 is coupled with a proximal portion 9070 of the access device 9060 and to a distal portion 9072 of the access device 9060 to selectively expand a distal skirt portion 9074. In some embodiments, the proximal portion 9070 comprises a collar portion 9076. In some embodiments, both the proximal collar portion 9076 and the distal skirt portion 9074 can be expanded simultaneously. Movement of a support mount or viewing element mount 9078, in some embodiments, can trigger expansion and/or rotation of portions of the access device 9060.

Some access devices having expanding proximal portions are now described in more detail. FIG. 187 is a plan view of one embodiment of an access device 9080 that includes an expandable proximal portion 9082, shown in a flat pattern detail, and a distal portion 9084, a portion of which is shown schematically. The schematic representation of the distal portion 9084 signifies that the proximal portion 9082 can be combined with any distal portion disclosed or incorporated by reference herein, or any other suitable distal portion. Preferably, the proximal portion 9082, when in the flat state, as illustrated in FIG. 187, has a generally rectangular shape defined by a distal edge 9086, a proximal edge 9088, a first longitudinal edge 9090, and a second longitudinal edge 9092. The distal edge 9086 of the proximal portion 9082 is located at or adjacent to the distal portion 9084. The proximal edge 9088 of the proximal portion 9082 is located at or adjacent the proximal end of the access device 9080. The flat pattern view of the proximal portion 9082 suggests many suitable manufacturing processes. For example, the proximal portion 9082 can be stamped out of sheet metal of a suitable thickness, or formed in any other suitable manner.

The proximal portion 9082 also includes at least one pair of flex fingers 9094, 9096. The pair of flex fingers 9094, 9096 preferably includes a latch finger 9094 located on the first longitudinal edge 9090 and a catch finger 9696 located on the second longitudinal edge 9092. In the illustrated embodiment, four pairs of flex fingers are provided. Any suitable number of flex fingers could be provided.

The catch finger 9096 and the latch finger 9094 preferably are elongate members that are configured to overlap, as discussed more fully below, such that the catch finger 9096 engages the latch finger 9094. When the flex fingers overlap to engage in this manner, the flex fingers are said to be "inter-digitated." Whether there are one, two, three, four or more pairs of flex fingers, the flex fingers may be said to be inter-digitated when they overlap and engage each other in this manner. As discussed more fully below, the flex fingers preferably are configured so that when the flex fingers are inter-digitated, the proximal portion 9082 can be suitably sized for a wide variety of surgical procedures. This arrangement of interdigitated flex fingers is one form of an expansion means for the proximal portion 9082.

In one embodiment, the catch and latch fingers 9096, 9094 preferably are located at the same position longitudinally (i.e., at the same position along a line extending from the distal edge 9086 to the proximal edge 9088), but on opposite sides of the proximal portion 9082. One of the catch and latch fingers 9096, 9094 preferably has one or a series of detent holes 9098 formed therein. In the illustrated embodiment, the catch finger 9096 is provided with six latch holes or detent holes 9098, as shown in FIG. 187, while the latch finger 9094 is provided with a detent hook feature 9100. In another embodiment, the catch finger 9096 could be in the position of the latch finger 9094 in FIG. 187 and the latch finger 9094 could be in the position of the catch finger 9096 in FIG. 187. FIG. 188 shows the proximal portion 9082 of the access device 9080 in an overlapping configuration.

The detent holes 9098 preferably extend entirely through the thickness of the catch finger 9096, but could extend only partially therethrough. The detent holes 9098 also could be formed as depressions, rather then as holes in the catch finger 9096. In one embodiment, the detent hook feature 9100 comprises a spherical surface that protrudes from at least one side of the latch finger 9094. The detent holes 9098 and the detent hook feature 9100 are configured to engage each other in a secure manner so that they will not become disengaged inadvertently. Although only a single detent hook feature 9100 is located on the latch finger 9094, more could be provided so that when the flex fingers are engaged at least two detent hook features 9100 may engage at least two detent holes 9098. Such an arrangement may further decrease the likelihood of the catch and latch fingers 9096, 9094 inadvertently becoming disengaged. One skilled in the art should recognize that other suitable detent arrangements could be employed.

As discussed above, the proximal portion 9082 of the access device 9080 is expandable. In the embodiment illustrated by FIGS. 187-188, the detent arrangement, and in particular, the detent holes 9098 provide a range discrete positions to which the proximal portion 9082 can be expanded. Each of the six detent holes 9098 provides a position at which the detent hook feature 9100 of the latch member 9094 may engage the catch member 9096. The transverse cross-sectional size of the proximal portion 9082 may be expanded by indexing the detent hook feature 9100 from a detent hole 9098 farther from the second longitudinal edge 9092 to a detent hole nearer to the second longitudinal edge 9092.

Expansion of the proximal portion 9082 of the access device 9080 may be accomplished in any suitable manner. For example, an expander tool can be used to expand the proximal portion 9082 by indexing the detent hook feature 9100 from one detent hole 9098 to another. If the proximal portion 9082 is in its smallest configuration, e.g., the detent hook feature 9100 is located in the detent hole 9098 farthest from the second longitudinal edge 9092, an expander tool can be inserted into the proximal portion 9082 and can be partially expanded until the expander tool engages opposites sides of the inner surface of the proximal portion 9082. Further expansion of the expander tool can be applied to the opposite sides of the inner surface of the proximal portion until the force at the detent hook feature 9100 and the detent holes 9098 exceeds the force resisting the inadvertent disengagement of the detent. When such force is applied, the detent will become disengaged and the detent hook feature 9100 will disengage the detent hole 9098 in which it resides and the flex fingers will translate with respect to each other until the detent hook feature 9100 comes to rest in a subsequent detent hole. One example of an expander tool is shown in FIG. 220.

The transverse cross-sectional size of the proximal portion 9082 may be reduced in any suitable manner. In one approach, the detent hook feature 9100 is caused to disengage from the detent hole 9098 in which it resides and is subsequently indexed from a detent hole 9098 nearer to the second longitudinal edge 9092 to a detent hole 9098 farther from the second longitudinal edge 9092. As in expansion, the detent hook feature 9100 may become disengaged from the detent hole 9098 by the application of a force on the proximal portion 9082. For example, a compressive force could be applied to opposite outer surfaces of the proximal portion 9082.

Another manner of expanding or reducing the cross-sectional size of the proximal portion 9082 is illustrated in FIG. 189. The proximal portion 9082 is illustrated in FIG. 189 in a reduced cross-sectional size configuration. An unlocking member 9102 is configured to be insertable between the interdigitated flex fingers 9104. In one embodiment, the thickness of the unlocking member 9102 increases toward the proximal edge thereof (e.g., the edge farthest from the distal edge of the proximal portion 9082). As the unlocking member 9102 is advanced between the interdigitated flex fingers 9104, the flex fingers 9104 are separated progressively decreasing the degree of engagement of the detent hook feature 9100 and the detent hole 9098 in which it is inserted. An arrow A indicates the advancement of the unlocking member 9102 with respect to the interdigitated flex fingers 9104 to disengage the detent hook feature 9100 from the detent holes 9098.

FIG. 190 is a perspective view of one embodiment of an access assembly 9120. The access assembly 9120 includes an access device 9122 that includes a proximal portion 9124. The access assembly 9120 also includes a skin wrap 9126 that at least partially surrounds the proximal portion 9124. The proximal portion 9124 preferably includes a first longitudinally extending side 9128 and a second longitudinally extending side 9130 that adjustably overlap. The first longitudinally extending side 9128 preferably has a notch 9132 located on a major axis 9136 of the proximal portion 9124. The second longitudinally extending side 9130 preferably has a notch 9134 located on a major axis 9136 of the proximal portion. The notches 9132, 9134, preferably are located on the same major axis 9136. The notches 9132, 9134 may be used to identify one or more features on the access device 9122 or to couple the access device 9122 to a mounting fixture or other structure.

The skin wrap 9126 prevents inadvertent expansion of the proximal portion 9124 of the access device 9122. The skin wrap 9126 preferably is removable from the proximal portion 9124 when the proximal portion 9124 is to be expanded. In one embodiment, the skin wrap 9126 is a heat-shrunk plastic sleeve that completely surrounds a portion of the proximal portion 9124.

In one arrangement, a release device is coupled with the skin wrap 9126, e.g., between the skin wrap 9126 and the proximal portion 9124, and is capable of disengaging the skin wrap 9126 from the proximal portion 9124 to allow the proximal portion 9124 to expand. One form of the release device is a length of string.

After the proximal portion 9124 of the access device 9122 is released, the proximal portion 9124 may be expanded. An arrow B indicates motion of the proximal portion 9124, e.g., of the first longitudinal extending side 9128 with respect to the second longitudinally extending side 9130, that expands the cross-sectional size of the proximal portion 9124. This motion may be provided by the expander tool illustrated in FIG. 220, in the mounting fixture illustrated in FIGS. 267-270, or by any other suitable means. The access device 9120 may be closed by way of the opposite motion.

FIG. 191 illustrates a proximal portion of an access device 9140. The access device 9140 has an expandable proximal portion 9142. The proximal portion 9142 is covered by, or wrapped in, a stretchable member 9144. The terms "stretchable member," as used herein, are broad terms, and can include elastic members, coatings, films, meshes, or other materials, and can also include other resilient, deformable, pliable, ductile and/or expandable materials. In some embodiments, the stretchable member 9144 can be a polymer forming an outer coating about the proximal portion 9142 of the access device 9140. The proximal portion 9142 of the access device 9140 has inner and outer clamshells 9146, 9148 that can be moved apart or together to expand or contract the cross-sectional area of the proximal portion 9142. As the proximal portion 9142 expands, the stretchable member 9144 expands along with the inner and outer clamshells 9146, 9148 to maintain a relatively continuous outer surface about the proximal portion 9142 of the access device 9140. Maintaining a relatively continuous outer surface along the proximal portion 9142 reduces the likelihood that tissue will encroach into the surgical space formed by a passage of the access device 9140.

FIG. 192 is a perspective view of a proximal end 9164 of a proximal portion 9162 of one embodiment of an access device 9160. In the illustrated embodiment, the proximal portion 9162 of the access device 9160 is expandable. The access device 9160 preferably has a plurality of notches 9166 formed along an upper surface or edge 9168 of the proximal portion 9162. When the proximal portion 9162 is expanded, the notches 9166 preferably can be aligned. A locking ring 9170 or support mount can be positioned over the expanded proximal portion 9162. The locking ring 9170 has one or more pins 9172 or tabs that can be configured to engage the notches 9166 at the proximal end 9164 of the access device 9160. The locking ring 9170 preferably maintains the proximal portion 9162 in the expanded configuration when applied at the proximal portion 9162. The locking ring 9170 has an opening 9174 to provide access to a passage 9176 of the access device 9160 and to a surgical location. In some embodiments, the locking ring 9170 can be formed as, or coupled with, an access device mounting fixture.

FIG. 193 is a perspective proximal end view of an access device 9180 having a pivot rivet. FIG. 193 illustrates another embodiment of an access device 9180 having an expandable proximal portion 9182. The access device 9180 has overlapping proximal segments. A first proximal segment 9184 is positioned generally within a second proximal segment 9186 such that the second proximal segment 9186 wraps around the first proximal segment 9184. In other embodiments, the proximal segments 9184, 9186 can be positioned in any suitable manner. As shown in the illustrated embodiment, slots 9188 are formed in one or more of the overlapping proximal segments 9184, 9186. Pins or rivets 9190 can be placed through the overlapping segments 9184, 9186 and into the slots 9188 to facilitate expansion or contraction of the proximal portion 9182. With reference to FIG. 193, the distal portion 9192 of the access device 9180 can have one or more slots 9194 formed in one or more skirt portions 9196 where the distal portion 9192 is coupled with the proximal portion 9182. A pivot rivet 9198 can be placed within the slots 9194 in the distal portion 9192 to couple the distal portion 9192 with the proximal portion 9182. The pivot rivet 9198 facilitates expansion of the distal portion 9192 of the access device 9180 in connection with the expansion of the proximal portion 9182. The pivot rivet 9198 and slot 9194 arrangement advantageously provides for smooth translation between expanded and contracted configurations and reduces the risk for binding of the distal portions 9192 of the access device 9180.

With reference to FIGS. 194-195, a proximal portion 9202 of one embodiment of an access device 9200 has a ratchet arrangement 9204 and/or an expansion lock. A surface 9206 of the proximal portion 9202 can be provided with one or a plurality of ridges, serrations, or notches 9208. An overlapping end 9210 of the proximal portion 9202 can be provided with a locking edge or ratchet mechanism 9212 to engage the ridges, serrations, or notches 9208 along the surface 9206 of the proximal portion 9202. The proximal portion 9202 can be expanded or contracted by moving the locking edge 9212 over the notched surface 9206. The amount of expansion can be adjusted as desired using the ratcheting and locking features.

FIG. 196 is a perspective view of another embodiment of an access device 9220 that includes a proximal portion 9222 and a distal portion 9224. As discussed more fully below, the proximal portion 9222 and the distal portion 9224 preferably are both expandable. The proximal portion 9222 includes a first longitudinally extending side 9226 and a second longitudinally extending side 9228 that adjustably overlap. The first longitudinally extending side 9226 preferably has a generally U-shaped configuration that extends from a first lateral side 9230, around a first longitudinal end 9232, to a second lateral side 9234 of the access device 9220. The second longitudinally extending side 9228 preferably has a generally U-shaped configuration that extends from the first lateral side 9230, around a second longitudinal end 9236, to the second lateral side 9234 of the access device 9220.

In one embodiment, the first longitudinally extending side 9226 adjustably receives a portion of the second longitudinally extending side 9228. For example, the open end of the "U" of the first longitudinally extending side 9226 is somewhat wider than the open end of the "U" of the second longitudinally extending side 9228 such that the open end of the "U" of the second longitudinally extending side 9228 can be received with the open end of the "U" of the first longitudinally extending side 9226. In one embodiment, the first and second longitudinally extending sides 9226, 9228 are adjustably engaged by way of a first pin-in-slot arrangement 9238. One form of the first pin-in-slot arrangement 9238 provides corresponding control slots 9240, 9242 on each of the first and second longitudinally extending sides 9226, 9228 on each of the first and second lateral sides 9232, 9234 of the access device 9220. A pin 9246 extends at least partially through both of the slots 9240, 9242 so that the first and second longitudinally extending sides 9226, 9228 are joined together. A second pin-in-slot arrangement 9238 similar to the pin-in-slot arrangement 9238 preferably is provided on the second lateral side 9234 of the access device 9220.

In one embodiment, the adjustable engagement of the first and second longitudinally extending sides 9226, 9228 also includes a ratchet arrangement 9248 wherein corresponding rows of ratchet teeth are provided on an overlapping portion of the first and second longitudinally extending sides 9226, 9228. The ratchet arrangement 9248 enables discrete adjustment and expansion of the proximal portion 9222 and also provides a means to lock the access device 9220 in place with any desired degree of expansion.

The proximal portion 9222 and the distal portion 9224 may also be coupled in any suitable manner. For example, the proximal portion 9222 and the distal portion 9224 may be coupled by one or more pin-in-slot arrangements. In one embodiment, a third pin-in-slot arrangement 9250, a fourth pin-in-slot arrangement 9252, and a fifth pin-in-slot arrangement 9254 join the distal portion 9224 with the proximal portion 9222. The third pin-in-slot arrangement 9250 joins a second longitudinally extending side 9256 of the distal portion 9224 to the second longitudinally extending side 9228 of the proximal portion 9222 at the second longitudinal end 9236 of the access device 9220. The third pin-and-slot arrangement 9250 can take any suitable form, but preferably is similar to the first pin-in-slot arrangement 9240. A sixth pin-in-slot arrangement similar to the third pin-in-slot arrangement 9250 preferably is provided on the first longitudinal end 9232 of the side of the access device 9220.

The fourth pin-in-slot arrangement 9252 joins a second longitudinally extending side 9256 of the distal portion 9224 to the second longitudinally extending side 9228 of the proximal portion 9222 at the first lateral side 9230 of the access device 9220. The fourth pin-and-slot arrangement 9252 can take any suitable form, but preferably is similar to the first pin-in-slot arrangement 9240, except as set forth below. The fourth pin-and-slot arrangement 9252 preferably includes an arcuate control slot formed in at least one of the second longitudinally extending side 9256 of the distal portion 9224 and in the second longitudinally extending side 9228 of the proximal portion 9222. A seventh pin-in-slot arrangement substantially similar to the fourth pin-in-slot arrangement 9252 preferably is provided on the second lateral side 9234 of the access device 9220.

The fifth pin-in-slot arrangement 9254 joins a first longitudinally extending side 9258 of the distal portion 9224 to the first longitudinally extending side 9226 of the proximal portion 9222 at the first lateral side 9230 of the access device 9220. The fifth pin-and-slot arrangement 9254 can take any suitable form, but preferably is similar to the first pin-in-slot arrangement 9240, except as set forth below. The fifth pin-and-slot arrangement 9254 preferably includes an arcuate control slot formed in at least one of the first longitudinally extending side 9258 of the distal portion 9224 and in the first longitudinally extending side 9226 of the proximal portion 9222. In the illustrated embodiment, the fourth and fifth pin-in-slot arrangements 9252, 9254 share at least one slot. An eighth pin-in-slot arrangement substantially similar to the fifth pin-in-slot arrangement 9254 preferably is provided on the second lateral side 9234 of the access device 9220.

The access device 9220 also provides a first actuator 9260 and a second actuator 9262. The first and second actuators 9260, 9262 preferably are in the form of rods that extend proximally of the proximal portion 9222. The first actuator 9260 may extend from the first longitudinally extending side 9226 of the proximal portion 9222 or of the first longitudinally extending side 9258 of the distal portion 9224 (e.g., as a discrete or an integral component thereof). The second actuator 9262 may extend from the second longitudinally extending side 9228 of the proximal portion 9222 or of the second longitudinally extending side 9256 of the distal portion 9224 (e.g., as a discrete or an integral component thereof). The first and second actuators 9260, 9262 can be handled by a medical practitioner to expand the access device 9220, e.g., by applying a force thereon to impart movement in a direction indicated by arrows H.

FIG. 197 shows contraction of the access device 9220, e.g., to configure the access device 9220 for insertion or withdrawal from the body. Movement of the access device 9220 from the expanded configuration to the un-expanded configuration is indicated by arrows I. FIG. 198 shows expansion of the access device 9220, e.g. to provide a working space for a surgical procedure. As in FIG. 196, movement is indicated by the arrows H.

Embodiments featuring various methods and structures for achieving distal expansion are described in further detail below. With reference to FIGS. 199-201, one embodiment of an access device 9280 has an expandable distal portion 9282 with anchor portions 9284 to fix the extent of the expansion of the distal portion 9282. The access device 9280 is configured to be expanded without the use of an expansion tool. The access device 9280 has a proximal collar portion 9286 coupled with a distal portion 9282 having right and left skirt halves 9288, 9290. The distal portion 9282 is coupled with the proximal portion 9286 at a pivot location 9292. The left and right skirt halves 9288, 9290 comprise anchor portions 9284. In some embodiments, the anchor portions 9284 can comprise a plurality of teeth. In the illustrated embodiment, the access device 9280 has a low profile configuration for insertion. In the low profile configuration, the skirt portions 9288, 9290 can be wrapped in an overlapping configuration. Upon insertion, the anchor portions 9284 are configured to be positioned in a fixed location. The access device 9280 is expanded from the low profile configuration to an expanded configuration by rotating the proximal portion 9286 of the access device 9280. In the illustrated embodiment, the access device 9280 is rotated in a clockwise direction to achieve expansion. The anchor portions 9284 preferably are held stationary while the access device 9280 is rotated. In some embodiments, the anchor portions 9284 can engage the tissue of the patient to maintain a stationary position. In some embodiments, a length 9294 of the distal portion 9282 in the expanded configuration is about three times greater than a length 9296 of the distal portion 9282 in the low profile configuration. To remove the access device 9280, the proximal portion 9286 is rotated in the opposite direction. In the illustrated embodiment, rotating the proximal portion 9286 in a counterclockwise direction returns the access device 9280 to the low profile configuration for removal.

FIGS. 202-203 illustrate one embodiment of an access device 9300 having an inflatable portion. In the illustrated embodiment, the access device 9300 incorporates a hoop skirt balloon system. In a deployed configuration, highly pressurized hoop balloons 9302 hold a skirt section 9304 and a collar section 9306 open to provide access to a surgical location. Inflation ports 9308, 9310 can be provided for the collar section 9306 and for the skirt section 9304. In one embodiment, the access device 9300 comprises an oval-shaped mounting ring 9312 near a proximal portion 9314 of the access device 9300. The hoop balloons 9302 are sized so that when inflated, the cross sectional area at a distal portion 9316 of the access device 9300 is greater than the cross-sectional area at a proximal portion 9314 of the access device 9300. The access device 9300 can be constructed with hoop balloons 9302 connected with web material 9318 or any other suitable material. When inflated, the hoop balloons 9302 are relatively more rigid than the web material 9318 connecting adjacent hoop balloons 9302. The flexibility of the compliant web material 9318 between the hoop balloons 9302 generally allows the proximal portion 9314 of the access device 9300 to be manipulated to provide better access and visualization of the surgical area. The flexibility of the hoop skirt balloon arrangement is advantageous for reaching some anatomical structures. The access device 9300 can be inflated by hand pump or by a pressure cartridge, such as, for example, a $CO_2$ cartridge. The access device 9300 can be deflated using a vacuum pump. In other embodiments, pressure can be released by simply opening the inflation ports 9308, 9310.

With reference to FIG. 204, in one embodiment, a collapsible access device 9320 comprises semicircular, semi-oblong, or a combination of semi-circular and semi-oblong bands 9322 interleaved together. Individual bands 9322 can pivot, or pivot and translate, along an internal track 9324. The bands 9322 can be configured so that a proximal portion 9326 of the access device 9320 has cross-sectional area that is generally smaller than the cross-sectional area at a distal portion 9328 of the access device 9320, in the expanded configuration. In the reduced profile configuration, the semicircular bands 9322 can be positioned in a collapsible arrangement, each band 9322 fitting at least partially within the next larger size band 9322. To deploy the access device 9320 into the expanded configuration, one or more internal rods 9330 can be provided in the internal track 9324 to push the bands 9322 toward the expanded configuration.

With reference to FIGS. 205-206, one embodiment of an access device 9340 includes a plurality of weaved bands 9342. The bands 9342 preferably are stainless steel bands; however, other materials can be used. The bands 9342 are coupled with first and second end collars 9344, 9346 at the proximal and distal ends 9348, 9350 of the access device 9340. In one embodiment, the end collars 9344, 9346 preferably are formed of an elastomeric overmold. In other embodiments any suitable material can be used. In the access device 9340 of the illustrated embodiment, the cross-sectional area of the access device 9340 can be increased or reduced without the use of an expanding tool. Pulling up on the proximal collar 9344 reduces the cross-sectional area of the access device 9340 for insertion. Pushing down on the proximal collar 9344 increases the cross-sectional area to provide increased access to the surgical location.

FIG. 207 is a cross-sectional view of one embodiment of an access device 9360 having a generally spherical joint 9362 similar in function to a ball joint located between a proximal 9364 and a distal portion 9366. The spherical joint 9362 includes in one embodiment a first spherical surface 9368 and a second spherical surface 9370 facing the first spherical surface 9368. The surfaces 9368, 9370 are configured so that the proximal portion 9364 can be manipulated with respect to the distal portion 9366 in a multitude of directions to enhance access to and visualization of a surgical location. In the illustrated embodiment, the proximal portion 9364 can be pivoted about multiple axes.

FIG. 208 is a schematic view of another embodiment of an inflatable access device 9380 that is shown applied across an incision in a patient's skin 9382. The access device 9380 has a positionable passageway 9384. The access device 9380 preferably comprises a balloon skirt 9386 along a distal portion 9388 of the access device 9380. In the expanded configuration, the balloon skirt 9386 is inflated and defines a passage 9390 that has a cross-sectional area at a distal location 9392 that is greater than a cross-sectional area at a more proximal location 9394. In some embodiments, the balloon portion 9386 can be positioned at least partially outside the patient. For example, the balloon 9386 can extend above the skin incision 9382, in some embodiments. The balloon 9386 has an inflation fill port 9396 in one embodiment. The access device 9380 has collar portion 9398 that can be positioned inside an opening in the balloon skirt portion 9386. In one embodiment, the collar 9398 is movable to various positions because of the flexibility of the balloon portion 9386. The proximal collar portion 9398 can be easily repositioned while in the opening of the balloon skirt 9386 to better access a surgical location. In use, a dilator can be used to expand the incision 9382 in the patient's skin. The access device 9380, with the balloon 9386 deflated, is inserted into the patient. The balloon 9386 is inflated to retract tissue and provide an expanded surgical area. In some embodiments, the collar 9398 can be inserted simultaneously with the deflated balloon 9386. In some embodiments, the collar portion 9398 can be inserted after inflation of the balloon skirt portion 9386. The flexibility of the balloon skirt portion 9386 enables the collar 9398 to be manipulated, angled, or rotated to achieve access and visualization of the surgical location as desired.

With reference to FIG. 209, an access device 9400 has a proximal portion 9402 with a generally oval-shaped cross-section, a distal portion 9404 with right and left skirt portions 9406, 9408, and a plurality of leaves 9410 positioned between the right and left skirt portions 9406, 9408. In other embodiments, the proximal portion 9402 can have any other oblong shaped cross section. Three leaves 9410 are coupled with the proximal portion 9402 of the access device 9400 in one embodiment. A first leaf 9412 is coupled with the left skirt portion 9408. A second leaf 9414 is coupled with the right skirt portion 9406. The third leaf 9416 is coupled with the first and second leaves 9412, 9414. The leaves 9410 can translate over each other and move from a contracted configuration to an expanded configuration. The access device 9400 of the illustrated embodiment is particularly advantageous because the distal portion 9404, in the expanded configuration, can accommodate surgical procedures across up to four or more adjacent vertebrae. In one embodiment, the distal portion 9404 of the access device 9400 can expand up to about 120 mm.

With reference to FIG. 210, an access device 9420 has a generally oval-shaped proximal portion 9422 and an expandable distal portion 9424. The expandable distal portion 9424 has left and right skirt portions 9426, 9428. The left and right skirt portions 9426, 9428 are coupled with the proximal portion 9422 with pins or rivets 9430. The distal portion 9424 comprises first and second slide members 9432, 9424 coupled with the proximal portion 9422 on either side of the access device 9420. The slide members 9432, 9434 preferably comprise slot portions 9436. The distal portion 9424 of the access device 9420 comprises first and second extension members 9438, 9440 on each side. In the illustrated embodiment, the first extension member 9438 is coupled with the left skirt portion 9426 via a pin, or a rivet, or another suitable coupling member 9442. The second extension member 9440 is coupled with the right skirt portion 9428 via a pin, or a rivet, or another suitable coupling member 9444. The first and second extension members 9438, 9444 are coupled with the slot 9436 of the slide member 9432. In one embodiment, the slide member 9432 and the first and second extension members 9438, 9440 form a linkage enabling the expansion of the distal portion 9424. The distal portion 9424 of the access device 9420 comprises a flexible mesh 9446 extending between the slide member 9432 and the left and right skirt portions 9438, 9440. The flexible mesh 9446 can comprise any type of flexible material including stretchable materials, e.g., polymeric materials, elastomeric materials, or metal mesh constructions. In the illustrated embodiment, the first and second extension members 9438, 9440 are coupled with the slide member 9432 by a coupling member 9450 at a bottom portion of the slot 9436 in an expanded configuration. In one embodiment, in the expanded configuration, the first and second extension members 9438, 9440 act as a locking structure to maintain the skirt portion 9426, 9428 in the expanded configuration. In the expanded configuration, the flexible mesh 9446 preferably reduces the amount of tissue that can penetrate into a passage 9448 defined by the access device 9420. To return the access device 9420 to the low profile configuration, the coupling member 9450 is raised in the slot 9436 so that the left and right skirt portions 9426, 9428 are drawn together as the extension members 9438, 9440 move toward the center of the access device 9420. The access device 9420 of the illustrated embodiment is particularly useful in surgical procedures involving multiple spinal levels.

With reference to FIG. 211, an access device 9460 has a proximal portion 9462 and an expandable distal portion 9464. The proximal portion 9462 can have a circular cross-section, an oval cross-section, or another oblong shaped cross-section. The distal portion 9464 of the access device 9460 comprises a plurality of blades 9466. The blades 9466 are coupled with an intermediate ring 9468. The intermediate ring 9468 is coupled with the proximal portion 9462 of the access device 9460. The proximal portion 9462 of the access device 9460 preferably can pivot with respect to the intermediate ring 9468 and with respect to the distal portion 9464 of the access device 9460. The blades 9466 can be positioned in a collapsed configuration for insertion into a patient and can be fanned out into an expanded configuration to provide space for performing a surgical procedure. The blades 9466 preferably pivot with respect to the intermediate ring 9468. The intermediate ring 9468 enables the access device 9460 and the proximal and distal portions 9462, 9464 to be positioned in or to have a plurality of pivot configurations.

FIGS. 212-213 illustrate another embodiment of access device 9480. The access device 9480 has a proximal portion 9482 and a distal portion 9484. The access device 9480 has an intermediate ring 9486 configured to expand or contract the distal portion 9484 of the access device 9480. In the illustrated embodiment, the proximal portion 9482 has an oval-shaped cross-section. The distal portion 9484 of the access device 9480 has left and right skirt portions 9488, 9490. The distal portion 9484 of the access device 9480 also has first and second mesh leaves 9492, 9494 coupled with the proximal portion 9482 of the access device 9480. In the illustrated embodiment, the mesh leaves 9492, 9494 include a mesh 9496 and a frame member 9498. The frame member 9498 surrounds the mesh 9496. In one embodiment, the frame 9498 is configured to collapse along at least one edge to enable the frame member 9498 to take on a low profile configuration. For example, one edge of the frame 9498 may have a gap formed therein. In some embodiments, e.g., where the frame member 9498 is collapsible, the mesh 9496 is a stretchy member that can expand as the access device 9480 is deployed. The frame member 9498, in combination with the mesh 9496, provides sufficient rigidity to prevent tissue encroachment, to retract tissue, or to retract tissue and prevent tissue encroachment. In some embodiments, movement of the intermediate ring 9486 can actuate the expansion or contraction of the access device 9480 at the distal portion 9484. With reference to FIGS. 212-213, moving the intermediate ring 9486 proximally acts to contract the distal portion 9484 of the access device 9480. Moving the intermediate ring 9486 distally acts to expand the distal portion 9484 of the access device 9480. The mesh 9496 material can be a metal weave, a polymeric material, or any other suitable material for preventing or minimizing the intrusion of tissue into the surgical space.

With reference to FIGS. 214-215, an access device 9500 is provided having a proximal portion 9502 and an expandable distal portion 9504. The access device 9500 has an intermediate ring 9506 coupled with the proximal portion 9502 of the access device 9500 and also coupled with the distal portion 9504 of the access device 9500. The intermediate ring 9506 in some embodiments can be configured to actuate the expandable distal portion 9504 from an expanded configuration to a contracted configuration. The distal portion 9504 of the access device 9500 in the illustrated embodiment comprises a plurality of wire loops 9508 coupled with left and right skirt portions 9510, 9512 of the distal portion 9504. The wire loop portions 9508 preferably act to limit tissue intrusion into a surgical space defined within the access device 9500. In the illustrated embodiment, movement of the intermediate ring 9506 proximally acts to expand the distal portion 9504 of the access device 9500. Moving the intermediate ring 9506 distally acts to contract the distal portion 9504 of the access device 9500.

With reference to FIGS. 216-219, an access device 9520 has a proximal portion 9522 and an expandable distal portion 9524. The access device 9520 preferably is configured to be expanded or contracted configuration by manipulating a proximal portion 9522 of the access device 9520. The distal portion 9524 has left and right skirt portions 9526, 9528. In the illustrated embodiment, the left and right skirt portions 9526, 9528 are coupled with, or integrally formed with, proximal skirt extensions 9530. The proximal skirt extensions 9530 are configured to cooperate with a collar portion 9532 to form a proximal portion 9522 of the access device 9520. The left and right skirt portions 9526, 9528 comprise holes or slots 9534 for receiving a coupling device 9536, such as a pin or a rivet. The left and right skirt portions 9526, 9528 can pivot about the coupling device 9536. In the illustrated embodiment, the collar portion 9532 is coupled with the left and right skirt portions 9526, 9528 by the rivet on first and second sides of the access device 9520. The left and right skirt portions 9526, 9528 can have flexed hinge points 9538 where the skirt portion is formed or coupled with the proximal skirt extensions 9530. The access device 9520 can be actuated from a closed position to an open position by pulling up on the proximal skirt extension 9530 while pushing down on the proximal collar portion 9532. Pushing down on the proximal collar portion 9530 forces the skirt portions 9526, 9528 to pivot about the flexed hinge points 9538 and rotate the skirt portions 9526, 9528 into the expanded configuration. The access device 9520 is returned to a closed position by pressing down on the proximal skirt extensions 9530 and pulling up on the proximal collar portion 9532. Manufacturing an access device 9520 according to the illustrated embodiment advantageously reduces the number of parts associated with providing an access device 9520, thereby reducing the expense and cost of production.

FIGS. 220-221 show one embodiment of an access device 9540 having a proximal portion 9542 and a distal portion 9544. An expander tool 9546, which may be used to increase the cross-sectional area of the distal portion 9544, is shown in FIG. 220 inserted into the access device 9540.

The distal portion 9544 includes a first longitudinally extending side 9548 and a second longitudinally extending side 9550 with a tab-in-slot engagement arrangement. In one arrangement, a locking tab 9552 with a latch hook 9554 is provided on opposing sides of the second longitudinally extending side 9550 of the distal portion 9544 and a catch slot 9556 is provided on opposing sides of the first longitudinally extending side 9548 of the distal portion 9544. The catch slot 9556 is configured to receive the latch hook 9554 which causes the first and second longitudinally extending sides 9548, 9550 to be engaged, preventing transverse motion of the sides 9548, 9550 with respect to each other. The catch slot 9556 and latch hook 9554 can be positioned such that their engagement occurs when the distal portion 9544 is expanded or to be engaged when the distal portion 9544 is contracted. Thus, the tab-in-slot engagement arrangement may prevent inadvertent expansion or inadvertent contraction of the distal portion 9544. In another embodiment, a plurality of slots similar to the slot 9556 can be provided to enable discrete expansion positions for the distal portion 9544.

The latch hooks 9554 and the catch slots 9556 preferably are located on or near a minor axis of the distal portion 9544. This facilitates expansion of the distal portion 9544. For example, the expansion of the distal portion 9544 may be achieved by first inserting the expander tool 9546 into the distal portion 9544 through the proximal portion 9542. The expander tool 9546 may then be aligned with the latch hooks 9554 which extend through the catch slots 9544 into an enclosed volume 9558 in the reduced cross-sectional size arrangement of the distal portion 9544, which volume 9558 is defined at least in part by the distal portion 9544. The proximal end of the expander tool 9546 may then be actuated to cause the distal portion thereof to engage the latch hooks 9554. A pair of arrows C indicate actuation of the expander tool 9546 to engage the latch hooks 9554. Further actuation of the expander tool 9546 causes the latch hooks 9554 to be moved outside of the catch slots 9556 so that the first and second sides 9548, 9550 of the distal portion 9544 no longer engage each other.

The expander tool 9546 may then be rotated about 90 degrees so that the distal portion thereof may engage a major axis of the distal portion 9544. Expansion of the expander tool 9546 causes the distal portion thereof to engage an inner surface of the distal portion 9544. Further expansion thereof causes the distal portion 9544 to be further expanded. Where the distal portion 9544 is provided with a plurality of catch slots 9556, the expansion along the major axis may index the distal portion 9544 to a selected discrete location. Where a single catch slot 9556 is provided, the distal portion 9544 may be expanded to a discrete expanded position. In this case, the latch hook 9554 will not be in engagement with a catch slot 9556 in the un-expanded configuration. Thus, the motion indicated by the arrows C will not be needed. Of course, where desired, the distal portion 9544 could be expanded to any position between the un-expanded position and the position at which the latch hook 9554 and the catch slot 9556 become engaged if suitable conditions exist to prevent the inadvertent contraction of the distal portion 9544.

In another embodiment, a distal portion is provided with a single catch slot and a single latch hook which is received by the catch slot in the un-expanded configuration. Expansion of this embodiment is similar to the expansion described above except that after the latch hook is disengaged from the catch slot, as discussed above, the distal portion may be expanded to any of a range of positions.

In one embodiment, one or more rivets are provided to maintain flap contact, e.g., on the proximal edge of the distal portion 9544.

In another embodiment, each of the sides is provided with one latch hook and one catch slot. In particular, FIG. 221 shows a portion of another embodiment of a distal portion that includes a first longitudinally extending side 9548a that includes a locking tab 9552a with a latch hook 9554a and a catch slot 9556a. The catch slot 9556a and the latch hook 9554a are located across the first longitudinally extending side 9548a from one another. These structures are configured to engage corresponding structures on a second longitudinally extending side (not shown). The expansion of the distal portion constructed from the first longitudinally extending side 9548a and the corresponding second longitudinally extending side is expandable as discussed above in connection with the distal portion 9544.

FIG. 222 is a cross-sectional view of a portion of an access device 9560 with a deployment mechanism 9564. The access device 9560 includes a proximal portion 9568 and a distal portion 9572. Engagement of the proximal and distal portions 9568, 9572 is at least in part defined by a pivot assembly 9576 that includes a pivot notch 9580 and a pivot finger 9584, as shown in FIG. 224. The pivot assembly 9576 enables the distal portion 9572 and the proximal portion 9568 to pivot with respect to each other.

The deployment mechanism 9564 preferably includes a pull strap 9588 and a plurality of catch hooks 9592. Preferably three catch hooks 9592 are provided. The catch hooks 9592 are configured to engage a portion of the proximal portion 9568 of the access device 9560 when the deployment mechanism is moved to a deployed position. The pull strap 9588 is an elongate member that has a distal end 9596 and a proximal end 9600. Preferably, a rivet 9604 (or other suitable fastener) is provided to couple the distal end 9596 of the pull strap 9588 with the distal portion 9572 of the access device 9560. The proximal end 9600 of the pull strap 9588 preferably includes a pull feature, such as a through-hole 9608, that provides a means to exert a force on the pull strap 9588. Application of a force on the pull strap 9588 is illustrated by an arrow D in FIG. 222.

An arrow D illustrates motion that actuates the deployment mechanism 9564 from the un-deployed configuration (FIG. 222) to the deployed configuration (FIG. 223) to deploy the access device 9560. In one embodiment, the pull strap 9588 has a length sufficient to allow the hooks 9592 to extend proximal of the proximal end of the proximal portion 9568. Preferably the hooks 9592 are also configured to engage the proximal end of the proximal portion 9568, as illustrated in FIG. 223. The access device 9560 is thereby locked into the expanded state illustrated in FIG. 223. The pivot assembly 9576 permits the distal portion 9572 of the access device 9560 to move with respect to the proximal portion 9568 when the force applied to the pull strap 9566 is transmitted to the distal portion 9572. In particular, the pivot finger 9584 pivots in the pivot notch 9580 as the distal portion 9572 extends outwardly.

An arrow E in FIG. 223 illustrates further expansion of the access device 9560. In particular, where further expansion of the distal portion 9572 is desired, an expander tool, such as the expander tool 9556 of FIG. 220 may be inserted into the access device 9560. A force urging greater expansion of the distal portion 9572, which is illustrated by the arrow E, may be applied by the expander tool 9556. Deployment may be assisted by the expander tool 9556 in this manner.

Movement of the deployment mechanism 9564 from the deployed position back to the un-deployed position may be achieved by providing a force and movement of the proximal end 9600 of the pull strap 9588 as indicated by an arrow F. This force and movement moves the catch hook 9592 off of the proximal end of the proximal portion 9568. The pivot finger 9584 is then free to pivot in the pivot notch 9580, allowing the distal portion 9572 to move from the deployed position (FIG. 223) back to the un-deployed position (FIG. 222), or to a less deployed, but not fully un-deployed position.

FIG. 225 is a perspective view of another embodiment of an access device 9620 having a proximal portion 9622, a distal portion 9624 that has a first configuration for insertion and a second configuration after being inserted and expanded, and a lock 9626. The second configuration is illustrated in FIG. 225. The access device 9620 is configured to be locked into at least the second configuration.

In the illustrated embodiment, the distal portion 9624 comprises a sheet portion 9628 that is an arcuate in shape if rolled flat. However, when coupled with the proximal portion 9622 and in the second configuration, the sheet portion 9628 of the distal portion 9624 forms a frusto-conical shape with an area of overlap 9632. The area of overlap 9632 is the area where a first edge 9636 of the sheet portion 9628 extends some distance over a second edge 9640. A first area 9644 of the sheet portion 9628 adjacent the first edge 9636 extends outside of a second area 9648 of the sheet portion 9628 adjacent the second edge 9640. Thus, the first area 9644 forms an outside surface while the second area forms an inside surface of the distal portion 9624.

The lock 9626 can take many forms. FIG. 225-226 illustrate a J-hook lock 9652. The J-hook lock 9652 includes a J-shaped lock tab 9656 and a locking slot 9660. The locking slot 9660 is formed in the sheet portion 9628 at a location selected to provide sufficient expansion of the distal portion 9624. The J-shaped lock tab 9656 is movable from a first location outside the locking slot 9660 to a second location within the locking slot 9660. In the first location, the J-shaped lock tab 9656 extends from the first area 9644 (e.g., the outer surface) around the distal end of the distal portion 9624 to the second area 9648 (e.g., the inner surface). See FIG. 226.

Movement of the J-shaped lock tab 9656 to the second location is indicated by an arrow G in FIG. 225. The J-shaped lock tab 9656 extends from the first area 9644 (e.g., the outer surface), through the locking slot 9660, and around the second edge 9640 when in the second position. In the second position, the J-shaped locking tab 9656 prevents movement of the second area 9648 with respect to first area 9644 to lock the distal portion 9624 in the second configuration.

In the illustrated embodiment, the first and second areas 9644, 9648 are two ends of a single curled sheet. In another embodiment, the first and second areas 9644, 9648 may be overlapping portions of two different curled elongate sheets that generally extend along longitudinal axes located between the two sheets. Other embodiments of distal portions and other access devices can employ a lock similar to the lock 9626.

FIG. 227 is a partial distal-end view of an access device similar to the access device 9620 showing another embodiment of a lock 9626a. The lock 9626a includes an area of overlap 9632a. In the area of overlap 9632a, a first area 9644a of a sheet portion 9628a adjacent a first edge 9636a generally extends outside of a second area 9646a of the sheet portion 9628a adjacent a second edge 9640a. An undulation 9660 is formed at a location selected to provide sufficient expansion of the access device with which the lock 9626a is used. The undulation provides a notch 9664 into which the first edge 9636a rests in the second configuration. Inadvertent collapse of the access device with which the lock 9626a is used is thereby prevented.

FIG. 228 is a partial distal-end view of an access device similar to the access device illustrated in FIG. 225, showing another embodiment of a lock 9626b. The lock 9626b is formed at a first edge 9636b and a second edge 9640b. The first and second edges 9636b, 9640b are formed with one or more interlocking protrusions such that when the distal portion of the access device having the lock 9626b is expanded a desired amount, the protrusion(s) on the first and second edge 9636b, 9640b engage one another in a manner that prevents inadvertent collapse of the distal portion.

With reference to FIGS. 229-231, additional embodiments of access devices having locking elements are illustrated. In the first embodiment, the access device 9670 has a proximal portion 9672 and a distal expandable portion 9674. The distal expandable portion has left and right skirt components 9676, 9678. The left and right skirt components 9676, 9678 are coupled with the proximal portion 9672 of the access device 9676 with a rivet 9680. The left and right skirt components 9676, 9678 comprise slots 9682, 9684. A rivet 9686 is placed within the slots 9682, 9684 of the right and left skirt components 9676, 9678. The left and right skirt components 9676, 9678 can be overlapped to slide relative one another from a contracted configuration to an expanded configuration. At a distal portion 9674 of the access device 9670, a spring tab 9688 is formed in the right skirt component 9678. As the distal portion 9674 of the access device 9670 is expanded, and the left skirt portion 9676 moves relative the right skirt portion 9678, the spring tab 9688 is configured to pop out to hold the left skirt component 9676 in the expanded configuration relative the right skirt component 9678. The spring tab 9688 acts to lock the skirt in the open position. The spring tab 9688 has an access hole so that the spring tab 9688 can be manipulated with an instrument to unlock or disengage the tab hook prior to returning the access device 9670 to the reduced profile configuration.

In another embodiment illustrated in FIGS. 230-231, an access device 9690 has a proximal portion 9692 and a distal portion 9694. The distal portion 9694 has left and right skirt components 9696, 9698 coupled with a proximal portion 9692 of the access device 9690 via a rivet 9700. The left and right skirt components 9696, 9698 comprise slots 9702, 9704 and a rivet 9706 to couple the left and right skirt components 9696, 9698 together. As the left and right skirt components 9696, 9698 are expanded, the rivet 9700 travels along the slots 9702, 9704. A clip 9708 is provided on one of the left and right skirt components 9696, 9698. The clip 9708 can be a piece of metal shaped in the form of a "J". In the illustrated embodiment, the clip 9708 is coupled with the skirt component 9696 using a rivet 9710, or other coupling mechanisms, to allow the clip 9708 to rotate relative to the skirt component 9696. In the illustrated embodiment, the J clip 9708 is coupled with the left skirt component 9696. The right skirt component 9698 comprises a slot 9712 for receiving the clip 9708 when the distal portion 9694 of the access device 9690 is in the fully expanded configuration. The clip 9708 can be manipulated with a surgical instrument to hold open the distal portion 9694 of the access device 9690 in the expanded configuration. The tab 9714 on the end of the clip preferably is strong enough to withstand the forces placed on the distal portion 9694 of the access device 9690.

FIGS. 232-234 illustrate one embodiment of a retractor 9720 or access device that may advantageously be deployed to enable surgical procedures to be performed minimally invasively. The retractor 9720 is similar to those of FIGS. 191 and 210, except as set forth below. In addition, the retractor 9720 advantageously can be coupled with a viewing element mount arrangement that enables expansion of the retractor, particularly at the proximal end. An example of such an arrangement is discussed below in connection with FIG. 271 and in greater detail in U.S. patent application Ser. No. 10/845,389, filed May 13, 2004, bearing the title ACCESS DEVICE FOR MINIMALLY INVASIVE SURGERY.

FIGS. 232-234 show that the retractor 9720 includes an elongate body 9722 and an expandable shroud 9724. The term "shroud" is used in its ordinary sense to mean something that covers, screens, or guards and is a broad term and it includes flexible and expandable structures that at least partially cover, screen, or guard an access device, a retractor, an elongate body, a passage, a working space, or a surgical field. The term "shroud" includes structures that at least partially cover, screen, or guard a passage, a working space, or a surgical field from encroachment of tissue displaced by an access device, a retractor, or an elongate body when applied to a patient. As discussed more fully below, the arrangement of the retractor 9720 and the shroud 9724 enable the retractor 9720 to expand to create an enlarged surgical field whereby surgical procedures may be facilitated. The expandable shroud 9724 enables the elongate body 9722 to be relatively simple while creating a relatively large surgical field and at the same time remaining low-profile during insertion.

In some embodiments, the elongate body 9722 has a distal portion 9726 and a proximal portion 9728 that are discrete members. In other embodiments, the retractor 9720 has an elongate body 9722 that comprises a portion similar to the distal portion 9726 without the proximal portion 9728. In other embodiments, the retractor 9720 has a portion similar to the proximal portion 9728 without the distal portion 9726.

In one embodiment, the distal portion 9726 comprises a first elongated member 9730 and a second elongate member 9732. The first and second elongate members 9730, 9732 are generally semicircular in transverse cross-section in one embodiment and are generally oval in another embodiment. The first and second elongate members 9730, 9732 can be other suitable shapes as well, such as any suitable oblong shape. In the illustrated embodiment, the first and second elongate members 9730, 9732 are generally semicircular and have about the same radius of curvature. The first elongate member has a first elongate edge 9734 and the second elongate member has a second elongate edge 9736.

The elongate body 9722 is able to be positioned in a multiplicity of positions, as discussed in greater detail below. One of the positions of the elongate body 9722 is a low-profile or closed position, which is shown in FIG. 232. In the low-profile position, the first longitudinal edge 9734 is positioned very close to the second longitudinal edge 9736. In one arrangement, a circle is defined within the first and second elongate members 9730, 9732 when the elongate body is in the closed position.

The elongate body 9722 also has an outer surface 9738 and an inner surface 9740. The inner surface 9740 at least partially defines a passage 9742 that provides access for a surgeon to a surgical location so that a surgeon can perform a surgical procedure, as discussed herein. In one embodiment, the closed or low-profile configuration, the elongate body 9722 fully encloses the passage 9782. As discussed more fully below, when the elongate body 9722 is in an expanded configuration, the passage 9782 is only partially defined by the inside surface of the elongate body 9722. Two expanded configurations are illustrated in FIGS. 233 and 234. In the illustrated embodiment, the inner surface of the elongate body is located on the first and the second elongate members 9730, 9732.

As discussed above, in some embodiments, the elongate body 9722 comprises discrete proximal and distal portions 9728, 9726. The proximal portion preferably comprises a first proximal side portion 9742 and a second proximal side portion 9744. The first proximal side portion 9742 has a third longitudinal edge 9746. The second proximal side portion 9744 has a fourth longitudinal edge 9748. The first and second proximal side portions are movable relative to each other such that the third and fourth longitudinal edges 9750, 9752 can be positioned in close proximity to each other or spaced apart, e.g., by a selected amount, as discussed more fully below.

In one embodiment, each of the first and second proximal side portions 9742, 9744 has a corresponding inside surface 9750, 9752 that at least partially defining the passage. As discussed more fully below, the proximal portion 9728 is capable of having a circular transverse cross-section in one configuration. The proximal portion 9728 preferably also is capable of having or at least partially defining an oval configuration, or other suitable configuration, such as oblong, in other embodiments.

Preferably the proximal portion 9728 is coupled with the distal portion 9726 in a manner that permits the distal portion 9726 to pivot with respect to the proximal portion 9728. The distal portion 9726 may be enabled to pivot by configuring the elongate body 9722 with one or more pivot joints 9754.

As discussed above, the retractor preferably includes an expandable shroud 9724. The shroud 9724 may be made of any suitable material that can stretch during expansion of the elongate body 9722 (or while the elongate body is in the enlarged configuration). In one embodiment, the shroud 9724 is coupled with the elongate body 9722. In one embodiment, the expandable shroud 9724 is an expandable sleeve that is positioned over the elongate body 9722. The shroud 9724 preferably is positioned over at least the distal portion 9726 where the elongate body 9722 comprises proximal and distal portions 9728, 9726. In other embodiments, the expandable shroud 9724 is positioned over only one of the proximal and distal portions 9728, 9726 where both proximal and distal portions 9728, 9726 form part of the retractor 9720.

In one arrangement, the expandable shroud 9724 is configured to extend at least from the first longitudinal edge 9734 to the second longitudinal edge 9736. In another embodiment, the expandable shroud 9724 is configured to extend at least from the third longitudinal edge 9746 to the fourth longitudinal edge 9748. In one arrangement, the expandable shroud 9724 is configured to extend at least from the first longitudinal edge 9734 to the second longitudinal edge 9736 and from the third longitudinal edge 9746 to the fourth longitudinal edge 9748. In some embodiments, the expandable shroud 9724 does not extend all the way around the first and second elongate members 9730, 9732 or all the way around the first and second proximal side portions 9742, 9744.

In some embodiments, the retractor also includes a first linkage 9756 that is coupled with the elongate body 9722. In one embodiment, the first linkage 9756 includes a first link member 9758 and a second link member 9760 that is coupled with the first link member 9758 at a pivot joint 9762. The first link member 9758 may be coupled with the first elongate member 9730 adjacent the first longitudinal edge 9734. The second link member 9760 may be coupled with the second elongate member 9732 adjacent the second longitudinal edge 9736. In the illustrated embodiment a second linkage member 9764 is provided and is coupled with the elongate body 9722 on the opposite side of the elongate body 9722.

In one embodiment, the first linkage 9756 has a collapsed configuration (shown in FIG. 232) and extended configurations. A first extended configuration is shown in FIG. 233 and a second extended configuration is shown in FIG. 234. As discussed above, in the illustrated embodiment, a corresponding second linkage 9764 is provided that couples a third longitudinal edge 9766 and a fourth longitudinal edge 9768 of the elongate body 9722. The third longitudinal edge 9766 is located on an opposite side of the elongate body 9722 from the first longitudinal edge 9734 and the fourth longitudinal edge 9768 is located on an opposite side of the elongate body 9722 from the second longitudinal edge 9736.

The retractor of FIGS. 232-234 operates to provide access to a surgical location within a patient. In particular, the elongate body 9722 is capable of having a low-profile configuration for insertion into the patient. One suitable configuration for insertion is one wherein the passage 9782 has a generally circular cross-section. This may be achieved by moving the first and second elongate bodies 9730, 9732 and/or the first and second proximal side portions 9742, 9744 toward each other until the longitudinal edges 9734, 9736 are adjacent to each other. Other configurations may also be accommodated. For example, the inside surfaces of the elongate body 9722 can be configured with a curved transverse cross-section that is not circular.

Insertion of the retractor 9720 into the patient may be performed in any suitable manner. For example, one or more dilators or obturators may be used to form an expanded channel into the patient, as discussed herein. As also discussed herein, where a retractor has a non-circular configuration, one or more dilators with non-circular transverse cross-sectional profiles may be used.

Once the retractor 9720 is advanced to the surgical location within the patient, the elongate body 9722 can be expanded. Where the technique for providing access employs a retractor with discrete proximal and distal portions 9728, 9726, multi-stage expansion can be employed. For example, as shown in FIG. 233, the distal portion 9726 may be expanded from the low-profile configuration to an enlarged configuration. In the enlarged configuration, the first longitudinal edge 9734 is spaced apart from the second longitudinal edge 9736. The expandable shroud 9724 is configured to extend from the first longitudinal edge 9734 to the second longitudinal edge 9736 when the first and second edges 9734, 9736 are spaced apart. The shroud 9724 partially defines the passage 9782. In the expanded configuration of FIG. 233, the cross-sectional area of the passage 9782 at a first location 9770 is greater than the cross-sectional area of the passage 9782 at a second location 9772, wherein the first location 9770 is distal to the second location 9772.

The retractor 9720 may be actuated from the low-profile configuration to the expanded configuration by any suitable technique. For example, the linkages 9756, 9764 may be articulated to force the distal ends of the first and second elongate bodies 9730, 9732 apart. In one embodiment, the linkages 9756, 9764 are located outside the passage 9782. As a result, the retractor 9720 is configured to be expanded from the outside of the passage 9782. This advantageously enables all the space in the passage 9782 to be used for procedures. In another embodiment, the linkages 9756, 9764 are located within the passage 9782. This arrangement is advantageous in that the linkages can more freely rotate in the enclosed space. In another embodiment, the linkage may be partly within the passage and partly outside to provide a combination of these benefits while maintaining the retractor in a relatively low-profile.

FIG. 234 illustrates a second stage of expansion of the retractor 9720. In particular, the proximal portion 9728 has been actuated to increase the size of the passage 9782 in the proximal portion 9728. This is achieved by moving the proximal side portions 9742, 9744 away from each other. In this expanded configuration, the linkages 9756, 9764 generally maintain the same position as is shown in the first stage of expansion of FIG. 233. As a result, the first and second elongate members 9730, 9732 are tilted so that the outside surfaces thereof are at a less-steep angle. This tilts the distal edges of the first and second elongate members 9730, 9732 to a generally flat orientation (e.g., in or nearly in a plane perpendicular to a longitudinal axis of the passage 9782).

The retractor 9720 provides for multi-state expansion while maintaining the passage 9782 in a substantially entirely enclosed configuration. The expanded or enlarged configurations enable procedures to be performed across one, two, three, or more than three adjacent vertebrae. The retractor 9720 can also be only partially expanded as is needed for the procedure.

Embodiments having an expandable shroud can also be employed advantageously in procedures such as the lateral or postero-lateral placement of replacement disks, as well as other developing procedures. FIG. 234A illustrates methods of applying an implant 9790, e.g. an intervertebral replacement disc, through the retractor 9720. Some methods for applying an implant are described further in U.S. patent application Ser. No. 10/842,651, filed May 10, 2004, which is hereby incorporated by reference herein in its entirety. With reference to FIG. 234A, the retractor 9720 preferably is actuated to the expanded configuration and the implant 9790 is delivered laterally as indicated by the arrow 9794 to a surgical location defined by the distal portion 9726 of the retractor 9720 at one lateral side of the vertebra V1 and into an interbody space I. In other techniques alternative approaches can be used. In one application, in order to facilitate insertion of the implant 9790, visualization of the surgical site may be achieved in any suitable manner, e.g., by use of a viewing element, as discussed herein. In one procedure, a gripping apparatus 9792, is coupled with one or more portions and/or surfaces of the implant 9790 to facilitate insertion of the implant 9790. The gripping apparatus 9792 and the implant 9790 are advanced through the proximal portion 9728 of the retractor 9720, through the surgical space, and into the interbody space I to deliver the implant 9790. In some embodiments, the method of applying an implant 9790 can be performed using other retractors or access devices described herein.

The retractor 9720 is particularly advantageous for delivering implants that are elongated. For example, some replacement discs are generally planar structures that are elongated in at least one dimension. The expandability of the proximal portion 9728 facilitates insertion of such an elongated implant. The proximal portion 9728 can be expanded such that the passage defined therein is long enough along the direction of expansion to accommodate a long dimension of an elongated implant. The degree of expansion of the proximal portion 9728 can be decreased after the elongated implant reaches the distal portion 9726 of the retractor 9720. This reduces the length of time that the skin and adjacent tissue is expanded in the region of the proximal portion 9728. In another technique, an implant that is elongated in at least one dimension can be oriented during delivery through the retractor 9720 such that the long dimension of the implant is transverse to the direction of expansion of the proximal portion 9728. In one technique, the proximal portion 9728 is expanded so that a gap at least as wide as the thickness of the implant is formed and is covered by the shroud 9724. The shroud 9724 can be configured to be flexible enough so that it can be deflected outward (e.g., perpendicular to the direction of expansion of the proximal portion 9728) to accommodate an implant with a long dimension that is greater than the width of the passage 9784 when the shroud 9724 is not deflected. Thus, an implant with a long dimension greater than the width of the elongate body 9722 in the proximal portion 9728 of the retractor 9720 can be delivered in a transverse orientation.

FIGS. 235-239 show another access device or retractor 9800 that is particularly advantageous in some application for retracting tissue to provide access to a surgical location (e.g., a spinal location) within a patient. The retractor 9800 is similar to the access devices described above in connection with FIGS. 123-150, except as set forth below. One feature of the retractor 9800 is that a proximal portion thereof is able to tilt relative to a distal portion to provide enhanced visibility of a surgical location (e.g., adjacent a spinal location), particularly of the far reaches of a surgical field exposed by the retractor 9800. As discussed further below, the proximal portion is able to tilt about at least two axes in one embodiment.

The retractor 9800 generally includes an elongate body 9804 and a passage 9808. The elongate body 9804 has a proximal portion 9812 and a distal portion 9816 in one embodiment. Where proximal and distal portions 9812, 9816 are provided these portions may be discrete portions of the elongate body 9804 or may be discrete, contiguous, or remote regions thereof. As with many of the embodiments described herein, the retractor 9800 can be configured such that the cross-sectional area of the passage 9808 at a first location is greater than the cross-sectional area of said passage at a second location, where the first location is distal to the second location. When in this expanded configuration, at least one of (and preferably both of) the first and the second locations are in the distal portion 9816. This configuration may be achieved by any suitable technique, such as those described herein (e.g., by expanding the distal portion 9816 with an expander tool).

The elongate body 9804 defines a length 9820 between the proximal portion 9812 and the distal portion 9816 along a longitudinal axis 9824. The length 9820 is sufficient such that the distal portion 9816 can be positioned inside the patient adjacent the spinal location while the proximal portion 9812 is accessible. The proximal portion 9812 preferably is accessible to the surgeon during a surgical procedure. In some applications, the retractor 9800 is applied such that at least a portion of the proximal portion 9812 remains outside the patient's body during the procedure.

In one embodiment, the elongate body 9804 is configured such that a transverse cross-section thereof has a first dimension 9828 that is longer than a second dimension 9832. The first dimension 9828 is perpendicular to the second dimension 9832. In one embodiment, the transverse cross-section of the elongate body 9804 or of the proximal portion 9812 is generally oblong. In another embodiment, the transverse cross-section of the elongate body 9804 or of the proximal portion 9812 is generally oval. In another embodiment, the transverse cross-section of the elongate body 9804 or of the proximal portion 9812 is generally circular.

The passage 9808 extends through the elongate body 9804 between the proximal portion 9812 and the distal portion 9816. Preferably, the passage 9808 is sized such that a plurality of surgical instruments may be advanced to the surgical location in connection with any suitable surgical technique, such as those disclosed herein. In some techniques, it is advantageous to be able to advance more than one surgical instrument through the passage 9808 at the same time. Advancement of surgical instruments to the surgical location may be facilitated by providing a generally smooth inside surface 9840 in the elongate body 9804.

The elongate body 9804 is configured such that the proximal portion 9812 may be tilted relative to the distal portion 9816 in a first direction generally aligned with the first dimension 9828 and in a second direction generally aligned with the second dimension 9832. In one embodiment, the elongate body 9804 is configured such that a portion of the elongate body 9804 may be rotated about a first axis 9844 such that the proximal portion 9812 may be tilted relative to the distal portion 9816. Also, the elongate body 9804 may be configured such that a portion of the elongate body 9804 may be rotated about a second axis 9848 such that the proximal portion 9812 may be tilted relative to the distal portion 9816. In this arrangement, the first axis 9844 is perpendicular to the second axis 9848. The tilting about the second axis is illustrated in FIG. 238, where a longitudinal axis 9824*a* of a portion of the passage 9808 corresponding to the proximal portion 9812 of the retractor 9800 is shown at an angle of a relative to the longitudinal axis 9824 of the elongate body 9804. In this position, visibility of a portion of the surgical field adjacent a lateral (or medial) side of the retractor 9800 may be enhanced. A second dashed line is shown in FIG. 238 opposite the longitudinal axis 9824*a* on the opposite side of the longitudinal axis 9824. This dashed line represents a range of motion of the proximal portion 9812 tilted to the opposite side about the axis 9848.

In one embodiment, the retractor 9800 has a coupling 9860 to enable tilting of the proximal portion 9812 relative to the distal portion 9816. The coupling 9860 preferably is located between the proximal and distal portions 9812, 9186. The coupling 9860 includes a gimbal ring 9864 and a plurality of pivot joints 9868 in one embodiment. The gimbal ring 9864 can take any suitable form and generally is an intermediate structure that enables the proximal and distal portions 9812, 9816 to not be directly coupled together so that they may be independently tilted about at least two axes. The gimbal ring 9864 preferably includes a first pair of apertures 9870 on opposite sides thereof. The first pivot axis 9844 may extend through the first pair of apertures 9870. The gimbal ring 9864 can also include a second pair of apertures 9872 located on opposite sides thereof. The second pivot axis 9848 may extend through the second pair of apertures 9872. The first pivot axis 9844 is perpendicular to the second pivot axis 9848 in one embodiment.

The pivot joints 9868 may include a member 9874 about which at least one of the gimbal ring 9864, the proximal portion 9812, and the distal portion 9816 can rotate. The member 9874 can be any suitable structure and in one embodiment is a rivet.

To assemble the retractor 9800, a member 9874 is extended through each of the apertures 9872 and a corresponding pair of apertures 9876 in the proximal portion 9812 and another member 9874 is extended through each of the apertures 9870 and a corresponding pair of apertures 9878 in the distal portion 9816. This arrangement of the retractor 9800 is relatively simple and thus can be easily assembled and used. Also, this arrangement provides the advantage of being able to enhance the visibility of the outer edges of the retractor 9800 when it is expanded by enabling the proximal portion 9812 of the elongate body 9804 to be tilted relative to the distal portion 9816, which is generally fixed in position when deployed within the patient.

Another embodiment that is similar to the embodiment discussed above in connection with FIGS. 235-239 is the embodiment discussed in connection with FIG. 207, wherein a ball joint-like arrangement is provided. This arrangement provides a first semi-spherical surface and a second semi-spherical surface. The second semi-spherical surface is configured to mate with the first semispherical surface and to enable a proximal portion of a retractor to be tilted relative to a distal portion thereof in a multiplicity of positions.

In another embodiment, the retractor 9800 does not have discrete proximal and distal portions 9812, 9816. Rather, a portion of the elongate body 9804 is made more flexible than the rest of the elongate body. The more flexible section is large enough and flexible enough to enhance visibility of the surgical field to an extent similar to that provided by the coupling and pin joint embodiments and to the ball joint embodiments discussed above. The more flexible section, in one embodiment, comprises a bellows that can expand and contract in response to a force being applied near the proximal end of the elongate body. In one arrangement, the bellows is configured so that a minimum force is required to begin to tilt the proximal portion so that the proximal portion will hold its position unless the surgeon desires to reposition it.

FIGS. 240-241 illustrate an obturator 9900 coupled with an access device 9902. In some embodiments, an obturator 9900 and a retractor, or an access device 9902, can be assembled and packaged together in a kit to be readily inserted into a patient. In such an embodiment, the access device 9902 is packaged in a generally tubular unexpanded shape. The proximal portion 9904 of the obturator can comprise handgrip features 9906, such as raised or lowered gripping portions, to facilitate manipulating and inserting the access device 9902 into the patient. In some embodiments, the obturator 9900 comprises a ledge 9928 to interface with the proximal end 9910 of the access device 9902. In some embodiments, the obturator 9900 can be cannulated 9912 for optional use over sequential dilators. The obturator 9960 can be used in expandable spinal access systems. The obturator 9900 can have a round or oblong shaped cross-section. With reference to FIGS. 242-243, in one embodiment, an obturator 9920 can be used for insertion of a multi-pivot oval access device 9922, such as that described with reference to FIGS. 235-239.

FIGS. 244-284 illustrate some additional embodiments of access device mounting fixtures. According to some embodiments, a viewing element or a viewing element mounting fixture can be provided for use with an access device. Viewing elements or viewing element mounting fixtures can comprise different configurations and structures. Some embodiments of viewing elements or viewing element mounting fixtures can comprise for example, ball joints that rotate and pivot, coiled springs, sliding rails, planetary gears, hose clamps, split shaft collars, spirograph-type configurations, and C-linkage type configurations. Still other embodiments are contemplated. Viewing element and viewing element mounting fixtures will be described in more detail below. Additionally, other types of mounting fixtures and support elements will be described.

As discussed above, the access devices described herein may be advantageously incorporated into a surgical assembly, similar to the surgical assembly 9000 illustrated in FIG. 182. This arrangement frees up the hands of the surgeon and provides stability to the access device 9006 and the space created for surgical procedures, among other advantages. One approach to incorporating the access devices into a surgical assembly is to provide an access device mounting fixture.

FIG. 244 shows one embodiment of a viewing element mount 10040 that provides adjustable, e.g., slidable, coupling of a viewing element 10042 to an access device or an access device mounting fixture (not shown). In the illustrated embodiment, the viewing element mount 10040 includes a carrier arm 10044, a support ring 10048, and a viewing element joint 10052. The carrier arm 10044 has an elongate shape with a proximal end 10056 and a distal end 10060. The carrier arm 10044 preferably also has an adjustment slot 10064 extending between the proximal and distal ends 10056, 10060. The adjustment slot 10064 permits the carrier arm 10044 to translate with respect to the support structure, as indicated by an arrow K and to pivot. Preferably a locking mechanism 10068 is provided, such as a lock knob, about which the carrier arm 10044 can be rotated, as indicated by arrows L.

The support ring 10048 is an annular member, in one embodiment, that defines an aperture 10072. The aperture 10072 provides a tool path and sight line opening through which a surgical location can be accessed and/or monitored. Preferably, the support ring 10048 is rotatable about an axis 10076 (which may correspond with the center of the tool path and sight line) extending through the center of the aperture 10072, as indicated by arrows M. The rotation of the support ring 10048 permits the rotatable adjustment of the viewing element 10042 about a proximal portion of an access device.

In one embodiment, the viewing element joint 10052 is supported by the support ring 10048 at a location near the aperture 10072. The viewing element joint 10052 is a ball joint in one embodiment. One skilled in the art should recognize that a ball joint will provide pitch adjustment, as indicated by arrows N, yaw adjustment, as indicated by arrows O, and roll adjustment, as indicated by arrows P, to the viewing element 10042. In one form, the ball joint also provide translational elevation adjustment, as indicated by arrows Q. In one embodiment, the translation of the viewing element 10042 is achieved by rotational advancement, e.g., by way of mating threads, as indicated by the helical arrow Q'.

The viewing element mount 10040 advantageously provides flexible adjustment of the viewing element 10042, after which the viewing element 10042 can be focused via a focusing knob 10080.

FIG. 245 shows another embodiment of a surgical assembly 10100 that is similar to the surgical assembly 9000. The surgical assembly 10100 includes a linkage 10104 that connects a viewing element support 10108 to a surgical assembly support 10112. The linkage 10104 is any suitable mechanical coupling that extends from the surgical assembly support 10112 to a location above an access device 10114. The linkage 10104 movably supports the viewing element support 10108, and thereby movably supports a viewing element 10116.

The linkage 10104 preferably is a two member linkage that permits a wide range of positioning of the viewing element support 10108 in two dimensions. The viewing element support 10108 is preferably rotatably coupled with one end of the linkage 10104, as is illustrated by arrows R. In one embodiment, the viewing element support 10108 is a camera mount. The viewing element 10116 can be rotated about an axis 10120 that extend through the viewing element 10116 and the viewing element support 10108. The surgical assembly 10100 thus is able to provide flexible positioning of the viewing element 10116 with respect to an access device 10124.

FIG. 246 is another embodiment of a surgical assembly 10140 that is similar to the surgical assembly 9000, except as set forth below. The surgical assembly 10140 includes a surgical assembly support 10144, an access assembly 10148, and a viewing assembly 10152. The access assembly 10148 and viewing assembly 10152 are coupled with a distal end of the surgical assembly support 10144. The access assembly 10148 includes an access device or retractor 10156 and an access device mounting fixture 10160.

The viewing assembly 10152 includes a viewing element 10162, an elongate member 10164 and an arcuate member 10168 located on the distal end of the elongate member 10164. The elongate member 10164 is translatably coupled with the distal end of the surgical assembly support 10144, as indicated by arrows S. The viewing element 10162 is coupled with the arcuate member 10168, preferably by way of a viewing element mount 10170, for translation about the arcuate member 10168, as indicated by arrows T. The motion indicated by the arrows S and T allows the viewing element 10162 to be positioned as desired in any location about the proximal end of the access device 10156.

FIG. 247 is another embodiment of a surgical assembly 10180 that is similar to the surgical assembly 9000, except as set forth below. The surgical assembly 10180 includes a surgical assembly support 10184, an access assembly 10188, and a viewing assembly 10192. The access assembly 10188 and viewing assembly 10192 are coupled with a distal end of the surgical assembly support 10184. The access assembly 10188 includes an access device or retractor 10196 and an access device mounting fixture 10200. The access device 10198 may be any suitable access device.

The viewing assembly 10192 includes a viewing assembly support arm 10204, a viewing element support fixture 10208 coupled with a distal end of the viewing assembly support arm 10204, and a viewing element mounted in the viewing element support fixture 10208. The proximal end of the viewing assembly support arm 10204 is coupled with a positioning element 10212. The positioning element 10212 includes a wheel 10216 in one form that is rotatably coupled with the surgical assembly 10180 at a first location 10220 near an outer perimeter thereof. The viewing assembly support arm 10204 is rotatably coupled with the wheel 10216 at a second location 10224 spaced from the first location 10220. The first and second locations 10220, 10224 are selected to provide a wide range of positions about the proximal end of the access device 10196, two of which are illustrated in FIG. 248.

FIG. 249 illustrates a portion of another embodiment of a surgical assembly. In particular, a viewing assembly 10240 includes a viewing element 10244 and a viewing element support 10248. The viewing element support 10248 includes a track 10252 with gear teeth 10254 and a race 10256, in one embodiment. The gear teeth 10254 are configured to mate with gear teeth 10262 of an internal gear 10264. The viewing element 10244 is coupled with the internal gear 10264 whereby the viewing element 10244 may be positioned about the track 10252 at any desired location.

With reference to FIGS. 250-251, a viewing element support mount 10280 comprises a scope mounting hole 10282 coupled with an expandable and contractible clamping element 10284. The clamping element 10284 has a plurality of notches or holes 10286. The clamping element 10284 can be adjusted to fit around a proximal portion of an access device. The clamping element 10284 is adjustable to accommodate proximal portions having different shapes or sizes. A gear or ratchet mechanism 10288 can be coupled with the clamping element 10284 to adjust the size of the clamping element 10284. The clamping element 10284 can be used with oblong shaped access devices, as well as with circular shaped access devices.

With reference to FIGS. 252-253, a viewing element support assembly 10300 is illustrated. A viewing element 10302 is configured to be received in a viewing element support block 10304. The viewing element support block 10304 comprises a clamp 10306 and a clamp release button 10308. The viewing element support block 10304 can be inserted onto a viewing element support platform 10310. The viewing element support platform 10310 preferably is configured to be coupled with a proximal portion of an access device 10314. In the illustrated embodiment, the viewing element support platform 10310 has a slot 10312 with a T-shaped cross-section for receiving a clamping member 10306 of the viewing element support block 10304. When the clamp member 10306 of the viewing element support block 10304 is placed in the viewing element support platform 10310, and into the T-shaped slot 10312, the viewing element support block 10304 can be positioned at a plurality of locations in the T-shaped slot 10312. The viewing element support block 10304 can be positioned around the periphery of the proximal portion of the access device 10314. The viewing element 10302 can be positioned within the access device 10314 at any desired location. The viewing element support block 10304 can be repositioned within the T-shaped slot 10312 by pressing the clamp release button 10308 and moving the viewing element support block 10304. When a desired position is achieved, the clamp release button 10308 is released and the clamp 10306 preferably clamps to the T-shaped slot 10312. The embodiment shown in FIGS. 252-253 provides for positioning of viewing elements in desired locations within the access device.

With reference to FIGS. 254-255, another embodiment of viewing element support portion 10320 is illustrated. The viewing element 10322 is configured to be received in the viewing element support block 10324. The viewing element support block 10324 has a C-shaped clamp 10326 and a clamp release button 10328. In the illustrated embodiment, the viewing element comprises a camera 10330. The viewing element support block 10324 is configured to be coupled with a viewing element support platform 10332. The C clamp 10326 of the viewing element support block 10324 can be positioned over an edge 10334 of the viewing element support platform 10332. The viewing element 10322 can extend into an opening 10336 in the viewing element support platform 10332 and into an access device 10338. The viewing element support block 10324 can be unclamped from the viewing element support platform 10332 and repositioned to various locations on the viewing element support platform 10332.

With reference to FIG. 256, one embodiment of viewing element support mount 10340 has a viewing element 10342 coupled with a viewing element support block 10344. The viewing element 10342 in some embodiments can include a camera 10346. The viewing element support block 10344 can comprise an air pressure port 10348 and an air pressure release valve 10350. In the illustrated embodiment, the viewing element support block 10344 is coupled with a viewing element support platform 10352 by creating a vacuum between the viewing element support platform 10352 and the viewing element support block 10344. The viewing element support platform 10352 in one embodiment has a substantially smooth surface. The viewing element support platform 10352 has an opening 10354 configured to receive a proximal portion of an access device 10356. The viewing element support block 10344 is positioned in a desired location on the viewing element support platform 10352 so that the viewing element 10342 can be positioned within the access device 10356 for viewing the surgical location. FIG. 257 is a side view of the viewing element support mount 10340 in FIG. 256. With reference to FIG. 257, a cavity 10358 is provided for generating the vacuum with sealed portions 10360 surrounding the cavity.

With reference to FIGS. 258-259, a viewing element support mount 10380 has a viewing element 10382 coupled with a viewing element support block 10384 having a suction cup 10386. The suction cup 10386 of the viewing element support block 10384 is configured to be coupled with a viewing element support platform 10388. In one embodiment, the viewing element support platform 10388 is formed with a polished glass plate. The viewing element support block 10384 has a suction release button 10390 to enable to the viewing element support block 10384 to be removed and repositioned on the viewing element support platform 10388. In some embodiments, the viewing element 10382 can comprise a camera 10392. The viewing element support block 10384 can be coupled with the viewing element support platform 10388 at various locations.

FIGS. 260-261 illustrates another embodiment of a viewing element support mount 10400 having a viewing element support block 10404 with a suction cup 10402. The viewing element support block 10404 is shown in different states. The viewing element support block 10404 has a suction cup 10402 in a free state 10406 with a spring 10408 in tension. The viewing element support block 10404 is shown in a compression state 10410 with the controls 10408 released. Following the compression state 10410, the viewing element support block 10404 is in a suction state 10414 and is coupled with a viewing element support platform 10416. Actuating the controls 10412 causes the device to pull up on the lip of the suction cup 10402 to release the suction at the release state 10418. The viewing element support block 10404 is then returned to the free state 10406. Any other suitable coupling method can be used for coupling a viewing element to a viewing element support mount.

With reference to FIG. 262, an access device 10440 has a fixed proximal portion 10442 coupled with a viewing element 10444 and a viewing element support mount 10446. The viewing element 10444 can be coupled with the viewing element support mount 10446 with a ball joint to enable the viewing element 10444 to pivot and rotate relative to the viewing element support mount 10446 and the access device 10440. In other embodiments, the proximal portion 10442 of the access device 10440 can be rotated and/or pivoted.

FIGS. 263-264 show further embodiments of viewing assemblies for adjustably coupling a viewing element to an access device mounting fixture. FIG. 263 shows a surgical assembly 10460 that is similar to the surgical assembly 9000, except as set forth below. The surgical assembly 10460 includes a surgical assembly support and an access assembly in phantom, and a viewing assembly 10464. The access assembly and viewing assembly 10464 are coupled with a distal end of the surgical assembly support.

The viewing assembly 10464 is coupled with the surgical assembly in a suitable manner. For example, in one embodiment, the viewing assembly 10464 is coupled with a portion of an access assembly. In one embodiment, a ball joint connection 10468 is provided between the viewing assembly 10464 and a jaw 10472 of an access device mounting fixture. A linkage 10476 preferably extends between the ball joint connection 10468 and a viewing element 10480. In the embodiment of FIG. 263, the linkage 10476 comprises a first member 10484A, a second member 10484B, and a third member 10484C. Each of the first, second, and third members 10484A, 10484B, 10484C are coupled by ball joints 10488A, 10488B. The viewing element 10480 can be coupled with the member 10484C by way of a ball joint 10492. Arrows 10496 indicate that the viewing element 10480 is adjustable in pitch, yaw, roll, and elevation. FIG. 264 illustrates a similar arrangement wherein a two member linkage is provided. The two members of the linkage are joined by a ball joint.

The ball joint and linkage systems shown in FIGS. 263-264 can include pneumatic or hydraulic actuation and position control. FIGS. 265-266 illustrate one such arrangement. FIG. 265 illustrates a linkage 10500 that includes a first member 10504 and a second member 10508 joined by a ball joint 10512. The position of the first member 10504 and the second member 10508 can be fixed by any suitable means, such as by a clamp 10514. The second member 10508 includes a body portion 10520, a clamping jaw 10524, and a clamp pivot 10528 about which the body portion 10520 and the clamping jaw 10524 pivot under pneumatic or hydraulic actuation.

The ball joint 10512 is shown in greater detail in FIG. 266. The ball joint includes a ball 10532, a clamping socket 10536 and a series of passages. A first passage 10540 extends through the ball 10532 between the clamping socket 10536 and the first member 10504. Fluid may be conducted downstream from the ball 10532 to another ball joint or other linkage member. The upstream end of the first passage 10540 nearest to the clamping socket 10536 communicates with a second passage 10544 that is located between the ball 10532 and the clamping socket 10536. The second passage communicates with a third passage 10548 extending between the second passage 10544 and a fourth passage 10552 formed between the body portion 10520 and the clamping jaw 10524. An O-ring seal 10556 (or any other suitable sealing arrangement) may be provided to force a fluid in the fourth passage 10552 into the third passage 10548. A fifth passage 10560 communicates with the fourth passage 10552 and extends into the body portion 10520. The fifth passage 10560 is in fluid communication with a source of fluid pressure.

The series of passages shown in FIG. 266 enable clamping of the ball joint 10512. In one arrangement, fluid pressure is dissipated in the passages, allowing the ball 10532 to move freely in the ball joint 10512. The first member 10504 (which may be coupled with a viewing element) may then be repositioned with respect to the second member 10508. When the desired position is reached, the fluid pressure in the passages may be applied. This pressure is communicated to the second passage 10544 wherein the pressure is applied to the side of the ball 10532 opposite the first member 10504. The ball 10532 is thereby forced up against the body portion 10520 of the second member 10508. The pressure of the ball 10532 up against the body portion 10520 of the second member 10508 causes the ball 10532 to be immobilized temporarily. The fluid used to actuate the clamping may be gas, e.g., air, or liquid, e.g., water.

The pneumatic or hydraulic actuation and position control arrangement of FIGS. 263-266 preferably is able to hold securely the weight of a surgical viewing element, such as a camera and/or a fiber light cable. The arrangements of FIGS. 263-266 advantageously keep the mounting fixtures out of tool path and sight lines. Another approach for clamping the viewing assemblies of FIGS. 263-266 would employ a friction fit, alone or in combination with a pneumatic or hydraulic fluid clamp.

FIG. 267 is a top view of one embodiment of an access device mounting fixture 10600 for adjustably mounting an access device. The access device mounting fixture 10600 includes a first jaw 10604 and a second jaw 10608. The first and second jaws 10604, 10608 are configured to couple to an access device in a suitable manner, e.g., to clamp an access device, to adjustably mount an access device, etc.

The access device mounting fixture 10600 also includes means to adjust the position of the jaws 10604, 10608 with respect to each other. In one form, the mounting fixture 10600 includes a box joint pivot 10612 that is actuated by a screw and nut arrangement 10616. In particular, a support arm 10620 extends proximally of a pivot location 10624. The first jaw 10604 extends between a proximal end 10628, which is coupled with the support arm 10620 at the pivot location 10624, and a distal end 10632, which is configured to be coupled with an access device. The first jaw 10604 has a bore 10636 extending transversely therethrough at a location between the proximal end 10628 and the distal end 10632. The bore 10636 is configured to receive a portion of the screw and nut arrangement 10616 for adjustment of the access device mounting fixture. The jaw 10604 also includes an access device engagement portion 10640 near the distal end 10632. The access device engagement portion 10640 preferably has an arcuate inside shape, which is circular in one embodiment. Other suitable shapes, such as oval shapes, may also be employed in connection with the access device engagement portion 10640. Further details of the engagement portion 10640 are discussed below in connection with FIG. 269.

The second jaw 10608 extends between a proximal end 10644, which is coupled with the support arm 10620 at the pivot location 10624, and a distal end 10648, which also is configured to coupled with an access device. The pivot jaws 10604, 10608 are thus enabled to pivot with respect to each other and are supported proximally by the support arm 10620. The first jaw 10608 has a bore 10652 extending transversely therethrough at a location between the proximal end 10644 and the distal end 10648. The bore 10652 is configured to receive a portion of the screw and nut arrangement 10616 for adjustment of the access device mounting fixture 10600. The jaw 10608 also includes an access device engagement portion 10656 near the distal end 10648. The access device engagement portion 10656 preferably has an arcuate inside shape, which is circular in one embodiment. Other suitable shapes, such as oval shapes, may also be employed in connection with the access device engagement portion 10656. Further details of the engagement portion 10656 are discussed below in connection with FIG. 269.

In one form the screw and nut arrangement 10616 includes an advancement element 10660 which is connected to a screw 10664. The advancement element 10660 preferably is a side-mounted wheel. The screw 10664 is threaded and is sized to extend through the bore 10652 and at least partially through the bore 10636. The bore 10636 preferably is sized to receive a ball nut 10668 which has threads that engage threads on the screw 10664. Thus by turning the side-mounted wheel, the ball nut 10668 is advanced toward the wheel, which causes the jaws 10604, 10608 to be advanced toward each other. Advancement of the jaws 10604, 10608 causes the access device engagement portions 10640, 10658 to be advanced toward each other, which could cause an access device coupled therewith to be reduced in size, e.g., un-expanded. If the jaws 10604, 10608 are moved in the opposite direction, an access device coupled therewith would be expanded thereby.

FIG. 268 shows another embodiment of an access device mounting fixture 10680, which is similar to the mounting fixture 10600 except as detailed below. The mounting fixture 10680 includes a first jaw 10684, a second jaw 10688, and a jack screw arrangement 10692 that is coupled with the jaws 10684, 10688 such that the jack screw 10692 can actuate the jaws 10684, 10688. A double arrow J illustrates that motion of the jaws 10684, 10688 away from each other enables expansion of an access device, such as the access devices described or incorporated by reference herein.

FIG. 269 is a detail view of an access device engagement portion 10696 of the jaw 10688. The cross-sectional profile of the engagement portion 10696 may take the form of an inverted "J". This arrangement provides a channel 10704 that extends around the bottom surface of the jaw 10684. A similar channel may be formed on the jaw 10684 such that when the jaws 10684, 10688 are brought together completely, a circular channel is formed on the bottom surface of the mounting fixture 10680. The shape of the channel 10704 need not be circular. The channel shape could be any shape that corresponds with a shape of a proximal end of an access device. In another embodiment, the engagement portion 10696 may be relatively short, forming a hook-like feature.

As shown in FIG. 269, the channel 10704 is configured to receive a proximal end 10708 of a proximal portion 10712 of an access device 10716. One skilled in the art should recognize that further clamping devices can be provided to maintain the elevation of an access device with respect to the mounting fixture 10680. Also, in some procedures, the patient may at least partially support the access device.

FIG. 270 shows another embodiment of an access device mounting fixture 10740. The access device mounting fixture 10740 is similar to those hereinbefore described, except as set forth below. The access device mounting fixture 10740 includes a first jaw 10744 and a second jaw 10748. The first and second jaws 10744, 10748 are translatably mounted, such that the second jaw 10748 may be moved at least between a first position 10752 and a second position 10756. The first position 10752 corresponds to an un-expanded position (e.g., an un-expanded position or configuration of an access device). The second position 10756 corresponds to an expanded position (e.g., an expanded position or configuration of an access device).

One embodiment of a translatable coupling of the jaws 10744, 10748 is illustrated in FIG. 70. A pin 10760 is received within corresponding recesses 10764A, 10764B formed in the first and second jaws 10744, 10748. In the illustrated embodiment, the pin 10760 is positioned distal of an access device engagement portion of the jaws 10744, 10748, but the pin 10760 could be located elsewhere as well. A translation actuator 10768 is located near a proximal end of the jaw 10748. The translation actuator 10768 can take any form, e.g., a screw that engages threads associated with the jaw 10744. The translation actuator 10768 has a wheel 10772 for advancement in one embodiment. The translatable coupling of the access device mounting fixture 10740 provides linear motion of the jaw 10744 with respect to the jaw 10748.

FIGS. 271-272 show one embodiment of a viewing element mount 10800. The viewing element mount 10800 provides adjustable coupling of a viewing element 10802 to an access device or an access device mounting fixture. The viewing element mount is spring loaded and can be positioned in a contracted configuration or an expanded configuration. In a contracted configuration, spring loaded elements 10804, 10806 are compressed and side portions 10808, 10810 of the mount are positioned near one another. The contracted mount 10800 preferably can engage an access device having an expandable proximal portion when the access device is in the contracted configuration. When the access device is to be expanded at the proximal portion, the support mount 10800 can also be positioned in an expanded configuration. The side portions 10808, 10810 of support mount can be separated. The spring loaded elements 10804, 10806 preferably snap into position between the side portions 10808, 10810 to maintain a generally continuous surface around the proximal portion of the access device for mounting or supporting the viewing element 10802 when the access device and the support mount 10800 are in expanded configurations. In the illustrated embodiment, the viewing element 10802 has a pair of adjustable roller mounts 10812, 10814, for engaging the support mount 10800.

With reference to FIG. 273, a viewing element support mount 10820 comprises first and second side portions 10822, 10824. The viewing element support portion 10826 is expandable from a contracted configuration to an expanded configuration. Side portions 10822, 10824 are coupled with one another via a linkage mechanism 10828. In a contracted configuration, the first and second side portions 10822, 10824 are positioned generally near one another and the linkage mechanisms 10828 are in a generally folded position. In the expanded configuration, the first and second side portions 10822, 10824 are spaced from one another and the linkage mechanisms 10828 are in an extended locked position. In the expanded configuration, the linkage mechanisms 10828 in the locked configuration form a continuous surface 10830 between the top of the first side portion 10822 and the top of the second side portion 10824 such that a viewing element can be mounted at various positions along the expanded viewing element support portion 10826.

With reference to FIG. 274, another embodiment of an expandable viewing element support mount 10840 is illustrated. In the viewing element support mount 10840 of the illustrated embodiment, side portions 10842, 10844 of the viewing element support mount 10840 have a generally C-shaped cross-section. A coiled spring 10846 is deployed within the side portions 10842, 10844 of the viewing element support mount 10840. A viewing element 10848 is configured to slide relative to the side portions 10842, 10844 of the viewing element support mount 10840 when the viewing element support mount 10840 is in the expanded configuration. The coiled spring 10846 can actuate the side portions 10842, 10844 of the viewing element support mount 10840 between the first configuration and the second configuration.

With reference to FIG. 275, in one embodiment of a viewing element support mount 10860 a proximal portion 10862 of the support mount 10860 comprises a ball joint 10864 and a jack screw 10866 for manipulating the viewing element support mount 10860 to a desired position relative any access device. Near a distal end 10868 of the viewing element support mount 10860, an extended visualization window 10870 is provided. Additionally, a viewing element pivot mount 10872 is placed in a distal portion of the viewing element support mount 10860.

With reference to FIGS. 276-280, another embodiment of a viewing element support mount 10880 is illustrated. The viewing element support mount 10880 includes a ball joint 10882 at a proximal portion of the handle 10884. A jack screw 10886 is also provided to provide elevation and rotation of the viewing element support mount 10880. The viewing element support mount 10880 has an arm portion 10888 that extends downward toward an access device coupling location 10890. The viewing element 10892 can be rotated in the viewing element support location 10894. In one embodiment, the viewing element support mount 10880 can be coupled with a generally oval-shaped proximal portion of an access device 10896. The viewing element support mount 10880 can be pivoted or rotated to move the viewing element 10892 to various positions along the proximal portion of the access device 10896. In one embodiment, a viewing element support portion 10898 can swing approximately 60 degrees to follow along a sidewall of an oval-shaped collar of an access device 10896. In one embodiment, the viewing element 10892 comprises a camera. In some embodiments, the camera can have approximately 300 degrees of rotary translation about the axis of the scope as shown in FIG. 277. In one embodiment, the viewing element support portion 10898 has a generally kidney-shaped viewing window that can be positioned over the access device 10896 and the viewing element 10892 can be positioned at locations along the viewing window.

With reference to FIGS. 281-283, an access device mounting system 10900 is provided with a simplified mount control arm 10902 for coupling with an access device 10904. In the illustrated embodiment, a distal portion 10906 of the mount control arm 10902 is coupled with a proximal portion 10908 of the access device 10904. The handle portion 10910 of the mount control arm 10902 can be coupled with a vacuum pressure system similar to those described previously with respect to the mount control arms. A pressure release button 10912 can be configured on the mount control arm 10902. The simplified structure for the mount control arm 10902 can provide for increase visualization of the surgical location within the access device 10904 and can minimize the hardware associated with supporting the access device 10904 in the desired position.

FIG. 284 is a perspective view of a surgical assembly 10920 having a thumb-wheel lock and/or a cam lever lock. One embodiment of an access device support assembly 10922 comprises an access device 10924 with a proximal portion 10926 and an expandable distal portion 10928. A simplified access device mounting fixture 10930 comprises a yoke adjustment. In one embodiment, the access device mounting fixture 10930 can comprise a thumb-wheel lock 10932. In another embodiment, the access device mounting fixture 10930 can comprise a cam lever lock 10934. The mounting fixture 10930 preferably comprises a vacuum release button 10934 in some embodiments.

The various devices, methods and techniques described above provide a number of ways to carry out the invention. Of course, it is to be understood that not necessarily all objectives or advantages described may be achieved with any particular embodiment described herein. Also, although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

Many of the systems, apparatuses, methods, and features described herein can be combined with many of the systems, apparatuses, methods and features disclosed in the following patents and patent applications. The entire disclosure of all of the following patents and patent applications is hereby incorporated by reference herein and made a part of this specification: U.S. Pat. Nos. 6,361,488 (issued Mar. 26, 2002), 6,530,880 (issued Mar. 11, 2003), 6,648,888 (issued Nov. 18, 2003), 6,652,553 (issued Nov. 25, 2003), 6,641,583 (issued Nov. 4, 2003), 6,554,832 (issued Apr. 29, 2003), 6,673,074 (issued Jan. 6, 2004), U.S. patent application Ser. Nos. 09/821,666 (filed Mar. 29, 2001, published Oct. 3, 2002 as Publication No. U.S. 2002/0143328A1), 09/824,411 (filed Apr. 2, 2001, published Oct. 3, 2002 as Publication No. U.S. 2002/0143330A1), 09/921,326 (filed Aug. 2, 2001, published Feb. 6, 2003 as Publication No. U.S. 2003/0028191A1), 09/940,402 (filed Aug. 27, 2001, published Feb. 27, 2003 as Publication No. US 2003/0040656A1), 10/075,668 (filed Feb. 13, 2002, published Aug. 14, 2003 as Publication No. U.S. 2003/0153911A1), 10/087,489 (filed Mar. 1, 2002, published Sep. 4, 2003 as Publication No. U.S. 2003/0167058A1), 10/178,875 (filed Jun. 24, 2002, published Dec. 25, 2003 as Publication No. U.S. 2003/0236529A1), 10/280,489 (filed Oct. 25, 2002, published Apr. 17, 2003 as Publication No. US 2003/0073998A1), 10/280,799 (filed Oct. 25, 2002), Ser. No. 10/361,887 (filed Feb. 10, 2003, published Aug. 14, 2003 as Publication No. US 2003/0153927A1), 10/658,736 (filed Sep. 9, 2003), 10/678,744 (filed Oct. 2, 2003), 10/693,815 (filed Oct. 24, 2003), 10/693,250 (filed Oct. 24, 2003), 10/693,663 (filed Oct. 24, 2003), 10/842,651 (filed May 10, 2004), 10/845,389 (filed May 13, 2004) U.S. Provisional Applications No. 60/471,431 (filed May 16, 2003), 60/497,763 (filed Aug. 26, 2003), 60/497,822 (filed Aug. 26, 2003), 60/513,796 (filed Oct. 22, 2003), 60/513,013 (filed Oct. 23, 2003), 60/514,559 (filed Oct. 24, 2003), 60/545,587 (filed Feb. 18, 2004), 60/558,296 (filed Mar. 31, 2004), 60/579,643 (filed Jun. 15, 2004).

What is claimed is:

1. A device for retracting tissue to provide access to a spinal location within a patient, said device comprising:
   a proximal portion partially defining a first portion of a path through which surgical instruments can be inserted to the surgical location;
   a distal portion partially defining a second portion of the path;
   a first joint located on a first side of the device; and a second joint located on a second side of the device opposite the first joint; a gimbal ring, wherein the first and second joints are pivot joints;
   wherein said proximal portion defining the first portion of the path is capable of being moved relative to said distal portion about a first axis extending through the first and second joints and about a second axis that is perpendicular to the first axis.

2. The device of claim 1, wherein the gimbal ring comprises a first pair of apertures on opposite sides thereof through which a first pivot axis extends and a second pair of apertures located on opposite sides thereof through which a second pivot axis extends, the first pivot axis being perpendicular to the second pivot axis.

3. The device of claim 2, wherein a first pair of joints are formed at the first pair of apertures and a second pair of joints are formed at the second pair of apertures, each of the first pair of joints comprising a member about which at least one of the gimbal ring and the proximal portion can rotate, each of the second pair of joints comprising a member about which at least one of the gimbal ring and the distal portion can rotate.

4. The device of claim 1, wherein the first and second joints are formed in part by the distal portion and further comprising a third joint partially formed by the proximal portion.

5. The device of claim 1, further comprising a fourth joint coupled with the proximal portion, the third and fourth joints being on opposite sides of the device, wherein the second axis extends through the third and fourth joints.

6. The device of claim 1, wherein the first portion of the path has a first longitudinal axis and the second portion of the path has a second longitudinal axis, wherein the proximal portion is configured to be moved relative to the distal portion such that the first and second longitudinal axes are not coaxial.

* * * * *